(12) United States Patent
Breslin et al.

(10) Patent No.: US 9,238,656 B2
(45) Date of Patent: Jan. 19, 2016

(54) IMIDAZO[4,5-B]PYRIDINE DERIVATIVES AS ALK AND JAK MODULATORS FOR THE TREATMENT OF PROLIFERATIVE DISORDERS

(71) Applicant: Cephalon, Inc., Frazer, PA (US)

(72) Inventors: Henry J. Breslin, Lansdale, PA (US); Matthew A. Curry, Coatesville, PA (US); Diane E. Gingrich, Downingtown, PA (US); Keith S. Learn, Perkiomenville, PA (US); Gregory R. Ott, Media, PA (US); Jason C. Wagner, Coatesville, PA (US)

(73) Assignee: Cephalon, Inc., Frazer, PA (US)

( * ) Notice: Subject to any disclaimer, the term of this patent is extended or adjusted under 35 U.S.C. 154(b) by 0 days.

(21) Appl. No.: 14/446,411

(22) Filed: Jul. 30, 2014

(65) Prior Publication Data

US 2014/0350011 A1 Nov. 27, 2014

Related U.S. Application Data

(63) Continuation of application No. PCT/US2013/023778, filed on Jan. 30, 2013.

(60) Provisional application No. 61/592,074, filed on Jan. 30, 2012.

(51) Int. Cl.

| | | |
|---|---|---|
| C07D 493/08 | (2006.01) |
| C07D 491/107 | (2006.01) |
| C07D 471/04 | (2006.01) |
| A61K 31/47 | (2006.01) |
| A61K 31/437 | (2006.01) |
| A61K 31/444 | (2006.01) |
| A61K 31/4545 | (2006.01) |
| A61K 31/496 | (2006.01) |
| A61K 31/506 | (2006.01) |
| A61K 31/5377 | (2006.01) |
| A61P 35/00 | (2006.01) |

(52) U.S. Cl.
CPC ............ *C07D 493/08* (2013.01); *C07D 471/04* (2013.01); *C07D 491/107* (2013.01)

(58) Field of Classification Search
CPC . C07D 471/04; C07D 491/107; C07D 493/08
See application file for complete search history.

(56) References Cited

U.S. PATENT DOCUMENTS

| | | | | | |
|---|---|---|---|---|---|
| 2007/0129364 A1* | 6/2007 | Dong | .................... | C07D 471/04 514/232.8 |
| 2007/0208053 A1* | 9/2007 | Arnold | ................. | C07D 471/04 514/300 |
| 2008/0300267 A1* | 12/2008 | Okram | ................. | C07D 471/04 514/275 |
| 2009/0048249 A1* | 2/2009 | Chiu | .................... | C07D 471/04 514/234.2 |
| 2011/0312908 A1* | 12/2011 | Gray | ..................... | C07D 239/42 514/46 |
| 2012/0277228 A1* | 11/2012 | Sutton | .................. | C07D 471/04 514/234.5 |
| 2014/0194418 A1* | 7/2014 | Vasudevan | ........... | C07D 471/04 514/233.2 |
| 2015/0011557 A1* | 1/2015 | Schiemann | .......... | C07D 403/04 514/250 |

FOREIGN PATENT DOCUMENTS

| | | |
|---|---|---|
| WO | WO 96/29993 | 10/1996 |
| WO | WO 2004/016611 | * 2/2004 |
| WO | WO 2004/099204 | * 11/2004 |
| WO | WO 2007/007919 | * 1/2007 |
| WO | WO 2007/077949 | 1/2007 |
| WO | WO 2007/072017 | * 6/2007 |
| WO | WO 2007/077949 | * 7/2007 |
| WO | WO 2009/001021 | * 12/2008 |

OTHER PUBLICATIONS

Angeles et al., "Enzyme-Linked Immunosorbent Assay for trkA Tyrosine Kinase Activity," *Analytical Biochemistry* (1996) 236, pp. 49-55.
Argetsinger et al., "Identification of JAK2 as a Growth Hormone Receptor-Associated Tyrosine Kinase," *Cell* (1993) 74, pp. 237-244.
Armitage et al., *Cancer: Principle and Practice of Oncology*, 6$^{th}$ ed. (2001), pp. 2256-2316.
Bai et al., "Nucleophosmin-anaplastic lymphoma kinase associated with anaplastic large-cell lymphoma activates the phosphatidylinositol 3-kinase/Akt antiapoptotic signaling pathway," *Blood* (2000) 96, pp. 4319-4327.
Bai et al., "Nucleophosmin-Anaplastic Lymphoma Kinase of Large-Cell Anaplastic Lymphoma is a Constitutively Active Tyrosine Kinase that Utilizes Phospholipase C-γ to Mediate its Mitogenicity," *Molecular and Cellular Biology* (1998) 18, pp. 6951-6961.
Baxter et a., "Acquired mutation of the tyrosine kinase JAK2 in human myeloproliferative disorders," *Lancet* (2005) 365, pp. 1054-1061.

(Continued)

*Primary Examiner* — Joseph Kosack
*Assistant Examiner* — Amanda L Aguirre

(57) ABSTRACT

This application relates to compounds of the Formula I

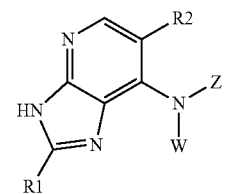

as defined herein, and/or salts thereof. This application further relates to compositions and methods of using these compounds and/or salts thereof. The compounds of Formula I are useful as ALK and JAK modulators for the treatment of proliferative disorders.

28 Claims, No Drawings

(56) References Cited

OTHER PUBLICATIONS

Benekli et al., "Signal transducer and activator of transcription proteins in leukemias," *Blood* (2003) 101, pp. 2940-2954.
Bilsland et al., "Behavioral and Neurochemical Alterations in Mice Deficient in Anaplastic Lymphoma Kinase Suggest Therapeutic Potential for Psychiatric Indictions," *Neuropsychopharmacology* (2008) 33, pp. 685-700.
Chen et al., "Oncogenic mutations of ALK kinase in neuroblastoma," *Nature* (2008) 455, pp. 971-974.
Cheng et al., "Anaplastic Lymphoma Kinase as a Therapeutic Target in Anaplastic Large Cell Lymphoma, Non-Small Cell Lung Cancer and Neuroblastoma," *Anti-Cancer Agents in Med. Chem.* (2010) 10, pp. 236-249.
Chiarle et al., "The anaplastic lymphoma kinase in the pathogenesis of cancer," *Nature Review Cancer* (2008) 8, pp. 11-23.
Choi et al., "Identification of Novel Isoforms of the EML4-ALK Transforming Gene in Non-Small Cell Lung Cancer," *Cancer Res.* (2008) 68, pp. 4971-4976.
Christensen et al., "Cytoreductive antitumor activity of PF-2341066, a novel inhibitor of anaplastic lymphoma kinase and c-Met, in experimental models of anaplastic large-cell lymphoma," *Mol. Cancer Ther.* (2007) 6, pp. 3314-3322.
Desai et al., "Clonal Evolution of Resistance to Imatinib in Patients with Metastatic Gastrointestinal Stromal Tumors," *Clin. Cancer Res.* (2007) 13, pp. 5398-5405.
Engelman et al., "Mechanisms of Acquired Resistance to Epidermal Growth Factor Receptor Tyrosine Kinase Inhibitors in Non-Small Cell Lung Cancer," *Clin. Cancer Res.* (2008) 14, pp. 2895-2899.
Engelman et al., "Acquired resistance to tyrosine kinase inhibitors during cancer therapy," *Curr. Opin. Genetics & Development* (2008) 18, pp. 73-79.
Ergin et al., "Inhibition of tyrosine kinase activity induces caspase-dependent apoptosis in anaplastic large cell lymphoma with NPM-ALK (p80) fusion protein," *Experimental Hematology* (2001) 29, pp. 1082-1090.
Falini et al., "Lymphomas Expressing ALK Fusion Protein(s) Other Than NPM-ALK," *Blood* (1999) 94, pp. 3509-3515.
Galkin et al., "Identification of NVP-TAE684, a potent, selective, and efficacious inhibitor of NPM-ALK," *Proc. Natl. Acad. Sci.* (2007) 104, pp. 270-275.
George et al., "Activating mutations in ALK provide a therapeutic target in neuroblastoma," *Nature* (2008) 455, pp. 975-978.
Grande et al., "Target Oncogenic ALK: A Promising Strategy for Cancer Treatment," *Mol. Cancer Ther.* (2011) 10, pp. 569-579.
Griesinger et al., "A BCR-JAK2 Fusion Gene as the Result of a t(9;22)(p24;q11.2) Translocation in a Patient with a Clinically Typical Chronic Myeloid Leukemia," *Genes, Chromosomes & Cancer* (2005) 44, pp. 329-333.
Iwahara et al., "Molecular characterization of ALK, a receptor tyrosine kinase expressed specifically in the nervous system," *Oncogene* (1997) 14, pp. 439-449.
James et al., "A unique clonal JAK2 mutation leading to constitutive signaling causes polycythaemia vera," *Nature* (2005) 434, pp. 1144-1148.
Janoueix-Lerosey et al., "Somatic and germline activating mutations of the ALK kinase receptor in neuroblastoma," *Nature* (2008) 455, pp. 967-970.
Koivunen et al., "EML4-ALK Fusion Gene and Efficacy of an ALK Kinase Inhibitor in Lung Cancer," *Clin. Cancer Res.* (2008) 14, pp. 4275-4283.
Kuefer et al., "Retrovirus-Mediated Gene Transfer of NPM-ALK Causes Lymphoid Malignaucy in Mice," *Blood* (1997) 90, pp. 2901-2910.
Kutok et al., "Molecular Biology of Anaplastic Lymphoma Kinase-Positive Anaplastic Large-Cell Lymphoma," *J. Clin. Oncology* (2002) 20, pp. 3691-3702.
Lacronique et al., "A Tel-JAK2 Fusion Protein with Constitutive Kinase Activity in Human Leukemia," *Science* (1997) 278, pp. 1309-1312.
Lawrence et al., "TPM3-ALK and TPM4-ALK Oncogenes in Inflammatory Myofibroblastic Tumors," *Am. J. Pathology* (2000) 157, pp. 377-384.
Levine et al., "Activating mutation in the tyrosine kinase JAK2 in polycythemia vera, essential thrombocythemia, and myeloid metaplasia with myelofibrosis," *Cancer Cell* (2005) 7, pp. 387-397.
Liu et al., "BCR-ABL mutants spread resistance to non-mutated cells through a paracrine mechanism," *Leukemia* (2008) 22, pp. 791-799.
Mano, "Non-solid oncogenes in solid tumors: EML4-ALK fusion genes in lung cancer," *Cancer Sci.* (2008) 99, pp. 2349-2355.
McDermott et al., "Genomic Alterations of Anaplastic Lymphoma Kinase May Sensitize Tumors to Anaplastic Lymphoma Kinase Inhibitors," *Cancer Res.* (2008) 68, pp. 3389-3395.
Mentlein et al., "Pleiotrophin, an angiogenic and mitogenic growth factor, is expressed in human gliomas," *J. Neurochem.* (2002) 83, pp. 747-753.
Morris et al., "ALK$^+$ CD30$^+$ Lymphomas: A Distinct Molecular Genetic Subtype of Non-Hodgkin's Lymphoma," *Br. J. Haematology* (2001) 113, pp. 275-295.
Morris et al., "ALK, the chromosome 2 gene locus altered by the t(2;5) in non-Hodgkin's lymphoma, encodes a novel neural receptor tyrosine kinase that is highly related to leukocyte tyrosine kinase (LTK)," *Oncogene* (1997) 14, pp. 2175-2188.
Mosse et al., "Identification of ALK as a major familial neuroblastoma predisposition gene," *Nature* (2008) 455, pp. 930-936.
Nicholson et al., "Tyrosine kinase JAK1 is associated with the granulocyte-colony-stimulating factor receptor and both become tyrosine-phosphorylated after receptor activation," *Proc. Natl. Acad. Sci.* (1994) 91, pp. 2985-2988.
Palmer et al., "Anaplastic lymphoma kinase: signaling in development and disease," *Biochem. J.* (2009) 420, pp. 345-361.
Passoni et al., "Mutation-Independent Anaplastic Lymphoma Kinase Overexpression in Poor Prognosis Neuroblastoma Patients," *Cancer Res.* (2009) 69, pp. 7338-7346.
Peeters et al., "Fusion of TEL, the ETS-Variant Gene 6 (ETV6) to the Receptor-Associated Kinase JAK2 as a Result of t(9;12) in a Lymphoid and t(9;15;12) in a Myeloid Leukemia," *Blood* (1997) 90, pp. 2535-2540.
Piva et al., "Ablation of oncogenic ALK is a viable therapeutic approach for anaplastic large-cell lymphomas," *Blood* (2006) 107, pp. 689-697.
Powers et al., "Pleiotrophin Signaling through Anaplastic Lymphoma Kinase is Rate-limiting for Glioblastoma Growth," *J. Biological Chem.* (2002) 277, pp. 14153-14158.
Reiter et al., "The t(8;9)(p22;p24) is a Recurrent Abnormally in Chronic and Acute Leukemia that Fuses PCM1 to JAK2," *Cancer Res.* (2005) 65, pp. 2662-2667.
Rotin et al., "SH2 domains prevent tyrosine dephosphorylation of the EGF receptor: identification of Tyr992 as the high-affinity binding site for SH2 domains of phospholipase Cγ," *EMBO Journal* (1992) 11; pp. 559-567.
Shah et al., "Mechanisms of resistance to ST1571 in Philadelphia chromosome-associated leukemias," *Oncogene* (2003) 22, pp. 7389-7395.
Shannon et al., "JAKing up hematopoietic proliferation," *Cancer Cell* (2005) 7, pp. 291-293.
Silvennoinen et al., "Structure of the murine JAK2 protein-tyrosine kinase and its role in interleukin 3 signal transduction," *Proc. Natl. Acad. Sci.* (1993) 90, pp. 8429-8433.
Slupianek et al., "Role of Phosphatidylinositol 3-Kinase-Akt Pathway in Nucleophosmin/Anaplastic Lymphoma Kinase-mediated Lymphomagenesis," *Cancer Res.* (2001) 61, pp. 2194-2199.
Soda et al., "Identification of the transforming EML4-ALK fusion gene in non-small-cell lung cancer," *Nature* (2007) 448, pp. 561-566.
Soda et al., "A mouse model for EML4-ALK-positive lung cancer," *Proc. Natl. Acad. Sci.* (2008) 105, pp. 19893-19897.
Stoica et al., "Identification of Anaplastic Lymphoma Kinase as a Receptor for the Growth Factor Pleiotrophin," *J. Biological Chem.* (2001) 276, pp. 16772-16779.

(56) References Cited

OTHER PUBLICATIONS

Takemoto et al., "Proliferation of adult T cell leukemia/lymphoma cells is associated with the constitutive activation of JAK/STAT proteins," *Proc. Natl. Acad. Sci.* (1997) 94, pp. 13897-13902.

Takeuchi et al., "KIF5B-ALK, a Novel Fusion Oncokinase Identified by an Immunohistochemistry-based Diagnostic System for ALK-positive Lung Cancer," *Clin. Cancer Res.* (2009) 15; pp. 3143-3149.

Turturro et al., "Model of Inhibition of the NPM-ALK Kinase Activity by Herbimycin A," *Clin. Cancer Res.* (2002) 8, pp. 240-245.

Walz et al., "Activated JAK2 with the V617F Point Mutation Promotes $G_1$/S Phase Transition," *J. Biological Chem.* (2006) 281, pp. 18177-18183.

Webb et al., "Anaplastic lymphoma kinase: role in cancer pathogenesis and small-molecule inhibitor development for therapy," *Expert Rev. Anticancer Ther.* (2009) 9, pp. 331-356.

Witthuhn et al., "JAK2 Associates with the Erythropoietin Receptor and is Tyrosine Phosphorylated and Activated Following Stimulation with Erythropoietin," *Cell* (1993) 74, pp. 227-236.

\* cited by examiner

IMIDAZO[4,5-B]PYRIDINE DERIVATIVES AS ALK AND JAK MODULATORS FOR THE TREATMENT OF PROLIFERATIVE DISORDERS

SUMMARY

This application relates to compounds of the Formula I

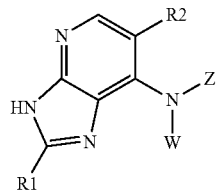

wherein:
W is H and Z is selected from

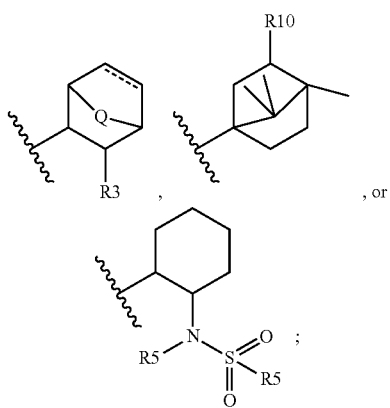

or
W and Z are taken together to form

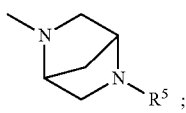

$R^1$ is selected from $(C_6-C_{10})$aryl, aminophenyl, $(C_2-C_9)$heterocycloalkyl, $(C_1-C_9)$heteroaryl or a group of formula

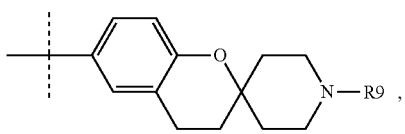

wherein any of the foregoing may be optionally substituted with one or more $R^6$ groups;
$R^2$ is selected from hydrogen or halogen;
$R^3$ is selected from $CH_2OH$ or $CONR^4R^5$;
Q is selected from $CH_2$ or O;
"------" is either present so as to form a double bond or is absent;

$R^4$ and $R^5$ are each independently selected from H, $(C_1-C_6)$alkyl, $(C_3-C_8)$cycloalkyl, $(C_1-C_6)$alkyl$(C_3-C_8)$cycloalkyl, or $(C_1-C_6)$alkyl-$OR^9$, wherein any of the foregoing except H may be optionally substituted with one or more $R^7$;

Each $R^6$ is independently selected from $(C_0-C_4)$alkyl$CO_2R^8$, $(C_0-C_4)$alkyl$CON(R^8)_2$, $(C_0-C_4)$alkyl$COR^8$, $(C_0-C_4)$alkylN$(R^8)_2$, $(C_0-C_4)$alkyl$OR^9$, $(C_1-C_6)$alkoxy, $(C_1-C_6)$alkoxy$(C_2-C_9)$heterocycloalkyl, $(C_1-C_6)$alkoxy$(C_3-C_8)$cycloalkyl, $(C_1-C_6)$alkyl, $(C_1-C_6)$alkyl$(C_1-C_9)$heteroaryl, $(C_1-C_6)$alkyl$(C_2-C_9)$heterocycloalkyl, $(C_1-C_6)$alkyl$(C_3-C_8)$cycloalkyl, $(C_1-C_6)$alkyl$(C_6-C_{10})$aryl, $(C_1-C_9)$heteroaryl, $(C_2-C_6)$alkenyl, $(C_2-C_9)$heterocycloalkyl, $(C_2-C_9)$heterocycloalkyloxy, $(C_3-C_8)$cycloalkyl, $(C_3-C_8)$cycloalkyloxy, $(C_3-C_9)$heterocycloalkenyl, $(C_6-C_{10})$aryl, cyano, halo$(C_1-C_6)$alkoxy, halo$(C_1-C_6)$alkyl, halogen, $O(C_0-C_4)$alkyl$CO_2R^8$, $O(C_0-C_4)$alkyl$CON(R^8)_2$, $O(C_0-C_4)$alkyl$COR^8$, $PO((C_1-C_4)$alkyl$)_2$ or $O(C_0-C_4)$alkylN$(R^8)_2$, wherein any of the foregoing except for halogen, may be optionally substituted with one or more $R^7$;

Each $R^7$ is independently selected from $(C_0-C_4)$alkyl$CO_2R^8$, $(C_0-C_4)$alkyl$CON(R^8)_2$, $(C_0-C_4)$alkyl$COR^8$, $(C_0-C_4)$alkyl$OR^9$, $(C_1-C_6)$alkoxy, $(C_1-C_6)$alkyl, $(C_1-C_6)$alkyl$(C_1-C_9)$heteroaryl, $(C_1-C_6)$alkyl$(C_2-C_9)$heterocycloalkyl, $(C_1-C_6)$alkyl$(C_3-C_8)$cycloalkyl, $(C_1-C_6)$alkyl$(C_6-C_{10})$aryl, $(C_6-C_{10})$aryl, $(C_1-C_9)$heteroaryl, $(C_2-C_9)$heterocycloalkyl, $(C_2-C_9)$heterocycloalkyl optionally substituted with $(C_1-C_6)$alkyl, $(C_3-C_8)$cycloalkyl, $(C_6-C_{10})$aryl, halo$(C_1-C_6)$alkoxy, halo$(C_1-C_6)$alkyl, halogen, hydroxy$(C_1-C_6)$alkyl, $PO((C_1-C_4)$alkyl$)_2$, or hydroxy$(C_1-C_6)$alkyl$(C_1-C_6)$alkoxy;

Each $R^8$ is independently selected from H, $(C_1-C_6)$alkyl, $(C_2-C_9)$heterocycloalkyl, or two $R^8$ are taken together with the nitrogen atom to which they are attached to form $(C_2-C_9)$heterocycloalkyl, wherein any of the foregoing except for H, may be optionally substituted with $(C_1-C_6)$alkyl, $(C_1-C_6)$alkoxy, halo$(C_1-C_6)$alkyl, halo$(C_1-C_6)$alkoxy, halogen, $(C_0-C_4)$alkyl$CO_2R^9$, $(C_0-C_4)$alkylN$(R^9)_2$ or $(C_0-C_4)$alkyl$OR^9$;

$R^9$ is independently selected from H or $(C_1-C_6)$alkyl; and $R^{10}$ is independently a carbonyl or a hydroxyl group.

This application also relates to salts of the compounds of Formula I as well as compositions comprising compounds of Formula I and/or salts of compounds of Formula I. The compounds of Formula I and their pharmaceutically acceptable salts are useful for treating diseases or disorders mediated by one or more tyrosine kinases such as, for example, JAK (Janus kinase) and/or ALK (Anaplastic Lymphoma Kinase).

BACKGROUND

The compounds of the present application are modulators of anaplastic lymphoma kinase (ALK) and Janus Kinase (JAK) and have a number of therapeutic applications, particularly in the treatment of proliferative diseases or disorders including certain cancers as well as hematological malignancies. Specifically, the compounds of the present application inhibit ALK and/or JAK2 kinase. Advantageously, the compounds inhibit both ALK and JAK2 kinase.

Receptor tyrosine kinases (RTKs) are enzymes which span the cell membrane and possess an extracellular ligand binding domain, a transmembrane domain, and a cytoplasmic (intracellular) tyrosine kinase domain (catalytic domain). The intracellular portion participates in cellular signal transduction by phosphorylating specific tyrosine residues in RTK substrate proteins which in turn triggers other transduction events (signal propagation). As a result, tyrosine kinases influence a number of aspects of cellular responses, such as proliferation, growth, differentiation, migration, metabolism and programmed cell death (apoptosis). It has been shown that many of these tyrosine kinases are frequently mutated and/or aberrantly expressed in a number of human disease states such as, for example, breast cancer, gastrointestinal cancers (colon, rectal, and/or stomach cancers), leukemia, ovarian cancer, and pancreatic cancer.

Some examples of RTKs that mediate various cellular responses associated with hyperproliferative disease states include c-erbB-2, c-met, tie-2, PDGFr, FGFr, and EGFR. As such, compounds that selectively inhibit or modulate the activity of one or more tyrosine kinases could provide significant therapeutic benefit in a variety of hyperproliferative disease states in mammals, including humans.

Anaplastic lymphoma kinase (ALK) is a transmembrane-spanning receptor tyrosine kinase, which belongs to the insulin receptor (IR) RTK superfamily. The most abundant expression of ALK occurs primarily in the central and peripheral nervous systems, suggesting a possible role for ALK in the development and function of the nervous system. (Iwahara, T. et al., *Oncogene*, 1997, 14(4), 439-449; Morris, S. W. et al., *Oncogene*, 1997, 14(18), 2175-2188). Mouse studies suggest that ALK may regulate the function of the frontal cortex and hippocampus in the adult brain, making ALK a possible target for psychiatric conditions such as schizophrenia and depression. (Bilsland, J. G., et al. *Neuropsychopharmacology*, 2008, 33(3), 685-700).

ALK is also implicated in the oncogenesis and progression of various human cancers. Specifically, an ALK inhibitor would be expected to either permit durable cures when administered as a single therapeutic agent or combined with current chemotherapy for ALCL, IMT, NSCLC, DLBCL, systemic histiocytosis, glioblastoma and other tumor types. Alternatively, an ALK inhibitor could be used in a maintenance role to prevent cancer recurrence or in patient populations that develop resistance to other therapies.

FAK (focal adhesion kinase), JAK (Janus kinase), Lck, Src, and Abl are examples of non-receptor (cytoplasmic) protein tyrosine kinases (NRPTKs). Initially, NRPTKs were identified in the context of cell growth and differentiation but subsequently the constitutive activation or abherrent expression of NRPTKs has been found to be associated with disease states characterized by abnormal cell growth, in particular cancer, in mammals.

The Janus kinase family (JAKs) consists of 4 members: JAK1, JAK2, JAK3 and TYK2. This family of kinases signals downstream from extracellular cytokines as well as various growth factor receptors. For example, the STAT (signal transduction and transcription) family of transcription factors is the principal, but not exclusive, target for JAKs. Constitutive JAK/STAT signaling is thought to play a critical role in oncogenesis and the progression of many different types of tumors by promoting multiple mechanisms of tumor pathogenesis, including cell proliferation, anti-apoptotic signaling, angiogenesis and tumor immune evasion (Yu et al. 2004). Moreover, constitutively activated JAK/STAT signaling is found in many tumor types, but not in normal tissues (Yu et al. 2004; Benekli et al. 2003). The ability of the JAK/STAT pathway to mediate resistance to apoptosis is particularly important, as most anti-cancer drugs affect tumors by inducing apoptosis.

The importance of these kinases in cellular survival is made evident by the fact that the loss of JAKs is often accompanied by immunodeficiency and non-viability in animal models (Aringer, M., et al.). The JAK family of enzymes is characterized by a number of JAK homology (JH) domains, including a carboxy-terminal protein tyrosine kinase domain (JH1) and an adjacent kinase-like domain (JH2), which is thought to regulate the activity of the JH1 domain (Harpur, A. G., et al.). The four JAK isoforms transduce different signals by being associated specifically with certain cytokine receptors, and activating a subset of downstream genes. For example, JAK2 associates with cytokine receptors specific for interleukin-3 (Silvennoinen, O., et al., *Proc Natl Acad Sci USA*, 1993, 90(18): p. 8429-33), erythropoietin (Witthuhn, B. A., et al., *Cell*, 1993, 74(2): p. 227-36), granulocyte colony stimulating factor (Nicholson, S. E., et al., *Proc Natl Acad Sci USA*, 1994, 91(8): p. 2985-8), and growth hormone (Argetsinger, L. S., et al., *Cell*, 1993, 74(2): p. 237-44).

The JAK family of enzymes has become an interesting set of targets for various hematological and immunological disorders; JAK2 specifically is currently under study as a viable target for neoplastic disease, especially leukemias and lymphomas (Benekli, M., et al., *Blood*, 2003. 101(8): p. 2940-54; Peeters, P., et al., *Blood*, 1997. 90(7): p. 2535-40; Reiter, A., et al., *Cancer Res*, 2005. 65(7): p. 2662-7; Takemoto, S., et al., *Proc Natl Acad Sci USA*, 1997. 94(25): p. 13897-902) as well as solid tumors (Walz, C., et al., *J Biol Chem*, 2006. 281(26): p. 18177-83), and other myeloproliferative disorders such as polycythemia vera (Baxter, E. J., et al., *Lancet*, 2005. 365 (9464): p. 1054-61; James, C., et al., *Nature*, 2005. 434(7037): p. 1144-8; Levine, R. L., et al., *Cancer Cell*, 2005. 7(4): p. 387-97; Shannon, K. and R. A. Van Etten, *Cancer Cell*, 2005. 7(4): p. 291-3), due to its activation of downstream effector genes involved in proliferation. JAK2 is also known to be mutated in hematologic malignancies, such that it no longer requires ligand binding to the cytokine receptor and is instead in a state of constitutive activation. This can occur through translocation between the JAK2 gene with genes encoding the ETV6, BCR or PCM1 proteins (Peeters, P., et al.; Reiter, A., et al.; Griesinger, F., et al., *Genes Chromosomes Cancer*, 2005. 44(3): p. 329-33; Lacronique, V., et al., *Science*, 1997. 278(5341): p. 1309-12) to create an oncogenic fusion protein, analogous to the BCR-ABL protein seen in chronic myelogenous leukemia. Overactivation of JAK2 can also occur through mutation of the JAK2 sequence itself for example, the myeloproliferative disease polycythemia vera is associated with a point mutation that causes a valine-to-phenylalanine substitution at amino acid 617 (JAK2 V617F) (Walz, C., et al.).

DETAILED DESCRIPTION

The following provides additional non-limiting details of the compound described or disclosed herein, including compounds of the general Formula I as well as subgenera, various species and/or specific embodiments thereof. The section titles used in this application are for indexing and search purposes only and should not be construed as limiting in any way.

In one aspect this application provides compounds of the Formula I

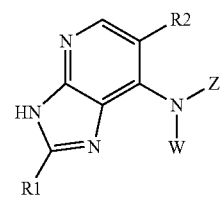

or salts thereof wherein:
W is H and Z is selected from

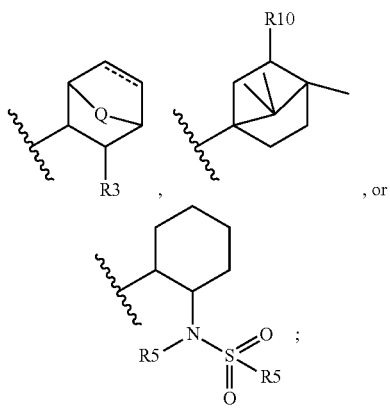

, or or
W and Z are taken together to form

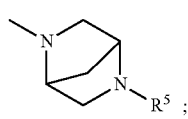

;

$R^1$ is selected from $(C_6-C_{10})$aryl, aminophenyl, $(C_2-C_9)$heterocycloalkyl, $(C_1-C_9)$heteroaryl or a group of formula

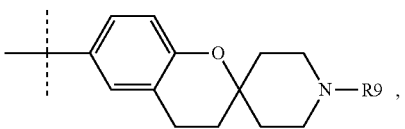

wherein any of the foregoing may be optionally substituted with one or more $R^6$ groups;
$R^2$ is selected from hydrogen or halogen;
$R^3$ is selected from $CH_2OH$ or $CONR^4R^5$;
Q is selected from $CH_2$ or O;
"------" is either present so as to form a double bond or is absent;
$R^4$ and $R^5$ are each independently selected from H, $(C_1-C_6)$alkyl, $(C_3-C_8)$cycloalkyl, $(C_1-C_6)$alkyl$(C_3-C_8)$cycloalkyl, or $(C_1-C_6)$alkyl-$OR^9$ wherein any of the foregoing except for H may be optionally substituted with one or more $R^7$;
Each $R^6$ is independently selected from $(C_0-C_4)$alkyl$CO_2R^8$, $(C_0-C_4)$alkyl$CON(R^8)_2$, $(C_0-C_4)$alkyl$COR^8$, $(C_0-C_4)$alkyl$N(R^8)_2$, $(C_0-C_4)$alkyl$OR^9$, $(C_1-C_6)$alkoxy, $(C_1-C_6)$alkoxy$(C_2-C_9)$heterocycloalkyl, $(C_1-C_6)$alkoxy$(C_3-C_8)$cycloalkyl, $(C_1-C_6)$alkyl, $(C_1-C_6)$alkyl$(C_1-C_9)$heteroaryl, $(C_1-C_6)$alkyl$(C_2-C_9)$heterocycloalkyl, $(C_1-C_6)$alkyl$(C_3-C_8)$cycloalkyl, $(C_1-C_6)$alkyl$(C_6-C_{10})$aryl, $(C_1-C_9)$heteroaryl, $(C_2-C_6)$alkenyl, $(C_2-C_9)$heterocycloalkyl, $(C_2-C_9)$heterocycloalkyloxy, $(C_3-C_8)$cycloalkyl, $(C_3-C_8)$cycloalkyloxy, $(C_3-C_9)$heterocycloalkenyl, $(C_6-C_{10})$aryl, cyano, halo$(C_1-C_6)$alkoxy, halo$(C_1-C_6)$alkyl, halogen, $O(C_0-C_4)$alkyl$CO_2R^8$, $O(C_0-C_4)$alkyl$CON(R^8)_2$, $O(C_0-C_4)$alkyl$COR^8$, $PO((C_1-C_4)$alkyl$)_2$, or $O(C_0-C_4)$alkyl$N(R^8)_2$, wherein any of the foregoing except for halogen, may be optionally substituted with one or more $R^7$;

Each $R^7$ is independently selected from $(C_0-C_4)$alkyl$CO_2R^8$, $(C_0-C_4)$alkyl$CON(R^8)_2$, $(C_0-C_4)$alkyl$COR^8$, $(C_0-C_4)$alkyl$OR^9$, $(C_1-C_6)$alkoxy, $(C_1-C_6)$alkyl, $(C_1-C_6)$alkyl$(C_1-C_9)$heteroaryl, $(C_1-C_6)$alkyl$(C_2-C_9)$heterocycloalkyl, $(C_1-C_6)$alkyl$(C_3-C_8)$cycloalkyl, $(C_1-C_6)$alkyl$(C_6-C_{10})$aryl, $(C_1-C_9)$heteroaryl, $(C_2-C_9)$heterocycloalkyl, $(C_2-C_9)$heterocycloalkyl optionally substituted with $(C_1-C_6)$alkyl, $(C_3-C_8)$cycloalkyl, $(C_6-C_{10})$aryl, halo$(C_1-C_6)$alkoxy, halo$(C_1-C_6)$alkyl, halogen, hydroxy$(C_1-C_6)$alkyl, $PO((C_1-C_4)$alkyl$)_2$, or hydroxy$(C_1-C_6)$alkyl$(C_1-C_6)$alkoxy;

Each $R^8$ is independently selected from H, $(C_1-C_6)$alkyl, $(C_2-C_9)$heterocycloalkyl, or two $R^8$ are taken together with the nitrogen atom to which they are attached to form $(C_2-C_9)$heterocycloalkyl, wherein any of the foregoing except for H, may be optionally substituted with $(C_1-C_6)$alkyl, $(C_1-C_6)$alkoxy, halo$(C_1-C_6)$alkyl, halo$(C_1-C_6)$alkoxy, halogen, $(C_0-C_4)$alkyl$CO_2R^9$, $(C_0-C_4)$alkyl$N(R^9)_2$ or $(C_0-C_4)$alkyl$OR^9$;

$R^9$ is independently selected from H or $(C_1-C_6)$alkyl; and
$R^{10}$ is independently a carbonyl or a hydroxyl group.

In some embodiments, Z is

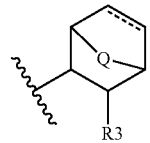

.

In other embodiments, Z is

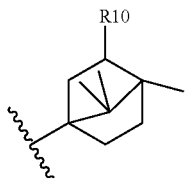

In other embodiments, Z is

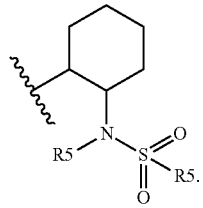

In some specific embodiments, Z is selected from:

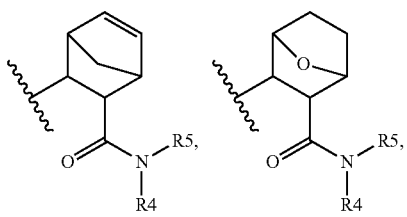

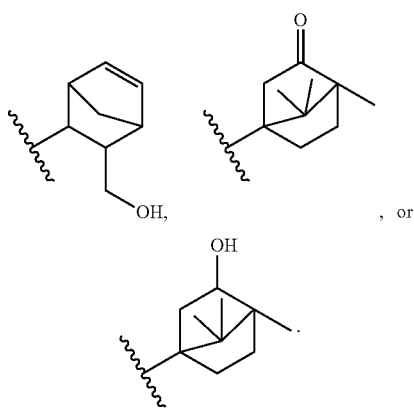

In some embodiments, Z is selected from:

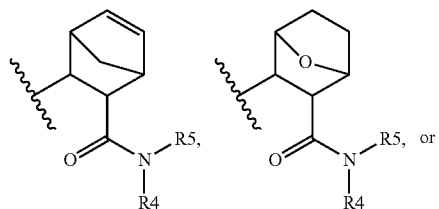

In other embodiments, Z is selected from:

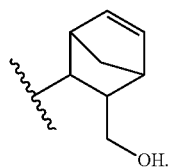

In still other embodiments, Z is:

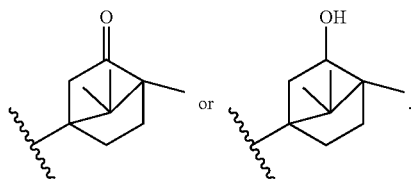 [SMILES: *C12CCC(C)(C(=O)C1)C2(C)C ; *C12CCC(C)(C(O)C1)C2(C)C]

In yet other embodiments, this application provides compounds of Formula I where W and Z are taken together to form

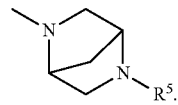

In other embodiments, $R^2$ is selected from hydrogen, chlorine or bromine.

In still other embodiments, Q is $CH_2$. In other embodiments, Q is O.

In other embodiments, "------" is present so as to form a double bond. In other embodiments, "------" is absent.

In still other embodiments, $R^1$ is selected from $(C_6-C_{10})$aryl, $(C_2-C_9)$heterocycloalkyl, or $(C_1-C_9)$heteroaryl, where any of the foregoing groups may be optionally substituted with one or more $R^6$ groups. In other embodiments, $R^1$ is selected from $(C_6-C_{10})$aryl or $(C_1-C_9)$heteroaryl, where any of the foregoing groups may be optionally substituted with one or more $R^6$ groups. In still other embodiments, $R^1$ is $(C_6-C_{10})$aryl optionally substituted with one or more $R^6$ groups. In yet other embodiments, $R^1$ is $(C_1-C_9)$heteroaryl, optionally substituted with one or more $R^6$ groups. In still other embodiments, $R^1$ is $(C_2-C_9)$heterocycloalkyl, optionally substituted with one or more $R^6$ groups. In yet other embodiments, $R^1$ is a group of formula

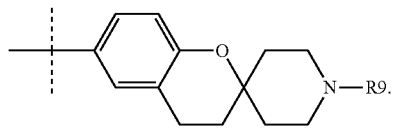

In other embodiments, this application provides compounds of Formula I where:
W is H and Z is

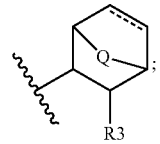

where "------" is present so as to form a double bond and Q is $CH_2$. In some embodiments, $R^1$ is selected from aminophenyl, $(C_6-C_{10})$aryl, $(C_2-C_9)$heterocycloalkyl and $(C_1-C_9)$heteroaryl, preferably $R^1$ is selected from phenyl, piperidinyl, pyrazolyl, pyridinyl, pyrimidinyl, furanyl, pyrrolyl, thiophenyl, thiazolyl, isoxazolyl, tetrahydroimidazopyridinyl, or aminophenyl, wherein each of the foregoing may be optionally substituted with one or more $R^6$ groups; $R^2$ is selected from halogen, preferably bromine or chlorine; $R^3$ is $CONR^4R^5$. In some of these embodiments it is preferred that $R^4$ and $R^5$ are each independently selected from hydrogen, methyl, isopropyl, hydroxyethyl, or cyclopropyl.

Compounds exemplifying this embodiment include, but are not limited to, the following:
(1S,2S,3R,4R)-3-[6-Chloro-2-(4-morpholin-4-ylmethyl-phenyl)-3H-imidazo[4,5-b]pyridine-7-ylamino]-bicyclo[2.2.1]hept-5-ene-2-carboxylic acid amide;
(1S,2S,3R,4R)-3-[6-Chloro-2-(4-morpholin-4-yl-phenyl)-3H-imidazo[4,5-b]pyridine-7-ylamino]-bicyclo[2.2.1]hept-5-ene-2-carboxylic acid amide;

(1S,2S,3R,4R)-3-[6-Chloro-2-(3-methoxy-phenyl)-3H-imi-
dazo[4,5-b]pyridin-7-ylamino]-bicyclo[2.2.1]hept-5-ene-
2-carboxylic acid amide;
(1S,2S,3R,4R)-3-[6-Chloro-2-(4-methoxy-phenyl)-3H-imi-
dazo[4,5-b]pyridine-7-ylamino]-bicyclo[2.2.1]hept-5-
ene-2-carboxylic acid amide;
(1S,2S,3R,4R)-3-[6-Chloro-2-(3-morpholin-4-yl-phenyl)-
3H-imidazo[4,5-b]pyridine-7-ylamino]-bicyclo[2.2.1]
hept-5-ene-2-carboxylic acid amide;
(1S,2S,3R,4R)-3-[6-Chloro-2-(1-methyl-1H-pyrazol-4-yl)-
3H-imidazo[4,5-b]pyridine-7-ylamino]-bicyclo[2.2.1]
hept-5-ene-2-carboxylic acid amide;
(1S,2S,3R,4R)-3-[6-Chloro-2-(2-methoxy-phenyl)-3H-imi-
dazo[4,5-b]pyridine-7-ylamino]-bicyclo[2.2.1]hept-5-
ene-2-carboxylic acid amide;
(1S,2S,3R,4R)-3-{6-Chloro-2-[4-(4-methyl-piperazin-1-
yl)-phenyl]-3H-imidazo[4,5-b]pyridine-7-ylamino}-bicy-
clo[2.2.1]hept-5-ene-2-carboxylic acid amide;
3-[7-((1R,2R,3S,4S)-3-Carbamoyl-bicyclo[2.2.1]hept-5-en-
2-ylamino)-6-chloro-3H-imidazo[4,5-b]pyridin-2-yl]-
piperidine-1-carboxylic acid tert-butyl ester;
of (1S,2S,3R,4R)-3-[6-Chloro-2-(3-dimethylamino-phe-
nyl)-3H-imidazo[4,5-b]pyridin-7-ylamino]-bicyclo
[2.2.1]hept-5-ene-2-carboxylic acid amide;
(1S,2S,3R,4R)-3-(6-Chloro-2-piperidin-3-yl-3H-imidazo[4,
5-b]pyridin-7-ylamino)-bicyclo[2.2.1]hept-5-ene-2-car-
boxylic acid amide; (1S,2S,3R,4R)-3-(6-Chloro-2-piperi-
din-3-yl-3H-imidazo[4,5-b]pyridin-7-ylamino)-bicyclo
[2.2.1]hept-5-ene-2-carboxylic acid amide; (1S,2S,3R,
4R)-3-[6-Chloro-2-(4-piperazin-1-yl-phenyl)-3H-
imidazo[4,5-b]pyridin-7-ylamino]-bicyclo[2.2.1]hept-5-
ene-2-carboxylic acid amide;
(1S,2S,3R,4R)-3-[6-Chloro-2-(3-morpholin-4-ylmethyl-
phenyl)-3H-imidazo[4,5-b]pyridin-7-ylamino]-bicyclo
[2.2.1]hept-5-ene-2-carboxylic acid amide; (1S,2S,3R,
4R)-3-[6-Chloro-2-(4-dimethylamino-2-methoxy-
phenyl)-3H-imidazo[4,5-b]pyridine-7-ylamino]-bicyclo
[2.2.1]hept-5-ene-2-carboxylic acid amide; (1S,2S,3R,
4R)-3-[6-Chloro-2-(2-methoxy-4-trifluoromethoxy-
phenyl)-3H-imidazo[4,5-b]pyridine-7-ylamino]-bicyclo
[2.2.1]hept-5-ene-2-carboxylic acid amide; (1S,2S,3R,
4R)-3-[6-Chloro-2-(2-methoxy-4-morpholin-4-yl-
phenyl)-3H-imidazo[4,5-b]pyridine-7-ylamino]-bicyclo
[2.2.1]hept-5-ene-2-carboxylic acid amide; (1S,2S,3R,
4R)-3-{6-Chloro-2-[4-(4-methyl-piperazin-1-ylmethyl)-
phenyl]-3H-imidazo[4,5-b]pyridin-7-ylamino}-bicyclo
[2.2.1]hept-5-ene-2-carboxylic acid amide; (1S,2S,3R,
4R)-3-{6-Chloro-2-[2-methoxy-4-(4-methyl-piperazin-1-
yl)-phenyl]-3H-imidazo[4,5-b]pyridin-7-ylamino}-
bicyclo[2.2.1]hept-5-ene-2-carboxylic acid amide; (1S,
2S,3R,4R)-3-[6-Bromo-2-(4-dimethylamino-phenyl)-3H-
imidazo[4,5-b]pyridin-7-ylamino]-bicyclo[2.2.1]hept-5-
ene-2-carboxylic acid amide; (1S,2S,3R,4R)-3-[6-Bromo-
2-(3-dimethylamino-phenyl)-3H-imidazo[4,5-b]pyridin-
7-ylamino]-bicyclo[2.2.1]hept-5-ene-2-carboxylic acid
amide;
(1S,2S,3R,4R)-3-{6-Bromo-2-[4-(4-methyl-piperazin-1-
yl)-phenyl]-3H-imidazo[4,5-b]pyridin-7-ylamino}-bicy-
clo[2.2.1]hept-5-ene-2-carboxylic acid amide; (1S,2S,3R,
4R)-3-[6-Bromo-2-(4-morpholin-4-yl-phenyl)-3H-
imidazo[4,5-b]pyridin-7-ylamino]-bicyclo[2.2.1]hept-5-
ene-2-carboxylic acid amide; (1S,2S,3R,4R)-3-[6-Bromo-
2-(4-morpholin-4-ylmethyl-phenyl)-3H-imidazo[4,5-b]
pyridin-7-ylamino]-bicyclo[2.2.1]hept-5-ene-2-
carboxylic acid amide; (1S,2S,3R,4R)-3-[6-Bromo-2-(3-
morpholin-4-ylmethyl-phenyl)-3H-imidazo[4,5-b]
pyridin-7-ylamino]-bicyclo[2.2.1]hept-5-ene-2-
carboxylic acid amide; 3-[6-Bromo-7-((1R,2R,3S,4S)-3-
carbamoyl-bicyclo[2.2.1]hept-5-en-2-ylamino)-3H-
imidazo[4,5-b]pyridin-2-yl]-piperidine-1-carboxylic acid
tert-butyl ester;
(1S,2S,3R,4R)-3-[6-Bromo-2-(3-morpholin-4-yl-phenyl)-
3H-imidazo[4,5-b]pyridin-7-ylamino]-bicyclo[2.2.1]
hept-5-ene-2-carboxylic acid amide; (1S,2S,3R,4R)-3-[6-
Bromo-2-(4-dimethylamino-2-methoxy-phenyl)-3H-
imidazo[4,5-b]pyridin-7-ylamino]-bicyclo[2.2.1]hept-5-
ene-2-carboxylic acid amide; (1S,2S,3R,4R)-3-[6-Bromo-
2-(1-methyl-1H-pyrazol-4-yl)-3H-imidazo[4,5-b]pyridin-
7-ylamino]-bicyclo[2.2.1]hept-5-ene-2-carboxylic acid
amide; (1S,2S,3R,4R)-3-[2-(4-Dimethylamino-phenyl)-
3H-imidazo[4,5-b]pyridin-7-ylamino]-bicyclo[2.2.1]
hept-5-ene-2-carboxylic acid amide; (1S,2S,3R,4R)-3-[2-
(3-Dimethylamino-phenyl)-3H-imidazo[4,5-b]pyridin-7-
ylamino]-bicyclo[2.2.1]hept-5-ene-2-carboxylic acid
amide; (1S,2S,3R,4R)-3-{2-[4-(4-Methyl-piperazin-1-
yl)-phenyl]-3H-imidazo[4,5-b]pyridin-7-ylamino}-bicy-
clo[2.2.1]hept-5-ene-2-carboxylic acid amide;
(1S,2S,3R,4R)-3-[2-(4-Morpholin-4-yl-phenyl)-3H-imi-
dazo[4,5-b]pyridin-7-ylamino]-bicyclo[2.2.1]hept-5-ene-
2-carboxylic acid amide; (1S,2S,3R,4R)-3-[2-(4-Morpho-
lin-4-ylmethyl-phenyl)-3H-imidazo[4,5-b]pyridin-7-
ylamino]-bicyclo[2.2.1]hept-5-ene-2-carboxylic acid
amide; (1S,2S,3R,4R)-3-[2-(3-Morpholin-4-ylmethyl-
phenyl)-3H-imidazo[4,5-b]pyridin-7-ylamino]-bicyclo
[2.2.1]hept-5-ene-2-carboxylic acid amide; 3-[7-((1R,2R,
3S,4S)-3-Carbamoyl-bicyclo[2.2.1]hept-5-en-2-
ylamino)-3H-imidazo[4,5-b]pyridin-2-yl]-piperidine-1-
carboxylic acid tert-butyl ester; (1S,2S,3R,4R)-3-[2-(4-
Dimethylamino-2-methoxy-phenyl)-3H-imidazo[4,5-b]
pyridin-7-ylamino]-bicyclo[2.2.1]hept-5-ene-2-
carboxylic acid amide; (1S,2S,3R,4R)-3-[2-(1-Methyl-
1H-pyrazol-4-yl)-3H-imidazo[4,5-b]pyridin-7-ylamino]-
bicyclo[2.2.1]hept-5-ene-2-carboxylic acid amide; (1S,
2S,3R,4R)-3-{6-Chloro-2-[2-methoxy-4-(4-morpholin-4-
yl-piperidin-1-yl)-phenyl]-3H-imidazo[4,5-b]pyridin-7-
ylamino}-bicyclo[2.2.1]hept-5-ene-2-carboxylic acid
amide; (1S,2S,3R,4R)-3-(6-Chloro-2-{2-methoxy-4-[4-
(4-methyl-piperazin-1-yl)-piperidin-1-yl]-phenyl}-3H-
imidazo[4,5-b]pyridin-7-ylamino)-bicyclo[2.2.1]hept-5-
ene-2-carboxylic acid amide; (1S,2S,3R,4R)-3-{2-[2-
Methoxy-4-(4-methyl-piperazin-1-yl)-phenyl]-3H-
imidazo[4,5-b]pyridin-7-ylamino}-bicyclo[2.2.1]hept-5-
ene-2-carboxylic acid amide; (1S,2S,3R,4R)-3-{6-
Bromo-2-[2-methoxy-4-(4-methyl-piperazin-1-yl)-
phenyl]-3H-imidazo[4,5-b]pyridin-7-ylamino}-bicyclo
[2.2.1]hept-5-ene-2-carboxylic acid amide;
(1S,2S,3R,4R)-3-{6-Bromo-2-[2-methoxy-4-(4-morpholin-
4-yl-piperidin-1-yl)-phenyl]-3H-imidazo[4,5b]pyridin-7-
ylamino}-bicyclo[2.2.1]hept-5-ene-2-carboxylic acid
amide;
(1S,2S,3R,4R)-3-(6-Bromo-2-{2-methoxy-4-[4-(4-methyl-
piperazin-1-yl)-piperidin-1-yl]-phenyl}-3H-imidazo[4,5-
b]pyridin-7-ylamino)-bicyclo[2.2.1]hept-5-ene-2-car-
boxylic acid amide; (1S,2S,3R,4R)-3-(2-{2-Methoxy-4-
[4-(4-methyl-piperazin-1-yl)-piperidin-1-yl]-phenyl}-
3H-imidazo[4,5-b]pyridin-7-ylamino)-bicyclo[2.2.1]
hept-5-ene-2-carboxylic acid amide; (1R,2R,3S,4S)-3-[6-
Chloro-2-(3-dimethylamino-phenyl)-3H-imidazo[4,5-b]
pyridine-7-ylamino]-bicyclo[2.2.1]hept-5-ene-2-
carboxylic acid amide; (1R,2R,3S,4S)-3-[6-Chloro-2-(3-
morpholin-4-yl-phenyl)-3H-imidazo[4,5-b]pyridine-7-
ylamino]-bicyclo[2.2.1]hept-5-ene-2-carboxylic acid
amide; (1R,2R,3S,4S)-3-{6-Chloro-2-[4-(4-methyl-piper-
azin-1-yl)-phenyl]-3H-imidazo[4,5-b]pyridine-7- ylamino}-bicyclo[2.2.1]hept-5-ene-2-carboxylic acid amide; (1R,2R,3S,4S)-3-{6-Chloro-2-[2-methoxy-4-(4-morpholin-4-yl-piperidin-1-yl)-phenyl]-3H-imidazo[4,5-b]pyridin-7-ylamino}-bicyclo[2.2.1]hept-5-ene-2-carboxylic acid amide; (1R,2R,3S,4S)-3-{6-Chloro-2-[2-methoxy-4-(4-methyl-piperazin-1-yl)-phenyl]-3H-imidazo[4,5-b]pyridin-7-ylamino}-bicyclo[2.2.1]hept-5-ene-2-carboxylic acid amide; 4-{2-[7-((1R,2R,3S,4S)-3-Carbamoyl-bicyclo[2.2.1]hept-5-en-2-ylamino)-6-chloro-3H-imidazo[4,5-b]pyridine-2-yl]-5-methoxy-phenyl]-piperidinej-1-carboxylic acid tert-butyl ester (1S,2S,3R,4R)-3-[6-Chloro-2-(4-methoxy-2-piperidin-4-yl-phenyl)-3H-imidazo[4,5-b]pyridine-7-ylamino]-bicyclo[2.2.1]hept-5-ene-2-carboxylic acid amide; (1S,2S,3R,4R)-3-(6-Chloro-2-{2-[1-((R)-2-hydroxypropyl)-piperidin-4-yl]-4-methoxy-phenyl}-3H-imidazo[4,5-b]pyridin-7-ylamino)-bicyclo[2.2.1]hept-5-ene-2-carboxylic acid amide; (1S,2S,3R,4R)-3-(6-Chloro-2-{2-[1-((S)-2-hydroxypropyl)-piperidin-4-yl]-4-methoxy-phenyl}-3H-imidazo[4,5-b]pyridin-7-ylamino)-bicyclo[2.2.1]hept-5-ene-2-carboxylic acid amide; (1S,2S,3R,4R)-3-(6-Chloro-2-{2-[1-((S)-2,3-dihydroxypropyl)-piperidin-4-yl]-4-methoxy-phenyl}-3H-imidazo[4,5-b]pyridin-7-ylamino)-bicyclo[2.2.1]hept-5-ene-2-carboxylic acid amide;
(1S,2S,3R,4R)-3-[6-Chloro-2-(2-chloro-4-morpholin-4-yl-phenyl)-3H-imidazo[4,5-b]pyridin-7-ylamino]-bicyclo[2.2.1]hept-5-ene-2-carboxylic acid amide; (1S,2S,3R,4R)-3-[6-Chloro-2-(2-methyl-4-morpholin-4-yl-phenyl)-3H-imidazo[4,5-b]pyridin-7-ylamino]-bicyclo[2.2.1]hept-5-ene-2-carboxylic acid amide; (1S,2S,3R,4R)-3-[6-Chloro-2-(1,3-dimethyl-5-morpholin-4-yl-1H-pyrazol-4-yl)-3H-imidazo[4,5-b]pyridin-7-ylamino]-bicyclo[2.2.1]hept-5-ene-2-carboxylic acid amide; (1S,2S,3R,4R)-3-[6-Chloro-2-(2-methoxy-pyridin-3-yl)-3H-imidazo[4,5-b]pyridin-7-ylamino]-bicyclo[2.2.1]hept-5-ene-2-carboxylic acid amide; (1S,2S,3R,4R)-3-{6-Bromo-2-[4-(4-methyl-piperazin-1-ylmethyl)-phenyl]-3H-imidazo[4,5-b]pyridin-7-ylamino-bicyclo[2.2.1]hept-5-ene-2-carboxylic acid amide; (1S,2S,3R,4R)-3-[6-Bromo-2-(2-methoxy-pyridin-3-yl)-3H-imidazo[4,5-b]pyridin-7-ylamino]-bicyclo[2.2.1]hept-5-ene-2-carboxylic acid amide;
(1S,2S,3R,4R)-3-[6-Bromo-2-(2-morpholin-4-yl-pyridin-3-yl)-3H-imidazo[4,5-b]pyridin-7-ylamino]-bicyclo[2.2.1]hept-5-ene-2-carboxylic acid amide; (1S,2S,3R,4R)-3-[6-Bromo-2-(4-methoxy-pyridin-3-yl)-3H-imidazo[4,5-b]pyridin-7-ylamino]-bicyclo[2.2.1]hept-5-ene-2-carboxylic acid amide; (1S,2S,3R,4R)-3-[6-Bromo-2-(2-pyrazol-1-yl-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(2-pyrrolidin-1-yl-pyridin-3-yl)-3H-imidazo[4,5-b]pyridin-7-ylamino]-bicyclo[2.2.1]hept-5-ene-2-carboxylic acid amide;
(1S,2S,3R,4R)-3-[6-Chloro-2-(2-morpholin-4-yl-pyridin-3-yl)-3H-imidazo[4,5-b]pyridine-7-ylamino]-bicyclo[2.2.1]hept-5-ene-2-carboxylic acid amide; (1S,2S,3R,4R)-3-[6-Chloro-2-(4-methoxy-pyridin-3-yl)-3H-imidazo[4,5-b]pyridine-7-ylamino]-bicyclo[2.2.1]hept-5-ene-2-carboxylic acid amide; (1S,2S,3R,4R)-3-[6-Bromo-2-(2,6-dimethoxy-phenyl)-3H-imidazo[4,5-b]pyridin-7-ylamino]-bicyclo[2.2.1]hept-5-ene-2-carboxylic acid amide; (1S,2S,3R,4R)-3-(6-Bromo-2-pyrimidin-5-yl-3H-imidazo[4,5-b]pyridin-7-ylamino)-bicyclo[2.2.1]hept-5-ene-2-carboxylic acid amide; (1S,2S,3R,4R)-3-(6-Bromo-2-furan-3-yl-3H-imidazo[4,5-b]pyridin-7-ylamino)-bicyclo[2.2.1]hept-5-ene-2-carboxylic acid amide; (1S,2S,3R,4R)-3-[6-Bromo-2-(1-methyl-1H-pyrrol-2-yl)-3H-imidazo[4,5-b]pyridin-7-ylamino]-bicyclo[2.2.1]hept-5-ene-2-carboxylic acid amide;
(1S,2S,3R,4R)-3-[6-Bromo-2-(5-methyl-furan-2-yl)-3H-imidazo[4,5-b]pyridin-7-ylamino]-bicyclo[2.2.1]hept-5-ene-2-carboxylic acid amide; (1S,2S,3R,4R)-3-(6-Bromo-2-thiophen-3-yl-3H-imidazo[4,5-b]pyridin-7-ylamino)-bicyclo[2.2.1]hept-5-ene-2-carboxylic acid amide; (1S,2S,3R,4R)-3-[6-Bromo-2-(6-morpholin-4-yl-pyridin-3-yl)-3H-imidazo[4,5-b]pyridin-7-ylamino]-bicyclo[2.2.1]hept-5-ene-2-carboxylic acid amide;
(1R,2S,3R,4S)-3-{6-Bromo-2-[4-(4-methyl-piperazin-1-yl)-phenyl]-3H-imidazo[4,5-b]pyridin-7-ylamino}-bicyclo[2.2.1]heptane-2-carboxylic acid amide; (1S,2S,3R,4R)-3-[6-Chloro-2-(6-methoxy-pyridin-2-yl)-3H-imidazo[4,5-b]pyridin-7-ylamino]-bicyclo[2.2.1]hept-5-ene-2-carboxylic acid amide; (1S,2S,3R,4R)-3-[6-Chloro-2-(3-pyrazol-1-yl-phenyl)-3H-imidazo[4,5-b]pyridin-7-ylamino]-bicyclo[2.2.1]hept-5-ene-2-carboxylic acid amide; (1S,2S,3R,4R)-3-[6-Chloro-2-(2-morpholin-4-yl-pyridin-4-yl)-3H-imidazo[4,5-b]pyridin-7-ylamino]-bicyclo[2.2.1]hept-5-ene-2-carboxylic acid amide;
(1S,2S,3R,4R)-3-[6-Chloro-2-(2-fluoro-phenyl)-3H-imidazo[4,5-b]pyridin-7-ylamino]-bicyclo[2.2.1]hept-5-ene-2-carboxylic acid amide; 1S,2S,3R,4R)-3-[6-Chloro-2-(3-fluoro-phenyl)-3H-imidazo[4,5-b]pyridin-7-ylamino]-bicyclo[2.2.1]hept-5-ene-2-carboxylic acid amide; (1S,2S,3R,4R)-3-[6-Chloro-2-(4-fluoro-phenyl)-3H-imidazo[4,5-b]pyridin-7-ylamino]-bicyclo[2.2.1]hept-5-ene-2-carboxylic acid amide; (1S,2S,3R,4R)-3-[6-Chloro-2-(2-methoxy-4-morpholin-4-yl-phenyl)-3H-imidazo[4,5-b]pyridine-7-ylamino]-bicyclo[2.2.1]hept-5-ene-2-carboxylic acid amide; (1S,2S,3R,4R)-3-{6-Chloro-2-[2-methoxy-4-(4-methyl-piperazin-1-ylmethyl)-phenyl]-3H-imidazo[4,5-b]pyridine-7-ylamino}-bicyclo[2.2.1]hept-5-ene-2-carboxylic acid amide; (1S,2S,3R,4R)-3-{6-Chloro-2-[2-methoxy-4-(4-methyl-piperazin-1-ylmethyl)-phenyl]-3H-imidazo[4,5-b]pyridine-7-ylamino}-bicyclo[2.2.1]hept-5-ene-2-carboxylic acid amide; (1S,2S,3R,4R)-3-{6-Chloro-2-[2-methoxy-4-pyrrolidin-1-ylmethyl)-phenyl]-3H-imidazo[4,5-b]pyridine-7-ylamino}-bicyclo[2.2.1]hept-5-ene-2-carboxylic acid amide; (1S,2S,3R,4R)-3-[6-Chloro-2-(2-methoxy-4-piperazin-1-ylmethyl-phenyl)-3H-imidazo[4,5-b]pyridine-7-ylamino]-bicyclo[2.2.1]hept-5-ene-2-carboxylic acid amide; (1S,2S,3R,4R)-3-(6-Chloro-2-{-4-[4-((S)-2-hydroxypropyl)-piperazin-1-ylmethyl]-2-methoxyphenyl}-3H-imidazo[4,5-b]pyridine-7-ylamino)-bicyclo[2.2.1]hept-5-ene-2-carboxylic acid amide; (1S,2S,3R,4R)-3-[6-Bromo-2-(2-methyl-4-morpholin-4-yl-phenyl)-3H-imidazo[4,5-b]pyridin-7-ylamino)-bicyclo[2.2.1]hept-5-ene-2-carboxylic acid amide; (1S,2S,3R,4R)-3-[6-Bromo-2-(2-fluoro-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(3-fluoro-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(4-fluoro-phenyl)-3H-imidazo[4,5-b]pyridin-7-ylamino]-bicyclo[2.2.1]hept-5-ene-2-carboxylic acid amide; (1S,2S,3R,4R)-3-(6-Chloro-2-{4-[4-((R)-2-hydroxypropyl)-piperazin-1-ylmethyl]-2-methoxyphenyl}-3H-imidazo[4,5-b]pyridine-7-ylamino)-bicyclo[2.2.1]hept-5-ene-2-carboxylic acid amide; (1S,2S,3R,4R)-3-(6-Chloro-2-{4-[1-((S)-2-hydroxypropyl)-piperidin-4-yl]-2-methoxyphenyl}-3H-imidazo[4,5-b]pyridine-7-ylamino)-bicyclo[2.2.1]hept-5-ene-2-carboxylic acid amide;

(1S,2S,3R,4R)-3-[6-Bromo-2-(2-chloro-4-morpholin-4-yl-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(3-chloro-4-morpholin-4-yl-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(2-morpholin-4-yl-pyridin-4-yl)-3H-imidazo[4,5-b]pyridin-7-ylamino]-bicyclo[2.2.1]hept-5-ene-2-carboxylic acid amide; (1S,2S,3R,4R)-3-[6-Chloro-2-(3-chloro-4-morpholin-4-yl-phenyl)-3H-imidazo[4,5-b]pyridin-7-ylamino]-bicyclo[2.2.1]hept-5-ene-2-carboxylic acid amide; (1S,2S,3R,4R)-3-[6-Chloro-2-(4-dimethylaminomethyl-2-methoxyphenyl)-3H-imidazo[4,5-b]pyridine-7-ylamino)-bicyclo[2.2.1]hept-5-ene-2-carboxylic acid amide; (1S,2S,3R,4R)-3-[6-Chloro-2-(3-chloro-4-morpholin-4-yl-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(6-trifluoromethyl-pyridin-3-yl)-3H-imidazo[4,5-b]pyridin-7-ylamino]-bicyclo[2.2.1]hept-5-ene-2-carboxylic acid amide; (1S,2S,3R,4R)-3-(6-Chloro-2-[4-((R)-3-hydroxy-pyrrolidin-1-ylmethyl)-2-methoxyphenyl]-3H-imidazo[4,5-b]pyridine-7-ylamino)-bicyclo[2.2.1]hept-5-ene-2-carboxylic acid amide; (1S,2S,3R,4R)-3-(6-chloro-2-(4-morpholinophenyl)-3H-imidazo[4,5-b]pyridin-7-ylamino)-N,N-dimethylbicyclo[2.2.1]hept-5-ene-2-carboxamide; (1S,2S,3R,4R)-3-(6-chloro-2-(4-morpholinophenyl)-3H-imidazo[4,5-b]pyridin-7-ylamino)-N-isopropylbicyclo[2.2.1]hept-5-ene-2-carboxamide; (1S,2S,3R,4R)-3-(6-chloro-2-(1-methyl-1H-pyrazol-4-yl)-3H-imidazo[4,5-b]pyridin-7-ylamino)-N-isopropylbicyclo[2.2.1]hept-5-ene-2-carboxamide;

(1S,2S,3R,4R)-3-(6-chloro-2-(4-(4-methylpiperazin-1-yl)phenyl)-3H-imidazo[4,5-b]pyridin-7-ylamino)-N-(2-hydroxyethyl)bicyclo[2.2.1]hept-5-ene-2-carboxamide;

(1S,2S,3R,4R)-3-(6-chloro-2-(thiazol-5-yl)-3H-imidazo[4,5-b]pyridin-7-ylamino)bicyclo[2.2.1]hept-5-ene-2-carboxamide; (1S,2S,3R,4R)-3-(6-chloro-2-(2-methylthiazol-5-yl)-3H-imidazo[4,5-b]pyridin-7-ylamino)bicyclo[2.2.1]hept-5-ene-2-carboxamide; (1S,2S,3R,4R)-3-(6-chloro-2-(4-chloro-2-(4-methylpiperazin-1-yl)thiazol-5-yl)-3H-imidazo[4,5-b]pyridin-7-ylamino)bicyclo[2.2.1]hept-5-ene-2-carboxamide;

(1S,2S,3R,4R)-3-(6-chloro-2-(5,6,7,8-tetrahydroimidazo[1,2-a]pyridin-2-yl)-3H-imidazo[4,5-b]pyridin-7-ylamino)bicyclo[2.2.1]hept-5-ene-2-carboxamide;

(1S,2S,3R,4R)-3-[6-Chloro-2-(3-chloro-phenyl)-3H-imidazo[4,5-b]pyridin-7-ylamino]-bicyclo[2.2.1]hept-5-ene-2-carboxylic acid amide; (1S,2S,3R,4R)-3-[6-Chloro-2-(4-chloro-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(3-chloro-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(4-chloro-phenyl)-3H-imidazo[4,5-b]pyridin-7-ylamino]-bicyclo[2.2.1]hept-5-ene-2-carboxylic acid amide; (1S,2S,3R,4R)-3-(6-Chloro-2-{4-[1((S)-2-hydroxypropyl)-1,2,3,6-tetrahydro-pyridin-4-yl]-2-methoxyphenyl}-3H-imidazo[4,5-b]pyridine-7-ylamino)-bicyclo[2.2.1]hept-5-ene-2-carboxylic acid amide;

(1S,2S,3R,4R)-3-[6-Chloro-2-(3-cyano-phenyl)-3H-imidazo[4,5-b]pyridin-7-ylamino]-bicyclo[2.2.1]hept-5-ene-2-carboxylic acid amide; (1S,2S,3R,4R)-3-[6-Chloro-2-(4-cyano-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(3-cyano-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(4-cyano-phenyl)-3H-imidazo[4,5-b]pyridin-7-ylamino]-bicyclo[2.2.1]hept-5-ene-2-carboxylic acid amide; (1S,2S,3R,4R)-3-[6-Chloro-2-(2-methoxy-5-morpholin-4-ylphenyl)-3H-imidazo[4,5-b]pyridine-7-ylamino]-bicyclo[2.2.1]hept-5-ene-2-carboxylic acid amide; 4-{4-[7-((1R,2R,3S,4S)-3-Carbamoyl-bicyclo[2.2.1]hept-5-en-2-ylamino)-6-chloro-3H-imidazo[4,5-b]pyridine-2-yl]-pyrazol-1-yl}-piperidine-1-carboxylic acid tert-butyl ester; (1S,2S,3R,4S)-3-{2-[4-(4-Acetyl-piperazin-1-ylmethyl)-2-methoxyphenyl]-6-chloro-3H-imidazo[4,5-b]pyridine-7-ylamino}-bicyclo[2.2.1]hept-5-ene-2-carboxylic acid amide; (1S,2S,3R,4R)-3-(6-chloro-2-(4-(4-methylpiperazin-1-yl)phenyl)-3H-imidazo[4,5-b]pyridin-7-ylamino)-N-methylbicyclo[2.2.1]hept-5-ene-2-carboxamide; (1S,2S,3R,4R)-3-(6-chloro-2-(2-methoxy-4-morpholinophenyl)-3H-imidazo[4,5-b]pyridin-7-ylamino)-N-methylbicyclo[2.2.1]hept-5-ene-2-carboxamide; (1S,2S,3R,4R)-3-(6-chloro-2-(4-(4-methylpiperazin-1-yl)phenyl)-3H-imidazo[4,5-b]pyridin-7-ylamino)-N-isopropyl bicyclo[2.2.1]hept-5-ene-2-carboxamide; (1S,2S,3R,4R)-3-(6-chloro-2-(2-methoxy-4-morpholinophenyl)-3H-imidazo[4,5-b]pyridin-7-ylamino)-N-(2-hydroxyethyl)bicyclo[2.2.1]hept-5-ene-2-carboxamide; (1S,2S,3R,4R)-3-(6-chloro-2-(2-methoxythiazol-5-yl)-3H-imidazo[4,5-b]pyridin-7-ylamino)bicyclo[2.2.1]hept-5-ene-2-carboxamide; (1S,2S,3R,4R)-3-(6-chloro-2-(2-(4-methylpiperazin-1-yl)thiazol-5-yl)-3H-imidazo[4,5-b]pyridin-7-ylamino)bicyclo[2.2.1]hept-5-ene-2-carboxamide; tert-butyl 4-(7-((1R,2R,3S,4S)-3-carbamoylbicyclo[2.2.1]hept-5-en-2-ylamino)-6-chloro-3H-imidazo[4,5-b]pyridin-2-yl)piperidine-1-carboxylate; (1S,2S,3R,4R)-3-(6-chloro-2-(2-morpholinothiazol-5-yl)-3H-imidazo[4,5-b]pyridin-7-ylamino)bicyclo[2.2.1]hept-5-ene-2-carboxamide; (1S,2S,3R,4R)-3-[6-Chloro-2-(2-chloro-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(2-chloro-phenyl)-3H-imidazo[4,5-b]pyridin-7-ylamino]-bicyclo[2.2.1]hept-5-ene-2-carboxylic acid amide; (1S,2S,3R,4R)-3-[6-Chloro-2-(2-methoxy-3-morpholin-4-ylmethyl-phenyl)-3H-imidazo[4,5-b]pyridine-7-ylamino]-bicyclo[2.2.1]hept-5-ene-2-carboxylic acid amide; (1S,2S,3R,4R)-3-[6-Chloro-2-(1-methyl-piperidin-4-yl)-3H-imidazo[4,5-b]pyridin-7-ylamino]-bicyclo[2.2.1]hept-5-ene-2-carboxylic acid amide;

(1S,2S,3R,4R)-3-[6-Chloro-2-(1,3,5-trimethyl-1H-pyrazol-4-yl)-3H-imidazo[4,5-b]pyridin-7-ylamino]-bicyclo[2.2.1]hept-5-ene-2-carboxylic acid amide; (1S,2S,3R,4R)-3-[6-Bromo-2-(1,3,5-trimethyl-1H-pyrazol-4-yl)-3H-imidazo[4,5-b]pyridin-7-ylamino]-bicyclo[2.2.1]hept-5-ene-2-carboxylic acid amide; (1S,2S,3R,4R)-3-(6-Chloro-2-{4-[1-(R)-2-hydroxy-3-methoxypropyl)-piperidin-4-yl]-2-methoxyphenyl}-3H-imidazo[4,5-b]pyridine-7-ylamino}-bicyclo[2.2.1]hept-5-ene-2-carboxylic acid amide; (1S,2S,3R,4R)-3-{6-Chloro-2-[4-((S)-3-hydroxy-pyrrolidin-1-ylmethyl)-2-methoxyphenyl]-3H-imidazo[4,5-b]pyridine-7-ylamino}-bicyclo[2.2.1]hept-5-ene-2-carboxylic acid amide;

(1S,2S,3R,4R)-3-(6-chloro-2-(1-methyl-1H-pyrazol-4-yl)-3H-imidazo[4,5-b]pyridin-7-ylamino)-N-methylbicyclo[2.2.1]hept-5-ene-2-carboxamide; (1S,2S,3R,4R)-3-(6-chloro-2-(4-morpholinophenyl)-3H-imidazo[4,5-b]pyridin-7-ylamino)-N-(2-hydroxyethyl)bicyclo[2.2.1]hept-5-ene-2-carboxamide; (1S,2S,3R,4R)-3-(6-chloro-2-(2-methoxy-4-(4-methylpiperazin-1-yl)phenyl)-3H-imidazo[4,5-b]pyridin-7-ylamino)-N-(2-hydroxyethyl)

bicyclo[2.2.1]hept-5-ene-2-carboxamide; (1S,2S,3R,4R)-3-(6-chloro-2-(4-(4-methylpiperazin-1-yl)phenyl)-3H-imidazo[4,5-b]pyridin-7-ylamino)-N-isopropyl-bicyclo[2.2.1]hept-5-ene-2-carboxamide; (1S,2S,3R,4R)-3-[2-(4-Allyl-2-methoxy-phenyl)-6-chloro-3H-imidazo[4,5-b]pyridine-7-ylamino}-bicyclo[2.2.1]hept-5-ene-2-carboxylic acid amide; (1S,2S,3R,4R)-3-(6-chloro-2-(2-methoxy-4-morpholinophenyl)-3H-imidazo[4,5-b]pyridin-7-ylamino)-N,N-dimethylbicyclo[2.2.1]hept-5-ene-2-carboxamide; (1S,2S,3R,4R)-3-(6-chloro-2-(2-methoxy-4-morpholinophenyl)-3H-imidazo[4,5-b]pyridin-7-ylamino)-N,N-dimethylbicyclo[2.2.1]hept-5-ene-2-carboxamide; (1S,2S,3R,4R)-3-(6-chloro-2-(2-methoxy-4-(4-methylpiperazin-1-yl)phenyl)-3H-imidazo[4,5-b]pyridin-7-ylamino)-N,N-dimethylbicyclo[2.2.1]hept-5-ene-2-carboxamide;

(1S,2S,3R,4R)-3-[6-Chloro-2-(1-piperidin-4-yl-1H-pyrazol-4-yl)-3H-imidazo[4,5-b]pyridine-7-ylamino]-bicyclo[2.2.1]hept-5-ene-2-carboxylic acid amide; (1S,2S,3R,4R)-3-(6-Chloro-2-{1-[1-R)-2-hydroxypropyl)-piperidin-4-yl]-1H-pyrazol-4-yl}-3H-imidazo[4,5-b]pyridine-7-ylamino)-bicyclo[2.2.1]hept-5-ene-2-carboxylic acid amide;

(1S,2S,3R,4R)-3-(6-Chloro-2-{1-[1-((S)-2-hydroxypropyl)-piperidin-4-yl]-1H-pyrazol-4-yl}-3H-imidazo[4,5-b]pyridine-7-ylamino)-bicyclo[2.2.1]hept-5-ene-2-carboxylic acid amide; (1S,2S,3R,4R)-3-(6-Chloro-2-{1-[1-((R)-2-hydroxy-3-methoxy-propyl)-piperidin-4-yl]-1H-pyrazol-4-yl}-3H-imidazo[4,5-b]pyridine-7-ylamino)-bicyclo[2.2.1]hept-5-ene-2-carboxylic acid amide; (1S,2S,3R,4R)-3-(6-Chloro-2-pyridin-3-yl-3H-imidazo[4,5-b]pyridin-7-ylamino)-bicyclo[2.2.1]hept-5-ene-2-carboxylic acid amide;

(1S,2S,3R,4R)-3-[6-Chloro-2-(4-chloro-2-dimethylamino-thiazol-5-yl)-3H-imidazo[4,5-b]pyridin-7-ylamino]-bicyclo[2.2.1]hept-5-ene-2-carboxylic acid amide; (1S,2S,3R,4R)-3-[6-Bromo-2-(4-chloro-2-dimethylamino-thiazol-5-yl)-3H-imidazo[4,5-b]pyridin-7-ylamino]-bicyclo[2.2.1]hept-5-ene-2-carboxylic acid amide; (1S,2S,3R,4R)-3-{2-[1-(1-Acetyl-piperidin-4-yl)-1H-pyrazol-4-yl]-6-chloro-3H-imidazo[4,5-b]pyridine-7-ylamino}-bicyclo[2.2.1]hept-5-ene-2-carboxylic acid amide; 4-{4-[7-((1R,2R,3S,4S)-3-Carbamoyl-bicyclo[2.2.1]hept-5-ene-2-ylamino)-6-chloro-3H-imidazo[4,5-b]pyridine-2-yl]-pyrazol-1-yl}-piperidine-1-carboxylic acid ethylamide; (1S,2S,3R,4R)-3-{6-Chloro-2-[2-methoxy-4-(morpholine-4-carbonyl)-phenyl]-3H-imidazo[4,5-b]pyridine-7-ylamino}-bicyclo[2.2.1]hept-5-ene-2-carboxylic acid amide; (1S,2S,3R,4R)-3-(6-Chloro-2-{4-[1-((R)-2-hydroxy-propyl)-piperidin-4-yl]-2-methoxy-phenyl}-3H-imidazo[4,5-b]pyridin-7-ylamino)-bicyclo[2.2.1]hept-5-ene-2-carboxylic acid amide; (1S,2S,3R,4R)-3-{6-Chloro-2-[2-methoxy-4-(1-methyl-piperidin-4-yl)-phenyl]-3H-imidazo[4,5-b]pyridin-7-ylamino}-bicyclo[2.2.1]hept-5-ene-2-carboxylic acid amide; (1S,2S,3R,4R)-3-(6-Chloro-2-{4-[1-((R)-2,3-dihydroxy-propyl)-piperidin-4-yl]-2-methoxy-phenyl}-3H-imidazo[4,5-b]pyridin-7-ylamino)-bicyclo[2.2.1]hept-5-ene-2-carboxylic acid amide; (1S,2S,3R,4R)-3-(6-Chloro-2-{4-[1-((S)-2-hydroxy-3-methoxy-propyl)-piperidin-4-yl]-2-methoxy-phenyl}-3H-imidazo[4,5-b]pyridin-7-ylamino)-bicyclo[2.2.1]hept-5-ene-2-carboxylic acid amide;

(1S,2S,3R,4R)-3-[6-Chloro-2-(4-methyl-2-piperidin-4-yl-thiazol-5-yl)-3H-imidazo[4,5-b]pyridine-7-ylamino]-bicyclo[2.2.1]hept-5-ene-2-carboxylic acid amide; (1S,2S,3R,4R)-3-{2-[4-(4-Acetyl-piperazin-1-ylmethyl)-phenyl]-6-bromo-3H-imidazo[4,5-b]pyridin-7-ylamino}-bicyclo[2.2.1]hept-5-ene-2-carboxylic acid amide; (1S,2S,3R,4R)-3-{2-[4-(4-Acetyl-piperazin-1-ylmethyl)-phenyl]-6-chloro-3H-imidazo[4,5-b]pyridin-7-ylamino}-bicyclo[2.2.1]hept-5-ene-2-carboxylic acid amide; (1S,2S,3R,4R)-3-{2-[2-(1-Carbamoylmethyl-piperidin-4-yl)-4-methyljj-thiazol-5-yl]-6-chloro-3H-imidazo[4,5-b]pyridine-7-ylamino}-bicyclo[2.2.1]hept-5-ene-2-carboxylic acid amide; (1S,2S,3R,4R)-3-{2-[1-(1-Carbamoylmethyl-piperidin-4-yl)-1H-pyrazol-4-yl]-6-chloro-3H-imidazo[4,5-b]pyridine-7-ylamino}-bicyclo[2.2.1]hept-5-ene-2-carboxylic acid amide; (1S,2S,3R,4R)-3-{2-[1-(1-Carbamoylmethyl-piperidin-4-yl)-1H-pyrazol-4-yl]-6-chloro-3H-imidazo[4,5-b]pyridine-7-ylamino}-bicyclo[2.2.1]hept-5-ene-2-carboxylic acid amide; (1S,2S,3R,4R)-3-(6-chloro-2-(3-methoxyphenyl)-3H-imidazo[4,5-b]pyridin-7-ylamino)bicyclo[2.2.1]hept-5-ene-2-carboxamide; (1S,2S,3R,4R)-3-(6-chloro-2-(3-(2-morpholinoethoxy)phenyl)-3H-imidazo[4,5-b]yridine-7-ylamino)yridin[2.2.1]hept-5-ene-2-carboxamide; (1S,2S,3R,4R)-3-(6-chloro-2-(2-methoxy-4-morpholinophenyl)-3H-imidazo[4,5-b]pyridin-7-ylamino)-N-isopropylbicyclo[2.2.1]hept-5-ene-2-carboxamide;

(1S,2S,3R,4R)-3-(6-chloro-2-(2-methoxy-4-(4-methylpiperazin-1-yl)phenyl)-3H-imidazo[4,5-b]pyridin-7-ylamino)-N-methylbicyclo[2.2.1]hept-5-ene-2-carboxamide;

(1S,2S,3R,4R)-3-(6-chloro-2-(4-morpholinophenyl)-3H-imidazo[4,5-b]pyridin-7-ylamino)-N-methylbicyclo[2.2.1]hept-5-ene-2-carboxamide; (1S,2S,3R,4R)-3-(6-chloro-2-(1-methyl-1H-pyrazol-4-yl)-3H-imidazo[4,5-b]pyridin-7-ylamino)-N-(2-hydroxyethyl)bicyclo[2.2.1]hept-5-ene-2-carboxamide; (1S,2S,3R,4R)-3-(6-chloro-2-(4-(4-methylpiperazin-1-yl)phenyl)-3H-imidazo[4,5-b]pyridin-7-ylamino)-N,N-dimethylbicyclo[2.2.1]hept-5-ene-2-carboxamide; (1S,2S,3R,4R)-3-(6-chloro-2-(5,6,7,8-tetrahydroimidazo[1,2-a]pyridin-2-yl)-3H-imidazo[4,5-b]pyridin-7-ylamino)bicyclo[2.2.1]hept-5-ene-2-carboxamide; 2-(4-(7-((1R,2R,3S,4S)-3-carbamoylbicyclo[2.2.1]hept-5-en-2-ylamino)-6-chloro-3H-imidazo[4,5-b]pyridin-2-yl)phenoxy)acetic acid; (1S,2S,3R,4R)-3-(6-chloro-2-(4-(2-morpholinoethoxy)phenyl)-3H-imidazo[4,5-b]pyridin-7-ylamino)bicyclo[2.2.1]hept-5-ene-2-carboxamide; 4-(7-((1R,2R,3S,4S)-3-carbamoylbicyclo[2.2.1]hept-5-en-2-ylamino)-6-chloro-3H-imidazo[4,5-b]pyridin-2-yl)benzoic acid; (1S,2S,3R,4R)-3-(6-chloro-2-(4-hydroxyphenyl)-3H-imidazo[4,5-b]pyridin-7-ylamino)bicyclo[2.2.1]hept-5-ene-2-carboxamide; (1S,2S,3R,4R)-3-(6-chloro-2-(4-methoxyphenyl)-3H-imidazo[4,5-b]pyridin-7-ylamino)bicyclo[2.2.1]hept-5-ene-2-carboxamide; (1S,2S,3R,4R)-3-(6-chloro-2-(3-hydroxyphenyl)-3H-imidazo[4,5-b]pyridin-7-ylamino)pyridin[2.2.1]hept-5-ene-2-carboxamide; (1S,2S,3R,4R)-3-(6-Chloro-2-phenylamino-3H-imidazo[4,5-b]pyridine-7-ylamino)-bicyclo[2.2.1]hept-5-ene-2-carboxylic acid amide; 2-(3-(7-((1R,2R,3S,4S)-3-carbamoylbicyclo[2.2.1]hept-5-en-2-ylamino)-6-chloro-3H-imidazo[4,5-b]pyridin-2-yl)phenoxy)acetic acid; (1S,2S,3R,4R)-3-(2-(3-(2-amino-2-oxoethoxy)phenyl)-6-chloro-3H-imidazo[4,5-b]pyridin-7-ylamino)bicyclo[2.2.1]hept-5-ene-2-carboxamide; (1S,2S,3R,4R)-3-(2-(4-(2-amino-2-oxoethoxy)phenyl)-6-chloro-3H-imidazo[4,5-b]pyridin-7-ylamino)bicyclo[2.2.1]hept-5-ene-2-carboxamide;

(1S,2S,3R,4R)-3-[6-Chloro-2-(4-chloro-2-morpholin-4-yl-thiazol-5-yl)-3H-imidazo[4,5-b]pyridin-7-ylamino]-bicyclo[2.2.1]hept-5-ene-2-carboxylic acid amide; (1S,2S,3R, 4R)-3-[6-Bromo-2-(4-chloro-2-morpholin-4-yl-thiazol-5-yl)-3H-imidazo[4,5-b]pyridin-7-ylamino]-bicyclo[2.2.1]hept-5-ene-2-carboxylic acid amide; (1S,2S,3R,4R)-3-(6-chloro-2-(4-(2-(dimethylamino)ethoxy)phenyl)-3H-imidazo[4,5-b]pyridin-7-ylamino)bicyclo[2.2.1]hept-5-ene-2-carboxamide; (1S,2S,3R,4R)-3-((6-chloro-2-(4-chloro-2-(4-methylpiperazin-1-yl)thiazol-5-yl)-3H-imidazo[4,5-b]pyridin-7-yl)amino)-N-isopropylbicyclo[2.2.1]hept-5-ene-2-carboxamide; (1S,2S,3R,4R)-3-((6-chloro-2-(4-chloro-2-(4-methylpiperazin-1-yl)thiazol-5-yl)-3H-imidazo[4,5-b]pyridin-7-yl)amino)-N,N-dimethylbicyclo[2.2.1]hept-5-ene-2-carboxamide; (1S,2S,3R,4R)-3-[6-Chloro-2-(2-methoxy-phenylamino)-3H-imidazo[4,5-b]pyridine-7-ylamino]-bicyclo[2.2.1]hept-5-ene-2-carboxylic acid amide; (1S,2S,3R,4R)-3-(6-chloro-2-(3-(1-methylpiperidin-4-yloxy)phenyl)-3H-imidazo[4,5-b]pyridin-7-ylamino)bicyclo[2.2.1]hept-5-ene-2-carboxamide; (1S,2S,3R,4R)-3-(6-chloro-2-(3-(2-(dimethylamino)ethoxy)phenyl)-3H-imidazo[4,5-b]yridine-7-ylamino)yridin[2.2.1]hept-5-ene-2-carboxamide;
(1S,2S,3R,4R)-3-(6-chloro-2-(3-(2-(4-methylpiperazin-1-yl)-2-oxoethoxy)phenyl)-3H-imidazo[4,5-b]yridine-7-ylamino)yridin[2.2.1]hept-5-ene-2-carboxamide;
(1S,2S,3R,4R)-3-(6-chloro-2-(4-(2-(4-methylpiperazin-1-yl)-2-oxoethoxy)phenyl)-3H-imidazo[4,5-b]pyridin-7-ylamino)bicyclo[2.2.1]hept-5-ene-2-carboxamide; 2-(3-(7-((1R,2R,3S,4S)-3-carbamoylbicyclo[2.2.1]hept-5-en-2-ylamino)-6-chloro-3H-imidazo[4,5-b]yridine-2-yl)benzamido)acetic acid; (1S,2S,3R,4R)-3-[6-Chloro-2-(2-methoxy-4-morpholin-4-ylmethyl-phenylamino)-3H-imidazo[4,5-b]pyridine-7-ylamino]-bicyclo[2.2.1]hept-5-ene-2-carboxylic acid amide; (1S,2S,3R,4R)-3-[6-Chloro-2-(4-chloro-2-morpholin-4-yl-thiazol-5-yl)-3H-imidazo[4,5-b]pyridin-7-ylamino]-bicyclo[2.2.1]hept-5-ene-2-carboxylic acid dimethylamide; (1S,2S,3R,4R)-3-[6-Chloro-2-(4-chloro-2-morpholin-4-yl-thiazol-5-yl)-3H-imidazo[4,5-b]pyridin-7-ylamino]-bicyclo[2.2.1]hept-5-ene-2-carboxylic acid isopropylamide; (1S,2S,3R,4R)-3-(6-chloro-2-(4-(1-methylpiperidin-4-yloxy)phenyl)-3H-imidazo[4,5-b]pyridin-7-ylamino)bicyclo[2.2.1]hept-5-ene-2-carboxamide; (1S,2S,3R,4R)-3-(6-chloro-2-(4-(4-methylpiperazine-1-carbonyl)phenyl)-3H-imidazo[4,5-b]pyridin-7-ylamino)bicyclo[2.2.1]hept-5-ene-2-carboxamide; (1S,2S,3R,4R)-3-(6-chloro-2-(3-(2-(dimethylamino)ethylcarbamoyl)phenyl)-3H-imidazo[4,5-b]pyridine-7-ylamino)yridin[2.2.1]hept-5-ene-2-carboxamide; (1S,2S,3R,4R)-3-(6-chloro-2-(3-(4-methylpiperazine-1-carbonyl)phenyl)-3H-imidazo[4,5-b]pyridin-7-ylamino)bicyclo[2.2.1]hept-5-ene-2-carboxamide; (1S,2S,3R,4R)-3-(6-chloro-2-(3-(2-(4-(2-hydroxypropyl)piperazin-1-yl)-2-oxoethoxy)phenyl)-3H-imidazo[4,5-b]pyridin-7-ylamino)bicyclo[2.2.1]hept-5-ene-2-carboxamide; (1S,2S,3R,4R)-3-(6-chloro-2-(4-(2-(4-methylpiperazin-1-yl)ethoxy)phenyl)-3H-imidazo[4,5-b]pyridin-7-ylamino)bicyclo[2.2.1]hept-5-ene-2-carboxamide; (1S,2S,3R,4R)-3-(6-chloro-2-(3-(piperazine-1-carbonyl)phenyl)-3H-imidazo[4,5-b]pyridin-7-ylamino)bicyclo[2.2.1]hept-5-ene-2-carboxamide; (1S,2S,3R,4R)-3-[6-Chloro-2-(4-chloro-2-pyrrolidin-1-yl-thiazol-5-yl)-3H-imidazo[4,5-b]pyridin-7-ylamino]-bicyclo[2.2.1]hept-5-ene-2-carboxylic acid isopropylamide; (1S,2S,3R,4R)-3-[6-Chloro-2-(4-chloro-2-pyrrolidin-1-yl-thiazol-5-yl)-3H-imidazo[4,5-b]pyridin-7-ylamino]-bicyclo[2.2.1]hept-5-ene-2-carboxylic acid amide;
(1S,2S,3R,4R)-3-[6-Bromo-2-(4-chloro-2-pyrrolidin-1-yl-thiazol-5-yl)-3H-imidazo[4,5-b]pyridin-7-ylamino]-bicyclo[2.2.1]hept-5-ene-2-carboxylic acid amide; (1S,2S,3R,4R)-3-{6-Chloro-2-[4-chloro-2-((R)-3-hydroxy-pyrrolidin-1-yl)-thiazol-5-yl]-3H-imidazo[4,5-b]pyridin-7-ylamino}-bicyclo[2.2.1]hept-5-ene-2-carboxylic acid dimethylamide;
(1S,2S,3R,4R)-3-{6-Chloro-2-[4-chloro-2-((R)-3-hydroxy-pyrrolidin-1-yl)-thiazol-5-yl]-1H-imidazo[4,5-b]pyridin-7-ylamino}-bicyclo[2.2.1]hept-5-ene-2-carboxylic acid isopropylamide; (1S,2S,3R,4R)-3-{6-Chloro-2-[4-chloro-2-((R)-3-hydroxy-pyrrolidin-1-yl)-thiazol-5-yl]-1H-imidazo[4,5-b]pyridin-7-ylamino}-bicyclo[2.2.1]hept-5-ene-2-carboxylic acid isopropylamide; (1S,2S,3R,4R)-3-{6-Bromo-2-[4-chloro-2-((R)-3-hydroxy-pyrrolidin-1-yl)-thiazol-5-yl]-3H-imidazo[4,5-b]pyridin-7-ylamino}-bicyclo[2.2.1]hept-5-ene-2-carboxylic acid amide; (1S,2S,3R,4R)-3-[6-Chloro-2-(4-chloro-2-pyrrolidin-1-yl-thiazol-5-yl)-3H-imidazo[4,5-b]pyridin-7-ylamino]-bicyclo[2.2.1]hept-5-ene-2-carboxylic acid cyclopropylamide; (1S,2S,3R,4R)-3-{6-Chloro-2-[4-chloro-2-((R)-3-hydroxy-pyrrolidin-1-yl)-thiazol-5-yl]-3H-imidazo[4,5-b]pyridin-7-ylamino}-bicyclo[2.2.1]hept-5-ene-2-carboxylic acid cyclopropylamide;
(1S,2S,3R,4R)-3-[6-Chloro-2-(4-chloro-2-morpholin-4-yl-thiazol-5-yl)-3H-imidazo[4,5-b]pyridin-7-ylamino]-bicyclo[2.2.1]hept-5-ene-2-carboxylic acid cyclopropylamide;
(1S,2S,3R,4R)-3-(6-chloro-2-(4-(piperazine-1-carbonyl)phenyl)-3H-imidazo[4,5-b]pyridin-7-ylamino)bicyclo[2.2.1]hept-5-ene-2-carboxamide; (1S,2S,3R,4R)-3-{6-Chloro-2-[4-(2-dimethylamino-ethylcarbamoyl)-phenyl]-3H-imidazo[4,5-b]yridine-7-ylamino}-bicyclo[2.2.1]hept-5-ene-2-carboxylic acid amide; (1S,2S,3R,4R)-3-(6-chloro-2-(4-(4-(2-hydroxypropyl)piperazine-1-carbonyl)phenyl)-3H-imidazo[4,5-b]pyridine-7-ylamino)pyridin[2.2.1]hept-5-ene-2-carboxamide; (1S,2S,3R,4R)-3-(6-chloro-2-(4-(1-(2-hydroxypropyl)piperidin-4-yloxy)phenyl)-3H-imidazo[4,5-b]pyridin-7-ylamino)bicyclo[2.2.1]hept-5-ene-2-carboxamide; (1S,2S,3R,4R)-3-(6-chloro-2-(3-(1-(2-hydroxypropyl)piperidin-4-yloxy)phenyl)-3H-imidazo[4,5-b]pyridine-7-ylamino)pyridin[2.2.1]hept-5-ene-2-carboxamide; 1S,2S,3R,4R)-3-(6-chloro-2-(3-(4-(2-hydroxypropyl)piperazine-1-carbonyl)phenyl)-3H-imidazo[4,5-b]pyridine-7-ylamino)pyridin[2.2.1]hept-5-ene-2-carboxamide; (1S,2S,3R,4R)-3-(6-chloro-2-(4-(2-(4-(2-hydroxypropyl)piperazin-1-yl)-2-oxoethoxy)phenyl)-3H-imidazo[4,5-b]pyridin-7-ylamino)bicyclo[2.2.1]hept-5-ene-2-carboxamide; 4-(3-(7-((1R,2R,3S,4S)-3-carbamoylbicyclo[2.2.1]hept-5-en-2-ylamino)-6-chloro-3H-imidazo[4,5-b]yridine-2-yl)benzoyl)piperazine-2-carboxylic acid; 2-(4-(7-((1R,2R,3S,4S)-3-carbamoylbicyclo[2.2.1]hept-5-en-2-ylamino)-6-chloro-3H-imidazo[4,5-b]pyridine-2-yl)benzamido)acetic acid; (1S,2S,3R,4R)-3-(6-Chloro-2-{4-[2-(4-methyl-piperazin-1-yl)-ethoxy]-phenyl}-3H-imidazo[4,5-b]pyridin-7-ylamino)-bicyclo[2.2.1]hept-5-ene-2-carboxylic acid dimethylamide; (1S,2S,3R,4R)-3-{6-Chloro-2-[4-(2-dimethylamino-ethoxy)-phenyl]-3H-imidazo[4,5-b]pyridin-7-ylamino}-bicyclo[2.2.1]hept-5-ene-2-carboxylic acid dimethylamide; 2-(4-(7-((1R,2R,3S,4S)-3-carbamoylbicyclo(2.2.1)hept-5-en-2-ylamino)-6-chloro-3H-imidazo[4,5-b]pyridine-2-yl)benzamido)-3-hydroxypropanoic acid; 4-(4-(7-((1R,2R,3S,4S)-3- carbamoylbicyclo[2.2.1]hept-5-en-2-ylamino)-6-chloro-3H-imidazo[4,5-b]yridine-2-yl)benzoyl)piperazine-2-carboxylic acid;

2-(3-(7-((1R,2R,3S,4S)-3-carbamoylbicyclo-(2.2.1)hept-5-en-2-ylamino)-6-chloro-3H-imidazo[4,5-b]pyridine-2-yl)benzamido)-3-hydroxypropanoic acid.

In other embodiments, this application provides compounds of Formula I where W is H, Z is

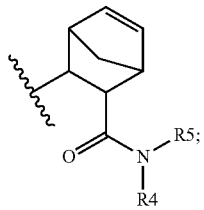

$R^1$ is

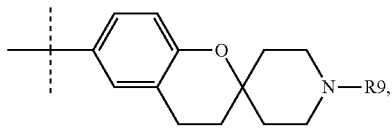

optionally substituted with one or more $R^6$ groups; $R^2$ is selected from chlorine or bromine; and $R^4$, $R^5$, and $R^9$ are each H.

Compounds exemplifying this embodiment include, but are not limited to, the following:

(1S,2S,3R,4R)-3-[(6-bromo-2-spiro[chromane-2,4'-piperidine]-6-yl-3H-imidazo[4,5-b]pyridin-7-yl)amino]bicyclo[2.2.1]hept-5-ene-2-carboxamide and (1S,2S,3R,4R)-3-[(6-chloro-2-spiro[chromane-2,4'-piperidine]-6-yl-3H-imidazo[4,5-b]pyridin-7-yl)amino]bicyclo[2.2.1]hept-5-ene-2-carboxamide.

In yet other embodiments, this application provides compounds of Formula I where W and Z are taken together to form

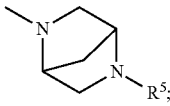

$R^1$ is selected from $(C_6-C_{10})$aryl that is optionally substituted with one or more $R^6$ groups; $R^2$ is halogen; and $R^5$ is selected from H, $(C_1-C_6)$alkyl, or $(C_0-C_4)$alkyl$CO_2(C_1-C_4)$alkyl wherein $(C_1-C_6)$alkyl, or $(C_0-C_4)$alkyl$CO_2(C_1-C_4)$alkyl may be optionally substituted with one or more $R^7$. In some preferred embodiments, W and Z are taken together to form

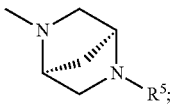

$R^1$ is phenyl optionally substituted with a methoxy group; $R^2$ is chlorine; and $R^5$ is selected from H, propan-2-ol, or $CO_2$t-butyl.

Compounds exemplifying this embodiment include, but are not limited to, the following:

(1S,4S)-5-[6-Chloro-2-(2-methoxy-4-morpholinj-4-yl-phenyl)-3H-imidazo[4,5-b]pyridine-7-yl]-2,5-diaza-bicyclo[2.2.1]heptane-2-carboxylic acid tert-butyl ester;

6-Chloro-7-(1S,4S)-2,5-diaza-bicyclo[2.2.1]hept-2-yl-2-(2-methoxy-4-morpholin-4-yl-phenyl)-3H-imidazo[4,5-b]pyridine;

(S)-1-{(1S,4S)-5-[6-Chloro-2-(methoxy-4-morpholin-4-yl-phenyl)-3H-imidazo[4,5-b]pyridine-7-yl]-2,5-diaza-bicyclo[2.2.1]hept-2-yl}-propan-2-ol.

In other embodiments, this application provides compounds of Formula I where W is H and Z is

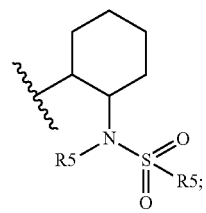

$R^1$ is $(C_6-C_{10})$aryl optionally substituted with one or more $R^6$ groups, with phenyl optionally substituted with one or more $R^6$ groups being more preferred; $R^2$ is halogen, preferably chlorine; and each $R^5$ is independently selected from H or $(C_1-C_6)$alkyl, with hydrogen and methyl being more preferred.

Compounds exemplifying this embodiment include, but are not limited to, the following:

N-[(1R,2R)-2-(6-Chloro-2-{2-methoxy-4-[4-(4-methyl-piperazin-1-yl)-piperidin-1-yl]-phenyl}-3H-imidazo[4,5-b]pyridin-7-ylamino)-cyclohexyl]-methanesulfonamide;

N-((1R,2R)-2-{6-Chloro-2-[4-(4-methyl-piperazin-1-ylmethyl)-phenyl]-3H-imidazo[4,5-b]pyridine-7-ylamino}-cyclohexyl)-methanesulfonamide;

N-{(1R,2R)-2-[6-Chloro-2-(2-methoxy-4-morpholin-4-yl-methyl-phenyl)-3H-imidazo[4,5-b]pyridine-7-ylamino]-cyclohexyl}-methanesulfonamide;

N-((1R,2R)-2-{6-Chloro-2-[2-methoxy-4-(4-methyl-piperazin-1-ylmethyl)-phenyl]-3H-imidazo[4,5-b]pyridine-7-ylamino}-cyclohexyl)-methanesulfonamide;

N-{(1R,2R)-2-[6-Chloro-2-(2-methoxy-4-morpholin-4-yl-phenyl)-3H-imidazo[4,5-b]pyridine-7-ylamino]-cyclohexyl}-methanesulfonamide;

N-((1R,2R)-2{6-Chloro-2-[2-methoxy-4-(4-morpholin-4-yl-piperidin-1-yl)-phenyl]-3H-imidazo[4,5-b]pyridine-7-ylamino}-cyclohexyl)-methanesulfoneamide;

N-{(1R,2R)-2-[6-Chloro-2-(2-methoxy-5-morpholin-4-yl-methyl-phenyl)-3H-imidazo[4,5-b]pyridine-7-ylamino]-cyclohexyl}-methanesulfonamide;

N-((1R,2R)-2-{6-Chloro-2-[4-((R)-3-hydroxy-pyrrolidin-1-ylmethyl)-2-methoxy-phenyl]-3H-imidazo[4,5-b]pyridine-7-ylamino}-cyclohexyl)-methanesulfonamide.

In still another embodiment, this application provides compounds of Formula I where W is H and Z is

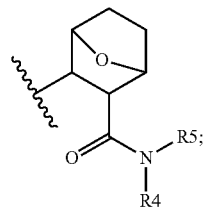

R¹ is selected from $(C_6\text{-}C_{10})$aryl or $(C_1\text{-}C_9)$heteroaryl either of which may be optionally substituted with one or more $R^6$; and $R^2$ is halogen. In some preferred embodiments, $R^1$ is selected from phenyl or pyrazolyl, either of which may be optionally substituted with one or more $R^6$, most preferably $R^6$ is selected from $(C_1\text{-}C_6)$alkyl, $(C_1\text{-}C_6)$alkoxy and $(C_0\text{-}C_6)$alkyl$(C_2\text{-}C_9)$heterocycloalkyl; and $R^2$ is chloride. In further preferred embodiments, each $R^6$ is independently selected from methyl, methoxy, and morpholinyl.

Compounds exemplifying this embodiment include, but are not limited to, the following:
(1S,2R,3S,4R)-3-(6-chloro-2-(1-methyl-1H-pyrazol-4-yl)-3H-imidazo[4,5-b]pyridin-7-ylamino)-7-oxabicyclo[2.2.1]heptane-2-carboxamide;
(1S,2R,3S,4R)-3-(6-chloro-2-(4-morpholinophenyl)-3H-imidazo[4,5-b]pyridin-7-ylamino)-7-oxabicyclo[2.2.1]heptane-2-carboxamide;
(1S,2R,3S,4R)-3-(6-chloro-2-(2-methoxy-4-morpholinophenyl)-3H-imidazo[4,5-b]pyridin-7-ylamino)-7-oxabicyclo[2.2.1]heptane-2-carboxamide.

In yet another embodiment, this application provides compounds of Formula I where W is H and Z is

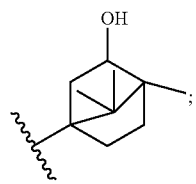 [SMILES: *C12CCC(C)(C(O)C1)C2(C)C]

R¹ is selected from $(C_6\text{-}C_{10})$aryl or $(C_1\text{-}C_9)$heteroaryl either of which may be optionally substituted with one or more $R^6$; and $R^2$ is halogen. In some preferred embodiments $R^1$ is selected from phenyl or pyrazolyl, either of which may be optionally substituted with one or more $R^6$, most preferably $R^6$ is selected from $(C_1\text{-}C_6)$alkyl, $(C_1\text{-}C_6)$alkoxy and $(C_0\text{-}C_6)$alkyl$(C_2\text{-}C_9)$heterocycloalkyl; and $R^2$ is chloride. In further preferred embodiments, each $R^6$ is independently selected from methyl, methoxy, and morpholinyl.

Compounds exemplifying this embodiment include, but are not limited to, the following:
4-(6-chloro-2-(2-methoxy-4-morpholinophenyl)-3H-imidazo[4,5-b]pyridin-7-ylamino)-1,7,7-trimethylbicyclo[2.2.1]heptan-2-ol;
(4S)-4-(6-chloro-2-(1-methyl-1H-pyrazol-4-yl)-3H-imidazo[4,5-b]pyridin-7-ylamino)-1,7,7-trimethylbicyclo[2.2.1]heptan-2-ol;
4-(6-chloro-2-(4-morpholinophenyl)-3H-imidazo[4,5-b]pyridin-7-ylamino)-1,7,7-trimethylbicyclo[2.2.1]heptan-2-ol.

In yet another embodiment, this application provides compounds of Formula I where W is H and Z is

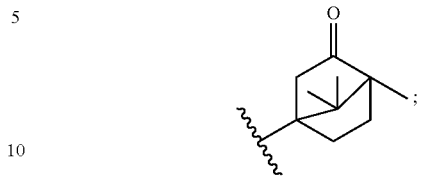

R¹ is selected from $(C_6\text{-}C_{10})$aryl or $(C_1\text{-}C_9)$heteroaryl either of which may be optionally substituted with one or more $R^6$; and $R^2$ is halogen. In some preferred embodiments $R^1$ is selected from phenyl or pyrazolyl, either of which may be optionally substituted with one or more $R^6$, most preferably $R^6$ is selected from $(C_1\text{-}C_6)$alkyl, $(C_1\text{-}C_6)$alkoxy and $(C_0\text{-}C_6)$alkyl$(C_2\text{-}C_9)$heterocycloalkyl; and $R^2$ is chloride. In further preferred embodiments, each $R^6$ is independently selected from methyl, methoxy, and morpholinyl.

Compounds exemplifying this embodiment include, but are not limited to, the following:
4-(6-chloro-2-(4-morpholinophenyl)-3H-imidazo[4,5-b]pyridin-7-ylamino)-1,7,7-trimethylbicyclo[2.2.1]heptan-2-one;
4-(6-chloro-2-(2-methoxy-4-morpholinophenyl)-3H-imidazo[4,5-b]pyridin-7-ylamino)-1,7,7-trimethylbicyclo[2.2.1]heptan-2-one;
4-(6-chloro-2-(1-methyl-1H-pyrazol-4-yl)-3H-imidazo[4,5-b]pyridin-7-ylamino)-1,7,7-trimethylbicyclo[2.2.1]heptan-2-one.

In another aspect, this application relates to pharmaceutically acceptable salts of the compounds described herein.

In another aspect, this application relates to compositions comprising one or more compounds of the general Formula I or a salt thereof. In some specific embodiments, the salt is a pharmaceutically acceptable salt. In some specific embodiments, the composition comprises at least one pharmaceutically acceptable excipient. In other specific embodiments, the composition further comprises at least one additional therapeutically active agent.

In another aspect, this application relates to methods of treating diseases or disorders mediated by at least one of ALK (Anaplastic Lymphoma Kinase) or a member of the JAK (Janus kinase) family of kinases comprising administering a therapeutically effective amount of a compound of the general Formula I or a pharmaceutically acceptable salt thereof. In some embodiments, the disease or disorder is mediated by at least one of ALK or JAK2. In some specific embodiments, the disease or disorder mediated by at least one of ALK or JAK2 is cancer. In further specific embodiments, the disease or disorder mediated by at least one of ALK or JAK2 is a cancer selected from colon cancer, breast cancer, non-small cell lung cancer, neuroblastoma, esophageal squamous carcinoma, hemangioma, head and neck squamous cell carcinoma, prostate cancer, myeloid leukemia, melanoma, glioblastoma, astrocytoma, anaplastic large cell lymphoma, inflammatory myofibroblastic tumor, myeloproliferative neoplasms (MPN) or other solid tumors. In other specific embodiments, the method further comprises administration of at least one additional therapeutically active agent.

In another aspect, this application relates to methods for treating a hyperproliferative disease or disorder for which inhibition of at least one of ALK or JAK2 is indicated comprising administering a therapeutically effective amount of a compound of the general Formula I or a pharmaceutically acceptable salt thereof. In some specific embodiments, a compound of Formula I preferentially inhibits the JAK2 enzyme in vitro. In other specific embodiments, a compound of Formula I preferentially inhibits the ALK enzyme in vitro. As used herein, the term "preferentially inhibits" refers to a difference of at least about 10 fold between, for example, $IC_{50}$ values. In still other specific embodiments, the compound of Formula I is substantially equipotent against both the ALK and JAK2 enzymes in vitro. As used herein, the term "substantially equipotent" refers to a difference between, for example, $IC_{50}$ values, of no greater than about 3 fold.

DEFINITIONS

The compounds and intermediates described herein may be named according to either the IUPAC (International Union for Pure and Applied Chemistry) or CAS (Chemical Abstracts Service) nomenclature systems. It should be understood that unless expressly stated to the contrary, when the terms "compounds of Formula I" or more simply "compounds" are used in this application these terms refer to and include all salts of the compounds described by and/or with reference to Formula I (including any subformulae of Formula I).

The various hydrocarbon-containing moieties described herein may be described using a prefix designating the minimum and maximum number of carbon atoms in the moiety, i.e. "$(C_a-C_b)$". For example, $(C_a-C_b)$alkyl indicates an alkyl moiety of the integer "a" to the integer "b" carbon atoms, inclusive. Certain moieties may also be described according to the minimum and maximum number of members with or without specific reference to a particular atom or overall structure. For example, the terms "a to b-membered" or "having between a to b members" refer to a moiety having the integer "a" to the integer "b" number of atoms, inclusive.

As used herein by itself or in conjunction with another term or terms, "alkyl" refers to straight or branched hydrocarbon groups containing a requisite number of carbon atoms. Unless otherwise defined, an alkyl group may have between one to eight carbon atoms, inclusive. As used herein, alkyl groups may be optionally substituted with between one to four substituents. Representative examples of alkyl groups include, but are not limited to, e.g., methyl, ethyl, n-propyl, isopropyl, n-butyl, isobutyl, sec-butyl, t-butyl, etc.

As used herein by itself or in conjunction with another term or terms, "alkoxy", refers to straight or branched hydrocarbon groups containing a requisite number of carbon atoms bonded to an oxygen atom. Unless otherwise defined, an alkoxy group may have between one to eight carbon atoms, inclusive. As used herein, alkoxy groups may be optionally substituted with between one to four substituents. Representative examples of alkoxy groups include, but are not limited to, e.g. methoxy, ethoxy, tert-butoxy, etc.

As used herein by itself or in conjunction with another term or terms, "alkenyl" refers to straight or branched hydrocarbon groups containing a requisite number of carbon atoms and at least one double bond. Unless otherwise defined, an alkenyl group may have between two to eight carbon atoms, inclusive. As used herein, alkenyl groups may be optionally substituted with between one to four substituents. Representative examples of alkenyl groups include, but are not limited to, e.g. ethenyl, 2-propenyl (allyl), iso-propenyl, 2-methyl-1-propenyl, etc.

As used herein by itself or in conjunction with another term or terms, "alkynyl" refers to straight or branched hydrocarbon groups containing a requisite number of carbon atoms and at least one triple bond. Unless otherwise defined, an alkynyl group may have between two to eight carbon atoms, inclusive. As used herein, alkynyl groups may be optionally substituted with between one to four substituents. Representative examples of alkynyl groups include, but are not limited to, e.g. ethynyl, propynyl, butynyl, etc.

As used herein by itself or in conjunction with another term or terms, "aromatic" refers to monocyclic and polycyclic ring systems containing 4n+2 pi electrons, where n is an integer. As used herein, aromatic refers to and includes ring systems that contain only carbon atoms (i.e. "aryl") as well as ring systems that contain at least one heteroatom selected from N, O or S (i.e. "heteroaromatic" or "heteroaryl"). As used herein, an aromatic ring system may be optionally substituted with between one to four substituents.

As used herein by itself or in conjunction with another term or terms, "non-aromatic" refers to a monocyclic or polycyclic ring system having at least one isolated double bond, i.e. a double bond that is not part of a conjugated pi system. As used herein, non-aromatic refers to and includes ring systems that contain only carbon atoms as well as ring systems that contain at least one heteroatom selected from N, O or S. A non-aromatic ring system may be optionally substituted with between one to four substituents.

As used herein by itself or in conjunction with another term or terms, "aryl" refers to monocyclic and polycyclic aromatic hydrocarbon ring systems containing a requisite number of carbon atoms and may be optionally substituted with between one to four substituents. Unless otherwise defined, an aryl group may have between six to ten carbon atoms, inclusive. Representative examples include, but are not limited to, e.g., phenyl, 9H-fluorenyl, azulenyl, anthracenyl, napthalenyl, etc., and may be optionally substituted with between one to four substituents.

As used herein by itself or in conjunction with another term or terms, "arylalkyl" refers to alkyl groups, as defined above, having an aryl group, as defined above, as a substituent. Arylalkyl groups may be optionally substituted with between one to four substituents. Representative examples include, but are not limited to, e.g., benzyl, phenylethyl, etc.

As used herein by themselves or in conjunction with another term or terms, "aryloxy" and "arylalkoxy" refer to aryl groups, as defined above, that are bonded directly to an oxygen atom or to an alkoxy group, as defined above, respectively. Representative examples include, but are not limited to, e.g., phenoxy, benzyloxy, phenylethoxy, and may be optionally substituted with between one to four substituents.

As used herein by itself or in conjunction with another term or terms, "aminophenyl" refers to a phenyl group having an amine as a substituent. It should be understood that aminophenyl refers to and includes primary, secondary or tertiary amines. As used herein, an aminophenyl group may be optionally substituted with between one to four substituents.

As used herein by themselves or in conjunction with another term or terms, "carbocyclic" and "carbocycle" refer to monocyclic and polycyclic ring systems that contain only carbon atoms in the ring(s), i.e. hydrocarbon ring systems, without regard to aromaticity. Thus, carbocyclic and carbocycle refer to and include ring systems that are saturated or unsaturated, aromatic or non-aromatic, as well as ring systems having fully saturated, aromatic and/or non-aromatic portions. The terms carbocyclic and carbocycle further include bridged, fused, and spirocyclic ring systems. Carbocycles may be optionally substituted with between one to four substituents. Representative examples include, but are not limited to, e.g., cyclopropyl, cyclobutyl, 1,3-dimethylcyclopentyl, cyclohexyl, phenyl, napthyl, cyclohexenyl, 2,3-dihydro-indenyl, 1,2,3,4-tetrahydro-naphthalene, spiro[3.4]

octanyl, bicycle[2.2.1]hept-5-enyl, adamantanyl, norbornanyl, bicyclo[2.2.1]heptanyl, etc.

As used herein by themselves or in conjunction with another term or terms, "halo" and "halogen" include fluorine, chlorine, bromine, and iodine atoms and substituents.

As used herein by itself or in conjunction with another term, "haloalkyl refers to alkyl groups, as defined above, having one or more hydrogen atoms replaced by halogen atoms, as defined above. It should be understood that where there is more than one halogen atom present in a haloalkyl group, the halogen atoms may be the same or different and/or may be located on the same carbon atom or on different carbon atoms. Representative examples of haloalkyl groups include, but are not limited to, e.g., difluoromethyl, trifluoromethyl, chloromethyl, 3-bromo-2-chloro-propyl, 2,2-dibromoethyl, 2-bromo-2-chloro-ethyl, 1,1,2,2,3,3,4,4-octafluoro-butyl, etc.

As used herein by itself or in conjunction with another term or terms, "haloalkoxy" refers to haloalkyl groups, as defined above, bonded to an oxygen atom. Representative examples of haloalkoxy groups include, but are not limited to, e.g., difluoromethoxy, trifluoromethoxy, chloromethoxy, 2,2-dibromoethoxy, 3-bromo-2-chloro-propoxy, 1,1,2,2,3,3,4,4-octafluoro-butoxy, etc.

As used herein by itself or in conjunction with another term or terms, "cycloalkyl" refers to monocyclic and polycyclic hydrocarbon ring systems containing a requisite number of carbon atoms and may be optionally substituted with between one to four substituents. Cycloalkyl refers to and includes ring systems that are fully saturated or contain at least one unsaturated bond, as well as ring systems with fully saturated, aromatic or non-aromatic portions, such as, for example, 1,2,3,4-tetrahydro-naphthalenyl. It should be understood that these terms further refer to and include bridged and/or fused polycyclic structures such as, for example, bicyclo[3.2.1] octanyl, bicyclo[5.2.0]nonanyl, bicyclo[2.2.1]hept-5-enyl and the like, as well as spirocyclic ring systems such as, for example, spiro[3.4]octanyl, spiro[3.5]nonyl and the like. Other representative examples of cycloalkyl groups include, but are not limited to, e.g., cyclopropyl, methylcyclopropyl, cyclobutyl, cyclobutenyl, isopropylcyclobutyl, cyclopentyl, 1,3-dimethylcyclopentyl, cyclohexyl, cyclohexenyl, cycloheptyl, 2,3-dihydro-1H-inden-2-yl, norbornyl, decahydronaphthalenyl, etc.

As used herein by themselves or in conjunction with another term or terms, "cycloalkyloxy" or "cycloalkoxy" refer to a cycloalkyl group having a requisite number of carbon atoms bonded directly to an oxygen atom or an alkoxy group, respectively. As used herein, cycloalkyloxy may be optionally substituted with between one to four substituents. Representative examples include, but are not limited to, e.g., cyclopropyloxy, cyclobutyloxy, cyclopentyloxy, 2-cyclopentyl-ethoxy, cyclohexyl-methoxy, cyclohex-3-yloxy, etc.

As used herein by themselves or in conjunction with another term or terms, "heterocycloalkyl", "heterocycle", and "heterocyclic" refer to monocyclic and polycyclic ring systems containing a requisite number of carbon atoms and at least one heteroatom selected from N, O, or S. These terms further refer to and include ring systems that are fully saturated or contain at least one double bond, such as for example 2-pyrrolinyl and tetrahydropyridinyl, as well as ring systems with fully saturated, aromatic and/or non-aromatic portions. It should be understood that polycyclic heterocycloalkyl groups further include fused, bridged and spirocyclic ring systems and ring systems in which the N or S is oxidized, i.e. 1,1-dioxide-thiomorpholinyl, 1-oxo-piperidinyl. It should also be understood that the incorporation of "heterocycloalkenyl" in the claims is not intended to limit the broader definition of heterocycloalkyl or cycloalkyl. As used herein, heterocycloalkyl, heterocycle, and heterocyclic groups may be optionally substituted with between one to four substituents. Representative examples of heterocycloalkyl groups include, but are not limited to, e.g., oxiranyl, thiaranyl, aziridinyl, oxetanyl, thiatanyl, azetidinyl, tetrahydrofuranyl, tetrahydrothiophenyl, pyrrolidinyl, dihydrofuranyl, tetrahydropyranyl, pyranyl, tetrahydrothiopyranyl, thiopyranyl, piperidinyl, 1,4-dioxanyl, 1,4-oxathianyl, morpholinyl, thiomorpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thieazepanyl, 1,4-diazepanyl, 1,2-tetrahydrothiazin-2-yl, 1,3-tetrahydrothiazin-3-yl, tetrahydrothiadiazinyl, 1,2-tetrahydrodiazin-2-yl, 1,3-tetrahydrodiazin-1-yl, tetrahydroazepinyl, chromanyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, 7-oxa-1-aza-spiro[4.4]nonanyl, 3-azabicyclo[3.1.0]hexanyl, indolinyl, octahydro-1H-indolyl, octahydro-2H-pyrido[1,2-a]pyrazinyl, 3-azabicyclo[4.1.0]heptanyl, 3,4-dihydro-2H-pyranyl, 1,2,3,4-tetrahydropyridinyl, etc.

As used herein by itself or in conjunction with another term or terms, "heterocycloalkylalkyl" refer to alkyl groups, as defined above, having a heterocycloalkyl group, as defined above, as a substituent. As used herein, heterocycloalkylalkyl groups may be optionally substituted with between one to four substituents. Representative examples include, but are not limited to, e.g., piperidinylmethyl, pyrrolidinylethyl, etc.

As used herein by themselves or in conjunction with another term or terms, "heterocycloalkyloxy" and "heterocycloalkylalkoxy" respectively refer to a heterocycloalkyl or a heterocycloalkylalkyl group, as defined above, bonded to an oxygen atom. As used herein, heterocycloalkyloxy and heterocycloalkylalkoxy groups may be optionally substituted with between one to four substituents. Representative examples include, but are not limited to, e.g., pyrrolidin-3-yloxy, piperidin-4-yloxy, azepan-4-yloxy, pyrrolidin-1-ylethoxy, pyrrolidin-2-ylmethoxy, etc.

As used herein by themselves or in conjunction with another term or terms, "heteroaryl" and "heteroaromatic" refer to monocyclic and polycyclic aromatic ring systems containing a requisite number of carbon atoms, as described above, and at least one heteroatom selected from N, O, or S. As used herein, heteroaromatic and heteroaryl ring system refer to and include polycyclic ring systems that contain aromatic portions, while other portions of the ring system may be fully saturated or non-aromatic. Heteroaromatic or heteroaryl rings may be optionally substituted with between one to four substituents. Representative examples include, but are not limited to, e.g., pyrrolyl, furanyl, thiophenyl, thienyl, pyrazolyl, imidazolyl, isoxazolyl, oxazolyl, isothiazolyl, thiazolyl, 1,2,3-triazolyl, 1,2,4-triazolyl, tetrazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridinyl (pyridyl), pyridazinyl, pyrimidinyl, pyrazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl, 1,2,3,4-tetrahydro-isoquinolinyl, 2,3-dihydro-1H-isoindolyl, 1,3,4,5-tetrahydro-benzo[b]azepin-2-one, 1,3,4,5-Tetrahydro-benzo[d]azepin-2-one, 2,3,4,5-Tetrahydro-benzo[c]azepin-1-one, 1,2,4,5-Tetrahydro-benzo

[c]azepin-3-one, 2,3,4,5-Tetrahydro-1H-benzo[b]azepinyl, 2,3,4,5-Tetrahydro-1H-benzo[d]azepinyl, 2,3,4,5-Tetrahydro-1H-benzo[c]azepinyl, etc.

As used herein by itself of in conjunction with another term or terms, "a bond", refers to and includes, a direct bond, a double bond (which may be denoted as —CH═CH—) or a triple bond (which may be denoted as —C≡C—) unless expressly stated otherwise.

As used herein by itself or in conjunction with another term or terms, "pharmaceutically acceptable" indicates that the designated entity such as for example, e.g. carrier, vehicle, diluent, excipient, salt or prodrug, is generally chemically and/or physically compatible with the other ingredients comprising a formulation, and/or is generally physiologically compatible with the recipient thereof.

As used herein by themselves or in conjunction with another term or terms, "subject(s)" and "patient(s)", refer to mammals, including humans.

As used herein by itself or in conjunction with another term or terms, "substituted" indicates that a hydrogen atom on a molecule has been replaced with a different atom or group of atoms and the atom or group of atoms replacing the hydrogen atom is a "substituent." It should be understood that the terms "substituent", "substituents", "moiety", "moieties", "group", or "groups" refer to substituent(s) when used in conjunction with the phrase " . . . optionally substituted by one or more . . . " unless otherwise specified.

As used herein, representative examples of substituents include, but are not limited to, e.g., hydrogen (may be denoted as H), halogen (may be referenced to as halo), $(C_1-C_8)$alkyl, $(C_1-C_8)$alkoxy, $(C_1-C_8)$alkoxy$(C_1-C_6)$alkyl, carboxyl (may be denoted as —COOH), formyl, $(C_1-C_6)$acyl, halo$(C_1-C_6)$alkyl, halo$(C_1-C_6)$alkoxy, hydroxyl (may be denoted as —OH), nitro (may be denoted as —NO$_2$), cyano (may be denoted as —CN), amino (may be denoted as —NH$_2$), mono- or di-$(C_1-C_6)$alkylamino (may be denoted as —NHR, —NRR, —NRR', or —N(R)$_2$), oxo (may be denoted as ═O or carbonyl), $(C_6-C_{10})$aryl, $(C_6-C_{10})$aryloxy, $(C_1-C_8)$alkyl$(C_6-C_{10})$aryl, $(C_1-C_8)$alkoxy$(C_6-C_{10})$aryl, $(C_2-C_9)$heteroaryl, $(C_2-C_9)$heteroaryloxy, $(C_1-C_8)$alkyl$(C_2-C_9)$heteroaryl, $(C_1-C_8)$alkoxy$(C_2-C_9)$heteroaryl, $(C_1-C_8)$alkoxycarbonyl (may be denoted as —COOR), $(C_3-C_{14})$cycloalkyl, $(C_1-C_8)$alkyl$(C_3-C_{14})$cycloalkyl, $(C_3-C_{14})$cycloalkyloxy, $(C_1-C_8)$alkoxy$(C_3-C_{14})$cycloalkyl, $(C_2-C_{14})$heterocycloalkyl, $(C_1-C_8)$alkyl$(C_2-C_{14})$heterocycloalkyl, $(C_2-C_{14})$heterocycloalkyloxy, $(C_1-C_8)$alkoxy$(C_2-C_{14})$heterocycloalkyl, $(C_0-C_6)$alkyl$(C_1-C_8)$alkoxycarbonyl (may be denoted $(C_0-C_6)$alkylCO$_2$R), $(C_1-C_6)$alkylsulfinyl (may be denoted —SOR), $(C_1-C_8)$alkylsulfonyl (may be denoted as —SO$_2$R), $(C_1-C_8)$alkylsulfide (may be denoted as —SR), mono- and di-$(C_1-C_8)$alkylaminocarbonyl (may be denoted as NH$_2$CO—, —NH$_2$CO—, —NRCO—, NR$_2$CO—), $(C_1-C_8)$acylthio, PO$((C_1-C_6)$alkyl$)_2$, etc.

As used herein, the terms "treating", "treated", and "treatment", whether used alone or in conjunction with another term or terms, include preventative (e.g., prophylactic), ameliorative, palliative, and curative uses and results, or any combination thereof. It should be understood that the terms "preventing" and "preventative" and "prophylactic" are not absolute but rather refer to uses and results where the administration of a compound or composition diminishes the likelihood or seriousness of a condition, symptom, or disease state, and/or delays the onset of a condition, symptom, or disease state for a period of time. In some embodiments, the terms "treating", "treated", and "treatment" refer to curative uses and results as well as uses and results that diminish or reduce the severity of a particular condition, symptom, disorder, or disease described herein.

As used herein, the terms "therapeutic" and "therapeutically effective amount", whether used alone or in conjunction with another term or terms, denote an amount of a compound, composition or medicament that (a) treats or prevents a particular disease, condition or disorder; (b) attenuates, ameliorates or eliminates one or more symptoms of a particular disease, condition or disorder; (c) prevents or delays the onset of one or more symptoms of a particular disease, condition or disorder described herein. It should be understood that the terms "therapeutic" and "therapeutically effective" encompass any one of the aforementioned effects (a)-(c), either alone or in combination with any of the others (a)-(c).

As used herein, the term "therapeutically active agent", whether used alone or in conjunction with another term or terms, refers to any compound, i.e. a drug, that has been found to be useful in the treatment of a disease or disorder and is not described by Formula I.

The compounds (including final products and intermediates) described herein may be isolated and used per se or may be isolated in the form of a salt. It should be understood that the terms "salt(s)" and "salt form(s)" used by themselves or in conjunction with another term or terms encompasses all inorganic and organic salts, including industrially acceptable salts, as defined herein, and pharmaceutically acceptable salts, as defined herein, unless otherwise specified. As used herein, industrially acceptable salts are salts that are generally suitable for manufacturing and/or processing (including purification) as well as for shipping and storage, but may not be salts that are typically administered for clinical or therapeutic use. Industrially acceptable salts may be prepared on a laboratory scale, i.e. multi-gram or smaller, or on a larger scale, i.e. up to and including a kilogram or more. Pharmaceutically acceptable salts, as used herein, are salts that are generally chemically and/or physically compatible with the other ingredients comprising a formulation, and/or are generally physiologically compatible with the recipient thereof. Pharmaceutically acceptable salts may be prepared on a laboratory scale, i.e. multi-gram or smaller, or on a larger scale, i.e. up to and including a kilogram or more. It should be understood that pharmaceutically acceptable salts are not limited to salts that are typically administered or approved (by a regulatory authority such as FDA) for clinical or therapeutic use in humans. A practitioner of ordinary skill will readily appreciate that some salts are both industrially acceptable as well as pharmaceutically acceptable salts. It should be understood that all such salts, including mixed salt forms, are within the scope of the application.

In general, salts of the present application can be prepared in situ during the isolation and/or purification of a compound (including intermediates), or by separately reacting the compound (or intermediate) with a suitable organic or inorganic acid or base (as appropriate) and isolating the salt thus formed. The degree of ionisation in the salt may vary from completely ionised to almost non-ionised. In practice, the various salts may be precipitated (with or without the addition of one or more co-solvents and/or anti-solvents) and collected by filtration or the salts may be recovered by evaporation of solvent(s). Salts of the present application may also be formed via a "salt switch" or ion exchange/double displacement reaction, i.e. reaction in which one ion is replaced (wholly or in part) with another ion having the same charge. One skilled in the art will appreciate that the salts may be prepared and/or isolated using a single method or a combination of methods.

Representative salts include, but are not limited to, acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate and the like. Other examples of representative salts include alkali or alkaline earth metal cations such as sodium, lithium, potassium, calcium, magnesium, and the like, as well as non-toxic ammonium, quaternary ammonium and amine cations including, but not limited to, ammonium, tetramethylammonium, tetraethylammonium, lysine, arginine, benzathine, choline, tromethamine, diolamine, glycine, meglumine, olamine and the like.

Certain compounds of Formula I may have two or more asymmetric centers and therefore can exist in a number of stereoisomeric configurations. Consequently, such compounds can be synthesized and/or isolated as mixtures of enantiomers and/or as individual (pure) enantiomers, as well as diastereomers and mixtures of different diastereomers. It should be understood that for those compounds of the general Formula I and any subgenera, species and/or specific embodiments that contain one or more stereogenic centers includes all stereoisomers including single enantiomers and diastereomers and mixtures thereof in all ratios.

In practice, resolution and isolation of pure enantiomers can be achieved using methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, the specific stereoisomers may be synthesized by using an optically active starting material, by asymmetric synthesis using optically active reagents, substrates, catalysts or solvents, or by converting one stereoisomer into the other by asymmetric transformation or inversion.

Compounds of Formula I that exist as diastereoisomers may be isolated by methods known to those skilled in the art, for example, by crystallization, gas-liquid or liquid chromatography. Alternatively, intermediates in the course of a synthesis that exist as racemic mixtures may be subjected to resolution by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, specific stereoisomers may be synthesized by asymmetric synthesis using optically active reagents, substrates, catalysts or solvents, or by converting one stereoisomer into the other by asymmetric transformation or inversion.

Compounds of the application may be administered as prodrugs. The term "prodrug" refers to a compound that is transformed in vivo to yield a compound of Formula I. The in vivo transformation may occur by various mechanisms, such as hydrolysis, in the blood or other biological fluids.

A prodrug of a compound of Formula I may be formed in a conventional manner with one or more functional groups in the compound, such as an amino, hydroxyl or carboxyl group. For example, if a compound of Formula I contains a carboxylic acid functional group, a prodrug can comprise: (1) an ester formed by the replacement of a hydrogen of the acid group with a group such as ($C_1$-$C_6$)alkyl or ($C_6$-$C_{10}$) aryl; (2) an activated ester formed by the replacement of the hydrogen of the acid group with groups such as —($CR_2$)COOR', where $CR_2$ is a spacer and R can be groups such as H or methyl and R' can be groups such as ($C_1$-$C_6$)alkyl or ($C_6$-$C_{10}$) aryl; and/or (3) a carbonate formed by the replacement of the hydrogen of the acid with groups such as CHROCOOR' where R can be groups such as H or methyl and R' can be groups such as ($C_1$-$C_6$)alkyl or ($C_6$-$C_{10}$)aryl. Similarly, if a compound of Formula I contains an alcohol functional group, a prodrug can be formed via the replacement of the hydrogen of the alcohol with groups such as ($C_1$-$C_6$)alkanoyloxymethyl or ($C_1$-$C_6$) alkanoyloxyaryl or by forming an ester via condensation with, for example, an amino acid. Where a compound of Formula I contains a primary or secondary amino group, a prodrug may comprise, for example, an amide formed by the replacement of one or both of the hydrogens of the amino group with ($C_1$-$C_{10}$)alkanoyl or ($C_6$-$C_{10}$)aroyl. Other prodrugs of amines are well known to those skilled in the art. Alternatively, certain compounds of Formula I may themselves act as prodrugs of other compounds of Formula I.

Discussions regarding prodrugs and their use can be found in, for example, "Prodrugs as Novel Delivery Systems," T. Higuchi and W. Stella, Vol. 14 of the ACS Symposium Series, and *Bioreversible Carriers in Drug Design*, Pergamon Press, 1987 (ed. E B Roche, American Pharmaceutical Association).

PREPARATIONS AND EXAMPLES

In general, compounds of the general Formula I may be prepared by the methods described in the Schemes, Preparations and Experimental sections of the present application. It should be understood that the methods set forth herein are intended for illustrative purposes and are not to be construed as limiting the scope of the disclosure.

Unless otherwise indicated, the variables shown or referenced in any general Schemes are defined as above or as defined in the Claims.

For example, one method for the preparation of compounds of Formula I involves the reaction of a halo pyridine compound (A) with an aldehyde of the formula $R^1$CHO under conditions resulting in the formation of the imidazopyridine ring system of Formula I. Details of the various reaction conditions are set forth, for example, in the Examples below.

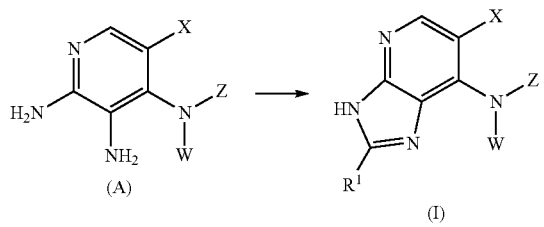

Alternative synthetic routes, reagents, intermediates, starting materials, and methods which are known in the chemical arts can be used or adapted in practice to prepare compounds of Formula I, particularly in light of the scope of the present disclosure in combination with the knowledge of one of ordinary skill in the art. Such alternatives and modifications should be understood as being within the spirit and scope of the present application and the claims.

Utilities

Various compounds of the general Formula I are useful in inhibiting the activity of one or more tyrosine kinases or in inhibiting the downstream events resulting from or mediated by the activation of one or more tyrosine kinases. By inhibiting the activity of more than one tyrosine kinase, various compounds of Formula I can potentially suppress multiple mechanisms underlying disease states such as tumor formation and progression. In one embodiment, various compounds of Formula I are inhibitors of ALK. In another embodiment various compounds of Formula I are inhibitors of JAK2. In a further embodiment various compounds of Formula I are dual inhibitors of ALK and JAK2.

In one embodiment, various compounds of the general Formula I are useful in inhibiting or suppressing uncontrolled cell proliferation, anti-apoptotic signalling, tumor immune evasion, metastasis, angiogenesis, tumorigenesis, and/or tumor growth in mammalian (including human) cancers. Examples of such cancers include: colon cancer, breast cancer, non-small cell lung cancer, neuroblastoma, esophageal squamous carcinoma, hemangioma, head and neck squamous cell carcinoma, prostate cancer, myeloid leukemia, melanoma, glioblastoma, astrocytoma, anaplastic large cell lymphoma, inflammatory myofibroblastic tumor, myeloproliferative neoplasms (MPN) and other solid tumors.

JAK2

Most tumors, in particular solid ones, are characterized by constitutive JAK2 activation. There is a large body of preclinical evidence demonstrating tumor-promoting activities of JAK2 signaling, such as antitumor activity of JAK2 inhibitors in animal models. JAK2 contributes to tumor growth and progression through multiple mechanisms including increased tumor cell proliferation and survival, increased tumor angiogenesis and immune evasion. Not surprisingly, JAK2/STAT activation correlates with more malignant and metastatic phenotype, and is often associated with a refractory and relapsing disease. In contrast, JAK3 activation is not well documented in human tumors, and does not seem to play a critical role in tumorigenesis (except in some hematopoietic tumors). Various studies suggest that JAK3 inhibition offers no obvious additional benefits for antitumor activity of JAK2 inhibitors (Pesu, 2008). Thus, preferential or selective inhibition of JAK2 is a more critical target for antitumor therapies.

JAK3

JAK3 expression is generally limited to hematopoietic cells where it specifically associates with so called common gamma chain ($\gamma_c$ receptor or CD132, a cytokine receptor subunit for IL-2, IL-4, IL-7, IL-15, IL-21 and others. These receptors are critical for proper functioning of immune system and genetic ablation of JAK3 (or gamma receptor) in mice resulted in a severe combined immunodeficiency (SCID). SCID mice have small thymuses, absence of lymph nodes and reduced numbers of thymocytes, CD8+ and NK cells; also, development of B cells is severely impaired. Importantly, mutations in JAK3 and gamma chain in human result in a very similar phenotype and account for most clinical cases of SCID. Thus, inhibition of JAK3 can result in a suppression of immune responses and severe immunodeficiency (Borie, 2003 and O'Shea, 2004). Consequently, JAK3 inhibitors have been developed as a novel class of immunosuppressant to treat transplant rejection and autoimmune diseases. The most advanced inhibitor, CP-690,550, prevented graft rejection in multiple animal models, including in cynomolgus monkey and its activity was associated with decrease in CD8 and NK cells. In Phase I and Phase II clinical studies, CP-690,550 showed clinical efficacy in de novo kidney allograft recipients; however, increased incidence of infections was also observed. By 6 months post-transplant, significantly more patients developed infections and cytomegalovirus disease in a treated group. Additionally, 20% of subjects receiving CP-690,550 at 30 mg BID developed polyoma-associated nephropathy. These observations indicate that JAK3 inhibition results in immunodeficiency, which in cancer patients, can accelerate disease progression and complicate treatments due to additional toxicities. In particular, cancer patients undergoing multiple rounds of various and toxic therapies are often immunocompromised and additional toxicities in this area are highly undesirable.

In view of the above, compounds that preferentially inhibit JAK2 over JAK3 should exhibit antitumor activity while avoiding immunosuppressive effects associated with JAK3 inhibition. The potential immunosuppressant toxicities related to non-preferential JAK2 inhibitors, i.e., dual JAK2/JAK3 inhibitors, might be dose limiting and could decrease the therapeutic window.

JAK/STAT

The JAK/STAT pathway is the major signaling cascade downstream from cytokine and growth factor receptors including growth hormone, prolactin and leptin (Rane et al. 2002; Levy et al. 2002; Baker et al. 2007). The signaling cascade consists of the family of non-receptor tyrosine kinases, Janus kinases (JAK) and transcription factors, STATs (signal transduction and transcription). Activated JAKs phosphorylate and activate STATs, allowing formation of homo- and heterodimers that translocate to the nucleus to regulate the transcription of STAT-dependent genes. In addition, STATs can be directly phosphorylated by non-receptor tyrosine kinases like Src or Abl. Under normal physiological conditions ligand-dependent activation of JAK/STAT signaling is transient and tightly regulated (Alexander 2002; Shuai et al. 2003).

JAK/STAT Signaling in Tumors

Constitutive activation of JAKs and STATs occurs in a wide spectrum of human cancers, both solid and hematopoietic, and is often correlated with a more malignant and metastatic phenotype and refractory tumors (Ferrajoli et al. 2006; Yu et al. 2004). In most tumors JAK2/STAT activation is mediated by constitutive expression of cytokines (IL-6, IL-4, GM-CSF) and/or by inactivation of endogenous repressors of the JAK/STAT pathway, including members of the suppressor of cytokine signaling (SOCS) family or phosphatase SHP-1. In some tumors, activating mutations in JAK1 (Flex et al. 2008), JAK2, JAK3 or JAK2 chimeric molecules are directly implicated in tumorigenesis. In addition, amplification of the JAK2 locus occurred in 35% of Hodgkin's lymphoma (HL) and 50% of primary mediastinal B-cell lymphoma (PMBL) cases (Melzner et al. 2005). Among hematological cancers, ABC-DLBCL accounts for the majority of non-Hodgkin's lymphoma (NHL) mortality with these tumors expressing high levels of activated STAT3 and showing resistance to conventional cytotoxic therapies. ABC-DLBCL cells are dependent on JAK2/STAT signaling and the inactivation of STAT3 by siRNA or small molecule JAK2 inhibition suppressed proliferation and induced apoptosis in these tumor cell lines (Ding et al. 2008).

The ectopic expression of JAK1, JAK2 and JAK3, as well as STAT3 and STAT5 results in oncogenic transformation in recipient cells, demonstrating that the activated JAK2/STAT pathway was sufficient to mediate oncogenesis in various solid and hematological tumors (Bromberg et al. 1999; Knoops et al. 2008; Scheeren et al. 2008). Inhibition of JAK2/STAT signaling in various tumor cells, including prostate, breast, colon, lung carcinomas, gliomas, and leukemias and lymphomas resulted in inhibition of growth, induction of apoptosis and suppression of tumor growth in vivo (Yu et al. 2004; Li et al. 2004; Iwamaru et al. 2007; Gao et al. 2007; Ding et al. 2008). Constitutively activated JAK2/STAT signaling in tumor cells not only promoted uncontrolled cell proliferation and anti-apoptotic signaling, but also mediated tumor immune evasion and angiogenesis (Kortylewski et al. 2005; Nefedova et al. 2007). Therefore, inhibitors of JAK/STAT signaling offer the potential to suppress multiple mechanisms underlying tumor formation and progression.

Molecular Mechanisms: JAK/STAT-Mediated Tumor Cell Survival

Activation of the JAK2/STAT pathway mediates increased survival of tumor cells by up regulating expression of multiple antiapoptotic proteins, including Bcl-2, Bcl-$X_L$, Mcl-1, survivin and others (Yu et al. 2004). Increased anti-apoptotic signaling protects tumor cells from therapy-induced cell death, a major factor contributing to drug resistance. In many tumor models inhibitors of JAK2/STAT signaling suppressed expression of anti-apoptotic proteins, decreased the apoptotic threshold and induced chemo-sensitization. Administration of non-selective JAK inhibitors like AG490 chemosensitized various tumor cell lines to multiple targeting drugs including cisplatin, fludarabine, adriamycin and doxorubicin (Alas et al. 2003). Constitutive JAK2 activation is often triggered by cytokines expressed in para- or auto-crine fashion. Elevated tumor and circulating cytokine levels are frequently detected in cancer patients and are associated with increased metastasis, drug resistance and disease relapse. High levels of IL-6 were found in 50% of patients with breast, pancreatic and lung carcinomas, HNSCC and various lymphomas (Grivennikov et al. 2008).

Acquired drug resistance can be mediated by a cytokine-driven adaptive activation of the JAK2/STAT pathway and could be overcome by the administration of JAK2 inhibitors (Wang et al. 2008), providing additional support for the role of activated JAK2/STAT signaling in cell survival and drug resistance in a variety of tumors.

Molecular Mechanisms: JAK/STAT-Mediated Tumor Immune Evasion

Constitutive activation of the JAK2/STAT pathway in tumor cells suppresses tumor immunosurveillance and dendritic cell (DC) maturation and promotes proliferation of T regulatory cells. Abnormal differentiation and accumulation of DCs in the tumor environment is the major contributor to immune evasion and is mediated by tumor-derived cytokines whose expression is driven by constitutive JAK2/STAT signaling (Nefedova et al. 2007). Pharmacological inhibition of JAK2 by JCI-124 overcame DC maturation block and promoted anti-tumor immune responses in cell culture and animal models (Nefedova et al. 2005). In this context, JAK2 inhibitors could be used against multiple tumors as immunostimulants in a maintenance phase of therapy. Immunosuppression mediated by IL-6-driven JAK2/STAT signaling in DCs could be reversed by inhibition of JAK2 activation (Bharaduwaj et al. 2007).

Constitutive Activation of JAK2/STAT Signaling: Inactivation of Endogenous Repressors:

Activation of the JAK/STAT pathway in normal cells is transient and is negatively regulated by endogenous suppressors, members of the SOCS family and phosphatases, which can directly inhibit activity of JAKs. In addition, SOCS proteins facilitate proteosomal degradation of activated JAKs. In tumors, SOCS proteins and/or phosphatase SHP-1 are frequently inactivated by promoter methylation or specific deletions (Yoshikava et al. 2001; Weber at al. 2005; Melzner et al. 2006; Weniger et al. 2006).

Clinical Implications:

The widespread inactivation of endogenous suppressors of JAK2/STAT signaling indicates a genetically-driven selective pressure suggesting that constitutive activation of the JAK2/STAT pathway is critical for growth/survival advantage of tumor cells. A frequent inactivation of endogenous repressors of the JAK2/STAT pathway combined with high levels of cytokines present in multiple tumors provides a molecular rationale for the constitutive activation of JAK2/STAT signaling observed in numerous human tumors. Tumors with constitutive JAK2 signaling can readily be identified via their JAK2 mutational status, STAT activation (pSTAT levels) or promoter methylation profiles using conventional diagnostic techniques. Such information can be used to try to determine which tumors may be sensitive to small molecule JAK2 inhibitors.

ALK

While the physiological role of ALK receptor has not been well defined, involvement of ALK in the oncogenesis of various human cancers has been well documented and characterized. For example, approximately sixty percent of anaplastic large cell lymphomas (ALCL) are associated with a chromosome mutation that generates a fusion protein consisting of nucleophosmin (NMP) and the intracellular domain of ALK. (Armitage, J. O. et al., *Cancer: Principle and Practice of Oncology*, 6$^{th}$ edition, 2001, 2256-2316; Kutok J. L. & Aster J. C., *J. Clin. Oncol.*, 2002, 20, 3691-3702). This mutant protein, NMP-ALK, possesses a constitutively active tyrosine kinase domain that is responsible for its oncogenic property through activation of downstream effectors. (Falini, B. et al., *Blood*, 1999, 94, 3509-3515; Morris, S. W. et al., *Brit. J. Haematol.*, 2001, 113, 275-295; Duyster et al.; Kutok & Aster). Experimental data have demonstrated that the aberrant expression of constitutively active ALK is directly implicated in the pathogenesis of ALCL and that inhibition of ALK can markedly impair the growth of ALK+ lymphoma cells (Kuefer, Mu et al. *Blood*, 1997, 90, 2901-2910; Bai, R. Y. et al., *Mol. Cell Biol.*, 1998, 18, 6951-6961; Bai, R. Y. et al., *Blood*, 2000, 96, 4319-4327; Ergin, M. et al., *Exp. Hematol.*, 2001, 29, 1082-1090; Slupianek, A. et al., *Cancer Res.*, 2001, 61, 2194-2199; Turturro, F. et al., *Clin. Cancer Res.*, 2002, 8, 240-245). The constitutively activated chimeric ALK has also been demonstrated in about 60% of inflammatory myofibroblastic tumors (IMTs), a slow-growing sarcoma that mainly affects children and young adults. (Lawrence, B. et al., *Am. J. Pathol.*, 2000, 157, 377-384; Duyster et al.). Other ALK fusion genes resulting in the generation of oncogenic ALK fusion proteins with constitutive phosphorylation/activation of ALK have been detected in diffuse large B-cell lymphoma (DLBCL), systemic histiocytosis, and most notably, in non-small cell lung cancer (NSCLC). (Palmer, R. H. et al., *Biochem. J.*, 2009, 420(3), 345-361; Chiarle, R. et al., *Nat. Rev. Cancer*, 2008, 8(1), 11-23; Mano, H., *Cancer Sci*, 2008, 99(12), 2349-2355).

ALK and its putative ligand, pleiotrophin, are also overexpressed in human glioblastomas (Stoica, G. et al., *J. Biol. Chem.*, 2001, 276, 16772-16779). In mouse studies, depletion of ALK reduced glioblastoma tumor growth and prolonged animal survival (Powers, C. et al., *J. Biol. Chem.*, 2002, 277, 14153-14158; Mentlein, R. et al, *J. Neurochem.*, 2002, 83, 747-753).

Besides NPM-ALK, various other ALK fusion genes were subsequently detected in ALCL, inflammatory myofibroblastic tumor (IMT), diffuse large B-cell lymphoma (DLBCL), systemic histiocytosis, and most notably, in non-small cell lung cancer (NSCLC), resulting in the generation of oncogenic ALK fusion proteins with constitutive phosphorylation/activation of ALK, which plays causative role in tumorgenesis by aberrant phosphorylation of intracellular downstream substrates (Webb, T. R. et al., Expert Rev. Anti-cancer Ther., 2009, 9, 331-356; Palmer, R. H. et al., Biochem. J., 2009, 420, 345-361; Chiarle, R. et al., Nature Rev. Cancer, 2008, 8, 11-23; Mano H., Cancer Sci., 2008, 99, 2349-2355). In NSCLC, at least seven isoforms of an oncogenic fusion gene comprised of portions of the echinoderm microtubule-associated protein-like 4 (EML4) gene and ALK gene were identified in about 3-15% patients examined (Soda, M. et al., Nature, 2007, 448, 561-566; Choi Y. L. et al., Cancer Res., 2008, 68, 4971-4976; Takeuchi, K. et al., Clin. Cancer Res., 2009, 15, 3143-3149). Experimental data indicate that inhibition of ALK could markedly impair the growth of ALK-positive lymphoma and lung cancer cells in vitro and in vivo, indicating that ALK-positive ALCL and NSCLC cells displayed "ALK oncogene addiction" (Piva, R. et al., Blood, 2006, 107, 689-697; Wan, W. et al., 2006; Galkin, A. V. et al., Proc. Natl. Acad. Sci. USA, 2007, 104, 270-275; Christensen, J. G. et al., Mol. Cancer. Ther., 2007, 6, 3389-3395; Soda, M. et al., Proc. Natl. Acad. Sci. USA, 2008, 105, 19893-19897; Koivunen, J. P. et al., Clin. Cancer Res., 2008, 14, 4275-4283). Recently, it has also been reported that germline mutations in ALK are the cause of most hereditary neuroblastoma cases, and ALK activation by mutation and/or gene amplification is functionally relevant in high-risk sporadic neuroblastoma (Mosse, Y. P. et al., Nature, 2008, 455, 930-936; Chen, Y. et al., Nature, 2008, 455, 971-974; George, R. E. et al., Nature, 2008, 455, 975-978; Janoueix-Lerosey, I. et al., Nature, 2008, 455, 967-970; McDermott, U. et al., Cancer Res., 2008, 68, 3389-3395; Passoni, L. et al., Cancer Res., 2009, 69, 7338-7346). Attenuation and inhibition of ALK activating mutants or wild type (WT) receptor resulted in profound growth inhibition in human neuroblastoma cell lines (Mosse, Y. P. et al., Nature, 2008, 455, 930-936; Chen, Y. et al., Nature, 2008, 455, 971-974; George, R. E. et al., Nature, 2008, 455, 975-978; Janoueix-Lerosey, I. et al., Nature, 2008, 455, 967-970; McDermott, U. et al., Cancer Res., 2008, 68, 3389-3395; Passoni, L. et al., Cancer Res., 2009, 69, 7338-7346), indicating that the ALK receptor, either the activating mutants or overexpressed WT form, is a critical player in neuroblastoma development. Altogether, these findings indicate that ALK is a major therapeutic target for human cancers and inhibition of ALK with a small molecule ALK inhibitor would offer a potentially more effective and less toxic therapy for patients with ALK-positive tumors than conventional chemotherapy.

Human cancers are notoriously heterogeneous, even in so-called "oncogene addicted" tumors, since some cancer cells likely contain additional oncogenic event(s) or redundant active signaling pathways which may render the cancer cells less dependent on the primary oncogene for growth and survival (Hanahan, D. and Weinberg, R. A., Cell, 2000, 100, 57-70). As such, concomitant inhibition of the secondary oncogenic event(s) in those cancer cells would likely lead to increase the efficacy of treatment with a kinase inhibitor, either by combination therapy or developing a small molecule inhibitor against both the primary and secondary targets.

On the other hand, although kinase inhibitors have been extremely effective in specific patient populations with tumors containing mutated, oncogenic forms of protein tyrosine kinases (PTK), clinical studies thus far have shown that some patients eventually develop resistance to these drugs, either due to the selection of cancer cells with mutations in the targeted PTK or the induction of compensatory oncogenic signaling pathways (Shah, N. P. and Sawyers, C. L., Oncogene, 2003, 22, 7389-7395; Engelman, J. A. and Settleman, J., Curr. Opin. Genet. Develop., 2008, 18, 1-7; Liu, J. et al., Leukemia, 2008, 22, 791-799; Desai, J. et al., Clin. Cancer Res., 2007, 13, 5398-5405; Engelman, J. A. and Janne, P. A., Clin. Cancer Res., 2008, 14, 2895-2899). In that regard, a kinase inhibitor simultaneously inhibiting two or more critical, non-redundant signaling pathways may prevent or decrease the incidence of resistant tumors.

Assays and Model Systems and Methods

The compounds described herein were tested for their ability to inhibit the activity of a number of different kinases as described below. In general, the compounds of Formula I were found to effectively inhibit the activity of at least one or more of the kinases tested.

In one aspect, various compounds of the general Formula I may inhibit one of the kinases tested. Such compounds may be referred to as selectively inhibiting or preferentially inhibiting a particular kinase. For example, in one embodiment particular compounds of the general Formula I may selectively or preferentially inhibit ALK. In another embodiment, particular compounds of the general Formula I may selectively or preferentially inhibit JAK2.

In another aspect, various compounds of the general Formula I may inhibit two of the kinases tested. Such compounds may be referred to as dual inhibitors. For example, in one embodiment particular compounds of the general Formula I may inhibit both JAK2 and ALK to some degree. In another embodiment, particular compounds of the general Formula I may inhibit both JAK2 and ALK to substantially the same degree. Such compounds may be referred to as being substantially equipotent inhibitors of JAK2 and ALK.

In another aspect, various compounds of the general Formula I may inhibit either ALK or JAK2 in addition to at least one other kinase to some degree. In one embodiment, particular compounds of the general Formula I, may be selective or preferential inhibitors of either ALK or JAK2 in addition to at least one other kinase.

In yet another aspect, particular compounds of the general Formula I may inhibit both ALK or JAK2 in addition to inhibiting at least one other kinase to some degree. In one embodiment, particular compounds of the general Formula I may be substantially equipotent inhibitors of both ALK and JAK2 and also inhibit at least one other kinase.

In Vitro Assays:

JAK2 Kinase:

Compounds were tested for their ability to inhibit the kinase activity of baculovirus-expressed JAK2 kinase using the time-resolved fluorescence (TRF) detection system. The assays were run in 96-well Costar high binding plates (Corning Costar Cat#3922, Corning, N.Y.). The plates were coated with 100 μL/well of 10 μg/mL Neutravidin (Pierce #31000, Rockford, Ill.) in TBS at 37° C. for 2 h, followed by 100 μL/well of 1 μg/mL 15-mer peptide substrate (biotinyl-amino-hexanoyl-EQEDEPEGDYFEWLE-amide, Infinity Biotech Research and Resource, Aston, Pa.) at 37° C. for 1 h. The JAK2 kinase assay mixture (total volume=100 μL/well) consisting of 20 mM HEPES (pH 7.2), 0.2 μM ATP, 1 mM $MnCl_2$, 0.1% BSA, and test compound (diluted in DMSO; 2.5% DMSO final in assay) was added to the assay plate. Enzyme (15 ng/mL JAK2) was added and the reaction was allowed to proceed at room temperature for 20 min. Detection of the phosphorylated product was performed by adding 100 μL/well of Eu-N1 labeled PY100 antibody diluted 1:5000 or 1:10000 in 0.25% BSA in TBS-T (PerkinElmer #AD0041). Samples were incubated at room temperature for 1 h, followed by addition of 100 μL enhancement solution (PerkinElmer #1244-105). Plates were agitated for 10 min and the fluorescence of the resulting solution measured using the PerkinElmer EnVision® 2102 or 2104 multi-label plate reader. Inhibition data were analyzed using ActivityBase (IDBS, Guilford, UK). $IC_{50}$ values were calculated by plotting percent inhibition versus $log_{10}$ of the concentration of compound and fitting to the nonlinear regression sigmoidal dose-response (variable slope) equation in XLFit (IDBS, Guilford, UK).

ALK Kinase:

Example compounds were tested for their ability to inhibit the kinase activity of baculovirus-expressed ALK using a modification of the ELISA protocol reported for trkA in Angeles, T. S. et al., *Anal. Biochem.* 1996, 236, 49-55, which is incorporated herein by reference in its entirety. Phosphorylation of the substrate, phospholipase C-gamma (PLC-γ) generated as a fusion protein with glutathione S-transferase (GST) as reported in Rotin, D. et al., *EMBO J.* 1992, 11, 559-567, which is incorporated herein by reference in its entirety, was detected with a europium-labeled anti-phosphotyrosine antibody and measured by time-resolved fluorescence (TRF). Briefly, each 96-well plate was coated with 100 μL/well of 10 μg/mL substrate (GST-PLC-γ) in Tris-buffered saline (TBS). The assay mixture (total volume=100 μL/well) consisting of 20 mM HEPES, pH 7.2, 1 μM ATP ($K_m$ level), 5 mM $MnCl_2$, 0.1% BSA, 2.5% DMSO, and various concentrations of test compound was then added to the assay plate. The reaction was initiated by adding enzyme (30 ng/mL ALK) and was allowed to proceed at 37° C. for 15 minutes. Detection of the phosphorylated product was performed by adding 100 μL/well of Eu-N1 labeled PT66 antibody (Perkin Elmer #AD0041). Incubation at 37° C. then proceeded for 1 hour, followed by addition of 100 μL enhancement solution (Wallac #1244-105). The plate was gently agitated and after thirty minutes, the fluorescence of the resulting solution was measured using the PerkinElmer EnVision™ 2102 (or 2104) multilabel plate reader.

Data analysis was performed using ActivityBase (IDBS, Guilford, UK). $IC_{50}$ values were calculated by plotting percent inhibition versus $log_{10}$ of the concentration of compound and fitting to the nonlinear regression sigmoidal dose-response (variable slope) equation in XLFit (IDBS, Guilford, UK).

The compounds described herein were tested according to procedures described above. The results of these tests are set forth below in Table 1. Unless otherwise noted, $IC_{50}$ nm values are designed as follows:

<100 nM = ++++
100-1000 nM = +++
1000-10,000 nM = ++
>10,000 nM = +

| Example | ALK Potency | JAK2 Potency |
|---|---|---|
| I | ++++ | ++++ |
| III | ++++ | ++++ |
| IV | ++++ | ++++ |
| V | +++ | ++++ |
| VI | +++ | ++++ |
| VII | ++++ | ++++ |
| VIII | +++ | ++++ |
| IX | ++++ | ++++ |
| X | ++++ | ++++ |
| XI | + | + |
| XII | +++ | ++++ |
| XIII | + | + |
| XIV | + | + |
| XV | ++++ | ++++ |
| XVI | ++++ | ++++ |
| XVII | ++++ | ++++ |
| XVIII | ++++ | +++ |
| XIX | ++++ | ++++ |
| XX | ++++ | ++++ |
| XXI | ++++ | ++++ |
| XXII | ++++ | ++++ |
| XXIII | ++++ | ++++ |
| XXIV | + | +++ |
| XXV | + | +++ |
| XXVI | ++ | ++++ |
| XXVII | +++ | +++ |
| XXVIII | +++ | +++ |
| XXIX | + | ++ |
| XXX | ++ | +++ |
| XXXI | ++ | +++ |
| XXXII | ++ | ++ |
| XXXIII | +++ | +++ |
| XXXIV | ++ | + |
| XXXV | +++ | +++ |
| XXXVI | + | ++ |
| XXXVII | + | ++ |
| XXXVIII | ++++ | ++++ |
| XXXIX | + | + |
| XL | ++++ | ++++ |
| XLI | ++++ | ++++ |
| XLII | ++++ | +++ |
| XLIII | ++++ | ++++ |
| XLIV | ++++ | ++++ |
| XLV | ++++ | ++++ |
| XLVI | ++++ | ++++ |
| XLVII | ++++ | ++++ |
| XLVIII | ++++ | ++++ |
| XLIX | ++++ | +++ |
| L | +++ | ++++ |
| LI | ++++ | ++++ |
| LII | ++++ | +++ |
| LIII | ++++ | ++++ |
| LIV | ++++ | ++++ |
| LV | ++++ | ++++ |
| LVI | ++++ | ++++ |
| LVII | ++++ | ++++ |
| LVIII | ++++ | ++++ |
| LIX | ++++ | ++++ |
| LX | ++++ | ++++ |
| LXI | +++ | ++++ |
| LXII | ++++ | ++++ |
| LXIII | ++++ | ++++ |
| LXIV | ++++ | ++++ |
| LXV | ++++ | ++++ |
| LXVI | +++ | ++++ |
| LXVII | +++ | ++++ |
| LXVIII | +++ | ++++ |
| LXIX | ++++ | ++++ |
| LXX | ++++ | ++ |
| LXXI | ++++ | ++ |
| LXXI | ++++ | ++ |
| LXXII | ++++ | + |
| LXXIV | +++ | + |

| | <100 nM = ++++ 100-1000 nM = +++ 1000-10,000 nM = ++ >10,000 nM = + | |
|---|---|---|
| Example | ALK Potency | JAK2 Potency |
| LXXV | ++++ | ++ |
| LXXVI | ++++ | ++++ |
| LXXVII | ++++ | ++++ |
| LXXVIII | ++++ | ++++ |
| LXXIX | ++++ | ++++ |
| LXXX | ++++ | ++++ |
| LXXXI | ++++ | ++++ |
| LXXXII | +++ | +++ |
| LXXXIII | ++++ | ++++ |
| LXXXIV | ++++ | ++++ |
| LXXXV | +++ | ++++ |
| LXXXVI | + | ++ |
| LXXXVII | + | ++ |
| LXXXVIII | ++ | ++ |
| LXXXIX | + | ++ |
| XC | + | ++ |
| XCI | + | ++ |
| XCII | + | ++ |
| XCIII | + | + |
| XCIV | + | ++ |
| XCV | ++ | ++ |
| XCVI | ++++ | ++++ |
| XCVII | ++++ | ++++ |
| XCVIII | ++++ | ++++ |
| XCIX | +++ | + |
| C | ++++ | ++++ |
| CI | ++++ | ++++ |
| CII | ++ | ++ |
| CIII | ++++ | +++ |
| CIV | ++ | +++ |
| CV | ++ | ++ |
| CVI | ++ | ++ |
| CVII | +++ | ++++ |
| CVIII | +++ | ++++ |
| CIX | ++++ | ++++ |
| CX | +++ | ++++ |
| CXI | ++++ | ++++ |
| CXII | ++++ | ++++ |
| CXIII | ++++ | ++++ |
| CXIV | ++++ | ++++ |
| CXV | ++++ | ++++ |
| CXVI | ++++ | ++++ |
| CXVII | ++++ | ++++ |
| CXVIII | ++++ | ++++ |
| CXIX | ++++ | ++++ |
| CXX | ++++ | ++++ |
| CXXI | +++ | ++++ |
| CXXII | ++ | ++ |
| CXXIII | ++++ | +++ |
| CXXIV | ++++ | ++++ |
| CXXV | ++ | ++++ |
| CXXVI | +++ | ++++ |
| CXXVII | +++ | ++++ |
| CXXVIII | +++ | ++++ |
| CXXIX | +++ | ++++ |
| CXXX | ++++ | ++++ |
| CXXXI | ++++ | ++++ |
| CXXXII | +++ | ++++ |
| CXXXIII | +++ | ++++ |
| CXXXIV | ++++ | ++++ |
| CXXXV | +++ | ++++ |
| CXXXVI | +++ | ++++ |
| CXXXVII | +++ | ++++ |
| CXXXVIII | +++ | ++++ |
| CXXXIX | ++ | ++++ |
| CXL | +++ | ++++ |
| CXLI | +++ | ++++ |
| CXLII | +++ | ++++ |
| CXLIII | +++ | ++++ |
| CXLIV | +++ | ++++ |
| CXLV | +++ | ++++ |
| CXLVI | +++ | ++++ |
| CXLVII | +++ | ++++ |
| CXLVIII | +++ | ++++ |
| CXLIX | +++ | ++++ |
| CL | ++ | + |
| CLI | ++++ | ++++ |
| CLII | ++++ | ++++ |
| CLIV | ++++ | ++++ |
| CLV | ++++ | ++++ |
| CLVI | ++++ | ++++ |
| CLVII | ++++ | ++++ |
| CLX | ++++ | ++++ |
| CLXI | ++++ | ++++ |
| CLXII | ++++ | ++++ |
| CLXIII | ++++ | + |
| CLXIV | ++++ | ++++ |
| CLXV | +++ | ++ |
| CLXVI | ++++ | ++++ |
| CLXVII | ++++ | ++++ |
| CLXVIII | ++++ | ++++ |
| CLXIX | +++ | ++ |
| CLXX | ++++ | ++++ |
| CLXXI | ++++ | ++++ |
| CLXXII | ++++ | +++ |
| CLXXIII | ++++ | +++ |
| CLXXIV | ++++ | +++ |
| CLXXV | ++++ | +++ |
| CLXXVII | +++ | ++++ |
| CLXXVIII | ++++ | ++++ |
| CLXXIX | +++ | +++ |
| CLXXX | +++ | +++ |
| CLXXXI | ++++ | ++++ |
| CLXXXII | ++++ | ++++ |
| CLXXXIII | ++++ | +++ |
| CLXXXIV | ++++ | +++ |
| CLXXXV | ++++ | ++++ |
| CLXXXVI | +++ | ++++ |
| CLXXXVII | +++ | +++ |
| CLXXXVIII | ++ | ++ |
| CLXXXIX | +++ | ++++ |
| CXC | ++++ | ++++ |
| CXCI | ++++ | ++ |
| CXCII | +++ | + |
| CXCIII | ++++ | +++ |
| CXCIV | ++++ | ++++ |
| CXCV | ++++ | ++ |
| CXCVI | ++++ | + |
| CXCVII | ++++ | +++ |
| CXCVIII | + | ++++ |
| CXCIX | ++ | ++++ |
| CC | +++ | +++ |
| CCI | + | ++++ |
| CCII | + | ++++ |
| CCIII | +++ | +++ |
| CCIV | ++ | ++++ |
| CCV | + | +++ |
| CCVI | +++ | ++ |
| CCVII | +++ | ++++ |
| CCVIII | +++ | ++++ |
| CCIX | +++ | ++++ |
| CCX | ++++ | ++++ |
| CCXI | ++++ | ++++ |
| CCXII | ++++ | ++++ |
| CCXIII | +++ | ++++ |
| CCXIV | +++ | +++ |
| CCXV | ++ | ++ |
| CCXVII | ++ | ++++ |
| CCXVIII | +++ | ++++ |
| CCXIX | ++++ | ++++ |
| CCXX | ++++ | ++++ |
| CCXXI | +++ | ++++ |

41
-continued

|  |  |  |
|---|---|---|
| <100 nM = ++++ | | |
| 100-1000 nM = +++ | | |
| 1000-10,000 nM = ++ | | |
| >10,000 nM = + | | |

| Example | ALK Potency | JAK2 Potency |
|---|---|---|
| CCXXII | ++++ | ++++ |
| CCXXIII | +++ | ++++ |
| CCXXIV | ++++ | ++++ |
| CCXXV | +++ | ++++ |
| CCXXVI | ++++ | ++++ |
| CCXXVII | ++ | ++++ |
| CCXXVIII | +++ | ++++ |
| CCXXIX | ++ | ++++ |
| CCXXX | +++ | ++++ |
| CCXXXI | ++++ | ++++ |
| CCXXXII | ++++ | ++++ |
| CCXXXIII | +++ | ++++ |
| CCXXXIV | +++ | ++++ |
| CCXXXVII | ++++ | ++++ |
| CCXXXVII | ++++ | +++ |
| CCXXXVIII | +++ | ++++ |
| CCXXXIX | ++++ | ++++ |
| CCXL | +++ | ++++ |
| CCXLI | +++ | ++++ |
| CCXLII | ++++ | ++++ |
| CCXLIII | ++++ | ++++ |
| CCXLIV | ++++ | ++++ |
| CCXLV | ++++ | ++++ |
| CCXLVI | +++ | ++++ |
| CCXLVII | ++++ | ++++ |
| CCXLVIII | ++++ | ++++ |
| CCXLIX | ++++ | ++++ |
| CCL | ++++ | ++++ |
| CCLI | ++++ | ++++ |
| CCLII | ++++ | ++++ |
| CCLIII | ++++ | ++ |
| CCLIV | ++++ | ++++ |
| CCLXIII | +++ | ++++ |
| CCLXIV | ++++ | ++++ |

PREPARATIVE EXAMPLES

The compounds described below or in Table 1 above are non-limiting examples of compounds encompassed by the general Formula I that were prepared and characterized according to one or more of the procedures outlined below or generally described herein. The preparation of various intermediates and starting materials are also described below or are generally described herein.

$^1$H NMR (Nuclear Magnetic Resonance) spectra were in all cases consistent with the proposed structures. Characteristic chemical shifts (δ) are given in parts per million (ppm) using conventional abbreviations for the designation of major peaks: s=singlet, d=doublet, t=triplet, m=multiplet, dd=doublet of doublets, ddd=doublet of doublet of doublets, q=quartet, b=broad.

Final compounds and intermediates were also characterized by one or more of the following: $^1$H NMR, HPLC retention times, mass spectrometry (MS) and reported as (MH)+, i.e. the molecular ion plus hydrogen, and/or melting point ranges.

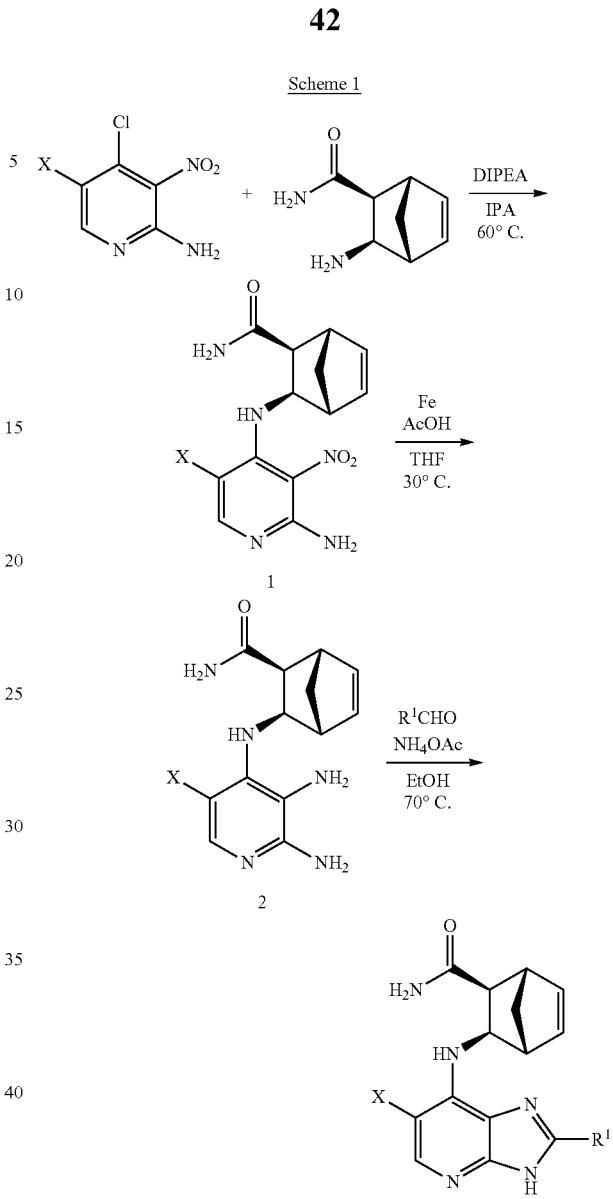

Scheme 1

Synthesis of (1S,2S,3R,4R)-3-(2-Amino-5-chloro-3-nitro-pyridin-4-ylamino)-bicyclo[2.2.1]hept-5-ene-2-carboxylic acid amide (Compound 1—X=Cl)

4,5-Dichloro-3-nitro-pyridin-2-ylamine (1.01 g, 4.86 mmol) and (1S,2S,3R,4R)-3-Amino-bicyclo[2.2.1]hept-5-ene-2-carboxylic acid amide trifluoroacetic acid salt (1.5 g, 5.5 mmol) were combined with N,N-diisopropylethylamine (3.3 g, 26 mmol) in isopropanol (15 mL) and heated at 60° C. overnight. The reaction was permitted to cool to room temperature and the orange solid which had formed was isolated by filtration. The solid was washed with 3 mL cold isopropanol and was dried in an air stream to afford 1.493 g (95%) of the desired product.

$^1$H NMR (d-chloroform): 7.82 (br s, 1H), 6.54 (br s, 2H), 6.29 (m, 1H), 6.23 (m, 1H), 5.71 (br s, 1H), 5.47 (br s, 1H), 4.30 (m, 1H), 3.09 (s, 1H), 2.80 (s, 1H), 2.56 (d, J=7 Hz, 1H), 2.44 (d, J=10 Hz, 1H), 1.71 (d, J=9 Hz, 1H). MS: 323.94 (M+H). HPLC retention time: 1.75 minutes (G Method).

Syntheses of Compound 1 where X=Br, H were effected similarly.

Synthesis of (1S,2S,3R,4R)-3-(2,3-Diamino-5-chloro-pyridin-4-ylamino)-bicyclo[2.2.1]hept-5-ene-2-carboxylic acid amide (Compound 2—X=Cl)

(1S,2S,3R,4R)-3-(2-Amino-5-chloro-3-nitro-pyridin-4-ylamino)-bicyclo[2.2.1]hept-5-ene-2-carboxylic acid amide (100 mg, 0.3 mmol) was dissolved in a mixture of tetrahydrofuran (1 mL) and acetic acid (1.6 mL). Powdered iron (121 mg, 2.162 mmol) was added and the mixture was stirred at 30° C. for four hours. Two drops of water was added and suspended solids were removed by filtration. The solid was washed with ethyl acetate (5 mL) and the combined filtrates were portioned between ethyl acetate and saturated sodium bicarbonate solution. The organics were extracted with ethyl acetate (3×25 mL), were dried (sodium sulfate) and were concentrated. Purification was effected via ISCO chromatography (12 g silica cartridge: gradient elution—0 to 15% MeOH:DCM) to afford 77 mg (80%) of the title compound as a tan solid. $^1$H NMR (d-chloroform): 7.49 (s, 1H), 6.18-6.20 (m, 4H), 6.09 (m, 1H), 4.51 (d, J=11 Hz, 1H), 4.09 (br s, 2H), 3.79 (d, J=9 Hz, 1H), 2.97 (s, 1H), 2.64 (s, 1H), 2.53 (d, J=8 Hz, 1H), 2.32 (d, J=9 Hz, 1H), 2.06 (s, 1H), 1.66 (d, J=9 Hz, 1H). MS: 294.99 (M+H). HPLC retention time: 1.62 minutes (G Method).

Synthesis of Compound 2 where X=Br, H were effected similarly.

Compound I

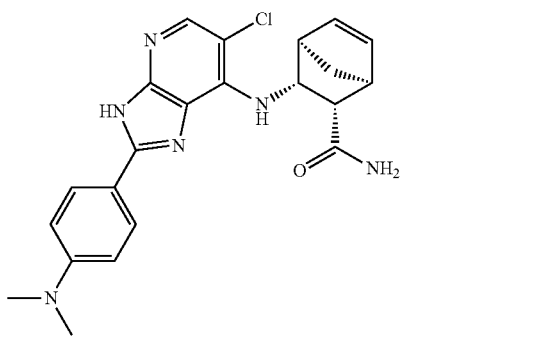

Synthesis of (1S,2S,3R,4R)-3-[6-Chloro-2-(4-dimethylamino-phenyl)-3H-imidazo[4,5-b]pyridin-7-ylamino]-bicyclo[2.2.1]hept-5-ene-2-carboxylic acid amide (Compound I)

(1S,2S,3R,4R)-3-(2,3-Diamino-5-chloro-pyridin-4-ylamino)-bicyclo[2.2.1]hept-5-ene-2-carboxylic acid amide (77 mg, 0.26 mmol) and 4-(dimethylamino)benzaldehyde (54 mg, 0.36 mmol) were combined and heated in 8 mL nitrobenzene at 140° C. for six hours. The reaction was concentrated and purified by reverse phase chromatography on a Gilson chromatograph to afford 16 mg (14%) of the title compound. $^1$H NMR (d-chloroform): 13.55 (br s, 1H), 7.99 (m, 3H), 6.84 (m, 2H), 6.62 (br s, 1H), 6.36 (m, 2H), 5.45 (d, J=9 Hz, 1H), 5.37 (s, 1H), 5.21 (t, J=9 Hz, 1H), 3.19 (s, 1H), 3.11 (s, 6H), 2.92 (m, 2H), 2.35 (d, J=9 Hz, 1H), 1.76 (d, J=9 Hz, 1H). MS: 424.05 (M+H). HPLC retention time: 2.39 minutes (G Method).

Compound III

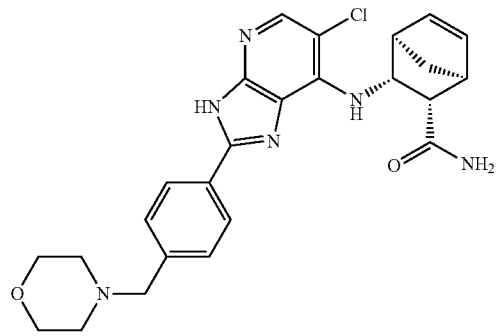

Synthesis of (1S,2S,3R,4R)-3-[6-Chloro-2-(4-morpholin-4-ylmethyl-phenyl)-3H-imidazo[4,5-b]pyridine-7-ylamino]-bicyclo[2.2.1]hept-5-ene-2-carboxylic acid amide-trifluoroacetate salt (Compound III)

(1S,2S,3R,4R)-3-(2,3-Diamino-5-chloro-pyridin-4-ylamino)-bicyclo[2.2.1]hept-5-ene-2-carboxylic acid amide (16 mg, 0.054 mmol) and 4-morpholin-4-ylmethylbenzaldehyde (12 mg, 0.058 mmol) were dissolved in ethanol (2.0 mL) and treated with ammonium acetate (5.2 mg, 0.068 mmol). The reaction was heated to 70° C. overnight. The reaction was concentrated and the organics were partitioned between dichloromethane and saturated sodium bicarbonate solution (50 mL each). Concentration followed by reverse phase chromatography on a Gilson chromatograph afforded desired fractions which were subjected to lyophilization to afford 16 mg (63%) of the title compound. $^1$H NMR (d-chloroform): 16.18 (br s, 1H), 8.78 (d, J=8 Hz, 1H), 8.20 (s, 1H), 8.17 (s, 1H), 7.84 (s, 1H), 7.65 (s, 1H), 7.62 (s, 1H), 6.51 (m, 1H), 6.45 (m, 1H), 5.85 (br s, 1H), 5.56 (br s, 1H), 5.36 (t, J=8 Hz, 1H), 4.26 (m, 2H), 4.00 (t, J=5 Hz, 4H), 3.40 (m, 2H), 3.18 (s, 1H), 3.04 (s, 1H), 2.96 (m, 2H), 2.67 (d, J=8 Hz, 1H), 2.32 (d, J=9 Hz, 1H), 2.75 (m, 1H), 1.68 (d, J=9 Hz, 1H). MS: 480.03 (M+H). HPLC retention time: 1.79 minutes (G Method).

Compound IV

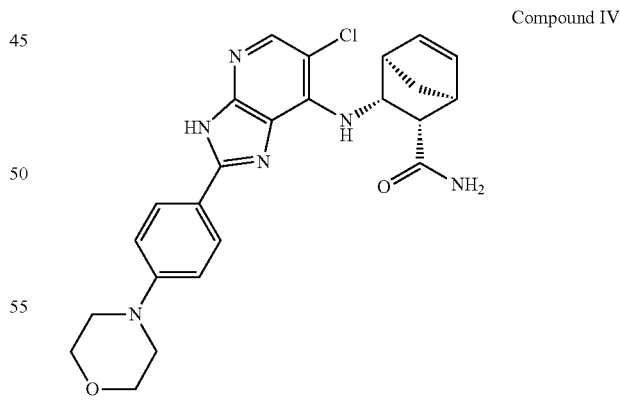

Synthesis of (1S,2S,3R,4R)-3-[6-Chloro-2-(4-morpholin-4-yl-phenyl)-3H-imidazo[4,5-b]pyridine-7-ylamino]-bicyclo[2.2.1]hept-5-ene-2-carboxylic acid amide (Compound IV)

In the same fashion as for Compound III, (1S,2S,3R,4R)-3-(2,3-Diamino-5-chloro-pyridin-4-ylamino)-bicyclo[2.2.1]

hept-5-ene-2-carboxylic acid amide and 4-morpholin-4-yl-benzaldehyde were reacted to produce the title compound (20%). ¹H NMR (d-chloroform): 15.43 (br s, 1H), 8.06 (d, J=9 Hz, 1H), 8.00 (d, J=9 Hz, 2H), 7.77 (s, 1H), 7.02 (d, J=9 Hz, 2H), 6.50 (m, 1H), 6.42 (m, 1H), 5.91 (br s, 1H), 5.53 (br s, 1H), 5.40 (t, J=8 Hz, 1H), 3.90 (t, J=5 Hz, 4H), 3.30 (t, J=5 Hz, 4H), 3.17 (s, 1H), 3.04 (s, 1H), 2.68 (d, J=8 Hz, 1H), 2.38 (d, J=9 Hz, 1H), 1.67 (d, J=9 Hz, 1H). MS: 466.07 (M+H). HPLC retention time: 2.42 minutes (G Method).

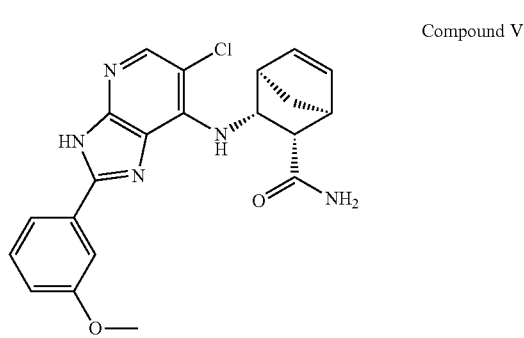 [SMILES: COc1cccc(-c2nc3c(N[C@H]4[C@@H](C(N)=O)[C@@H]5C=C[C@H]4C5)c(Cl)cnc3[nH]2)c1]

Compound V

Synthesis of (1S,2S,3R,4R)-3-[6-Chloro-2-(3-methoxy-phenyl)-3H-imidazo[4,5-b]pyridine-7-ylamino]-bicyclo[2.2.1]hept-5-ene-2-carboxylic acid amide (Compound V)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 3-methoxybenzaldehyde were reacted to produce the title compound (34%). ¹H NMR (d-chloroform): 15.77 (br s, 1H) 8.43 (d, J=8 Hz, 1H), 7.80 (s, 1H), 7.67 (s, 1H), 7.66 (m, 1H), 7.44 (t, J=8 Hz, 1H), 7.04 (d, J=8 Hz, 1H), 6.51 (m, 1H), 6.42 (m, 1H), 5.93 (br s, 1H), 5.55 (br s, 1H), 5.36 (t, J=8 Hz, 1H), 3.93 (s, 3H), 3.17 (s, 1H), 3.05 (s, 1H), 2.69 (d, J=8 Hz, 1H), 2.32 (d, J=9 Hz, 1H), 1.67 (d, J=9 Hz, 1H). MS: 466.07 (M+H). HPLC retention time: 2.42 minutes (G Method).

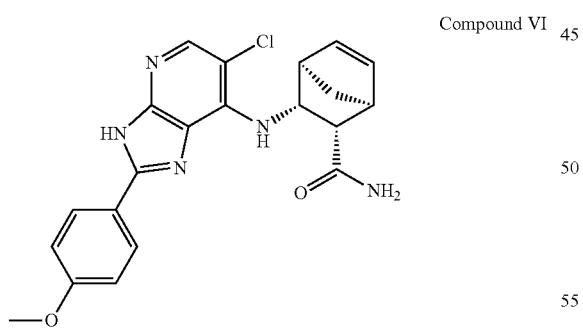

Compound VI

Synthesis of (1S,2S,3R,4R)-3-[6-Chloro-2-(4-methoxy-phenyl)-3H-imidazo[4,5-b]pyridine-7-ylamino]-bicyclo[2.2.1]hept-5-ene-2-carboxylic acid amide (Compound VI)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 4-methoxybenzaldehyde were reacted to produce the title compound (16%). ¹H NMR (d-chloroform): 15.54 (br s, 1H) 8.23 (d, J=9 Hz, 1H), 8.06 (d, J=9 Hz, 2H), 7.79 (s, 1H), 7.06 (d, J=9 Hz, 2H), 6.51 (m, 1H), 6.42 (m, 1H), 5.86 (br s, 1H), 5.46 (br s, 1H), 5.39 (t, J=8 Hz, 1H), 3.91 (s, 3H), 3.17 (s, 1H), 3.05 (s, 1H), 2.68 (d, J=9 Hz, 1H), 2.33 (d, J=9 Hz, 1H), 1.68 (d, J=10 Hz, 1H). MS: 466.07 (M+H). HPLC retention time: 2.42 minutes (G Method).

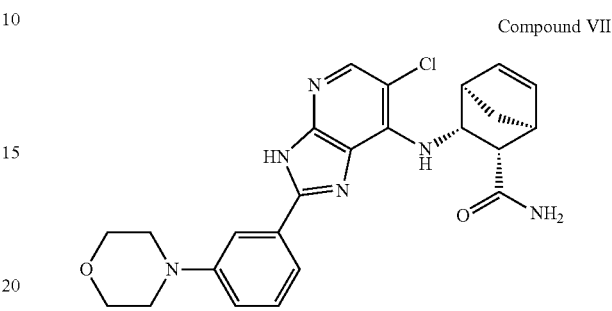

Compound VII

Synthesis of (1S,2S,3R,4R)-3-[6-Chloro-2-(3-morpholin-4-yl-phenyl)-3H-imidazo[4,5-b]pyridine-7-ylamino]-bicyclo[2.2.1]hept-5-ene-2-carboxylic acid amide (Compound VII)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 3-morpholin-j4-yl-benzaldehyde were reacted to produce the title compound (69%). ¹H NMR (d-chloroform): 15.96 (br s, 1H) 8.37 (d, J=9 Hz, 1H), 7.83 (s, 1H), 7.71 (s, 1H), 7.59 (d, J=8 Hz, 1H), 7.40 (t, J=8 Hz, 1H), 7.06 (dd, J=2.8 Hz, 1H), 6.48 (m, 1H), 6.42 (m, 1H), 6.07 (br s, 1H), 5.86 (br s, 1H), 5.37 (t, J=8 Hz, 1H), 3.94 (m, 4H), 3.33 (m, 4H), 3.17 (s, 1H), 3.03 (s, 1H), 2.71 (d, J=8 Hz, 1H), 2.31 (d, J=9 Hz, 1H), 1.67 (d, J=9 Hz, 1H). MS: 466.07 (M+H). HPLC retention time: 2.41 minutes (G Method).

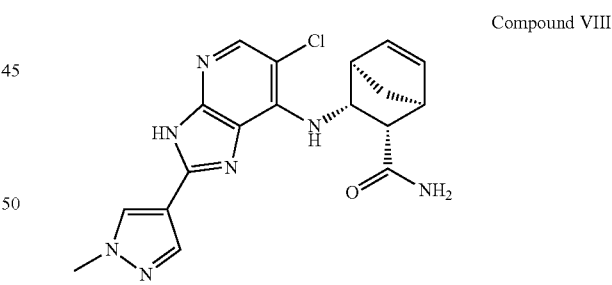

Compound VIII

Synthesis of (1S,2S,3R,4R)-3-[6-Chloro-2-(1-methyl-1H-pyrazol-4-yl)-3H-imidazo[4,5-b]pyridine-7-ylamino]-bicyclo[2.2.1]hept-5-ene-2-carboxylic acid amide (Compound VIII)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 1-Methyl-1H-pyrazole-4-carbaldehyde were reacted to produce the title compound (88%). ¹H NMR (d-chloroform): 15.26 (br s, 1H) 8.26 (d, J=8 Hz, 1H), 8.04 (s, 1H), 8.02 (s, 1H), 7.78 (s, 1H), 6.45 (m, 1H), 6.41 (m, 1H), 5.99 (s, 1H), 5.70 (s, 1H), 5.31 (t, J=8 Hz, 1H), 4.02 (s, 3H), 3.16 (s, 1H), 3.00 (s, 1H), 2.68 (d, J=8 Hz, 1H), 2.29 (d, J=9 Hz, 1H), 1.66 (d, J=10 Hz, 1H). MS: 385.06 (M+H). HPLC retention time: 1.90 minutes (G Method).

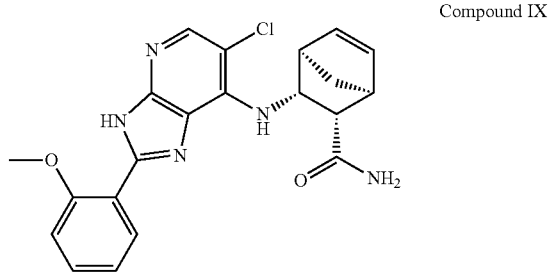 [SMILES: COc1ccccc1-c1nc2c(N[C@H]3[C@@H](C(N)=O)[C@@H]4C=C[C@H]3C4)c(Cl)cnc2[nH]1]

Compound IX

Synthesis of (1S,2S,3R,4R)-3-[6-Chloro-2-(2-methoxy-phenyl)-3H-imidazo[4,5-b]pyridin-7-ylamino]-bicyclo[2.2.1]hept-5-ene-2-carboxylic acid amide (Compound IX)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 2-methoxybenzaldehyde were reacted to produce the title compound (96%). $^1$H NMR (d-chloroform): 13.89 (br s, 1H) 8.31 (dd, J=1.8 Hz, 1H), 8.10 (d, J=9 Hz, 1H), 7.84 (s, 1H), 7.46 (m, 1H), 7.10 (t, J=8 Hz, 1H), 7.04 (d, J=8 Hz, 1H), 6.49 (m, 1H), 6.43 (m, 1H), 6.07 (br s, 1H), 5.60 (br s, 1H), 5.39 (t, J=8 Hz, 1H), 4.15 (s, 3H), 3.16 (s, 1H), 3.01 (s, 1H), 2.73 (d, J=9 Hz, 1H), 2.33 (d, J=9 Hz, 1H), 1.67 (d, J=9 Hz, 1H). MS: 411.04 (M+H). HPLC retention time: 2.58 minutes (G Method).

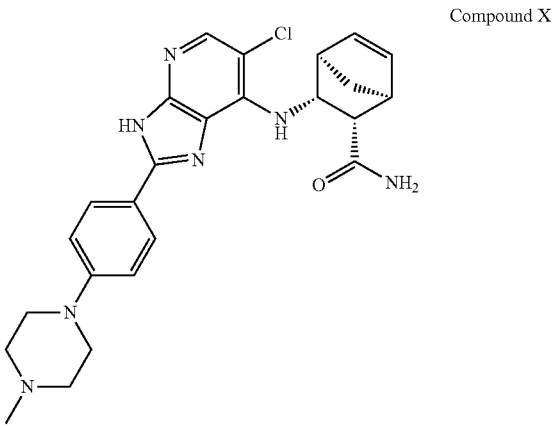 [SMILES: CN1CCN(c2ccc(-c3nc4c(N[C@H]5[C@@H](C(N)=O)[C@@H]6C=C[C@H]5C6)c(Cl)cnc4[nH]3)cc2)CC1]

Compound X

Synthesis of (1S,2S,3R,4R)-3-{6-Chloro-2-[4-(4-methyl-piperazin-1-yl)-phenyl]-3H-imidazo[4,5-b]pyridine-7-ylamino}-bicyclo[2.2.1]hept-5-ene-2-carboxylic acid amide trifluoroacetic acid salt (Compound X)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 4-(4-Methyl-piperazin-1-yl)-benzaldehyde were reacted to produce the title compound (88%). $^1$H NMR (d-chloroform): 15.58 (br s, 1H) 8.36 (d, J=9 Hz, 1H), 8.00 (d, J=9 Hz, 2H), 7.78 (s, 1H), 7.02 (d, J=9 Hz, 2H), 6.48 (m, 1H), 6.41 (m, 1H), 5.99 (s, 1H), 5.61 (s, 1H), 5.35 (t, J=9 Hz, 1H), 3.38-3.93 (m, 8H), 3.17 (s, 1H), 3.04 (m, 1H), 3.02 (s, 1H), 2.91 (s, 3H), 2.69 (d, J=9 Hz, 1H), 2.31 (d, J=9 Hz, 1H), 1.67 (d, J=9 Hz, 1H). MS: 479.11 (M+H). HPLC retention time: 1.81 minutes (G Method).

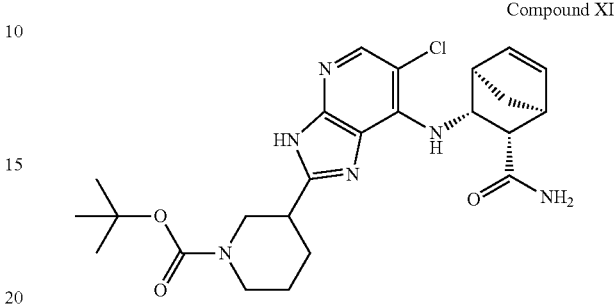

Compound XI

Synthesis of 3-[7-((1R,2R,3S,4S)-3-Carbamoyl-bicyclo[2.2.1]hept-5-en-2-ylamino)-6-chloro-3H-imidazo[4,5-b]pyridine-2-yl]-piperidine-1-carboxylic acid tert-butyl ester (Compound XI)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 3-formyl-piperidine-1-carboxylic acid tert-butyl ester were reacted to produce the title compound (65%). $^1$H NMR (d-chloroform): 15.20 (br s, 1H), 8.42 (m, 1H), 7.83 (s, 1H), 6.45 (m, 1H), 6.38 (m, 1H), 5.90 (m, 1H), 5.64 (s, 1H), 5.25 (m, 1H), 4.03 (m, 1H), 2.80-3.25 (m, 5H), 2.62 (t, J=8 Hz, 1H), 2.39 (d, J=10 Hz, 2H), 1.32-2.00 (m, 14H). MS: 488.07 (M+H). HPLC retention time: 2.67 minutes (G Method).

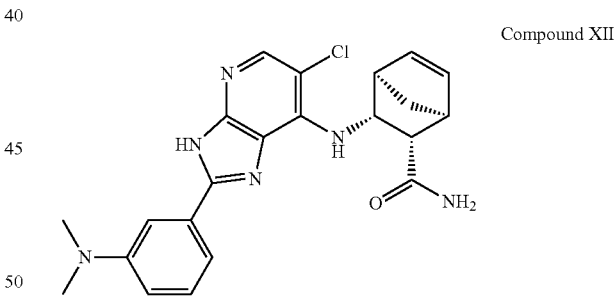

Compound XII

Synthesis of (1S,2S,3R,4R)-3-[6-Chloro-2-(3-dimethylamino-phenyl)-3H-imidazo[4,5-b]pyridin-7-ylamino]-bicyclo[2.2.1]hept-5-ene-2-carboxylic acid amide (Compound XII)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 3-Dimethylamino-benzaldehyde were reacted to produce the title compound (86%). $^1$H NMR (d-chloroform): 16.5 (br s, 1H), 8.37 (d, J=8 Hz, 1H), 7.83 (s, 1H), 7.72 (s, 1H), 7.61 (d, J=8 Hz, 1H), 7.45 (t, J=8 Hz, 1H), 7.06 (dd, J=2.8 Hz, 1H), 6.51 (m, 1H), 6.42 (m, 1H), 5.98 (m, 1H), 5.62 (m, 1H), 5.38 (t, J=8 Hz, 1H), 3.17 (s, 1H), 3.13 (s, 6H), 3.06 (s, 1H), 2.71 (d, J=8 Hz, 1H), 2.33

(d, J=8 Hz, 1H), 1.68 (d, J=8 Hz, 1H). MS: 424.04 (M+H). HPLC retention time: 2.06 minutes (G Method).

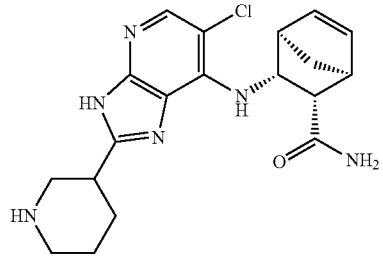

Compound XIII

Synthesis of both diastereomers of (1S,2S,3R,4R)-3-(6-Chloro-2-piperidin-3-yl-3H-imidazo[4,5-b]pyridin-7-ylamino)-bicyclo[2.2.1]hept-5-ene-2-carboxylic acid amide trifluoroacetic acid salts (Compounds XIII and XIV)

3-[7-((1R,2R,3S,4S)-3-Carbamoyl-bicyclo[2.2.1]hept-5-en-2-ylamino)-6-chloro-3H-imidazo[4,5-b]pyridin-2-yl]-piperidine-1-carboxylic acid tert-butyl ester (31 mg, 0.064 mmol) was stirred with 4M hydrogen chloride in 1,4-dioxane (3 mL) at 40° C. overnight. The reaction was concentrated and subjected to reverse phase chromatography on a Gilson chromatograph. Two products were collected corresponding to individual (stereochemistry not determined) diastereomers differing at the 3-position of the piperidine ring. Lyophilization of respective fractions affords:

First eluting diastereomer (8 mg, 30%)—¹H NMR (d6-DMSO): 12.89 (br s, 1H), 8.63 (m, 2H), 7.97 (s, 1H), 7.80 (s, 1H), 7.42 (br s, 1H), 7.27 (s, 1H), 6.58 (m, 2H), 4.97 (t, J=8 Hz, 1H), 3.63 (m, 1H), 3.29 (m, 3H), 2.97 (m, 1H), 2.88 (s, 1H), 2.73 (s, 1H), 2.33 (m, 1H), 2.19 (d, J=9 Hz, 2H), 1.86 (m, 1H), 1.75 (m, 2H), 1.36 (d, J=9 Hz, 1H). MS: 388.14 (M+H). HPLC retention time: 1.49 minutes (G Method).

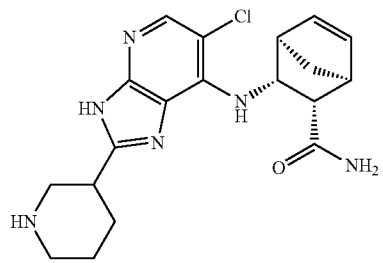

Compound XIV

Second eluting diastereomers (7 mg, 30%)—¹H NMR (d6-DMSO): 12.96 (br s, 1H), 8.74 (m, 2H), 8.00 (s, 1H), 7.80 (s, 1H), 7.51 (m, 1H), 7.27 (s, 1H), 6.38 (m, 1H), 6.33 (m, 1H), 4.95 (t, J=8 Hz, 1H), 3.63 (d, J=10 Hz, 1H), 3.14-3.36 (m, 3H), 2.99 (s, 1H), 2.89 (s, 1H), 2.76 (s, 1H), 2.57 (d, J=9 Hz, 1H), 2.26 (m, 1H), 2.18 (d, J=9 Hz, 1H), 1.91 (m, 1H), 1.76 (m, 2H), 1.36 (d, J=9 Hz, 1H). MS: 388.13 (M+H). HPLC retention time: 1.54 minutes (G Method).

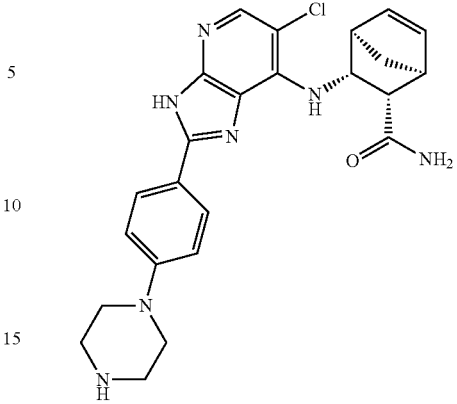

Compound XV

Synthesis of (1S,2S,3R,4R)-3-[6-Chloro-2-(4-piperazin-1-yl-phenyl)-3H-imidazo[4,5-b]pyridin-7-ylamino]-bicyclo[2.2.1]hept-5-ene-2-carboxylic acid amide trifluoroacetic acid salt (Compound XV)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 4-(4-Formyl-phenyl)-piperazine-1-carboxylic acid tert-butyl ester were reacted to produce an initial tert-butyl carbamate condensation product. This material was treated with 4N hydrochloric acid in dioxane at 40° C. overnight. Concentration followed by reverse phase chromatography on a Gilson chromatograph afforded fractions which were lyophilized to afford the title compound (43%). ¹H NMR (d6-DMSO): 13.19 (br s, 1H), 8.77 (m, 2H), 8.04 (s, 1H), 8.02 (s, 1H), 7.95 (s, 1H), 7.78 (s, 1H), 7.13-7.45 (m, 4H), 6.38 (m, 2H), 5.17 (t, J=8 Hz, 1H), 3.49 (m, 4H), 3.26 (m, 4H), 2.91 (s, 1H), 2.80 (s, 1H), 2.62 (d, J=8 Hz, 1H), 2.23 (d, J=9 Hz, 1H), 1.40 (d, J=9 Hz, 1H). MS: 465.09 (M+H). HPLC retention time: 1.79 minutes (G Method).

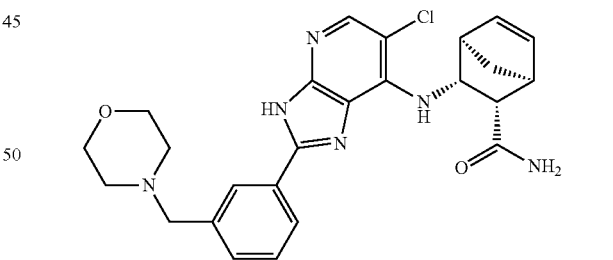

Compound XVI

Synthesis of (1S,2S,3R,4R)-3-[6-Chloro-2-(3-morpholin-4-ylmethyl-phenyl)-3H-imidazo[4,5-b]pyridin-7-ylamino]-bicyclo[2.2.1]hept-5-ene-2-carboxylic acid amide trifluoroacetic acid salt (Compound XVI)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 3-Morpholin-4-ylmethyl-benzaldehyde were reacted to produce the title compound (77%). ¹H NMR (d-chloroform): 8.78 (d, J=8 Hz, 1H), 8.20 (m, 1H), 8.09 (s, 1H), 7.85 (s, 1H), 7.63 (m, 2H), 6.42-6.50 (m, 2H), 6.01 (s, 1H), 5.61 (s, 1H), 5.38 (t, J=8 Hz, 1H), 4.37 (d, J=13 Hz, 1H), 4.27 (d, J=13 Hz, 1H), 3.99 (m, 4H), 3.53 (m, 2H), 3.18 (s, 1H), 3.05 (m, 1H), 3.04 (s, 1H), 2.70 (d, J=8 Hz, 1H), 2.32 (d, J=9 Hz, 1H), 1.68 (d, J=9 Hz, 1H). MS: 480.09 (M+H). HPLC retention time: 1.81 minutes (G Method).

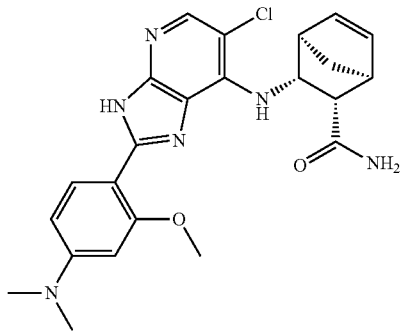

Compound XVII

Synthesis of (1S,2S,3R,4R)-3-[6-Chloro-2-(4-dimethylamino-2-methoxy-phenyl)-3H-imidazo[4,5-b]pyridine-7-ylamino]-bicyclo[2.2.1]hept-5-ene-2-carboxylic acid amide (Compound XVII)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 4-Dimethylamino-2-methoxy-benzaldehyde were reacted to produce the title compound (52%). $^1$H NMR (d-chloroform): 13.60 (br s, 1H), 8.16 (d, J=9 Hz, 1H), 7.79 (s, 1H), 7.44 (br s, 1H), 6.35-6.50 (m, 3H), 6.24 (d, J=2 Hz, 1H), 5.94 (s, 1H), 5.43 (t, J=8 Hz, 1H), 5.31 (br s, 1H), 4.16 (s, 3H), 3.27 (s, 1H), 3.10 (s, 6H), 3.02 (s, 1H), 2.72 (d, J=8 Hz, 1H), 2.35 (d, J=9 Hz, 1H), 1.70 (d, J=10 Hz, 1H). MS: 454.07 (M+H). HPLC retention time: 2.61 minutes (G Method).

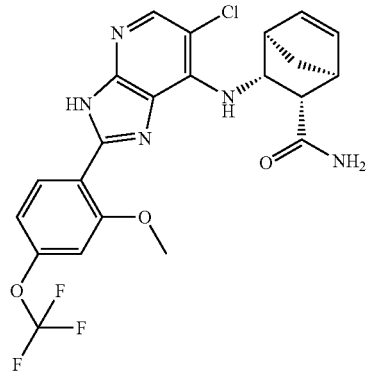

Compound XVIII

Synthesis of (1S,2S,3R,4R)-3-[6-Chloro-2-(2-methoxy-4-trifluoromethoxy-phenyl)-3H-imidazo[4,5-b]pyridine-7-ylamino]-bicyclo[2.2.1]hept-5-ene-2-carboxylic acid amide (Compound XVIII)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 2-Methoxy-4-trifluoromethoxy-benzaldehyde were reacted to produce the title compound (60%). $^1$H NMR (d-chloroform): 13.94 (br s, 1H), 8.31 (d, J=9 Hz, 1H), 8.20 (d, J=9 Hz, 1H), 7.83 (s, 1H), 6.97 (d, J=9 Hz, 1H), 6.82 (s, 1H), 6.44 (m, 2H), 6.24 (s, 1H), 5.82 (s, 1H), 5.35 (d, J=9 Hz, 1H), 4.11 (s, 3H), 3.17 (s, 1H), 2.97 (s, 1H), 2.74 (d, J=8 Hz, 1H), 2.31 (d, J=9 Hz, 1H), 1.65 (d, J=9 Hz, 1H). MS: 495.00 (M+H). HPLC retention time: 3.12 minutes (G Method).

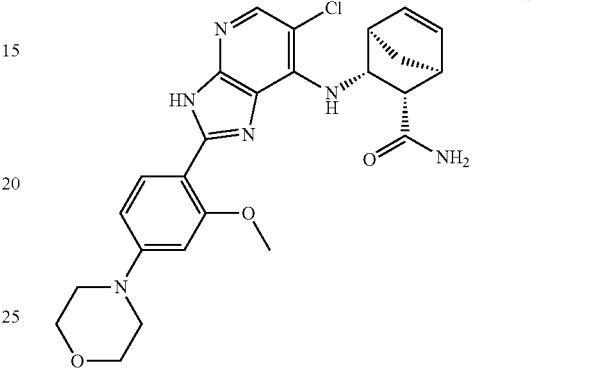

Compound XIX

Synthesis of (1S,2S,3R,4R)-3-[6-Chloro-2-(2-methoxy-4-morpholin-4-yl-phenyl)-3H-imidazo[4,5-b]pyridine-7-ylamino]-bicyclo[2.2.1]hept-5-ene-2-carboxylic acid amide (Compound XIX)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 2-Methoxy-4-morpholin-4-yl-benzaldehyde were reacted to produce the title compound (90%). $^1$H NMR (d-chloroform): 13.72 (br s, 1H), 8.19 (d, J=8 Hz, 1H), 7.81 (s, 1H), 7.76 (d, J=9 Hz, 1H), 6.62 (dd, J=2.9 Hz, 1H), 6.47 (m, 2H), 6.40 (dd, J=2.6 Hz, 1H), 5.95 (br s, 1H), 5.48 (br s, 1H), 5.42 (d, J=8 Hz, 1H), 4.15 (s, 3H), 3.91 (t, J=5 Hz, 4H), 3.33 (t, J=5 Hz, 4H), 3.16 (s, 1H), 3.02 (s, 1H), 2.71 (d, J=8 Hz, 1H), 2.34 (d, J=9 Hz, 1H), 1.69 (d, J=9 Hz, 1H). MS: 496.06 (M+H). HPLC retention time: 2.48 minutes (G Method).

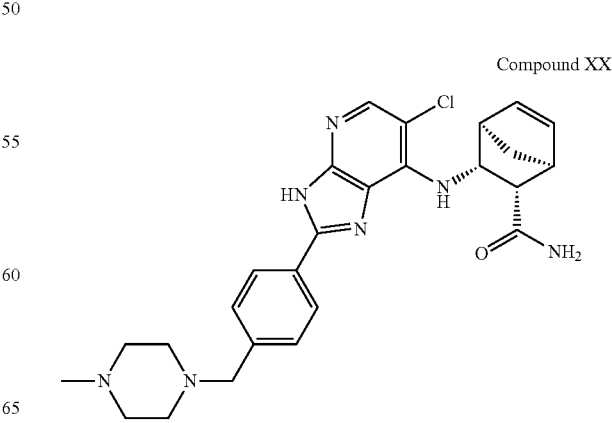

Compound XX

Synthesis of (1S,2S,3R,4R)-3-{6-Chloro-2-[4-(4-methyl-piperazin-1-ylmethyl)-phenyl]-3H-imidazo[4,5-b]pyridin-7-ylamino}-bicyclo[2.2.1]hept-5-ene-2-carboxylic acid amide; compound with trifluoroacetic acid bis trifluoroacetic acid salt (Compound XX)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 4-(4-Methyl-piperazin-1-ylmethyl)-benzaldehyde were reacted to produce the title compound (60%). $^1$H NMR (d-chloroform): 16.00 (br s, 1H), 8.64 (d, J=8 Hz, 1H), 8.12 (d, J=8 Hz, 1H), 7.85 (s, 1H), 7.56 (d, J=8 Hz, 1H), 6.50 (m, 1H), 6.44 (m, 1H), 5.86 (br s, 1H), 5.60 (br s, 1H), 5.37 (t, J=8 Hz, 1H), 3.93 (s, 3H), 3.10-3.60 (m, 10H), 3.06 (s, 1H), 2.05 (s, 4H), 2.67 (d, J=9 Hz, 1H), 2.32 (d, J=9 Hz, 1H), 1.68 (d, J=9 Hz, 1H). MS: 493.14 (M+H). HPLC retention time: 1.68 minutes (G Method).

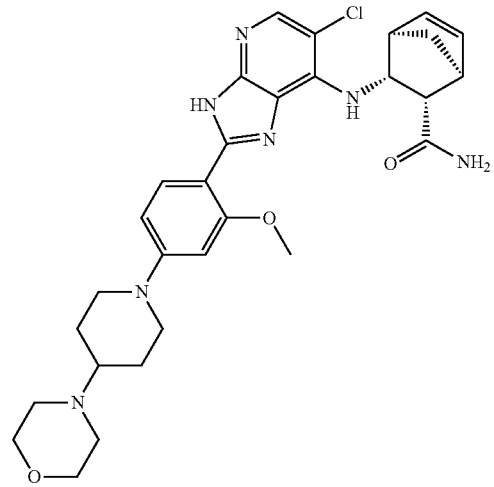

Compound XXII

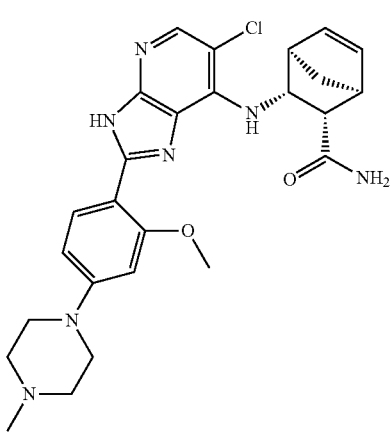

Compound XXI

Synthesis of (1S,2S,3R,4R)-3-{6-Chloro-2-[2-methoxy-4-(4-morpholin-4-yl-piperidin-1-yl)-phenyl]-3H-imidazo[4,5-b]pyridin-7-ylamino}-bicyclo[2.2.1]hept-5-ene-2-carboxylic acid amide (Compound XXII)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 2-Methoxy-4-(4-morpholin-4-yl-piperidin-1-yl)-benzaldehyde were reacted to produce the title compound (75%). $^1$H NMR (d-6 DMSO): 12.50 (br s, 1H), 9.85 (br s, 1H), 8.09 (s, 1H), 8.04 (d, J=9 Hz, 1H), 7.83 (br s, 1H), 7.29 (s, 1H), 6.77 (d, J=9 Hz, 1H), 6.66 (s, 1H), 6.38 (s, 2H), 5.15 (m, 1H), 3.95-4.30 (m, 7H), 3.69 (t, J=10 Hz, 2H), 3.48 (m, 3H), 3.13 (m, 2H), 2.82-2.96 (m, 4H), 2.63 (d, J=8 Hz, 1H), 2.11-2.26 (m, 3H), 2.08 (s, 1H), 1.69 (m, 2H), 1.41 (d, J=9 Hz, 1H). MS: 579.20 (M+H). HPLC retention time: 1.91 minutes (G Method).

Compound XXIII

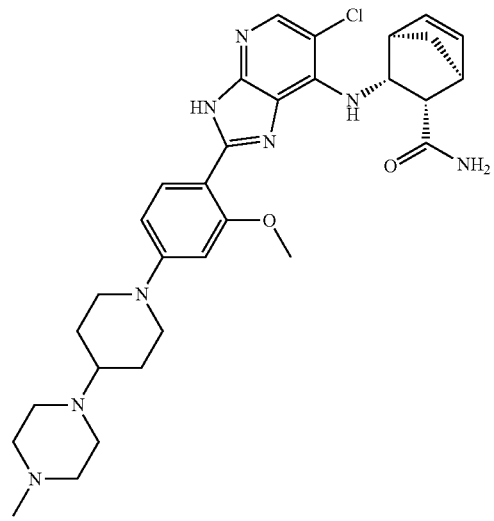

Synthesis of (1S,2S,3R,4R)-3-{6-Chloro-2-[2-methoxy-4-(4-methyl-piperazin-1-yl)-phenyl]-3H-imidazo[4,5-b]pyridin-7-ylamino}-bicyclo[2.2.1]hept-5-ene-2-carboxylic acid amide trifluoroacetic acid salt (Compound XXI)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 2-Methoxy-4-(4-methyl-piperazin-1-yl)-benzaldehyde were reacted to produce the title compound (62%). $^1$H NMR (d-chloroform): 13.76 (br s, 1H), 8.21 (d, J=8 Hz, 1H), 7.97 (d, J=8 Hz, 1H), 7.80 (s, 1H), 6.62 (d, J=8 Hz, 1H), 6.47 (s, 1H), 6.46 (m, 1H), 6.42 (br s, 1H), 6.07 (br s, 1H), 5.40 (t, J=9 Hz, 1H), 4.11 (s, 3H), 3.65-3.90 (m, 4H), 3.40-3.60 (m, 2H), 3.16 (s, 1H), 3.03 (m, 1H), 2.99 (s, 1H), 2.92 (s, 3H), 2.72) d, J=8 Hz, 1H), 2.32 (d, J=9 Hz, 1H), 1.80-2.10 (m, 2H), 1.68 (d, J=9 Hz, 1H). MS: 509.14 (M+H). HPLC retention time: 1.82 minutes (G Method).

Synthesis of (1S,2S,3R,4R)-3-(6-Chloro-2-{2-methoxy-4-[4-(4-methyl-piperazin-1-yl)-piperidin-1-yl]-phenyl}-3H-imidazo[4,5-b]pyridin-7-ylamino)-bicyclo[2.2.1]hept-5-ene-2-carboxylic acid amide (Compound XXIII)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 2-Methoxy-4-[4-(4-methyl-piperazin-1-yl)-piperidin-1-yl]-benzaldehyde were reacted to produce the title compound (60%). $^1$H NMR (d-chloroform): 10.62 (br s, 1H), 8.22 (d, J=9 Hz, 1H), 7.98 (s, 1H), 6.66 (m, 2H), 6.50 (s, 1H), 6.33 (d, J=10 Hz, 2H), 5.07-5.19 (m, 2H), 4.03 (s, 3H), 3.90 (d, J=11 Hz, 2H), 3.49 (s, 2H), 3.17 (s, 1H), 2.89 (m, 4H), 2.65 (m, 4H), 2.46 (m, 4H), 232 (m, 1H), 2.31 (s, 3H), 1.97 (d, J=11 Hz, 2H), 1.60-1.79 (m, 3H). MS: 592.22 (M+H). HPLC retention time: 1.76 minutes (G Method).

Synthesis of (1R,2R,3S,4S)-3-[6-Chloro-2-(3-morpholin-4-yl-phenyl)-3H-imidazo[4,5-b]pyridine-7-ylamino]-bicyclo[2.2.1]hept-5-ene-2-carboxylic acid amide (Compound XXV)

In the same fashion as for Compound III, (1R,2R,3S,4S)-3-(2,3-Diamino-5-chloro-pyridin-4-ylamino)-bicyclo[2.2.1]hept-5-ene-2-carboxylic acid amide and 3-Morpholin-4-yl-benzaldehyde were reacted to produce the title compound (11%). $^1$H NMR (d-chloroform): 16.12 (br s, 1H), 8.42 (d, J=9 Hz, 1H), 7.83 (s, 1H), 7.74 (s, 1H), 7.64 (d, J=8 Hz, 1H), 7.44 (t, J=8 Hz, 1H), 7.07 (d, J=8 Hz, 1H), 6.50 (m, 1H), 6.42 (m, 1H), 5.90 (br s, 1H), 5.65 (br s, 1H), 5.40 (t, J=8 Hz, 1H), 3.94 (m, 4H), 3.34 (m, 4H), 3.18 (s, 1H), 3.07 (s, 1H), 2.69 (d, J=8 Hz, 1H), 2.33 (d, J=9 Hz, 1H), 1.69 (d, J=9 Hz, 1H). MS: 465.15 (M+H). HPLC retention time: 2.39 minutes (G Method).

Compound XXIV

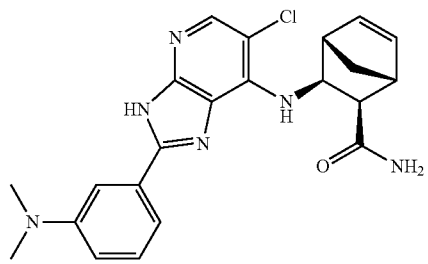

Synthesis of (1R,2R,3S,4S)-3-[6-Chloro-2-(3-dimethylamino-phenyl)-3H-imidazo[4,5-b]pyridine-7-ylamino]-bicyclo[2.2.1]hept-5-ene-2-carboxylic acid amide (Compound XXIV)

In the same fashion as for Compound III, (1R,2R,3S,4S)-3-(2,3-Diamino-5-chloro-pyridin-4-ylamino)-bicyclo[2.2.1]hept-5-ene-2-carboxylic acid amide and 3-Dimethylamino-benzaldehyde were reacted to produce the title compound (58%). $^1$H NMR (d-chloroform): 16.03 (br s, 1H), 8.36 (d, J=9 Hz, 1H), 7.82 (s, 1H), 7.74 (s, 1H), 7.61 (d, J=9 Hz, 1H), 7.45 (t, J=8 Hz, 1H), 7.09 (t, J=8 Hz, 1H), 6.50 (m, 1H), 6.42 (m, 1H), 6.04 (m, 1H), 5.69 (m, 1H), 5.37 (t, J=7 Hz, 1H), 3.17 (s, 1H), 3.13 (s, 6H), 3.04 (s, 1H), 2.71 (d, J=9 Hz, 1H), 2.33 (d, J=9 Hz, 1H), 1.68 (d, J=9 Hz, 1H). MS: 423.15 (M+H). HPLC retention time: 2.05 minutes (G Method).

Compound XXV

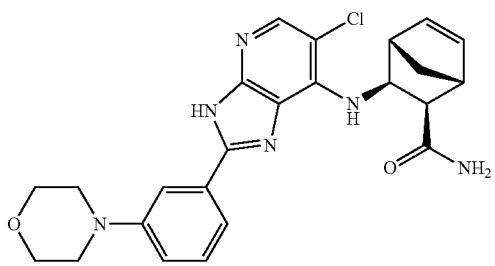

Compound XXVI

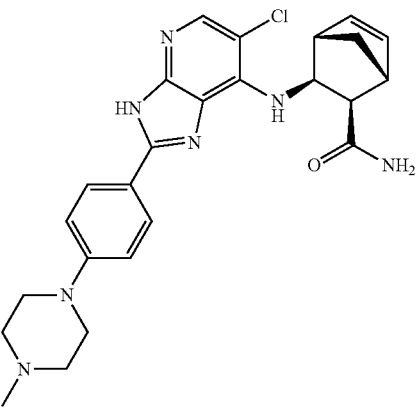

Synthesis of (1R,2R,3S,4S)-3-{6-Chloro-2-[4-(4-methyl-piperazin-1-yl)-phenyl]-3H-imidazo[4,5-b]pyridine-7-ylamino}-bicyclo[2.2.1]hept-5-ene-2-carboxylic acid amide (Compound XXVI)

In the same fashion as for Compound III, (1R,2R,3S,4S)-3-(2,3-Diamino-5-chloro-pyridin-4-ylamino)-bicyclo[2.2.1]hept-5-ene-2-carboxylic acid amide and 4-(4-Methyl-piperazin-1-yl)-benzaldehyde were reacted to produce the title compound (66%). $^1$H NMR (d-chloroform): 15.63 (br s, 1H) 8.36 (d, J=9 Hz, 1H), 8.02 (d, J=9 Hz, 2H), 7.78 (s, 1H), 7.03 (d, J=9 Hz, 2H), 6.48 (m, 1H), 6.42 (m, 1H), 5.95 (s, 1H), 5.59 (s, 1H), 5.54 (t, J=8 Hz, 1H), 3.38-3.92 (m, 8H), 3.17 (s, 1H), 3.04 (m, 1H), 3.02 (s, 1H), 2.91 (s, 3H), 2.68 (d, J=9 Hz, 1H), 2.32 (d, J=9 Hz, 1H), 1.67 (d, J=9 Hz, 1H). MS: 478.15 (M+H). HPLC retention time: 1.79 minutes (G Method).

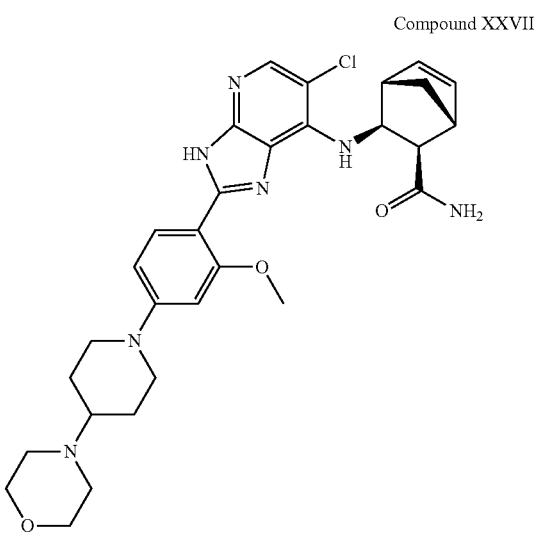 [SMILES: COc1cc(N2CCC(N3CCOCC3)CC2)ccc1-c1nc2c(N[C@@H]3[C@H](C(N)=O)[C@H]4C=C[C@@H]3C4)c(Cl)cnc2[nH]1]

Compound XXVII

Synthesis of (1R,2R,3S,4S)-3-{6-Chloro-2-[2-methoxy-4-(4-morpholin-4-yl-piperidin-1-yl)-phenyl]-3H-imidazo[4,5-b]pyridin-7-ylamino}-bicyclo[2.2.1]hept-5-ene-2-carboxylic acid amide (Compound XXVII)

In the same fashion as for Compound III, (1R,2R,3S,4S)-3-(2,3-Diamino-5-chloro-pyridin-4-ylamino)-bicyclo[2.2.1]hept-5-ene-2-carboxylic acid amide and 2-Methoxy-4-(4-morpholin-4-yl-piperidin-1-yl)-benzaldehyde were reacted to produce the title compound (8%). $^1$H NMR (d-6 DMSO): 12.26 (br s, 1H), 9.70 (br s, 1H), 8.02 (m, 1H), 7.79 (s, 1H), 7.42 (br s, 1H), 7.26 (s, 1H), 6.78 (d, J=9 Hz, 1H), 6.66 (s, 1H), 6.38 (s, 2H), 5.17 (m, 1H), 4.11 (m, 2H), 4.03 (m, 2H), 4.00 (s, 3H), 3.68 (m, 2H), 3.48 (m, 4H), 3.12 (m, 2H), 2.92-2.77 (m, 3H), 2.63 (d, J=8 Hz, 1H), 2.24 (m, 1H), 2.13 (m, 2H), 1.68 (m, 2H), 1.40 (d, J=9 Hz, 1H). MS: 578.20 (M+H). HPLC retention time: 1.92 minutes (G Method).

Compound XXVIII

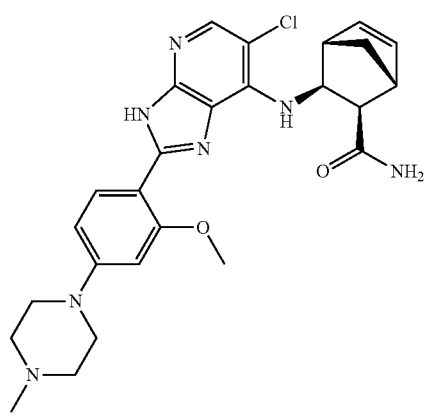

Synthesis of (1R,2R,3S,4S)-3-{6-Chloro-2-[2-methoxy-4-(4-methyl-piperazin-1-yl)-phenyl]-3H-imidazo[4,5-b]pyridin-7-ylamino}-bicyclo[2.2.1]hept-5-ene-2-carboxylic acid amide (Compound XXVIII)

In the same fashion as for Compound III, (1R,2R,3S,4S)-3-(2,3-Diamino-5-chloro-pyridin-4-ylamino)-bicyclo[2.2.1]hept-5-ene-2-carboxylic acid amide and 2-Methoxy-4-(4-methyl-piperazin-1-yl)-benzaldehyde were reacted to produce the title compound (5%). $^1$H NMR (d-6 DMSO): 12.19 (br s, 1H), 9.67 (br s, 1H), 8.05 (d, J=8 Hz, 1H), 7.94 (s, 1H), 7.77 (s, 1H), 7.18 (m, 1H), 6.79 (d, J=8 Hz, 1H), 6.71 (s, 1H), 6.35 (s, 2H), 5.20 (m, 1H), 4.07 (d, J=8 Hz, 2H), 3.98 (s, 3H), 3.28-2.18 (m, 11H), 1.45 (m, 2H), 1.39 (m, 1H). MS: 508.1 (M+H). HPLC retention time: 1.82 minutes (G Method).

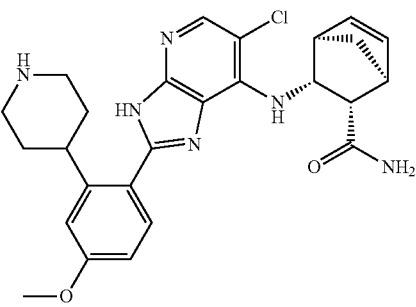

Compound XXIX

Synthesis of 4-{2-[7-((1R,2R,3S,4S)-3-Carbamoyl-bicyclo[2.2.1]hept-5-en-2-ylamino)-6-chloro-3H-imidazo[4,5-b]pyridine-2-yl}-5-methoxy-phenyl]-piperidinej-1-carboxylic acid tert-butyl ester (Compound XXIX)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 4-(2-Formyl-5-methoxy-phenyl)-piperidine-1-carboxylic acid tert-butyl ester were reacted to produce the title compound (31%). $^1$H NMR (d-chloroform): 14.13 (br s, 1H), 7.85 (br s, 1H), 7.70 (d, J=8 Hz, 1H), 6.99 (s, 1H), 6.97 (d, J=8 Hz, 1H), 6.33 (s, 1H), 6.28 (s, 1H), 6.16 (s, 1H), 5.89 (m, 1H), 5.47 (m, 1H), 5.26 (t, J=8 Hz, 1H), 4.19 (m, 2H), 3.94 (s, 3H), 3.87 (m, 1H), 3.13 (s, 1H), 2.89 (s, 1H), 2.72 (m, 4H), 2.36 (d, J=9 Hz, 1H), 1.89 (m, 2H), 1.73 (d, J=10 Hz, 2H), 1.51 (s, 9H). MS: 593.2 (M+H). HPLC retention time: 3.15 minutes (G Method).

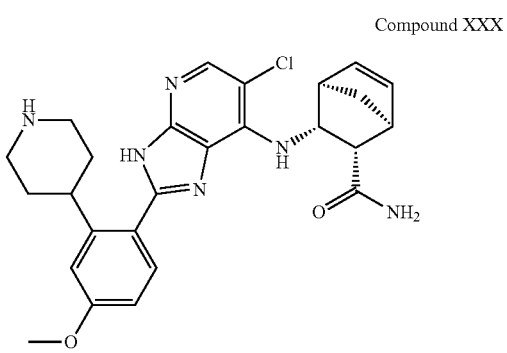 [SMILES: COc1ccc(-c2nc3c(N[C@H]4[C@@H](C(N)=O)[C@@H]5C=C[C@H]4C5)c(Cl)cnc3[nH]2)c(C2CCNCC2)c1]

Compound XXX

Synthesis of (1S,2S,3R,4R)-3-[6-Chloro-2-(4-methoxy-2-piperidin-4-yl-phenyl)-3H-imidazo[4,5-b]pyridine-7-ylamino]-bicyclo[2.2.1]hept-5-ene-2-carboxylic acid amide (Compound XXX)

4-{2-[7-((1R,2R,3S,4S)-3-Carbamoyl-bicyclo[2.2.1]hept-5-en-2-ylamino)-6-chloro-3H-imidazo[4,5-b]pyridine-2-yl]-5-methoxy-phenyl}-piperidinej-1-carboxylic acid tert-butyl ester (Compound XXIX) (754 mg, 1.27 mmol) was treated with 4M hydrogen chloride in dioxane (50 mL, 200 mmol) at 60° C. for three hours. The reaction was concentrated, taken up into dichloromethane, neutralized with saturated sodium bicarbonate solution. The organics were concentrated onto Celite and purified via ISCO chromatography (gradient elution on a 40 g silica cartridge: 0 to 100% (2:20:78 ammonia:methanol:dichloromethane):methanol to afford 265 mg (63%) of the title compound as a white solid. Mp 199-200° C. $^1$H NMR (d-6 DMSO): 7.95 (s, 1H), 7.81 (br s, J=1H), 7.55 (d, J=8 Hz, 1H), 7.20 (m, 2H), 6.95 (m, 2H), 6.28 m (1H), 6.17 (m, 1H), 5.16 (t, J=8 Hz, 1H), 3.84 (s, 3H), 3.64 (m, 1H), 2.95 (m, 2H), 2.86 (s, 1H), 2.76 (s, 1H), 2.58 (d, J=8 Hz, 1H), 2.49-2.39 (m, 4H), 2.26 (d, J=8 Hz, 1H), 1.77 (d, J=10 Hz, 1H), 1.60 (m, 2H), 1.47 (m, 1H), 1.38 (d, J=8 Hz, 1H). MS: 493.1 (M+H). HPLC retention time: 1.98 minutes (G Method).

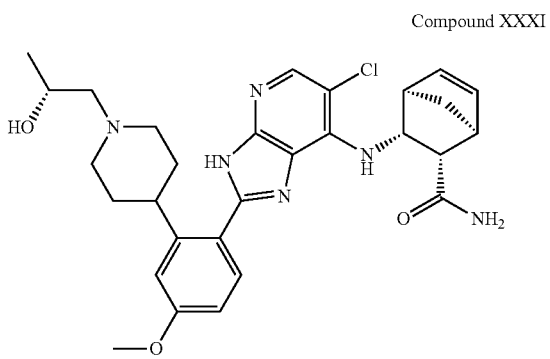 [SMILES: COc1ccc(-c2nc3c(N[C@H]4[C@@H](C(N)=O)[C@@H]5C=C[C@H]4C5)c(Cl)cnc3[nH]2)c(C2CCN(C[C@@H](C)O)CC2)c1]

Compound XXXI

Synthesis of (1S,2S,3R,4R)-3-(6-Chloro-2-{2-[1-((R-2-hydroxyporpyl)-piperidin-4-yl]-4-methoxyphenyl}-3H-imidazo[4,5-b]pyridin-7-ylamino)-bicyclo[2.2.1]hept-5-ene-2-carboxylic acid amide (Compound XXXI)

(1S,2S,3R,4R)-3-[6-Chloro-2-(4-methoxy-2-piperidin-4-yl-phenyl)-3H-imidazo[4,5-b]pyridine-7-ylamino]-bicyclo[2.2.1]hept-5-ene-2-carboxylic acid amide (Compound XXX) (60 mg, 0.1 mmol) was stirred with (S)-propylene oxide (11.0 mg, 1.5 mmol) in methanol (5 mL) in a sealed tube overnight. The reaction was concentrated and the product purified by reverse phase chromatography (Gilson). Desired fractions were collected, combined, and neutralized by partitioning between dichloromethane and saturated sodium bicarbonate solution. The organic layer was separated, dried (magnesium sulfate) and concentrated to afford the title compound as a white solid (22 mg, 30%). Mp 186-7. $^1$H NMR (d-chloroform): 14.14 (br s, 1H), 7.82 (s, J=1H), 7.65 (d, J=8 Hz, 1H), 7.06 (s, 1H), 6.95 (d, J=8 Hz, 1H), 6.28 (m, 3H), 5.73 (m, 1H), 5.54 (m, 1H), 5.22 (t, J=8 Hz, 1H), 3.95 (s, 3H), 3.90 (m, 1H), 3.72 (m, 1H), 3.13 (m, 2H), 2.90 (m, 2H), 2.72 (d, J=9 Hz, 1H), 2.33 (m, 4H), 1.97-1.69 (m, 6H), 1.28 (s, 1H), 1.18 (d, J=5 Hz, 3H). MS: 551.19 (M+H). HPLC retention time: 1.98 minutes (G Method).

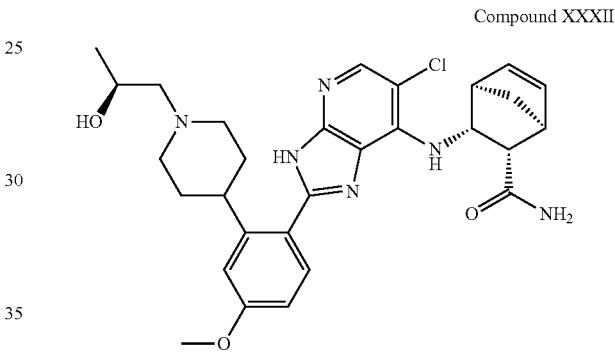

Compound XXXII

Synthesis of (1S,2S,3R,4R)-3-(6-Chloro-2-{2-[1-((S)-2-hydroxypropyl)-piperidin-4-yl]-4-methoxyphenyl}-3H-imidazo[4,5-b]pyridin-7-ylamino)-bicyclo[2.2.1]hept-5-ene-2-carboxylic acid amide (Compound XXXII)

(1S,2S,3R,4R)-3-[6-Chloro-2-(4-methoxy-2-piperidin-4-yl-phenyl)-3H-imidazo[4,5-b]pyridine-7-ylamino]-bicyclo[2.2.1]hept-5-ene-2-carboxylic acid amide (Compound XXX) (60 mg, 0.1 mmol) was stirred with (R)-propylene oxide (8.0 mg, 1.0 mmol) in methanol (5 mL) in a sealed tube overnight. The reaction was concentrated and the product purified by reverse phase chromatography (Gilson). Desired fractions were collected, combined, and neutralized by partitioning between dichloromethane and saturated sodium bicarbonate solution. The organic layer was separated, dried (magnesium sulfate) and concentrated to afford the title compound as a white solid 9 mg, 10%). $^1$H NMR (d-chloroform): 13.83 (br s, 1H), 7.89 (s, 1H), 7.66 (d, J=8 Hz, 1H), 7.07 (s, 1H), 6.97 (d, J=8 Hz, 1H), 6.32-6.28 (m, 3H), 5.62 (m, 1H), 5.22 (m, 2H), 3.95 (s, 3H), 3.87 (m, 1H), 3.70 (m, 1H), 3.15 (s, 1H), 3.07 (m, 1H), 2.93 (m, 2H), 2.74 (d, J=7 Hz, 1H), 2.36 (m, 4H), 1.99 (m, 3H), 1.76 (m, 3H), 1.28 (s, 1H), 1.18 (d, J=5 Hz, 3H). MS: 551.18 (M+H). HPLC retention time: 1.99 minutes (G Method).

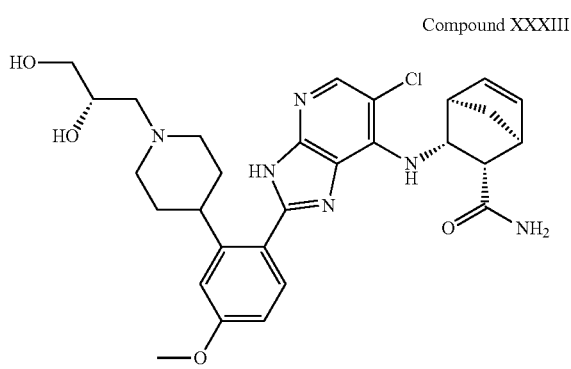 [SMILES: COc1ccc(-c2nc3c(N[C@H]4[C@@H](C(N)=O)[C@@H]5C=C[C@H]4C5)c(Cl)cnc3[nH]2)c(C2CCN(C[C@H](O)CO)CC2)c1]

Compound XXXIII

Synthesis of 1S,2S 3R,4R)-3-(6-Chloro-2-{2-[1-((S)-2,3-dihydroxypropyl)-piperidin-4-yl]-4-methoxy-phenyl}-3H-imidazo[4,5-b]pyridin-7-ylamino)-bicyclo[2.2.1]hept-5-ene-2-carboxylic acid amide (Compound XXXIII)

(1S,2S,3R,4R)-3-[6-Chloro-2-(4-methoxy-2-piperidin-4-yl-phenyl)-3H-imidazo[4,5-b]pyridine-7-ylamino]-bicyclo[2.2.1]hept-5-ene-2-carboxylic acid amide (Compound XXX) (60 mg, 0.1 mmol) was stirred with (R)-1-oxiranyl-methanol (14.0 mg, 1.5 mmol) in methanol (5 mL) in a sealed tube overnight. The reaction was concentrated and the product purified by reverse phase chromatography (Gilson). Desired fractions were collected, combined, and lyophilized to afford the title compound as a white lyophilate (46 mg, 70%). $^1$H NMR (d-chloroform): 9.16 (br s, 1H), 8.03 (s, 1H), 7.65 (m, 2H), 7.30 (m, 1H), 7.02 (d, J=9 Hz, 1H), 6.95 (s, 1H), 6.32 (s, 1H), 6.17 (s, 1H), 5.52 (br m, 1H), 5.15 (m, 1H), 3.87 (m, 1H), 3.85 (s, 3H), 3.65-3.26 (m, 8H), 3.22-2.70 (m, 5H), 2.24 (d, J=9 Hz, 1H), 2.12 (m, 4H), 1.94 (m, 1H), 1.28 (s, 1H), 1.18 (d, J=5 Hz, 3H). MS: 567.17 (M+H). HPLC retention time: 1.91 minutes (G Method).

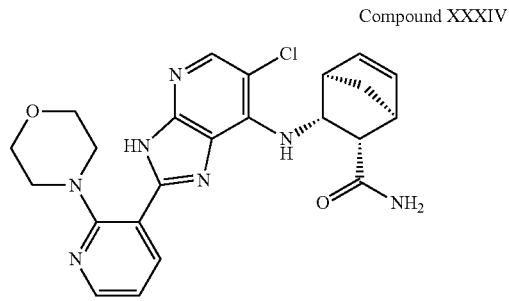 [SMILES: NC(=O)[C@@H]1[C@H](Nc2c(Cl)cnc3[nH]c(-c4cccnc4N4CCOCC4)nc23)[C@H]2C=C[C@@H]1C2]

Compound XXXIV

Synthesis of (1S,2S,3R,4R)-3-[6-Chloro-2-(2-morpholin-4-yl-pyridin-3-yl)-3H-imidazo[4,5-b]pyridine-7-ylamino]-bicyclo[2.2.1]hept-5-ene-2-carboxylic acid amide (Compound XXXIV)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 2-morpholinyl-4-yl-pyridine-3-carbaldehyde were reacted to produce the title compound (52%). $^1$H NMR (d-chloroform): 8.49 (br s, 1H), 8.36 (s, 1H), 8.25 (s, 1H), 8.04 (d, J=7 Hz, 1H), 7.91 (s, 1H), 7.32 (s, 1H), 7.13 (t, J=7 Hz, 1H), 6.36 (s, 2H), 5.05 (t, J=7 Hz, 1H), 3.68 (m, 4H), 3.09 (m, 4H), 2.90 (m, 2H), 2.62 (d, J=7 Hz, 1H), 2.18 (d, J=7 Hz, 1H), 1.42 (d, J=8 Hz, 1H) MS: 466.16 (M+H). HPLC retention time: 1.95 minutes (G Method).

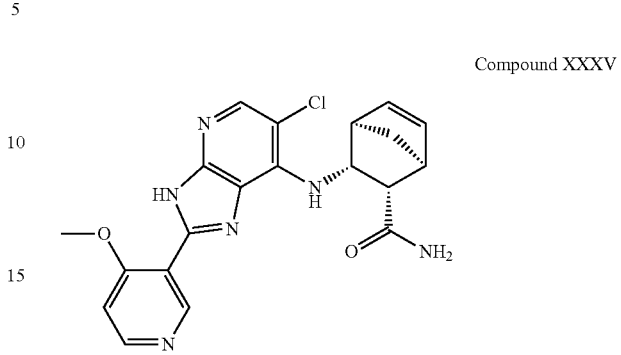

Compound XXXV

Synthesis of (1S,2S,3R,4R)-3-[6-Chloro-2-(4-methoxy-pyridin-3-yl)-3H-imidazo[4,5-b]pyridine-7-ylamino]-bicyclo[2.2.1]hept-5-ene-2-carboxylic acid amide (Compound XXXV)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 4-methoxy-pyridine-3-carbaldehyde were reacted to produce the title compound (89%). $^1$H NMR (d-6 DMSO): 13.16 (br s, 1H), 9.19 (s, 1H), 8.81 (s, 1H), 8.10 (s, 1H), 7.83 (s, 1H), 7.70 (m, 2H), 7.28 (s, 1H), 6.40 (s, 1H), 6.38 (s, 1H), 5.10 (t, J=7 Hz, 1H), 4.21 (s, 3H), 2.92 (s, 1H), 2.85 (s, 1H), 2.63 (d, J=8 Hz, 1H), 2.23 (d, J=8 Hz, 1H), 1.41 (d, J=8 Hz, 1H). MS: 411.14 (M+H). HPLC retention time: 1.60 minutes (G Method)

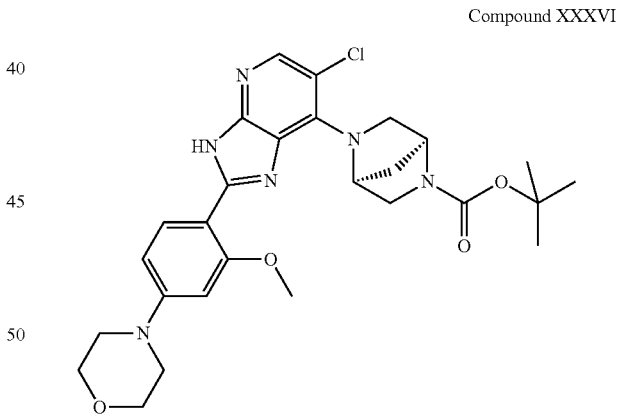

Compound XXXVI

Synthesis of (1S,4S)-5-[6-Chloro-2-(2-methoxy-4-morpholinj-4-yl-phenyl)-3H-imidazol-[4,5-b]pyridine-7-yl]-2,5-diaza-bicyclo[2.2.1]heptane-2-carboxylic acid tert-butyl ester (Compound XXXVI)

In the same fashion as for Compound III, (1S,4S)-5-(2,3-Diamino-5-chloro-pyridin-4-yl)-2,5-diaza-bicyclo[2.2.1]heptane-2-carboxylic acid tert-butyl ester and 2-methoxy-4-morpholin-4-yl-benzaldehyde were reacted to produce the title compound (50%). $^1$H NMR (d-6 DMSO): 12.23 (br s, 1H), 8.01 (d, J=8 Hz, 1H), 7.93 (s, 1H), 6.67 (d, J=8 Hz, 1H), 6.63 (s, 1H), 5.71 (d. J=53 Hz, 1H), 4.48 (d, J=22 Hz, 1H), 4.30 (d, J=9 Hz, 1H), 3.96 (s, 3H), 3.76 (s, 4H), 3.62 (m, 1H), 3.52 (m, 2H), 3.27 (s, 4H), 1.97 (m, 2H), 1.36 (m, 9H). MS: 541.23 (M+H). HPLC retention time: 3.02 minutes (G Method).

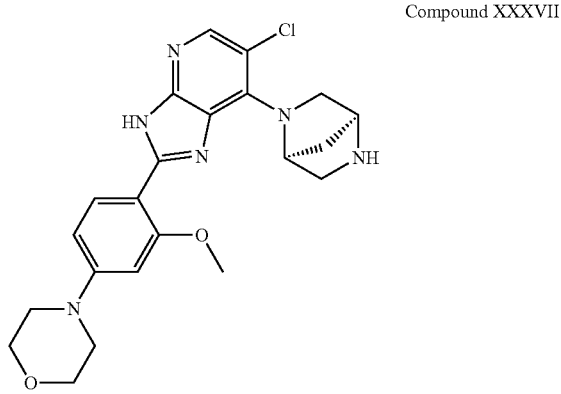 [SMILES: COc1cc(N2CCOCC2)ccc1-c1nc2c(N3C[C@@H]4C[C@H]3CN4)c(Cl)cnc2[nH]1]

Compound XXXVII

Synthesis of 6-Chloro-7-(1S,4S)-2,5-diaza-bicyclo[2.2.1]hept-2-yl-2-(2-methoxy-4-morpholin-4-yl-phenyl)-3H-imidazo[4,5-b]pyridine hydrochloride (Compound XXXVII)

(1S,4S)-5-[6-Chloro-2-(2-methoxy-4-morpholinj-4-yl-phenyl)-3H-imidazo[4,5-b]pyridine-7-yl]-2,5-diaza-bicyclo[2.2.1]heptane-2-carboxylic acid tert-butyl ester derived above (174 mg, 0.322 mmol) was reacted with 4M hydrogen chloride in 1,4-dioxane (10 mL) at 60° C. for 72 hours. The reaction was permitted to cool and a green solid was isolated by filtration and dried in vacuo. $^1$H NMR (d-6 DMSO): 12.42 (br s, 1H), 9.34 (br s, 1H), 8.77 (br s, 1H), 8.03 (m, 2H), 6.66 (m, 2H), 5.76 (s, 1H), 4.48 (s, 2H), 4.34 (d, J=9 Hz, 1H), 3.97 (s, 2H), 3.88 (d, J=9 Hz, 2H), 3.77 (s, 3H), 3.57 (m, 1H), 3.28 (s, 4H), 2.19 (d, J=9 Hz, 2H), 2.04 (d, J=9 Hz, 1H). MS: 441.18 (M+H). HPLC retention time: 1.79 minutes (G Method).

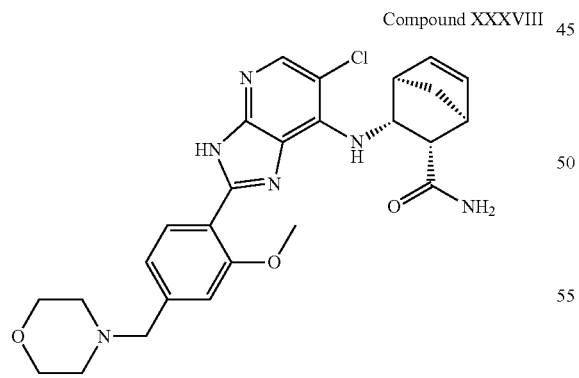

Compound XXXVIII

Synthesis of (1S,2S,3R,4R)-3-[6-Chloro-2-(2-methoxy-4-morpholin-4-yl-phenyl)-3H-imidazo[4,5-b]pyridine-7-ylamino]-bicyclo[2.2.1]hept-5-ene-2-carboxylic acid amide (Compound XXXVIII)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 2-methoxy-4-morpholin-4-yl-benzaldehyde were reacted to produce the title compound (65%). $^1$H NMR (d-chloroform): 13.88 (br s, 1H), 8.25 (m, 2H), 7.77 (s, 1H), 7.18 (s, 1H), 7.07 (d, J=7 Hz, 1H), 6.42 (m, 3H), 5.81 (s, 1H), 5.29 (t, J=7 Hz, 1H), 4.53 (d, J=9 Hz, 1H), 4.10-3.94 (m, 10H), 3.68 (m, 1H), 3.35 (m, 1H), 3.16 (s, 1H), 2.92 (s, 1H), 2.77 (d, J=8 Hz, 1H), 2.38 (d, J=9 Hz, 1H), 1.63 (d, J=9 Hz, 1H). MS: 509.16 (M+H). HPLC retention time: 1.82 minutes (G Method).

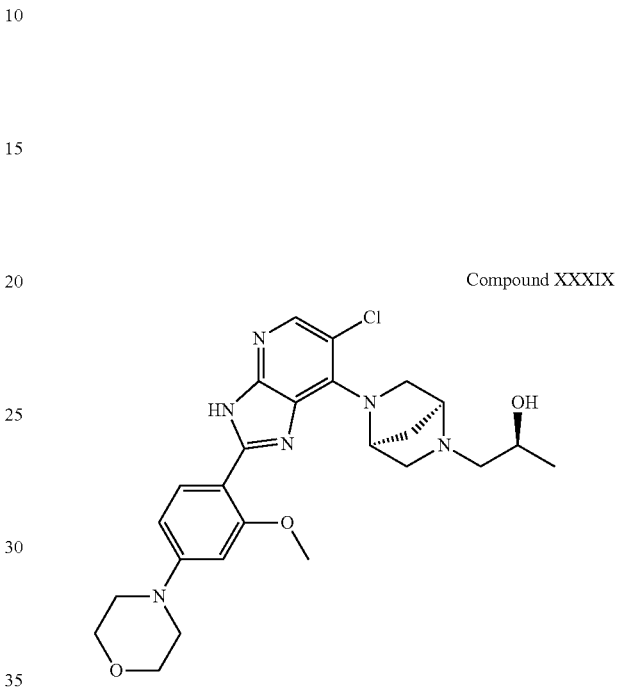

Compound XXXIX

Synthesis of (S)-1-[(1S,4S)-5-[6-Chloro-2-(methoxy-4-morpholin-4-yl-phenyl)-3H-imidazo[4,5-b]pyridine-7-yl]-2,5-diaza-bicyclo[2.2.1]hept-2-yl]-propan-2-ol (Compound XXXIX)

6-Chloro-7-(1S,4S)-2,5-diaza-bicyclo[2.2.1]hept-2-yl-2-(2-methoxy-4-morpholin-4-yl-phenyl)-3H-imidazo[4,5-b]pyridine hydrochloride (Compound XXXVII) (50 mg, 0.1 mmol), (S)-2-methyl-oxirane (7.30 mg, 0.126 mmol), pyridine (10.2 μL, 0.126 mmol), and methanol (3.0 mL) were stirred in a sealed tube at room temperature overnight. An additional equivalent each of epoxide and Hunig's base were added and the mixture was heated at 80° C. overnight. The mixture was concentrated and the material was subjected to purification via reverse phase chromatography (Gilson) to afford the title compound as a yellow lyophilate (26 mg, 50%). $^1$H NMR (d-chloroform): 13.63 (br s, 1H), 8.10 (m, 1H), 7.90 (s, 1H), 7.71 (s, 1H), 7.55 (s, 1H), 6.59 (m, 1H), 6.46 (s, 1H), 4.62 (m, 1H), 4.35 (m, 1H), 4.24 (t, J=7 Hz, 2H), 4.15 (s, 3H), 3.92 (s, 4H), 3.35 (s, 4H), 3.14 (m, 2H), 2.38 (m, 1H), 1.71 (m, 1H), 1.44 (m, 2H), 1.32 (m, 1H), 0.94 (m, 3H). MS: 499.18 (M+H). HPLC retention time: 1.83 minutes (G Method).

Compound XL

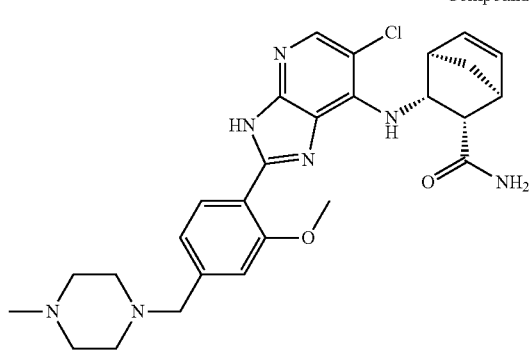

Synthesis of (1S,2S,3R,4R)-3-{6-Chloro-2-[2-methoxy-4-(4-methyl-piperazin-1-ylmethyl)-phenyl]-3H-imidazo[4,5-b]pyridin-7-ylamino}-bicyclo[2.2.1]hept-5-ene-2-carboxylic acid amide (Compound XL)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 2-methoxy-4-(4-methyl-piperazin-1-ylmethyl)-benzaldehyde bis trifluoroacetate were reacted to produce the title compound (18%). $^1$H NMR (d-chloroform): 10.74 (s, 1H), 8.34 (d, J=7 Hz, 1H), 8.03 (s, 1H), 7.12 (m, 2H), 6.37 (m, 3H), 5.55 (d, J=8 Hz, 1H), 5.20 (t, J=7 Hz, 1H), 5.14 (br s, 1H), 4.08 (s, 3H), 3.58 (s, 2H), 3.18 (s, 1H), 2.91 (s, 1H), 2.88 (d, J=7 Hz, 1H), 2.52 (m, 4H), 2.36 (m, 1H), 2.33 (s, 3H), 1.74 (m, 4H), 1.29 (m, 1H). MS: 522.2 (M+H). HPLC retention time: 1.71 minutes (G Method).

Compound XLI

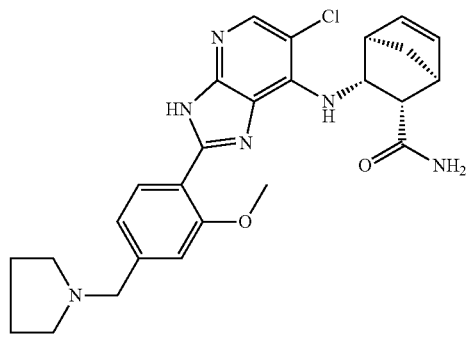

Synthesis of (1S,2S,3R,4R)-3-{6-Chloro-2-[2-methoxy-4-pyrrolidin-1-ylmethyl)-phenyl]-3H-imidazo[4,5-b]pyridin-7-ylamino}-bicyclo[2.2.1]hept-5-ene-2-carboxylic acid amide (Compound XLI)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 2-methoxy-4-pyrrolidin-1-ylmethyl-benzaldehyde were reacted to produce the title compound (10%). $^1$H NMR (d-6 DMSO): 12.39 (s, 1H), 8.09 (m, 1H), 7.96 (s, 1H), 7.77 (s, 1H), 7.27-7.07 (m, 4H), 6.37 (m, 2H), 5.76 (s, 1H), 5.20 (m, 1H), 3.96 (s, 3H), 3.65 (s, 2H), 3.34 (m, 2H), 2.89 (s, 1H), 2.79 (s 1H), 2.69-2.34 (m, 4H), 2.24 (m, 1H), 1.73 (m, 4H), 1.39 (m, 1H). MS: 493.18 (M+H). HPLC retention time: 1.86 minutes (G Method).

Compound XLII

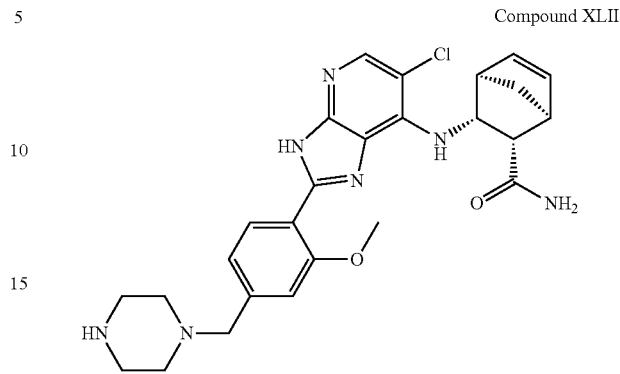

Synthesis of (1S,2S,3R,4R)-3-[6-Chloro-2-(2-methoxy-4-piperazin-1-ylmethyl-phenyl)-3H-imidazo[4,5-b]pyridin-7-ylamino]-bicyclo[2.2.1]hept-5-ene-2-carboxylic acid amide (Compound XLII)

In the same fashion as for Compound III, (1S,2S,3R,4R)-3-(2,3-Diamino-5-chloro-pyridin-4-ylamino)-bicyclo[2.2.1]hept-5-ene-2-carboxylic acid amide and 4-(4-formyl-3-methoxy-benzyl)-piperazine-1-carboxylic acid tert-butyl ester were reacted to produce a material which following treatment with trifluoroacetic acid at 40° C. for four hours, followed by concentration and neutralization afforded the title compound (10%). $^1$H NMR (d-4 methanol): 8.30 (d, J=7 Hz, 1H), 8.11 (s, 1H), 7.40 (s, 1H), 7.27 (d, J=7 Hz, 1H), 6.47 (m, 2H), 5.09 (m, 1H), 4.34 (m, 2H), 4.13 (s, 3H), 3.73 (s, 1H), 3.56 (s, 4H), 3.44 (s, 4H), 3.07 (s 1H), 3.02 (s, 1H), 2.75 (s, J=8 Hz, 1H), 2.18 (m, 2H), 1.87 (s, 1H), 1.58 (d, J=8 Hz, 1H), 1.30 (s, 1H). MS: 508.2 (M+H). HPLC retention time: 1.66 minutes (G Method).

Compound XLIII

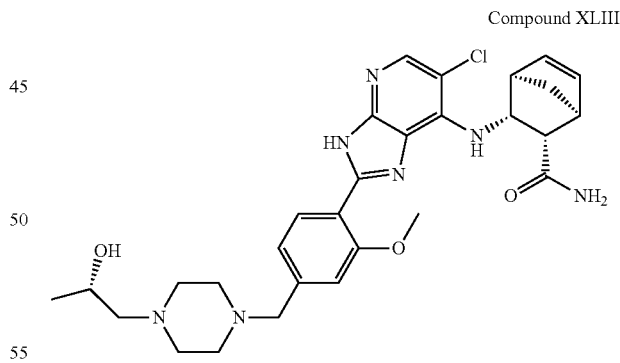

Synthesis of (1S,2S,3R,4R)-3-(6-Chloro-2-{4-[4-((S)-2-hydroxypropyl)-piperazin-1-ylmethyl]-2-methoxyphenyl}-3H-imidazo[4,5-b]pyridin-7-ylamino)-bicyclo[2.2.1]hept-5-ene-2-carboxylic acid amide (Compound XLIII)

(1S,2S,3R,4R)-3-[6-Chloro-2-(2-methoxy-4-piperazin-1-ylmethyl-phenyl)-3H-imidazo[4,5-b]pyridin-7-ylamino]-bicyclo[2.2.1]hept-5-ene-2-carboxylic acid amide (Compound XLII above) (45 mg, 0.088 mmol) was reacted with (S)-(−)-propylene oxide (7.7 mg, 0.13 mmol) in methanol (5 mL) at 60° C. in a sealed tube for six hours. The reaction was concentrated to afford the title compound as a rust colored solid (14 mg, 28%). Mp 142-6° C. ¹H NMR (d-chloroform): 10.76 (br s, 1H), 8.34 (d, J=9 Hz, 1H), 8.04 (s, 1H), 7.12 (m, 2H), 6.37 (m, 3H), 5.57 (d, J=9 Hz, 1H), 5.19 (m, 2H), 4.08 (s, 3H), 3.84 (m, 1H), 3.58 (s, 2H), 3.49 (m, 1H), 3.18 (s, 1H), 2.92 (s 1H), 2.87 (d, J=9 Hz, 1H), 2.72 (m, 2H), 2.62-2.39 (m, 2H), 2.35 (d, J=0 Hz, 1H), 2.26 (m, 1H), 1.76 (d, J=7 Hz, 1H), 1.31 (m, 1H), 1.15 (d, J=9 Hz, 3H). MS: 566.21 (M+H). HPLC retention time: 1.71 minutes (G Method).

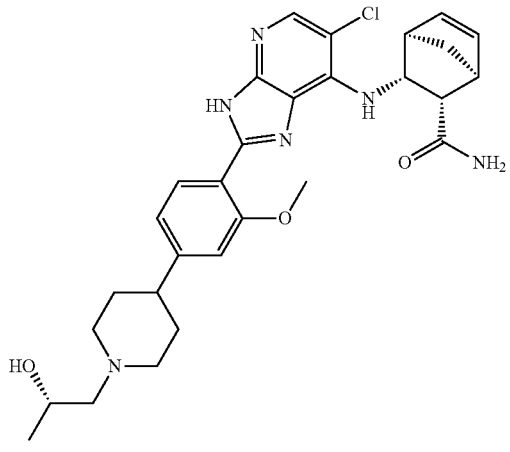

Compound XLV

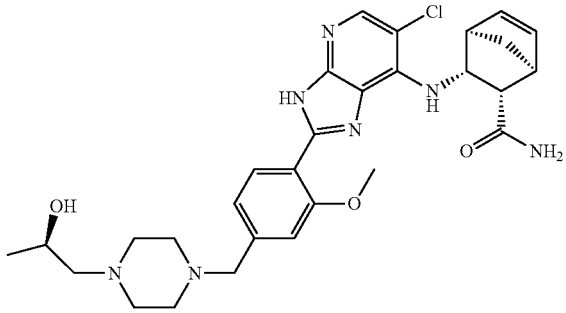

Compound XLIV

Synthesis of (1S,2S,3R,4R)-3-(6-Chloro-2-{4-[1-((S)-2-hydroxypropyl)-piperidin-4-yl]-2-methoxyphenyl}-3H-imidazo[4,5-b]pyridine-7-ylamino)-bicyclo[2.2.1]hept-5-ene-2-carboxylic acid amide (Compound XLV)

In a similar fashion as for the synthesis of III, (1S,2S,3R,4R)-3-(2,3-Diamino-5-chloro-pyridin-4-ylamino)-bicyclo[2.2.1]hept-5-ene-2-carboxylic acid amide and 4-[1-((S)-2-hydroxypropyl)-piperidin-4-yl]-2-methoxy-benzaldehyde were reacted to produce the title compound (70%). ¹H NMR (d-chloroform): 10.81 (br s, 1H), 8.33 (d, J=9 Hz, 1H), 8.01 (s, 1H), 7.03 (d, J=9 Hz, 1H), 6.94 (s, 1H), 6.42 (s, 1H), 6.35 (m, 2H), 5.55 (d, J=8 Hz, 1H), 5.27 (br s, 1H), 5.20 (t, J=9 Hz, 1H), 4.07 (s, 3H), 3.89 (m, 1H), 3.58 (m, 1H), 3.18 (m, 2H), 2.97 (d, J=11 Hz, 1H), 2.92 (s, 1H), 2.87 (d, J=11 Hz, 1H), 2.61 (m, 1H), 2.49-2.24 (m, 4H), 2.08 (t, J=11 Hz, 1H), 1.94-1.71 (m, 5H), 1.18 (d, J=7 Hz, 3H). MS: 551.2 (M+H). HPLC retention time: 1.84 minutes (G Method).

Synthesis of (1S,2S,3R,4R)-3-(6-Chloro-2-{4-[4-((R)-2-hydroxypropyl)-piperazin-1-ylmethyl]-2-methoxyphenyl}-3H-imidazo[4,5-b]pyridine-7-ylamino)-bicyclo[2.2.1]hept-5-ene-2-carboxylic acid amide (Compound XLIV)

In a similar fashion as for the synthesis of Compound XLIII, (1S,2S,3R,4R)-3-[6-Chloro-2-(2-methoxy-4-piperazin-1-ylmethyl-phenyl)-3H-imidazo[4,5-b]pyridine-7-ylamino]-bicyclo[2.2.1]hept-5-ene-2-carboxylic acid amide was reacted with (R)-(−)-propylene oxide to afford the title compound as an orange solid (32%). Mp 157-9° C. ¹H NMR (d-chloroform): 10.72 (br s, 1H), 8.35 (d, J=9 Hz, 1H), 8.05 (s, 1H), 7.04 (m, 2H), 6.37 (m, 3H), 5.56 (d, J=9 Hz, 1H), 5.20 (t, J=8 Hz, 1H), 5.12 (s, 1H), 4.08 (s, 3H), 3.84 (m, 1H), 3.59 (s, 2H), 3.48 (m, 1H), 3.18 (s, 1H), 2.92 (s 1H), 2.88 (d, J=8 Hz, 1H), 2.73 (m, 2H), 2.61-2.41 (m, 5H), 2.37-2.22 (m, 3H), 2.19 (s, 1H), 1.76 (d, J=9 Hz, 1H), 1.15 (d, J=7 Hz, 3H). MS: 566.23 (M+H). HPLC retention time: 1.71 minutes (G Method).

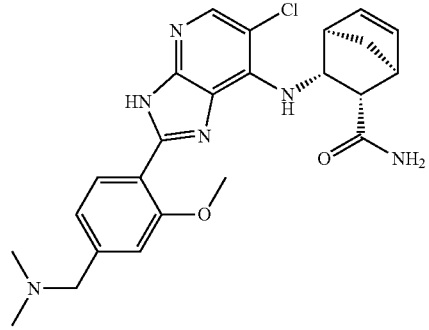

Compound XLVI

Synthesis of (1S,2S,3R,4R)-3-[6-Chloro-2-(4-dimethylaminomethyl-2-methoxyphenyl)-3H-imidazo[4,5-b]pyridine-7-ylamino)-bicyclo[2.2.1]hept-5-ene-2-carboxylic acid amide, trifluoroacetic acid salt (Compound XLVI)

In a similar fashion as for the synthesis of III, (1S,2S,3R,4R)-3-(2,3-Diamino-5-chloro-pyridin-4-ylamino)-bicyclo

[2.2.1]hept-5-ene-2-carboxylic acid amide and 4-dimethylaminomethyl-2-methoxy-benzaldehyde were reacted to produce following lyophilization of desired reverse-phase hplc fractions the title compound (63%). ¹H NMR (d-chloroform): 13.99 (s, 1H), 13.71 (br s, 1H), 8.33 (d, J=8 Hz, 1H), 8.26 (d, J=9 Hz, 1H), 7.80 (s, 1H), 7.24 (s, 1H), 7.11 (d, J=7 Hz, 1H), 6.44 (s, 2H), 6.23 (s, 1H), 5.62 (s, 1H), 5.36 (d, J=7 Hz, 1H), 4.45 (d, J=9 Hz, 1H), 4.13 (d, J=9 Hz, 1H), 4.09 (s, 3H), 3.16 (s, 1H), 2.96 (s, 1H), 2.91 (s, 3H), 2.81 (s, 3H), 2.76 (d, J=7 Hz, 1H), 2.32 (d, J=7 Hz, 1H), 1.65 (d, J=7 Hz, 1H). MS: 467.16 (M+H). HPLC retention time: 1.76 minutes (G Method).

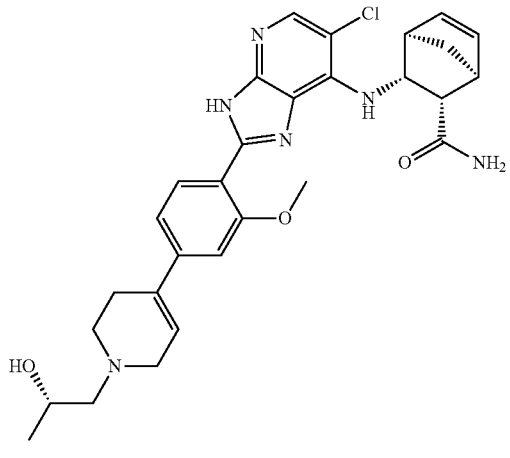

Compound XLVIII

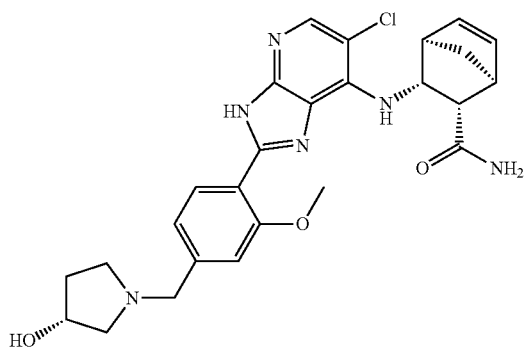

Compound XLVII

Synthesis of (1S,2S,3R,4R)-3-(6-Chloro-2-[4-[1((S)-2-hydroxypropyl)-1,2,3,6-tetrahydro-pyridin-4-yl]-2-methoxyphenyl]-3H-imidazo[4,5-b]pyridine-7-ylamino)-bicyclo[2.2.1]hept-5-ene-2-carboxylic acid amide (Compound XLVIII)

In a similar fashion as for the synthesis of III, (1S,2S,3R,4R)-3-(2,3-Diamino-5-chloro-pyridin-4-ylamino)-bicyclo[2.2.1]hept-5-ene-2-carboxylic acid amide and 4[1-((S)-2-hydroxypropyl)-1,2,3,6-tetrahydro-pyridin-4-yl]-2-methoxybenzaldehyde were reacted to produce the title compound (44%). ¹H NMR (d-4 methanol): 8.26 (d, J=7 Hz, 1H), 7.94 (s, 1H), 7.24 (m, 2H), 6.42 (m, 2H), 6.31 (s, 1H), 5.33 (m, 1H), 4.29 (m, 1H), 4.11 (s, 3H), 4.07 (m, 2H), 3.65 (m, 2H), 3.39-3.27 (m, 6H), 3.17 (m, 1H), 3.07-2.85 (m, 4H), 2.77 (d, J=7 Hz, 1H), 2.34 (d, J=7 Hz, 1H), 1.57 (d, J=7 Hz, 1H), 1.56 (d, J=7 Hz, 1H), 1.30 (d, J=7 Hz, 3H). MS: 549.19 (M+H). HPLC retention time: 1.86 minutes (G Method).

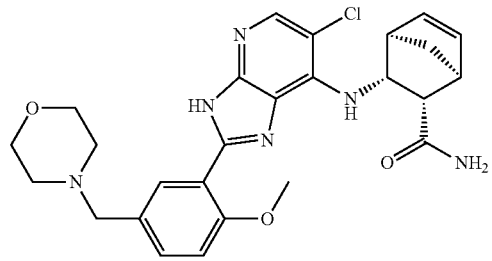

Compound XLIX

Synthesis of (1S,2S,3R,4R)-3-(6-Chloro-2-[4-((R)-3-hydroxy-pyrrolidin-1-ylmethyl)-2-methoxyphenyl]-3H-imidazo[4,5-b]pyridine-7-ylamino)-bicyclo[2.2.1]hept-5-ene-2-carboxylic acid amide (Compound XLVII)

In a similar fashion as for the synthesis of III, (1S,2S,3R,4R)-3-(2,3-Diamino-5-chloro-pyridin-4-ylamino)-bicyclo[2.2.1]hept-5-ene-2-carboxylic acid amide and 4-(R)-3-hydroxy-pyrrolidin-1-ylmethyl)-2-methoxybenzaldehyde were reacted to produce the title compound (63%). ¹H NMR (d-chloroform): 10.81 (br s, 1H), 8.32 (d, J=7 Hz, 1H), 8.02 (s, 1H), 7.09 (m, 2H), 6.42 (s, 1H), 6.35 (m, 2H), 5.58 (d, J=8 Hz, 1H), 5.33 (m, 1H), 5.21 (t, J=7 Hz, 1H), 4.39 (m, 1H), 4.05 (s, 3H), 3.69 (m, 2H), 3.17 (s, 1H), 2.95-2.84 (m, 3H), 2.73 (d, J=8 Hz, 1H), 2.59 (m, 1H), 2.42-2.32 (m, 2H), 2.23 (m, 1H), 1.81 (m, 1H), 1.74 (d, J=7 Hz, 1H). MS: 509.19 (M+H). HPLC retention time: 1.69 minutes (G Method).

Synthesis of (1S,2S,3R,4R)-3-[6-Chloro-2-(2-methoxy-5-morpholin-4-ylphenyl)-3H-imidazo[4,5-b]pyridine-7-ylamino)-bicyclo[2.2.1]hept-5-ene-2-carboxylic acid amide (Compound XLIX)

In a similar fashion as for the synthesis of III, (1S,2S,3R,4R)-3-(2,3-Diamino-5-chloro-pyridin-4-ylamino)-bicyclo[2.2.1]hept-5-ene-2-carboxylic acid amide and 2-methoxy-5-morpholin-4-ylmethylbenzaldehyde were reacted to produce the title compound (60%). ¹H NMR (d-chloroform): 10.71 (s, 1H), 8.42 (s, 1H), 8.05 (s, 1H), 7.41 (d, J=7 Hz, 1H), 7.05 (d, J=8 Hz, 1H), 6.46 (m, 1H), 6.39 (m, 1H), 6.25 (s, 1H), 5.82 (d, J=8 Hz, 1H), 5.25 (t, J=7 Hz, 1H), 5.16 (m, 1H), 4.07 (s, 3H), 3.74 (m, 4H), 3.57 (s, 2H), 3.19 (s, 1H), 2.96 (d, 1H), 2.85 (d, J=7 Hz, 1H), 2.52 (s, 4H), 2.37 (d, J=7 Hz, 1H), 1.75 (d, J=7 Hz, 1H). MS: 509.2 (M+H). HPLC retention time: 1.73 minutes (G Method).

Compound L

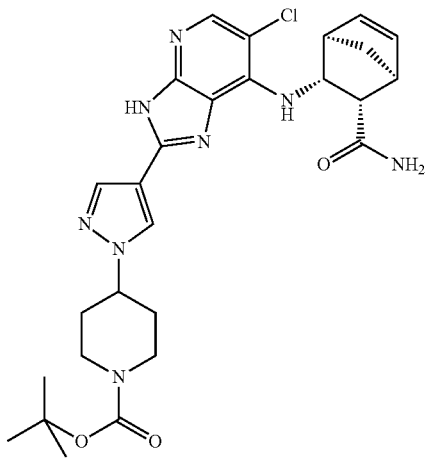

Synthesis of 4-{4-[7-((1R,2R,3S,4S)-3-Carbamoyl-bicyclo[2.2.1]hept-5-en-2-ylamino)-6-chloro-3H-imidazo[4,5-b]pyridine-2-yl]-pyrazol-1-yl}-piperidine-1-carboxylic acid tert-butyl ester (Compound L)

In a similar fashion as for the synthesis of III, (1S,2S,3R,4R)-3-(2,3-Diamino-5-chloro-pyridin-4-ylamino)-bicyclo[2.2.1]hept-5-ene-2-carboxylic acid amide and 4-(4-formyl-pyrazol-1-yl)-piperidine-1-carboxylic acid tertj-butyl ester were reacted to produce the title compound (10%). ¹H NMR (d-chloroform): 8.06-7.92 (m, 3H), 6.37 (m, 2H), 6.27 (s, 1H), 5.90 (s, 1H), 5.82 (d, J=8 Hz, 1H), 5.16 (t, J=7 Hz, 1H), 4.45-4.26 (m, 3H), 3.16 (s, 1H), 2.97 (m, 2H), 2.89 (s, 1H), 2.79 (d, J=7 Hz, 1H), 2.33 (d, J=7 Hz, 1H), 2.27 (d, J=11 Hz, 2H), 2.02 (m, 2H), 1.76-1.57 (m, 2H), 1.52 (s, 9H). MS: 553.2 (M+H). HPLC retention time: 2.64 minutes (G Method).

Compound LI

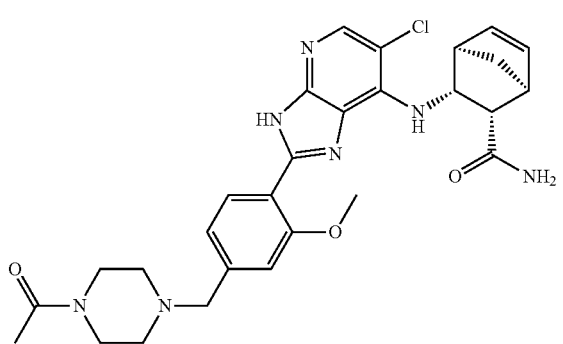

Synthesis of (1S,2S,3R,4S)-3-{2-[4-(4-Acetyl-piperazin-1-ylmethyl)-2-methoxyphenyl]-6-chloro-3H-imidazo[4,5-b]pyridine-7-ylamino}-bicyclo[2.2.1]hept-5-ene-2-carboxylic acid amide (Compound LI)

(1S,2S,3R,4R)-3-[6-Chloro-2-(2-methoxy-4-piperazin-1-ylmethyl-phenyl)-3H-imidazo[4,5-b]pyridine-7-ylamino]-bicyclo[2.2.1]hept-5-ene-2-carboxylic acid amide (Compound XLII) (254 mg, 0.5 mmol) was dissolved in anhydrous dichloromethane (10 mL) and treated with acetic anhydride (1 mL, 10.0 mmol) and triethylamine (1.0 mL, 7.2 mmol) for one hour at ambient temperature. The reaction was concentrated and the product was purified by reverse phase chromatography (Gilson) to afford following neutralization of desired fractions a pale yellow solid as the title compound (91 mg, 30%). Mp 109-113° C. ¹H NMR (d-chloroform): 11.12 (br s, 1H), 8.34 (d, J=7 Hz, 1H), 7.99 (s, 1H), 7.11 (m, 2H), 6.37 (m, 3H), 5.72 (d, J=7 Hz, 1H), 5.36 (m, 1H), 5.22 (t, J=8 Hz, 1H), 4.10 (s, 3H), 3.66 (m, 2H), 3.59 (s, 2H), 3.50 (m, 2H), 3.17 (s 1H), 2.92 (s, 1H), 2.85 (d, J=7 Hz, 1H), 2.48 (m, 4H), 2.34 (d, J=8 Hz, 1H), 2.10 (s, 3H), 1.73 (d, J=7 Hz, 1H). MS: 550.2 (M+H). HPLC retention time: 1.70 minutes (G Method).

Compound LII

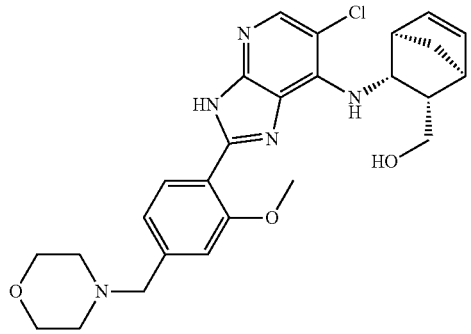

Synthesis of {(diexo)-3-[6-Chloro-2-(2-methoxy-4-morpholin-4-ylmethylphenyl)-3H-imidazo[4,5-b]pyridine-7-ylamino]-bicyclo[2.2.1]hept-5-en-2-yl}-methanol (Compound LII)

In a similar fashion as for the synthesis of III, (diexo)-3-(2,3-diamino-5-chloro-pyridin-4-ylamino)-bicyclo[2.2.1]hept-5-en-2-yl)-methanol and 2-methoxy-4-morpholin-4-yl-methyl-benzaldehyde were reacted to produce the title compound (81%). Mp 115-117° C. ¹H NMR (d-chloroform): 10.74 (s, 1H), 8.36 (d, J=8 Hz, 1H), 8.04 (s, 1H), 7.10 (m, 2H), 6.42 (m, 1H), 6.28 (m, 1H), 5.43 (d, J=7 Hz, 1H), 5.01 (t, J=7 Hz, 1H), 4.06 (s, 3H), 3.96 (m, 1H), 3.81 (m, 1H), 3.74 (m, 4H), 3.56 (s, 2H), 2.93 (s, 1H), 2.84 (s, 1H), 2.76 (m, 1H), 2.48 (m, 4H), 2.23 (m, 1H), 1.91 (d, J=7 Hz, 1H), 1.62 (d, J=8 Hz, 1H). MS: 496.2 (M+H). HPLC retention time: 1.86 minutes (G Method).

Compound LIII

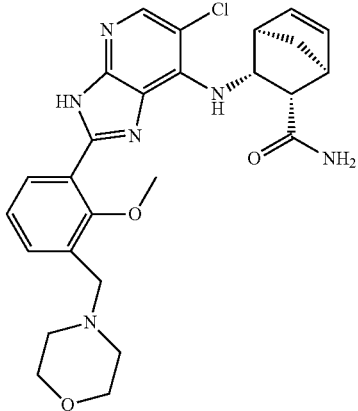

Synthesis of (1S,2S,3R,4R)-3-[6-Chloro-2-(2-methoxy-3-morpholin-4-ylmethyl-phenyl)-3H-imidazo[4,5-b]pyridine-7-ylamino]-bicyclo[2.2.1]hept-5-ene-2-carboxylic acid amide (Compound LIII)

In a similar fashion as for the synthesis of III, (1S,2S,3R,4R)-3-(2,3-Diamino-5-chloro-pyridin-4-ylamino)-bicyclo[2.2.1]hept-5-ene-2-carboxylic acid amide and 2-methoxy-3-morpholin-4-ylmethylbenzaldehyde were reacted to produce the title compound (70%). Mp. 133-7° C. $^1$H NMR (d-chloroform): 12.03 (br s, 1H), 8.18 (d, J=7 Hz, 1H), 8.13 (s, 1H), 7.56 (d, J=7 Hz, 1H), 7.29 (t, J=8 Hz, 1H), 6.37 (m, 2H), 6.29 (s, 1H), 5.82 (d, J=7 Hz, 1H), 5.41 (s, 1H), 5.25 (t, J=7 Hz, 1H), 3.83 (s, 3H), 3.75 (m, 4H), 3.67 (s, 2H), 3.17 (s, 1H), 2.94 (s, 1H), 2.83 (d, J=7 Hz, 1H), 2.58 (m, 4H), 2.36 (d, J=7 Hz, 1H). MS: 509.2 (M+H). HPLC retention time: 1.71 minutes (G Method).

Compound LIV

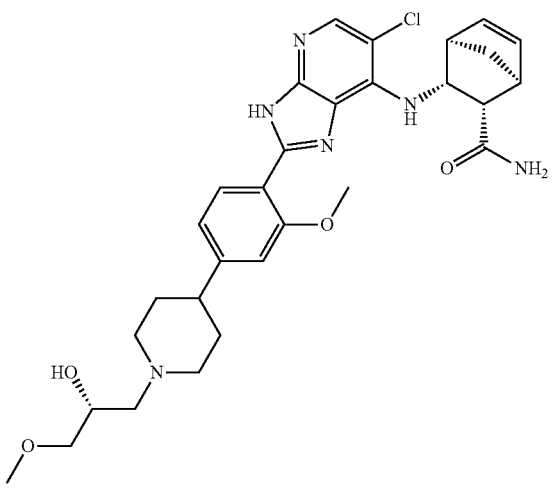

Synthesis of (1S,2S 3R,4R)-3-(6-Chloro-2-{4-[1-(R)-2-hydroxy-3-methoxypropyl)-piperidin-4-yl]-2-methoxyphenyl}-3H-imidazo[4,5-b]pyridine-7-ylamino}-bicyclo[2.2.1]hept-5-ene-2-carboxylic acid amide (Compound LIV)

In a similar fashion as for the synthesis of III, (1S,2S,3R,4R)-3-(2,3-Diamino-5-chloro-pyridin-4-ylamino)-bicyclo[2.2.1]hept-5-ene-2-carboxylic acid amide and 4-[1-(R)-2-hydroxy-3-methoxypropyl)-piperidin-4-yl]-2-methoxybenzaldehyde were reacted to produce the title compound as a yellow solid (40%). Mp. 116-22° C. $^1$H NMR (d-chloroform): 10.84 (br s, 1H), 8.32 (d, J=7 Hz, 1H), 8.00 (s, 1H), 7.03 (d, J=7 Hz, 1H), 6.93 (s, 1H), 6.43 (s, 1H), 6.36 (m, 2H), 5.57 (d, J=7 Hz, 1H), 5.31 (s, 1H), 5.19 (t, J=7 Hz, 1H), 4.07 (s, 3H), 3.95 (m, 1H), 3.48 (m, 1H), 3.43 (s, 3H), 3.42 (m, 1H), 3.17 (m, 2H), 3.01 (d, J=10 Hz, 1H), 2.90 (s, 1H), 2.87 (d, J=7 Hz, 1H), 2.67-2.30 (m, 5H), 2.13 (t, J=10 Hz, 1H), 1.96-1.70 (m, 5H). MS: 581.26 (M+H). HPLC retention time: 1.84 minutes (G Method).

Compound LV

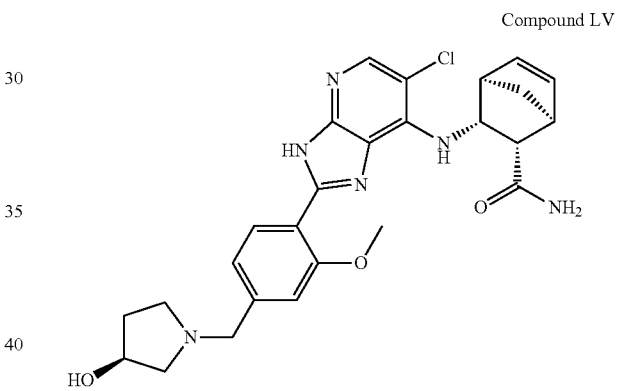

Synthesis of (1S,2S,3R,4R)-3-{6-Chloro-2-[4-((S)-3-hydroxy-pyrrolidin-1-ylmethyl)-2-methoxyphenyl]-3H-imidazo[4,5-b]pyridine-7-ylamino}-bicyclo[2.2.1]hept-5-ene-2-carboxylic acid amide (Compound LV)

In a similar fashion as for the synthesis of III, (1S,2S,3R,4R)-3-(2,3-Diamino-5-chloro-pyridin-4-ylamino)-bicyclo[2.2.1]hept-5-ene-2-carboxylic acid amide and 4-(S)-3-hydroxy-pyrrolidin-1-ylmethyl)-2-methoxybenzaldehyde were reacted to produce the title compound as a yellow solid (40%). Mp. 205-8° C. $^1$H NMR (d-4 methanol): 8.22 (d, J=8 Hz, 1H), 7.91 (m, 2H), 7.22 (s, 1H), 7.08 (d, J=8 Hz, 1H), 6.43 (m, 1H), 6.38 (m, 1H), 5.40 (d, J=10 Hz, 1H), 4.39 (m, 1H), 4.08 (s, 3H), 3.72 (m, 1H), 3.33 (m, 4H), 3.00 (s, 1H), 2.89 (s, 1H), 2.86-2.74 (m, 3H), 2.59 (m, 2H), 2.35 (d, J=8 Hz, 1H), 2.19 (m, 1H), 1.78 (m, 1H), 1.57 (d, J=8 Hz, 1H). MS: 509.17 (M+H). HPLC retention time: 1.71 minutes (G Method).

Compound LVI

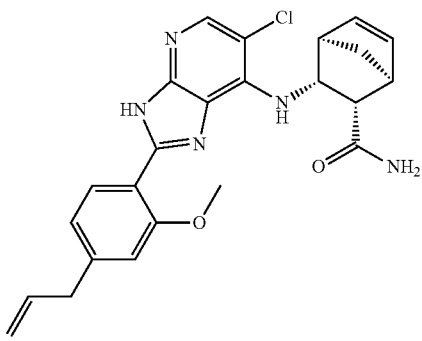

Synthesis of (1S,2S,3R,4R)-3-[2-(4-Allyl-2-methoxy-phenyl)-6-chloro-3H-imidazo[4,5-b]pyridine-7-ylamino]-bicyclo[2.2.1]hept-5-ene-2-carboxylic acid amide (Compound LVI)

In a similar fashion as for the synthesis of III, (1S,2S,3R,4R)-3-(2,3-Diamino-5-chloro-pyridin-4-ylamino)-bicyclo[2.2.1]hept-5-ene-2-carboxylic acid amide and 4-allyl-2-methoxybenzaldehyde were reacted to produce the title compound as a yellow solid (12%). Mp. 123-6° C. $^1$H NMR (d-chloroform): 10.83 (br s, 1H), 8.32 (d, J=8 Hz, 1H), 8.02 (s, 1H), 7.00 (d, J=7 Hz, 1H), 6.91 (s, 1H), 6.46-6.31 (m, 3H), 6.00 (m, 1H), 5.55 (d, J=10 Hz, 1H), 5.28-5.12 (m, 4H), 4.05 (s, 3H), 3.48 (d, J=7 Hz, 1H), 3.18 (s, 1H), 2.91 (s, 1H), 2.87 (d. J=7 Hz, 1H), 2.35 (d, J=8 Hz, 1H), 1.75 (d, J=8 Hz, 1H). MS: 449.9 (M+H). HPLC retention time: 2.94 minutes (G Method).

Compound LVII

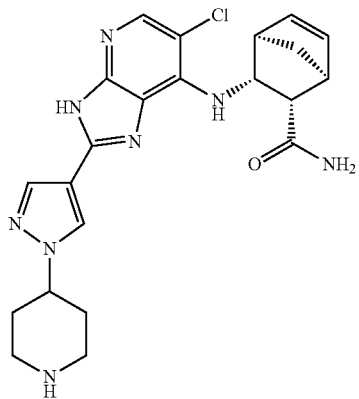

Synthesis of (1S,2S,3R,4R)-3-[6-Chloro-2-(1-piperidin-4-yl-1H-pyrazol-4-yl)-3H-imidazo[4,5-b]pyridine-7-ylamino]-bicyclo[2.2.1]hept-5-ene-2-carboxylic acid amide (Compound LVII)

(1S,2S,3R,4R)-3-(2,3-Diamino-5-chloro-pyridin-4-ylamino)-bicyclo[2.2.1]hept-5-ene-2-carboxylic acid amide and 4-(4-formyl-pyrazol-1-yl)-piperidine-1-carboxylic acid tert-butyl ester were reacted in a similar fashion as for the synthesis of III. The resulting product was treated with 20 equivalents of trifluoroacetic acid in dichloromethane at 40° C. overnight. The solution was concentrated and neutralized to afford the title compound as a tan solid (64%). Mp. 203-5° C. $^1$H NMR (d-4 methanol): 8.27 (s, 1H), 8.07 (s, 1H), 7.89 (s, 1H), 6.42 (m, 1H), 6.37 (m, 1H), 5.32 (m, 1H), 4.87 (m, 3H), 4.44 (m, 1H), 3.33 (m, 2H), 3.25 (m, 2H), 2.98 (s, 1H), 2.90-2.72 (m, 4H), 2.36 (d, J=8 Hz, 1H), 2.20 (m, 2H), 2.04 (m, 2H), 1.57 (d, J=8 Hz, 1H). MS: 452.9 (M+H). HPLC retention time: 1.60 minutes (G Method).

Compound LVIII

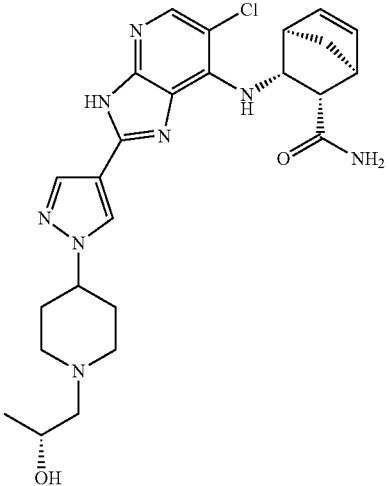

Synthesis of (1S,2S,3R,4R)-3-(6-Chloro-2-{1-[1-((R)-2-hydroxypropyl)-piperidin-4-yl]-1H-pyrazol-4-yl}-3H-imidazo[4,5-b]pyridine-7-ylamino)-bicyclo[2.2.1]hept-5-ene-2-carboxylic acid amide (Compound LVIII)

(1S,2S,3R,4R)-3-[6-Chloro-2-(1-piperidin-4-yl-1H-pyrazol-4-yl)-3H-imidazo[4,5-b]pyridine-7-ylamino]-bicyclo[2.2.1]hept-5-ene-2-carboxylic acid amide (Compound LVII above) (100 mg, 0.2 mmol) was combined with (R)-(−)-propylene oxide (25.6 mg, 0.442 mmol) and MP-Carbonate (140 mg, 0.442 mmol) in methanol (10 mL) and stirred in a sealed tube overnight. The product was filtered and the filtrate concentrated to afford a solid which was purified via reverse phase chromatography (Gilson) to afford following extractive neutralization of fractions and concentration the title compound as a white solid. $^1$H NMR (d-chloroform): 14.01 (br s, 1H), 7.92 (s, 1H), 7.83 (s, 1H), 7.69 (s, 1H), 7.13 (br s, 1H), 6.83 (s, 1H), 6.37 (1, 2H), 6.15 (d, J=9 Hz, 1H), 5.25 (t, J=9 Hz, 1H), 4.26 (m, 1H), 3.89 (m, 1H), 3.22 (d, J=10 Hz, 1H), 3.11 (s, 1H), 2.99 (d, J=10 Hz, 1H), 2.86 (s, 1H), 2.81 (m, 2H), 2.66-2.13 (m, 7H), 2.03 (m, 2H), 1.61 (d, J=10 Hz, 1H), 1.22 (d, J=7 Hz, 3H). MS: 510.9 (M+H). HPLC retention time: 1.59 minutes (G Method).

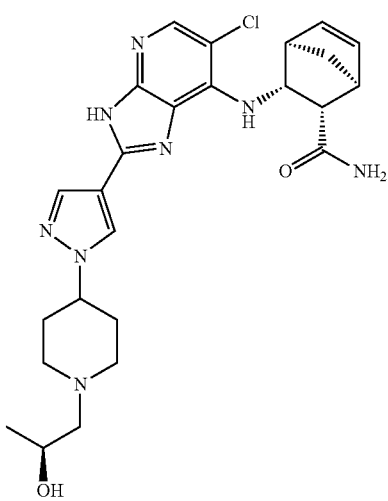

Compound LIX

Synthesis of (1S,2S,3R,4R)-3-(6-Chloro-2-{1-[1((S)-2-hydroxypropyl)-piperidin-4-yl]-1H-pyrazol-4-yl}-3H-imidazo[4,5-b]pyridine-7-ylamino)-bicyclo[2.2.1]hept-5-ene-2-carboxylic acid amide (Compound LIX)

In a similar fashion as for the synthesis of LVIII but employing (S)-(−)-propylene oxide, the title compound was obtained as a white solid (60%). $^1$H NMR (d-6 DMSO): 12.95 (br s, 1H), 8.28 (s, 1H), 8.03 (s, 1H), 7.87 (s, 1H), 6.44 (s, 1H), 6.33 (s, 1H), 5.10 (m, 1H), 4.27 (m, 1H), 4.06 (s, 1H), 3.77 (m, 1H), 3.32 (m, 1H), 2.98 (m, 2H), 2.86 (s, 1H), 2.74 (s, 1H), 2.60 (m, 1H), 2.51 (m, 3H), 2.22 (m, 5H), 2.01 (m, 4H), 1.34 (m, 3H). MS: 511.0 (M+H). HPLC retention time: 1.59 minutes (G Method).

Synthesis of (1S,2S,3R,4R)-3-(6-Chloro-2-{1-[1-((R)-2-hydroxy-3-methoxy-propyl)-piperidin-4-yl]-1H-pyrazol-4-yl}-3H-imidazo[4,5-b]pyridine-7-ylamino)-bicyclo[2.2.1]hept-5-ene-2-carboxylic acid amide (Compound LX)

In a similar fashion as for the synthesis of LVIII but employing (R)-2-methoxymethyl-oxirane, the title compound was obtained as a white solid (40%). $^1$H NMR (d-6 DMSO): 12.98 (br s, 1H), 8.29 (s, 1H), 8.05 (s, 1H), 7.88 (s, 1H), 6.44 (s, 1H), 6.33 (s, 1H), 5.10 (d, J=7 Hz, 1H), 4.59 (m, 1H), 4.28 (m, 1H), 3.77 (m, 1H), 3.37-3.20 (m, 9H), 3.00 (m, 2H), 2.87 (s, 1H), 2.74 (s, 1H), 2.59 (d, J=8 Hz, 1H), 2.44-1.92 (m, 8H), 1.36 (m, 1H). MS: 541.0 (M+H). HPLC retention time: 1.64 minutes (G Method).

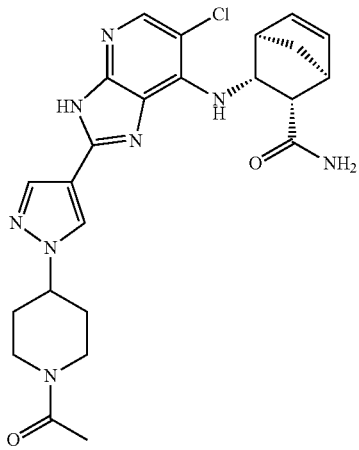

Compound LXI

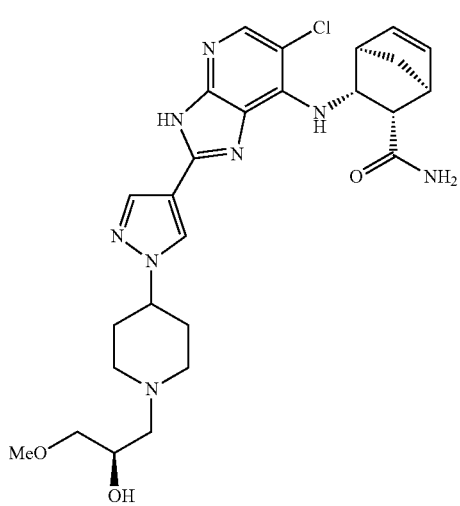

Compound LX

Synthesis of (1S,2S,3R,4R)-3-{2-[1-(1-Acetyl-piperidin-4-yl)-1H-pyrazol-4-yl]-6-chloro-3H-imidazo[4,5-b]pyridine-7-ylamino}-bicyclo[2.2.1]hept-5-ene-2-carboxylic acid amide (Compound LXI)

(1S,2S,3R,4R)-3-[6-Chloro-2-(1-piperidin-4-yl-1H-pyrazol-4-yl)-3H-imidazo[4,5-b]pyridine-7-ylamino]-bicyclo[2.2.1]hept-5-ene-2-carboxylic acid amide (100 mg, 0.20 mmol) and acetic anhydride (45.1 mg, 0.442 mmol) were combined in pyridine (1 mL) and stirred at ambient temperature overnight. The mixture was concentrated and the crude product was purified employing reverse phase chromatography (Gilson) to afford following lyophilization of desired fractions a white lyophilate—the title compound (100%). $^1$H NMR (d-chloroform): 8.38 (d, J=8 Hz, 1H), 8.12 (s, 2H), 7.80 (s, 1H), 6.48 (m, 1H), 6.43 (m, 1H), 5.81 (br s, 1H), 5.40 (br s, 1H), 5.35 (m, 1H), 4.81 (m, 1H), 4.47 (m, 1H), 4.04 (m, 1H), 3.31 (t, J=8 Hz, 1H), 3.17 (s, 1H), 3.03 (s, 1H), 2.82 (m, 1H), 2.65 (m, 1H), 2.36-1.98 (m, 8H), 1.67 (d, J=8 Hz, 1H), 1.26 (d, J=8 Hz, 1H). MS: 494.9 (M+H). HPLC retention time: 1.88 minutes (G Method).

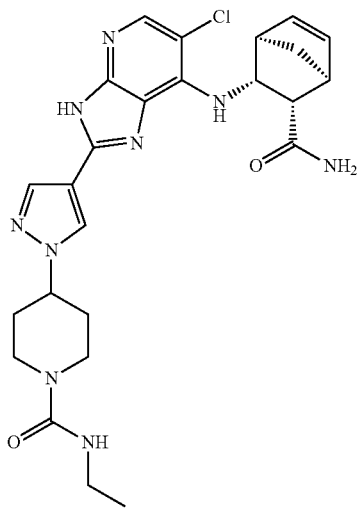

Compound LXII

Synthesis of 4-{4-[7-((1R,2R,3S,4S)-3-Carbamoyl-bicyclo[2.2.1]hept-5-ene-2-ylamino)-6-chloro-3H-imidazo[4,5-b]pyridine-2-yl]-pyrazol-1-yl)-piperidine-1-carboxylic acid ethylamide (Compound LXII)

In a similar fashion as for the synthesis of Compound LXI, (1S,2S,3R,4R)-3-[6-Chloro-2-(1-piperidin-4-yl-1H-pyrazol-4-yl)-3H-imidazo[4,5-b]pyridine-7-ylamino]-bicyclo[2.2.1]hept-5-ene-2-carboxylic acid amide was reacted with ethyl isocyanate to afford the title compound as a white lyophilate (70%). $^1$H NMR (d-chloroform): 8.36 (d, J=8 Hz, 1H), 8.11 (s, 2H), 7.87 (s, 1H), 6.47 (m, 1H), 6.42 (m, 1H), 5.81 (br s, 1H), 5.45 (br s, 1H), 5.36 (m, 1H), 4.42 (m, 2H), 4.15 (m, 2H), 3.33 (m, 2H), 3.17 (s, 1H), 3.02 (m, 3H), 2.67 (d, J=9 Hz, 1H), 2.33 (d, J=9 Hz, 1H), 2.23 (m, 2H), 2.10 (m, 3H), 1.69 (d, J=8 Hz, 1H), 1.20 (t, J=9 Hz, 1H). MS: 524.21 (M+H). HPLC retention time: 1.96 minutes (G Method).

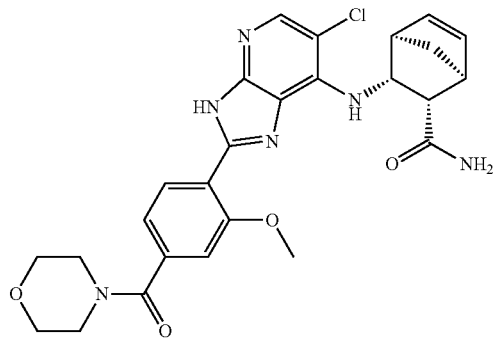

Compound LXIII

Synthesis of (1S,2S,3R,4R)-3-{6-Chloro-2-[2-methoxy-4-(morpholine-4-carbonyl)-phenyl]-3H-imidazo[4,5-b]pyridine-7-ylamino}-bicyclo[2.2.1]hept-5-ene-2-carboxylic acid amide (Compound LXIII): pyridine-7-ylamino}-bicyclo[2.2.1]hept-5-ene-2-carboxylic acid amide (Compound LXIII)

In a similar fashion as for the synthesis of III, (1S,2S,3R,4R)-3-(2,3-Diamino-5-chloro-pyridin-4-ylamino)-bicyclo[2.2.1]hept-5-ene-2-carboxylic acid amide and 2-methoxy-4-(morpholine-4-carbonyl-benzaldehyde were reacted to produce the title compound (100%). $^1$H NMR (d-chloroform): 10.95 (br s, 1H), 8.40 (d, J=8 Hz, 1H), 8.01 (s, 1H), 7.19 (s, 1H), 7.13 (m, 1H), 6.48 (br s, 1H), 6.35 (s, 2H), 6.01 (m, 1H), 5.63 (br s, 1H), 5.11 (t, J=7 Hz, 1H), 4.07 (s, 3H), 3.94-3.38 (m, 8H), 3.14 (s, 1H), 2.90 (s, 1H), 2.78 (d, J=8 Hz, 1H), 2.34 (d, J=8 Hz, 1H), 1.68 (d, J=8 Hz, 1H). MS: 522.9 (M+H). HPLC retention time: 2.08 minutes (G Method).

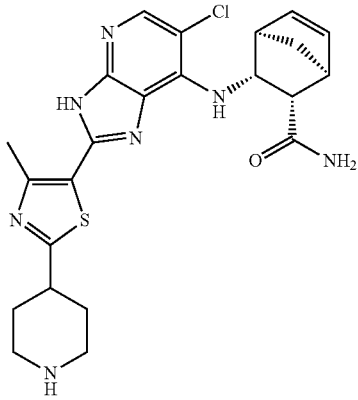

Compound LXIV

Synthesis of (1S,2S,3R,4R)-3-[6-Chloro-2-(4-methyl-2-piperidin-4-yl-thiazol-5-yl)-3H-imidazo[4,5-b]pyridine-7-ylamino]-bicyclo[2.2.1]hept-5-ene-2-carboxylic acid amide (Compound LXIV)

In a similar fashion as for the synthesis of III, (1S,2S,3R,4R)-3-(2,3-diamino-5-chloro-pyridin-4-ylamino)-bicyclo[2.2.1]hept-5-ene-2-carboxylic acid amide and 4-(5-formyl-4-methyl-thiazol-2-yl)-piperidine-1-carboxylic acid tertj-butyl ester were reacted to produce 4-{5-[7-((1R,2R,3S,4S)-3-carbamoyl-bicyclo[2.2.1]hept-5-en-2-ylamino)-6-chloro-3H-imidazo[4,5-b]pyridine-2-yl]-4-methyl-thiazol-2-yl}-piperidine-1-carboxylic acid tert-butyl ester (90%). This latter compound (1.83 mmol) was subjected to reaction with trifluoroacetic acid (20 mL) in dichloromethane (80 mL) at 40° C. for sixteen hours. The reaction mixture was concentrated and the product was purified by reverse phase chromatography (Gilson) to afford, following neutralization with saturated sodium bicarbonate solution and filtration, the title compound as a white solid (28%). $^1$H NMR (d-6 DMSO): 7.91 (s, 1H), 7.75 (s, 1H), 7.22 (s, 1H), 7.03 (m, 1H), 6.33 (m 2H), 5.16 (m, 1H), 3.04 (m, 3H), 2.86 (s, 1H), 2.81-2.57 (m, 9H), 2.23 (m, 1H), 1.97 (m, 2H), 1.58 (m, 2H), 1.39 (m, 1H). MS: 483.9 (M+H). HPLC retention time: 1.71 minutes (G Method).

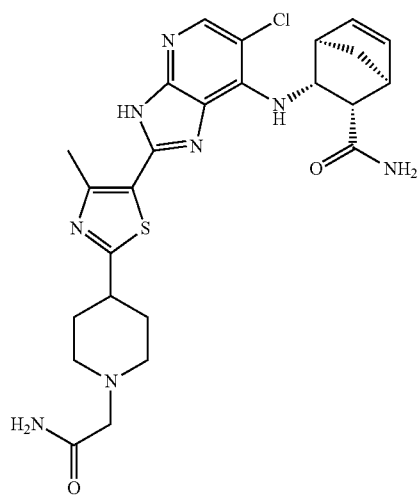

Compound LXV

Synthesis of (1S,2S,3R,4R)-3-{2-[2-(1-Carbamoyl-methyl-piperidin-4-yl)-4-methyl]j-thiazol-5-yl]-6-chloro-3H-imidazo[4,5-b]pyridine-7-ylamino}-bicyclo[2.2.1]hept-5-ene-2-carboxylic acid amide (Compound LXV)

(1S,2S,3R,4R)-3-[6-Chloro-2-(4-methyl-2-piperidin-4-yl-thiazol-5-yl)-3H-imidazo[4,5-b]pyridine-7-ylamino]-bicyclo[2.2.1]hept-5-ene-2-carboxylic acid amide (Compound LXIV above) (50 mg, 0.103 mmol), iodoacetamide (19 mg, 0.103 mmol), and MP-carbonate (31.6 mg, 0.100 mmol) were combined in N,N-dimethylformamide (1 mL) and heated at 40° C. overnight. Solids were removed by filtration and the filtrate was concentrated. The crude product was purified by reverse phase chromatography (Gilson) to afford, following lyophilization and neutralization, the title compound as a white solid (71%). $^1$H NMR (d-6 DMSO): 9.69 (br s, 1H), 7.99 (m, 2H), 7.78 (s, 1H), 7.27 (s, 1H), 6.36 (m, 2H), 5.08 (m 1H), 3.60 (m, 2H), 3.37-3.12 (m, 3H), 2.89 (s, 1H), 2.79 (s, 1H), 2.72 (s, 3H), 2.71 (m, 1H), 2.59 (m, 1H), 2.35-2.18 (m, 5H), 2.10 (m, 2H), 1.40 (m, 1H). MS: 541.0 (M+H). HPLC retention time: 1.66 minutes (G Method).

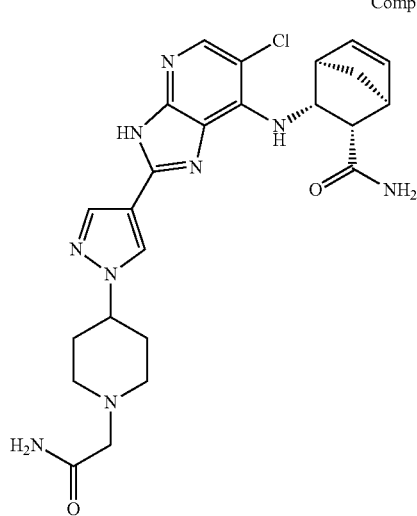

Compound LXVI

Synthesis of (1S,2S,3R,4R)-3-{2-[1-(1-Carbamoyl-methyl-piperidin-4-yl)-1H-pyrazol-4-yl]-6-chloro-3H-imidazo[4,5-b]pyridine-7-ylamino}-bicyclo[2.2.1]hept-5-ene-2-carboxylic acid amide, trifluoroacetic acid salt (Compound LXVI)

In a similar fashion as for the synthesis of Compound LXIV, Compound LVII was combined with iodoacetamide to afford the title compound as a white lyophilate (80%). $^1$H NMR (d-6 DMSO): 13.06 (br s, 1H), 9.81 (br s, 1H), 8.30 (s, 1H), 8.09 (s, 1H), 7.96 (m, 2H), 7.76 (m, 2H), 7.25 (m, 2H), 6.43 (m, 1H), 6.34 (m, 1H), 5.08 (m, 1H), 4.61 (m, 1H), 3.96 (m, 2H), 3.26 (m, 3H), 2.90 (s, 1H), 2.77 (s, 1H), 2.60 (m, 1H), 2.43-2.15 (m, 6H), 1.37 (m, 1H). MS: 509.9 (M+H). HPLC retention time: 1.55 minutes (G Method).

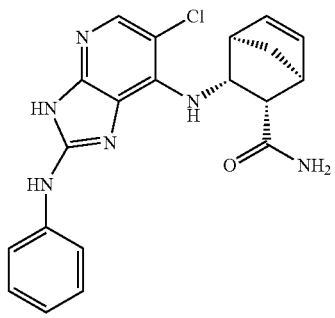

Compound LXVII

Synthesis of (1S,2S,3R,4R)-3-(6-Chloro-2-phenylamino-3H-imidazo[4,5-b]pyridine-7-ylamino)-bicyclo[2.2.1]hept-5-ene-2-carboxylic acid amide (Compound LXVII)

(1S,2S,3R,4R)-3-(2,3-Diamino-5-chloro-pyridin-4-ylamino)-bicyclo[2.2.1]hept-5-ene-2-carboxylic acid amide (100 mg, 0.5 mmol), isothiocyanatobenzene (60 L, 0.5 mmol), and PS-carbodiimide (769 mg, 1.01 mmol) were heated overnight at 70° C. in a sealed tube with tetrahydrofuran (10 mL). The solids were removed by filtration and the filtrate was concentrated. The organics were purified by reverse phase chromatography (Gilson) to afford, following neutralization and concentration, the title compound as a yellow solid (21%). $^1$H NMR (d-4 methanol): 7.73 (m, 3H), 7.29 (m, 2H), 6.98 (m, 1H), 6.44 (m, 1H), 6.40 (m, 1H), 5.31 (m, 1H), 4.88 (m, 3H), 2.98 (s, 1H), 2.89 (s, 1H), 2.73 (m, 1H), 2.37 (m, 1H), 1.57 (m, 1H), 1.30 (m, 2H). MS: 394.9 (M+H). HPLC retention time: 2.33 minutes (G Method).

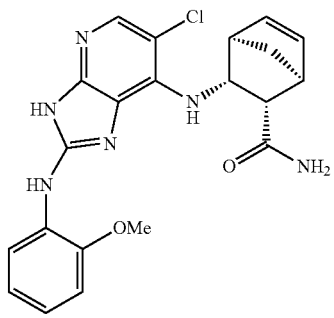

Compound LXVIII

Synthesis of (1S,2S,3R,4R)-3-[6-Chloro-2-(2-methoxy-phenylamino)-3H-imidazo[4,5-b]pyridine-7-ylamino]-bicyclo[2.2.1]hept-5-ene-2-carboxylic acid amide (Compound LXVIII)

In a similar fashion as for the synthesis of Compound LXVII, (1S,2S,3R,4R)-3-(2,3-Diamino-5-chloro-pyridin-4-ylamino)-bicyclo[2.2.1]hept-5-ene-2-carboxylic acid amide was reacted with 1-isothiocyanatoj-2-methoxybenzene to afford the title compound as a tan solid (17%). $^1$H NMR (d-chloroform): 8.26 (br s, 1H), 7.96 (br s, 1H), 7.51 (m, 2H), 7.05 (m, 1H), 6.95 (m, 3H), 6.46 (m, 1H), 6.41 (m, 1H), 6.21 (m, 1H), 5.68 (s, 1H), 5.14 (m, 1H), 3.93 (m, 3H), 3.13 (s, 1H), 2.98 (s, 1H), 2.72 (m, 1H), 2.34 (m, 1H), 1.69 (m, 1H). MS: 424.9 (M+H). HPLC retention time: 2.42 minutes (G Method).

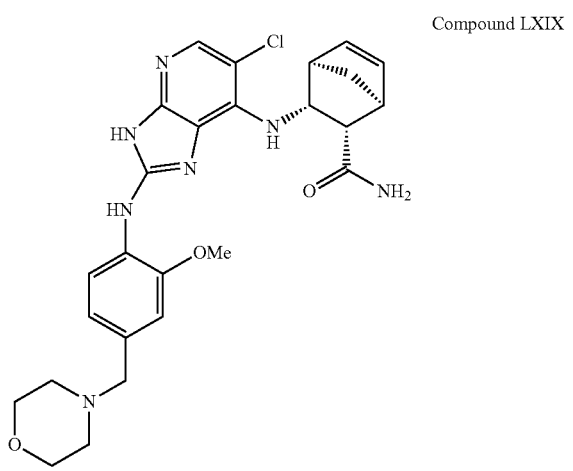 [SMILES: COc1cc(CN2CCOCC2)ccc1Nc1nc2c(N[C@H]3[C@@H](C(N)=O)[C@@H]4C=C[C@H]3C4)c(Cl)cnc2[nH]1]

Compound LXIX

Synthesis of (1S,2S,3R,4R)-3-[6-Chloro-2-(2-methoxy-4-morpholin-4-ylmethyl-phenylamino)-3H-imidazo[4,5-b]pyridine-7-ylamino]-bicyclo[2.2.1]hept-5-ene-2-carboxylic acid amide (Compound LXIX)

In a similar fashion as for the synthesis of Compound LXVII, (1S,2S,3R,4R)-3-(2,3-Diamino-5-chloro-pyridin-4-ylamino)-bicyclo[2.2.1]hept-5-ene-2-carboxylic acid amide was reacted with 4-(4-isothiocyanato-3-methoxybenzyl)-morpholine to afford the title compound as a tan solid (11%). $^1$H NMR (d-6 DMSO): 10.0 (br m, 1H), 8.78 (m, 1H), 8.62 (m, 1H), 7.86 (m, 2H), 7.36 (m, 1H), 7.25 (m, 1H), 7.10 (m, 1H), 6.43 (m, 2H), 5.08 (m, 1H), 4.34 (m, 2H), 3.98 (s, 3H), 3.29 (m, 4H), 3.12 (m, 4H), 2.92 (s, 1H), 2.86 (s, 1H), 2.62 (m, 1H), 2.21 (m, 1H), 1.69 (m, 1H), 1.44 (m, 1H). MS: 524.02 (M+H). HPLC retention time: 1.74 minutes (G Method).

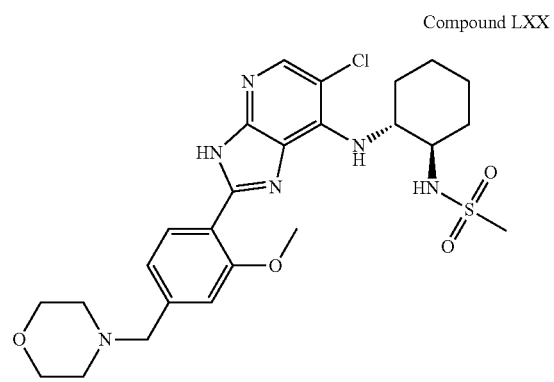 [SMILES: COc1cc(CN2CCOCC2)ccc1-c1nc2c(N[C@@H]3CCCC[C@H]3NS(C)(=O)=O)c(Cl)cnc2[nH]1]

Compound LXX

Synthesis of N-{(1R,2R)-2-[6-Chloro-2-(2-methoxy-4-morpholin-4-ylmethyl-phenyl)-3H-imidazo[4,5-b]pyridine-7-ylamino]-cyclohexyl}-methanesulfonamide, trifluoroacetic acid salt (Compound LXX)

In a similar fashion as for the synthesis of Compound A (X=Cl), 4,5-dichloro-3-nitro-pyridin-2-ylamine was reacted with N-((1R,2R)-2-amino-cyclohexyl)-methanesulfonamide to afford N-[(1R,2R)-2-(2-amino-5-chloro-3-nitro-pyridin-4-ylamino)-cyclohexyl]-methanesulfonamide (72%) which was subjected to hydrogenation with iron in acetic acid in a similar fashion as for Compound B to afford N-[(1R,2R)-2-(2,3-diamino-5-chloro-pyridin-4-ylamino)-cyclohexyl]-methanesulfonamide (66%). This latter material was then reacted with 2-methoxy-4-morpholin-4-ylmethyl-benzaldehyde in a similar fashion as for the synthesis of Compound III to afford the title compound as a yellow lyophilate (70%). $^1$H NMR (d-chloroform): 13.39 (br s, 1H), 8.30 (d, J=8 Hz, 1H), 8.23 (s, 1H), 7.19 (m, 1H), 7.12 (s, 1H), 7.03 (d, J=8 Hz, 1H), 6.76 (d, J=8 Hz, 1H), 5.05 (m, 1H), 4.97 (m, 1H), 4.12-3.81 (m, 6H), 3.64 (s, 3H), 3.48 (m, 1H), 3.25 (m, 1H), 3.12 (s, 3H), 3.06 (m, 1H), 2.83 (m, 1H), 2.22 (m, 2H), 2.01-1.60 (m, 4H), 1.44 (m, 2H), 1.25 (m, 1H). MS: 549.0 (M+H). HPLC retention time: 1.85 minutes (G Method).

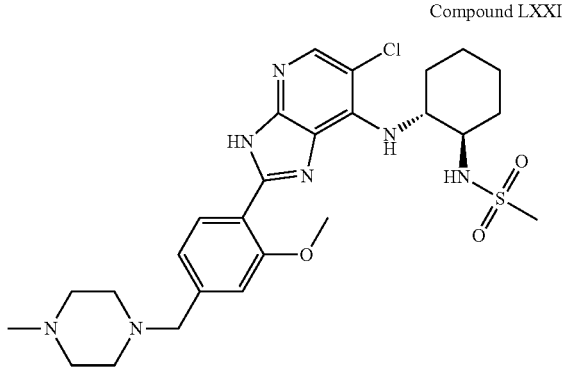

Compound LXXI

Synthesis of N-((1R,2R)-2-{6-Chloro-2-[2-methoxy-4-(4-methyl-piperazin-1-ylmethyl)-phenyl]-3H-imidazo[4,5-b]pyridine-7-ylamino}-cyclohexyl)-methanesulfonamide, trifluoroacetic acid salt (Compound LXXI)

In a similar fashion as for the synthesis of Compound LXX, N-[(1R,2R)-2-(2,3-diamino-5-chloro-pyridin-4-ylamino)-cyclohexyl]-methanesulfonamide was reacted with 2-methoxy-4-(4-methylj-piperazin-1-ylmethyl)-benzaldehyde to afford the title compound as a pale yellow lyophilate (50%). $^1$H NMR (d-chloroform): 13.53 (br s, 1H), 8.37 (d, J=8 Hz, 1H), 8.16 (s, 1H), 7.12 (d, J=7 Hz, 1H), 7.03 (s, 1H), 6.97 (m, 1H), 6.66 (d, J=7 Hz, 1H), 5.14 (m, 1H), 4.47 (d, J=9 Hz, 1H), 3.95 (d, J=9 Hz, 1H), 3.66 (s, 3H), 3.61-3.28 (m, 10H), 3.08 (s, 3H), 2.87 (s, 3H), 2.30 (m, 1H), 2.17 (m, 1H), 1.96 (m, 1H), 1.80 (m, 2H), 1.48 (m, 2H), 1.31 (m, 1H). MS: 562.0 (M+H). HPLC retention time: 1.76 minutes (G Method).

Compound LXXIII

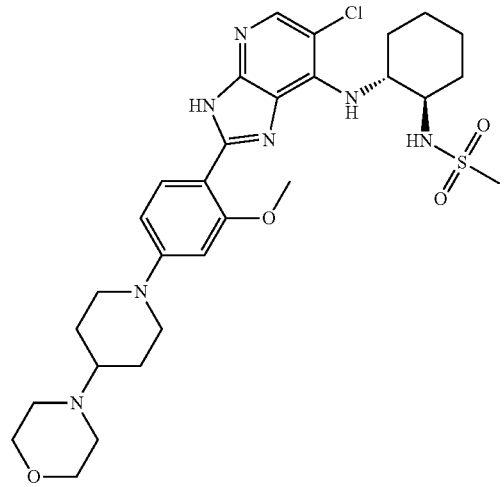

Synthesis of N-((1R,2R)-2{6-Chloro-2-[2-methoxy-4-(4-morpholin-4-yl-piperidin-1-yl)-phenyl]-3H-imidazo[4,5-b]pyridine-7-ylamino}-cyclohexyl)-methanesulfoneamide, trifluoroacetic acid salt (Compound LXXIII)

In a similar fashion as for the synthesis of Compound LXXII, N-[(1R,2R)-2-(2,3-diamino-5-chloro-pyridin-4-ylamino)-cyclohexyl]-methanesulfonamide was reacted with 2-methoxy-4-(4-morpholin-4-yl-piperidin-1-yl)-benzaldehyde to afford the title compound as a tan lyophilate (50%). $^1$H NMR (d-chloroform): 13.09 (br s, 1H), 8.18 (d, J=8 Hz, 1H), 8.10 (s, 1H), 7.14 (m, 1H), 6.64 (d, J=8 Hz, 1H), 6.46 (m, 1H), 6.18 (s, 1H), 5.03 (m, 1H), 4.16-3.90 (m, 6H), 3.79 (s, 3H), 3.77 (m, 1H), 3.63 (m, 1H), 3.44 (m, 1H), 3.24 (m, 1H), 3.05 (s, 3H), 3.03 (m, 2H), 3.00 (m, 2H), 2.88 (m, 2H), 2.46-1.68 (m, 9H), 1.45 (m, 2H), 1.28 (m, 2H). MS: 618.1 (M+H). HPLC retention time: 1.98 minutes (G Method).

Compound LXXII

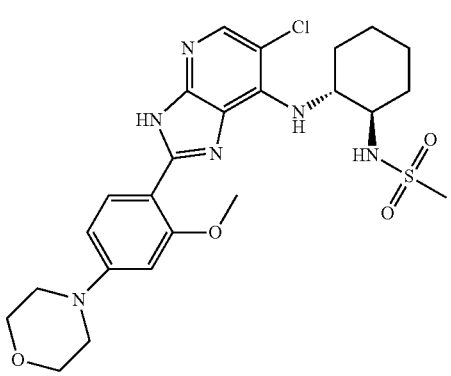

Synthesis of N-{(1R,2R)-2-[6-Chloro-2-(2-methoxy-4-morpholin-4-yl-phenyl)-3H-imidazo[4,5-b]pyridine-7-ylamino]-cyclohexyl}-methanesulfonamide, trifluoroacetic acid salt (Compound LXXII)

In a similar fashion as for the synthesis of Compound LXXI, N-[(1R,2R)-2-(2,3-diamino-5-chloro-pyridin-4-ylamino)-cyclohexyl]-methanesulfonamide was reacted with 2-methoxy-4-morpholin-4-yl-benzaldehyde to afford the title compound as a mustard yellow lyophilate (60%). $^1$H NMR (d-chloroform): 13.26 (br s, 1H), 8.21 (d, J=8 Hz, 1H), 8.05 (s, 1H), 6.83 (m, 1H), 6.65 (d, J=8 Hz, 1H), 6.30 (m, 2H), 5.11 (m, 1H), 3.94 (m, 4H), 3.85 (s, 3H), 3.44 (m, 1H), 3.33 (m, 4H), 2.98 (s, 3H), 2.32 (m, 1H), 2.23 (m, 1H), 1.97-1.64 (m, 4H), 1.55-1.25 (m, 3H). MS: 535.0 (M+H). HPLC retention time: 2.57 minutes (G Method).

Compound LXXIV

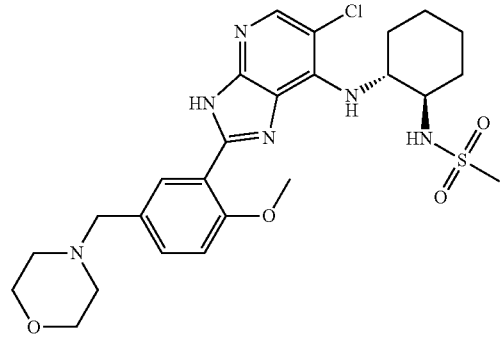

Synthesis of N-{(1R,2R)-2-[6-Chloro-2-(2-methoxy-5-morpholin-4-ylmethyl-phenyl)-3H-imidazo[4,5-b]pyridine-7-ylamino]-cyclohexyl}-methanesulfonamide, trifluoroacetic acid salt (Compound LXXIV)

In a similar fashion as for the synthesis of Compound LXXII, N-[(1R,2R)-2-(2,3-diamino-5-chloro-pyridin-4- ylamino)-cyclohexyl]-methanesulfonamide was reacted with 2-methoxy-5-morpholin-4-ylmethyl-benzaldehyde to afford the title compound as a yellow lyophilate (70%). ¹H NMR (d-chloroform): 13.50 (br s, 1H), 8.30 (s, 1H), 8.25 (s, 1H), 7.62 (d, J=7 Hz, 1H), 7.10 (d, J=7 Hz, 1H), 6.84 (d, J=7 Hz, 1H), 6.64 (m, 1H), 4.95 (m, 1H), 4.47 (d, J=9 Hz, 1H), 4.12 (d, J=9 Hz, 1H), 3.99 (m, 4H), 3.74 (s, 3H), 3.49 (m, 1H), 3.33 (m, 1H), 3.08 (s, 3H), 2.82 (m, 1H), 2.26 (m, 2H), 2.02-1.40 (m, 7H), 3.00 (m, 2H), 1.30 (m, 2H). MS: 549.0 (M+H). HPLC retention time: 1.86 minutes (G Method).

Compound LXXV

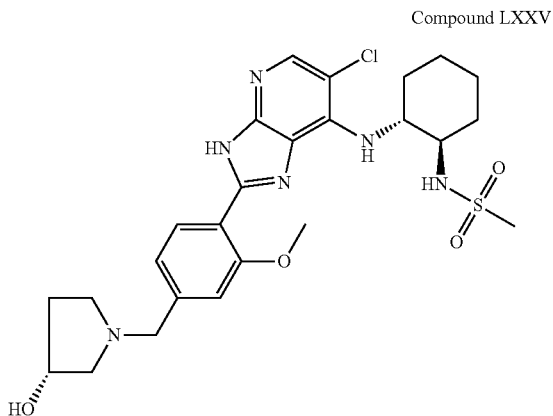 [SMILES: COc1cc(CN2CC[C@@H](O)C2)ccc1-c1nc2c(N[C@@H]3CCCC[C@H]3NS(C)(=O)=O)c(Cl)cnc2[nH]1]

Synthesis of N-((1R,2R)-2-{6-Chloro-2-[4-((R)-3-hydroxy-pyrrolidin-1-ylmethyl)-2-methoxy-phenyl]-3H-imidazo[4,5-b]pyridine-7-ylamino}-cyclohexyl)-methanesulfonamide, trifluoroacetic acid salt (Compound LXXV)

In a similar fashion as for the synthesis of Compound LXXII, N-[(1R,2R)-2-(2,3-diamino-5-chloro-pyridin-4-ylamino)-cyclohexyl]-methanesulfonamide was reacted with 4-((R)-3-hydroxy-pyrrolidin-1-ylmethyl)-2-methoxy-benzaldehyde to afford the title compound as a yellow lyophilate (30%). ¹H NMR (d-chloroform): 13.27 (br s, 1H), 8.38 (m, 1H), 8.22 (s, 1H), 7.43 (m, 1H), 7.11 (m, 1H), 7.02 (m, 1H), 6.82 (m, 1H), 5.08 (m, 1H), 4.72 (m, 1H), 4.52 (m, 1H), 4.34 (m, 1H), 3.96 (m, 1H), 3.84 (m, 1H), 3.58 (s, 3H), 3.52 (m, 2H), 3.14 (s, 3H), 3.07 (m, 1H), 2.44 (m, 1H), 2.32-2.13 (m, 5H), 1.95 (m, 1H), 1.81 (m, 2H), 1.44 (m, 2H), 1.24 (m, 1H). MS: 548.9 (M+H). HPLC retention time: 1.84 minutes (G Method).

Compound LXXVI

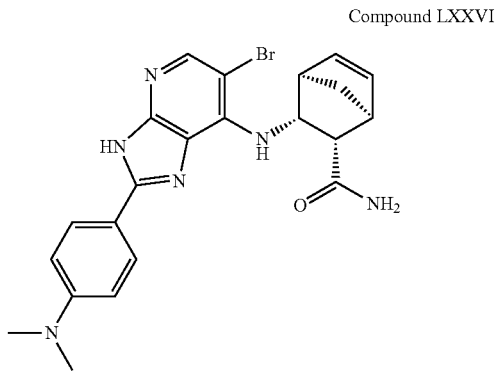 [SMILES: CN(C)c1ccc(-c2nc3c(N[C@H]4[C@@H](C(N)=O)[C@@H]5C=C[C@H]4C5)c(Br)cnc3[nH]2)cc1]

Synthesis of (1S,2S,3R,4R)-3-[6-Bromo-2-(4-dimethylamino-phenyl)-3H-imidazo[4,5-b]pyridin-7-ylamino]-bicyclo[2.2.1]hept-5-ene-2-carboxylic acid amide (Compound LXXVI)

(1S,2S,3R,4R)-3-(2,3-Diamino-5-bromo-pyridin-4-ylamino)-bicyclo[2.2.1]hept-5-ene-2-carboxylic acid amide (1.30 mg, 0.386 mmol), 4-(dimethylamino)benzaldehyde (63.3 mg, 0.424 mmol) and ammonium acetate (59.4 mg, 0.771 mmol) were heated in ethanol (5 mL) at 70° C. for 18 hours. The desired product precipitated from the reaction mixture. The mixture was diluted with ethyl ether (5 mL) and filtered. The remaining solid was dried under high vacuum to afford 85 mg (47%) of the title compound. mp: 264-265° C., ¹H NMR (300 MHz, DMSO-d⁶): 12.73 (s, 1H), 7.96 (d, J=8 Hz, 2H), 7.84 (d, J=4 Hz, 1H), 7.65 (s, 1H), 7.15 (s, 1H), 6.81 (d, J=8 Hz, 2H), 6.70 (d, J=8 Hz, 1H), 6.37 (d, J=8 Hz, 1H), 6.32 (s, 2H), 3.89 (br s, 1H), 2.99 (s, 6H), 2.87 (s, 1H), 2.75 (s, 1H), 2.60 (d, J=7 Hz, 1H), 2.24 (d, J=8 Hz, 1H), 1.42 (d, J=8 Hz, 1H). MS: 467, 469 (M+H), HPLC: 2.43 min (G method).

Compound LXXVII

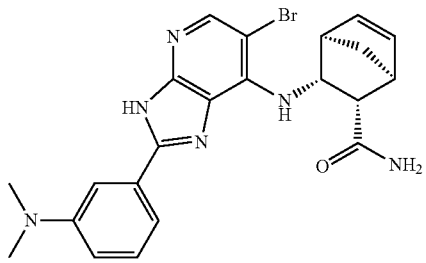

Synthesis of (1S,2S,3R,4R)-3-[6-Bromo-2-(3-dimethylamino-phenyl)-3H-imidazo[4,5-b]pyridin-7-ylamino]-bicyclo[2.2.1]hept-5-ene-2-carboxylic acid amide (Compound LXXVII)

In a similar fashion to Compound LXXVI, (1S,2S,3R,4R)-3-(2,3-Diamino-5-bromo-pyridin-4-ylamino)-bicyclo[2.2.1] hept-5-ene-2-carboxylic acid amide (1.30 mg, 0.386 mmol) and 3-(dimethylamino)benzaldehyde were reacted to produce 105 mg (58%) of the title compound. mp: 220-221° C., ¹H NMR (300 MHz, DMSO-d⁶): 13.02 (s, 1H), 7.90 (d, 1H), 7.66 (s, 1H), 7.50 (s, 1H), 7.47 (d, J=8 Hz, 1H), 7.30 (t, J=8 Hz, 1H), 7.15 (s, 1H), 6.86 (m, 1H), 6.81 (d, J=8 Hz, 1H), 6.40 (d, J=5 Hz, 1H), 6.33 (s, 2H), 2.98 (s, 6H), 2.87 (s, 1H), 2.77 (s, 1H), 2.60 (d, J=8 Hz, 1H), 2.24 (d, J=8 Hz, 1H), 1.42 (d, J=8 Hz, 1H). MS: 467, 469 (M+H), HPLC: 2.13 min (G method).

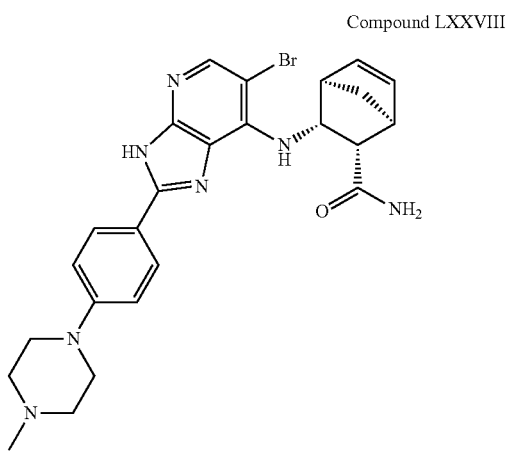 [SMILES: CN1CCN(c2ccc(-c3nc4c(N[C@H]5[C@@H](C(N)=O)[C@@H]6C=C[C@H]5C6)c(Br)cnc4[nH]3)cc2)CC1]

Compound LXXVIII

Synthesis of (1S,2S,3R,4R)-3-{6-Bromo-2-[4-(4-methyl-piperazin-1-yl)-phenyl]-3H-imidazo[4,5-b]pyridin-7-ylamino}-bicyclo[2.2.1]hept-5-ene-2-carboxylic acid amide (Compound LXXVIII)

In a similar fashion to Compound LXXVI, (1S,2S,3R,4R)-3-(2,3-Diamino-5-bromo-pyridin-4-ylamino)-bicyclo[2.2.1]hept-5-ene-2-carboxylic acid amide (40.0 mg, 0.118 mmol) and 4-(4-methyl-piperazin-1-yl)-benzaldehyde (26.6 mg, 0.130 mmol) were reacted to produce 30 mg (49%) of the title compound. mp: 215-218° C., $^1$H NMR (300 MHz, DMSO-d$^6$): 13.02 (s, 1H), 7.99 (s, 1H), 7.97 (s, 2H), 7.73 (s, 1H), 7.20 (s, 1H), 7.07 (d, J=8 Hz, 2H), 6.99 (d, J=8 Hz, 1H), 6.37 (br s, 2H), 5.27 (t, J=8 Hz, 1H), 3.32 (s, 6H), 2.88 (s, 1H), 2.75 (s, 1H), 2.60 (d, J=7 Hz, 1H), 2.45 (br s, 4H), 2.23 (s, 4H). MS: 522, 524 (M+H), HPLC: 1.86 min (G method).

Compound LXXIX

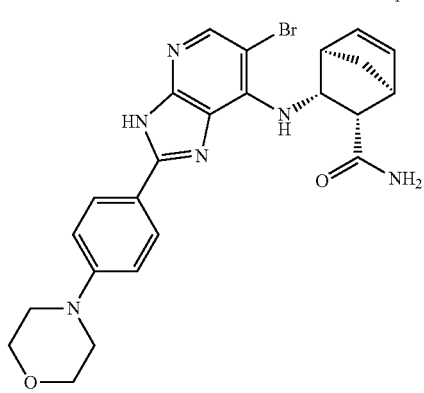

Synthesis of (1S,2S,3R,4R)-3-[6-Bromo-2-(4-morpholin-4-yl-phenyl)-3H-imidazo[4,5-b]pyridin-7-ylamino]-bicyclo[2.2.1]hept-5-ene-2-carboxylic acid amide (Compound LXXIX)

In a similar fashion to Compound LXXVI, (1S,2S,3R,4R)-3-(2,3-Diamino-5-bromo-pyridin-4-ylamino)-bicyclo[2.2.1]hept-5-ene-2-carboxylic acid amide (40.0 mg, 0.118 mmol) and 4-morpholin-4-yl-benzaldehyde (24.9 mg, 0.130 mmol) were reacted to produce 45 mg (75%) of the title compound. mp: 283-284° C., $^1$H NMR (300 MHz, DMSO-d$^6$): 12.97 (s, 1H), 8.22 (s, 1H), 8.00 (d, J=8 Hz, 2H), 7.93 (s, 1H), 7.65 (s, 1H), 7.11 (s, 1H), 7.03 (d, J=8 Hz, 2H), 6.98 (d, J=8 Hz, 1H), 6.36 (br s, 1H), 6.33 (br s, 1H), 5.27 (t, J=8 Hz, 1H), 3.77 (br s, 4H), 2.88 (s, 1H), 2.77 (s, 1H), 2.62 (d, J=7 Hz, 1H), 2.26 (br s, 4H), 1.39 (d, J=8 Hz, 1H). MS: 509, 511 (M+H), HPLC: 2.31 min (G method).

Compound LXXX

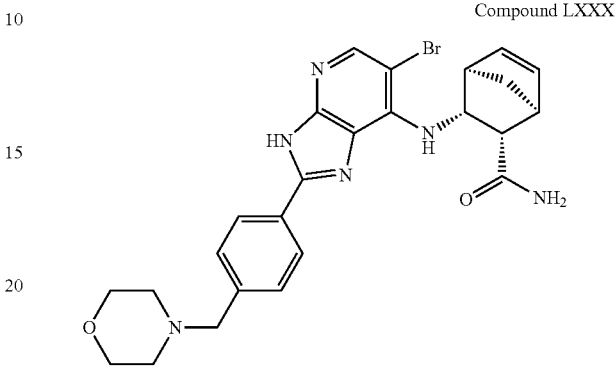

Synthesis of (1S,2S,3R,4R)-3-[6-Bromo-2-(4-morpholin-4-ylmethyl-phenyl)-3H-imidazo[4,5-b]pyridin-7-ylamino]-bicyclo[2.2.1]hept-5-ene-2-carboxylic acid amide (Compound LXXX)

(1S,2S,3R,4R)-3-(2,3-Diamino-5-bromo-pyridin-4-ylamino)-bicyclo[2.2.1]hept-5-ene-2-carboxylic acid amide (40.0 mg, 0.118 mmol), 4-morpholin-4-ylmethyl-benzaldehyde (26.7 mg, 0.130 mmol) and ammonium acetate (59.4 mg, 0.771 mmol) were heated in ethanol (5 mL) at 70° C. for 18 hours. The reaction mixture was concentrated and the product was purified by reverse phase chromatography (Gilson) to afford, following neutralization with saturated sodium bicarbonate solution and filtration, the title compound 35 mg (57%). mp: 217-219° C., $^1$H NMR (300 MHz, DMSO-d$^6$): 13.27 (s, 1H), 8.10 (d, J=9 Hz, 2H), 8.03 (s, 1H), 7.76 (s, 1H), 7.48 (d, J=8 Hz, 2H), 7.22 (s, 1H), 7.16 (d, J=8 Hz, 1H), 6.41 (br s, 1H), 6.37 (br s, 1H), 5.23 (t, J=8 Hz, 1H), 3.59 (br s, 4H), 3.53 (s, 2H), 2.89 (s, 1H), 2.78 (s, 1H), 2.39 (br s, 4H), 2.25 (d, J=8 Hz, 1H), 1.90 (s, 1 h), 1.39 (d, J=8 Hz, 1H). MS: 523, 525 (M+H), HPLC: 1.82 min (G method).

Compound LXXXI

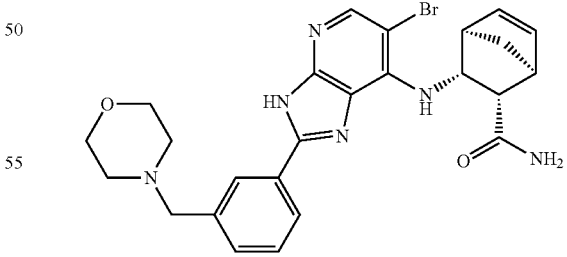

Synthesis of (1S,2S,3R,4R)-3-[6-Bromo-2-(3-morpholin-4-ylmethyl-phenyl)-3H-imidazo[4,5-b]pyridin-7-ylamino]-bicyclo[2.2.1]hept-5-ene-2-carboxylic acid amide (Compound LXXXI)

In a similar fashion to Compound LXXVI, (1S,2S,3R,4R)-3-(2,3-Diamino-5-bromo-pyridin-4-ylamino)-bicyclo[2.2.1]

hept-5-ene-2-carboxylic acid amide (40.0 mg, 0.118 mmol) and 3-morpholin-4-ylmethyl-benzaldehyde (26.7 mg, 0.130 mmol) were reacted to produce 35 mg (57%) of the title compound. mp: 184-185° C., $^1$H NMR (300 MHz, CDCl$_3$): 8.13 (s, 1H), 8.04 (s, 1H), 7.98 (s, 1H), 7.47 (s, 2H), 6.40 (d, J=8 Hz, 2H), 6.24 (s, 1H), 6.14 (br s, 1H), 6.10 (d, J=8 Hz, 1H), 5.28 (t, J=8 Hz, 1H), 3.74 (br s, 4H), 3.64 (s, 2H), 3.17 (s, 1H), 3.07 (s, 6H), 2.94 (s, 1H), 2.80 (d, J=8 Hz, 1H), 2.54 (s, 3H), 2.35 (d, J=8 Hz, 1H), 2.13 (s, 1H), 1.70 (d, J=8 Hz, 1H). MS: 523, 525 (M+H), HPLC: 1.84 min (G method).

and 3-morpholin-4-yl-benzaldehyde (24.9 mg, 0.130 mmol) were reacted to produce 54 mg (90%) of the title compound. mp: 232-234° C., $^1$H NMR (300 MHz, DMSO-d$^6$): 12.90 (s, 1H), 8.24 (s, 1H), 8.19 (s, 1H), 7.97 (s, 1H), 7.92 (s, 1H), 7.66 (s, 1H), 6.95 (d, J=8 Hz, 1H), 6.41 (br s, 1H), 6.31 (br s, 1H), 5.17 (t, J=8 Hz, 1H), 3.93 (s, 3H), 3.45 (m, 1H), 3.18 (s, 1H), 2.87 (s, 1H), 2.74 (s, 1H), 2.59 (d, J=8 Hz, 1H), 2.25 (d, J=8 Hz, 1H), 1.89 (s, 1H), 1.38 (d, J=8 Hz, 1H). MS: 509, 511 (M+H), HPLC: 2.43 min (G method).

Compound LXXXII

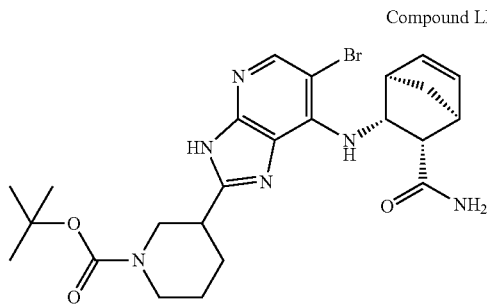

Compound LXXXIV

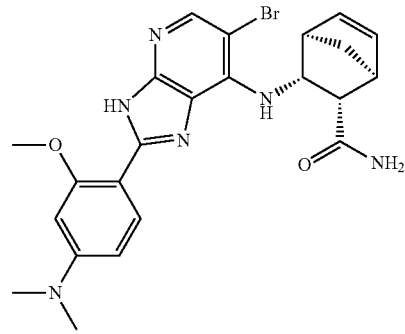

Synthesis of 3-[6-Bromo-7-((1R,2R,3S,4S)-3-carbamoyl-bicyclo[2.2.1]hept-5-en-2-ylamino)-3H-imidazo[4,5-b]pyridin-2-yl]-piperidine-1-carboxylic acid tert-butyl (Compound LXXXII)

In a similar fashion to Compound LXXX, (1S,2S,3R,4R)-3-(2,3-Diamino-5-bromo-pyridin-4-ylamino)-bicyclo[2.2.1]hept-5-ene-2-carboxylic acid amide (40.0 mg, 0.118 mmol) and 3-formyl-piperidine-1-carboxylic acid tert-butyl ester (27.7 mg, 0.130 mmol) were reacted to produce 36 mg (57%) of the title compound. mp: 172-177° C., $^1$H NMR (300 MHz, DMSO-d$^6$): 12.64 (s, 1H), 7.96 (s, 1H), 7.72 (s, 1H), 7.19 (s, 1H), 6.98 (m, 1H), 6.31 (s, 2H), 5.76 (s, 2H), 5.09 (m, 1H), 4.19 (br s, 1H), 3.84 (br s, 1H), 3.38 (m, 1H), 2.86 (m, 4H), 2.68 (s, 1H), 2.57 (d, J=8 Hz, 1H), 2.21 (d, J=8 Hz, 1H), 2.16 (br s, 1H). MS: 531, 533 (M+H), HPLC: 2.70 min (G method).

Synthesis of (1S,2S,3R,4R)-3-[6-Bromo-2-(4-dimethylamino-2-methoxy-phenyl)-3H-imidazo[4,5-b]pyridin-7-ylamino]-bicyclo[2.2.1]hept-5-ene-2-carboxylic acid amide (Compound LXXXIV)

In a similar fashion to Compound LXXVI, (1S,2S,3R,4R)-3-(2,3-Diamino-5-bromo-pyridin-4-ylamino)-bicyclo[2.2.1]hept-5-ene-2-carboxylic acid amide (40.0 mg, 0.118 mmol) and 4-dimethylamino-2-methoxy-benzaldehyde (23.3 mg, 0.130 mmol) were reacted to produce 25 mg (43%) of the title compound. mp: 218-220° C., $^1$H NMR (300 MHz, DMSO-d$^6$): 13.00 (s, 1H), 8.24 (s, 1H), 8.00 (s, 1H), 7.96 (s, 1H), 7.73 (s, 1H), 6.99 (d, J=8 Hz, 2H), 6.43 (br s, 1H), 6.33 (br s, 1H), 5.16 (t, J=8 Hz, 1H), 3.94 (s, 3H), 2.87 (s, 1H), 2.73 (s, 1H), 2.59 (d, J=7 Hz, 1H), 2.23 (d, J=8 Hz, 1H), 1.90 (s, 1H), 1.37 (d, J=8 Hz, 1H). MS: 497, 499 (M+H), HPLC: 2.65 min (G method).

Compound LXXXIII

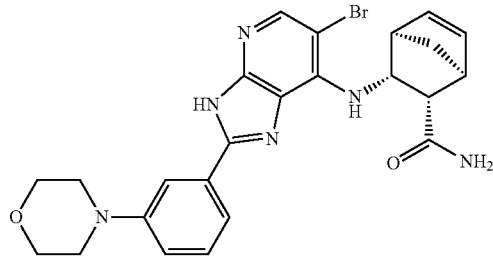

Compound LXXXV

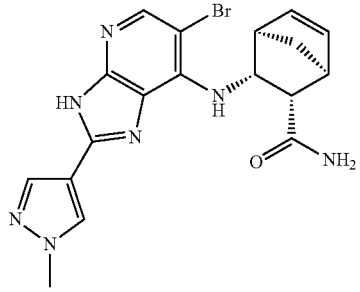

Synthesis of (1S,2S,3R,4R)-3-[6-Bromo-2-(3-morpholin-4-yl-phenyl)-3H-imidazo[4,5-b]pyridin-7-ylamino]-bicyclo[2.2.1]hept-5-ene-2-carboxylic acid amide (Compound LXXXIII)

In a similar fashion to Compound LXXVI, (1S,2S,3R,4R)-3-(2,3-Diamino-5-bromo-pyridin-4-ylamino)-bicyclo[2.2.1]hept-5-ene-2-carboxylic acid amide (40.0 mg, 0.118 mmol)

Synthesis of (1S,2S,3R,4R)-3-[6-Bromo-2-(1-methyl-1H-pyrazol-4-yl)-3H-imidazo[4,5-b]pyridin-7-ylamino]-bicyclo[2.2.1]hept-5-ene-2-carboxylic acid amide (Compound LXXXV)

In a similar fashion to Compound LXXVI, (1S,2S,3R,4R)-3-(2,3-Diamino-5-bromo-pyridin-4-ylamino)-bicyclo[2.2.1]

hept-5-ene-2-carboxylic acid amide (40.0 mg, 0.118 mmol) and 1-methyl-1H-pyrazole-4-carbaldehyde (14.3 mg, 0.130 mmol) were reacted to produce 23 mg (45%) of the title compound. mp: 255-258° C., $^1$H NMR (300 MHz, DMSO-d$^6$): 11.99 (s, 1H), 7.99 (d, J=8 Hz, 1H), 7.96 (s, 1H), 7.72 (s, 1H), 7.19 (s, 1H), 6.88 (d, J=8 Hz, 1H), 6.49 (d, J=8 Hz, 1H), 6.35 (m, 2H), 5.30 (t, J=8 Hz, 1H), 4.34 (m, 1H), 3.97 (s, 2H), 3.02 (s, 4H), 2.87 (s, 1H), 2.74 (s, 1H), 2.61 (d, J=8 Hz, 1H), 2.26 (d, J=8 Hz, 1H), 1.38 (d, J=8 Hz, 1H). MS: 428, 430 (M+H), HPLC: 1.94 min (G method).

Compound LXXXVI

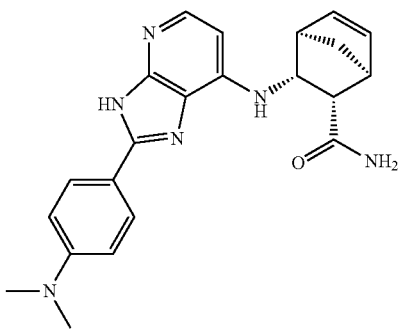

Synthesis of (1S,2S,3R,4R)-3-[2-(4-Dimethylamino-phenyl)-3H-imidazo[4,5-b]pyridin-7-ylamino]-bicyclo[2.2.1]hept-5-ene-2-carboxylic acid amide (Compound LXXXVI)

In a similar fashion to Compound LXXVI, (1S,2S,3R,4R)-3-(2,3-Diamino-pyridin-4-ylamino)-bicyclo[2.2.1]hept-5-ene-2-carboxylic acid amide (50.0 mg, 0.193 mmol) and 4-(dimethylamino)benzaldehyde (31.6 mg, 0.212 mmol) were reacted to produce 25 mg (33%) of the title compound. mp: 245-251° C., $^1$H NMR (300 MHz, DMSO-d$^6$): 12.73 (s, 1H), 7.96 (d, J=8 Hz, 2H), 7.84 (d, J=4 Hz, 1H), 7.65 (s, 1H), 7.15 (s, 1H), 6.81 (d, J=8 Hz, 2H), 6.70 (d, J=8 Hz, 1H), 6.37 (d, J=8 Hz, 1H), 6.32 (s, 2H), 3.89 (br s, 1H), 2.99 (s, 6H), 2.87 (s, 1H), 2.75 (s, 1H), 2.60 (d, J=7 Hz, 1H), 2.24 (d, J=8 Hz, 1H), 1.42 (d, J=8 Hz, 1H). MS: 389 (M+H), HPLC: 1.97 min (G method).

Compound LXXXVII

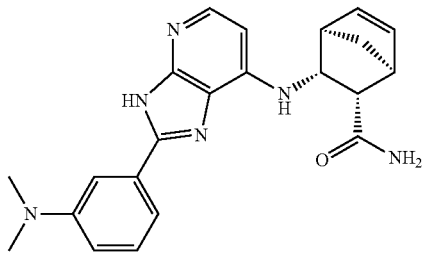

Synthesis of (1S,2S,3R,4R)-3-[2-(3-Dimethylamino-phenyl)-3H-imidazo[4,5-b]pyridin-7-ylamino]-bicyclo[2.2.1]hept-5-ene-2-carboxylic acid amide (Compound LXXXVII)

(1S,2S,3R,4R)-3-(2,3-Diamino-pyridin-4-ylamino)-bicyclo[2.2.1]hept-5-ene-2-carboxylic acid amide (50.0 mg, 0.193 mmol) and 3-dimethylamino-benzaldehyde (31.6 mg, 0.212 mmol) were combined with ammonium acetate (29.7 mg, 0.386 mmol) and heated in ethanol (2.5 mL) at 70° C. for 18 h. The reaction mixture was concentrated and chromatographed by reverse phase preparative HPLC. The desired fractions were neutralized with bicarb solution and extracted into EtOAc. The organic layer was dried over MgSO$_4$, filtered and concentrated. This residue was triturated in ethyl ether and filtered to yield 28 mg (37%) of the title compound. mp: 200-204° C., $^1$H NMR (300 MHz, DMSO-d$^6$): 13.02 (s, 1H), 7.90 (d, 1H), 7.66 (s, 1H), 7.50 (s, 1H), 7.47 (d, J=8 Hz, 1H), 7.30 (t, J=8 Hz, 1H), 7.15 (s, 1H), 6.86 (m, 1H), 6.81 (d, J=8 Hz, 1H), 6.40 (d, J=5 Hz, 1H), 6.33 (s, 2H), 2.98 (s, 6H), 2.87 (s, 1H), 2.77 (s, 1H), 2.60 (d, J=8 Hz, 1H), 2.24 (d, J=8 Hz, 1H), 1.42 (d, J=8 Hz, 1H). HPLC: 1.63 min (G method), MS: 389 (M+H).

Compound LXXXVIII

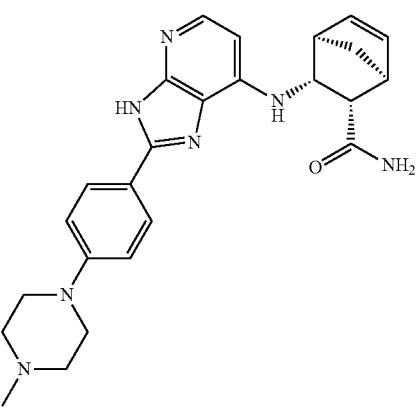

Synthesis of (1S,2S,3R,4R)-3-{2-[4-(4-Methyl-piperazin-1-yl)-phenyl]-3H-imidazo[4,5-b]pyridin-7-ylamino}-bicyclo[2.2.1]hept-5-ene-2-carboxylic acid amide (Compound LXXXVIII)

In a similar fashion to Compound LXXXVII, (1S,2S,3R,4R)-3-(2,3-Diamino-pyridin-4-ylamino)-bicyclo[2.2.1]hept-5-ene-2-carboxylic acid amide (50.0 mg, 0.193 mmol) and 4-(4-methyl-piperazin-1-yl)-benzaldehyde (43.3 mg, 0.212 mmol) were reacted to produce 16 mg (19%) of the title compound. mp: 220-222° C., $^1$H NMR (300 MHz, DMSO-d$^6$): 12.81 (s, 1H), 7.98 (d, J=8 Hz, 2H), 7.85 (d, J=5 Hz, 1H), 7.66 (s, 1H), 7.16 (s, 1H), 7.04 (d, J=8 Hz, 2H), 6.75 (m, 1H), 6.37 (d, J=8 Hz, 1H), 6.33 (s, 2H), 3.88 (br s, 1H), 3.32 (s, 6H), 2.88 (s, 1H), 2.75 (s, 1H), 2.60 (d, J=8 Hz, 1H), 2.45 (br s, 4H), 1.42 (d, J=8 Hz, 1H). MS: 444 (M+H), HPLC: 1.57 min (G method).

Compound LXXXIX

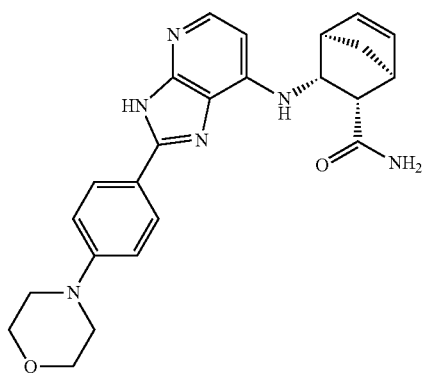

Synthesis of (1S,2S,3R,4R)-3-[2-(4-Morpholin-4-yl-phenyl)-3H-imidazo[4,5-b]pyridin-7-ylamino]-bicyclo[2.2.1]hept-5-ene-2-carboxylic acid amide (Compound LXXXIX)

In a similar fashion to Compound LXXXVII, (1S,2S,3R,4R)-3-(2,3-Diamino-pyridin-4-ylamino)-bicyclo[2.2.1]hept-5-ene-2-carboxylic acid amide (50.0 mg, 0.193 mmol) and 4-morpholin-4-yl-benzaldehyde (36.9 mg, 0.193 mmol) were reacted to produce 24 mg (29%) of the title compound. mp: 240-244° C., $^1$H NMR (300 MHz, DMSO-d$^6$): 12.83 (s, 1H), 8.00 (d, J=8 Hz, 2H), 7.86 (d, J=8 Hz, 1H), 7.66 (s, 1H), 7.16 (s, 1H), 7.06 (d, J=8 Hz, 2H), 6.77 (d, J=8 Hz, 1H), 6.38 (d, J=8 Hz, 1H), 6.33 (s, 2H), 3.88 (br s, 1H), 3.76 (s, 4H), 3.31 (s, 3H), 2.87 (s, 1H), 2.75 (s, 1H), 2.60 (d, J=8 Hz, 1H), 2.24 (d, J=8 Hz, 1H), 1.42 (d, J=8 Hz, 1H). MS: 431 (M+H), HPLC: 1.99 min (G method).

Compound XC

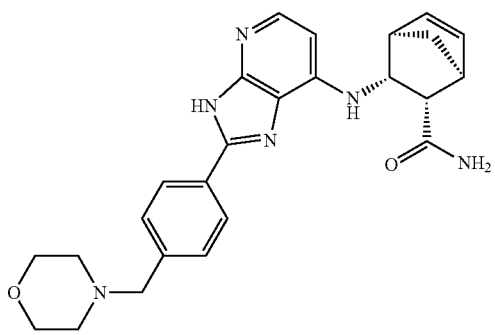

Synthesis of (1S,2S,3R,4R)-3-[2-(4-Morpholin-4-ylmethyl-phenyl)-3H-imidazo[4,5-b]pyridin-7-ylamino]-bicyclo[2.2.1]hept-5-ene-2-carboxylic acid amide (Compound XC)

In a similar fashion to Compound LXXXVII, (1S,2S,3R,4R)-3-(2,3-Diamino-pyridin-4-ylamino)-bicyclo[2.2.1]hept-5-ene-2-carboxylic acid amide (50.0 mg, 0.193 mmol) and 4-morpholin-4-ylmethyl-benzaldehyde (43.5 mg, 0.212 mmol) were reacted to produce 27 mg (32%) of the title compound. mp: 240-244° C., $^1$H NMR (300 MHz, DMSO-d$^6$): 13.06 (s, 1H), 8.09 (d, J=8 Hz, 2H), 7.91 (d, 1H), 7.67 (s, 1H), 7.45 (d, J=8 Hz, 1H), 7.16 (s, 1H), 6.88 (m, 1H), 6.41 (d, J=8 Hz, 1H), 6.33 (s, 1H), 3.88 (br s, 1H), 3.59 (br s, 4H), 3.52 (s, 2H), 2.88 (s, 1H), 2.76 (s, 1H), 2.60 (d, J=8 Hz, 1H), 2.38 (s, 4H), 2.23 (d, J=8 Hz, 1H), 1.43 (d, J=8 Hz, 1H). MS: 445 (M+H), HPLC: 1.51 min (G method).

Compound XCI

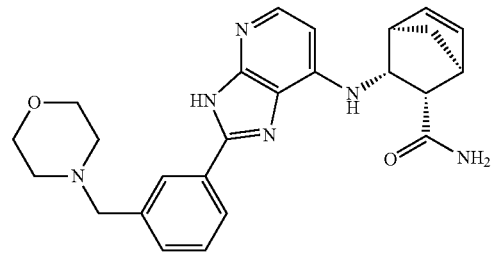

Synthesis of (1S,2S,3R,4R)-3-[2-(3-Morpholin-4-ylmethyl-phenyl)-3H-imidazo[4,5-b]pyridin-7-ylamino]-bicyclo[2.2.1]hept-5-ene-2-carboxylic acid amide (Compound XCI)

In a similar fashion to Compound LXXXVII, (1S,2S,3R,4R)-3-(2,3-Diamino-pyridin-4-ylamino)-bicyclo[2.2.1]hept-5-ene-2-carboxylic acid amide (50.0 mg, 0.193 mmol) and 3-morpholin-4-ylmethyl-benzaldehyde (43.5 mg, 0.212 mmol) were reacted to produce 29 mg (34%) of the title compound. mp: 240-244° C., $^1$H NMR (300 MHz, DMSO-d$^6$) 13.09 (s, 1H), 8.10 (s, 1H), 8.02 (d, J=8 Hz, 1H), 7.91 (d, J=8 Hz, 1H), 7.67 (s, 1H), 7.47 (t, J=8 Hz, 1H), 7.39 (m, 1H), 7.17 (s, 1H), 6.91 (m, 1H), 6.41 (d, J=8 Hz, 1H), 6.34 (s, 1H), 3.88 (br s, 1H), 3.60 (br s, 4H), 3.54 (s, 2H), 2.88 (s, 1H), 2.77 (s, 1H), 2.61 (d, J=8 Hz, 1H), 2.40 (s, 4H), 2.24 (d, J=8 Hz, 1H), 1.43 (d, J=8 Hz, 1H). MS: 445 (M+H), HPLC: 1.54 min (G method).

Compound XCII

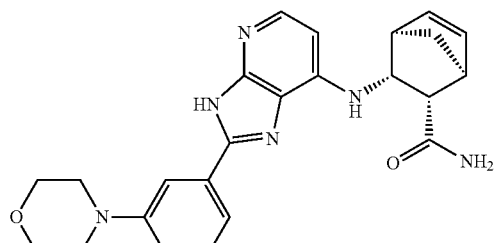

Synthesis of 3-[7-((1R,2R,3S,4S)-3-Carbamoyl-bicyclo[2.2.1]hept-5-en-2-ylamino)-3H-imidazo[4,5-b]pyridin-2-yl]-piperidine-1-carboxylic acid tert-butyl ester (Compound XCII)

In a similar fashion to Compound LXXXVII, (1S,2S,3R,4R)-3-(2,3-Diamino-pyridin-4-ylamino)-bicyclo[2.2.1]hept-5-ene-2-carboxylic acid amide (50.0 mg, 0.193 mmol) and 3-morpholin-4-ylmethyl-benzaldehyde (45.2 mg, 0.212 mmol) were reacted to produce 29 mg (34%) of the title compound. mp: 222-225° C., $^1$H NMR (300 MHz, DMSO-d$^6$): 13.03 (s, 1H), 7.90 (s, 1H), 7.70 (s, 1H), 7.66 (s, 1H), 7.62 (d, J=8 Hz, 1H), 7.36 (t, J=8 Hz, 1H), 7.15 (s, 1H), 7.03 (d, J=8 Hz, 1H), 6.86 (m, 1H), 6.40 (d, J=8 Hz, 1H), 6.33 (s, 2H), 3.79

(s, 4H), 3.32 (s, 4H), 2.87 (s, 1H), 2.77 (s, 1H), 2.60 (d, J=8 Hz, 1H), 2.24 (d, J=8 Hz, 1H), 1.43 (d, J=8 Hz, 1H). MS: 431 (M+H), HPLC: 1.94 min (G method).

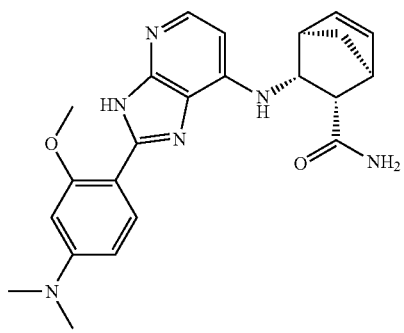

Compound XCIII

Synthesis of (1S,2S,3R,4R)-3-[2-(4-Dimethylamino-2-methoxy-phenyl)-3H-imidazo[4,5-b]pyridin-7-ylamino]-bicyclo[2.2.1]hept-5-ene-2-carboxylic acid amide (Compound XCIII)

In a similar fashion to Compound LXXXVII, (1S,2S,3R,4R)-3-(2,3-Diamino-pyridin-4-ylamino)-bicyclo[2.2.1]hept-5-ene-2-carboxylic acid amide (50.0 mg, 0.193 mmol) and 4-dimethylamino-2-methoxy-benzaldehyde (38.0 mg, 0.212 mmol) were reacted to produce 20 mg (29%) of the title compound. mp: 185-190° C., $^1$H NMR (300 MHz, DMSO-d$^6$): 11.78 (s, 1H), 8.00 (d, J=8 Hz, 1H), 7.85 (d, J=5 Hz, 1H), 7.65 (s, 1H), 7.14 (s, 1H), 6.69 (d, J=8 Hz, 2H), 6.46 (d, J=8 Hz, 1H), 6.36 (d, J=8 Hz, 1H), 6.32 (br s, 3H), 3.96 (s, 3H), 3.01 (s, 6H), 2.86 (s, 1H), 2.75 (s, 1H), 2.59 (d, J=8 Hz, 1H), 2.24 (d, J=8 Hz, 1H), 1.42 (d, J=8 Hz, 1H). MS: 419 (M+H), HPLC: 2.09 min (G method).

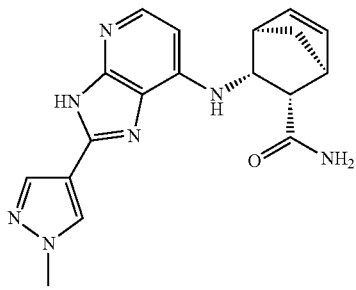

Compound XCIV (1S,2S,3R,4R)-3-[2-(1-Methyl-1H-pyrazol-4-yl)-3H-imidazo[4,5-b]pyridin-7-ylamino]-bicyclo[2.2.1]hept-5-ene-2-carboxylic acid amide In a similar fashion to Compound LXXXVII, (1S,2S,3R,4R)-3-(2,3-Diamino-pyridin-4-ylamino)-bicyclo[2.2.1]hept-5-ene-2-carboxylic acid amide (50.0 mg, 0.193 mmol) and 1-methyl-1H-pyrazole-4-carbaldehyde (23.4 mg, 0.212 mmol) were reacted to produce 19 mg (28%) of the title compound. mp: 236-238° C., $^1$H NMR (300 MHz, DMSO-d$^6$): 12.76 (s, 1H), 8.27 (s, 1H), 7.99 (s, 1H), 7.85 (s, 1H), 7.64 (s, 1H), 7.10 (s, 1H), 6.63 (m, 1H), 6.38 (s, 1H), 6.32 (m, 2H), 3.92 (s, 4H), 2.86 (s, 1H), 2.73 (s, 1H), 2.22 (s, 1H), 1.41 (s, 1H), 1.09 (s, 1H). MS: 350 (M+H), HPLC: 1.60 min (G method).

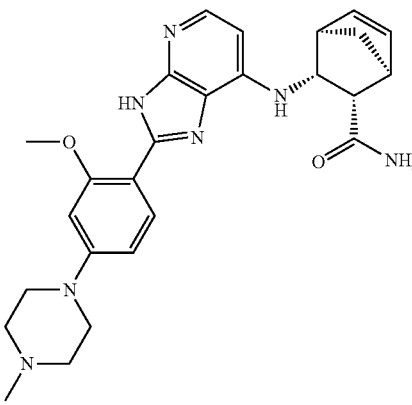

Compound XCV

Synthesis of (1S,2S,3R,4R)-3-{2-[2-Methoxy-4-(4-methyl-piperazin-1-yl)-phenyl]-3H-imidazo[4,5-b]pyridin-7-ylamino}-bicyclo[2.2.1]hept-5-ene-2-carboxylic acid amide (Compound XCV)

In a similar fashion to Compound LXXXVII, (1S,2S,3R,4R)-3-(2,3-Diamino-pyridin-4-ylamino)-bicyclo[2.2.1]hept-5-ene-2-carboxylic acid amide (50.0 mg, 0.193 mmol) and 2-methoxy-4-(4-methyl-piperazin-1-yl)-benzaldehyde (49.7 mg, 0.212 mmol) were reacted to produce 19 mg (21%) of the title compound. mp: 185-195° C., $^1$H NMR (300 MHz, DMSO-d$^6$): 11.87 (s, 1H), 8.01 (s, 1H), 7.87 (s, 1H), 7.65 (s, 1H), 7.16 (s, 1H), 6.73 (m, 1H), 6.68 (s, 1H), 6.60 (s, 1H), 6.37 (s, 1H), 6.32 (s, 2H), 3.95 (s, 4H), 2.86 (s, 1H), 2.75 (s, 1H), 2.24 (s, 4H), 1.42 (s, 1H), 1.24 (s, 1H). MS: 474 (M+H), HPLC: 1.59 min (G method).

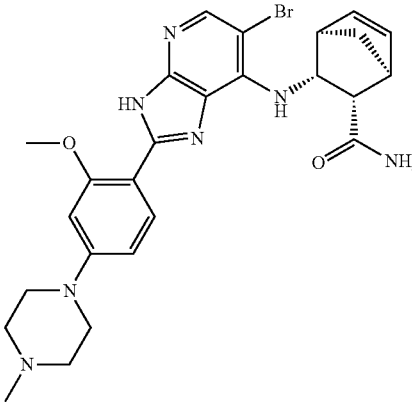

Compound XCVI

Synthesis of (1S,2S,3R,4R)-3-{6-Bromo-2-[2-methoxy-4-(4-methyl-piperazin-1-yl)-phenyl]-3H-imidazo[4,5-b]pyridin-7-ylamino}-bicyclo[2.2.1]hept-5-ene-2-carboxylic acid amide (Compound XCVI)

In a similar fashion to Compound LXXXVII, (1S,2S,3R,4R)-3-(2,3-Diamino-pyridin-4-ylamino)-bicyclo[2.2.1]

hept-5-ene-2-carboxylic acid amide (50.0 mg, 0.148 mmol) and 2-methoxy-4-(4-methyl-piperazin-1-yl)-benzaldehyde (38.1 mg, 0.163 mmol) were reacted to produce 15 mg (18%) of the title compound. mp: 185-195° C., $^1$H NMR (300 MHz, DMSO-d$^6$): 12.08 (s, 1H), 8.00 (s, 1H), 7.98 (s, 1H), 7.72 (s, 1H), 7.19 (s, 1H), 6.93 (d, J=8 Hz, 1H), 6.71 (d, J=8 Hz, 1H), 6.73 (m, 1H), 6.61 (s, 1H), 6.35 (s, 2H), 5.28 (t, J=8 Hz, 1H), 3.96 (s, 3H), 2.88 (s, 1H), 2.74 (s, 1H), 2.61 (d, J=8 Hz, 1H), 2.24 (s, 4H), 1.38 (s, 1H), 1.24 (s, 1H). MS: 554 (M+H), HPLC: 1.88 min (G method).

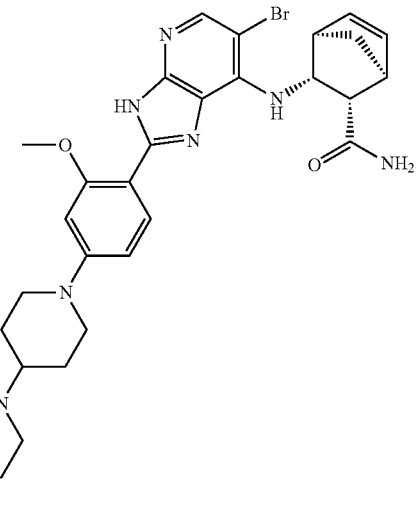

Compound XCVIII

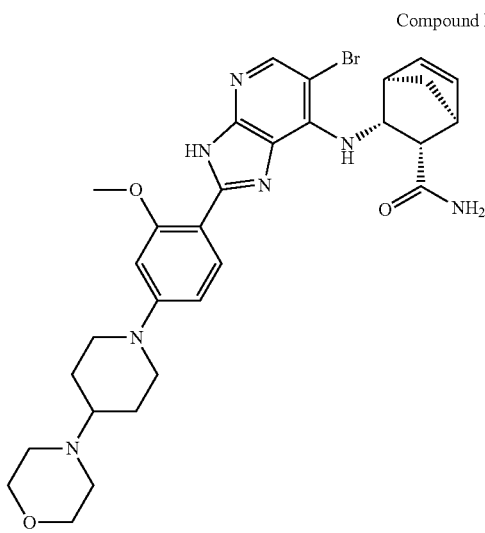

Compound XCVII

Synthesis of (1S,2S,3R,4R)-3-{6-Bromo-2-[2-methoxy-4-(4-morpholin-4-yl-piperidin-1-yl)-phenyl]-3H-imidazo[4,5-b]pyridin-7-ylamino}-bicyclo[2.2.1]hept-5-ene-2-carboxylic acid amide (Compound XCVII)

In a similar fashion to Compound LXXXVII, (1S,2S,3R,4R)-3-(2,3-Diamino-pyridin-4-ylamino)-bicyclo[2.2.1]hept-5-ene-2-carboxylic acid amide (50.0 mg, 0.148 mmol) and 2-methoxy-4-(4-morpholin-4-yl-piperidin-1-yl)-benzaldehyde (49.5 mg, 0.163 mmol) were reacted to produce 29 mg (32%) of the title compound. mp: 185-195° C., $^1$H NMR (300 MHz, DMSO-d$^6$): 12.06 (s, 1H), 7.99 (s, 1H), 7.97 (s, 1H), 7.72 (s, 1H), 7.20 (s, 1H), 6.92 (d, J=8 Hz, 1H), 6.71 (d, J=8 Hz, 1H), 6.59 (s, 1H), 6.35 (s, 1H), 5.28 (t, J=8 Hz, 1H), 3.95 (s, 4H), 3.90 (s, 1H), 3.58 (br s, 4H), 2.87-2.74 (m, 4H), 2.61 (d, J=8 Hz, 1H), 2.34 (d, J=8 Hz, 1H), 2.26 (d, J=8 Hz, 1H), 1.87 (d, J=8 Hz, 2H), 1.48 (q, J=8 Hz, 2H), 1.38 (d, J=12 Hz, 1H), 1.06 (t, J=8 Hz, 1H). MS: 622 (M+H), HPLC: 1.96 min (G method).

Synthesis of (1S,2S,3R,4R)-3-(6-Bromo-2-{2-methoxy-4-[4-(4-methyl-piperazin-1-yl)-piperidin-1-yl]-phenyl}-3H-imidazo[4,5-b]pyridin-7-ylamino)-bicyclo[2.2.1]hept-5-ene-2-carboxylic acid amide (Compound XCVIII)

In a similar fashion to Compound LXXXVII, (1S,2S,3R,4R)-3-(2,3-Diamino-pyridin-4-ylamino)-bicyclo[2.2.1]hept-5-ene-2-carboxylic acid amide (50.0 mg, 0.148 mmol) and 2-methoxy-4-[4-(4-methyl-piperazin-1-yl)-piperidin-1-yl]-benzaldehydebenzaldehyde (51.6 mg, 0.163 mmol) were reacted to produce 49 mg (52%) of the title compound. mp: 185-195° C., $^1$H NMR (300 MHz, DMSO-d$^6$): 12.05 (s, 1H), 7.99 (s, 1H), 7.97 (s, 1H), 7.72 (s, 1H), 7.20 (s, 1H), 6.92 (d, J=8 Hz, 1H), 6.70 (d, J=8 Hz, 1H), 6.59 (s, 1H), 6.35 (s, 1H), 5.28 (t, J=8 Hz, 1H), 3.95 (s, 3H), 3.92 (d, J=12 Hz, 2H), 2.87-2.74 (m, 4H), 2.61 (d, J=8 Hz, 1H), 2.34 (d, J=8 Hz, 1H), 2.26 (d, J=8 Hz, 1H), 2.13 (s, 3H), 1.84 (d, J=8 Hz, 2H), 1.48 (q, J=12 Hz, 2H), 1.38 (d, J=8 Hz, 1H), 1.09 (t, J=8 Hz, 1H). MS: 637 (M+H), HPLC: 1.85 min (G method).

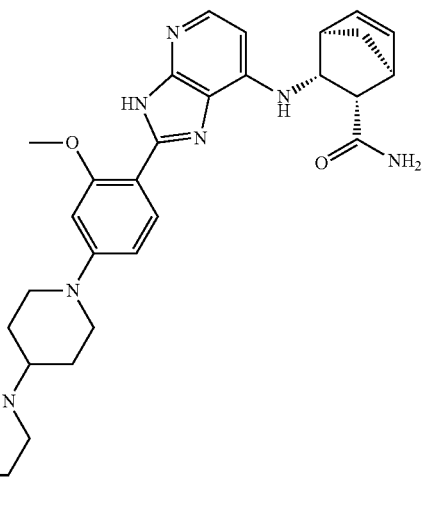

Compound XCIX

Synthesis of (1S,2S,3R,4R)-3-(2-{2-Methoxy-4-[4-(4-methyl-piperazin-1-yl)-piperidin-1-yl]-phenyl}-3H-imidazo[4,5-b]pyridin-7-ylamino)-bicyclo[2.2.1]hept-5-ene-2-carboxylic acid amide (Compound XCIX)

In a similar fashion to Compound LXXXVII, (1S,2S,3R,4R)-3-(2,3-Diamino-pyridin-4-ylamino)-bicyclo[2.2.1]hept-5-ene-2-carboxylic acid amide (50.0 mg, 0.193 mmol) and 2-methoxy-4-[4-(4-methyl-piperazin-1-yl)-piperidin-1-yl]-benzaldehyde (67.3 mg, 0.212 mmol) were reacted to produce 19 mg (20%) of the title compound. mp: 185-195° C., $^1$H NMR (300 MHz, DMSO-d$^6$): 11.84 (s, 1H), 7.99 (d, J=9 Hz, 1H), 7.87 (d, J=5 Hz, 1H), 7.65 (s, 1H), 7.16 (s, 1H), 6.72 (d, J=8 Hz, 1H), 6.67 (d, J=8 Hz, 1H), 6.58 (s, 1H), 6.37 (d, J=5 Hz, 1H), 6.32 (s, 2H), 3.95 (s, 3H), 3.90 (d, J=12 Hz, 2H), 2.87-2.74 (m, 4H), 2.59 (d, J=8 Hz, 1H), 2.33 (m, 4H), 2.23 (d, J=8 Hz, 1H), 2.14 (s, 3H), 1.86 (d, J=12 Hz, 2H), 1.50 (q, J=12 Hz, 2H), 1.42 (d, J=8 Hz, 1H). MS: 557 (M+H), HPLC: 1.58 min (G method).

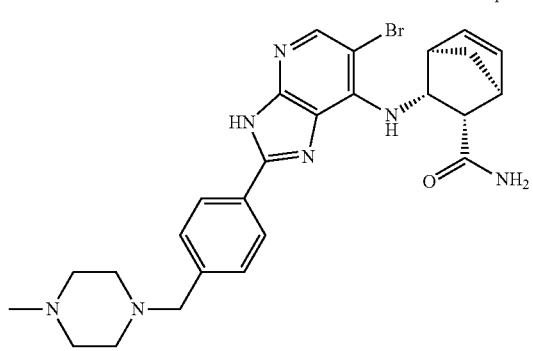

Compound C

Synthesis of (1S,2S,3R,4R)-3-{6-Bromo-2-[4-(4-methyl-piperazin-1-ylmethyl)-phenyl]-3H-imidazo[4,5-b]pyridin-7-ylamino-bicyclo[2.2.1]hept-5-ene-2-carboxylic acid amide (Compound C)

In a similar fashion to Compound LXXXVII, (1S,2S,3R,4R)-3-(2,3-Diamino-5-bromo-pyridin-4-ylamino)-bicyclo[2.2.1]hept-5-ene-2-carboxylic acid amide (50 mg, 0.148 mmol) and 4-(4-Methyl-piperazin-1-ylmethyl)-benzaldehyde (35.5 mg, 0.163 mmol) were reacted to produce 44 mg (55%) of the title compound. mp: 208-209° C., $^1$H NMR (300 MHz, DMSO-d$^6$): 13.27 (s, 1H), 8.09 (d, J=8 Hz, 2H), 8.03 (d, 1H), 7.76 (s, 1H), 7.46 (d, J=8 Hz, 2H), 7.22 (s, 1H), 7.15 (d, J=8 Hz, 1H), 6.41 (s, 1H), 6.37 (s, 1H), 5.23 (t, J=8 Hz, 1H), 3.52 (s, 2H), 2.89 (s, 1H), 2.78 (s, 1H), 2.62 (d, J=8 Hz, 1H), 2.39 (m, 4H), 2.25 (d, J=8 Hz, 1H), 2.16 (s, 3H), 1.39 (d, J=8 Hz, 1H). MS: 536, 538 (M+H), HPLC: 1.72 min (G method).

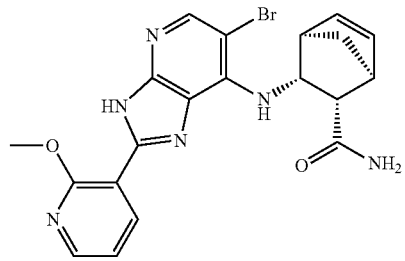

Compound CI

Synthesis of (1S,2S,3R,4R)-3-[6-Bromo-2-(2-methoxy-pyridin-3-yl)-3H-imidazo[4,5-b]pyridin-7-ylamino]-bicyclo[2.2.1]hept-5-ene-2-carboxylic acid amide (Compound CI)

In a similar fashion to Compound LXXXVII, (1S,2S,3R,4R)-3-(2,3-Diamino-5-bromo-pyridin-4-ylamino)-bicyclo[2.2.1]hept-5-ene-2-carboxylic acid amide (50 mg, 0.148 mmol) and 2-Methoxy-pyridine-3-carbaldehyde (22.3 mg, 0.163 mmol) were reacted to produce 43 mg (64%) of the title compound. mp: 201° C., $^1$H NMR (300 MHz, DMSO-d$^6$): 12.64 (s, 1H), 8.45 (d, J=8 Hz, 1H), 8.32 (s, 1H), 8.07 (s, 1H), 7.75 (s, 1H), 7.22 (m, 2H), 7.17 (d, J=8 Hz, 1H), 6.39 (s, 1H), 6.36 (s, 1H), 5.23 (t, J=8 Hz, 1H), 4.05 (s, 3H), 2.89 (s, 1H), 2.78 (s, 1H), 2.62 (d, J=8 Hz, 1H), 2.25 (d, J=8 Hz, 1H), 1.39 (d, J=8 Hz, 1H). MS: 455, 457 (M+H), HPLC: 2.39 min (G method).

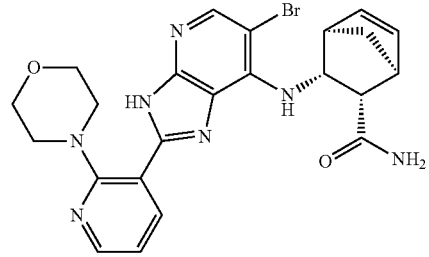

Compound CII

Synthesis of (1S,2S,3R,4R)-3-[6-Bromo-2-(2-morpholin-4-yl-pyridin-3-yl)-3H-imidazo[4,5-b]pyridin-7-ylamino]-bicyclo[2.2.1]hept-5-ene-2-carboxylic acid amide (Compound CII)

In a similar fashion to Compound LXXXVII, (1S,2S,3R,4R)-3-(2,3-Diamino-5-bromo-pyridin-4-ylamino)-bicyclo[2.2.1]hept-5-ene-2-carboxylic acid amide (50 mg, 0.148 mmol) and 2-Morpholin-4-yl-pyridine-3-carbaldehyde (31.2 mg, 0.163 mmol) were reacted to produce 32 mg (42%) of the title compound. mp: 150° C., $^1$H NMR (300 MHz, DMSO-d$^6$): 12.95 (s, 1H), 8.33 (d, J=5 Hz, 1H), 8.04 (s, 1H), 7.98 (d, J=8 Hz, 1H), 7.73 (s, 1H), 7.19 (s, 1H), 7.09 (m, 1H), 6.34 (s, 1H), 6.32 (s, 1H), 5.21 (t, J=8 Hz, 1H), 3.64 (s, 4H), 3.29 (s, 1H), 3.06 (m, 4H), 2.87 (s, 1H), 2.78 (s, 1H), 2.59 (d, J=8 Hz, 1H), 2.26 (d, J=8 Hz, 1H), 1.39 (d, J=8 Hz, 1H). MS: 510, 512 (M+H), HPLC: 2.02 min (G method).

Compound CIII

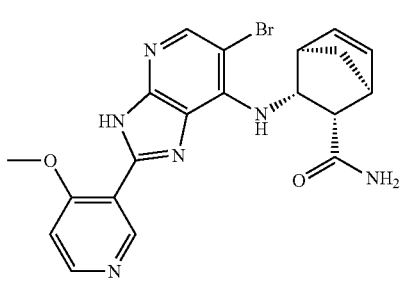

Synthesis of (1S,2S,3R,4R)-3-[6-Bromo-2-(4-methoxy-pyridin-3-yl)-3H-imidazo[4,5-b]pyridin-7-ylamino]-bicyclo[2.2.1]hept-5-ene-2-carboxylic acid amide (Compound CIII)

In a similar fashion to Compound LXXXVII, (1S,2S,3R,4R)-3-(2,3-Diamino-5-bromo-pyridin-4-ylamino)-bicyclo[2.2.1]hept-5-ene-2-carboxylic acid amide (50 mg, 0.148 mmol) and 4-Methoxy-pyridine-3-carbaldehyde (22.3 mg, 0.163) were reacted to produce 29 mg (43%) of the title compound. mp: 160° C., $^1$H NMR (300 MHz, DMSO-d$^6$): 12.69 (s, 1H), 9.11 (s, 1H), 8.54 (d, J=8 Hz, 1H), 8.07 (s, 1H), 7.74 (s, 1H), 7.27 (d, J=8 Hz, 1H), 7.21 (s, 1H), 7.17 (d, J=9 Hz, 1H), 6.35 (s, 2H), 5.26 (t, J=8 Hz, 1H), 4.02 (s, 3H), 3.38 (q, J=8 Hz, 1H), 3.32 (s, 1H), 2.89 (s, 1H), 2.78 (s, 1H), 2.63 (d, J=8 Hz, 1H), 2.26 (d, J=8 Hz, 1H), 1.40 (d, J=8 Hz, 1H), 1.09 (t, J=8 Hz, 1H). MS: 455, 457 (M+H), HPLC: 1.64 min (G method).

Compound CV

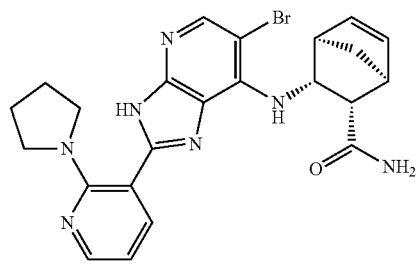

Synthesis of (1S,2S,3R,4R)-3-[6-Bromo-2-(2-pyrrolidin-1-yl-pyridin-3-yl)-3H-imidazo[4,5-b]pyridin-7-ylamino]-bicyclo[2.2.1]hept-5-ene-2-carboxylic acid amide (Compound CV)

In a similar fashion to Compound LXXXVII, (1S,2S,3R,4R)-3-(2,3-Diamino-5-bromo-pyridin-4-ylamino)-bicyclo[2.2.1]hept-5-ene-2-carboxylic acid amide (50 mg, 0.148 mmol) and 2-Pyrrolidin-1-yl-pyridine-3-carbaldehyde (28.6 mg, 0.163 mmol) were reacted to produce 24 mg (34%) of the title compound. mp: 190° C., $^1$H NMR (300 MHz, DMSO-d$^6$): 13.02 (s, 1H), 8.21 (m, 1H), 8.02 (s, 1H), 7.71 (d, J=8 Hz, 1H), 6.68 (s, 1H), 7.18 (s, 1H), 7.06 (d, J=8 Hz, 1H), 6.75 (t, 1H), 6.27 (m, 1H), 6.17 (m, 1H), 5.14 (t, J=8 Hz, 1H), 3.32 (s, 3H), 3.29 (s, 2H), 3.08 (m, 2H), 2.85 (s, 1H), 2.71 (s, 1H), 2.55 (d, J=8 Hz, 1H), 2.25 (d, J=8 Hz, 1H), 1.82 (m, 2H), 1.73 (m, 2H), 1.37 (d, J=8 Hz, 1H), 1.09 (t, J=8 Hz, 1H). MS: 494, 496 (M+H), HPLC: 3.19 min (G method).

Compound CIV

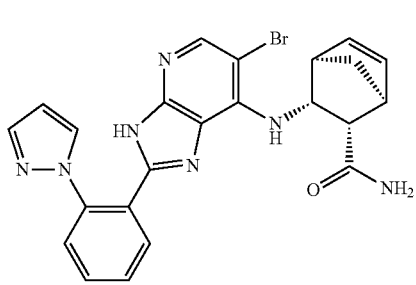

Synthesis of (1S,2S,3R,4R)-3-[6-Bromo-2-(2-pyrazol-1-yl-phenyl)-3H-imidazo[4,5-b]pyridin-7-ylamino]-bicyclo[2.2.1]hept-5-ene-2-carboxylic acid amide (Compound CIV)

In a similar fashion to Compound LXXXVII, (1S,2S,3R,4R)-3-(2,3-Diamino-5-bromo-pyridin-4-ylamino)-bicyclo[2.2.1]hept-5-ene-2-carboxylic acid amide (50 mg, 0.148 mmol) and 2-Pyrazol-1-yl-benzaldehyde (28 mg, 0.163 mmol) were reacted to produce 33 mg (45%) of the title compound. mp: 120° C., $^1$H NMR (300 MHz, DMSO-d$^6$): 12.88 (s, 1H), 8.00 (s, 1H), 7.82 (d, J=8 Hz, 1H), 7.77 (s, 1H), 7.66 (m, 3H), 7.60 (m, 1H), 7.57 (s, 1H), 7.16 (s, 1H), 7.04 (d, J=8 Hz, 1H), 6.37 (s, 1H), 6.22 (s, 1H), 6.10 (s, 1H), 4.87 (t, J=8 Hz, 1H), 3.32 (s, 1H), 2.80 (s, 1H), 2.16 (d, J=8 Hz, 1H), 1.31 (d, J=8 Hz, 1H). MS: 490, 492 (M+H), HPLC: 2.28 min (G method).

Compound CVI

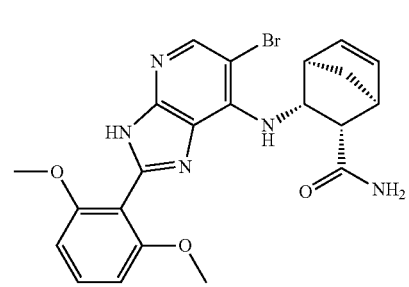

Synthesis of (1S,2S,3R,4R)-3-[6-Bromo-2-(2,6-dimethoxy-phenyl)-3H-imidazo[4,5-b]pyridin-7-ylamino]-bicyclo[2.2.1]hept-5-ene-2-carboxylic acid amide (Compound CVI)

In a similar fashion to Compound LXXXVII, (1S,2S,3R,4R)-3-(2,3-Diamino-5-bromo-pyridin-4-ylamino)-bicyclo[2.2.1]hept-5-ene-2-carboxylic acid amide (50 mg, 0.148 mmol) and 2,6-Dimethoxy-benzaldehyde (27 mg, 0.163 mmol) were reacted to produce 49 mg (68%) of the title compound. mp: 194-197° C., $^1$H NMR (300 MHz, DMSO-d$^6$): 12.6 (s, 1H), 8.00 (s, 1H), 7.57 (s, 1H), 7.45 (t, J=8 Hz, 1H), 7.12 (s, 1H), 6.80 (d, J=8 Hz, 2H), 6.23 (br s, 1H), 6.17 (br s, 1H), 5.14 (t, J=8 Hz, 1H), 3.73 (s, 6H), 2.84 (s, 1H), 2.69 (s, 1H), 2.54 (d, J=8 Hz, 1H), 2.25 (d, J=8 Hz, 1H), 2.09 (s, 1H), 1.38 (d, J=8 Hz, 1H). MS: 484, 486 (M+H), HPLC: 2.33 min (G method)

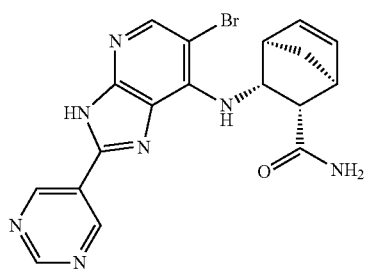

Compound CVII

Synthesis of (1S,2S,3R,4R)-3-(6-Bromo-2-pyrimidin-5-yl-3H-imidazo[4,5-b]pyridin-7-ylamino)-bicyclo[2.2.1]hept-5-ene-2-carboxylic acid amide (Compound CVII)

In a similar fashion to Compound LXXXVII, (1S,2S,3R,4R)-3-(2,3-Diamino-5-bromo-pyridin-4-ylamino)-bicyclo[2.2.1]hept-5-ene-2-carboxylic acid amide (50 mg, 0.148 mmol) and Pyrimidine-5-carbaldehyde (17.6 mg, 0.163 mmol) were reacted to produce 9.0 mg (14%) of the title compound. mp: >300° C., $^1$H NMR (300 MHz, DMSO-d$^6$): 13.7 (s, 1H), 9.42 (s, 2H), 9.28 (s, 1H), 8.10 (s, 1H), 7.77 (s, 1H), 7.35 (m, 1H), 7.23 (s, 1H), 6.39 (d, J=8 Hz, 1H), 5.22 (t, J=8 Hz, 1H), 3.3 (s, 1H), 2.90 (s, 1H), 2.78 (s, 1H), 2.63 (d, J=8 Hz, 1H), 2.25 (d, J=8 Hz, 1H), 1.40 (d, J=9 Hz, 1H). MS: 426, 428 (M+H), HPLC: 1.91 min (G method).

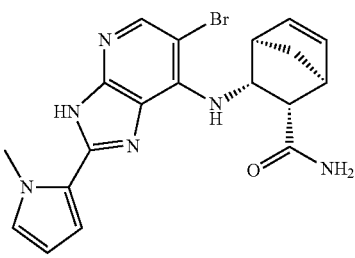

Compound CIX

Synthesis of (1S,2S,3R,4R)-3-[6-Bromo-2-(1-methyl-1H-pyrrol-2-yl)-3H-imidazo[4,5-b]pyridin-7-ylamino]-bicyclo[2.2.1]hept-5-ene-2-carboxylic acid amide (Compound CIX)

In a similar fashion to Compound LXXXVII, (1S,2S,3R,4R)-3-(2,3-Diamino-5-bromo-pyridin-4-ylamino)-bicyclo[2.2.1]hept-5-ene-2-carboxylic acid amide (50 mg, 0.148 mmol) and 1-Methyl-1H-pyrrole-2-carbaldehyde (17.7 mg, 0.163 mmol) were reacted to produce 38 mg (60%) of the title compound. mp: 293-295° C., $^1$H NMR (300 MHz, DMSO-d$^6$): 12.89 (s, 1H), 7.97 (s, 1H), 7.71 (s, 1H), 7.21 (s, 1H), 6.97 (s, 1H), 6.93 (br s, 2H), 6.35 (s, 1H), 6.28 (s, 1H), 6.14 (s, 1H), 5.26 (t, J=8 Hz, 1H), 4.05 (s, 3H), 3.32 (s, 1H), 3.29 (s, 1H), 2.85 (s, 1H), 2.73 (s, 1H), 2.59 (d, J=8 Hz, 1H), 2.26 (d, J=8 Hz, 1H), 1.40 (d, J=8 Hz, 1H). MS: 427, 429 (M+H), HPLC: 2.40 (G method).

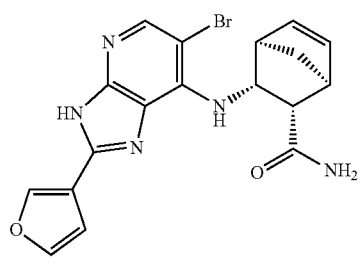

Compound CVIII

Synthesis of (1S,2S,3R,4R)-3-(6-Bromo-2-furan-3-yl-3H-imidazo[4,5-b]pyridin-7-ylamino)-bicyclo[2.2.1]hept-5-ene-2-carboxylic acid amide (Compound CVIII)

In a similar fashion to Compound LXXXVII, (1S,2S,3R,4R)-3-(2,3-Diamino-5-bromo-pyridin-4-ylamino)-bicyclo[2.2.1]hept-5-ene-2-carboxylic acid amide (50 mg, 0.148 mmol) and 3-Furaldehyde (15.6 mg, 0.163 mmol) were reacted to produce 33 mg (54%) of the title compound. mp: 231-232° C., $^1$H NMR (300 MHz, DMSO-d$^6$): 13.1 (s, 1H), 8.31 (s, 1H), 8.00 (s, 1H), 7.84 (s, 1H), 7.74 (br s, 1H), 7.21 (s, 1H), 7.10 (d, J=8 Hz, 1H), 7.01 (s, 1H), 6.40 (br s, 1H), 6.33 (br s, 1H), 5.15 (t, J=8 Hz, 1H), 2.87 (s, 1H), 2.74 (s, 1H), 2.60 (d, J=8 Hz, 1H), 2.23 (d, J=8 Hz, 1H), 1.37 (d, J=8 Hz, 1H). MS: 414-416 (M+H), HPLC: 2.27 min (G method)

Compound CX

Synthesis of (1S,2S,3R,4R)-3-[6-Bromo-2-(5-methyl-furan-2-yl)-3H-imidazo[4,5-b]pyridin-7-ylamino]-bicyclo[2.2.1]hept-5-ene-2-carboxylic acid amide (Compound CX)

In a similar fashion to Compound LXXXVII, (1S,2S,3R,4R)-3-(2,3-Diamino-5-bromo-pyridin-4-ylamino)-bicyclo[2.2.1]hept-5-ene-2-carboxylic acid amide (50 mg, 0.148 mmol) and 5-Methyl-2-furancarboxaldehyde (17.9 mg, 0.163 mmol) were reacted to produce 19 mg (30%) of the title compound. mp: 200-201° C., $^1$H NMR (300 MHz, DMSO-d$^6$): 13.17 (s, 1H), 8.00 (s, 1H), 7.74 (s, 1H), 7.20 (s, 1H), 7.06 (s, 1H), 6.36 (s, 1H), 6.33 (s, 1H), 5.16 (t, J=8 Hz, 1H), 3.32 (s, 1H), 2.87 (s, 1H), 2.73 (s, 1H), 2.60 (d, J=8 Hz, 1H), 2.40 (s, 3H), 2.23 (d, J=8 Hz, 1H), 1.37 (d, J=8 Hz, 1H). MS: 428, 430 (M+H), HPLC: 2.39 (G method).

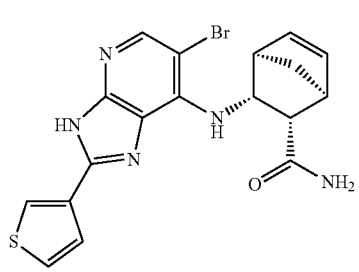

Compound CXI

Synthesis of (1S,2S,3R,4R)-3-(6-Bromo-2-thiophen-3-yl-3H-imidazo[4,5-b]pyridin-7-ylamino)-bicyclo[2.2.1]hept-5-ene-2-carboxylic acid amide (Compound CXI)

In a similar fashion to Compound LXXXVII, (1S,2S,3R,4R)-3-(2,3-Diamino-5-bromo-pyridin-4-ylamino)-bicyclo[2.2.1]hept-5-ene-2-carboxylic acid amide (50 mg, 0.148 mmol) and 3-Thiophenecarboxaldehyde (18.2 mg, 0.163 mmol) were reacted to produce 17 mg (27%) of the title compound. mp: 238-241° C., $^1$H NMR (300 MHz, DMSO-d$^6$): 13.21 (s, 1H), 8.19 (s, 1H), 8.01 (s, 1H), 7.75 (s, 1H), 7.72 (s, 2H), 7.22 (s, 1H), 7.13 (d, J=8 Hz, 1H), 6.40 (br s, 1H), 6.35 (br s, 1H), 5.19 (t, J=8 Hz, 1H), 3.31 (s, 2H), 3.29 (s, 1H), 2.88 (s, 1H), 2.76 (s, 1H), 2.61 (d, J=8 Hz, 1H), 2.24 (d, J=8 Hz, 1H), 1.38 (d, J=8 Hz, 1H). MS: 430, 432 (M+H), HPLC: 2.44 min (G method).

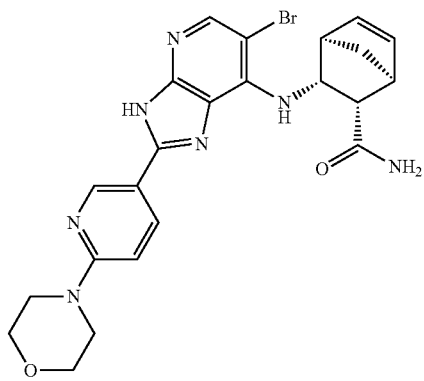

Compound CXII

Synthesis of (1S,2S,3R,4R)-3-[6-Bromo-2-(6-morpholin-4-yl-pyridin-3-yl)-3H-imidazo[4,5-b]pyridin-7-ylamino]-bicyclo[2.2.1]hept-5-ene-2-carboxylic acid amide (Compound CXII)

In a similar fashion to Compound LXXXVII, (1S,2S,3R,4R)-3-(2,3-Diamino-5-bromo-pyridin-4-ylamino)-bicyclo[2.2.1]hept-5-ene-2-carboxylic acid amide (50 mg, 0.148 mmol) and 6-Morpholin-4-yl-pyridine-3-carbaldehyde (31.2 mg, 0.163 mmol) were reacted to produce 56 mg (74%) of the title compound. mp: 288-290° C., $^1$H NMR (300 MHz, DMSO-d$^6$): 13.14 (s, 1H), 8.87 (s, 1H), 8.21 (d, J=8 Hz, 2H), 7.98 (s, 1H), 7.74 (s, 1H), 7.20 (s, 1H), 7.02 (m, 2H), 6.36 (s, 2H), 5.25 (t, J=8 Hz, 1H), 3.72 (br s, 4H), 3.57 (br s, 4H), 3.29 (s, 1H), 2.88 (s, 1H), 2.75 (s, 1H), 2.61 (d, J=7 Hz, 1H), 2.25 (d, J=8 Hz, 1H), 1.38 (d, J=8 Hz, 1H). MS: 510, 512 (M+H), HPLC: 1.96 min (G method).

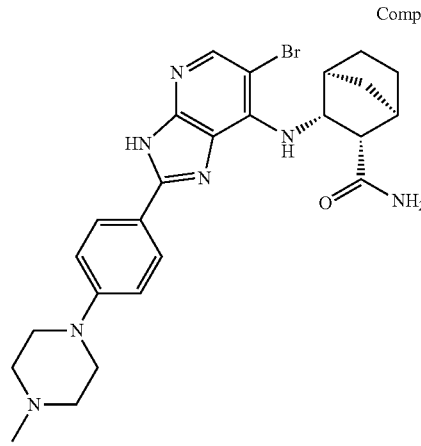

Compound CXIII

Synthesis of (1R,2S,3R,4S)-3-{6-Bromo-2-[4-(4-methyl-piperazin-1-yl)-phenyl]-3H-imidazo[4,5-b]pyridin-7-ylamino}-bicyclo[2.2.1]heptane-2-carboxylic acid amide (Compound CXIII)

Compound LXXVIII (50.0 mg, 0.0957 mmol) was hydrogenated in a Paar shaker at 20 psi H$_2$ for 2 hours. The reaction mixture was filtered through celite and the filtrate was concentrated. The residue was taken up into a small amount of methanol and filtered through a syringe before Gilson chromatography. The desired fractions were free-based with bicarb and extracted with DCM. The organics were dried over MgSO$_4$, filtered and concentrated. This residue was isolated as a 34 mg (68%) of solid by triturations with ether. mp: 256-258° C., $^1$H NMR (300 MHz, DMSO-d$^6$): 12.99 (s, 1H), 8.00 (d, J=8 Hz, 1H), 7.95 (s, 2H), 7.64 (s, 1H), 7.10 (s, 1H), 7.06 (d, J=8 Hz, 2H), 6.96 (d, J=8 Hz, 1H), 5.32 (t, J=8 Hz, 1H), 3.31 (s, 3H), 3.29 (s, 1H), 2.70 (d, J=9 Hz, 1H), 2.45 (br s, 4H), 2.31 (s, 1H), 2.23 (s, 3H), 2.15 (s, 1H), 2.07 (d, J=8 Hz, 1H), 1.52 (m, 3H), 1.27 (m, 1H), 1.10 (m, 1H). MS: 524, 526 (M+H), HPLC: 1.87 min (G method).

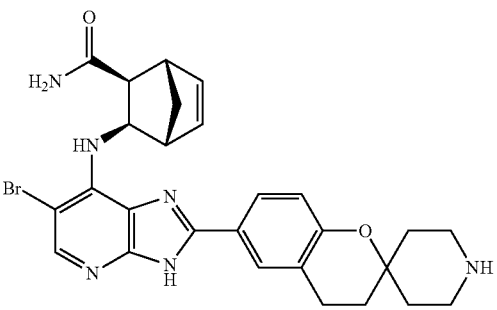

Compound CXIV

Synthesis of (1S,2S,3R,4R)-3-[(6-bromo-2-spiro[chromane-2,4'-piperidine]-6-yl-3H-imidazo[4,5-b]pyridin-7-yl)amino]bicyclo[2.2.1]hept-5-ene-2-carboxamide (Compound CXIV)

In a similar fashion to Compound LXXXVII, (1S,2S,3R,4R)-3-(2,3-Diamino-5-bromo-pyridin-4-ylamino)-bicyclo[2.2.1]hept-5-ene-2-carboxylic acid amide (50 mg, 0.148 mmol) and N-tert-butoxycarbonyl-6-carboxy-3,4-dihydrospiro[2H-1-benzopyran-2,4'-piperidine] (75.4 mg, 0.228 mmol) were reacted. The crude reaction was concentrated, then taken up into 4N HCl/dioxane and heated at 50° C. for 4 hours. The reaction mixture was then concentrated and chromatographed on Gilson HPLC 0-45% CH$_3$CN/H$_2$O. The desired fractions were lyophilized to produce 65 mg (47%) of the title compound as the TFA salt. mp: lyophilate, $^1$H NMR (300 MHz, DMSO-d$^6$): 13.19 (s, 1H), 8.59 (m, 1H), 8.42 (m, 1H), 8.03 (s, 1H), 7.92 (s, 1H), 7.89 (d, 1H), 7.76 (s, 1H), 7.25 (s, 2H), 7.00 (d, J=8 Hz, 1H), 6.38 (s, 2H), 5.19 (t, J=8 Hz, 1H), 3.23 (m, 2H), 3.14 (m, 2H), 2.88 (m, 3H), 2.78 (s, 1H), 2.62 (d, J=8 Hz, 1H), 2.24 (d, J=8 Hz, 1H), 1.96-1.85 (m, 4H), 1.39 (d, J=8 Hz, 1H). MS: 551 (M+H), HPLC: 1.94 min (G method).

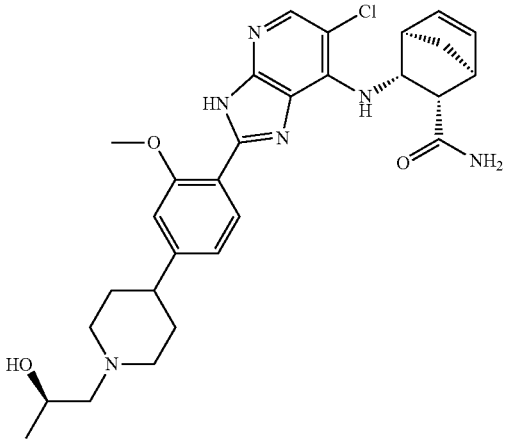

Compound CXVI

Synthesis of (1S,2S,3R,4R)-3-(6-(Chloro-2-{4-[1-((R)-2-hydroxy-propyl)-piperidin-4-yl]-2-methoxy-phenyl}-3H-imidazo[4,5-b]pyridin-7-ylamino)-bicyclo[2.2.1]hept-5-ene-2-carboxylic acid amide (Compound CXVI)

In a similar fashion to Compound LXXXVII, (1S,2S,3R,4R)-3-(2,3-Diamino-5-chloro-pyridin-4-ylamino)-bicyclo[2.2.1]hept-5-ene-2-carboxylic acid amide (50 mg, 0.148 mmol) and 4-[1-((R)-2-Hydroxy-propyl)-piperidin-4-yl]-2-methoxy-benzaldehyde (80 mg, 0.288 mmol) were reacted to produce 17 mg (12%) of the title compound. mp: >120° C., $^1$H NMR (300 MHz, CDCl$_3$): 10.70 (s, 1H), 8.34 (d, J=8 Hz, 1H), 8.04 (s, 1H), 7.04 (d, J=8 Hz, 1H), 6.94 (s, 1H), 6.39-6.35 (m, 3H), 5.51 (d, J=8 Hz, 1H), 5.19 (t, J=8 Hz, 1H), 5.07 (s, 1H), 4.08 (s, 3H), 3.89 (m, 1H), 3.19 (s, 2H), 2.98 (d, 1H), 2.91 (s, 1H), 2.88 (d, J=8 Hz, 1H), 2.62 (m, 1H), 2.46-2.22 (m, 5H). MS: 551 (M+H), HPLC: 1.89 min (G method).

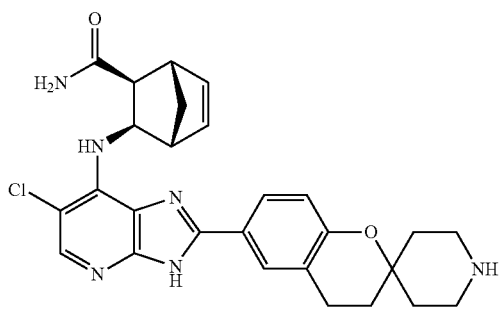

Compound CXV

Synthesis of (1S,2S,3R,4R)-3-[(6-chloro-2-spiro[chromane-2,4'-piperidine]-6-yl-3H-imidazo[4,5-b]pyridin-7-yl)amino]bicyclo[2.2.1]hept-5-ene-2-carboxamide (Compound CXV)

In a similar fashion to Compound LXXXVII, (1S,2S,3R,4R)-3-(2,3-Diamino-5-chloro-pyridin-4-ylamino)-bicyclo[2.2.1]hept-5-ene-2-carboxylic acid amide (50 mg, 0.148 mmol) and N-tert-butoxycarbonyl-6-carboxy-3,4-dihydrospiro[2H-1-benzopyran-2,4'-piperidine] (75.4 mg, 0.228 mmol) were reacted. The crude reaction was concentrated, then taken up into 4N HCl/dioxane and heated at 50° C. for 4 hours. The reaction mixture was then concentrated and chromatographed on Gilson HPLC 0-45% CH$_3$CN/H$_2$O. The desired fractions were neutralized with conc. bicarb. Attempted extraction into DCM and EtOAc failed but a solid formed in the sep funnel and was filtered. This solid was 7 mg (6%) of the title compound. mp: >250° C., $^1$H NMR (300 MHz, DMSO-d$^6$): 13.12 (s, 1H), 7.92 (s, 2H), 7.88 (d, 1H), 7.76 (s, 1H), 7.24 (s, 1H), 7.15 (d, J=8 Hz, 1H), 6.98 (d, J=8 Hz, 1H), 6.38 (s, 2H), 5.15 (t, J=8 Hz, 1H), 3.23 (m, 2H), 3.14 (m, 2H), 2.88 (m, 3H), 2.78 (s, 1H), 2.62 (d, J=8 Hz, 1H), 2.24 (d, J=8 Hz, 1H), 1.96-1.85 (m, 4H), 1.39 (d, J=8 Hz, 1H). MS: 505 (M+H), HPLC: 1.96 min (G method).

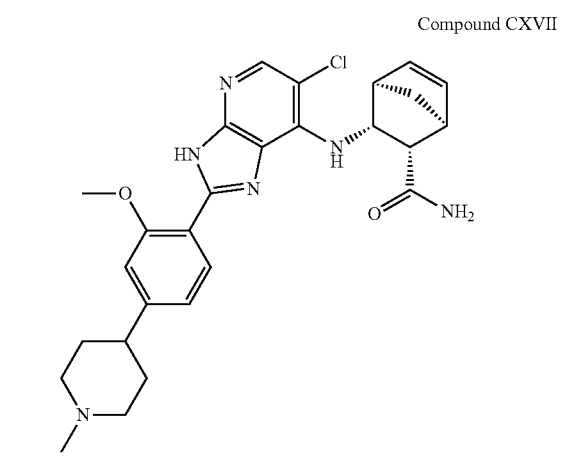 [SMILES: COc1cc(C2CCN(C)CC2)ccc1-c1nc2c(N[C@H]3[C@@H](C(N)=O)[C@@H]4C=C[C@H]3C4)c(Cl)cnc2[nH]1]

Compound CXVII

Synthesis of (1S,2S,3R,4R)-3-{6-Chloro-2-[2-methoxy-4-(1-methyl-piperidin-4-yl)-phenyl]-3H-imidazo[4,5-b]pyridin-7-ylamino}-bicyclo[2.2.1]hept-5-ene-2-carboxylic acid amide (Compound CXVII)

In a similar fashion to Compound LXXXVII, (1S,2S,3R,4R)-3-(2,3-Diamino-5-chloro-pyridin-4-ylamino)-bicyclo

[2.2.1]hept-5-ene-2-carboxylic acid amide (125 mg, 0.427 mmol) and 2-Methoxy-4-(1-methyl-piperidin-4-yl)-benzaldehyde (109.5 mg, 0.469 mmol) were reacted to produce 106 mg (49%) of the title compound. mp: 232-235° C., ¹H NMR (300 MHz, CDCl₃): 10.67 (s, 1H), 8.33 (d, J=8 Hz, 1H), 8.04 (s, 1H), 7.04 (d, J=8 Hz, 1H), 6.96 (s, 1H), 6.42 (m, 1H), 6.38 (m, 1H), 6.35 (m, 1H), 5.48 (d, J=8 Hz, 1H), 5.18 (t, J=8 Hz, 1H), 5.05 (s, 1H), 4.06 (s, 3H), 3.19 (s, 1H), 3.03 (d, J=10 Hz, 2H), 2.91 (m, 2H), 2.57 (m, 1H), 2.37 (s, 3H), 2.34 (s, 1H), 2.10 (m, 2H), 1.89 (m, 4H), 1.76 (d, J=8 Hz, 1H), 1.27 (s, 2H). MS: 507 (M+H), HPLC: 1.86 min (G method)

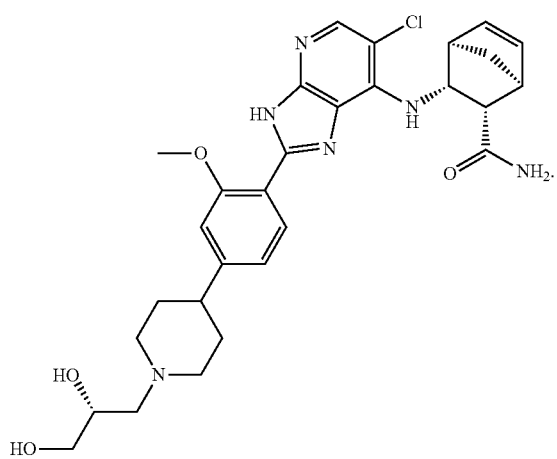

Compound CXVIII

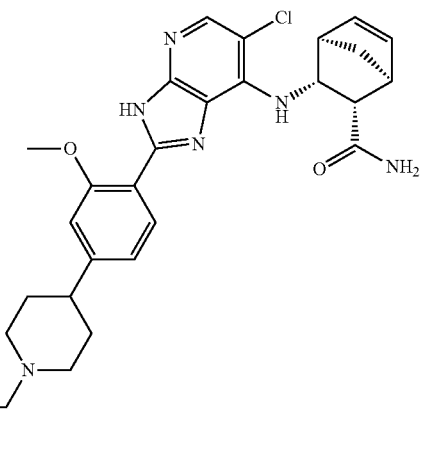

Compound CXIX

Synthesis of (1S,2S,3R,4R)-3-(6-Chloro-2-{4-[1-((S)-2-hydroxy-3-methoxy-propyl)-piperidin-4-yl]-2-methoxy-phenyl}-3H-imidazo[4,5-b]pyridin-7-ylamino)-bicyclo[2.2.1]hept-5-ene-2-carboxylic acid amide (Compound CXIX)

In a similar fashion to Compound LXXXVII, (1S,2S,3R,4R)-3-(2,3-Diamino-5-chloro-pyridin-4-ylamino)-bicyclo[2.2.1]hept-5-ene-2-carboxylic acid amide (109 mg, 0.373 mmol) and 4-[1-((S)-2-Hydroxy-3-methoxy-propyl)-piperidin-4-yl]-2-methoxy-benzaldehyde (126 mg, 0.410 mmol) were reacted to produce 102 mg (47%) of the title compound. mp: 189-191° C., ¹H NMR (300 MHz, CDCl₃): 10.67 (s, 1H), 8.35 (d, J=8 Hz, 1H), 8.04 (s, 1H), 7.04 (d, J=8 Hz, 1H), 6.94 (s, 1H), 6.39-6.35 (m, 3H), 5.51 (d, J=8 Hz, 1H), 5.19 (t, J=8 Hz, 1H), 5.07 (s, 1H), 4.08 (s, 3H), 3.89 (m, 1H), 3.19 (s, 2H), 2.98 (d, 1H), 2.91 (s, 1H), 2.88 (d, J=8 Hz, 1H), 2.62 (m, 1H), 2.46-2.22 (m, 5H). MS: 581 (M+H), HPLC: 1.90 min (G method).

Synthesis of (1S,2S,3R,4R)-3-(6-Chloro-2-{4-[1-((R)-2,3-dihydroxy-propyl)-piperidin-4-yl]-2-methoxy-phenyl}-3H-imidazo[4,5-b]pyridin-7-ylamino)-bicyclo[2.2.1]hept-5-ene-2-carboxylic acid amide (Compound CXVIII)

In a similar fashion to Compound LXXXVII, (1S,2S,3R,4R)-3-(2,3-Diamino-5-chloro-pyridin-4-ylamino)-bicyclo[2.2.1]hept-5-ene-2-carboxylic acid amide (63.4 mg, 0.216 mmol) and 4-[1-((R)-2,3-Dihydroxy-propyl)-piperidin-4-yl]-2-methoxy-benzaldehyde (69.6 mg, 0.469 mmol) were reacted to produce 12 mg (10%) of the title compound. mp: 209-211° C., ¹H NMR (300 MHz, CDCl₃): 10.67 (s, 1H), 8.35 (d, J=8 Hz, 1H), 8.04 (s, 1H), 7.04 (d, J=8 Hz, 1H), 6.94 (s, 1H), 6.39-6.35 (m, 3H), 5.51 (d, J=8 Hz, 1H), 5.19 (t, J=8 Hz, 1H), 5.07 (s, 1H), 4.08 (s, 3H), 3.89 (m, 1H), 3.19 (s, 2H), 2.98 (d, 1H), 2.91 (s, 1H), 2.88 (d, J=8 Hz, 1H), 2.62 (m, 1H), 2.46-2.22 (m, 5H). MS: 567 (M+H), HPLC: 1.83 min (G method).

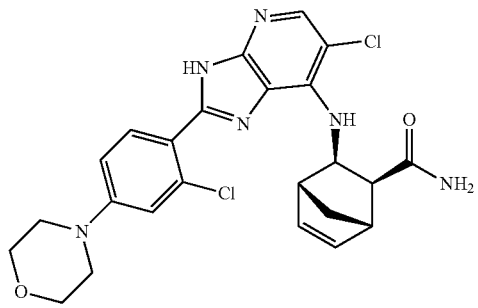

Compound CXX

(1S,2S,3R,4R)-3-[6-Chloro-2-(2-chloro-4-morpholin-4-yl-phenyl)-3H-imidazo[4,5-b]pyridin-7-ylamino]-bicyclo[2.2.1]hept-5-ene-2-carboxylic acid amide (Compound CXX)

In a similar fashion to Compound LXXXVII, (1S,2S,3R,4R)-3-(2,3-Diamino-5-chloro-pyridin-4-ylamino)-bicyclo

[2.2.1]hept-5-ene-2-carboxylic acid amide (50.00 mg, 0.1702 mmol), 2-Chloro-4-morpholin-4-yl-benzaldehyde (42.2 mg, 0.187 mmol), and Ammonium acetate (26.2 mg, 0.340 mmol) were reacted to produce 46.98 mg (45%) of the title compound. (300 MHz, DMSO-$d_6$) 12.89 (s, 1H), 7.95 (s, 1H), 7.72 (m, 2H), 7.21 (s, 1H), 7.09 (m, 3H), 6.30 (s, 2H), 5.18 (t, J=17 Hz, 8.5 Hz, 1H), 3.75 (s, 4H), 3.27 (s, 4H), 2.87 (s, 1H), 2.78 (s, 1H), 2.58 (d, J=8 Hz, 1H), 2.24 (d, J=8 Hz, 1H), 1.38 (d, J=8 Hz). MS=499 (M+H), HPLC: 2.47 min. (G Method).

Compound CXXI

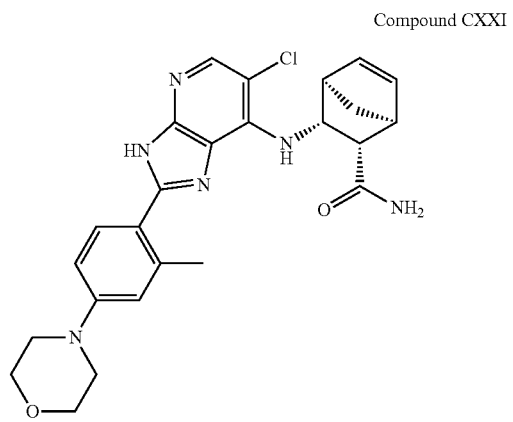 [SMILES: Cc1cc(N2CCOCC2)ccc1-c1nc2c(N[C@H]3[C@@H](C(N)=O)[C@@H]4C=C[C@H]3C4)c(Cl)cnc2[nH]1]

(1S,2S,3R,4R)-3-[6-Chloro-2-(2-methyl-4-morpholin-4-yl-phenyl)-3H-imidazo[4,5-b]pyridin-7-ylamino]-bicyclo[2.2.1]hept-5-ene-2-carboxylic acid amide (Compound CXXI)

In a similar fashion to Compound LXXXVII, (1S,2S,3R,4R)-3-(2,3-Diamino-5-chloro-pyridin-4-ylamino)-bicyclo[2.2.1]hept-5-ene-2-carboxylic acid amide (50.00 mg, 0.1702 mmol), 2-Methyl-4-morpholin-4-yl-benzaldehyde (38.4 mg, 0.187 mmol), and Ammonium acetate (26.2 mg, 0.340 mmol) were reacted to produce 28.37 mg (35%) of the title compound. (300 MHz, DMSO-$d_6$) 12.83 (s, 1H), 7.91 (s, 1H), 7.72 (m, 2H), 7.21 (s, 1H), 7.00 (d, J=9 Hz, 1H), 6.90 (s, 2H), 6.33 (s, 1H), 6.26 (s, 1H), 5.18 (t, J=17 Hz, 9 Hz, 1H), 3.75 (s, 4H), 3.22 (s, 4H), 2.86 (s, 1H), 2.75 (s, 1H), 2.59 (d, J=8 Hz, 1H), 2.25 (d, J=8 Hz, 1H), 1.39 (d, J=8 Hz). MS=479 (M+H), HPLC: 2.42 min. (G Method)

Compound CXXII

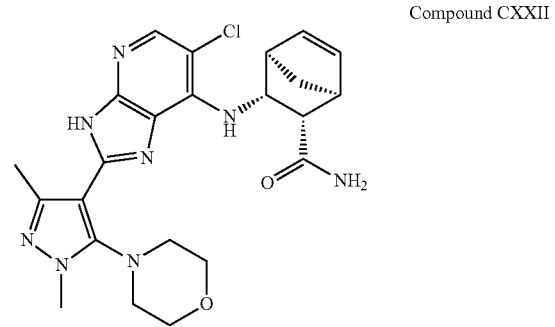 [SMILES: Cc1nn(C)c(N2CCOCC2)c1-c1nc2c(N[C@H]3[C@@H](C(N)=O)[C@@H]4C=C[C@H]3C4)c(Cl)cnc2[nH]1]

(1S,2S,3R,4R)-3-[6-Chloro-2-(1,3-dimethyl-5-morpholin-4-yl-1H-pyrazol-4-yl)-3H-imidazo[4,5-b]pyridin-7-ylamino]-bicyclo[2.2.1]hept-5-ene-2-carboxylic acid amide (Compound CXXII)

In a similar fashion to Compound LXXXVII, (1S,2S,3R,4R)-3-(2,3-Diamino-5-chloro-pyridin-4-ylamino)-bicyclo[2.2.1]hept-5-ene-2-carboxylic acid amide (50.00 mg, 0.1702 mmol), 1,3-Dimethyl-5-morpholin-4-yl-1H-pyrazole-4-carbaldehyde (39.2 mg, 0.187 mmol), and Ammonium acetate (26.2 mg, 0.340 mmol) were reacted to produce 28.80 mg (35%) of the title compound. (300 MHz, DMSO-$d_6$) 12.67 (s, 1H), 7.93 (s, 1H), 7.68 (m, 1H), 7.18 (s, 1H), 6.98 (d, J=8.5 Hz, 1H), 6.31 (d, J=15 Hz, 2H), 5.28 (t, J=17 Hz, 9 Hz, 1H), 3.65 (m, 7H), 3.04 (m, 4H), 2.94 (m, 2H), 2.84 (s, 1H), 2.74 (s, 1H), 2.57 (d, J=9 Hz, 1H), 2.27 (d, J=9 Hz, 1H), 2.18 (s, 3H), 1.40 (d, J=8 Hz, 1H). MS=483 (M+H), HPLC: 1.99 min. (G Method)

Compound CXXIII

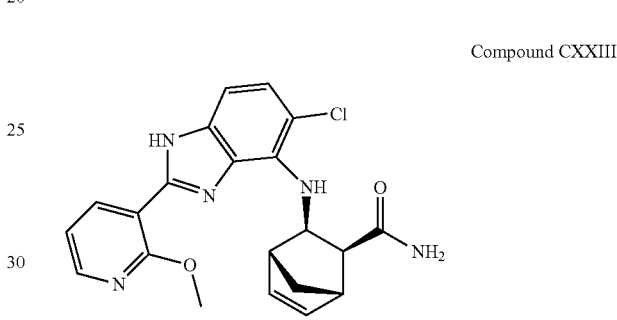

(1S,2S,3R,4R)-3-[6-Chloro-2-(2-methoxy-pyridin-3-yl)-3H-imidazo[4,5-b]pyridin-7-ylamino]-bicyclo[2.2.1]hept-5-ene-2-carboxylic acid amide (Compound CXXIII)

In a similar fashion to Compound LXXXVII, (1S,2S,3R,4R)-3-(2,3-Diamino-5-chloro-pyridin-4-ylamino)-bicyclo[2.2.1]hept-5-ene-2-carboxylic acid amide (50.00 mg, 0.1702 mmol), 2-Methoxy-pyridine-3-carbaldehyde (25.7 mg, 0.187 mmol), and Ammonium acetate (26.2 mg, 0.340 mmol) were reacted to produce 8.5 mg (12%) of the title compound. (300 MHz, DMSO-$d_6$) 12.61 (s, 1H), 8.46 (d, J=7.5 Hz, 1H), 8.31 (s, 1H), 7.99 (s, 1H), 7.76 (s, 1H), 7.21 (m, 3H), 6.38 (d, J=19 Hz, 2H), 5.17 (t, J=17 Hz, J=9 Hz, 1H), 4.05 (s, 3H), 2.89 (s, 1H), 2.80 (s, 1H), 2.61 (d, J=9 Hz, 1H), 2.24 (d, J=9 Hz, 1H), 1.39 (d, J=9 Hz, 1H). MS=411 (M+H), HPLC: 2.33 min. (G Method)

Compound CXXIV

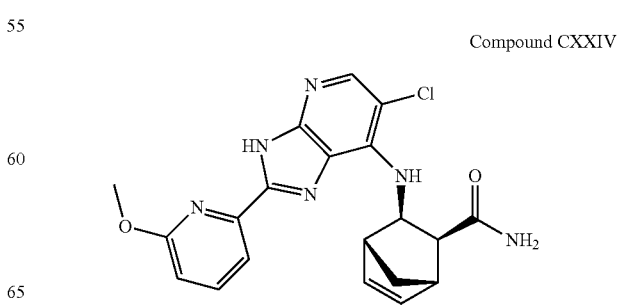

(1S,2S,3R,4R)-3-[6-Chloro-2-(6-methoxy-pyridin-2-yl)-3H-imidazo[4,5-b]pyridin-7-ylamino]-bicyclo[2.2.1]hept-5-ene-2-carboxylic acid amide (Compound CXXIV)

In a similar fashion to Compound LXXXVII, (1S,2S,3R,4R)-3-(2,3-Diamino-5-chloro-pyridin-4-ylamino)-bicyclo[2.2.1]hept-5-ene-2-carboxylic acid amide (50.00 mg, 0.1702 mmol), 6-Methoxy-pyridine-2-carbaldehyde (25.7 mg, 0.187 mmol), and Ammonium acetate (26.2 mg, 0.340 mmol) were reacted to produce 11.03 mg (19%) of the title compound. (300 MHz, DMSO-$d_6$) 13.30 (s, 1H), 8.01 (s, 1H), 7.89 (t, J=15 Hz, 7.5 Hz, 1H), 7.79 (m, 2H), 7.30 (d, J=9 Hz, 1H), 7.25 (s, 1H), 6.90 (d, J=8 Hz, 1H), 6.44 (s, 1H), 6.37 (s, 1H), 5.17 (t, J=17 Hz, J=9 Hz, 1H), 4.06 (s, 3H), 2.90 (s, 1H), 2.82 (s, 1H), 2.63 (d, J=8 Hz, 1H), 2.24 (d, J=8 Hz, 1H), 1.39 (d, J=8 Hz, 1H). MS=411 (M+H), HPLC: 2.53 min. (G Method)

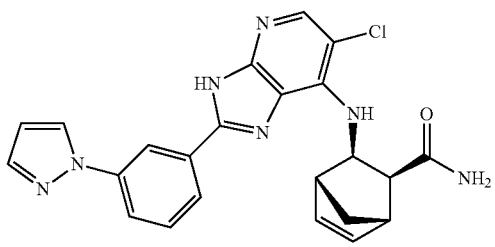

Compound CXXV

(1S,2S,3R,4R)-3-[6-Chloro-2-(3-pyrazol-1-yl-phenyl)-3H-imidazo[4,5-b]pyridin-7-ylamino]-bicyclo[2.2.1]hept-5-ene-2-carboxylic acid amide (Compound CXXV)

(1S,2S,3R,4R)-3-(2,3-Diamino-5-chloro-pyridin-4-ylamino)-bicyclo[2.2.1]hept-5-ene-2-carboxylic acid amide (50.00 mg, 0.1702 mmol), 3-Pyrazol-1-yl-benzaldehyde (32.2 mg, 0.187 mmol), and Ammonium acetate (26.2 mg, 0.340 mmol) were combined in Ethanol (2.21 mL, 37.8 mmol) in a reaction tube and heated at 80° C. overnight. Upon cooling, a precipitate formed. Reaction was diluted with 3 ml ethyl ether and cooled in an ice/water bath. The resulting solid was filtered, washed with cold ether and dried under hi-vacuum. Product is a white solid. Yield: 41.35 mg (54%) of the title compound. (300 MHz, DMSO-$d_6$) 13.39 (s, 1H), 8.68 (s, 1H), 8.53 (s, 1H), 8.06 (d, J=7.6 Hz, 1H), 7.98 (s, 1H), 7.93 (d, J=8 Hz, 1H), 7.81 (m, 2H), 7.67 (t, J=16 Hz, 8 Hz, 1H), 7.32 (d, J=8 Hz, 1H), 7.25 (s, 1H), 6.62 (s, 1H), 6.53 (s, 1H), 6.39 (s, 1H), 5.15 (t, J=17 Hz, J=9 Hz, 1H), 2.89 (d, J=17 Hz, 2H), 2.63 (d, J=8 Hz, 1H), 2.24 (d, J=8 Hz, 1H), 1.39 (d, J=8 Hz, 1H). MS=446 (M+H), HPLC: 2.51 min. (G Method)

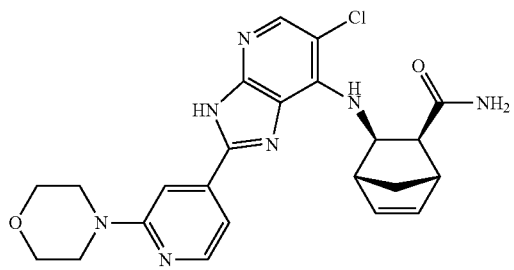

Compound CXXVI

(1S,2S,3R,4R)-3-[6-Chloro-2-(2-morpholin-4-yl-pyridin-4-yl)-3H-imidazo[4,5-b]pyridin-7-ylamino]-bicyclo[2.2.1]hept-5-ene-2-carboxylic acid amide (Compound CXXVI)

In a similar fashion compound to CXXV, (1S,2S,3R,4R)-3-(2,3-Diamino-5-chloro-pyridin-4-ylamino)-bicyclo[2.2.1]hept-5-ene-2-carboxylic acid amide (50.00 mg, 0.1702 mmol), 2-Morpholin-4-yl-pyridine-4-carbaldehyde (36.0 mg, 0.187 mmol) and Ammonium acetate (26.2 mg, 0.340 mmol) were reacted to yield 36.32 mg (46%) of the title compound. (300 MHz, DMSO-$d_6$) 12.35 (s, 1H), 8.26 (s, 1H), 7.79 (s, 1H), 7.52 (s, 1H), 7.38 (s, 2H), 7.25 (s, 1H), 6.39 (s, 2H), 5.15 (s, 1H), 3.75 (s, 4H), 3.54 (s, 4H), 2.90 (s, 1H), 2.80 (s, 1H), 2.62 (s, 1H), 2.26 (s, 1H), 1.38 (s, 1H). MS=466 (M+H), HPLC: 1.76 min. (G Method)

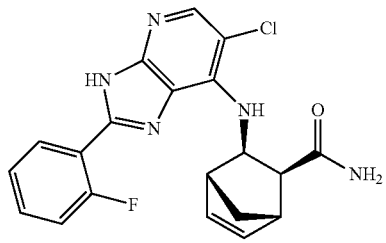

Compound CXXVII

(1S,2S,3R,4R)-3-[6-Chloro-2-(2-fluoro-phenyl)-3H-imidazo[4,5-b]pyridin-7-ylamino]-bicyclo[2.2.1]hept-5-ene-2-carboxylic acid amide (Compound CXXVII)

In a similar fashion compound to CXXV, (1S,2S,3R,4R)-3-(2,3-Diamino-5-chloro-pyridin-4-ylamino)-bicyclo[2.2.1]hept-5-ene-2-carboxylic acid amide (50.00 mg, 0.1702 mmol), Benzaldehyde, 2-fluoro-(23.2 mg, 0.187 mmol), and Ammonium acetate (26.2 mg, 0.340 mmol) were reacted to yield 27.56 mg (42%) of the title compound. (300 MHz, DMSO-$d_6$) 12.35 (s, 1H), 8.26 (s, 1H), 7.79 (s, 1H), 7.52 (s, 1H), 7.38 (s, 2H), 7.25 (s, 1H), 6.39 (s, 2H), 5.15 (s, 1H), 3.75 (s, 4H), 3.54 (s, 4H), 2.90 (s, 1H), 2.80 (s, 1H), 2.62 (s, 1H), 2.26 (s, 1H), 1.38 (s, 1H). MS=466 (M+H), HPLC: 1.76 min. (G Method)

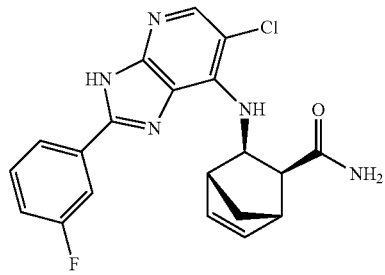

Compound CXXVIII (1S,2S,3R,4R)-3-[6-Chloro-2-(3-fluoro-phenyl)-3H-imidazo[4,5-b]pyridin-7-ylamino]-bicyclo[2.2.1]hept-5-ene-2-carboxylic acid amide (Compound CXXVIII)

In a similar fashion compound to CXXV, (1S,2S,3R,4R)-3-(2,3-Diamino-5-chloro-pyridin-4-ylamino)-bicyclo[2.2.1]hept-5-ene-2-carboxylic acid amide (50.00 mg, 0.1702 mmol), 3-FC$_6$H$_4$CHO (23.2 mg, 0.187 mmol) and Ammonium acetate (26.2 mg, 0.340 mmol) were reacted to yield 37.94 mg (56%) of the title compound. (300 MHz, DMSO-d$_6$) 13.40 (s, 1H), 7.99 (m, 2H), 7.91 (s, 1H), 7.78 (s, 1H), 7.60 (s, 1H), 7.29 (m, 3H), 6.39 (s, 2H), 5.15 (m, 1H), 2.90 (s, 1H), 2.80 (s, 1H), 2.62 (s, 1H), 2.26 (s, 1H), 1.38 (s, 1H). MS=398 (M+H), HPLC: 2.55 min. (G Method)

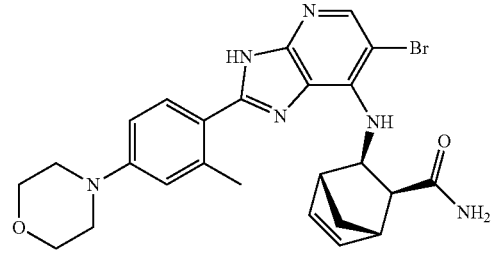

Compound CXXX (1S,2S,3R,4R)-3-[6-Bromo-2-(2-methyl-4-morpholin-4-yl-phenyl)-3H-imidazo[4,5-b]pyridin-7-ylamino]-bicyclo[2.2.1]hept-5-ene-2-carboxylic acid amide (Compound CXXX)

In a similar fashion to compound CXXV, (1S,2S,3R,4R)-3-(2,3-Diamino-5-bromo-pyridin-4-ylamino)-bicyclo[2.2.1]hept-5-ene-2-carboxylic acid amide (100.00 mg, 0.29568 mmol), 2-Methyl-4-morpholin-4-yl-benzaldehyde (66.8 mg, 0.325 mmol), and Ammonium acetate (45.6 mg, 0.591 mmol) were reacted to yield 48.7 mg (32%) of the title compound. (300 MHz, DMSO-d$_6$) 12.85 (s, 1H), 8.00 (s, 1H), 7.71 (m, 2H), 7.19 (s, 1H), 6.92 (m, 2H), 6.34 (s, 1H), 6.26 (s, 1H), 5.30 (t, J=17 Hz, 8. Hz, 1H), 3.75 (s, 4H), 3.22 (s, 4H), 2.85 (s, 1H), 2.73 (s, 1H), 2.65 (s, 3H), 2.59 (d, J=8 Hz, 1H) 2.24 (d, J=8 Hz, 1H), 1.38 (d, J=8 Hz, 1H). MS=525 (M+H), HPLC: 2.43 min. (G Method)

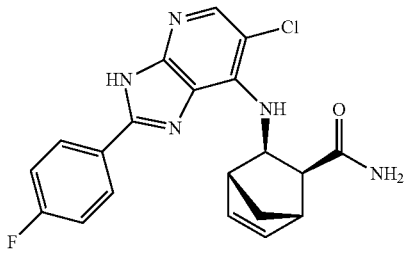

Compound CXXIX (1S,2S,3R,4R)-3-[6-Chloro-2-(4-fluoro-phenyl)-3H-imidazo[4,5-b]pyridin-7-ylamino]-bicyclo[2.2.1]hept-5-ene-2-carboxylic acid amide (Compound CXXIX)

In a similar fashion compound to CXXV, (1S,2S,3R,4R)-3-(2,3-Diamino-5-chloro-pyridin-4-ylamino)-bicyclo[2.2.1]hept-5-ene-2-carboxylic acid amide (50.00 mg, 0.1702 mmol), 4-Fluorobenzaldehyde (23.2 mg, 0.187 mmol), and Ammonium acetate (26.2 mg, 0.340 mmol) were reacted to yield 20.09 mg (30%) of the title compound. (300 MHz, DMSO-d$_6$) 13.31 (s, 1H), 8.18 (s, 2H), 7.96 (m, 1H), 7.77 (s, 1H), 7.41 (m, 2H), 7.23 (s, 2H), 6.40 (m, 2H), 5.18 (t, J=17 Hz, 8.5 Hz, 1H), 2.90 (s, 1H), 2.78 (s, 1H), 2.63 (d, J=8 Hz, 1H), 2.24 (d, J=8 Hz, 1H), 1.38 (d, J=8 Hz, 1H). MS=398 (M+H), HPLC: 2.54 min. (G Method)

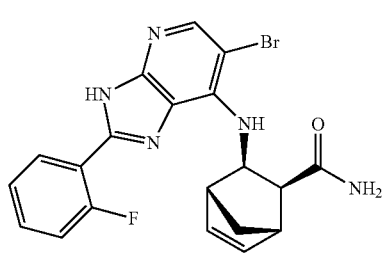

Compound CXXXI (1S,2S,3R,4R)-3-[6-Bromo-2-(2-fluoro-phenyl)-3H-imidazo[4,5-b]pyridin-7-ylamino]-bicyclo[2.2.1]hept-5-ene-2-carboxylic acid amide (Compound CXXXI)

In a similar fashion to compound CXXV, (1S,2S,3R,4R)-3-(2,3-Diamino-5-bromo-pyridin-4-ylamino)-bicyclo[2.2.1]hept-5-ene-2-carboxylic acid amide (100.00 mg, 0.29568 mmol), Benzaldehyde, 2-fluoro- (40.4 mg, 0.325 mmol), and Ammonium acetate (45.6 mg, 0.591 mmol) were reacted to yield 41.4 mg (32%) of the title compound. (300 MHz, DMSO-d$_6$) 13.05 (s, 1H), 8.07 (m, 2H), 7.75 (s, 1H), 7.55 (m, 1H), 7.41 (m, 2H), 7.21 (m, 2H), 6.35 (d, J=11 Hz, 2H), 5.21 (t, J=17 Hz, 8.5 Hz, 1H), 2.89 (s, 1H), 2.78 (s, 1H), 2.60 (d, J=9 Hz, 1H), 2.24 (d, J=9 Hz, 1H), 1.38 (d, J=9 Hz, 1H). MS=444 (M+H), HPLC: 2.42 min. (G Method)

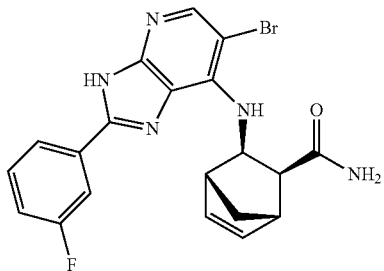

Compound CXXXII (1S,2S,3R,4R)-3-[6-Bromo-2-(3-fluoro-phenyl)-3H-imidazo[4,5-b]pyridin-7-ylamino]-bicyclo[2.2.1]hept-5-ene-2-carboxylic acid amide (Compound CXXXII)

In a similar fashion to compound CXXV, (1S,2S,3R,4R)-3-(2,3-Diamino-5-bromo-pyridin-4-ylamino)-bicyclo[2.2.1]hept-5-ene-2-carboxylic acid amide (100.00 mg, 0.29568 mmol), 3-FC$_6$H$_4$CHO (40.4 mg, 0.325 mmol) and Ammonium acetate (45.6 mg, 0.591 mmol) were reacted to yield 84.7 mg (65%) of the title compound. (300 MHz, DMSO-d$_6$) 13.33 (s, 1H), 8.18 (m, 2H), 8.04 (s, 1H), 7.75 (s, 1H), 7.41 (t, J=16.5 Hz, 8 Hz, 2H), 7.22 (s, 1H), 6.39 (d, J=15 Hz, 2H), 5.22 (t, J=17 Hz, 8.5 Hz, 1H), 2.89 (s, 1H), 2.78 (s, 1H), 2.62 (d, J=8 Hz, 1H), 2.24 (d, J=8 Hz, 1H), 1.39 (d, J=8 Hz, 1H). MS=444 (M+H), HPLC: 2.56 min. (G Method)

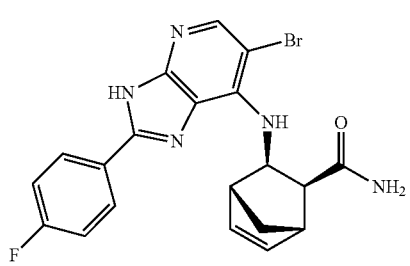

Compound CXXXIII (1S,2S,3R,4R)-3-[6-Bromo-2-(4-fluoro-phenyl)-3H-imidazo[4,5-b]pyridin-7-ylamino]-bicyclo[2.2.1]hept-5-ene-2-carboxylic acid amide (Compound CXXXIII)

In a similar fashion to compound CXXV, (1S,2S,3R,4R)-3-(2,3-Diamino-5-bromo-pyridin-4-ylamino)-bicyclo[2.2.1]hept-5-ene-2-carboxylic acid amide (100.00 mg, 0.29568 mmol), 4-Fluorobenzaldehyde (40.4 mg, 0.325 mmol), and Ammonium acetate (45.6 mg, 0.591 mmol) were reacted to yield 70.9 mg (54%) of the title compound. (300 MHz, DMSO-d$_6$) 13.42 (s, 1H), 8.06 (s, 1H), 7.99 (d, J=8 Hz, 1H), 7.90 (d, J=11 Hz, 1H), 7.76 (s, 1H), 7.61 (m, 1H), 7.33 (m, 1H), 7.24 (m, 2H) 6.39 (s, 2H), 5.21 (t, J=17 Hz, 8.5 Hz, 1H), 2.89 (s, 1H), 2.78 (s, 1H), 2.63 (d, J=8 Hz, 1H), 2.24 (d, J=8 Hz, 1H), 1.39 (d, J=8 Hz, 1H). MS=444 (M+H).

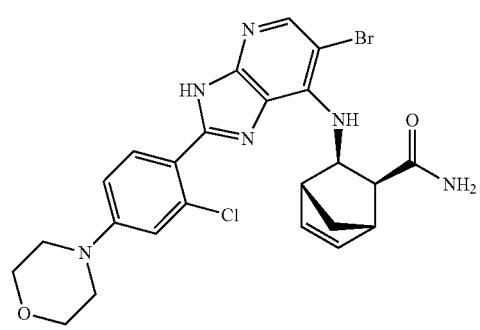

Compound CXXXIV (1S,2S,3R,4R)-3-[6-Bromo-2-(2-chloro-4-morpholin-4-yl-phenyl)-3H-imidazo[4,5-b]pyridin-7-ylamino]-bicyclo[2.2.1]hept-5-ene-2-carboxylic acid amide (Compound CXXXIV)

In a similar fashion to compound CXXV, (1S,2S,3R,4R)-3-(2,3-Diamino-5-bromo-pyridin-4-ylamino)-bicyclo[2.2.1]hept-5-ene-2-carboxylic acid amide (100.00 mg, 0.29568 mmol), 4-Fluorobenzaldehyde (40.4 mg, 0.325 mmol), and Ammonium acetate (45.6 mg, 0.591 mmol) were reacted to yield 70.9 mg (54%) of the title compound. (300 MHz, DMSO-d$_6$) 13.42 (s, 1H), 8.06 (s, 1H), 7.99 (d, J=8 Hz, 1H), 7.90 (d, J=11 Hz, 1H), 7.76 (s, 1H), 7.61 (m, 1H), 7.33 (m, 1H), 7.24 (m, 2H) 6.39 (s, 2H), 5.21 (t, J=17 Hz, 8.5 Hz, 1H), 2.89 (s, 1H), 2.78 (s, 1H), 2.63 (d, J=8 Hz, 1H), 2.24 (d, J=8 Hz, 1H), 1.39 (d, J=8 Hz, 1H). MS=444 (M+H).

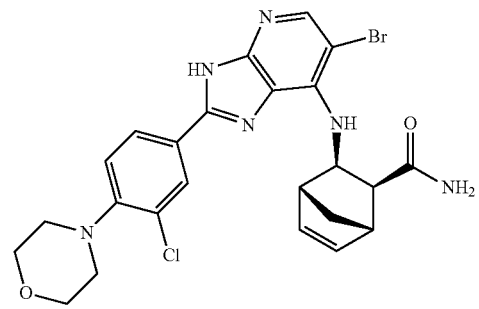

Compound CXXXV (1S,2S,3R,4R)-3-[6-Bromo-2-(3-chloro-4-morpholin-4-yl-phenyl)-3H-imidazo[4,5-b]pyridin-7-ylamino]-bicyclo[2.2.1]hept-5-ene-2-carboxylic acid amide (Compound CXXXV)

In a similar fashion to Compound CXXV, (1S,2S,3R,4R)-3-(2,3-Diamino-5-bromo-pyridin-4-ylamino)-bicyclo[2.2.1]hept-5-ene-2-carboxylic acid amide (100.00 mg, 0.29568 mmol), 3-Chloro-4-morpholin-4-yl-benzaldehyde (73.4 mg, 0.325 mmol), and Ammonium acetate (45.6 mg, 0.591 mmol) were reacted to produce 123.8 mg (77%) of the title compound. (300 MHz, DMSO-d$_6$) 13.27 (s, 1H), 8.18 (s, 1H), 8.06 (d, J=8 Hz, 1H), 8.02 (s, 1H), 7.74 (s, 1H), 7.33 (s, 1H), 7.22 (s, 1H), 7.17 (d, J=9 Hz, 1H), 6.30 (s, 2H), 5.20 (t, J=17 Hz, 8.5 Hz, 1H), 3.77 (m, 4H), 3.07 (m, 4H), 2.90 (s, 1H), 2.78 (s, 1H), 2.63 (d, J=9 Hz, 1H), 2.24 (d, J=9 Hz, 1H), 1.39 (d, J=9 Hz, 1H). MS=545 (M+H), HPLC: 2.67 min. (G Method)

Compound CXXXVI

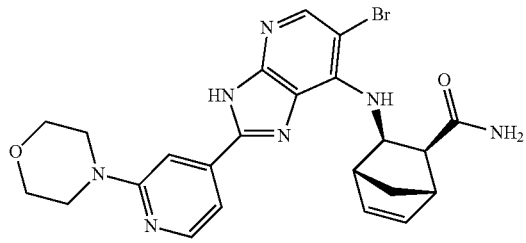

(1S,2S,3R,4R)-3-[6-Bromo-2-(2-morpholin-4-yl-pyridin-4-yl)-3H-imidazo[4,5-b]pyridin-7-ylamino]-bicyclo[2.2.1]hept-5-ene-2-carboxylic acid amide (Compound CXXXVI)

In a similar fashion to Compound CXXV, (1S,2S,3R,4R)-3-(2,3-Diamino-5-bromo-pyridin-4-ylamino)-bicyclo[2.2.1]hept-5-ene-2-carboxylic acid amide (57.57 mg, 0.1702 mmol), 2-Morpholin-4-yl-pyridine-4-carbaldehyde (36.0 mg, 0.187 mmol), and Ammonium acetate (26.2 mg, 0.340 mmol) were reacted to produce 75.1 mg (86%) of the title compound. (300 MHz, DMSO-$d_6$) 13.47 (s, 1H), 8.28 (d, J=5 Hz, 1H), 8.08 (s, 1H), 7.76 (s, 1H), 7.52 s, 1H), 7.36 (d, J=5 Hz, 1H), 7.33 (d, J=8 Hz, 1H), 7.24 (s, 1H), 6.39 (s, 2H), 5.20 (t, J=17 Hz, 8.5 Hz, 1H), 3.75 (m, 4H), 3.54 (s, 4H), 2.90 (s, 1H), 2.79 (s, 1H), 2.62 (d, J=8 Hz, 1H), 2.24 (d, J=8 Hz, 1H), 1.38 (d, J=8 Hz, 1H). MS=512 (M+H), HPLC: 1.78 min. (G Method)

Compound CXXXVII

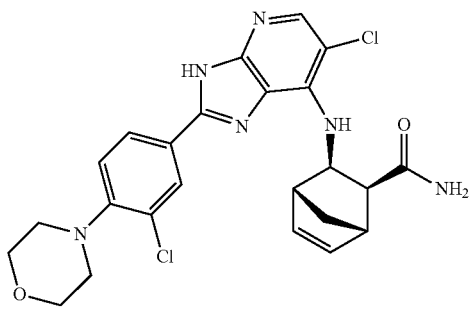

(1S,2S,3R,4R)-3-[6-Chloro-2-(3-chloro-4-morpholin-4-yl-phenyl)-3H-imidazo[4,5-b]pyridin-7-ylamino]-bicyclo[2.2.1]hept-5-ene-2-carboxylic acid amide (Compound CXXXVII)

In a similar fashion to Compound CXXV, (1S,2S,3R,4R)-3-(2,3-Diamino-5-chloro-pyridin-4-ylamino)-bicyclo[2.2.1]hept-5-ene-2-carboxylic acid amide (100.00 mg, 0.34042 mmol), 3-Chloro-4-morpholin-4-yl-benzaldehyde (84.5 mg, 0.374 mmol), and Ammonium acetate (52.5 mg, 0.681 mmol) were reacted to produce 62.66 mg (37%) of the title compound. (300 MHz, DMSO-$d_6$) 13.35 (s, 1H), 8.28 (d, J=5 Hz, 1H), 8.01 (s, 1H), 7.78 (s, 1H), 7.52 (m, 1H), 7.38 (m, 2H), 7.25 (s, 1H), 6.38 (m, 2H), 5.14 (t, J=16 Hz, 8 Hz, 1H), 3.76 (m, 4H), 3.54 (s, 4H), 2.91 (s, 1H), 2.81 (s, 1H), 2.63 (d, J=8 Hz, 1H), 2.22 (d, J=9 Hz, 1H), 1.39 (d, J=9 Hz, 1H). MS=466 (M-Cl+), HPLC: 1.76 min. (G Method)

Compound CXXXVIII

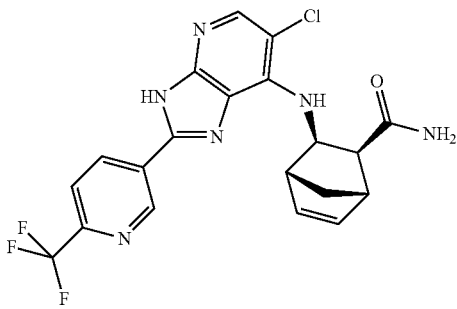

(1S,2S,3R,4R)-3-[6-Chloro-2-(3-chloro-4-morpholin-4-yl-phenyl)-3H-imidazo[4,5-b]pyridin-7-ylamino]-bicyclo[2.2.1]hept-5-ene-2-carboxylic acid amide (Compound CXXXVIII)

In a similar fashion to Compound LXXXVII, (1S,2S,3R,4R)-3-(2,3-Diamino-5-chloro-pyridin-4-ylamino)-bicyclo[2.2.1]hept-5-ene-2-carboxylic acid amide (75.00 mg, 0.2553 mmol), 6-Trifluoromethyl-pyridine-3-carbaldehyde (49.2 mg, 0.281 mmol), and Ammonium acetate (39.4 mg, 0.511 mmol) were reacted to produce 13.55 mg (12%) of the title compound. (300 MHz, DMSO-$d_6$) 9.45 (s, 1H), 8.69 (d, J=8 Hz, 1H), 8.13 (d, J=8 Hz, 1H), 8.03 (s, 1H), 7.79 (m, 2H), 7.44 (d, J=9 Hz, 1H), 7.25 (s, 1H), 6.44 (m, 1H), 6.31 (m, 1H), 5.18 (t, J=17 Hz, 8 Hz, 1H), 3.29 (s, 1H), 2.91 (s, 1H), 2.82 (s, 1H), 2.63 (d, J=9 Hz, 1H), 2.23 (d, J=8 Hz, 1H), 1.39 (d, J=8 Hz, 1H). MS=449 (M+H), HPLC: 2.65 min. (G Method)

Compound CXXXIX

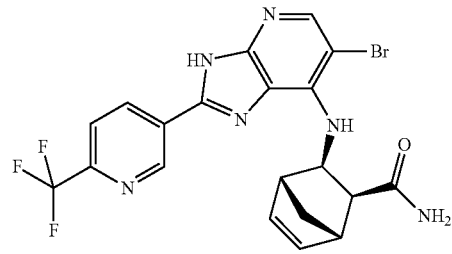

(1S,2S,3R,4R)-3-[6-Bromo-2-(6-trifluoromethyl-pyridin-3-yl)-3H-imidazo[4,5-b]pyridin-7-ylamino]-bicyclo[2.2.1]hept-5-ene-2-carboxylic acid amide (Compound CXXXIX)

In a similar fashion to Compound LXXXVII, (1S,2S,3R,4R)-3-(2,3-Diamino-5-bromo-pyridin-4-ylamino)-bicyclo[2.2.1]hept-5-ene-2-carboxylic acid amide (75.00 mg, 0.2218 mmol), 6-Trifluoromethyl-pyridine-3-carbaldehyde (42.7 mg, 0.244 mmol), and Ammonium acetate (34.2 mg, 0.444 mmol) were reacted to produce 5.98 mg (5%) of the title compound. (300 MHz, DMSO-$d_6$) 9.45 (s, 1H), 8.69 (d, J=9 Hz, 1H), 8.09 (m, 2H), 7.76 (s, 1H), 7.22 (s, 2H), 6.44 (m, 1H), 6.37 (m, 1H), 5.24 (t, J=17 Hz, 8 Hz, 1H), 2.89 (s, 1H), 2.79 (s, 1H), 2.66 (d, J=9 Hz, 1H), 2.63 (d, J=9 Hz, 1H), 2.25 (d, J=8 Hz, 1H), 1.39 (d, J=8 Hz, 1H). MS=493 (M+H), HPLC: 2.66 min. (G Method)

Compound CXL

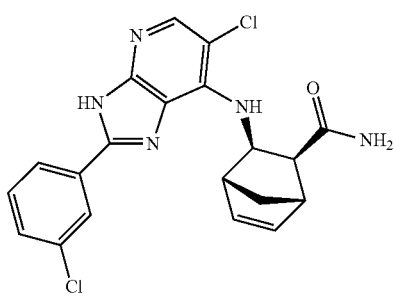

(1S,2S,3R,4R)-3-[6-Chloro-2-(3-chloro-phenyl)-3H-imidazo[4,5-b]pyridin-7-ylamino]-bicyclo[2.2.1]hept-5-ene-2-carboxylic acid amide (Compound CXL)

In a similar fashion to Compound CXXV, (1S,2S,3R,4R)-3-(2,3-Diamino-5-chloro-pyridin-4-ylamino)-bicyclo[2.2.1]hept-5-ene-2-carboxylic acid amide (75.00 mg, 0.2553 mmol), 3-Chlorobenzaldehyde (39.5 mg, 0.281 mmol), and Ammonium acetate (39.4 mg, 0.511 mmol) were reacted to produce 31.23 mg (30%) of the title compound. (300 MHz, DMSO-$d_6$) 13.42 (s, 1H), 8.19 (s, 1H), 8.10 (d, J=8 Hz, 1H), 7.98 (s, 1H), 7.78 (s, 1H), 7.62-7.53 (m, 2H), 7.32 (d, J=9 Hz, 1H), 7.25 (s, 1H), 6.39 (s, 2H), 5.18 (t, J=17 Hz, 9 Hz, 1H), 2.87 (s, 1H), 2.91 (s, 1H), 2.81 (d, J=8 Hz, 1H), 2.63 (d, J=8 Hz, 1H), 2.23 (d, J=8 Hz, 1H), 1.38 (d, J=8 Hz, 1H). MS=414 (M+H), HPLC: 2.73 min. (G Method)

Compound CXLII

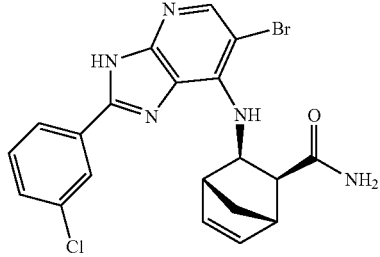

(1S,2S,3R,4R)-3-[6-Bromo-2-(3-chloro-phenyl)-3H-imidazo[4,5-b]pyridin-7-ylamino]-bicyclo[2.2.1]hept-5-ene-2-carboxylic acid amide (Compound CXLII)

In a similar fashion to Compound CXXV, (1S,2S,3R,4R)-3-(2,3-Diamino-5-bromo-pyridin-4-ylamino)-bicyclo[2.2.1]hept-5-ene-2-carboxylic acid amide (86.35 mg, 0.2553 mmol), 3-Chlorobenzaldehyde (39.5 mg, 0.281 mmol) and Ammonium acetate (39.4 mg, 0.511 mmol) were reacted to produce 62.33 mg (53%) of the title compound. (300 MHz, DMSO-$d_6$) 3.42 (s, 1H), 8.18 s, 1H), 8.09 (d, J=8 Hz, 1H), 8.05 (s, 1H), 7.76 (s, 1H), 7.62-7.53 (m, 2H), 7.27-7.22 (m, 2H), 6.38 (m, 2H), 5.19 (t, J=17 Hz, 9 Hz, 1H), 2.90 (s, 1H), 2.79 (s, 1H), 2.63 (d, J=8 Hz, 1H), 2.25 (d, J=8 Hz, 1H), 1.40 (d, J=8 Hz, 1H). MS=460 (M+H), HPLC: 2.75 min. (G Method)

Compound CXLI

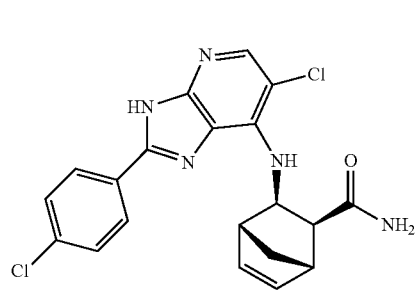

(1S,2S,3R,4R)-3-[6-Chloro-2-(4-chloro-phenyl)-3H-imidazo[4,5-b]pyridin-7-ylamino]-bicyclo[2.2.1]hept-5-ene-2-carboxylic acid amide (Compound CXLI)

In a similar fashion to Compound CXXV, (1S,2S,3R,4R)-3-(2,3-Diamino-5-chloro-pyridin-4-ylamino)-bicyclo[2.2.1]hept-5-ene-2-carboxylic acid amide (75.00 mg, 0.2553 mmol), 4-Chlorobenzaldehyde (39.5 mg, 0.281 mmol), and Ammonium acetate (39.4 mg, 0.511 mmol) were reacted to produce 39.8 mg (38%) of the title compound. (300 MHz, DMSO-$d_6$) 13.39 (s, 1H), 8.14 (d, J=9 Hz, 1H), 7.96 (s, 1H), 7.77 (s, 1H), 7.63 (d, J=9 Hz, 2H), 7.24 (m, 2H), 7.24 (s, 2H), 6.41 (s, 1H), 6.37 (m, 1H), 5.18 (t, J=17 Hz, 9 Hz, 1H), 2.89 (s, 1H), 2.79 (s, 1H), 2.63 (d, J=8 Hz, 1H), 2.23 (d, J=8 Hz, 1H), 1.38 (d, J=8 Hz, 1H). MS=414 (M+H), HPLC: 2.75 min (G Method)

Compound CXLIII

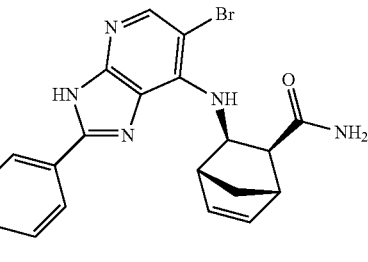

(1S,2S,3R,4R)-3-[6-Bromo-2-(4-chloro-phenyl)-3H-imidazo[4,5-b]pyridin-7-ylamino]-bicyclo[2.2.1]hept-5-ene-2-carboxylic acid amide (Compound CXLIII)

In a similar fashion to Compound CXXV, (1S,2S,3R,4R)-3-(2,3-Diamino-5-bromo-pyridin-4-ylamino)-bicyclo[2.2.1]hept-5-ene-2-carboxylic acid amide (86.35 mg, 0.2553 mmol), 4-Chlorobenzaldehyde (39.5 mg, 0.281 mmol) and Ammonium acetate (39.4 mg, 0.511 mmol) were reacted to produce 72.70 mg (63%) of the title compound. (300 MHz, DMSO-$d_6$) 13.39 (s, 1H), 8.14 (d, J=9 Hz, 1H), 8.04 (s, 1H), 7.75 (s, 1H), 7.63 (d, J=9 Hz, 2H), 7.21 (m, 2H), 6.41 (m, 1H), 6.37 (m, 1H), 5.21 (t, J=17 Hz, 9 Hz, 1H), 2.89 (s, 1H), 2.77 (s, 1H), 2.62 (d, J=9 Hz, 1H), 2.23 (d, J=9 Hz, 1H), 1.38 (d, J=9 Hz, 1H). MS=458 (M+H), HPLC: 2.77 min. (G Method)

Compound CXLIV

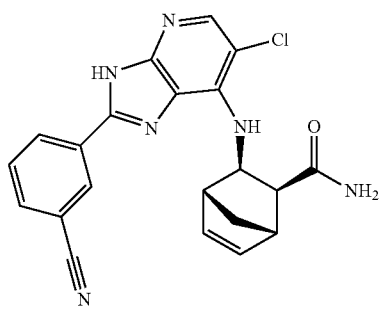

(1S,2S,3R,4R)-3-[6-Chloro-2-(3-cyano-phenyl)-3H-imidazo[4,5-b]pyridin-7-ylamino]-bicyclo[2.2.1]hept-5-ene-2-carboxylic acid amide (Compound CXLIV)

In a similar fashion to Compound CXXV, (1S,2S,3R,4R)-3-(2,3-Diamino-5-chloro-pyridin-4-ylamino)-bicyclo[2.2.1]hept-5-ene-2-carboxylic acid amide (75.00 mg, 0.2553 mmol), 3-cyanobenzaldehyde (36.8 mg, 0.281 mmol), and Ammonium acetate (39.4 mg, 0.511 mmol) were reacted to produce 72.70 mg (63%) of the title compound. (300 MHz, DMSO-d$_6$) 13.44 (s, 1H), 8.49 (s, 1H), 8.43 (d, J=8 Hz, 1H), 7.99 (s, 1H), 7.95 (d, J=8 Hz, 1H), 7.77 (m, 2H), 7.35 (d, J=9 Hz, 1H) 7.25 (s, 1H), 6.41 (m, 2H), 5.14 (t, J=17 Hz, 8.5 Hz, 1H), 2.91 (s, 1H), 2.81 (s, 1H), 2.63 (d, J=8 Hz, 1H), 2.23 (d, J=8 Hz, 1H), 1.39 (d, J=8 Hz, 1H). MS=405 (M+H), HPLC: 2.39 min. (G Method)

Compound CXLVI

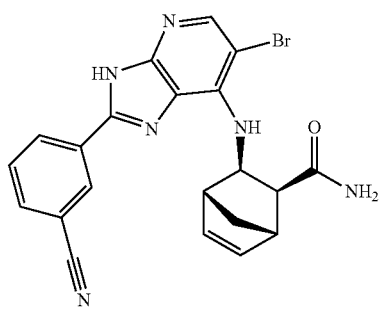

(1S,2S,3R,4R)-3-[6-Bromo-2-(3-cyano-phenyl)-3H-imidazo[4,5-b]pyridin-7-ylamino]-bicyclo[2.2.1]hept-5-ene-2-carboxylic acid amide (Compound CXLVI)

In a similar fashion to Compound CXXV, (1S,2S,3R,4R)-3-(2,3-Diamino-5-bromo-pyridin-4-ylamino)-bicyclo[2.2.1]hept-5-ene-2-carboxylic acid amide (75 mg, 0.22 mmol), 3-cyanobenzaldehyde (32.0 mg, 0.244 mmol, and Ammonium acetate (34.2 mg, 0.444 mmol) were reacted to produce 17.15 mg (17%) of the title compound. (300 MHz, DMSO-d$_6$) 13.49 (s, 1H), 8.49 (s, 1H), 8.43 (d, J=8 Hz, 1H), 7.95 (d, J=8 Hz, 1H), 7.82-7.74 (m, 2H), 7.23 (s, 1H), 6.40 (m, 2H), 5.18 (t, J=17 Hz, 9 Hz, 1H), 2.90 (s, 1H), 2.79 (s, 1H), 2.63 (d, J=9 Hz, 1H), 2.24 (d, J=9 Hz, 1H), 1.38 (d, J=9 Hz, 1H). MS=451 (M+2), HPLC: 2.43 min. (G Method)

Compound CXLV

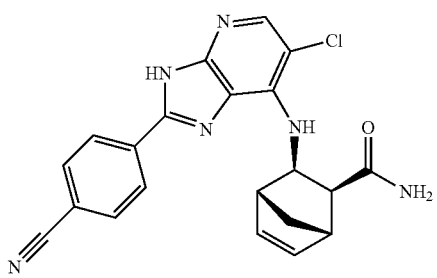

(1S,2S,3R,4R)-3-[6-Chloro-2-(4-cyano-phenyl)-3H-imidazo[4,5-b]pyridin-7-ylamino]-bicyclo[2.2.1]hept-5-ene-2-carboxylic acid amide (Compound CXLV)

In a similar fashion to Compound CXXV, (1S,2S,3R,4R)-3-(2,3-Diamino-5-chloro-pyridin-4-ylamino)-bicyclo[2.2.1]hept-5-ene-2-carboxylic acid amide (75.00 mg, 0.2553 mmol), 4-Formylbenzonitrile (36.8 mg, 0.281 mmol), and Ammonium acetate (39.4 mg, 0.511 mmol) were reacted to produce 17.15 mg (17%) of the title compound. (300 MHz, DMSO-d$_6$) 13.55 (s, 1H), 8.29 (d, J=8 Hz, 1H), 8.05-7.99 (m, 3H), 7.78 (s, 1H), 7.36 (m, 1H), 7.25 (s, 1H), 6.43 (m, 1H), 6.38 (m, 1H), 5.18 (t, J=17 Hz, 8.5 Hz, 1H), 2.90 (s, 1H), 2.81 (s, 1H), 2.62 (d, J=8 Hz, 1H), 2.24 (d, J=8 Hz, 1H), 1.38 (d, J=8 Hz, 1H). MS=405 (M+H), HPLC: 2.42 min. (G Method)

Compound CXLVII

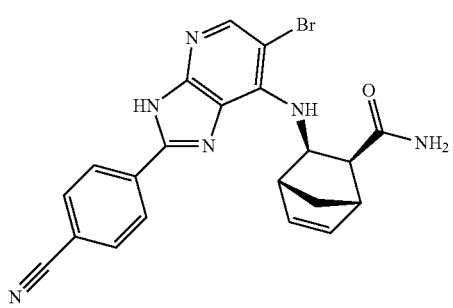

(1S,2S,3R,4R)-3-[6-Bromo-2-(4-cyano-phenyl)-3H-imidazo[4,5-b]pyridin-7-ylamino]-bicyclo[2.2.1]hept-5-ene-2-carboxylic acid amide (Compound CXLVII)

In a similar fashion to Compound CXXV, (1S,2S,3R,4R)-3-(2,3-Diamino-5-bromo-pyridin-4-ylamino)-bicyclo[2.2.1]hept-5-ene-2-carboxylic acid amide (75 mg, 0.22 mmol), 4-Formylbenzonitrile (32.0 mg, 0.244 mmol), and Ammonium acetate (34.2 mg, 0.444 mmol) were reacted to produce 47.01 mg (47%) of the title compound. (300 MHz, DMSO-d$_6$) 13.60 (s, 1H), 8.29 (d, J=8 Hz, 2H), 8.08 (s, 1H), 7.76 (s, 1H), 7.31 (m, 1H), 7.24 (s, 1H), 6.42 (m, 1H), 6.37 (m, 1H), 5.20 (t, J=17 Hz, 8.5 Hz, 1H), 2.90 (s, 1H), 2.79 (s, 1H), 2.62 (d, J=8 Hz, 1H), 2.24 (d, J=8 Hz, 1H), 1.38 (d, J=8 Hz, 1H). MS=451 (M+H), HPLC: 2.43 min. (G Method)

Compound CXLVIII

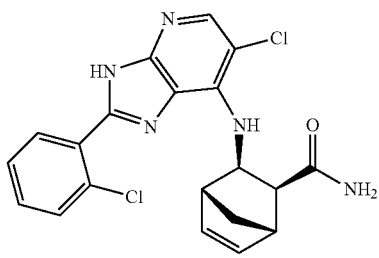

(1S,2S,3R,4R)-3-[6-Chloro-2-(2-chloro-phenyl)-3H-imidazo[4,5-b]pyridin-7-ylamino]-bicyclo[2.2.1]hept-5-ene-2-carboxylic acid amide (Compound CXLVIII)

In a similar fashion to Compound LXXXVII, (1S,2S,3R,4R)-3-(2,3-Diamino-5-chloro-pyridin-4-ylamino)-bicyclo[2.2.1]hept-5-ene-2-carboxylic acid amide (75.00 mg, 0.2553 mmol), 2-Chlorobenzaldehyde (39.4 mg, 0.281 mmol), and Ammonium acetate (39.4 mg, 0.511 mmol) were reacted to produce 24.35 mg (23%) of the title compound. (300 MHz, DMSO-$d_6$) 13.15 (s, 1H), 7.99 (s, 1H), 7.84 (m, 1H), 7.74 (s, 1H), 7.64 (m, 1H), 7.53 (m, 2H), 7.20 (m, 2H), 6.29 (s, 2H), 5.14 (t, J=17 Hz, 8.5 Hz, 1H), 2.86 (s, 1H), 2.79 (s, 1H), 2.58 (d, J=8 Hz, 1H), 2.23 (d, J=8 Hz, 1H), 1.38 (d, J=8 Hz, 1H). MS=414 (M+H), HPLC: 2.49 min. (G Method)

Compound CXLIX

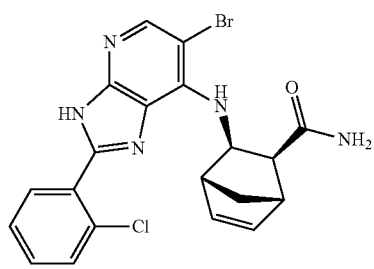

(1S,2S,3R,4R)-3-[6-Bromo-2-(2-chloro-phenyl)-3H-imidazo[4,5-b]pyridin-7-ylamino]-bicyclo[2.2.1]hept-5-ene-2-carboxylic acid amide (Compound CXLIX)

In a similar fashion to Compound LXXXVII, (1S,2S,3R,4R)-3-(2,3-Diamino-5-bromo-pyridin-4-ylamino)-bicyclo[2.2.1]hept-5-ene-2-carboxylic acid amide (75 mg, 0.22 mmol), 2-Chlorobenzaldehyde (34.3 mg, 0.244 mmol), and Ammonium acetate (34.2 mg, 0.444 mmol) were reacted to produce 50.82 mg (50%) of the title compound. (300 MHz, DMSO-$d_6$) 13.16 (s, 1H), 8.07 (s, 1H), 7.84 (m, 1H), 7.72 (s, 1H), 7.64 (m, 1H), 7.52 (m, 2H), 7.20 (s, 1H), 7.14 (d, J=9 Hz, 1H), 6.29 (s, 2H), 5.21 (t, J=17 Hz, 8.5 Hz, 1H), 2.86 (s, 1H), 2.77 (s, 1H), 2.57 (d, J=8 Hz, 1H), 2.24 (d, J=8 Hz, 1H), 1.38 (d, J=8 Hz, 1H). MS=460 (M+H), HPLC: 2.46 min. (G Method)

Compound CL

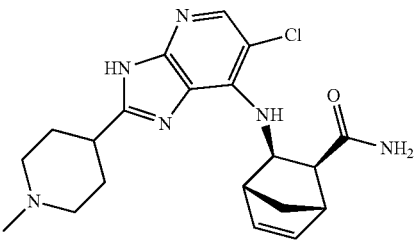

(1S,2S,3R,4R)-3-[6-Chloro-2-(1-methyl-piperidin-4-yl)-3H-imidazo[4,5-b]pyridin-7-ylamino]-bicyclo[2.2.1]hept-5-ene-2-carboxylic acid amide (Compound CL)

In a similar fashion to Compound LXXXVII, (1S,2S,3R,4R)-3-(2,3-Diamino-5-chloro-pyridin-4-ylamino)-bicyclo[2.2.1]hept-5-ene-2-carboxylic acid amide (75.00 mg, 0.2553 mmol), 1-Methyl-piperidine-4-carbaldehyde; hydrochloride (46.0 mg, 0.281 mmol), Ammonium acetate (39.4 mg, 0.511 mmol), and N,N-Diisopropylethylamine (53.37 uL, 0.3064 mmol) were reacted to produce 21.99 mg (21%) of the title compound. (300 MHz, DMSO-$d_6$) 12.52 (s, 1H), 7.86 (s, 1H), 7.72 (s, 1H), 7.18 (s, 1H), 6.95 (d, J=9 Hz, 1H), 6.29 (m, 2H), 5.09 (t, J=17 Hz, 8.5 Hz, 1H), 2.87-2.54 (m, 7H), 2.18 (s, 3H), 1.98 (m, 4H), 1.81 (m, 2H), 1.38 (d, J=8 Hz, 1H). MS=499 (M+H), HPLC: 2.47 min. (G Method)

Compound CLI

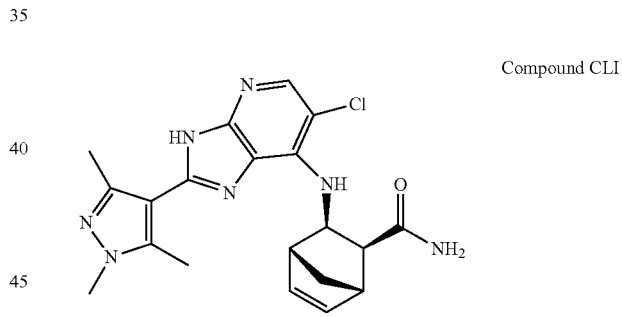

(1S,2S,3R,4R)-3-[6-Chloro-2-(1,3,5-trimethyl-1H-pyrazol-4-yl)-3H-imidazo[4,5-b]pyridin-7-ylamino]-bicyclo[2.2.1]hept-5-ene-2-carboxylic acid amide (Compound CLI)

In a similar fashion to Compound LXXXVII, (1S,2S,3R,4R)-3-(2,3-Diamino-5-chloro-pyridin-4-ylamino)-bicyclo[2.2.1]hept-5-ene-2-carboxylic acid amide (75.00 mg, 0.2553 mmol), 1,3,5-Trimethyl-1H-pyrazole-4-carbaldehyde (38.8 mg, 0.281 mmol), and Ammonium acetate (39.4 mg, 0.511 mmol) were reacted to produce 36.49 mg (37%) of the title compound. (300 MHz, DMSO-$d_6$) 12.47 (s, 1H), 7.91 (s, 1H), 7.72 (s, 1H), 7.21 (s, 1H), 7.00 (d, J=9 Hz, 1H), 6.32 (m, 1H), 6.26 (m, 1H), 5.17 (t, J=17 Hz, 9 Hz, 1H), 3.73 (s, 3H), 2.85 (s, 1H), 2.77 (s, 1H), 2.57 (d, J=8 Hz, 1H), 2.47 (s, 3H), 2.35 (s, 3H), 2.24 (d, J=8 Hz, 1H), 1.38 (d, J=8 Hz, 1H). MS=412 (M+H), HPLC: 1.97 min. (G Method)

Compound CLII

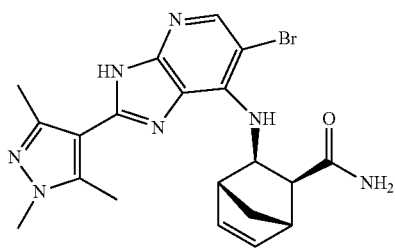

(1S,2S,3R,4R)-3-[6-Bromo-2-(1,3,5-trimethyl-1H-pyrazol-4-yl)-3H-imidazo[4,5-b]pyridin-7-ylamino]-bicyclo[2.2.1]hept-5-ene-2-carboxylic acid amide (Compound CLII)

In a similar fashion to Compound LXXXVII, (1S,2S,3R,4R)-3-(2,3-Diamino-5-bromo-pyridin-4-ylamino)-bicyclo[2.2.1]hept-5-ene-2-carboxylic acid amide (75 mg, 0.22 mmol), 1,3,5-Trimethyl-1H-pyrazole-4-carbaldehyde (33.7 mg, 0.244 mmol), and Ammonium acetate (34.2 mg, 0.444 mmol) were reacted to produce 63.66 mg (64%) of the title compound. (300 MHz, DMSO-$d_6$) 12.46 (s, 1H), 7.99 (s, 1H), 7.70 (s, 1H), 7.19 (s, 1H), 7.93 (d, J=9 Hz, 1H), 6.32 (m, 1H), 6.25 (m, 1H), 5.23 (t, J=17 Hz, 9 Hz, 1H), 3.76 (s, 3H), 2.85 (s, 1H), 2.75 (s, 1H), 2.57 (d, J=9 Hz, 1H), 2.47 (s, 3H), 2.35 (s, 3H), 2.25 (d, J=8 Hz, 1H), 1.39 (d, J=8 Hz, 1H). MS=458 (M+H), HPLC: 2.0 min. (G Method)

Compound CLIII

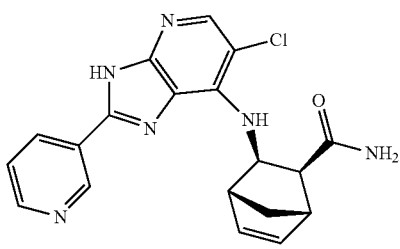

(1S,2S,3R,4R)-3-(6-Chloro-2-pyridin-3-yl-3H-imidazo[4,5-b]pyridin-7-ylamino)-bicyclo[2.2.1]hept-5-ene-2-carboxylic acid amide (Compound CLIII)

In a similar fashion to Compound LXXXVII, (1S,2S,3R,4R)-3-(2,3-Diamino-5-chloro-pyridin-4-ylamino)-bicyclo[2.2.1]hept-5-ene-2-carboxylic acid amide (75 mg, 0.26 mmol), 3-Pyridinecarboxaldehyde (26.4 uL, 0.281 mmol), and Ammonium acetate (39.4 mg, 0.511 mmol) were reacted to produce 5.5 mg (6%) of the title compound. (300 MHz, DMSO-$d_6$) 13.50 (s, 1H), 9.31 (s, 1H), 8.66 (d, J=5 Hz, 1H), 8.45 (d, J=8 Hz, 1H), 7.99 (s, 1H), 7.78 (s, 1H), 7.59 (q, J=13 Hz, 6 Hz, 1H), 7.29 (d, J=8 Hz, 1H), 7.24 (s, 1H), 6.42 (m, 1H), 6.37 (m, 1H), 5.18 (t, J=17 Hz, 8.5 Hz, 1H), 2.90 (s, 1H), 2.80 (s, 1H), 2.63 (d, J=8 Hz, 1H), 2.24 (d, J=8 Hz, 1H), 1.38 (d, J=8 Hz, 1H). MS=381 (M+H), HPLC: 1.69 min. (G Method)

Compound CLIV

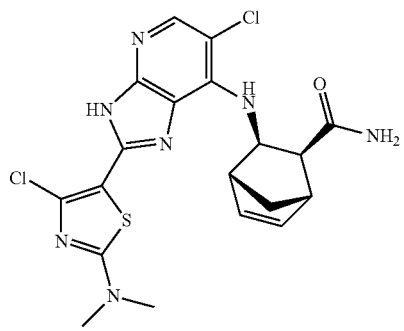

(1S,2S,3R,4R)-3-[6-Chloro-2-(4-chloro-2-dimethylamino-thiazol-5-yl)-3H-imidazo[4,5-b]pyridin-7-ylamino]-bicyclo[2.2.1]hept-5-ene-2-carboxylic acid amide (Compound CLIV)

In a similar fashion to Compound CXXV, (1S,2S,3R,4R)-3-(2,3-Diamino-5-chloro-pyridin-4-ylamino)-bicyclo[2.2.1]hept-5-ene-2-carboxylic acid amide (75.00 mg, 0.2553 mmol), 4-Chloro-2-dimethylamino-thiazole-5-carbaldehyde (53.5 mg, 0.281 mmol), and Ammonium acetate (39.4 mg, 0.511 mmol) were reacted to produce 29.03 mg (24%) of the title compound. (300 MHz, DMSO-$d_6$) 7.93 (s, 1H), 7.76 (s, 1H), 7.23 (m, 2H), 6.38-6.31 (m, 2H), 4.99 (t, J=17 Hz, 8.5 Hz, 1H), 3.11 (s, 6H), 2.87 (s, 4H), 2.75 (s, 1H), 2.58 (d, J=8 Hz, 1H), 2.19 (d, J=8 Hz, 1H), 1.36 (d, J=8 Hz, 1H). MS=464 (M+H), HPLC: 2.37 min. (G Method)

Compound CLV

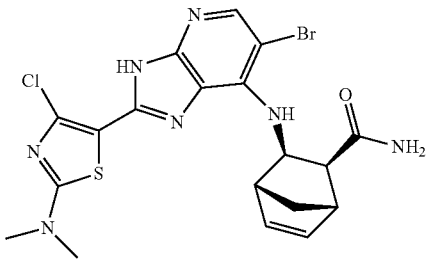

(1S,2S,3R,4R)-3-[6-Bromo-2-(4-chloro-2-dimethylamino-thiazol-5-yl)-3H-imidazo[4,5-b]pyridin-7-ylamino]-bicyclo[2.2.1]hept-5-ene-2-carboxylic acid amide (Compound CLV)

In a similar fashion to Compound CXXV, (1S,2S,3R,4R)-3-(2,3-Diamino-5-bromo-pyridin-4-ylamino)-bicyclo[2.2.1]hept-5-ene-2-carboxylic acid amide (75.00 mg, 0.2553 mmol), 4-Chloro-2-dimethylamino-thiazole-5-carbaldehyde (53.5 mg, 0.281 mmol), and Ammonium acetate (39.4 mg, 0.511 mmol) were reacted to produce 36.84 mg (33%) of the title compound. (300 MHz, DMSO-$d_6$) 12.56 (s, 1H), 8.00 (s, 1H), 7.73 (s, 1H), 7.18 (m, 2H), 6.34 (s, 2H), 5.04 (t, J=17 Hz, 8.5 Hz, 1H), 3.11 (s, 6H), 2.87 (s, 1H), 2.75 (s, 1H), 2.58 (s, 1H), 2.19 (d, J=8 Hz, 1H), 1.36 (d, J=8 Hz, 1H). MS=509 (M+H), HPLC: 2.39 min. (G Method).

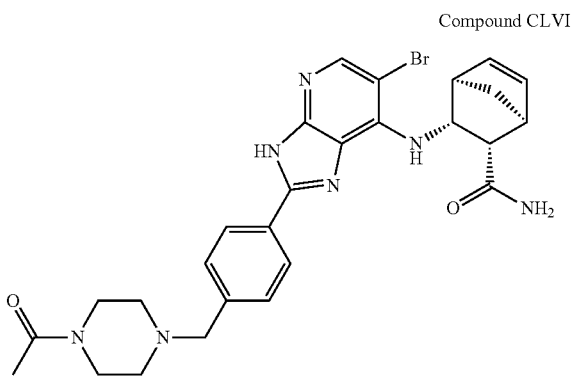 [SMILES: CC(=O)N1CCN(Cc2ccc(-c3nc4c(N[C@H]5[C@@H](C(N)=O)[C@@H]6C=C[C@H]5C6)c(Br)cnc4[nH]3)cc2)CC1]

Compound CLVI (1S,2S,3R,4R)-3-{2-[4-(4-Acetyl-piperazin-1-ylmethyl)-phenyl]-6-bromo-3H-imidazo[4,5-b]pyridin-7-ylamino}-bicyclo[2.2.1]hept-5-ene-2-carboxylic acid amide (Compound CLVI)

4-{4-[6-Bromo-7-((1R,2R,3S,4S)-3-carbamoyl-bicyclo[2.2.1]hept-5-en-2-ylamino)-3H-imidazo[4,5-b]pyridin-2-yl]-benzyl}-piperazine-1-carboxylic acid tert-butyl ester (172 mg, 0.276 mmol) was taken up into DCM and treated with TFA (3 ml) and stirred @ 40° C., O/N. the solution was then concentrated. The residue was taken up into methanol and treated with 900 mg mp carbonate for ½ hour. The resin was removed by filtration and filtrate concentrated. The residue was taken up into DCM/THF (~30 mL) and acetic anhydride (0.56 ml, 5.9 mmol) was added followed by triethylamine (0.56 ml, 4.0 mmol). Solution was stirred at RT for 1 hr and then concentrated. The residue was purified via reverse phase chromatography using a gradient of MeCN with 0.1% TFA in Water with 0.1% TFA on a Phenomenex Gemini-NX C18 AXIA column. Fractions containing desired product were poured into sat'd sodium bicarbonate and extracted with 3 portions of methylene chloride. The combined organic was dried over magnesium sulfate, filtered and evaporated to yield an off white solid, 28 mg, 18% yield. (300 MHz, DMSO-$d_6$) 13.28 (s, 1H), 8.10 (d, J=8 Hz, 2H), 8.02 (s, 1H), 7.75 (m, 1H), 7.48 (d, J=8 Hz, 2H), 7.19 (m, 2H), 6.44-6.33 (m, 2H), 5.23 (t, J=17 Hz, 9 Hz, 1H), 3.56 (s, 2H), 3.43 (s, 4H), 2.89 (s, 1H), 2.78 (s, 1H), 2.62 (d, J=8 Hz, 1H), 2.39 (s, 2H), 2.33 (s, 2H), 2.25 (d, J=8 Hz, 1H), 1.98 (s, 3H), 1.38 (d, J=8 Hz, 1H). MS=565 (M+H), HPLC: 1.5 min. (G Method)

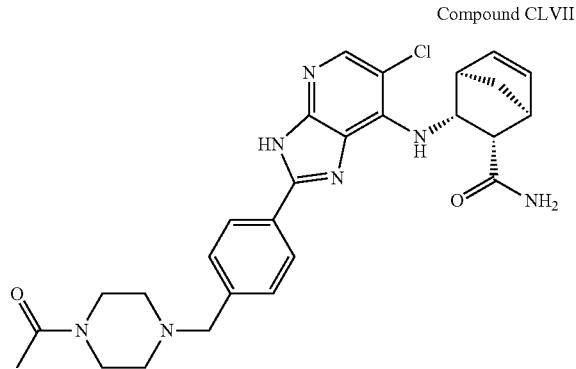 [SMILES: CC(=O)N1CCN(Cc2ccc(-c3nc4c(N[C@H]5[C@@H](C(N)=O)[C@@H]6C=C[C@H]5C6)c(Cl)cnc4[nH]3)cc2)CC1]

Compound CLVII (1S,2S,3R,4R)-3-[6-Chloro-2-(4-chloro-2-morpholin-4-yl-thiazol-5-yl)-3H-imidazo[4,5-b]pyridin-7-ylamino]-bicyclo[2.2.1]hept-5-ene-2-carboxylic acid amide (Compound CLVII)

[4-{4-[7-((1R,2R,3S,4S)-3-Carbamoyl-bicyclo[2.2.1]hept-5-en-2-ylamino)-6-chloro-3H-imidazo[4,5-b]pyridin-2-yl]-benzyl}-piperazine-1-carboxylic acid tert-butyl ester (159.0 mg, 0.2750 mmol) was taken up into Methylene chloride (8.4 mL, 130 mmol) and treated with Trifluoroacetic Acid (3 mL, 40 mmol) and stirred @ 40° C., O/N. The solution was then concentrated. The residue was taken up into methanol and treated with 900 mg mp carbonate for ½ hour. The resin was removed by filtration and filtrate concentrated. The residue was taken up into DCM/THF (~30 mL) and Acetic anhydride (0.56 mL, 5.9 mmol) was added followed by triethylamine Triethylamine (0.56 mL, 4.0 mmol). Solution was stirred at RT for 1 hr and then concentrated. The residue was purified via reverse phase chromatography using a gradient of MeCN with 0.1% TFA in Water with 0.1% TFA on a Phenomenex Gemini-NX C18 AXIA column. Fractions containing desired product were poured into sat'd sodium bicarbonate and extracted with 3 portions of methylene chloride. The combined organic was dried over magnesium sulfate, filtered and evaporated to yield a yellow solid, 15.00 mg, 10% yield. (300 MHz, DMSO-$d_6$) 13.26 (s, 1H), 8.10 (d, J=8 Hz, 2H), 7.95 (s, 1H), 7.78 (m, 1H), 7.48 (d, J=8 Hz, 2H), 7.22 (m, 2H), 6.44-6.33 (m, 2H), 5.17 (t, J=17 Hz, 9 Hz, 1H), 3.56 (s, 2H), 3.43 (m, 4H), 2.89 (s, 1H), 2.80 (s, 1H), 2.62 (d, J=9 Hz, 1H), 2.40 (m, 2H), 2.33 (m, 2H), 2.25 (d, J=8 Hz, 1H), 1.98 (s, 3H), 1.38 (d, J=8 Hz, 1H). MS=521 (M+H), HPLC: 1.47 min. (G Method)

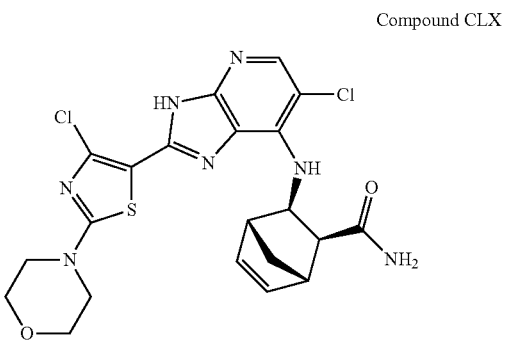 [SMILES: NC(=O)[C@@H]1[C@H](Nc2c(Cl)cnc3[nH]c(-c4sc(N5CCOCC5)nc4Cl)nc23)[C@H]2C=C[C@@H]1C2]

Compound CLX (1S,2S,3R,4R)-3-[6-Chloro-2-(4-chloro-2-morpholin-4-yl-thiazol-5-yl)-3H-imidazo[4,5-b]pyridin-7-ylamino]-bicyclo[2.2.1]hept-5-ene-2-carboxylic acid amide (Compound CLX)

In a similar fashion to Compound LXXXVII, 4-Chloro-2-morpholin-4-yl-thiazole-5-carbaldehyde (65 mg, 0.28 mmol), (1S,2S,3R,4R)-3-(2,3-Diamino-5-chloro-pyridin-4-ylamino)-bicyclo[2.2.1]hept-5-ene-2-carboxylic acid amide (75 mg, 0.26 mmol), and Ammonium acetate (98 mg, 1.3 mmol) were reacted to produce 13.87 mg (11%) of the title compound. (300 MHz, DMSO-$d_6$) 12.79 (s, 1H), 7.95 (s, 1H), 7.77 (s, 2H), 7.25 (s, 2H), 6.40-6.30 (m, 2H), 4.98 (t, J=17 Hz, 8.5 Hz, 1H), 3.72 (m, 4H), 3.27 (m, 4H), 3.48 (m, 4H), 2.87 (s, 1H), 2.75 (s, 1H), 2.57 (d, J=8 Hz, 1H), 2.19 (d, J=8 Hz, 1H), 1.36 (d, J=8 Hz, 1H). MS=507 (M+H), HPLC: 2.35 min. (G Method)

Compound CLXI

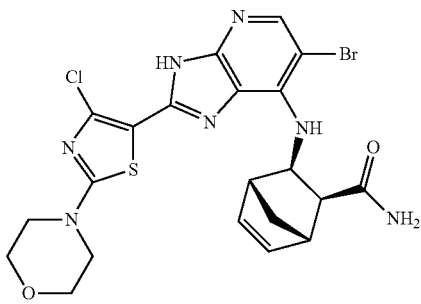

(1S,2S,3R,4R)-3-[6-Bromo-2-(4-chloro-2-morpholin-4-yl-thiazol-5-yl)-3H-imidazo[4,5-b]pyridin-7-ylamino]-bicyclo[2.2.1]hept-5-ene-2-carboxylic acid amide (Compound CLXI)

In a similar fashion to Compound LXXXVII, [A]-4-Chloro-2-morpholin-4-yl-thiazole-5-carbaldehyde (65 mg, 0.28 mmol) (1S,2S,3R,4R)-3-(2,3-Diamino-5-bromo-pyridin-4-ylamino)-bicyclo[2.2.1]hept-5-ene-2-carboxylic acid amide (86 mg, 0.26 mmol) and Ammonium acetate (98 mg, 1.3 mmol) were reacted to produce 13.91 mg (9.9%) of the title compound. (300 MHz, DMSO-$d_6$) 12.78 (s, 1H), 8.03 (s, 1H), 7.77 (s, 1H), 7.22 (m, 1H), 6.40-6.30 (m, 2H), 5.03 (t, J=17 Hz, 8.5 Hz, 1H), 3.73 (s, 4H), 3.48 (s, 4H), 2.87 (s, 1H), 2.73 (s, 1H), 2.56 (d, J=8 Hz, 1H), 2.20 (d, J=8 Hz, 1H), 1.38 (d, J=8 Hz, 1H). MS=551 (M+H), HPLC: 2.37 min. (G Method)

Compound CLXII

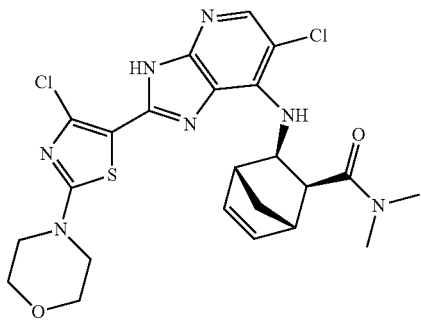

(1S,2S,3R,4R)-3-[6-Chloro-2-(4-chloro-2-morpholin-4-yl-thiazol-5-yl)-3H-imidazo[4,5-b]pyridin-7-ylamino]-bicyclo[2.2.1]hept-5-ene-2-carboxylic acid dimethylamide (Compound CLXII)

In a similar fashion to Compound LXXXVII, 4-Chloro-2-morpholin-4-yl-thiazole-5-carbaldehyde (75.00 mg, 0.3223 mmol), (1S,2S,3R,4R)-3-(2,3-Diamino-5-chloro-pyridin-4-ylamino)-bicyclo[2.2.1]hept-5-ene-2-carboxylic acid dimethylamide (93.35 mg, 0.2901 mmol) and Ammonium acetate (44.72 mg, 0.5802 mmol) were reacted to produce 24.34 mg (16%) of the title compound. (300 MHz, DMSO-$d_6$) 12.80 (s, 1H), 7.96 (s, 1H), 6.42-6.32 (m, 2H), 5.11 (t, J=17 Hz, 8.5 Hz, 1H), 3.73 (m, 4H), 3.48 (m, 4H), 3.01 (d, J=9 Hz, 1H), 2.94 (s, 3H), 2.86 (m, 4H), 2.82 (s, 1H), 2.11 (d, J=8 Hz, 1H), 1.42 (d, J=8 Hz, 1H). MS=533 (M+H), HPLC: 2.73 min. (G Method)

Compound CLXIII

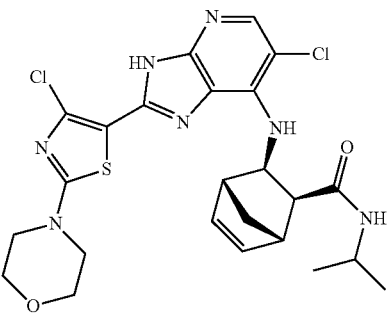

(1S,2S,3R,4R)-3-[6-Chloro-2-(4-chloro-2-morpholin-4-yl-thiazol-5-yl)-3H-imidazo[4,5-b]pyridin-7-ylamino]-bicyclo[2.2.1]hept-5-ene-2-carboxylic acid isopropylamide (Compound CLXIII)

In a similar fashion to Compound LXXXVII 4-Chloro-2-morpholin-4-yl-thiazole-5-carbaldehyde (75.00 mg, 0.3223 mmol), (1S,2S,3R,4R)-3-(2,3-Diamino-5-chloro-pyridin-4-ylamino)-bicyclo[2.2.1]hept-5-ene-2-carboxylic acid isopropylamide (97.42 mg, 0.2901 mmol), and Ammonium acetate (44.72 mg, 0.5802 mmol were reacted to produce 14.26 mg (9%) of the title compound. (300 MHz, DMSO-$d_6$) 12.78 (s, 1H), 8.11 (d, J=7.5 Hz, 1H), 7.94 (s, 1H), 6.95 (s, 1H), 6.39-6.29 (m, 2H), 4.98 (t, J=17 Hz, 8.5 Hz, 1H), 3.88 (m, 1H), 3.73 (m, 4H), 3.49 (m, 4H), 2.83 (s, 1H), 2.83 (s, 1H), 2.76 (s, 1H), 2.54 (d, J=8 Hz, 1H), 2.54 (d, J=8 Hz, 1H), 2.25 (d, J=8 Hz, 1H), 1.07 (d, J=6.5 Hz, 3H, 1.00 (d, J=6.5 Hz, 3H). MS=547 (M+H), HPLC: 2.92 min. (G Method)

Compound CLXIV

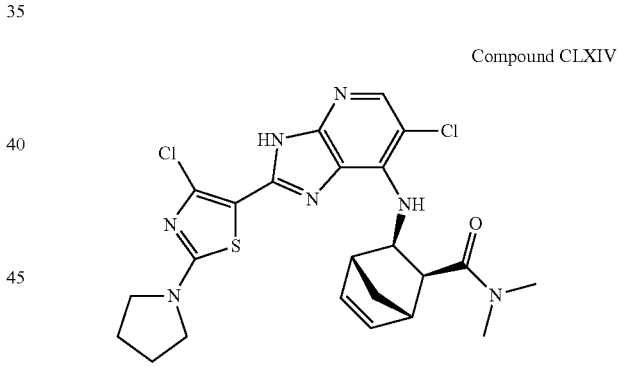

(1S,2S,3R,4R)-3-[6-Chloro-2-(4-chloro-2-pyrrolidin-1-yl-thiazol-5-yl)-3H-imidazo[4,5-b]pyridin-7-ylamino]-bicyclo[2.2.1]hept-5-ene-2-carboxylic acid dimethylamide (Compound CLXIV)

In a similar fashion to Compound LXXXVII 4-Chloro-2-pyrrolidin-1-yl-thiazole-5-carbaldehyde (69.84 mg, 0.3223 mmol), (1S,2S,3R,4R)-3-(2,3-Diamino-5-chloro-pyridin-4-ylamino)-bicyclo[2.2.1]hept-5-ene-2-carboxylic acid dimethylamide (93.35 mg, 0.2901 mmol and Ammonium acetate (44.72 mg, 0.5802 mmol) were reacted to produce 7.35 mg (5%) of the title compound. (300 MHz, DMSO-$d_6$) 13.50 (s, 1H), 7.94 (s, 1H), 6.67 (s, 1H), 6.38 (m, 2H), 5.12 (t, J=17 Hz, 8.5 Hz, 1H), 3.44 (m, 4H), 3.02 (d, J=9 Hz, 1H), 2.94 (s, 3H), 2.86 (m, 4H), 2.82 (s, 1H), 2.11 (d, J=8 Hz, 1H), 2.01 (m, 4H), 1.42 (d, J=8 Hz, 1H). MS=517 (M+H), HPLC: 2.96 min. (G Method)

Compound CLXV

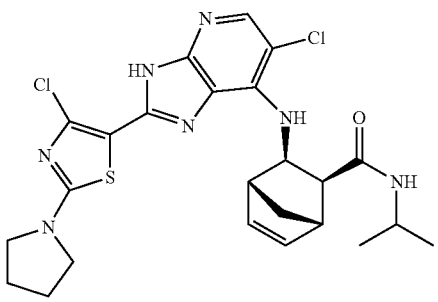

(1S,2S,3R,4R)-3-[6-Chloro-2-(4-chloro-2-pyrrolidin-1-yl-thiazol-5-yl)-3H-imidazo[4,5-b]pyridin-7-ylamino]-bicyclo[2.2.1]hept-5-ene-2-carboxylic acid isopropylamide (Compound CLXV)

In a similar fashion to Compound LXXXVII, 4-Chloro-2-pyrrolidin-1-yl-thiazole-5-carbaldehyde (69.84 mg, 0.3223 mmol), (1S,2S,3R,4R)-3-(2,3-Diamino-5-chloro-pyridin-4-ylamino)-bicyclo[2.2.1]hept-5-ene-2-carboxylic acid isopropylamide (97.42 mg, 0.2901 mmol), and Ammonium acetate (44.72 mg, 0.5802 mmol) were reacted to produce 5.21 mg (3.4%) of the title compound. (300 MHz, DMSO-$d_6$) 12.60 (s, 1H), 8.10 (d, J=8 Hz, 1H), 7.93 (s, 1H), 6.90 (s, 1H), 6.34 (m, 2H), 5.00 (t, J=17 Hz, 8.5 Hz, 1H), 3.88 (m, 1H), 3.44 (m, 4H), 2.83 (s, 1H), 2.76 (s, 1H), 2.55 (d, J=8 Hz, 1H), 2.24 (d, J=8 Hz, 1H), 2.01 (m, 4H), 1.37 (d, J=8 Hz, 1H), 1.07 (d, J=7 Hz, 3H), 1.00 (d, J=7 Hz, 3H). MS=531 (M+H), HPLC: 3.11 min. (G Method)

Compound CLXVI

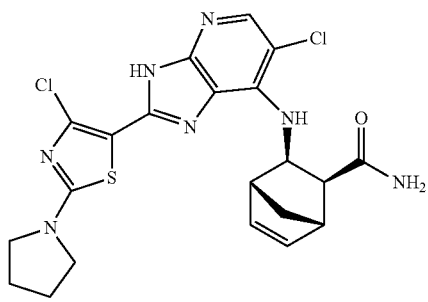

(1S,2S,3R,4R)-3-[6-Chloro-2-(4-chloro-2-pyrrolidin-1-yl-thiazol-5-yl)-3H-imidazo[4,5-b]pyridin-7-ylamino]-bicyclo[2.2.1]hept-5-ene-2-carboxylic acid amide (Compound CLXVI)

In a similar fashion to Compound LXXXVII, [A]-4-Chloro-2-pyrrolidin-1-yl-thiazole-5-carbaldehyde (204.9 mg, 0.9456 mmol), [B] (1S,2S,3R,4R)-3-(2,3-Diamino-5-chloro-pyridin-4-ylamino)-bicyclo[2.2.1]hept-5-ene-2-carboxylic acid amide (250 mg, 0.85 mmol) and Ammonium acetate (131.2 mg, 1.702 mmol) were reacted to produce 23.24 mg (6%) of the title compound. (300 MHz, DMSO-$d_6$) 12.89 (s, 1H), 7.95 (s, 1H), 7.72 (m, 2H), 7.21 (s, 1H), 7.09 (m, 3H), 6.30 (s, 2H), 5.18 (t, J=17 Hz, 8.5 Hz, 1H), 3.75 (s, 4H), 3.27 (s, 4H), 2.87 (s, 1H), 2.78 (s, 1H), 2.58 (d, J=8 Hz, 1H), 2.24 (d, J=8 Hz, 1H), 1.38 (d, J=8 Hz, 1H). MS=490 (M+H), HPLC: 2.57 min. (G Method)

Compound CLXVII

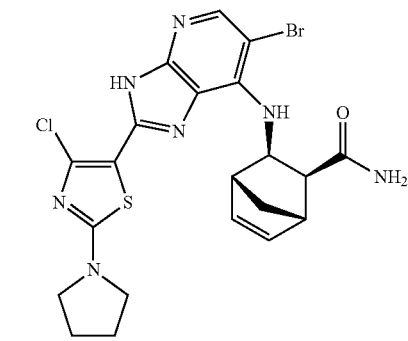

(1S,2S,3R,4R)-3-[6-Bromo-2-(4-chloro-2-pyrrolidin-1-yl-thiazol-5-yl)-3H-imidazo[4,5-b]pyridin-7-ylamino]-bicyclo[2.2.1]hept-5-ene-2-carboxylic acid amide (Compound CLXVII)

In a similar fashion to Compound LXXXVII, 4-Chloro-2-pyrrolidin-1-yl-thiazole-5-carbaldehyde (204.9 mg, 0.9456 mmol), (1S,2S,3R,4R)-3-(2,3-Diamino-5-bromo-pyridin-4-ylamino)-bicyclo[2.2.1]hept-5-ene-2-carboxylic acid amide (290 mg, 0.85 mmol), and Ammonium acetate (131.2 mg, 1.702 mmol) were reacted to produce 23.46 mg (5%) of the title compound. (300 MHz, DMSO-$d_6$) 2.68 (s, 1H), 8.00 (s, 1H), 7.74 (m, 2H), 7.23 (s, 1H), 7.13 (m, 1H), 6.38-6.31 (m, 2H), 5.05 (t, J=17 Hz, 8.5 Hz, 1H), 3.44 m, 4H), 2.87 (s, 1H), 2.73 (s, 1H), 2.58 (d, J=8 Hz, 1H), 2.21 (d, J=8 Hz, 1H), 2.01 (m, 5H). MS=535 (M+H), HPLC: 2.54 min. (G Method)

Compound CLXVIII (1S,2S,3R,4R)-3-{6-Chloro-2-[4-chloro-2-((R)-3-hydroxy-pyrrolidin-1-yl)-thiazol-5-yl]-3H-imidazo[4,5-b]pyridin-7-ylamino}-bicyclo[2.2.1]hept-5-ene-2-carboxylic acid dimethylamide (Compound CLXVIII)

In a similar fashion to Compound LXXXVII, 4-Chloro-2-(3-hydroxy-pyrrolidin-1-yl)-thiazole-5-carbaldehyde (180.77 mg, 0.77687 mmol), (1S,2S,3R,4R)-3-(2,3-Diamino-5-chloro-pyridin-4-ylamino)-bicyclo[2.2.1]hept-5-ene-2-carboxylic acid dimethylamide (200.00 mg, 0.62149 mmol) and Ammonium acetate (95.813 mg, 1.2430 mmol) were reacted to produce 35.95 mg (11%) of the title compound. (300 MHz, DMSO-$d_6$) 12.70 (s, 1H), 7.95 (s, 1H), 6.66 (s, 1H), 6.42-6.34 (m, 2H), 5.76 (s, 1H), 5.13 (m, 2H), 4.44 (s, 1H), 3.54 (m, 3H), 3.03 (d, J=9 Hz, 1H), 2.95 (s, 3H), 2.86 (m, 4H), 2.83 (m, 4H), 2.11 (d, J=9 Hz, 1H), 1.96 (m, 1H), 1.42 (d, J=9 Hz, 1H). MS=533 (M+H), HPLC: 2.33 min. (G Method)

Compound CLXIX

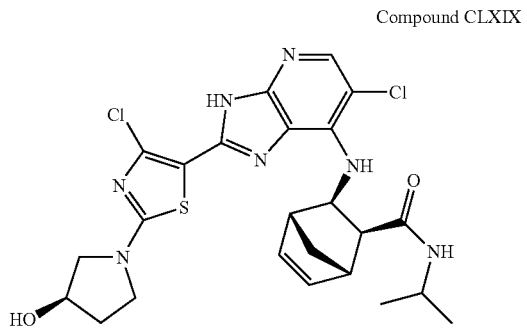 [SMILES: CC(C)NC(=O)[C@@H]1[C@H](Nc2c(Cl)cnc3[nH]c(-c4sc(N5CC[C@@H](O)C5)nc4Cl)nc23)[C@H]2C=C[C@@H]1C2]

(1S,2S,3R,4R)-3-{6-Chloro-2-[4-chloro-2-((R)-3-hydroxy-pyrrolidin-1-yl)-thiazol-5-yl]-1H-imidazo[4,5-b]pyridin-7-ylamino}-bicyclo[2.2.1]hept-5-ene-2-carboxylic acid isopropylamide (Compound CLXIX)

In a similar fashion to Compound LXXXVII, 4-Chloro-2-(3-hydroxy-pyrrolidin-1-yl)-thiazole-5-carbaldehyde (180.77 mg, 0.77687 mmol), (1S,2S,3R,4R)-3-(2,3-Diamino-5-chloro-pyridin-4-ylamino)-bicyclo[2.2.1]hept-5-ene-2-carboxylic acid isopropylamide (208.72 mg, 0.62149 mmol), and Ammonium acetate (95.813 mg, 1.2430 mmol) were reacted to produce 23.87 mg (7%) of the title compound. (300 MHz, DMSO-$d_6$) 12.60 (s, 1H), 8.10 (d, J=7 Hz, 1H), 7.92 (s, 1H), 6.38-6.31 (m, 2H), 5.16 (m, 1H), 5.02 (T, J=17 Hz, 9 Hz, 1H), 4.44 (s, 1H), 3.88 (m, 1H), 3.54 (m, 3H), 2.83 (s, 1H), 2.76 (s, 1H), 2.55 (d, J=8 Hz, 1H), 2.24 (d, J=8 Hz, 1H), 2.10 (m, 1H), 1.96 (m, 1H), 1.38 (d, J=8 Hz, 1H), 1.06 (d, J=7 Hz, 3H), 0.99 (d, J=7 Hz, 3H). MS=548 (M+H), HPLC: 2.52 min. (G Method)

Compound CLXX

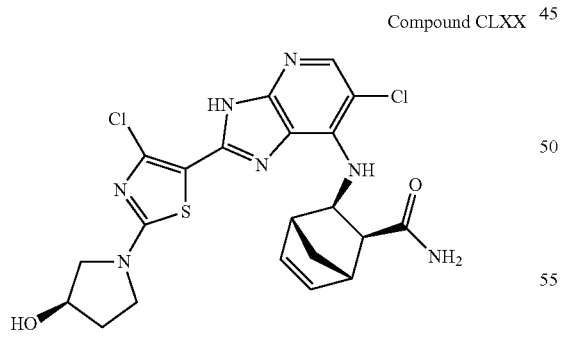

(1S,2S,3R,4R)-3-{6-Chloro-2-[4-chloro-2-((R)-3-hydroxy-pyrrolidin-1-yl)-thiazol-5-yl]-1H-imidazo[4,5-b]pyridin-7-ylamino}-bicyclo[2.2.1]hept-5-ene-2-carboxylic acid isopropylamide (Compound CLXX)

In a similar fashion to Compound LXXXVII, 4-Chloro-2-(3-hydroxy-pyrrolidin-1-yl)-thiazole-5-carbaldehyde (180.77 mg, 0.77687 mmol), (1S,2S,3R,4R)-3-(2,3-Diamino-5-chloro-pyridin-4-ylamino)-bicyclo[2.2.1]hept-5-ene-2-carboxylic acid amide (182.56 mg, 0.62149 mmol), and Ammonium acetate (95.813 mg, 1.2430 mmol) were reacted to produce 16.24 mg (5%) of the title compound. (300 MHz, DMSO-$d_6$) 12.68 (s, 1H), 7.92 (s, 1H), 7.75 (s, 1H), 7.23 (s, 1H), 7.17 (s, 1H), 6.38-6.31 (m, 2H), 5.15 (s, 1H), 5.00 (t, J=17 Hz, 8.5 Hz, 1H), 4.44 (s, 1H), 3.54 (m, 3H), 2.87 (s, 1H), 2.75 (s, 1H), 2.59 (d, J=8 Hz, 1H), 2.19 (d, J=8 Hz, 1H), 2.11 (m, 1H), 1.38 (d, J=8 Hz, 1H). MS=506 (M+H), HPLC: 2.04 min. (G Method)

Compound CLXXI

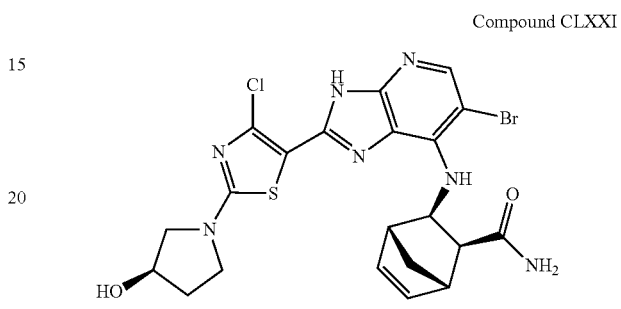

(1S,2S,3R,4R)-3-{6-Bromo-2-[4-chloro-2-((R)-3-hydroxy-pyrrolidin-1-yl)-thiazol-5-yl]-3H-imidazo[4,5-b]pyridin-7-ylamino}-bicyclo[2.2.1]hept-5-ene-2-carboxylic acid amide (Compound CLXXI)

In a similar fashion to Compound LXXXVII, 4-Chloro-2-(3-hydroxy-pyrrolidin-1-yl)-thiazole-5-carbaldehyde (180.77 mg, 0.77687 mmol), (1S,2S,3R,4R)-3-(2,3-Diamino-5-bromo-pyridin-4-ylamino)-bicyclo[2.2.1]hept-5-ene-2-carboxylic acid amide (210.19 mg, 0.62149 mmol), and Ammonium acetate (95.813 mg, 1.2430 mmol) were reacted to produce 13.82 mg (4%) of the title compound. (300 MHz, DMSO-$d_6$) 12.68 (s, 1H), 8.01 (s, 1H), 7.73 (s, 1H), 7.23 (s, 1H), 7.14 (s, 1H), 6.38-6.31 (m, 2H), 5.15 (s, 1H), 5.05 (t, J=17 Hz, 8.5 Hz, 1H), 4.44 (s, 1H), 3.54 (m, 3H), 2.87 (s, 1H), 2.73 (s, 1H), 2.59 (d, J=8 Hz, 1H), 2.21 (d, J=8 Hz, 1H), 2.10 (m, 1H), 1.96 (m, 1H), 1.38 (d, J=8 Hz, 1H). MS=553 (M+H), HPLC: 2.07 min. (G Method)

Compound CLXXII

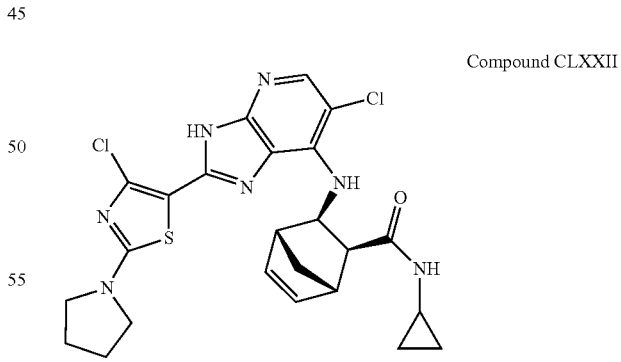

(1S,2S,3R,4R)-3-[6-Chloro-2-(4-chloro-2-pyrrolidin-1-yl-thiazol-5-yl)-3H-imidazo[4,5-b]pyridin-7-ylamino]-bicyclo[2.2.1]hept-5-ene-2-carboxylic acid cyclopropylamide (Compound CLXXII)

In a similar fashion to Compound LXXXVII, (1S,2S,3R,4R)-3-(2,3-Diamino-5-chloro-pyridin-4-ylamino)-bicyclo

[2.2.1]hept-5-ene-2-carboxylic acid cyclopropylamide (200 mg, 0.6 mmol), 4-Chloro-2-pyrrolidin-1-yl-thiazole-5-carbaldehyde (162.28 mg, 0.74892 mmol), and Ammonium acetate (92.439 mg, 1.1992 mmol) were reacted to produce 26.23 mg (8%) of the title compound. (300 MHz, DMSO-$d_6$) 12.68 (s, 1H), 8.31 (s, 1H), 7.94 (s, 1H), 6.93 (s, 1H), 6.38-6.31 (m, 2H), 4.99 (t, J=17 Hz, 8.5 Hz, 1H), 3.44 (m, 4H), 2.84 (s, 1H), 2.75 (s, 1H), 2.65 (m, 1H), 2.23 (d, J=8 Hz, 1H), 2.01 (m, 4H), 1.38 (d, J=8 Hz, 1H), 0.63 (m, 2H), 0.37 (m, 2H). MS=530 (M+H), HPLC: 2.90 min. (G Method)

Compound CLXXIII

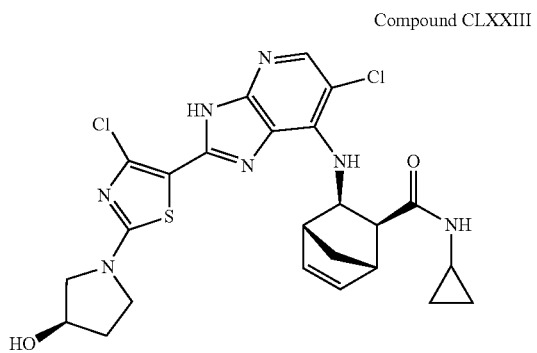 [SMILES: O=C(NC1CC1)[C@@H]1[C@H](Nc2c(Cl)cnc3[nH]c(-c4sc(N5CC[C@@H](O)C5)nc4Cl)nc23)[C@H]2C=C[C@@H]1C2]

(1S,2S,3R,4R)-3-[6-Chloro-2-[4-chloro-2-((R)-3-hydroxy-pyrrolidin-1-yl)-thiazol-5-yl]-3H-imidazo[4,5-b]pyridin-7-ylamino]-bicyclo[2.2.1]hept-5-ene-2-carboxylic acid cyclopropylamide (Compound CLXXIII)

In a similar fashion to Compound LXXXVII, 4-Chloro-2-(3-hydroxy-pyrrolidin-1-yl)-thiazole-5-carbaldehyde (174.40 mg, 0.74951 mmol), (1S,2S,3R,4R)-3-(2,3-Diamino-5-chloro-pyridin-4-ylamino)-bicyclo[2.2.1]hept-5-ene-2-carboxylic acid cyclopropylamide (200 mg, 0.6 mmol), and Ammonium acetate (92.439 mg, 1.1992 mmol) were reacted to produce 36.26 mg (10%) of the title compound. (300 MHz, DMSO-$d_6$) 12.68 (s, 1H), 8.30 (s, 1H), 7.94 (s, 1H), 6.93 (s, 1H), 6.38-6.30 (m, 2H), 4.99 (t, J=17 Hz, 8.5 Hz, 1H), 3.44 (m, 4H), 2.84 (s, 1H), 2.76 (s, 1H), 2.66 (m, 1H), 2.23 (d, J=8 Hz, 1H), 2.01 (m, 4H), 1.38 (d, J=8 Hz, 1H), 0.63 (m, 2H), 0.37 (m, 2H). MS=546 (M+H), HPLC: 2.35 min. (G Method)

Comppound CLXXIV

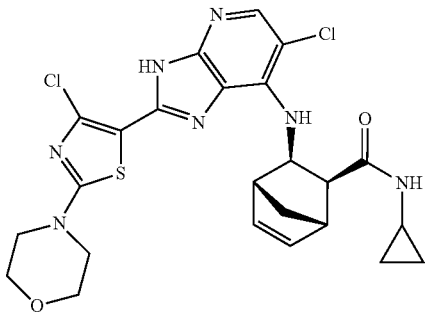

(1S,2S,3R,4R)-3-[6-Chloro-2-(4-chloro-2-morpholin-4-yl-thiazol-5-yl)-3H-imidazo[4,5-b]pyridin-7-ylamino]-bicyclo[2.2.1]hept-5-ene-2-carboxylic acid cyclopropylamide (Compound CLXXIV)

In a similar fashion to Compound LXXXVII, (1S,2S,3R,4R)-3-(2,3-Diamino-5-chloro-pyridin-4-ylamino)-bicyclo[2.2.1]hept-5-ene-2-carboxylic acid cyclopropylamide (200 mg, 0.6 mmol), 4-Chloro-2-morpholin-4-yl-thiazole-5-carbaldehyde (0.17426 g, 0.74892 mmol), and Ammonium acetate (92.439 mg, 1.1992 mmol) were reacted to produce 23.28 mg (7%) of the title compound. (300 MHz, DMSO-$d_6$) 12.68 (s, 1H), 8.30 (s, 1H), 7.94 (s, 1H), 6.93 (s, 1H), 6.38-6.30 (m, 2H), 4.99 (t, J=17 Hz, 8.5 Hz, 1H), 3.44 (m, 4H), 2.84 (s, 1H), 2.76 (s, 1H), 2.66 (m, 1H), 2.23 (d, J=8 Hz, 1H), 2.01 (m, 4H), 1.38 (d, J=8 Hz, 1H), 0.63 (m, 2H), 0.37 (m, 2H). MS=547 (M+H), HPLC: 2.72 min. (G Method)

Compound CLXXV

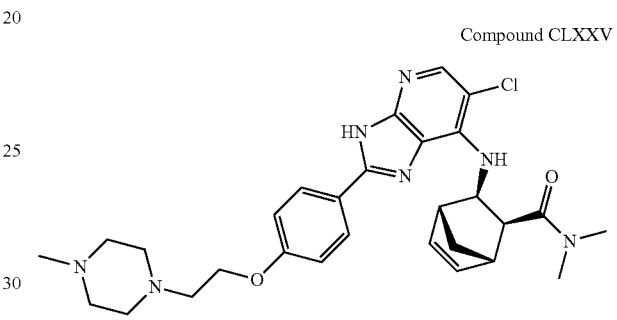

(1S,2S,3R,4R)-3-(6-Chloro-2-{4-[2-(4-methyl-piperazin-1-yl)-ethoxy]-phenyl}-3H-imidazo[4,5-b]pyridin-7-ylamino)-bicyclo[2.2.1]hept-5-ene-2-carboxylic acid dimethylamide (Compound CLXXV)

In a similar fashion to Compound LXXXVII, 4-(2-(4-methylpiperazin-1-yl)ethoxy)benzaldehyde (138 mg, 0.222 mmol), (1S,2S,3R,4R)-3-(2,3-Diamino-5-chloro-pyridin-4-ylamino)-bicyclo[2.2.1]hept-5-ene-2-carboxylic acid dimethylamide (78.7 mg, 0.244 mmol), and Ammonium acetate (34.3 mg, 0.444 mmol) were reacted to produce 34.61 mg (28%) of the title compound. (300 MHz, DMSO-$d_6$) 12.56 (s, 1H), 8.08 (d, J=8 Hz, 1H), 7.93 (s, 1H), 7.88 (s, 1H), 7.11 (d, J=8 Hz, 1H), 6.42 (m, 2H), 6.32 (s, 1H), 5.35 (m, 1H), 4.15 (m, 2H), 3.49 (m, 1H), 3.07 (d, J=8 Hz, 1H), 3.00 (d, J=8 Hz, 1H), 2.96-2.68 (m, 14H), 2.32 (s, 2H), 2.14 (s, 2H), 1.92 (m, 1H), 1.44 (m, 1H). MS=550 (M+H), HPLC: 1.91 min. (G Method)

Compound CLXXVII

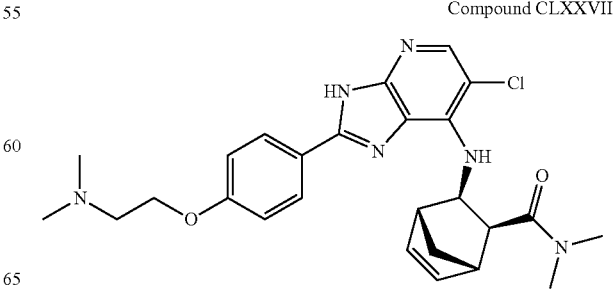

(1S,2S,3R,4R)-3-[6-Chloro-2-[4-(2-dimethylamino-ethoxy)-phenyl]-3H-imidazo[4,5-b]pyridin-7-ylamino]-bicyclo[2.2.1]hept-5-ene-2-carboxylic acid dimethylamide (Compound CLXXVII)

In a similar fashion to Compound LXXXVII, (1S,2S,3R,4R)-3-(2,3-Diamino-5-chloro-pyridin-4-ylamino)-bicyclo[2.2.1]hept-5-ene-2-carboxylic acid dimethylamide (78.7 mg, 0.244 mmol), 4-(2-(4-dimethylamin-1-yl)ethoxy)benzaldehyde (107 mg, 0.222 mmol), and Ammonium acetate (34.3 mg, 0.444 mmol) were reacted to produce 7.32 mg (7%) of the title compound. (300 MHz, DMSO-$d_6$) 12.55 (s, 1H), 8.08 (d, J=8 Hz, 1H), 7.92 (s, 1H), 7.87 (s, 1H), 7.11 (d, J=8 Hz, 1H), 6.42 (m, 1H), 6.32 (s, 1H), 5.36 (m, 2H), 4.13 (m, 1H), 3.10-2.59 (m, 18H), 2.14 (m, 1H), 1.90 (m, 1H), 1.45 (m, 1H). HPLC: 2.07 min. (G Method)

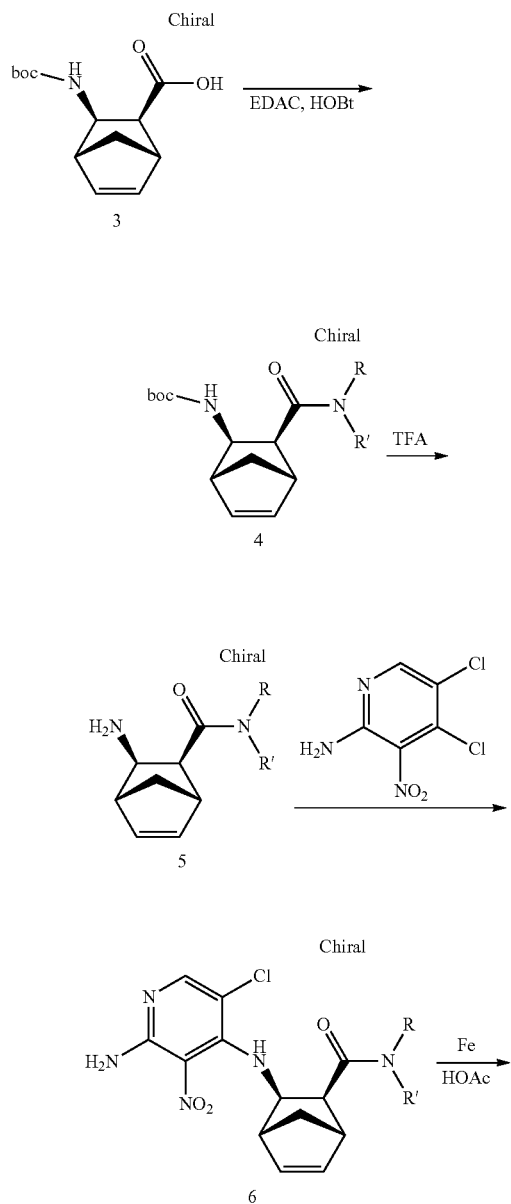

Scheme 2

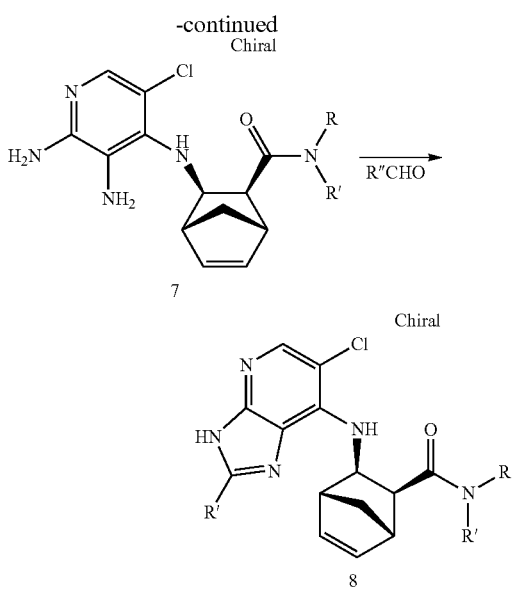

a: R = H; R' = Me
b: R = H; R' = i-Pr
c: R = R' = Me
d: R = H; R' = CH$_2$CH$_2$OH

General Procedure for the Synthesis of 4a,b,c,d:
(1S,2S,3R,4R)-3-tert-Butoxycarbonylamino-bicyclo[2.2.1]hept-5-ene-2-carboxylic acid (Compound 3) (1 eq), the appropriate amine (2 eq), N-(3-dimethylaminopropyl)-N'-ethylcarbodiimide hydrochloride (1.4 eq), 1-hydroxybenzotriazole hydrate (HOBt) (1 eq) and catalytic 4-dimethylaminopyridine were stirred in dichloromethane for 120 h when TLC showed completion of reaction. The reaction mixture was diluted with dichloromethane and washed with water, was dried and concentrated, and purified by column chromatography using silica gel (100-200 mesh).

4a:
Yield: 89%
$^1$H NMR: δ ($^1$H, 400 MHz, CDCl$_3$): 1.4 (9H, s), 1.57 (1H, d, J=8.8 Hz), 2.08 (1H, d, J=9.2 Hz), 2.32 (1H, J=8 Hz), 2.68 (1H, s), 2.77 (3H, d, J=4.8 Hz), 2.95 (1H, s), 3.85 (1H, t, J=8.4 Hz), 5.20 (1H, d, J=8.8 Hz), 5.73 (1H, bs), 6.18 (1H, s).

4b:
Yield: 94%
$^1$H NMR: δ ($^1$H, 400 MHz, CDCl$_3$): 1.0-1.2 (6H, m), 1.39 (9H, s), 1.52-1.60 (3H, m), 2.10 (1H, d, J=9.2 Hz), 2.20 (1H, d, J=7.2 Hz), 2.65 (1H, s), 2.88 (1H, s), 3.8-3.9 (1H, m), 4.0-4.1 (1H, m), 5.31 (1H, d, J=8.8 Hz), 5.38 (1H, bs), 6.15 (2H, d, J=6 Hz).

4c:
Yield: 90%
$^1$H NMR: δ ($^1$H, 400 MHz, CDCl$_3$): 1.41 (9H, s), 1.60 (1H, d, J=13.2 Hz), 2.69 (1H, s), 2.75 (1H, d, J=8.4 Hz), 2.92 (1H, s), 2.95 (3H, s), 2.99 (3H, s), 4.01 (1H, t, J=9.6 Hz), 4.94 (1H, d, J=10.4 Hz), 6.21 (2H, s).

4d:
Yield: 90%
$^1$H NMR: δ ($^1$H, 400 MHz, CDCl$_3$): 1.43 (9H, s), 1.59 (1H, d, J=8.4 Hz), 1.71 (1H, bs), 2.08 (1H, d, J=9.2 Hz), 2.37 (1H, d, J=8 Hz), 2.70 (1H, s), 2.86 (1H, bs), 2.97 (1H, s), 3.3-3.5 (2H, m), 3.69 (1H, bs), 3.89 (1H, t, J=8.4 Hz), 5.16 (1H, d, J=8.8 Hz), 6.20 (2H, bs).

General Procedure for Synthesis of 5a,b,c,d:
Compound 4a-d (1 eq) was dissolved in dichloromethane, cooled to 0° C. and treated with trifluoroacetic acid (20 eq).

The solution was stirred at room temperature for 3 h when TLC confirmed completion of reaction. Trifluoroacetic acid was removed by azeotroping with dichloromethane to afford compounds 5a-d as TFA salts.

5a:
Yield: 95%
$^1$H NMR: δ ($^1$H, 400 MHz, CDCl$_3$): 1.68 (1H, d, J=10 Hz), 2.21 (1H, d, J=10 Hz), 2.50 (1H, d, J=7.2 Hz), 2.79 (3H, d, J=4.0 Hz), 3.05 (2H, d, J=10.8 Hz), 3.48 (1H, bs), 3.81-3.94 (1H, m), 6.2-6.29 (1H, m), 6.31-6.4 (1H, m)

5b:
Yield: 95%

5c:
Yield: 96%
$^1$H NMR: δ ($^1$H, 400 MHz, CDCl$_3$): 1.68 (1H, d, J=9.6 Hz), 2.16 (1H, d, J=10 Hz), 2.85 (1H, d, J=6.8 Hz), 2.96 (1H, s), 2.98 (3H, s), 3.13 (3H, s), 3.46 (1H, bs), 6.2-6.3 (1H, m), 6.35-6.40 (1H, m).

5d:
Yield: quantitative
$^1$H NMR: δ ($^1$H, 400 MHz, CDCl$_3$): 1.69 (1H, d, J=10 Hz), 2.18 (1H, d, J=10.4 Hz), 2.49 (1H, d, J=8.5 Hz), 3.03 (1H, s), 3.07 (1H, s), 3.4-3.49 (1H, m), 3.5-3.6 (1H, m), 3.62-6.7 (1H, m), 4.3-4.47 (2H, m), 6.2-6.28 (1H, m), 6.3-6.42 (1H, m), 6.9-7.04 (1H, m).

General Procedure for Synthesis of 6a,b,c,d:

Compounds 5a-d (1.1 eq), 4,5-dichloro-3-nitropyridin-2-amine (1 eq) and diisopropylethylamine (5.3 eq) were heated in isopropanol at 60° C. for 15 h when an orange precipitate formed. TLC and LCMS indicated completion of reaction. The reaction mixtures were allowed to come to room temperature and the precipitates were filtered, washed well with isopropanol, and dried in vacuo.

6a:
Yield: 84%
$^1$H NMR: δ ($^1$H, 400 MHz, CDCl$_3$): 1.65 (1H, d, J=9.6 Hz), 2.40 (1H, d, J=8 Hz), 2.46 (1H, d, J=9.2 Hz), 2.74 (3H, d, J=4.4 Hz), 2.77 (1H, s), 3.01 (1H, s), 4.10-4.20 (1H, m), 5.68 (1H, bs), 6.1-6.2 (1H, m), 6.22-6.3 (1H, m), 6.37 (2H, bs), 7.81 (1H, s).
LCMS: (254 nm): [M+H]$^+$ 337.90 (96.14%)

6b:
Yield: 85%
$^1$H NMR: δ ($^1$H, 400 MHz, CDCl$_3$): 1.3-1.52 (6H, m), 1.60-1.70 (1H, m), 2.36 (1H, d, J=7.6 Hz), 2.46 (1H, d, J=9.6 Hz), 2.75 (1H, s), 3.01 (1H, s), 3.09-3.2 (1H, m), 3.6-3.8 (1H, m), 3.9-4.1 (1H, m), 4.17 (1H, bs), 5.55 (1H, d, J=6.8 Hz), 6.1-6.19 (1H, m), 6.2-6.28 (1H, m), 6.46 (1H, bs), 7.80 (1H, s), 8.33 (1H, bs), 11.25 (1H, bs)
LCMS: (254 nm): [M+H]$^+$ 366.10 (98.74%)

6c:
Yield: 75%
$^1$H NMR: δ ($^1$H, 400 MHz, CDCl$_3$): 1.64 (1H, d, J=9.2 Hz), 2.24 (1H, d, J=9.6 Hz), 2.84 (1H, d, J=5.2 Hz), 2.86 (1H, s), 2.93 (3H, s), 2.97 (3H, s), 3.01 (2H, s), 3.06-3.2 (1H, m), 4.28 (1H, bs), 6.2-6.23 (1H, m), 6.25-6.3 (1H, m), 6.37 (2H, m), 7.84 (1H, s).
LCMS: (254 nm): [M+H]$^+$ 351.90 (99.02%)

6d:
Yield: 85%
LCMS: (254 nm): [M+H]$^+$ 367.00 (100%)

General Procedure for Synthesis of 7a,b,c,d:

Compounds 6a-d (1 eq) were taken up into tetrahydrofuran (16 eq) and acetic acid (16 eq) and treated with powdered iron (7 eq). The mixtures were stirred at room temperature for 3-4 hours when TLC confirmed completion of reaction. The reaction mixtures were filtered through a bed of Celite, the bed being washed well with ethyl acetate. The filtrates were treated with satd. sodium bicarbonate solution to adjust the pH to neutral. The ethyl acetate layer was separated, washed well with water, dried, and concentrated to afford the products as reddish brown solids.

7a:
Yield: 82%
$^1$H NMR: δ ($^1$H, 400 MHz, CDCl$_3$): 1.66 (1H, d, J=7.6 Hz), 2.42 (1H, d, J=8.8 Hz), 2.58 (1H, d, J=4.4 Hz), 2.65 (1H, bs), 2.83 (3H, d, J=4.4 Hz), 2.95 (1H, bs), 3.7-3.9 (2H, m), 4.0-4.20 (2H, m), 4.56 (1H, d, J=11.2 Hz), 5.68 (1H, bs), 6.0-6.13 (1H, m), 6.16-6.2 (1H, m), 7.59 (1H, s).
LCMS: (254 nm): [M+H]$^+$ 308.05 (96.57%)

7b:
Yield: 75%
$^1$H NMR: δ ($^1$H, 400 MHz, CDCl$_3$): 1.11 (3H, d, J=6.4 Hz), 1.17 (3H, d, J=6.8 Hz), 1.63 (1H, d, J=8.8 Hz), 2.35 (1H, d, J=8 Hz), 2.41 (1H, d, J=9.2 Hz), 2.63 (1H, s), 2.92 (1H, s), 3.77 (1H, t, J=9.6 Hz), 4.0-4.2 (2H, m), 4.59 (1H, d, J=11.2 Hz), 5.52 (1H, d, J=7.6 Hz), 6.0-6.12 (1H, m), 6.15-6.20 (1H, m), 7.58 (1H, s).
LCMS: (254 nm): [M+H]$^+$ 336.00 (98.9%)

7c:
Yield: 50%
$^1$H NMR: δ ($^1$H, 400 MHz, CDCl$_3$): 1.65 (1H, d, J=8.8 Hz), 2.45 (1H, d, J=9.2 Hz), 2.60 (1H, s), 2.85 (1H, d, J=8.4 Hz), 2.95 (3H, s), 3.04 (3H, s), 3.21 (1H, bs), 3.98 (1H, t, J=8.8 Hz), 4.11 (2H, bs), 4.39 (1H, d, J=11.6 Hz), 6.1-6.18 (1H, m), 6.2-6.3 (1H, m), 7.61 (1H, s).
LCMS: (254 nm): [M+H]$^+$ 322.05 (98.41%)

7d:
Yield: 85%
$^1$H NMR: δ ($^1$H, 400 MHz, DMSO-d$_6$): 1.39 (1H, J=8.4 Hz), 2.32 (1H, s), 2.37 (1H, d, J=8.8 Hz), 2.66-2.82 (2H, m), 3.0-3.25 (3H, m), 3.30-3.40 (2H, m), 3.6-3.75 (1H, m), 4.18 (1H, s), 4.24 (1H, d, J=11.6 Hz), 4.6-4.7 (1H, m), 5.43 (2H, s), 6.0-6.1 (1H, m), 6.12-6.25 (1H, m), 7.30 (1H, s), 8.08 (1H, t, J=5.6 Hz).
LCMS: (254 nm): [M+H]$^+$ 337.00 (96.6%)

General Procedure for the Syntheses of Compounds CLXXVIII-CXCVII:

To a solution of compound 7a-d (1 eq) and the appropriate aldehyde (1.1 eq) in ethanol was added ammonium acetate (1.2 eq) and the reaction mixture was heated at 70° C. for 15-24 h. The reaction mixture was concentrated and the residue taken up into water and extracted with ethyl acetate. The combined organic extracts were washed with saturated sodium bicarbonate solution, were dried and were concentrated. The solid obtained was triturated with diethyl ether to obtain pure products in 25-55% yields. Some derivatives were purified by Prep HPLC.

Compound CLXXVIII

(1S,2S,3R,4R)-3-(6-chloro-2-(4-morpholinophenyl)-3H-imidazo[4,5-b]pyridin-7-ylamino)-N-methylbicyclo[2.2.1]hept-5-ene-2-carboxamide (Compound CLXXVIII)

Yield: 40%

NMR: δ ($^1$H, 400 MHz, DMSO-d$_6$): 1.38 (1H, d, 8.4 Hz), 2.27 (1H, d, J=8.8 Hz), 2.50-2.54 (1H, m), 2.59-2.65 (3H, m), 2.78 (1H, s), 2.85 (1H, s), 3.15-3.25 (4H, m), 3.60-3.80 (4H, m), 5.21 (1H, t, J=8 Hz), 6.34-6.39 (2H, m), 6.90 (1H, d, J=9.2 Hz), 7.08 (2H, d, J=8.8 Hz), 7.89-8.0 (2H, m), 8.22 (1H, d, J=4.4 Hz), 13.02 (1H, b s). LCMS (254 nm): [M+H]$^+$ 479.05 (98.66%).

HPLC: 98.35% (220 nm).

(1S,2S,3R,4R)-3-(6-chloro-2-(1-methyl-1H-pyrazol-4-yl)-3H-imidazo[4,5-b]pyridin-7-ylamino)-N-methylbicyclo[2.2.1]hept-5-ene-2-carboxamide (Compound CLXXX)

Yield: 23%

NMR: δ ($^1$H, 400 MHz, CDCl$_3$): 1.74 (1H, d, 8.4 Hz), 2.38 (1H, d, J=9.2 Hz), 2.80 (2H, d, J=7.2 Hz), 2.91 (1H, s), 3.00-3.20 (3H, m), 3.31-3.29 (6H, m), 3.80-4.00 (4H, m), 5.20-5.30 (1H, m), 5.50-5.60 (1H, m), 6.34 (2H, s), 6.72 (1H, S), 7.03 (2H, d, J=8.8 Hz), 7.96 (2H, d, J=8.8 Hz), 8.02 (1H, s).

LCMS (254 nm): [M+H]$^+$ 509.05 (96.27%).
HPLC: 95.61% (220 nm).

Compound CLXXIX

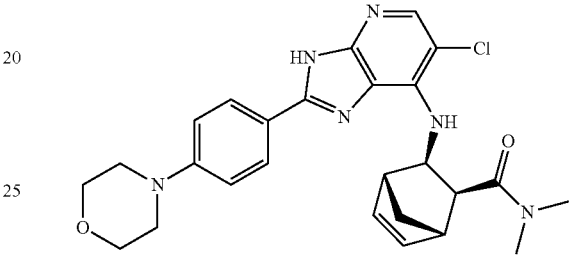

(1S,2S,3R,4R)-3-(6-chloro-2-(4-(4-methylpiperazin-1-yl)phenyl)-3H-imidazo[4,5-b]pyridin-7-ylamino)-N-methylbicyclo[2.2.1]hept-5-ene-2-carboxamide (Compound CLXXIX)

Yield: 35%

NMR: δ ($^1$H, 400 MHz, CDCl$_3$): 0.49 (3H, d, J=6.8 Hz), 0.86 (3H, d, J=6.8 Hz) 1.72 (1H, d, J=9.2 Hz), 2.39 (1H, d, J=8.8 Hz), 2.71 (1H, d, J=7.6 Hz), 2.91 (1H, s), 3.13 (1H, s), 3.25-3.40 (4H, m), 3.80-4.00 (5H, m), 5.20 (1H, t, J=8.4 Hz), 5.64 (1H, d, J=8.8 Hz), 6.25 (1H, d, J=8.0 Hz), 6.34 (1H, s), 7.06 (2H, d, J=8.8 Hz), 8.00 (2H, d, J=8.0 Hz), 13.9 (1H, bs).

LCMS (254 nm): [M+H]$^+$ 507.10 (98.075%).
HPLC: 97.7% (254 nm).

Compound CLXXXI

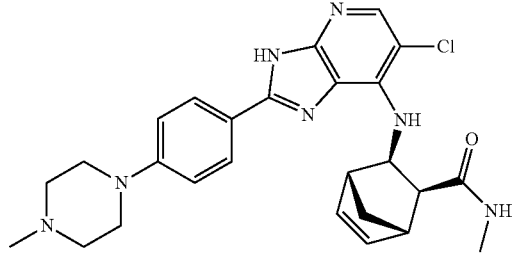

(1S,2S,3R,4R)-3-(6-chloro-2-(2-methoxy-4-morpholinophenyl)-3H-imidazo[4,5-b]pyridin-7-ylamino)-N-methylbicyclo[2.2.1]hept-5-ene-2-carboxamide (Compound CLXXXI)

Yield: 33%

NMR: δ ($^1$H, 400 MHz, CDCl$_3$): 1.16 (1H, d, J=9.2 Hz), 2.31 (1H, d, J=9.2 Hz), 2.94 (3H, s), 2.96 (3H, s), 3.01-3.15 (3H, m), 3.28-3.33 (4H, m), 3.92 (4H, t, J=4 Hz), 5.67 (1H, t, J=8.8 Hz), 6.07 (1H, d, J=9.6 Hz), 6.32-6.36 (1H, m), 6.46-6.48 (1H, m), 7.06 (2H, d, J=8.8 Hz), 8.04 (2H, d, J=8.4 Hz), 8.04 (1H, s).

LCMS (254 nm): [M+H]$^+$ 493.10 (98.75%).
HPLC: 99.81% (220 nm).

Compound CLXXX

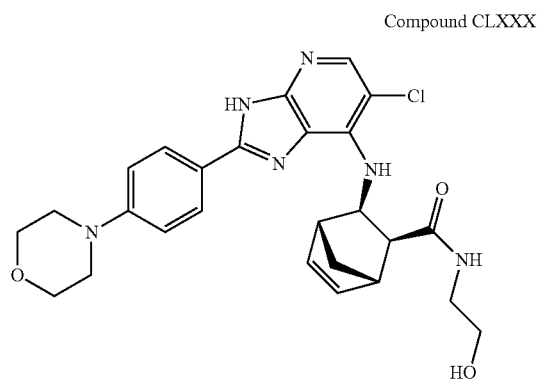 [SMILES: O=C(NCCO)[C@@H]1[C@H](Nc2c(Cl)cnc3[nH]c(-c4ccc(N5CCOCC5)cc4)nc23)[C@H]2C=C[C@@H]1C2]

Compound CLXXXII

(1S,2S,3R,4R)-3-(6-chloro-2-(2-methoxy-4-(4-methylpiperazin-1-yl)phenyl)-3H-imidazo[4,5-b]pyridin-7-ylamino)-N-methylbicyclo[2.2.1]hept-5-ene-2-carboxamide (Compound CLXXXII)

Yield: 55%

NMR: δ ($^1$H, 400 MHz, DMSO-d$_6$): 1.39 (1H, d, J=8.4 Hz), 2.26 (1H, d, J=8.8 Hz), 2.59 (1H, bs), 2.62 (3H, d, J=4.4

Hz), 2.80 (1H, s), 2.87 (3H, s), 3.02-3.16 (3H, m), 3.54 (2H, d, J=11.2 Hz), 4.0-4.35 (4H, m), 5.16 (1H, t, J=16.4 Hz), 6.35-6.39 (1H, m), 7.17 (2H, d, J=9.2 Hz), 7.96 (1H, s), 8.03 (2H, d, J=8.8 Hz), 8.26 (1H, d, J=4.4 Hz), 9.76 (1H, bs,), 13.23 (1H, bs).

LCMS (254 nm): [M+H]+ 492.10 (94.28%).

HPLC: 96.07% (220 nm).

7.17 (2H, d, J=9.2 Hz), 7.94 (1H, s), 8.03 (2H, d, J=8.8 Hz), 8.33 (1H, bs), 9.65 (1H, bs), 13.2 (1H, bs).

LCMS (254 nm): [M+H]+ 522.20 (100.0%).

HPLC: 99.56% (220 nm).

Compound CLXXXIII

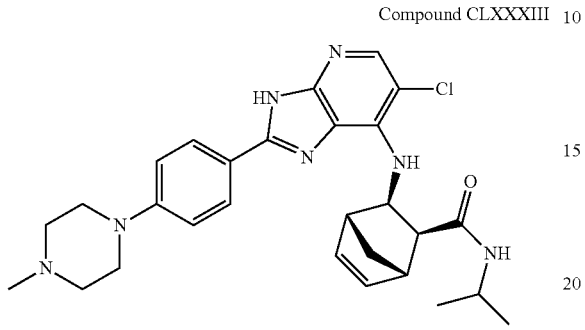

(1S,2S,3R,4R)-3-(6-chloro-2-(4-morpholinophenyl)-3H-imidazo[4,5-b]pyridin-7-ylamino)-N-isopropyl-bicyclo[2.2.1]hept-5-ene-2-carboxamide (Compound CLXXXIII)

Yield: 29%

NMR: δ (1H, 400 MHz, CDCl3): 1.04 (3H, d, J=6.4 Hz), 1.15 (3H, d, J=6.4 Hz), 1.63 (1H, d, J=9.2 Hz), 2.36 (1H, d, J=9.2 Hz), 2.47 (1H, d, J=8 Hz), 2.88 (3H, s), 2.90-3.20 (4H, m), 3.40-4.00 (6H, m), 4.06-4.08 (1H, m), 5.32 (1H, t, J=8 Hz), 5.68 (1H, d, J=8 Hz), 6.36-6.46 (2H, m), 7.02 (2H, d, J=8.8 Hz), 7.75 (1H, s), 8.02 (2H, d, J=8.8 Hz), 8.42 (1H, d, J=8.4 Hz).

LCMS (254 nm): [M+H]+ −520.10 (98.06%).

HPLC: 97.57% (254 nm).

Compound CLXXXIV

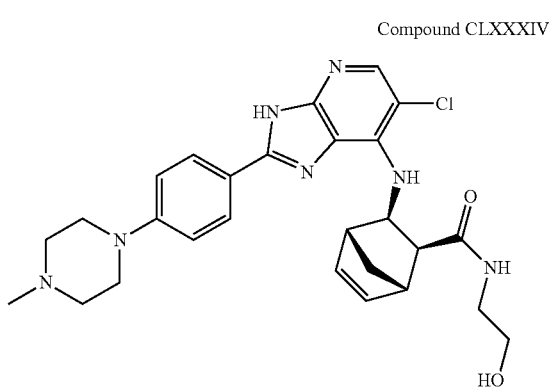 [SMILES: CN1CCN(c2ccc(-c3nc4c(N[C@H]5[C@@H](C(=O)NCCO)[C@@H]6C=C[C@H]5C6)c(Cl)cnc4[nH]3)cc2)CC1]

(1S,2S,3R,4R)-3-(6-chloro-2-(4-(4-methylpiperazin-1-yl)phenyl)-3H-imidazo[4,5-b]pyridin-7-ylamino)-N-isopropyl-bicyclo[2.2.1]hept-5-ene-2-carboxamide (Compound CLXXXIV)

Yield: 32%

NMR: δ (1H, 400 MHz, DMSO-d6): 1.39 (1H, d, 8.4 Hz), 2.27 (1H, d, J=8 Hz), 2.66 (1H, d, J=8 Hz), 2.80 (1H, s), 2.87 (3H, s), 3.02-3.17 (4H, m), 3.34-3.60 (4H, m), 3.60-4.20 (5H, m), 5.16 (1H, t, J=8.4 Hz), 6.35-6.40 (2H, m), 7.10 (1H, bs),

Compound CLXXXV

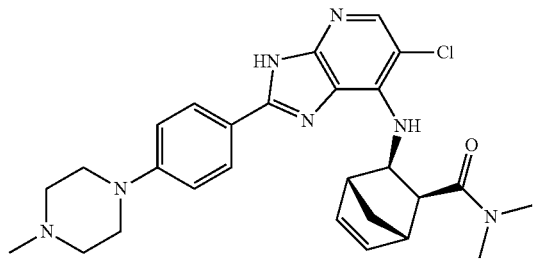

(1S,2S,3R,4R)-3-(6-chloro-2-(1-methyl-1H-pyrazol-4-yl)-3H-imidazo[4,5-b]pyridin-7-ylamino)-N-isopropylbicyclo[2.2.1]hept-5-ene-2-carboxamide (Compound CLXXXV)

Yield: 26%

NMR: δ (1H, 400M Hz, DMSO-d6): 1.44-1.63 (1H, m), 2.30 (1H, d, J=9.2 Hz), 2.39 (3H, s), 2.61-2.64 (4H, m), 2.92 (3H, s), 2.95 (3H, s), 2.98-3.08 (3H, m), 3.73 (4H, t, J=4.4 Hz), 5.67 (1H, t, J=9.2 Hz), 5.97 (1H, d, J=10 Hz), 6.31-6.41 (1H, m), 6.48-6.49 (1H, m), 7.05 (2H, d, J=9.2 Hz), 7.99 (2H, d, J=8.8 Hz), 8.02 (1H, s).

LCMS (254 nm): [M+H]+ 506.15 (99.35%).

HPLC: 97.5% (254 nm).

Compound CLXXXVI

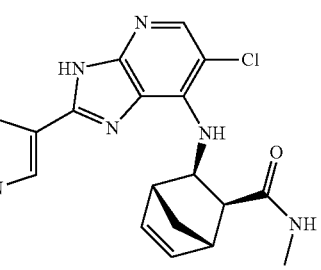

(1S,2S,3R,4R)-3-(6-chloro-2-(2-methoxy-4-morpholinophenyl)-3H-imidazo[4,5-b]pyridin-7-ylamino)-N-isopropylbicyclo[2.2.1]hept-5-ene-2-carboxamide (Compound CLXXXVI)

Yield: 55%

NMR: δ (1H, 400 MHz, DMSO-d6): 1.37 (1H, d, J=8.4 Hz), 2.25 (1H, d, J=8.8 Hz), 2.57 (1H, d, J=8.4 Hz), 2.61 (3H, d, J=4.0 Hz), 2.75 (1H, s) 2.84 (1H, s), 3.33-3.47 (1H, m), 3.93-3.97 (3H, m), 5.10 (1H, t, J=8.4 Hz), 6.30-6.32 (1H, m), 6.43-6.46 (1H, m), 6.88 (1H, d, J=9.2 Hz), 7.88 (1H, s), 7.99 (1H, s), 8.15-8.30 (1H, m).

LCMS (254 nm): [M+H]+ 398.00 (99.39%).

HPLC: 98.38% (220 nm).

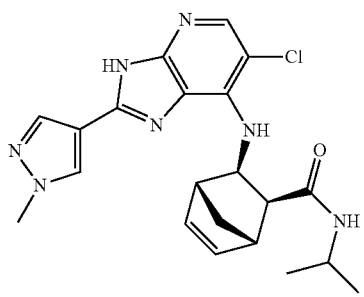

Compound CLXXXVII (1S,2S,3R,4R)-3-(6-chloro-2-(4-(4-methylpiperazin-1-yl)phenyl)-3H-imidazo[4,5-b]pyridin-7-ylamino)-N-isopropyl bicyclo[2.2.1]hept-5-ene-2-carboxamide (Compound CLXXXVII)

Yield: 44%

NMR: δ ($^1$H, 400 MHz, CDCl$_3$-D$_2$O exchange): 1.04 (3H, d, J=6.4 Hz), 1.15 (3H, d, J=6.4 Hz), 1.63 (1H, d, J=9.2 Hz), 2.36 (1H, d, J=9.2 Hz), 2.67 (1H, m), 2.88 (1H, s), 3.15 (1H, s), 3.75-3.9 (1H, m), 4.06 (3H, s), 5.32 (1H, t, J=8 Hz), 6.25 (2H, bs), 7.9-8.1 (3H, m).

LCMS: (254 nm): [M+H]$^+$ 426.0 (96.64%).

HPLC: 96.39% (254 nm).

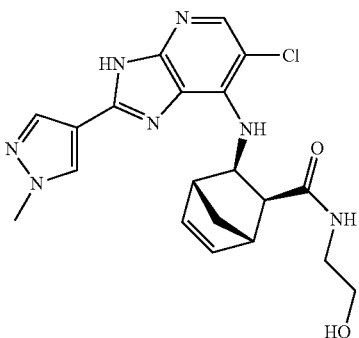

Compound CLXXXVIII (1S,2S,3R,4R)-3-(6-chloro-2-(4-morpholinophenyl)-3H-imidazo[4,5-b]pyridin-7-ylamino)-N-(2-hydroxyethyl)bicyclo[2.2.1]hept-5-ene-2-carboxamide (Compound CLXXXVIII)

Yield: 39%

NMR: δ ($^1$H, 400 MHz, DMSO-d$_6$): 1.37 (1H, d, J=8 Hz), 2.25 (1H, d, J=8 Hz), 2.62 (1H, d, J=8.4 Hz), 2.75 (1H, bs), 2.84 (1H, bs), 3.11-3.17 (3H, m), 3.25-3.50 (2H, m), 3.93 (3H, s), 4.66-4.68 (1H, m), 5.09 (1H, t, J=8.4 Hz), 6.28-6.32 (1H, m), 6.43-6.46 (1H, m), 6.86 (1H, d, J=8.8 Hz), 7.87 (1H, s), 7.99 (1H, s), 8.24 (1H, s), 8.30-8.32 (1H, m, J=5.2 Hz).

LCMS (254 nm): [M+H]$^+$ 428.00 (98.66%).

HPLC: 98.16% (254 nm).

F.

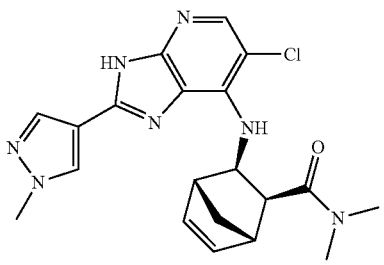

Compound CLXXXIX (1S,2S,3R,4R)-3-(6-chloro-2-(4-(4-methylpiperazin-1-yl)phenyl)-3H-imidazo[4,5-b]pyridin-7-ylamino)-N-(2-hydroxyethyl)bicyclo[2.2.1]hept-5-ene-2-carboxamide (Compound CLXXXIX)

Yield: 40%

NMR: δ ($^1$H, 400M Hz, CDCl$_3$): 1.65 (3H, d, J=9.2 Hz), 2.30 (1H, d, J=8.8 Hz), 2.92 (3H, s), 2.95 (3H, s), 2.98-3.09 (3H, m), 5.55 (1H, t, J=1.2 Hz), 6.08 (1H, d, J=10.0 Hz), 6.32-6.34 (2H, m), 6.42-6.42 (2H, m), 7.9 (1H, s), 8.02 (1H, d, J=7.6 Hz).

LCMS (254 nm): [M+H]$^+$ 412.10 (98.48%).

HPLC: 96.95% (254 nm).

Compound CXC (1S,2S,3R,4R)-3-(6-chloro-2-(1-methyl-1H-pyrazol-4-yl)-3H-imidazo[4,5-b]pyridin-7-ylamino)-N-(2-hydroxyethyl)bicyclo[2.2.1]hept-5-ene-2-carboxamide (Compound CXC)

Yield: 30%

NMR: δ ($^1$H, 400 MHz, CDCl$_3$): 1.41 (1H, d, J=8 Hz), 2.23 (1H, d, J=8.8 Hz), 2.60-2.62 (4H, m), 2.83 (1H, bs), 2.88 (1H, bs), 3.25-3.33 (4H, m), 3.76-3.92 (4H, m), 3.98 (3H, s), 5.0-5.2 (1H, m), 6.37 (2H, bs), 6.65 (1H, s), 6.75 (2H, d, J=9.2 Hz), 7.53 (1H, bs), 8.01 (2H, d, J=8.8 Hz), 8.30 (1H, bs), 12.30 (1H, bs).

LCMS (254 nm): [M+H]$^+$ 509.10 (96.12%).

HPLC: 99.42% (254 nm).

Compound CXCI

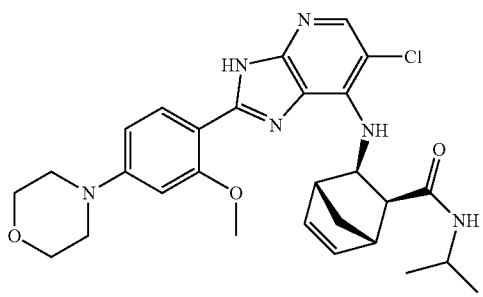

(1S,2S,3R,4R)-3-(6-chloro-2-(2-methoxy-4-mor-
pholinophenyl)-3H-imidazo[4,5-b]pyridin-7-
ylamino)-N-(2-hydroxyethyl)bicyclo[2.2.1]hept-5-
ene-2-carboxamide (Compound CXCI)

Yield: 30%

NMR: δ ($^1$H, 400 MHz, CDCl$_3$): 0.38 (3H, d, J=6.4 Hz), 0.79 (3H, d, J=6.4 Hz), 1.72 (1H, d, J=8.8 Hz), 2.36 (1H, d, J=8.8 Hz), 2.71 (1H, d, J=8 Hz), 2.86 (1H, bs), 3.13 (1H, bs), 3.38-3.42 (4H, m), 3.75-3.92 (5H, m), 4.04 (3H, s), 5.14 (1H, s), 5.32 (1H, s), 6.50 (1H, s), 6.65-6.70 (1H, m), 7.97 (1H, s), 8.26 (1H, s), 10.55 (1H, s).

LCMS (254 nm): [M+H]$^+$ 537.15 (96.12%).

HPLC: 98.01% (254 nm).

Compound CXCIII

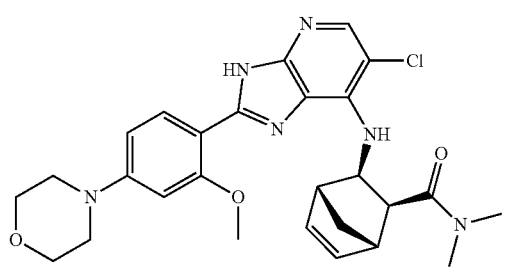

(1S,2S,3R,4R)-3-(6-chloro-2-(4-morpholinophenyl)-
3H-imidazo[4,5-b]pyridin-7-ylamino)-N,N-dimeth-
ylbicyclo[2.2.1]hept-5-ene-2-carboxamide (Com-
pound CXCIII)

Yield: 26%

NMR: δ ($^1$H, 400 MHz, CDCl$_3$): 1.65 (1H, d, J=9.6 Hz), 2.29 (d, 1H, J=9.6 Hz), 2.89 (3H, s), 2.93 (3H, s), 2.95-3.10 (3H, m), 3.25-3.35 (4H, m), 3.83-3.90 (4H, m), 4.03 (3H, s), 5.64 (1H, t, J=9.6 Hz), 5.82 (1H, bs), 6.31-6.33 (1H, m), 6.44-6.50 (2H, m), 6.67 (1H, d, J=10.8 Hz), 7.95 (1H, s), 8.30 (1H, d, J=8 Hz), 10.53 (1H, s).

LCMS (254 nm): [M+H]$^+$-%)-523.15 (99.08%).

HPLC: 97.15% (254 nm).

Compound CXCII

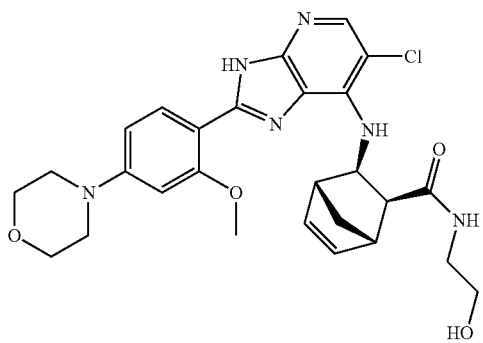

(1S,2S,3R,4R)-3-(6-chloro-2-(2-methoxy-4-(4-meth-
ylpiperazin-1-yl)phenyl)-3H-imidazo[4,5-b]pyridin-
7-ylamino)-N-(2-hydroxyethyl)bicyclo[2.2.1]hept-5-
ene-2-carboxamide (Compound CXCII)

Yield: 30%

NMR: δ ($^1$H, 400 MHz, CDCl$_3$): 1.74 (1H, d, J=9.2 Hz), 2.35 (1H, d, J=9.2 Hz), 2.79-2.81 (1H, m), 2.88 (1H, s), 2.99-3.04 (2H, m), 3.10-3.19 (1H, m), 3.19-3.35 (6H, m), 3.80-3.95 (5H, m), 4.06 (3H, s), 5.18-5.37 (2H, m), 6.30-6.40 (2H, m), 6.49-6.57 (1H, m), 6.60-6.70 (1H, m), 6.75-6.85 (1H, m), 7.95 (1H, s), 8.24 (1H, d, J=8.8 Hz), 11.0 (1H, bs).

LCMS (254 nm): [M+H]$^+$ 539.05 (97.73%).

HPLC: 93.43% (220 nm).

Compound CXCIV

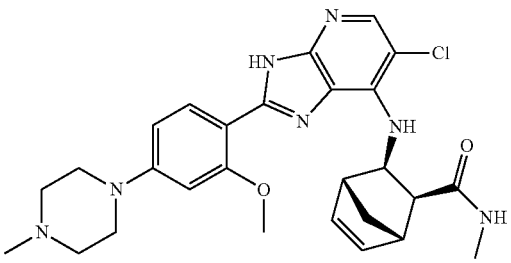

(1S,2S,3R,4R)-3-(6-chloro-2-(4-(4-methylpiperazin-
1-yl)phenyl)-3H-imidazo[4,5-b]pyridin-7-ylamino)-
N,N-dimethylbicyclo[2.2.1]hept-5-ene-2-carboxam-
ide (Compound CXCIV)

Yield: 39%

NMR: δ ($^1$H, 400M Hz, DMSO-d$_6$): 1.40 (1H, d, J=8.8 Hz), 2.25 (1H, d, J=8.4 Hz), 2.51-2.70 (4H, m), 2.82 (1H, s), 2.88 (4H, s), 3.00-3.30 (4H, m), 3.50-4.50 (7H, m), 5.10-5.20 (1H, m), 6.36 (2H, s), 6.50-6.90 (2H, m), 7.40 (1H, bs), 8.04 (1H, d, J=8.8 Hz), 8.24 (1H, s), 9.7 (1H, bs), 12.37 (1H, bs).

LCMS (254 nm): [M+H]$^+$ 521.95 (97.35%).

HPLC: 99.88% (220 nm).

Compound CXCV

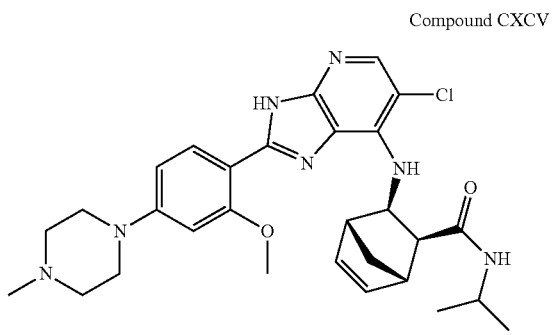 [SMILES: COc1cc(N2CCN(C)CC2)ccc1-c1nc2c(N[C@H]3[C@@H](C(=O)NC(C)C)[C@@H]4C=C[C@H]3C4)c(Cl)cnc2[nH]1]

(1S,2S,3R,4R)-3-(6-chloro-2-(2-methoxy-4-morpholinophenyl)-3H-imidazo[4,5-b]pyridin-7-ylamino)-N,N-dimethylbicyclo[2.2.1]hept-5-ene-2-carboxamide (Compound CXCV)

Yield: 70%

NMR: δ ($^1$H, 400M Hz, CDCl$_3$): 0.38 (3H, d, J=6.0 Hz), 0.80 (3H, d, J=6.4 Hz), 1.72 (1H, d, J=8.4 Hz), 2.0-2.8 (10H, m), 2.87 (1H, s), 3.14 (1H, s), 3.35-3.42 (4H, m), 3.75-3.84 (1H, m), 4.08 (3H, s), 5.16 (1H, t, J=8.0 Hz), 5.40 (1H, d, J=8.0 Hz), 6.19-6.28 (3H, m), 6.51 (1H, s), 6.67 (1H, d, J=8.8 Hz), 7.9 (1H, s), 8.24 (1H, d, J=8.4 Hz), 11.3 (1H, bs).

LCMS (254 nm): [M+H]$^+$ 550.15 (96.19%).

HPLC: 95.24% (254 nm).

Compound CXCVII

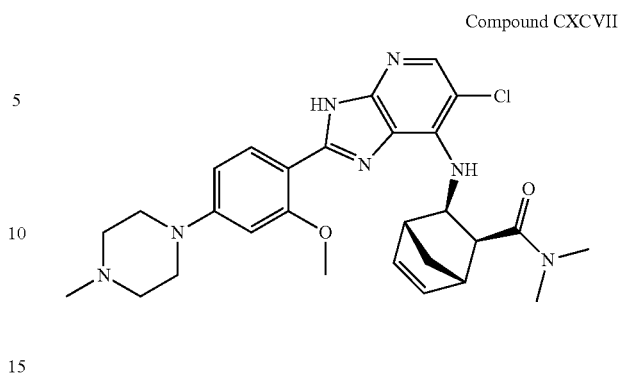

(1S,2S,3R,4R)-3-(6-chloro-2-(2-methoxy-4-(4-methylpiperazin-1-yl)phenyl)-3H-imidazo[4,5-b]pyridin-7-ylamino)-N,N-dimethylbicyclo[2.2.1]hept-5-ene-2-carboxamide (Compound CXCVII)

Yield: 75%

NMR: δ ($^1$H, 400M Hz, CDCl$_3$): 1.65 (1H, d, J=9.2 Hz), 2.0-2.10 (1H, m), 2.10 (3H, s), 2.28 (1H, d, J=9.2 Hz), 2.39 (3H, s), 2.50-2.68 (4H, m), 2.89 (3H, s), 2.93 (3H, s), 2.99-3.10 (3H, m), 3.30-3.40 (4H, m), 4.06 (3H, s), 5.67 (1H, t, J=8.8 Hz), 5.80-5.90 (1H, d, J=10 Hz), 6.33 (1H, bs), 6.45 (1H, bs), 6.51 (1H, s), 6.66 (1H, d, J=8.4 Hz), 7.89 (1H, s), 8.28 (1H, d, J=8.8 Hz), 11.23 (1H, s).

LCMS (254 nm): [M+H]$^+$ 536.20 (99.05%).

HPLC: 96.06% (254 nm).

Compound CXCVI

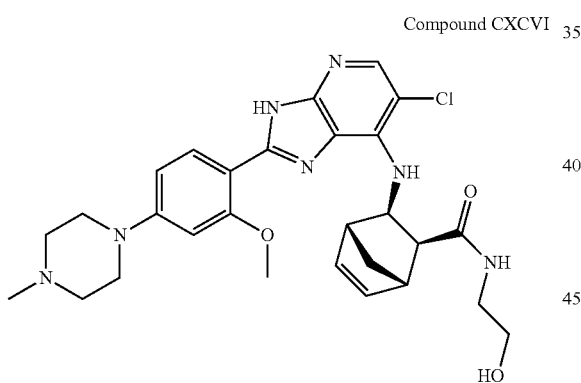

(1S,2S,3R,4R)-3-(6-chloro-2-(2-methoxy-4-morpholinophenyl)-3H-imidazo[4,5-b]pyridin-7-ylamino)-N,N-dimethylbicyclo[2.2.1]hept-5-ene-2-carboxamide (Compound CXCVI)

Yield: 36%

NMR: δ ($^1$H, 400 MHz, CDCl$_3$): 1.7-1.8 (1H, m), 2.0-2.50 (4H, m), 2.55-2.70 (4H, m), 2.81 (1H, s), 2.83 (1H, s), 2.89 (1H, s), 3.0-3.10 (2H, m), 3.15 (1H, s), 3.20-3.30 (2H, m), 3.30-3.40 (4H, m), 4.07 (3H, s), 5.10-5.25 (1H, m), 5.30-5.40 (1H, m), 6.30-6.40 (2H, m), 6.51 (1H, s), 6.67 (1H, d, J=8.4 Hz), 6.80-6.90 (1H, m), 7.94 (1H, s), 8.23 (1H, d, J=8.8 Hz), 11.3 (1H, bs).

LCMS (254 nm): [M+H]$^+$ 552.30 (96.09%).

HPLC: 95.16% (254 nm).

Scheme 3

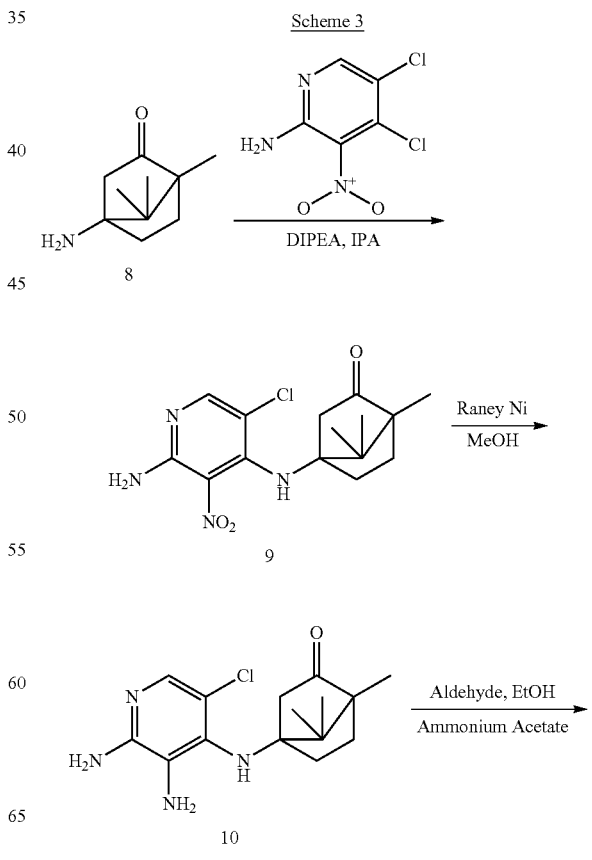

-continued

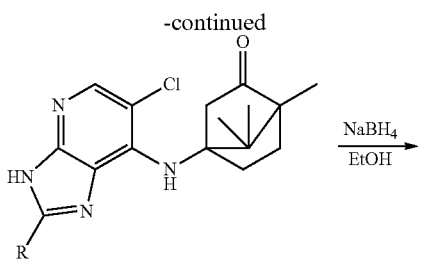

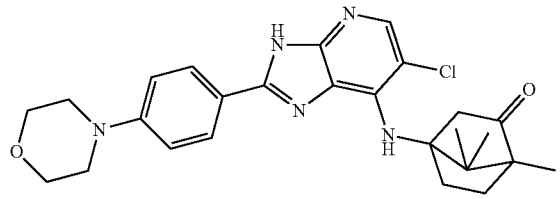

Synthesis of 4-(6-chloro-2-(4-morpholinophenyl)-3H-imidazo[4,5-b]pyridin-7-ylamino)-1,7,7-trimethylbicyclo[2.2.1]heptan-2-one (26b) (Compound CXCVIII)

4-(2,3-diamino-5-chloropyridin-4-ylamino)-1,7,7-trimethylbicyclo[2.2.1]heptan-2-one (10) (300 mg, 0.971 mmol), 4-morpholinobenzaldehyde (167 mg, 0.873 mmol) were taken in EtOH (15 ml) to which ammonium acetate (112 mg) was added and the reaction mixture was heated at 70° C. for 48 h. Crude LCMS showed the desired product along with trace of starting material. The reaction mixture was allowed to come to rt and the precipitated was filtered and washed well with ethanol to afford the desired product (466 mg, 23%) as a yellow solid. NMR: δ ($^1$H, 400M Hz, DMSO-$d_6$): 0.91 (3H, s), 0.92 (3H, s), 1.09 (3H, s), 1.40-1.50 (1H, m), 1.70-1.80 (2H, m), 2.40-2.60 (1H, m), 3.00-3.10 (1H, m), 3.20-3.30 (4H, m), 3.72-3.80 (5H, m), 5.37 (1H, s), 7.09 (2H, d, J=8.8 Hz), 7.99 (2H, d, J=8.8 Hz), 8.02 (1H, s), 13.15 (1H, s). LCMS (254 nm): [M+H]$^+$ 480.20 (95.88%) HPLC: 95.55% (220 nm)

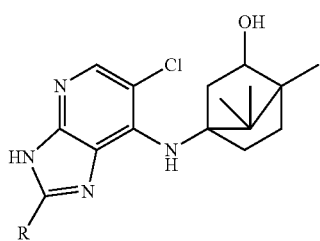

Synthesis of 4-(2-amino-5-chloro-3-nitropyridin-4-ylamino)-1,7,7-trimethylbicyclo[2.2.1]heptan-2-one (9)

4-amino-1,7,7-trimethylbicyclo[2.2.1]heptan-2-one (8) (1.1 g, 5.29 mmol)) and 4,5-dichloro-3-nitropyridin-2-amine (1 g, 4.81 mmol) were taken in IPA (30 ml) and DIPEA (4.6 ml, 26.44 mmol)) was added to the reaction mixture which was then heated at 60° C. for 24 h when TLC confirmed completion of reaction. The reaction mixture was cooled to rt and concentrated in vacuuo. Pure product (9) (1.63 g, 92%) was obtained as a yellow solid after purification by column chromatography using silica gel (100-200 mesh). NMR: δ ($^1$H, 400 MHz, CDCl$_3$): 0.87 (3H, s), 0.97 (3H, s), 1.05 (3H, s), 1.44-1.54 (1H, m), 1.70-1.80 (1H, m), 1.90-2.20 (1H, m), 2.30-2.40 (1H, m), 2.47 (1H, dd, J=3.2, 18.0 Hz), 2.88 (1H, d, J=18.4 Hz), 6.55 (2H, s), 7.85 (1H, s), 7.96 (1H, s) LCMS: (254 nm): [M+H]$^+$ 339.10 (86.27%)

Synthesis of 4-(2,3-diamino-5-chloropyridin-4-ylamino)-1,7,7-trimethylbicyclo[2.2.1]heptan-2-one (10)

4-(2-amino-5-chloro-3-nitropyridin-4-ylamino)-1,7,7-trimethylbicyclo[2.2.1]heptan-2-one (9) (1.5 g, 4.43 mmol) was added to a suspension of Raney Nickel (1 g) taken in MeOH (50 ml) and hydrogenated for 2 h when TLC confirmed completion of reaction. The reaction mixture was filtered through a bed of celite and the bed was washed well with MeOH. The filtrate was concentrated to afford the product (1.37 g, 77%) as a light grey solid. NMR: δ ($^1$H, 400 MHz, CD$_3$OD): 0.91 (3H, s), 0.96 (3H, s), 1.13 (3H, s), 1.20-1.35 (1H, m), 1.64-1.80 (2H, m), 2.06-2.18 (1H, m), 2.23 (1H, d, J=18 Hz), 2.61 (1H, dd, J=3.6, 18.0 Hz), 7.20 (1H, s) LCMS: (254 nm): [M+H]$^+$ 309.10 (89.4%)

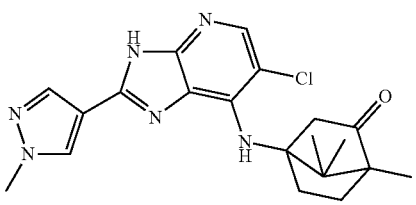

Synthesis of 4-(6-chloro-2-(1-methyl-1H-pyrazol-4-yl)-3H-imidazo[4,5-b]pyridin-7-ylamino)-1,7,7-trimethylbicyclo[2.2.1]heptan-2-one (Compound CXCIX)

4-(2,3-diamino-5-chloropyridin-4-ylamino)-1,7,7-trimethylbicyclo[2.2.1]heptan-2-one (10) (380 mg, 1.23 mmol), 1-methyl-1H-pyrazole-4-carbaldehyde (135 mg, 1.23 mmol) were taken in EtOH (15 ml) to which ammonium acetate (112 mg) was added and the reaction mixture was heated at 70° C. for 48 h. Crude LCMS showed the desired product along with trace of starting material. The reaction mixture was allowed to come to rt and the precipitated was filtered and washed well with ethanol to afford the desired product (478 mg, 25%) as an off white solid. NMR: δ ($^1$H, 400M Hz, DMSO-$d_6$): 0.90 (3H, s), 0.91 (3H, s), 1.09 (3H, s), 1.40-1.80 (3H, m), 2.30-2.60 (1H, m), 3.00-3.10 (1H, m), 3.51-3.70 (1H, m), 3.93 (3H, s), 5.36 (1H, s), 8.00 (1H, s), 8.04 (1H, s), 8.31 (1H, s), 13.09 (1H, s). LCMS (254 nm): [M+H]$^+$ 399.00 (96.43%). HPLC: 254 nm (94.06%)

Compound CC

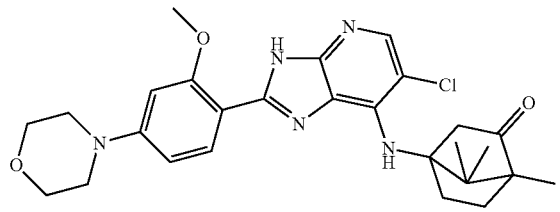

Compound CCII

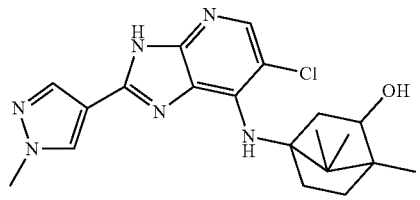

Synthesis of 4-(6-chloro-2-(2-methoxy-4-morpholinophenyl)-3H-imidazo[4,5-b]pyridin-7-ylamino)-1,7,7-trimethylbicyclo[2.2.1]heptan-2-one (Compound CC)

4-(2,3-diamino-5-chloropyridin-4-ylamino)-1,7,7-trimethylbicyclo[2.2.1]heptan-2-one (10) (300 mg, 0.97 mmol), 2-methoxy-4-morpholinobenzaldehyde (193 mg, 0.873 mmol) were taken in EtOH (15 ml) to which ammonium acetate (112 mg) was added and the reaction mixture was heated at 70° C. for 48 h. Crude LCMS showed the desired product along with trace of starting material. The reaction mixture was allowed to come to rt and the precipitated was filtered and washed well with ethanol to afford the desired product (495 mg, 24%) as an off white solid. NMR: δ ($^1$H, 400M Hz, DMSO-$d_6$): 0.91 (6H, s), 1.09 (3H, s), 1.40-1.50 (1H, m), 1.70-1.90 (2H, m), 2.40-2.60 (1H, m), 3.00-3.10 (1H, m), 3.20-3.40 (4H, m), 3.60-3.80 (5H, m), 3.94 (3H, s), 5.36 (1H, s), 6.64 (1H, s), 6.72 (1H, d, J=8.8 Hz), 7.94 (1H, d, J=8.8 Hz), 8.01 (1H, s), 12.29 (1H, s). LCMS (254 nm): [M+H]$^+$ 510.25 (98.08%). HPLC: (220 nm) 97.36%

Synthesis of (4S)-4-(6-chloro-2-(1-methyl-1H-pyrazol-4-yl)-3H-imidazo[4,5-b]pyridin-7-ylamino)-1,7,7-trimethylbicyclo[2.2.1]heptan-2-ol (Compound CCII)

To a suspension of 4-(6-chloro-2-(1-methyl-1H-pyrazol-4-yl)-3H-imidazo[4,5-b]pyridin-7-ylamino)-1,7,7-trimethylbicyclo[2.2.1]heptan-2-one (Compound CXCIX) (90 mg, 0.228 mmol) in ethanol NaBH$_4$ (85 mg, 2.26 mmol) was added and the reaction mixture was heated at 60° C. for 16 h when LCMS confirmed consumption of staring material and formation of desired product. The reaction mixture was allowed to come to rt and acidified to pH 5. Solvent was then removed and the residue was suspended in water and filtered. The residue was triturated with ether to afford the desired product (42 mg, 46%) as a white solid. NMR: δ ($^1$H, 400M Hz, DMSO-$d_6$): 0.88 (3H, s), 0.91 (3H, s), 1.09 (3H, s), 1.10-1.60 (4H, m), 2.75-2.90 (1H, m), 3.60-3.75 (1H, m), 3.94 (3H, s), 4.77 (1H, d, J=4.4 Hz), 5.21 (1H, s), 7.95 (1H, s), 8.03 (1H, s), 8.28 (1H, s), 12.99 (1H, s). LCMS (254 nm): [M+H]$^+$ 401.05 (96.59%). HPLC: 93.58% (220 nm)

Compound CCI

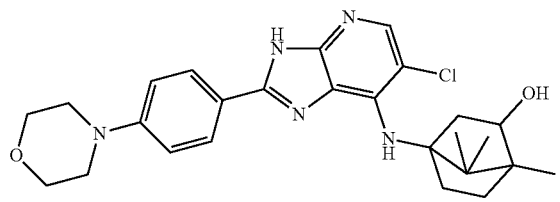

Compound CCIII

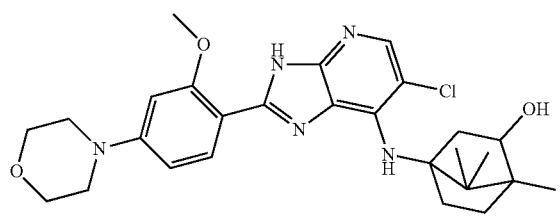

Synthesis of 4-(6-chloro-2-(4-morpholinophenyl)-3H-imidazo[4,5-b]pyridin-7-ylamino)-1,7,7-trimethylbicyclo[2.2.1]heptan-2-ol (Compound CCI)

To a suspension of 4-(6-chloro-2-(4-morpholinophenyl)-3H-imidazo[4,5-b]pyridin-7-ylamino)-1,7,7-trimethylbicyclo[2.2.1]heptan-2-one (Compound CXCVIII) (100 mg, 0.208 mmol) in ethanol NaBH$_4$ (78 mg, 2.08 mmol) was added and the reaction mixture was heated at 60° C. for 16 h when LCMS confirmed consumption of staring material and formation of desired product. The reaction mixture was allowed to come to rt and acidified to pH 5. Solvent was then removed and the residue was suspended in water and filtered. The residue was triturated with ether to afford the desired product (47 mg, 47%) as a white solid. NMR: δ ($^1$H, 400M Hz, DMSO-$d_6$): 0.88 (3H, s), 0.91 (3H, s), 1.09 (3H, s), 1.00-1.60 (4H, m), 2.80-2.90 (1H, m), 3.15-3.25 (4H, m), 3.60-3.70 (1H, m), 3.70-3.80 (4H, m), 4.80 (1H, d, J=4.4 Hz), 5.26 (1H, s), 7.10 (2H, d, J=8.8 Hz), 8.02 (2H, d, J=8.8 Hz), 13.04 (s, 1H). LCMS (254 nm): [M+H]$^+$ 482.15 (88.07%). HPLC: 86.94% (220 nm)

Synthesis 4-(6-chloro-2-(2-methoxy-4-morpholinophenyl)-3H-imidazo[4,5-b]pyridin-7-ylamino)-1,7,7-trimethylbicyclo[2.2.1]heptan-2-ol (Compound CCIII)

To a suspension of 4-(6-chloro-2-(2-methoxy-4-morpholinophenyl)-3H-imidazo[4,5-b]pyridin-7-ylamino)-1,7,7-trimethylbicyclo[2.2.1]heptan-2-one (Compound CC) (100 mg, 0.196 mmol) in ethanol NaBH$_4$ (74 mg, 1.96 mmol) was added and the reaction mixture was heated at 60° C. for 16 h when LCMS confirmed consumption of starting material and formation of desired product. The reaction mixture was allowed to come to rt and acidified to pH 5. Solvent was then removed and the residue was suspended in water and filtered. The residue was triturated with ether to afford the desired product (44 mg, 43%) as a light green solid. NMR: δ ($^1$H, 400M Hz, DMSO-$d_6$): 0.89 (3H, s), 0.91 (3H, s), 1.09 (3H, s), 1.00-1.60 (4H, m), 2.70-2.90 (1H, m), 3.20-3.30 (4H, m), 3.60-3.70 (1H, m), 3.70-3.80 (4H, m), 3.97 (3H, s), 5.35 (1H, s), 6.54 (1H, s), 6.74 (1H, d, J=8.8 Hz), 8.03 (2H, d, J=8.8 Hz), 12.26 (1H, s). LCMS (254 nm): [M+H]⁺ 512.15 (91.18%).
HPLC: (254 nm) 89.96% (220 nm)

Scheme 4

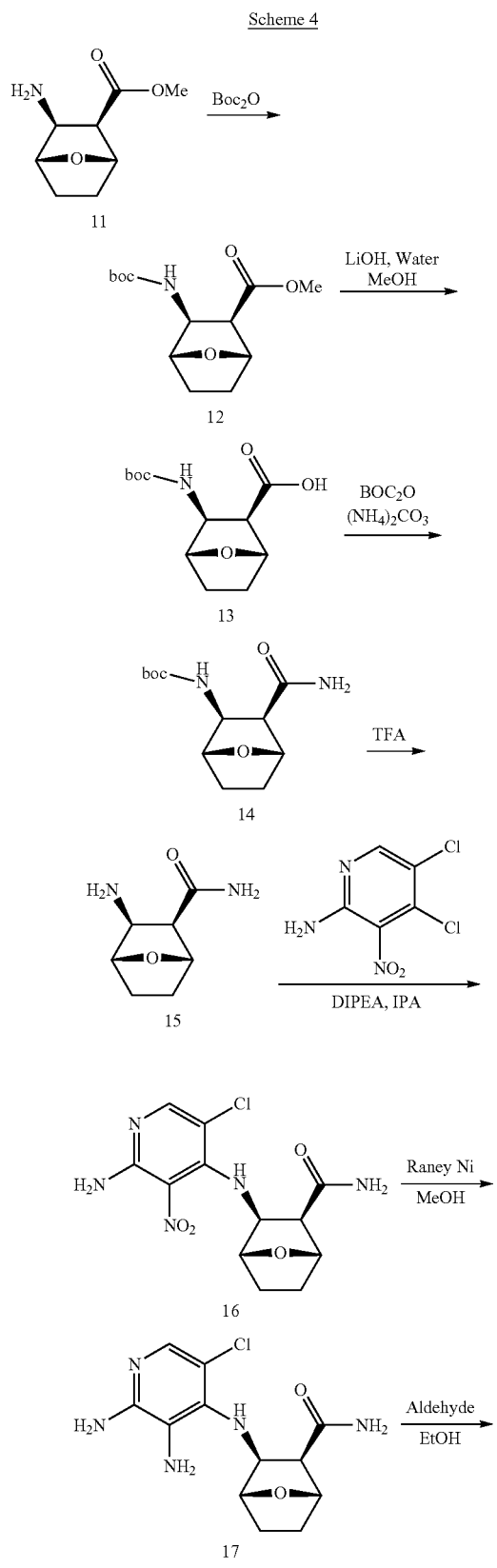

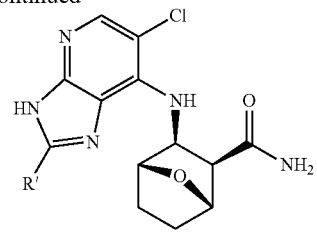

(1S,2R,3S,4R)-methyl 3-(tert-butoxycarbony-lamino)-7-oxabicyclo[2.2.1]heptane-2-carboxylate (12)

A solution of (1S,2R,3S,4R)-methyl 3-amino-7-oxabicyclo[2.2.1]heptane-2-carboxylate (11) (500 mg, 2.4 mmol), Et₃N (0.85 ml, 6 mmol) and BOC₂O (0.66 ml, 2.88 mmol) in acetonitrile was stirred at rt for 2 h and then heated at 80° C. for 30 min when TLC confirmed completion of reaction. Acetonitrile was removed and the crude product was purified by column chromatography using silica gel (100-200 mesh) to afford the desired compound (600 mg, 92%) as a colourless oil.

1S,2R,3S,4R)-3-(tert-butoxycarbonylamino)-7-oxabicyclo[2.2.1]heptane-2-carboxylic acid (13)

(1S,2R,3S,4R)-methyl 3-(tert-butoxycarbonylamino)-7-oxabicyclo[2.2.1]heptane-2-carboxylate (12) (600 mg, 2.2 mmol) was taken in MeOH/H₂O (3:1) and LiOH (265 mg, 11 mmol) was added at 0° C. The reaction mixture was allowed to come to rt and then stirred at rt for 16 h. MeOH was removed and saturated ammonium chloride solution was added. This was followed by extraction with DCM. The aqueous extract was acidified to pH 3 using 1N HCl and extracted with DCM again. The combined organic extracts was dried and concentrated to afford the desired product (450 mg, 87%) as an off white solid.

tert-Butyl(1R,2S,3R,4S)-3-carbamoyl-7-oxabicyclo[2.2.1]heptan-2-ylcarbamate (14)

(1S,2R,3S,4R)-3-(tert-butoxycarbonylamino)-7-oxabicyclo[2.2.1]heptane-2-carboxylic acid (13) (44 mg, 0.17 mmol) was taken in dioxane when pyridine (1.7 eq) was added followed by addition of BOC₂O. The reaction mixture was stirred at rt for 40 min when NH₄CO₃ (38 mg, 0.49 mmol) was added and the reaction mixture was stirred at rt for 15 h when TLC confirmed formation of product. The reaction mixture was concentrated and purified by column chromatography using silica gel (100-200 mesh) to afford the desired product (43 mg, 95%) as a yellow oil.

(1S,2R,3S,4R)-3-amino-7-oxabicyclo[2.2.1]heptane-2-carboxamide (15)

tert-butyl(1R,2S,3R,4S)-3-carbamoyl-7-oxabicyclo[2.2.1]heptan-2-ylcarbamate (14) (40 mg, 0.156 mmol) was taken in DCM and cooled to 0° C. when TFA (10 eq) was added and the reaction mixture was then stirred at rt for 3-4 h when TLC confirmed completion of reaction. TFA was removed and afforded the product (40 mg, quantitative) as a yellow oil.

(1S,2R,3S,4R)-3-(2-amino-5-chloro-3-nitropyridin-4-ylamino)-7-oxabicyclo[2.2.1]heptane-2-carboxamide (16)

(1S,2R,3S,4R)-3-amino-7-oxabicyclo[2.2.1]heptane-2-carboxamide (15) (170 mg, 0.67 mmol), 4,5-dichloro-3-nitropyridin-2-amine (127 mg, 0.6 mmol), DIPEA (5.5 eq) were taken in IPA and heated at 60° C. for 15 h when a yellow precipitate appeared. The precipitate was filtered, washed well with IPA and dried to afford the desired product, (198 mg, 34%).

1S,2R,3S,4R)-3-(2,3-diamino-5-chloropyridin-4-ylamino)-7-oxabicyclo[2.2.1]heptane-2-carboxamide (17)

To a suspension of Raney Nickel (70 mg) in MeOH (25 ml) (1S,2R,3S,4R)-3-(2-amino-5-chloro-3-nitropyridin-4-ylamino)-7-oxabicyclo[2.2.1]heptane-2-carboxamide (16) (150 mg, 0.458 mmol) was added and the reaction mixture was hydrogenated for 2 h at rt. The reaction mixture was filtered through a bed of celite and the bed was washed well with MeOH. The filtrate was concentrated to afford the product (131 mg, 96%) as a white solid. LCMS (254 nm): [M+H]$^+$ 298.10 (99.9%)

Compound CCIV

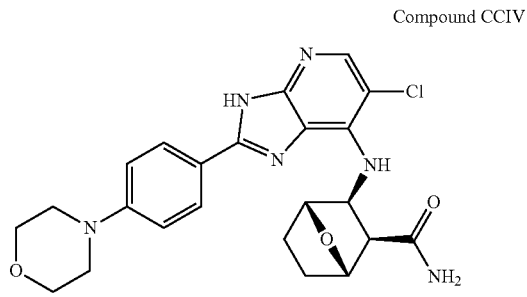 [SMILES: NC(=O)[C@@H]1[C@H](Nc2c(Cl)cnc3[nH]c(-c4ccc(N5CCOCC5)cc4)nc23)[C@H]2CC[C@@H]1O2]

Synthesis of (1S,2R,3S,4R)-3-(6-chloro-2-(4-morpholinophenyl)-3H-imidazo[4,5-b]pyridin-7-ylamino)-7-oxabicyclo[2.2.1]heptane-2-carboxamide (Compound CCIV)

(1S,2R,3S,4R)-3-(2,3-diamino-5-chloropyridin-4-ylamino)-7-oxabicyclo[2.2.1]heptane-2-carboxamide (17) (300 mg, 0.971 mmol), and 4-morpholinobenzaldehyde (167 mg, 0.873 mmol) were taken in EtOH (15 ml) to which ammonium acetate (112 mg) was added and the reaction mixture was heated at 70° C. for 48 h. Crude LCMS showed the desired product along with trace of starting material. The reaction mixture was allowed to come to rt and the precipitated was filtered and washed well with hot ethanol to afford the desired product (466 mg, 23%) as a yellow solid. NMR: δ ($^1$H, 400M Hz, DMSO-d$_6$): 1.50-1.80 (4H, m), 2.96 (1H, d, J=8.4 Hz), 3.23 (4H, s), 3.76 (4H, s), 4.33 (1H, d, J=4.5 Hz), 4.57 (1H, s), 5.49 (1H, t, J=8.8 Hz), 6.99 (1H, d, J=8.4 Hz), 7.08 (1H, d, J=8.4 Hz), 7.18 (1H, s), 7.62 (1H, s), 7.91 (1H, s), 8.02 (1H, d, J=8.0 Hz), 12.96 (1H, s). LCMS (254 nm): [M+H]$^+$ 469.15 (95.56%) HPLC: 91.64% (220 nm).

Compound CCV

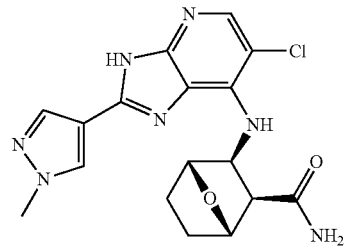

Synthesis of (1S,2R,3S,4R)-3-(6-chloro-2-(1-methyl-1H-pyrazol-4-yl)-3H-imidazo[4,5-b]pyridin-7-ylamino)-7-oxabicyclo[2.2.1]heptane-2-carboxamide (Compound CCV)

(1S,2R,3S,4R)-3-(2,3-diamino-5-chloropyridin-4-ylamino)-7-oxabicyclo[2.2.1]heptane-2-carboxamide (17) (90 mg, 0.302 mmol), 1-methyl-1H-pyrazole-4-carbaldehyde (30 mg, 0.272 mmol) were taken in EtOH (15 ml) to which ammonium acetate (35 mg) was added and the reaction mixture was heated at 70° C. for 48 h. Crude LCMS showed the desired product along with trace of starting material. The reaction mixture was allowed to come to rt and the precipitated was filtered and washed well with hot ethanol to afford the desired product (70 mg, 41%) as a white solid. NMR: δ ($^1$H, 400M Hz, DMSO-d$_6$): 1.40-1.80 (4H, m), 2.92 (1H, d, J=8.4 Hz), 3.92 (3H, s), 4.28 (1H, s), 4.56 (1H, s), 5.40-5.55 (1H, m), 6.82 (1H, s), 7.14 (1H, s), 7.1 (1H, s), 7.86 (1H, s), 7.99 (1H, s), 8.23 (1H, s).

LCMS (254 nm): [M+H]$^+$ 388.05 (98.20%). HPLC: 92.71% (220 nm)

Compound CCVI

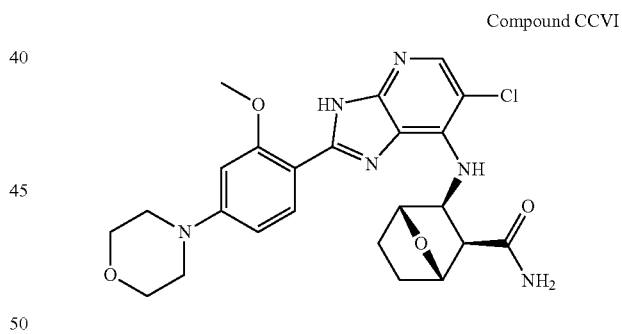

Synthesis of (1S,2R,3S,4R)-3-(6-chloro-2-(2-methoxy-4-morpholinophenyl)-3H-imidazo[4,5-b]pyridin-7-ylamino)-7-oxabicyclo[2.2.1]heptane-2-carboxamide (Compound CCVI)

(1S,2R,3S,4R)-3-(2,3-diamino-5-chloropyridin-4-ylamino)-7-oxabicyclo[2.2.1]heptane-2-carboxamide (17) (140 mg, 0.47 mmol), 2-methoxy-4-morpholinobenzaldehyde (93 mg, 0.42 mmol) were taken in EtOH (15 ml) to which ammonium acetate (40 mg) was added and the reaction mixture was heated at 70° C. for 48 h. Crude LCMS showed the desired product along with trace of starting material. The reaction mixture was allowed to come to rt and the precipitated was filtered and washed well with hot ethanol to afford the desired product (120 mg, 51%) as an off white solid. NMR: δ ($^1$H, 400M Hz, CDCl$_3$): 1.50-1.80 (4H, m), 2.95 (1H, d, J=8.4 Hz), 3.27 (4H, bs), 3.76 (4H, bs), 3.96 (3H, s), 4.32 (1H, d, J=4.4 Hz), 4.57 (1H, s), 5.51 (1H, t, J=4.4 Hz), 6.63 (1H, s), 6.69 (1H, d, J=8.4 Hz), 6.90 (1H, d, J=8.4 Hz), 7.18 (1H, s), 7.60 (1H, s), 7.91 (1H, s), 8.05 (1H, d, J=8.8 Hz), 12.14 (1H, s). LCMS (254 nm): [M+H]+ 499.00 (100%). HPLC: (254 nm) 97.68%.

In a similar fashion as for the synthesis of Compound CXCVII (Scheme 2), the following compounds were synthesized:

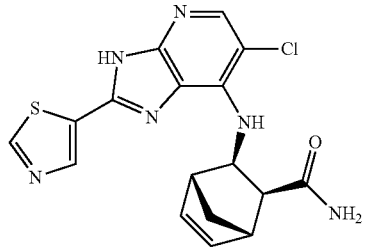

Compound CCVII

Synthesis of (1S,2S,3R,4R)-3-(6-chloro-2-(thiazol-5-yl)-3H-imidazo[4,5-b]pyridin-7-ylamino)bicyclo[2.2.1]hept-5-ene-2-carboxamide (Compound CCVII)

NMR: δ (1H, 400M Hz, DMSO-d6): 1.36 (1H, d, J=8.4 Hz), 2.19 (1H, d, J=8.8 Hz), 2.61 (1H, d, J=8 Hz), 2.70 (1H, s),), 2.89 (1H, s), 5.00 (1H, t, J=8 Hz), 6.29-6.37 (2H, m), 7.15-7.33 (2H, m), 7.78 (1H, bs), 7.97 (1H, s), 8.53 (1H, s), 9.18 (1H, s), 13.56 (1H, bs).

LCMS (254 nm): [M+H]+ 386.95 (91.69%).

HPLC: 90.16% (220 nm).

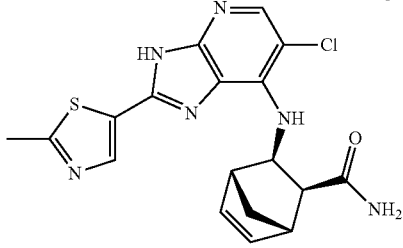

Compound CCVIII

Synthesis of (1S,2S,3R,4R)-3-(6-chloro-2-(2-methylthiazol-5-yl)-3H-imidazo[4,5-b]pyridin-7-ylamino)bicyclo[2.2.1]hept-5-ene-2-carboxamide (Compound CCVIII)

NMR: δ (1H, 400M Hz, DMSO-d6): 1.34 (1H, d, J=8 Hz), 2.21 (1H, d, J=8.4 Hz), 2.50-2.60 (1H, m), 2.67 (3H, s),), 2.70 (1H, s), 2.85 (1H, s), 5.13 (1H, t, J=8 Hz), 6.30-6.40 (2H, m), 6.71 (1H, bs), 7.14 (1H, bs), 7.72 (1H, bs), 7.81 (1H, s), 8.10 (1H, s).

LCMS (254 nm): [M+H]+ 400.9 (93.39%).

HPLC: 94.77% (220 nm).

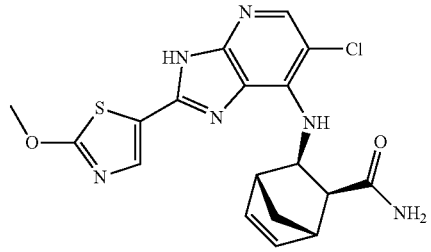

Compound CCIX

Synthesis of (1S,2S,3R,4R)-3-(6-chloro-2-(2-methoxythiazol-5-yl)-3H-imidazo[4,5-b]pyridin-7-ylamino)bicyclo[2.2.1]hept-5-ene-2-carboxamide (Compound CCIX)

NMR: δ (1H, 400M Hz, DMSO-d6): 1.35 (1H, d, J=9.2 Hz), 2.18 (1H, d, J=8.4 Hz), 2.58 (1H, d, J=8.4 Hz), 2.73 (1H, bs),), 2.87 (1H, bs), 4.09 (3H, s), 4.94 (1H, t, J=8 Hz), 6.33 (2H, bs), 7.20-7.30 (2H, m), 7.76 (1H, bs), 7.87 (1H, s), 7.93 (1H, s).

LCMS (254 nm): [M+H]+ 417.05 (98.01%).

HPLC: 97.37% (220 nm).

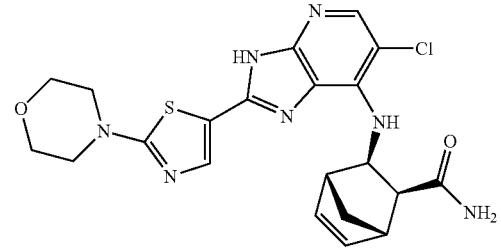

Compound CCX

Synthesis of (1S,2S,3R,4R)-3-(6-chloro-2-(2-morpholinothiazol-5-yl)-3H-imidazo[4,5-b]pyridin-7-ylamino)bicyclo[2.2.1]hept-5-ene-2-carboxamide (Compound CCX)

NMR: δ (1H, 400M Hz, DMSO-d6): 1.34 (1H, d, J=7.2 Hz), 2.18 (1H, d, J=8.4 Hz), 2.57 (1H, d, J=8.8 Hz), 2.73 (1H, bs),), 2.87 (1H, bs), 3.46-3.54 (4H, m), 3.70-3.76 (4H, m), 4.95 (1H, t, J=8 Hz), 6.33-6.36 (2H, m), 7.15 (1H, d, J=8.4 Hz), 7.23 (1H, bs), 7.76 (1H, bs), 7.88-7.90 (2H, m), 13.22 (1H, s).

LCMS (254 nm): [M+H]+ 471.95 (99.96%).

HPLC: 98.73% (220 nm).

Compound CCXI

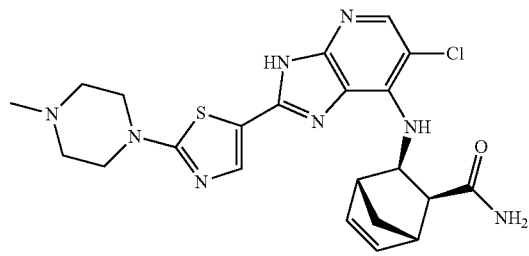

Synthesis of (1S,2S,3R,4R)-3-(6-chloro-2-(2-(4-methylpiperazin-1-yl)thiazol-5-yl)-3H-imidazo[4,5-b]pyridin-7-ylamino)bicyclo[2.2.1]hept-5-ene-2-carboxamide (Compound CCXI)

NMR: δ ($^1$H, 400M Hz, DMSO-$d_6$): 1.33-1.34 (1H, m), 2.28 (1H, s), 2.44 (3H, s), 2.49-2.51 (4H, m), 2.57 (1H, d, J=8.8 Hz), 2.73 (1H, s), 2.87 (1H, s), 3.49-3.51 (4H, m), 4.96 (1H, s), 6.33-6.37 (2H, m), 7.14 (1H, d, J=8.8 Hz), 7.23 (1H, s), 7.76 (1H, s), 7.88 (2H, s), 13.14 (1H, bs).

LCMS (254 nm): [M+H]$^+$ 485.05 (98.19%).

HPLC: 94.77% (254 nm).

Compound CCXIII

Synthesis of (1S,2S,3R,4R)-3-(6-chloro-2-(5,6,7,8-tetrahydroimidazo[1,2-a]pyridin-2-yl)-3H-imidazo[4,5-b]pyridin-7-ylamino)bicyclo[2.2.1]hept-5-ene-2-carboxamide (Compound CCXIII)

NMR: δ ($^1$H, 400M Hz, CDCl$_3$): 1.62 (1H, d, J=8.8 Hz), 1.92-2.22 (4H, m), 2.11 (2H, s), 2.30 (2H, d, J=8.8 Hz), 2.60-2.64 (2H, m), 2.84 (1H, s), 2.92-3.11 (2H, m), 3.08 (1H, s), 4.40-4.43 (2H, m), 5.17 (1H, t, J=8 Hz), 6.19-6.33 (1H, m), 6.34-6.35 (1H, m), 7.56 (1H, s), 7.91 (1H, s).

LCMS (254 nm): [M+H]$^+$ 424.00 (99.69%).

HPLC: 94.37% (220 nm).

Compound CCXII

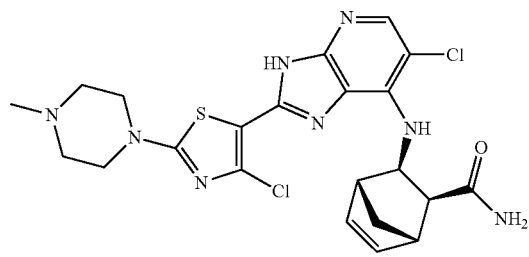

Synthesis of (1S,2S,3R,4R)-3-(6-chloro-2-(4-chloro-2-(4-methylpiperazin-1-yl)thiazol-5-yl)-3H-imidazo[4,5-b]pyridin-7-ylamino)bicyclo[2.2.1]hept-5-ene-2-carboxamide (Compound CCXII)

NMR: δ ($^1$H, 400M Hz, DMSO-$d_6$): 1.36 (1H, d, J=7.6 Hz), 2.16-2.30 (4H, m), 2.40-2.50 (4H, m), 2.57 (1H, d, J=8 Hz), 2.75 (1H, s), 2.87 (1H, s), 3.49 (4H, bs), 4.97 (1H, t, J=8 Hz), 6.33 (1H, bs), 6.35 (1H, bs), 7.25 (2H, s), 7.77 (1H, s), 7.93 (1H, s), 12.5 (1H, bs).

LCMS (254 nm): [M+H]$^+$ 519.00 (96.87%).

HPLC: 96.32% (220 nm).

Compound CCXIV

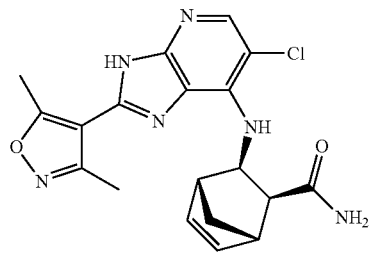

Synthesis of (1S,2S,3R,4R)-3-(6-chloro-2-(5,6,7,8-tetrahydroimidazo[1,2-a]pyridin-2-yl)-3H-imidazo[4,5-b]pyridin-7-ylamino)bicyclo[2.2.1]hept-5-ene-2-carboxamide (Compound CCXIV)

NMR: δ ($^1$H, 400M Hz, DMSO-$d_6$): 1.39 (1H, d, J=8.4 Hz), 2.24 (1H, d, J=9.2 Hz), 2.47 (3H, s), 2.58 (1H, d, J=8 Hz), 2.63 (3H, s), 2.77 (1H, s), 2.86 (1H, s), 5.14 (1H, t, J=8 Hz), 6.1-6.47 (2H, m), 7.23 (2H, s), 7.74 (1H, s), 7.97 (1H, s).

LCMS (254 nm): [M+H]$^+$ 399.30 (100%).

HPLC: 98.17% (254 nm).

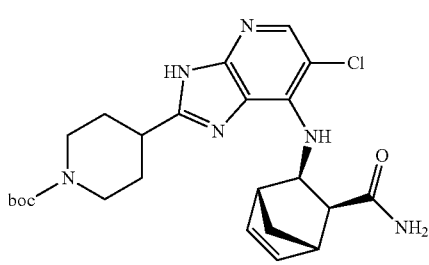

Compound CCXV

Synthesis of tert-butyl 4-(7-((1R,2R,3S,4S)-3-carbamoylbicyclo[2.2.1]hept-5-en-2-ylamino)-6-chloro-3H-imidazo[4,5-b]pyridin-2-yl)piperidine-1-carboxylate (Compound CCXV)

NMR: δ ($^1$H, 400M Hz, DMSO-$d_6$): 1.31 (1H, d, J=8.8 Hz), 1.37 (9H, s), 1.56-1.70 (2H, m), 1.91-198 (2H, m), 2.16 (1H, d, J=8.4 Hz), 2.52 (2H, d, J=8.4 Hz), 2.64 (1H, s), 2.82 (1H, s), 2.89-3.0 (4H, m), 5.03 (1H, t, J=8.4 Hz), 6.21-6.29 (2H, m), 6.95 (1H, d, J=8.8 Hz), 7.16 (1H, s), 7.68 (1H, s), 7.84 (1H, s).

LCMS (254 nm): [M+H]$^+$ 487.20 (96.90%).

HPLC: 95.48% (254 nm

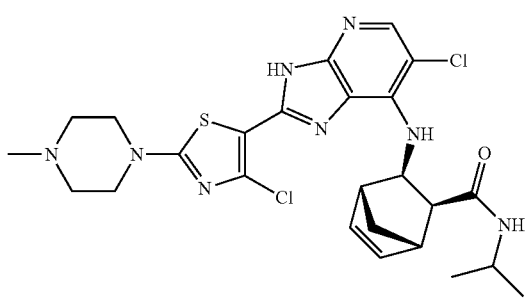

Compound CCXVI

(1S,2S,3R,4R)-3-((6-chloro-2-(4-chloro-2-(4-methylpiperazin-1-yl)thiazol-5-yl)-3H-imidazo[4,5-b]pyridin-7-yl)amino)-N-isopropylbicyclo[2.2.1]hept-5-ene-2-carboxamide (Compound CCXVI)

Yield: 13%.

NMR: δ ($^1$H, 400M Hz, CDCl$_3$): 1.12 (d, 3H, J=6.4 Hz), 1.19 (d, 3H, J=6.4 Hz), 1.58 (d, 1H, J=10.0 Hz), 1.60-2.10 (m, 1H), 2.29 (d, 1H, J=8.6 Hz), 2.45 (d, 1H, J=8.6 Hz), 2.91 (s, 3H), 3.02 (s, 1H), 3.10-3.60 (m, 4H), 3.80-4.20 (m, 4H), 4.76 (s, 1H), 4.96 (d, 1H, J=8.0 Hz), 6.36 (s, 2H), 7.79 (s, 1H).

LCMS (254 nm): [M+H]$^+$ 561.10.

HPLC: 96%.

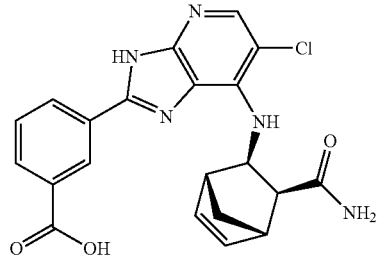

Compound CCXVII

Synthesis of 3-(7-((1R,2R,3S,4S)-3-carbamoylbicyclo[2.2.1]hept-5-en-2-ylamino)-6-chloro-3H-imidazo[4,5-b]pyridin-2-yl)benzoic acid (Compound CCXVII)

Yield: 55.5%.

NMR: δ ($^1$H, 400 MHz, DMSO-$d_6$): 1.40 (1H, d, J=8 Hz), 2.20 (1H, d, J=8.4 Hz), 2.64 (1H, d, J=8.4 Hz), 2.89 (1H, s), 2.93 (1H, s), 5.11 (1H, t, J=8 Hz), 6.30-6.50 (2H, m), 7.29 (1H, s), 7.60-7.85 (3H, m), 8.00-8.06 (2H, m), 8.35 (1H, d, J=7.6 Hz), 8.82 (1H, s), 13.67 (1H, bs).

LCMS (254 nm): [M+H]$^+$ 424.05 (99.3%).

HPLC: 99.37% (220 nm).

Synthesis of 4-(7-((1R,2R,3S,4S)-3-carbamoylbicyclo[2.2.1]hept-5-en-2-ylamino)-6-chloro-3H-imidazo[4,5-b]pyridin-2-yl)benzoic acid (Compound CCXVIII)

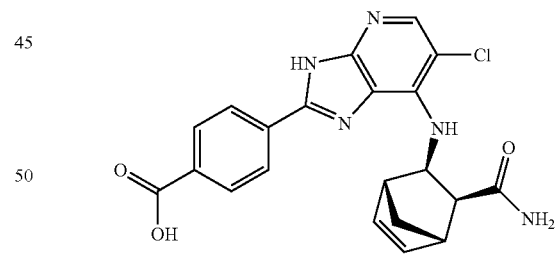

Compound CCXVIII

Yield: 58%.

NMR: δ ($^1$H, 400 MHz, DMSO-$d_6$): 1.39 (1H, d, J=8 Hz), 2.24 (1H, d, J=8.4 Hz), 2.62 (1H, d, J=8.4 Hz), 2.81 (1H, s), 2.90 (1H, s), 5.17 (1H, t, J=8 Hz), 6.30-6.50 (2H, m), 7.26 (1H, s), 7.32 (2H, d, J=8.8 Hz), 7.79 (1H, s), 7.99 (1H, s), 8.09 (2H, d, J=8 Hz), 8.24 (2H, d, J=8 Hz), 13.47 (1H, bs).

LCMS (254 nm): [M+H]$^+$ 424.00 (99.3%).

HPLC: 98.70% (254 nm), 96.65% (220 nm).

Scheme 5

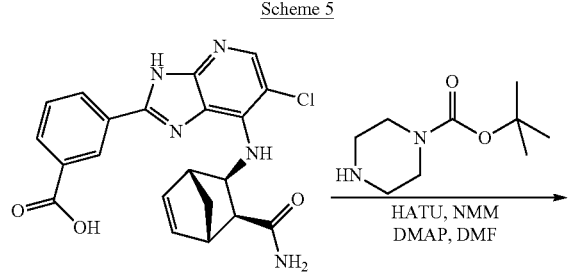

CXCVI

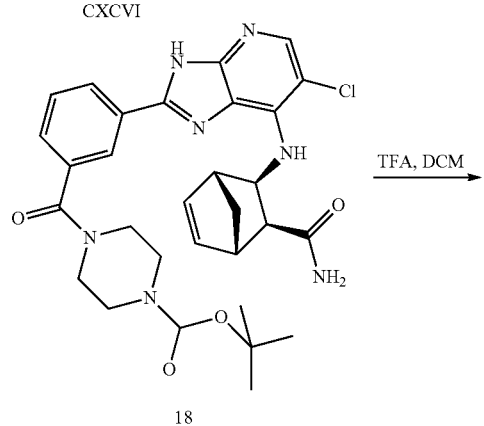

18

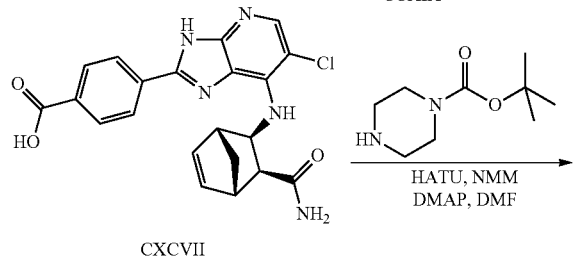

CXCVII

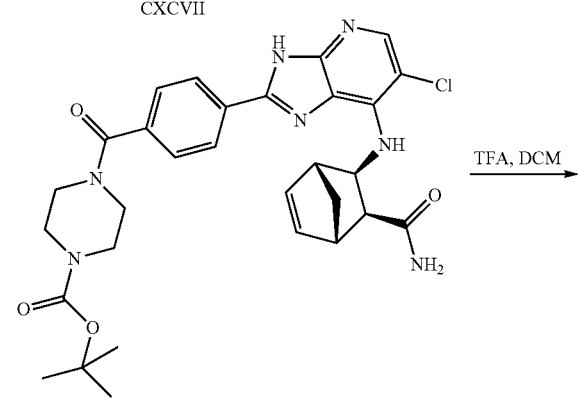

19

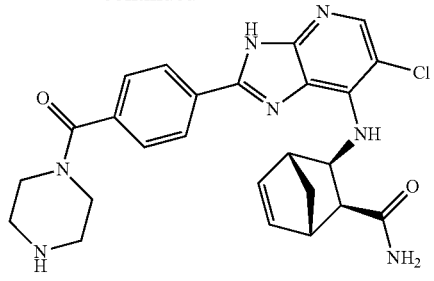

CCXX tert-butyl 4-(3-(7-((1R,2R,3S,4S)-3-carbamoylbicyclo[2.2.1]hept-5-en-2-ylamino)-6-chloro-3H-imidazo[4,5-b]pyridin-2-yl)benzoyl)piperazine-1-carboxylate (18)

To a solution of Compound CXCVII (100 mg, 0.235 mmol) in DMF (2 mL), tert-butyl piperazine-1-carboxylate (48 mg, 0.259 mmol), HATU (106 mg, 0.282 mg), NMM (60 mg, 0.587 mmol), DMAP (3 mg, 0.0235 mmol) were added. RM was stirred at RT for 16 h. RM was concentrated and column purification of crude afforded pure product (60 mg, 44%) as off white solid.

LCMS (254 nm): [M+H]$^+$ 592.15 (79.87%).

Compound CCXIX

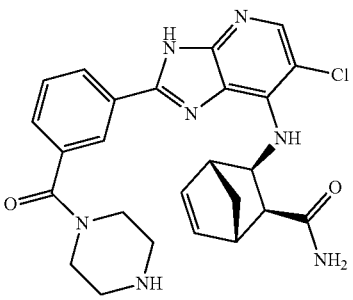

(1S,2S,3R,4R)-3-(6-chloro-2-(3-(piperazine-1-carbonyl)phenyl)-3H-imidazo[4,5-b]pyridin-7-ylamino)bicyclo[2.2.1]hept-5-ene-2-carboxamide (Compound CCXIX)

tert-butyl 4-(3-(7-((1R,2R,3S,4S)-3-carbamoylbicyclo[2.2.1]hept-5-en-2-ylamino)-6-chloro-3H-imidazo[4,5-b]pyridine-2-yl)benzoyl)piperazine-1-carboxylate (18) (160 mg, 0.27 mmol) was dissolved in 2 mL of 20% TFA solution in DCM. The reaction mixture was stirred at room temperature for 6 h. After 6 h, DCM was evaporated and the residue was triturated with ether to obtain the desired product (75 mg, 56% yield) as a light brown hygroscopic solid.

NMR: δ ($^1$H, 400 MHz, CD$_3$OD): 1.57 (1H, d, J=8.4 Hz), 2.30 (1H, d, J=8 Hz), 2.76 (1H, d, J=8 Hz), 2.96-3.20 (6H, m), 3.40-4.20 (4H, m), 5.28 (1H, bs), 6.40-6.50 (2H, m), 7.50-7.60 (1H, m), 7.63-7.75 (2H, m), 8.09 (1H, bs), 8.25 (1H, bs).

LCMS (254 nm): [M+H]$^+$ 492.05 (95.46%).

HPLC: 93.6% (254 nm).

Tert-butyl 4-(3-(7-((1R,2R,3S,4S)-3-carbamoylbicyclo[2.2.1]hept-5-en-2-ylamino)-6-chloro-3H-imidazo[4,5-b]pyridin-2-yl)benzoyl)piperazine-1-carboxylate (19)

To a solution of Compound CXCVIII (100 mg, 0.235 mmol) in DMF (2 mL), tert-butyl piperazine-1-carboxylate (48 mg, 0.259 mmol), HATU (106 mg, 0.282 mg), NMM (60 mg, 0.587 mmol), DMAP (3 mg, 0.0235 mmol) were added. RM was stirred at RT for 16 h. RM was concentrated and column purification of crude afforded pure product (32.44%) as LCMS (254 nm): [M+H]+ 592.0 (44.65%).

Compound CCXX

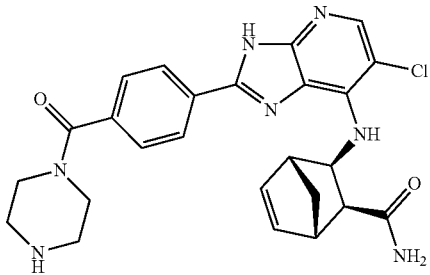

(1S,2S,3R,4R)-3-(6-chloro-2-(4-(piperazine-1-carbonyl)phenyl)-3H-imidazo[4,5-b]pyridin-7-ylamino)bicyclo[2.2.1]hept-5-ene-2-carboxamide (CCXX)

In an analogous manner to compound CCXIX, tert-butyl 4-(3-(7-((1R,2R,3S,4S)-3-carbamoylbicyclo[2.2.1]hept-5-en-2-ylamino)-6-chloro-3H-imidazo[4,5-b]pyridin-2-yl)benzoyl)piperazine-1-carboxylate (19) was reacted to yield the desired compound. (90.90%).
NMR: δ (¹H, 400 MHz, DMSO-d₆): 1.38 (1H, d, J=8.4 Hz), 2.24 (1H, d, J=8 Hz), 2.63 (1H, d, J=8.4 Hz), 2.82 (1H, bs), 2.91 (1H, bs), 3.19 (4H, bs), 3.3-3.8 (4H, m), 5.10-5.30 (1H, m), 6.30-6.60 (2H, m), 7.26 (1H, s), 7.39 (1H, d, J=7.6 Hz), 7.64 (2H, d, J=8 Hz), 7.79 (1H, s), 8.00 (1H, s), 8.23 (2H, d, J=8.0 Hz), 8.87 (1H, bs), 13.48 (1H, s).
LCMS (254 nm): [M+H]+ 492 (99.86%).
HPLC: 99.43% (254 nm), 99.16% (220 nm).

Compound CCXXI

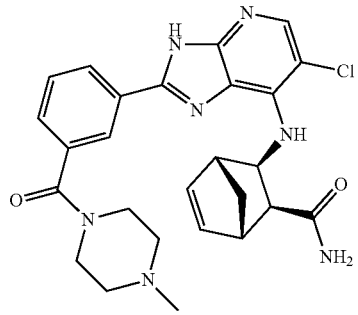

(1S,2S,3R,4R)-3-(6-chloro-2-(3-(4-methylpiperazine-1-carbonyl)phenyl)-3H-imidazo[4,5-b]pyridin-7-ylamino)bicyclo[2.2.1]hept-5-ene-2-carboxamide (Compound CCXXII)

To a solution of Compound CXCVII (100 mg, 0.235 mmol) in DMF (2 mL), 1-methylpiperzine (22 mg, 0.259 mmol), HATU (106 mg, 0.282 mg), NMM (60 mg, 0.587 mmol), DMAP (3 mg, 0.0235 mmol) were added. RM was stirred at RT for 16 h. RM was concentrated and column purification of crude afforded pure product (80 mg, 54.7%) as off white solid.
NMR: δ (¹H, 400 MHz, DMSO-d₆): 1.39 (1H, d, J=8 Hz), 2.22 (1H, d, J=8 Hz), 2.62 (1H, d, J=8 Hz), 2.84 (4H, s), 3.10-3.52 (4H, m), 3.70-4.60 (4H, m), 5.12 (1H, t, J=8 Hz), 6.39 (2H, s), 7.28 (1H, s), 7.60 (1H, d, J=7.6 Hz), 7.67 (1H, t, J=7.6 Hz), 7.82 (1H, s), 8.04 (1H, s), 8.24 (2H, m), 10.14 (1H, bs), 13.6 (1H, s).
LCMS (254 nm): [M+H]+ 506.05 (100.0%).
HPLC: 97.97% (254 nm).

Compound CCXXII

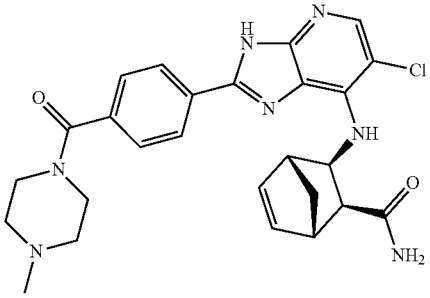

(1S,2S,3R,4R)-3-(6-chloro-2-(4-(4-methylpiperazine-1-carbonyl)phenyl)-3H-imidazo[4,5-b]pyridin-7-ylamino)bicyclo[2.2.1]hept-5-ene-2-carboxamide (Compound CCXXII)

In an analogous manner to Compound CCXXI, Compound CXCVIII was reacted with 1-Methylpiperzine to yield the desired compound (33.47%).
NMR: δ (¹H, 400 MHz, DMSO-d₆): 1.39 (1H, d, J=8.4 Hz), 2.10-2.70 (5H, m), 2.81 (1H, s), 2.90 (1H, s), 3.20-4.20 (8H, m), 5.16 (1H, t, J=8.4 Hz), 6.20-6.50 (2H, m), 7.20-7.35 (2H, m), 7.56 (2H, d, J=7.6 Hz), 7.78 (1H, s), 7.97 (1H, s), 8.19 (2H, d, J=8.4 Hz), 13.5 (1H, bs).
LCMS (254 nm): [M+H]+ 506.15 (98.58%).
HPLC: 94.42% (254 nm), 91.11% (220 nm).

Scheme 6

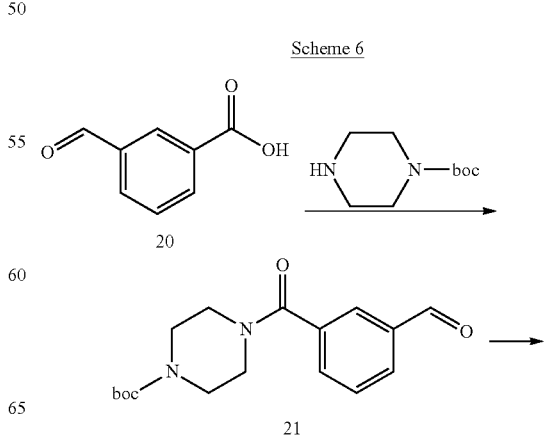

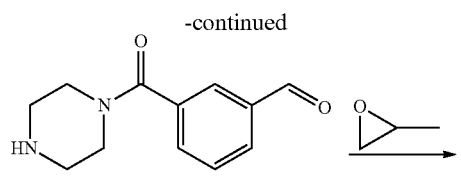

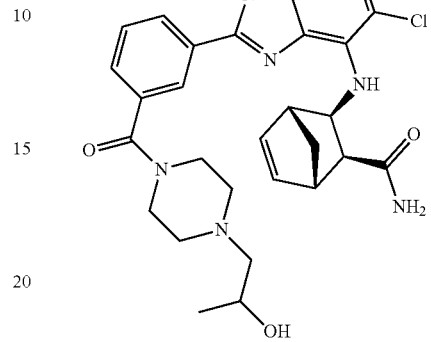

Compound CCXXIII tert-butyl 4-(3-formylbenzoyl)piperazine-1-carboxylate (21)

To a solution of 3-formylbenzoic acid (600 mg, 3.99 mmol) in DCM (12 mL) were added tert-butyl piperazine-1-carboxylate (818.8 mg, 4.40 mmol), HATU (1.82 g, 4.80 mmol), NMM (1.1 mL, 9.99 mmol), and DMAP (49 mg, 0.39 mmol) at 0° C. Reaction was stirred at RT for 16 h. TLC analysis indicated complete consumption of starting material. The reaction mixture was diluted with DCM and washed with water. Organic layer was separated and dried over $Na_2SO_4$ and concentrated. Column chromatography of crude material afforded pure product tert-butyl 4-(3-formylbenzoyl)piperazine-1-carboxylate as off-white solid (990 mg, 78%).

NMR: δ ($^1$H, 400 MHz, $CDCl_3$): 1.45 (9H, s), 3.2-4.0 (8H, m), 7.60 (1H, t, J=7.6 Hz), 7.66 (1H, d, J=7.6 Hz), 7.90 (1H, s), 7.94 (1H, d, J=7.6 Hz), 10.03 (1H, s).

3-(4-(2-hydroxypropyl)piperazine-1-carbonyl)benzaldehyde (23)

To a solution of tert-butyl 4-(3-formylbenzoyl)piperazine-1-carboxylate 21 (700 mg, 2.2 mmol) in DCM (5 mL) was added TFA (1.75 mL, 1.54 mmol) at 0° C. The reaction mixture was stirred at room temperature for 3 h. After 3 h, RM was washed with 10% sodium bicarbonate solution and concentrated. The crude material was dissolved in methanol (4 mL) and propylene oxide (892 mg, 15.3 mmol) was added. The reaction was heated at 55° C. for 15 h. TLC analysis indicated complete consumption of starting material. The reaction mixture was concentrated and purification of crude material by column chromatography (3% MeOH/DCM, Silica (230-400)) afforded product as white sticky solid (100 mg, 16.4%).

LCMS (254 nm): [M+H]$^+$ 276.90 (99.85%).

(1S,2S,3R,4R)-3-(6-chloro-2-(3-(4-(2-hydroxypropyl)piperazine-1-carbonyl)phenyl)-3H-imidazo[4,5-b]pyridine-7-ylamino)pyridin[2.2.1]hept-5-ene-2-carboxamide (Compound CCXXIII)

A suspension of 3-(4-(2-hydroxypropyl)piperazine-1-carbonyl)benzaldehyde 23 (124 mg, 0.44 mmol), (1S,2S,3R,4R)-3-(2,3-diamino-5-chloropyridin-4-ylamino)pyridin[2.2.1]hept-5-ene-2-carboxamide (120 mg, 0.40 mmol), ammonium acetate (47.35 mg, 0.61 mmol) in ethanol (2.5 mL) was heated at 70° C. for 16 h. Reaction was monitored by LCMS. Reaction mixture was cooled and ppt was filtered off then tittered with diisopropyl ether to afford product as yellow solid (55%).

MP: 183° C.

NMR: δ ($^1$H, 400 MHz, DMSO-$d_6$): 1.05 (3H, d, J=6 Hz), 1.39 (1H, d, J=8.4 Hz), 2.1-2.4 (5H, m), 2.63 (1H, d, J=8.4 Hz), 2.82 (1H, s), 2.90 (1H, s), 3.1-4.0 (5H, m), 4.35 (2H, d, J=3.6 Hz), 5.16 (1H, t, J=8.4 Hz), 6.38 (2H, bs), 7.2-7.3 (3H, m), 7.48 (2H, d, J=8 Hz), 7.63 (1H, t, J=7.6 Hz), 7.78 (1H, bs), 7.97 (1H, s), 8.16 (1H, bs), 8.20 (1H, d, J=8 Hz).

LCMS (254 nm): [M+H]$^+$ 550.0 (96.75%).

HPLC: (254 nm) 94.24%.

Scheme 7

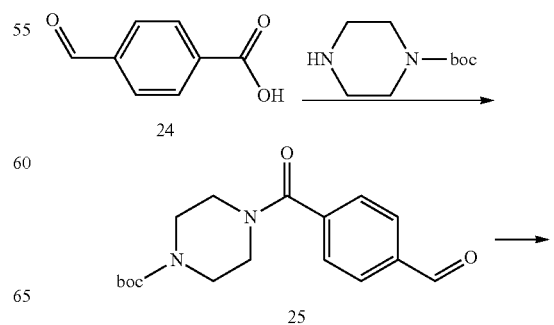

-continued

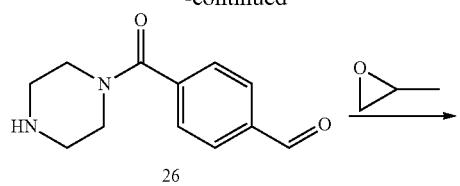

26

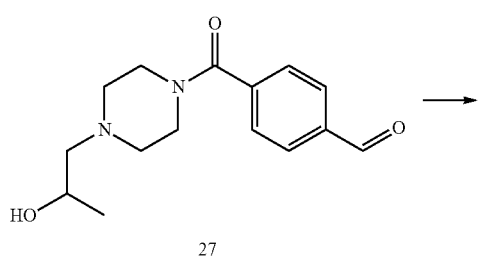

27

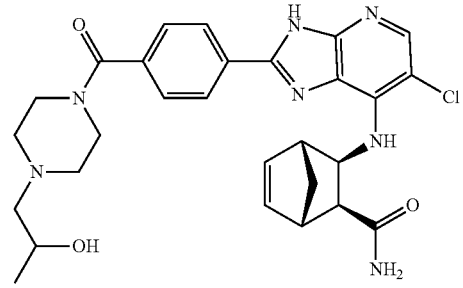

Compound CCXXIV tert-butyl 4-(4-formylbenzoyl)piperazine-1-carboxylate (25)

In an analogous manner to 21, 4-formylbenzoic acid (600 mg, 3.99 mmol) was reacted with tert-butyl piperazine-1-carboxylate (818.8 mg, 4.40 mmol) to afford desired product as off-white solid (1.1 g, 86.6%).

NMR: δ ($^1$H, 400 MHz, CDCl$_3$): 1.47 (9H, s), 3.2-4.0 (8H, m), 7.55 (2H, d, J=8.4 Hz), 7.94 (2H, d, J=8.0 Hz), 10.03 (1H, s).

4-(4-(2-hydroxypropyl)piperazine-1-carbonyl)benzaldehyde (27)

In an analagous manner to 23, tert-butyl 4-(4-formylbenzoyl)piperazine-1-carboxylate 26 (500 mg, 1.57 mmol) in DCM (10 mL) was reacted with TFA (1.17 mL, 15.72 mmol) to afford product as white sticky solid. Yield: 31.4%.

LCMS (254 nm): [M+H]$^+$ 276.95 (94.96%).

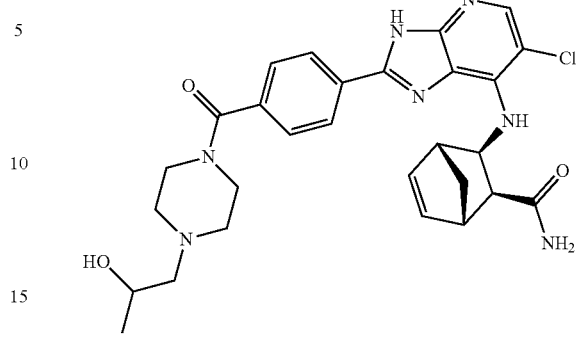

Compound CCXXIV (1S,2S,3R,4R)-3-(6-chloro-2-(4-(4-(2-hydroxypropyl)piperazine-1-carbonyl)phenyl)-3H-imidazo[4,5-b]pyridine-7-ylamino)pyridin[2.2.1]hept-5-ene-2-carboxamide (Compound CCXXIV)

In an analogous manner to Compound CCXXIII. (1S,2S,3R,4R)-3-(2,3-diamino-5-chloropyridin-4-ylamino) pyridin[2.2.1]hept-5-ene-2-carboxamide (238 mg, 0.81 mmol) was reacted with 4-(4-(2-hydroxypropyl)piperazine-1-carbonyl)benzaldehyde 4 (246 mg, 0.89 mmol) to afford product (Compound CCXXIV) as a yellow solid (80 mg, 18%).

NMR: δ ($^1$H, 400 MHz, DMSO-d$_6$): 1.04 (3H, d, J=6 Hz), 1.39 (1H, d, J=8 Hz), 2.1-2.4 (5H, m), 2.62 (1H, d, J=7.6 Hz), 2.81 (1H, s), 2.90 (1H, s), 3.2-3.9 (5H, m), 4.34 (2H, d, J=4 Hz), 5.17 (1H, t, J=8.4 Hz), 6.3-6.5 (2H, m), 7.2-7.3 (2H, m), 7.55 (2H, d, J=8.4 Hz), 7.78 (1H, bs), 7.98 (1H, s), 8.19 (2H, d, J=8 Hz).

MP: 224° C.

LCMS (254 nm): [M+H]$^+$ 550.12 (93.48%).

HPLC: (254 nm) 99.12%.

Scheme 8

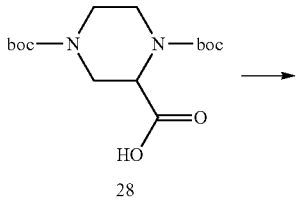

28

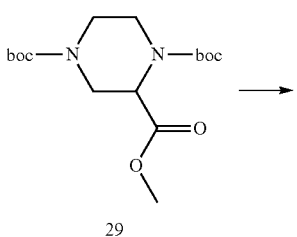

29

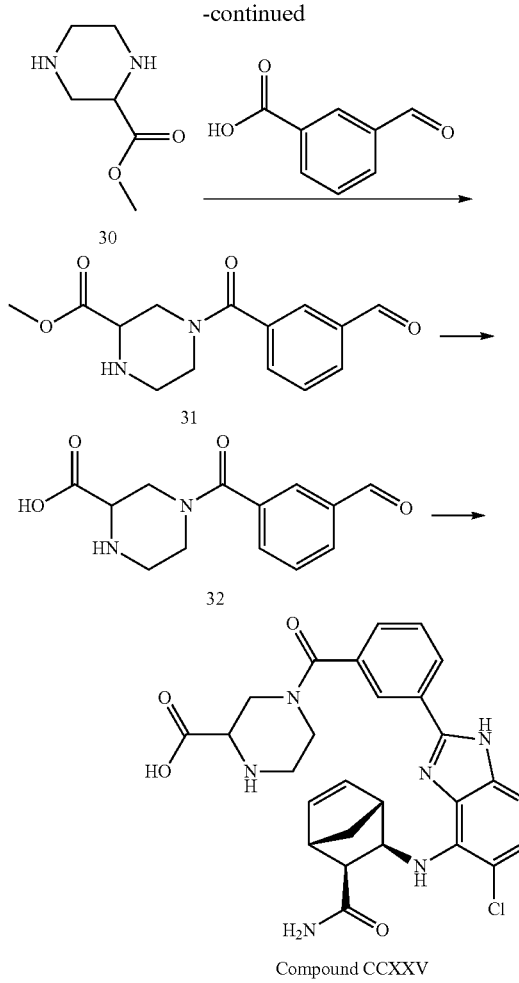

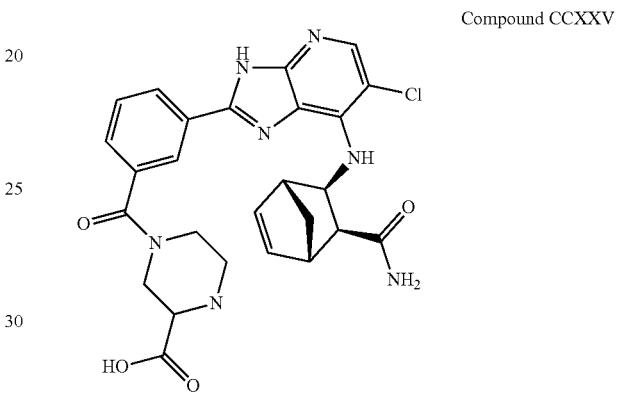

1,4-di-tert-butyl 2-methyl piperazine-1,2,4-tricarboxylate (29)

To a solution of 1,4-bis(tert-butoxycarbonyl)piperazine-2-carboxylic acid (2.5 g, 7.56 mol) in acetonitrile (25 mL) was added $Cs_2CO_3$ (3.93 g, 12.06 mol) with stirring at RT. After 15 min, MeI (2.34 g, 16.48 mol) was added. The reaction mixture was stirred at rt for 14 h. The reaction was monitored by TLC. When SM was finished, reaction mixture was filtered through celite pad and filtrate was concentrated. Column chromatography of crude material afforded product 1,4-di-tert-butyl 2-methyl piperazine-1,2,4-tricarboxylate (29) as white solid (2.35 g, 90%).

NMR: δ ($^1$H, 400 MHz, $CDCl_3$): 1.45 (18H, s), 2.6-3.5 (4H, m), 3.74 (3H, s), 3.8-5.0 (3H, m).

4-(3-formylbenzoyl)piperazine-2-carboxylic acid (32)

To a solution of 1,4-di-tert-butyl 2-methyl piperazine-1,2,4-tricarboxylate 29 (1.0 g, 2.9 mmol) in DCM (20 mL) was added TFA (2.31 g, 20.3 mmol) at 0° C. The reaction mixture was stirred at RT for 4 h. TLC analysis indicated complete conversion of SM. Reaction was concentrated to remove excess of TFA and sticky solid so obtained was taken in DCM (20 mL). To this suspension, HATU (1.65 g, 4.34 mmol), NMM (293 mg, 2.9 mmol), 3-formylbenzoic acid (435 mg, 2.9 mmol), and DMAP (10 mg) were added. Reaction mixture was stirred at RT for 16 h. The reaction was monitored by LCMS. The reaction mixture was diluted with DCM and washed with water; organic layer was separated, dried over $Na_2SO_4$ and concentrated under reduced pressure. The sticky solid so obtained was added to a solution of NaOH (65 mg, 1.6 mmol) in MeOH (5 mL). Reaction mixture was stirred at rt for 7 h. The reaction was monitored by TLC. When SM was completely consumed, reaction mixture was concentrated under vacuum. The solid was suspended in water and acidified to pH 6 using 1 N HCl. The suspension was filtered and the precipitate was triturated with ethanol to give 766 mg (20%) of 4-(3-formylbenzoyl)piperazine-2-carboxylic acid 32 as sticky solid.

LCMS (254 nm): $[M+H]^+$ 276.95 (100%).

4-(3-(7-(((1R,2R,3S,4S)-3-carbamoylbicyclo[2.2.1]hept-5-en-2-ylamino)-6-chloro-3H-imidazo[4,5-b]pyridine-2-yl)benzoyl)piperazine-2-carboxylic acid (Compound CCXXV)

In an analogous manner to CCXXIII, (1S,2S,3R,4R)-3-(2,3-diamino-5-chloropyridin-4-ylamino)pyridin[2.2.1]hept-5-ene-2-carboxamide 6 (150 mg, 0.51 mmol) was reacted with 4-(3-formylbenzoyl)piperazine-2-carboxylic acid 32 (147 mg, 0.56 mmol) to afforded Compound CCXXV (30 mg, 16.4%) as yellow solid.

M.P: 261° C.

NMR: δ ($^1$H, 400 MHz, DMSO-$d_6$—$D_2O$ exchange): 1.37 (1H, d, J=8 Hz), 2.19 (1H, d, J=8.4 Hz), 2.60 (2H, d, J=8 Hz), 2.78 (1H, s), 2.87 (1H, s), 2.9-3.0 (1H, m), 3.1-3.8 (6H, m), 5.12 (1H, d, J=7.6 Hz), 6.3-6.5 (2H, m), 7.5-7.7 (2H, m), 7.94 (1H, s), 8.0-8.3 (2H, m).

LCMS (254 nm): $[M+H]^+$ 536.15 (98.57%).

HPLC: (254 nm) 91.79%.

Scheme 9

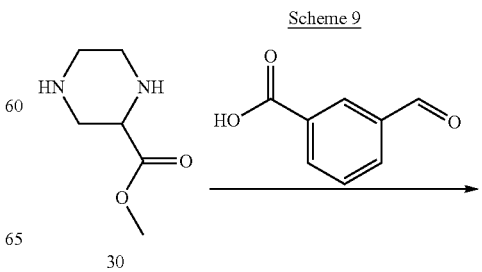

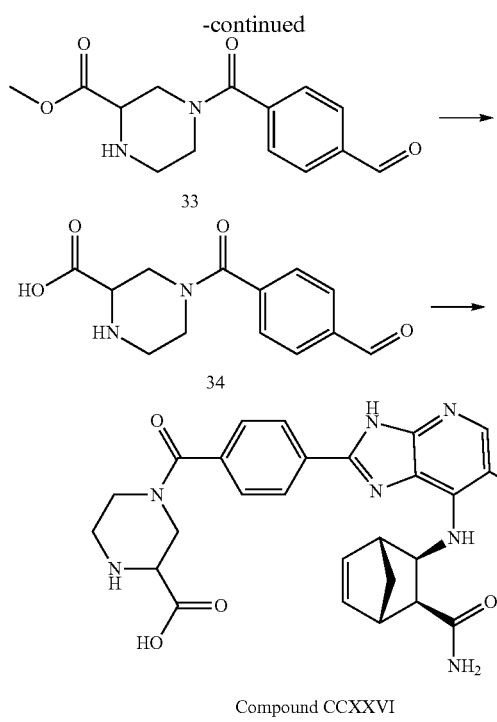

4-(4-formylbenzoyl)piperazine-2-carboxylic acid (34)

In an analogous manner to 32 1,4-di-tert-butyl 2-methyl piperazine-1,2,4-tricarboxylate 29 (1.0 g, 2.9 mmol) was reacted to give 766 mg (22%) of desired compound as sticky solid.

LCMS (254 nm): [M+H]$^+$ 276.95 (75.82%).

Compound CCXXVI

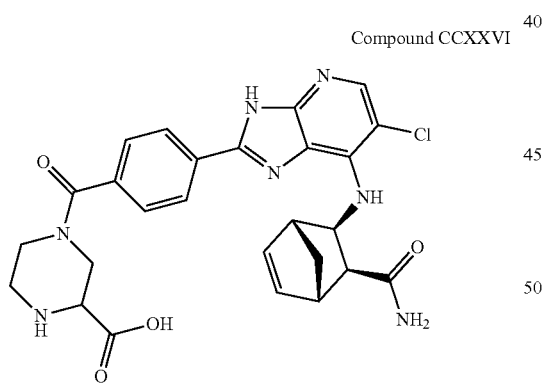

4-(4-(7-(((1R,2R,3S,4S)-3-carbamoylbicyclo[2.2.1] hept-5-en-2-ylamino)-6-chloro-3H-imidazo[4,5-b] 211pyridine-2-yl)benzoyl)piperazine-2-carboxylic acid (Compound CCXXVI)

In an analogous manner to CCXXIII, (1S,2S,3R,4R)-3-(2, 3-diamino-5-chloropyridin-4-ylamino)pyridin[2.2.1]hept-5-ene-2-carboxamide 6 (150 mg, 0.51 mmol) was reacted with 4-(4-formylbenzoyl)piperazine-2-carboxylic acid 34 (147 mg, 0.56 mmol) to afford Compound CCXXVI (30 mg, 11%) as yellow solid.

NMR: δ ($^1$H, 400 MHz, DMSO-d$_6$): 1.39 (1H, d, J=8.4 Hz), 2.24 (1H, d, J=8.4 Hz), 2.65 (2H, d, J=8.0 Hz), 2.81 (1H, s), 2.90 (1H, s), 2.96 (1H, t, J=11.6 Hz), 3.01-4.0 (6H, m), 5.1-5.2 (1H, m), 6.30-6.40 (2H, m), 7.2-7.3 (2H, m), 7.63 (2H, d, J=8 Hz), 7.80 (1H, bs), 7.80 (1H, s), 8.22 (2H, d, J=8 Hz), 13.46 (1H, bs).

LCMS (254 nm): [M+H]$^+$ 536.30 (94.14%).

HPLC: 94.64% (254 nm), 95.68% (220 nm).

Scheme 10

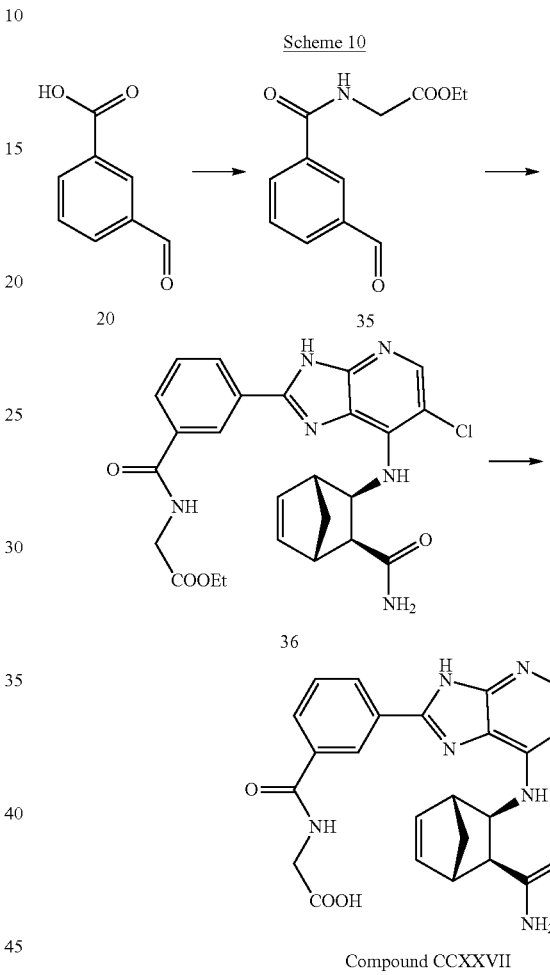

Compound CCXXVII

Ethyl 2-(3-formylbenzamido)acetate (35)

To a solution of 3-formylbenzoic acid 20 (0.1 g, 0.819 mmol) in DMF (2 mL) were added glycine ethyl ester (0.13 g, 0.98 mmol), HATU (0.37 g, 0.98 mmol), and NMM (0.2 g, (2.04 mmol). The reaction mixture was stirred at RT for 16 h. The reaction was monitored by LCMS. The reaction mixture was concentrated and column chromatographed to afford ethyl 2-(3-formylbenzamido)acetate 35 (146 mg).

Yield: 76%.

LCMS (254 nm): [M+H]$^+$ 235.95 (96.35%).

Ethyl 2-(3-(7-(((1R,2R,3S,4S)-3-carbamoylbicyclo [2.2.1]hept-5-en-2-ylamino)-6-chloro-3H-imidazo[4, 5-b]212yridine-2-yl)benzamido)acetate (36)

In an analogous manner to CCXXIII, (1S,2S,3R,4R)-3-(2, 3-diamino-5-chloropyridin-4-ylamino)212yridin[2.2.1] hept-5-ene-2-carboxamide (150 mg, 0.51 mmol) and ethyl 2-(3-formylbenzamido)acetate 35 (143 mg, 0.612 mmol) were reacted to afforded ethyl 2-(3-(7-((1R,2R,3S,4S)-3-carbamoylbicyclo[2.2.1]hept-5-en-2-ylamino)-6-chloro-3H-imidazo[4,5-b]212yridine-2-yl)benzamido)acetate 36 (120 mg, 46.3%).

LCMS (254 nm): [M+H]+ 509.10 (67.7%).

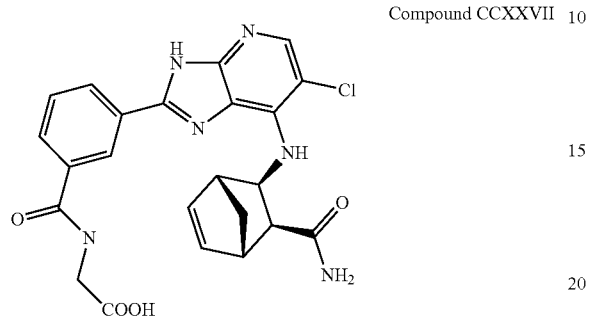

Compound CCXXVII 2-(3-(7-((1R,2R,3S,4S)-3-carbamoylbicyclo[2.2.1]
hept-5-en-2-ylamino)-6-chloro-3H-imidazo[4,5-b]
213yridine-2-yl)benzamido)acetic acid (Compound CCXXVII)

NaOH (19 mg, 0.47 μmol) was taken in MeOH/H2O (2:1; 3 mL) and added compound 36 (120 mg, 0.235 mmol). The reaction mixture was heated to 70° C. and stirred for 1 h. LCMS indicated complete consumption of starting material. The reaction mixture was concentrated under reduced pressure and the solid so obtained was suspended in H$_2$O and acidified with 1N HCl to pH 2. The solution was filtered and precipitated was triturated with ethanol to give desired product Compound CCXXVII as an off-white solid (113 mg, 68%).

NMR: δ ($^1$H, 400 MHz, DMSO-d$_6$ D$_2$O exchange): 1.38 (1H, d, J=8 Hz), 2.20 (1H, d, J=8.4 Hz), 2.63 (1H, d, J=8 Hz), 2.88 (1H, s), 3.81 (1H, s), 3.81 (2H, s), 5.12 (1H, d, J=7.6 Hz), 6.35-6.40 (1H, m), 6.46-6.51 (1H, m), 7.20-7.30 (1H, m), 7.64 (1H, t, J=8 Hz), 7.92 (1H, d, J=8 Hz), 7.95 (1H, s), 8.24 (1H, d, J=8 Hz), 8.66 (1H, s).

LCMS (254 nm): [M+H]+ 481.20 (97.79%).

HPLC: 95.91% (254 nm), 95.83% (220 nm).

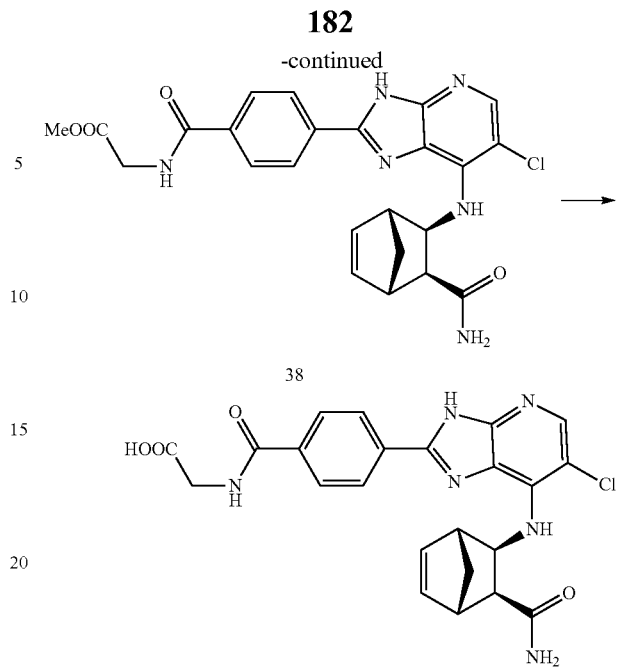

Methyl 2-(4-formylbenzamido)acetate (37)

In an analogous manner to 35, 4-formyl benzoic acid 24 (1.0 g, 6.66 mmol) was reacted with glycine methyl ester (653 mg, 7.33 mmol) to give 1.2 gm (81%) of methyl 2-(4-formylbenzamido)acetate 37 as an off-white solid (81%).

LCMS (254 nm): [M+H]+ 221.80 (99.81%)

Methyl 2-(4-(7-((1R,2R,3S,4S)-3-carbamoylbicyclo
[2.2.1]hept-5-en-2-ylamino)-6-chloro-3H-imidazo[4,
5-b]214yridine-2-yl)benzamido)acetate (38)

In an analogous manner to 36, methyl 2-(4-formylbenzamido)acetate 37 (226 mg, 1.02 mmol) and (1S,2S,3R,4R)-3-(2,3-diamino-5-chloropyridin-4-ylamino)pyridin[2.2.1]hept-5-ene-2-carboxamide (300 mg, 1.02 mmol) were reacted to obtain 120 mg (24%) of methyl 2-(4-(7-((1R,2R,3S,4S)-3-carbamoylbicyclo[2.2.1]hept-5-en-2-ylamino)-6-chloro-3H-imidazo[4,5-b]214yridine-2-yl)benzamido)acetate 38 as an off-white solid.

LCMS (254 nm): [M+H]+ 509.15 (47.48%)

2-(4-(7-((1R,2R,3S,4S)-3-carbamoylbicyclo[2.2.1]hept-5-en-2-ylamino)-6-chloro-3H-imidazo[4,5-b]pyridine-2-yl)benzamido)acetic acid (Compound CCXXVIII)

In an analogous manner to Compound CCXXVII, 38 (120 mg, 0.235 mmol) in was reacted to give 60 mg (53%) of Compound CCXXVIII as an off-white solid.

M.P: 291° C.

NMR: δ ($^1$H, 400 MHz, DMSO-$d_6$): 1.39 (1H, d, J=8.8 Hz), 2.23 (1H, d, J=8.4 Hz), 2.63 (1H, d, J=8.4 Hz), 2.81 (1H, s), 2.90 (1H, s), 3.93 (2H, d, J=5.6 Hz), 5.18 (1H, t, J=8.0 Hz), 6.3-6.5 (2H, m), 7.26 (1H, s), 7.30 (1H, d, J=8.8 Hz), 7.89 (1H, bs), 7.99 (1H, s), 8.02 (2H, d, J=8.0 Hz), 8.22 (2H, d, J=8.4 Hz), 8.88 (1H, bs), 13.44 (1H, s).

LCMS (254 nm): [M+H]$^+$ 481.15 (95.56%).

HPLC: 94.57% (220 nm).

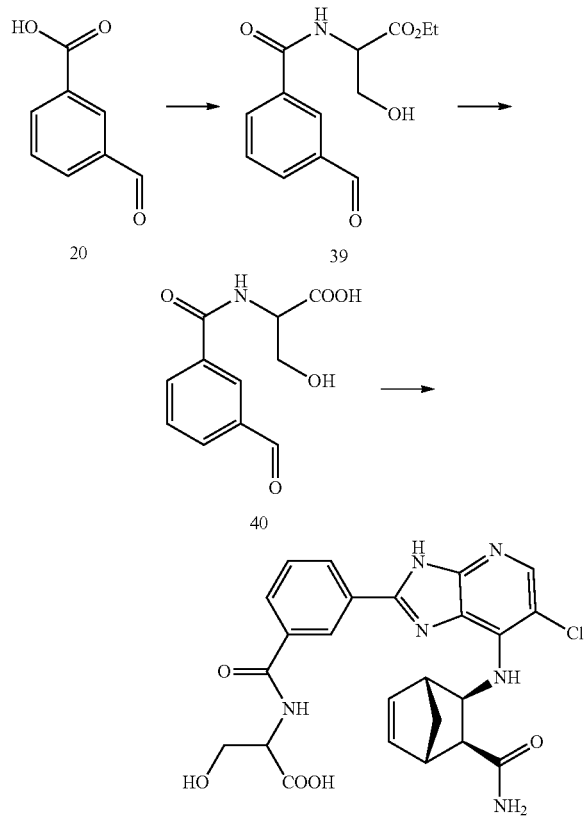

Scheme 12

Ethyl-2-(3-formylbenzamido)-3-hydroxypropane (39)

In an analogous manner to 35, 3-formyl benzoic acid 20 (1.0 g, 6.66 mmol) was reacted with ethyl 2-amino-3-hydroxypropanoate (975 mg, 7.33 mmol) to give 650 mg (36%) of 39 as an off-white sticky solid.

LCMS ⊗ 254 nm): [M+H]$^+$ 266.00 (93.64%).

Yield—36%.

Ethyl 2-(3-formylbenzamido)-3-hydroxypropanoic acid (40)

To a solution of compound 39 (200 mg, 0.75 mmol) in MeOH (2 ml) was added NaOH (120 mg, 3.01 mmol). The reaction mixture was stirred at r.t ° C. for 4 h. checked TLC, starting material consumed, adjust the pH up to 6 using 50% HCl and concentrated under vacuum to obtain 178 mg (100%) a white solid.

LCMS (254 nm): LCMS (254 nm): [M+Na]$^+$ 260.05 (87.03%).

Yield—100%.

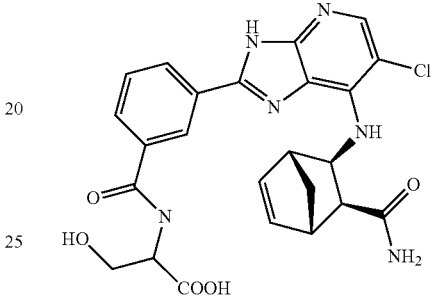

Compound CCXXIX

2-(3-(7-((1R,2R,3S,4S)-3-carbamoylbicyclo(2.2.1)hept-5-en-2-ylamino)-6-chloro-3H-imidazo[4,5-b]pyridine-2-yl)benzamido)-3-hydroxypropanoic acid (Compound CCXXIX)

In an analogous manner to Compound CCXXIII, ethyl 2-(3-formylbenzamido)-3-hydroxypropanoic acid (178 mg, 0.75 mmol) was reacted with (1S,2S,3R,4R)-3-(2,3-diamino-5-chloropyridin-4-ylamino)pyridin[2.2.1]hept-5-ene-2-carboxamide (198 mg, 0.67 mmol) to obtain 58 mg (16%) Compound CCXXIX as a yellow solid.

M.P: 243° C.

LCMS (254 nm): LCMS (254 nm): [M+H]$^+$ 511.10 (95.14%).

HPLC: 86.64% (254 nm).

NMR: δ ($^1$H, 400 MHz, DMSO-$d_6$): 1.38 (1H, d, J=8.0 Hz), 2.22 (1H, d, J=8.4 Hz), 2.64 (2H, d, J=8.4 Hz), 2.81 (1H, s), 2.90 (1H, s), 2.5-4.1 (5H, m), 5.16 (1H, t, J=8.0 Hz), 6.3-6.5 (2H, m), 7.23 (1H, s), 7.28 (1H, d, J=8.4 Hz), 7.64 (1H, t), 7.92 (1H, d, J=7.4 Hz), 7.96 (1H, s), 8.06 (1H, m,), 8.27 (1H, d, J=8.0 Hz), 8.68 (1H, s).

Scheme 13

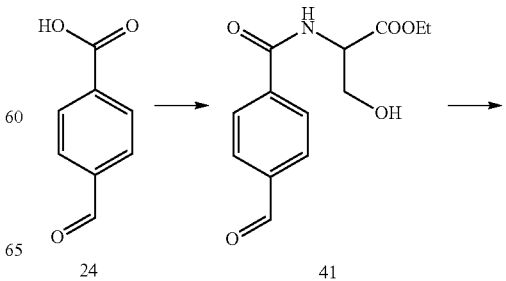

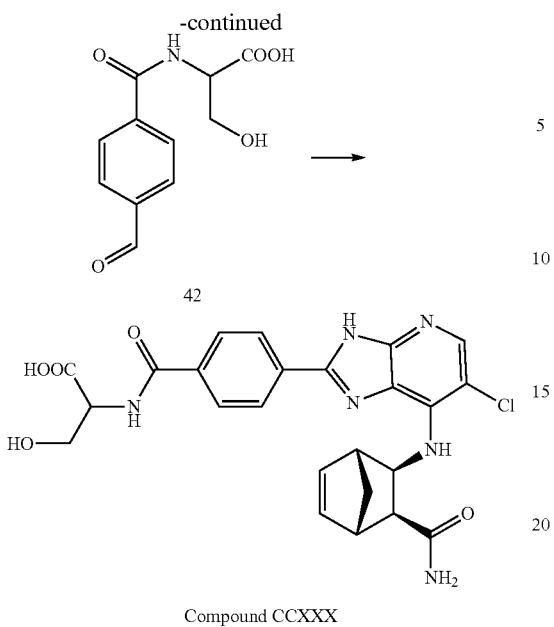

Ethyl 2-(4-formylbenzamido)-3-hydroxypropanoate (41)

In an analogous manner to 39, 4-formyl benzoic acid (24) (1.0 g, 6.66 mmol) and ethyl 2-amino-3-hydroxypropanoate (975 mg, 7.33 mmol) were reacted to yield 600 mg (34%) of 41 as an off-white sticky solid.

LCMS (254 nm): LCMS (254 nm): [M+H]$^+$ 266.05 (98.80%).

2-(4-formylbenzamido)-3-hydroxypropanoic acid (42)

In an analogous manner to 40, 41 (200 mg, 0.75 mmol) was reacted to obtain 157 mg (88%) a white solid.

LCMS (254 nm): LCMS (254 nm): [M+H]$^+$ 238.0 (83.69%).

Compound CCXXX

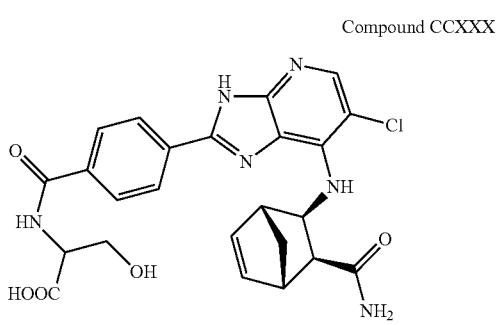 [SMILES: NC(=O)[C@@H]1[C@H](Nc2c(Cl)cnc3[nH]c(-c4ccc(C(=O)NC(CO)C(=O)O)cc4)nc23)[C@H]2C=C[C@@H]1C2]

2-(4-(7-((1R,2R,3S,4S)-3-carbamoylbicyclo(2.2.1) hept-5-en-2-ylamino)-6-chloro-3H-imidazo[4,5-b]pyridine-2-yl)benzamido)-3-hydroxypropanoic acid (Compound CCXXX)

In an analogous manner to CCXXIII, ethyl 2-(4-formylbenzamido)-3-hydroxypropanoic acid (157 mg, 0.66 mmol) was reacted with (1S,2S,3R,4R)-3-(2,3-diamino-5-chloropyridin-4-ylamino)pyridin[2.2.1]hept-5-ene-2-carboxamide (174 mg, 0.59 mmol) to obtain 17 mg yellow solid.

NMR: δ ($^1$H, 400 MHz, DMSO-d$_6$): 1.378 (1H, d, J=7.2 Hz), 2.21 (1H, d, J=8.4 Hz), 2.62 (1H, d, J=7.6 Hz), 2.80 (1H, s), 2.89 (1H, s), 2.99 (1H, bs), 3.2-4.0 (3H, m) 5.16 (1H, t, J=8.0 Hz), 6.3-6.5 (2H, m), 7.24 (1H, s), 7.41 (1H, bs,), 7.77 (2H, bs), 7.99 (1H, s), 8.04 (2H, d, J=8.0 Hz), 8.21 (2H, d, J=8.4 Hz), 8.48 (1H, d, J=7.6 Hz), 13.47 (1H, s).

M.P: 186° C.

LCMS (254 nm): LCMS (254 nm): [M+H]$^+$ 511.20 (96.25%).

HPLC: 98.12% (254 nm), 93.34% (220 nm).

Compound CCXXXI

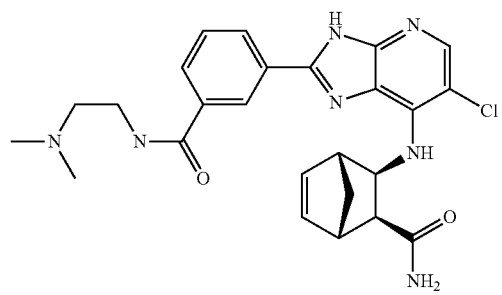

(1S,2S,3R,4R)-3-(6-chloro-2-(3-(2-(dimethylamino) ethylcarbamoyl)phenyl)-3H-imidazo[4,5-b]pyridine-7-ylamino)pyridin[2.2.1]hept-5-ene-2-carboxamide (Compound CCXXXI)

In an analogous manner to Compound CCXXI, Compound CXCVII was reacted with N,N-dimethyl-ethane-1,2-diamine to obtain Compound CXXXI (12%).

NMR: δ ($^1$H, 400 MHz, DMSO-d$_6$): 1.39 (1H, d, J=8 Hz), 2.22 (1H, d, J=8.4 Hz), 2.62 (2H, d, J=8 Hz), 2.86 (3H, s), 2.87 (3H, s), 2.91 (1H, s), 3.29 (2H, d, J=5.2 Hz), 3.66-3.71 (2H, m), 5.11 (1H, t, J=8 Hz), 6.38 (1H, bs), 6.51 (1H, bs), 7.27 (1H, s), 7.44 (1H, bs), 7.68 (1H, t, J=7.2 Hz), 7.80 (1H, s), 7.93 (1H, d, J=7.6 Hz), 7.99 (1H, s), 8.28 (1H, d, J=7.2 Hz), 8.72 (1H, s), 8.78 (1H, bs), 9.32 (1H, bs), 13.47 (1H, bs).

LCMS (254 nm): [M+H]$^+$ 494.10 (99.46%).

HPLC: 98.64% (254 nm), 98.79% (220 nm).

Scheme 13

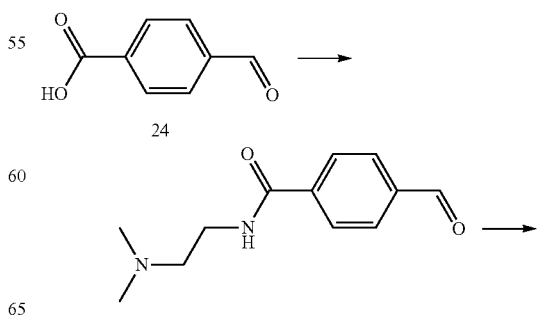

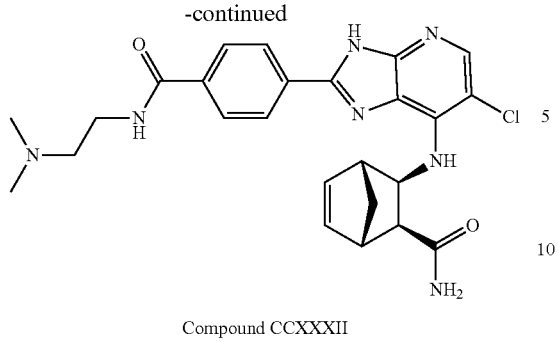

Compound CCXXXII

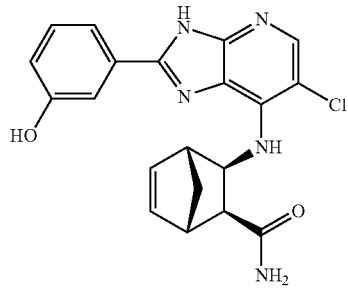

Compound CCXXXIII

N-(2-Dimethylamino-ethyl)-4-formyl-benzamide (43)

To a solution of 4-formylbenzoic acid (24) (300 mg, 1.99 mmol) in DCM (4 mL) were added N,N-dimethylethane-1,2-diamine (193.8 mg, 2.19 mmol), HATU (911.8 mg, 2.4 mmol), NMM (505 mg, 5.0 mmol), and DMAP (24 mg, 0.199 mg) at RT. The reaction mixture was stirred at RT for 16 h. The reaction was monitored by LCMS. After 16 h, RM was washed with water and organic layer was concentrated after drying over $Na_2SO_4$. Column purification of crude material afforded pure product as oil.
Yield: 95.67%.
LCMS (254 nm): [M+H]$^+$ 221.0 (82.15%).

(1S,2S,3R,4R)-3-(6-chloro-2-(3-hydroxyphenyl)-3H-imidazo[4,5-b]pyridin-7-ylamino)pyridin[2.2.1]hept-5-ene-2-carboxamide (Compound CCXXXIII)

Yield: 53%.
NMR: δ ($^1$H, 400 MHz, DMSO-d$_6$): 1.38 (1H, d, J=8.4 Hz), 2.23 (1H, d, J=8.4 Hz), 2.61 (1H, d, J=8.4 Hz), 2.79 (1H, s), 2.89 (1H, s), 5.15 (1H, t, J=16.8 Hz), 6.35-6.37 (1H, m), 6.45-6.46 (1H, m) 6.87 (1H, d, J=7.6 Hz), 7.19-7.24 (2H, m), 7.32 (1H, t, J=8 Hz), 7.56 (2H, d, J=2 Hz), 7.78 (1H, s), 7.94 (1H, s), 9.74 (1H, s), 13.2 (1H, s).
LCMS (254 nm): [M+H]$^+$ 396.10 (99.23%).
HPLC: 99.2% (254 nm), 95.9% (220 nm).

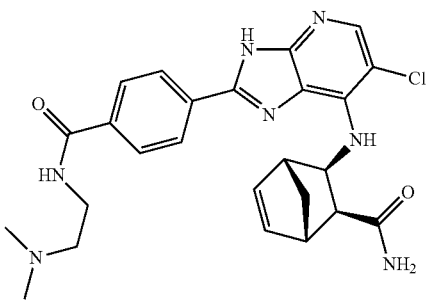

Compound CCXXXII

(1S,2S,3R,4R)-3-{6-Chloro-2-[4-(2-dimethylamino-ethylcarbamoyl)-phenyl]-3H-imidazo[4,5-b]pyridine-7-ylamino}-bicyclo[2.2.1]hept-5-ene-2-carboxylic acid amide (Compound CCXXXII)

In an analogous manner to Compound CCXXIII, (1S,2S,3R,4R)-3-(2,3-diamino-5-chloropyridin-4-ylamino)pyridin[2.2.1]hept-5-ene-2-carboxamide (250 mg, 0.851 mmol) and compound 43 (187 mg, 0.851 mmol were reacted to afford TFA salt of Compound CCXXXII as off-white solid product.
Yield: 12%.
NMR: δ ($^1$H, 400 MHz, CD$_3$OD): 1.57 (1H, d, J=8.8 Hz), 2.89 (1H, d, J=9.2 Hz), 2.77 (1H, d, J=8 Hz), 3.01 (6H, s), 3.05 (1H, s), 3.35 (1H, s), 3.43 (2H, t, J=5.6 Hz), 3.81 (2H, t, J=5.6 Hz), 5.29 (1H, d, J=7.6 Hz), 6.4-6.49 (2H, m), 8.04 (2H, d, J=8.0 Hz), 8.12 (1H, s), 8.22 (2H, d, J=8.4 Hz).
LCMS (254 nm): [M+H]$^+$ 494.10 (100%).
HPLC: (254 nm) 96%.
In an analogous manner as for the synthesis of Compound CCXXXII, Compounds CCXXXIII-CCXXXVI were prepared.

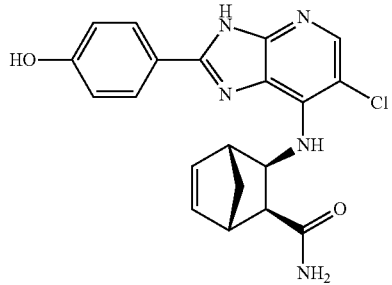

Compound CCXXXIV

(1S,2S,3R,4R)-3-(6-chloro-2-(4-hydroxyphenyl)-3H-imidazo[4,5-b]pyridin-7-ylamino)bicyclo[2.2.1]hept-5-ene-2-carboxamide (Compound CCXXXIV)

Yield: 45%.
NMR: δ ($^1$H, 400 MHz, DMSO-d$_6$): 1.39 (1H, d, J=8 Hz). 2.21 (1H, d, J=8 Hz), 2.62 (1H, d, J=8 Hz), 2.81 (H, s), 2.91 (1H, s), 4.28 (1H, bs), 5.15 (1H, bs), 6.37-6.40 (2H, m), 6.92 (2H, d, J=8 Hz), 7.27 (1H, s), 7.53 (1H, bs), 7.81 (1H, bs), 7.97 (2H, d, J=8.4 Hz), 9.9 (1H, bs,), 13.2 (1H, bs).
LCMS: (254 nm): [M+H]$^+$ 396.00 (99.9%).
HPLC: 99.215% (254 nm), 95.996% (220 nm).

Compound CCXXXV

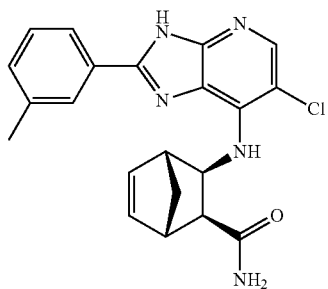

(1S,2S,3R,4R)-3-(6-chloro-2-(3-methoxyphenyl)-3H-imidazo[4,5-b]pyridin-7-ylamino)bicyclo[2.2.1]hept-5-ene-2-carboxamide (Compound CCXXXV)

Yield: 40%.

NMR: δ ($^1$H, 400 MHz, DMSO-d$_6$): 1.39 (1H, d, J=8.4 Hz), 2.24 (1H, d, J=8.4 Hz), 2.63 (1H, d, J=8.4 Hz), 2.81 (1H, s), 2.90 (1H, s), 3.40-3.50 (1H, m), 3.86 (3H, s), 5.18 (1H, t, J=8.4 Hz), 6.39 (2H, s), 7.06 (1H, d, J=8 Hz), 7.24 (2H, s), 7.46 (1H, t, J=8 Hz), 7.73-7.80 (3H, m), 7.96 (1H, s), 13.31 (1H, bs).

LCMS (254 nm): [M+H]$^+$ 409.95 (99.057%).

HPLC: 98.419% (254 nm), 98.212% (220 nm).

Compound CCXXXVI

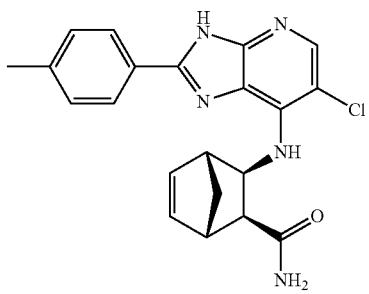

(1S,2S,3R,4R)-3-(6-chloro-2-(4-methoxyphenyl)-3H-imidazo[4,5-b]pyridin-7-ylamino)bicyclo[2.2.1]hept-5-ene-2-carboxamide (Compound CCXXXVI)

Yield: 30%.

NMR: δ ($^1$H, 400 MHz, DMSO-d$_6$): 1.38 (1H, d, J=8.4 Hz), 2.24 (1H, d, J=7.6 Hz), 2.33 (1H, m), 2.67 (1H, s), 2.79 (1H, s), 2.89 (1H, s), 3.83 (3H, s), 5.16-5.20 (1H, m), 6.37-6.40 (2H, m), 7.11 (2H, d, J=8.4 Hz), 7.23 (1H, bs), 7.76 (1H, s), 7.92 (1H, s), 8.08 (2H, d, J=8.4 Hz), 13.14 (1H, bs).

LCMS (254 nm): [M+H]$^+$ 410.00 (99.172%).

HPLC: 98.245% (254 nm), 98.489% (220 nm).

Scheme 14

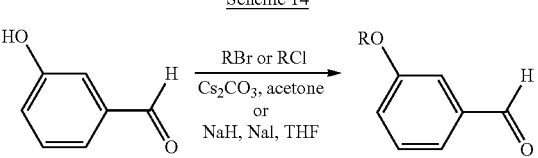

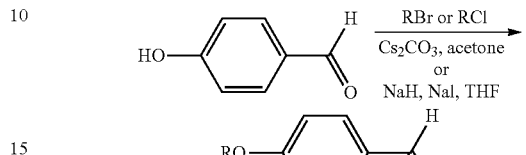

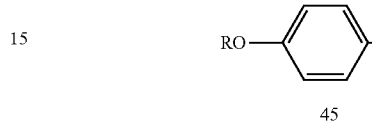

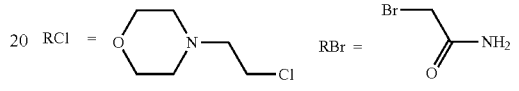

Synthesis of 3-(2-morpholinoethoxy)benzaldehyde (44a) and 4-(2-morpholinoethoxy)benzaldehyde (45a)

General Procedure:

3-hydroxy benzaldehyde/4-hydroxy benzaldehyde (1 eq) and 4-(2-chloroethyl)morpholine hydrochloride (1.1 eq) were taken in acetone to which Cs$_2$CO$_3$ (2 eq) was added and the reaction mixture was refluxed for 16 h when TLC indicated completion of reaction. The reaction mixture was cooled and filtered, the residue washed well with acetone. The filtrate was concentrated and purified by column chromatography using silica gel (100-200 mesh) to afford the pure product.

3-(2-morpholinoethoxy)benzaldehyde (44a)

colorless sticky oil
Yield: 38%.
LCMS: 95.4% (M$^+$+1).

4-(2-morpholinoethoxy)benzaldehyde (45a)

colorless sticky oil
Yield: 39%.
NMR: δ 2.53-2.62 (m, 4H), 2.284 (t, J=5.6 Hz, 2H), 3.695 (t, J=4.8 Hz, 4H), 4.232 (t, J=5.6 Hz, 2H), 7.091 (d, J=8.8 Hz, 2H), 7.85 (d, J=9.2 Hz, 2H), 9.817 (s, 1H).

Synthesis of 2-(3-formylphenoxy)acetamide (44b) and 2-(4-formylphenoxy)acetamide (45b)

General Procedure:

3-hydroxy benzaldehyde/4-hydroxy benzaldehyde (1 eq), 2-bromoacetamide (1.2 eq) and NaI (0.07 eq) were taken in THF and cooled to 0° C. to which NaH (3 eq) was added portionwise. The reaction mixture was allowed to come to rt and heated at 70° C. for 4 h when TLC confirmed completion of reaction. The reaction mixture was cooled to rt and quenched with cold water. Extraction was done with EtOAc. The combined organic extracts was dried, concentrated and purified by column chromatography using silica gel (100-200 mesh) to afford the pure product.

2-(3-formylphenoxy)acetamide (44b)

white solid
Yield: 43%.
NMR: δ 4.525 (s, 2H), 7.28-7.44 (m, 3H), 7.51-7.62 (m, 3H), 9.975 (s, 1H).

2-(4-formylphenoxy)acetamide (45b)

off white solid
Yield: 54%.
LCMS: 100% (M$^+$+1).

Compounds CCXXXVII-CCXL were synthesized in a similar fashion as for the synthesis of Compound CCXXXVI.

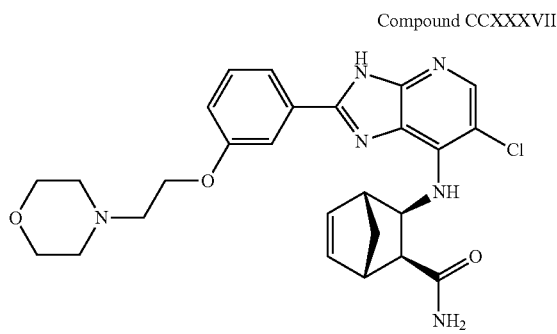 [SMILES: NC(=O)[C@@H]1[C@H](Nc2c(Cl)cnc3[nH]c(-c4cccc(OCCN5CCOCC5)c4)nc23)[C@H]2C=C[C@@H]1C2]
Compound CCXXXVII

(1S,2S,3R,4R)-3-(6-chloro-2-(3-(2-morpholinoethoxy)phenyl)-3H-imidazo[4,5-b]pyridine-7-ylamino)pyridin[2.2.1]hept-5-ene-2-carboxamide (Compound CCXXXVII)

Yield: 47% of an offwhite solid.
NMR: δ ($^1$H, 400 MHz, DMSO-d$_6$): 1.39 (1H, d, J=8.4 Hz), 2.24 (1H, d, J=8.8 Hz), 2.63 (1H, d, J=8 Hz), 2.75 (2H, t, J=5.6 Hz), 2.81 (1H, bs), 2.90 (1H, bs), 3.2-3.4 (4H, m), 3.5-3.7 (4H, m), 4.18 (2H, t, J=6.0 Hz), 5.17 (1H, t, J=8 Hz), 6.37 (2H, d, J=4.8 Hz), 7.05 (1H, d, J=8 Hz), 7.21-7.23 (2H, m), 7.44 (1H, t, J=7.6 Hz), 7.73-7.84 (3H, m), 7.96 (1H, s), 13.26 (1H, bs).
LCMS (254 nm): [M+H]$^+$ 509.10 (97.28%).
HPLC: 97.087% (254 nm), 96.340% (220 nm).

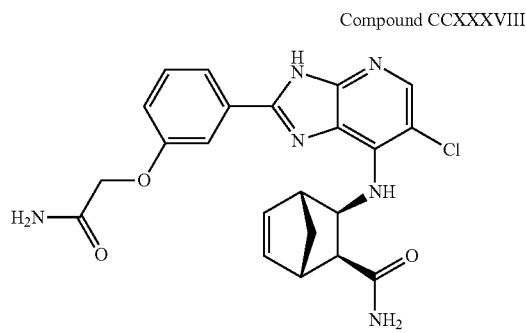 [SMILES: NC(=O)COc1cccc(-c2nc3c(N[C@H]4[C@@H](C(N)=O)[C@@H]5C=C[C@H]4C5)c(Cl)cnc3[nH]2)c1]
Compound CCXXXVIII

(1S,2S,3R,4R)-3-(2-(3-(2-amino-2-oxoethoxy)phenyl)-6-chloro-3H-imidazo[4,5-b]pyridin-7-ylamino)bicyclo[2.2.1]hept-5-ene-2-carboxamide (Compound CCXXXVIII)

Yield: 52% of an offwhite solid.
NMR: δ ($^1$H, 400 MHz, DMSO-d$_6$): 1.38 (1H, d, J=8.8 Hz), 2.23 (1H, d, J=8.4 Hz), 2.62 (1H, d, J=8.4 Hz), 2.79 (1H, s), 2.89 (1H, s), 5.17 (1H, t, J=8.0 Hz), 4.5 (2H, s), 6.40 (2H, m), 7.06 (1H, d, J=8 Hz), 7.42-7.56 (3H, m), 7.74-7.77 (3H, m), 7.96 (1H, bs), 13.21 (1H, bs).
LCMS (254 nm): [M+H]$^+$ 454.75 (95.96%).
HPLC: 94.30% (254 nm), 92.17% (220 nm).

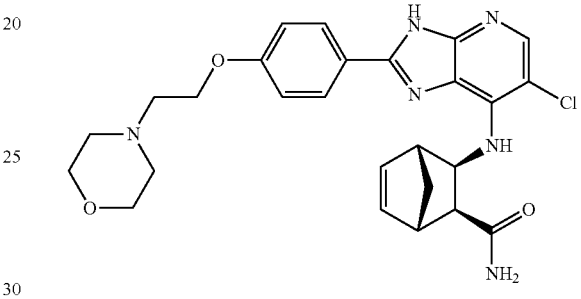
Compound CCXXXIX

(1S,2S,3R,4R)-3-(6-chloro-2-(4-(2-morpholinoethoxy)phenyl)-3H-imidazo[4,5-b]pyridin-7-ylamino)bicyclo[2.2.1]hept-5-ene-2-carboxamide (Compound CCXXXIX)

Yield: 35% of a brown sticky solid (TFA salt).
NMR: δ ($^1$H, 400 MHz, DMSO-d$_6$): 1.38 (1H, d, J=8.4 Hz), 2.22 (1H, d, J=8.4 Hz), 2.61 (1H, d, J=8.4 Hz), 2.81 (1H, s), 2.91 (1H, s), 3.1-3.97 (10H, m), 4.4-4.5 (2H, m), 5.15 (1H, t, J=8 Hz), 6.35-6.40 (2H, m), 7.19 (2H, d, J=8.8 Hz), 7.26 (1H, bs), 7.41 (1H, bs), 7.80 (1H, bs), 7.99 (1H, s), 8.11 (2H, d, J=8.8 Hz), 13.31 (1H, bs).
LCMS (254 nm): 509.05 [M+H]$^+$ (99.639%).
HPLC: 98.381% (254 nm), 96.899% (220 nm).

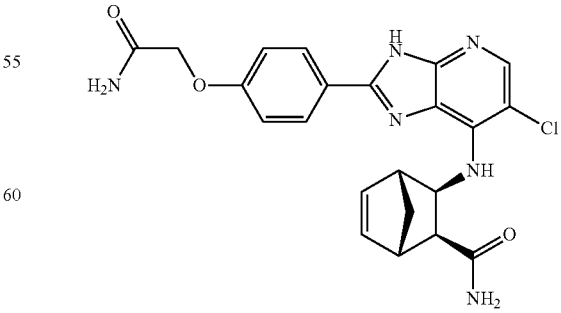
Compound CCXL (1S,2S,3R,4R)-3-(2-(4-(2-amino-2-oxoethoxy)phenyl)-6-chloro-3H-imidazo[4,5-b]pyridin-7-ylamino)bicyclo[2.2.1]hept-5-ene-2-carboxamide (Compound CCXL)
Yield: 27% of an off white solid.
NMR: δ (¹H, 400 MHz, DMSO-d₆): 1.38 (1H, d, J=8 Hz), 2.23 (1H, d, J=8.8 Hz), 2.62 (1H, d, J=8 Hz), 2.78 (1H, s), 2.89 (1H, s), 4.52 (2H, s), 5.18 (1H, t, J=8.4 Hz), 6.20-6.45 (2H, m), 7.10-7.14 (3H, m), 7.23 (1H, bs), 7.43 (1H, bs), 7.57 (1H, bs), 7.76 (1H, bs), 7.92 (1H, s), 8.07 (2H, d, J=8.8 Hz), 13.13 (1H, bs).
LCMS (254 nm): [M+H]⁺ 453.25 (94.74%).
HPLC: 92.39% (220 nm).
Scheme 15
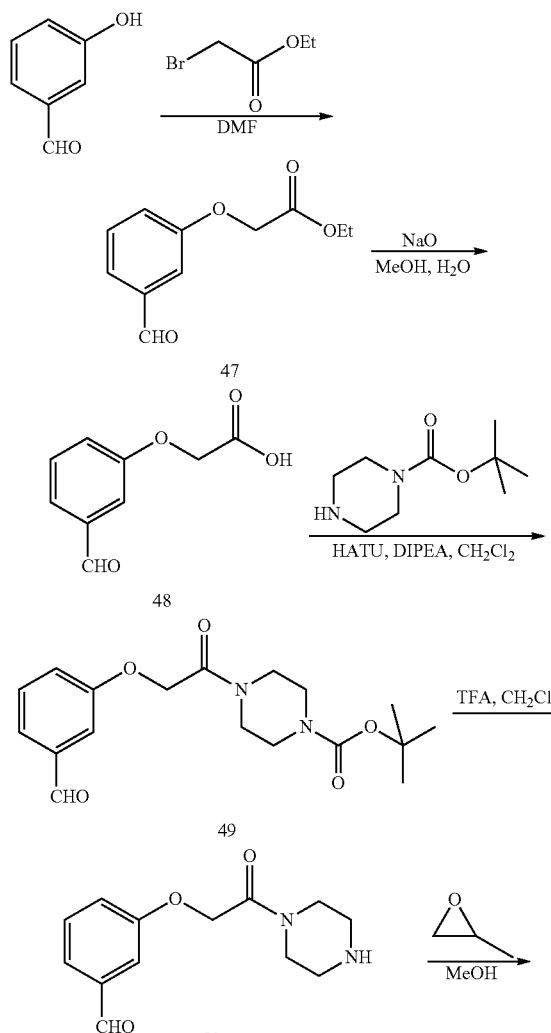
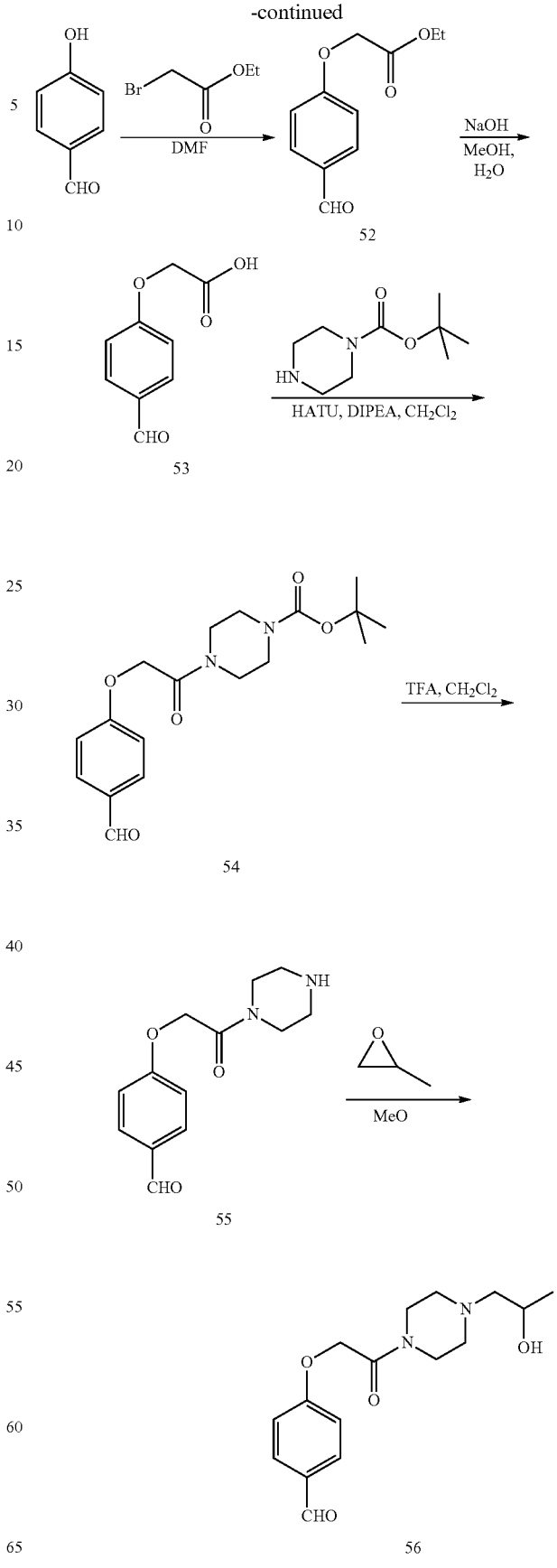

Ethyl 2-(3-formylphenoxy)acetate (47)

3-hydroxy benzaldehyde/ethyl 2-bromoacetate (1.1 eq) and K$_2$CO$_3$ (2 eq) were taken in DMF and heated at 80° C. for 16 h when TLC indicated completion of reaction. The reaction mixture was cooled to rt and poured into water. Extraction was done with DCM. The combined organic extracts was dried, concentrated and purified by column chromatography using silica gel (100-200 mesh) to afford the pure product (23%) as a colorless oil. NMR: δ 1.298 (t, J=7.2 Hz, 3H), 4.27 (q, J=7.2 Hz, 2H), 4.683 (s, 1H), 7.20-7.27 (m, 1H), 7.361 (s, 1H), 7.42-7.52 (m, 2H), 9.96 (s, 1H).

2-(3-Formylphenoxy)acetic acid (48)

ethyl 2-(3-formylphenoxy)acetate (47)/(1 eq) was taken in MeOH and cooled to 0° C. when NaOH (2 eq) solution was added drop wise. After completion of addition the reaction mixture was stirred at rt for 30 min. The reaction mixture was cooled to rt and acidified with dil HCl to attain pH 3 when a precipitate appeared which was filtered and washed well with water and dried well to yield a white solid (49%). NMR: δ 4.754 (s, 1H), 7.23-7.27 (m, 1H), 7.349 (s, 1H), 7.449 (d, J=4.8 Hz, 2H), 9.938 (s, 1H), 13.07 (s, 1H).

Tert-Butyl 4-(2-(3-formylphenoxy)acetyl)piperazine-1-carboxylate (49)

2-(3-formylphenoxy)acetic acid (48)/(1 eq), tert-butyl piperazine-1-carboxylate (1.5 eq) were taken in DCM to which HATU (1.3 eq) and DIPEA (2 eq) along with cat. DMAP were added and the traction mixture was stirred at rt for 16 h when TLC indicated completion of reaction. The reaction mixture was diluted with DCM and the organic extract was washed with water, dried and purified by column chromatography using silica gel (100-200 mesh) to afford the pure product (29%) as a colorless oil. LCMS: 91.65% (M$^+$+1-Boc).

3-(2-oxo-2-(piperazin-1-yl)ethoxy)benzaldehyde (50)

tert-butyl 4-(2-(3-formylphenoxy)acetyl)piperazine-1-carboxylate (49)/(5.55 mmol) was taken in DCM and cooled to 0° C. when TFA (5 ml) was added drop wise and then stirred at rt for 16 h when TLC confirmed completion of reaction. The reaction mixture was concentrated and neutralized with satd NaHCO$_3$ solution followed by extraction with DCM. The combined organic extracts was dried, concentrated and used directly for the next step (86%). LCMS: 98.12% (M$^+$+1).

3-(2-(4-(2-hydroxypropyl)piperazin-1-yl)-2-oxoethoxy)benzaldehyde (51)

3-(2-oxo-2-(piperazin-1-yl)ethoxy)benzaldehyde (50) (1 eq) was taken in MeOH to which propylene oxide (4 eq) was added and the reaction mixture was heated in a sealed tube at 70° C. for 16 h when LCMS showed completion of reaction. The reaction mixture was concentrated and purified by column chromatography using silica gel (100-200 mesh) to afford the pure product (50%) as a colorless oil. LCMS: 96.31% (M$^+$+1).

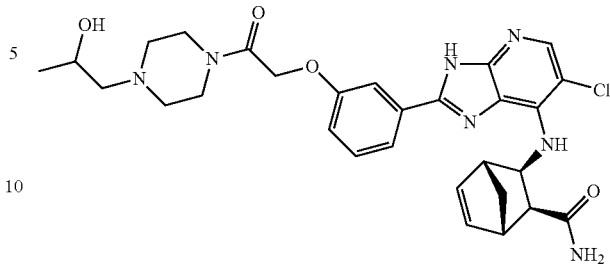

Compound CCXLI

(1S,2S,3R,4R)-3-(6-chloro-2-(3-(2-(4-(2-hydroxypropyl)piperazin-1-yl)-2-oxoethoxy)phenyl)-3H-imidazo[4,5-b]pyridin-7-ylamino)bicyclo[2.2.1]hept-5-ene-2-carboxamide (Compound CCXLI)

(1S,2S,3R,4R)-3-(2,3-Diamino-5-chloro-pyridin-4-ylamino)-bicyclo[2.2.1]hept-5-ene-2-carboxylic acid amide (1 eq.) and 3-(2-(4-(2-hydroxypropyl)piperazin-1-yl)-2-oxoethoxy)benzaldehyde (51) (1.1 eq) were reacted in an analogous manner as compound CCXXIII to yield the desired product (17%) as a yellow, sticky, TFA salt.

NMR: δ ($^1$H, 400 MHz, DMSO-d$_6$): 1.11 (3H, d, J=6.4 Hz), 1.12-1.20 (2H, m), 1.39 (1H, d, J=8.4 Hz), 2.23 (1H, d, J=8.0 Hz), 2.62 (1H, d, J=8.0 Hz), 2.81 (1H, s), 2.91 (1H, s), 2.99-3.30 (5H, m), 3.8-5.0 (5H, m), 5.15 (1H, t, J=8.8 Hz), 5.75 (1H, s), 6.38 (2H, s), 7.06 (1H, d, J=8.0 Hz), 7.26 (1H, s), 7.35 (1H, bs), 7.45 (1H, d, J=8 Hz), 7.70-7.78 (3H, m), 7.98 (1H, s), 9.63 (1H, bs), 13.34 (1H, bs), LCMS (254 nm): [M+H]$^+$ 580.10 (96.71%), HPLC: 95.75% (254 nm), 94.16% (220 nm).

Ethyl 2-(4-formylphenoxy)acetate (52)

In an analogous manner to compound 47, 4-hydroxy benzaldehyde (1 eq) and ethyl 2-bromoacetate (1.1 eq) were reacted to produce the desired product (52%) as a brown oil. NMR: δ 1.306 (t, J=6.8 Hz, 3H), 4.29 (q, J=7.2 Hz, 2H), 4.710 (s, 2H), 7.016 (d, J=8.8 Hz, 2H), 7.85 (d, J=8.8 Hz, 2H), 9.904 (s, 1H).

2-(4-Formylphenoxy)acetic acid (53)

Ethyl 2-(4-formylphenoxy)acetate (52) was treated in an analogous manner to compound 48 to yield the desired product (57%) as a white solid. NMR: δ 4.834 (s, 2H), 7.112 (d, J=7.2 Hz, 2H), 7.866 (d, J=7.6 Hz, 2H), 9.878 (s, 1H), 13.146 (s, 1H).

Tert-Butyl 4-(2-(4-formylphenoxy)acetyl)piperazine-1-carboxylate (54)

2-(4-Formylphenoxy)acetic acid (53) was treated in an analogous manner to Compound 49 to afford the desired product (74%) as a white solid. NMR: δ 1.461 (s, 9H), 3.38-3.64 (m, 8H), 4.802 (s, 2H), 2.06 (d, J=8.4 Hz, 2H), 7.85 (d, J=8.8 Hz, 2H), 9.899 (s, 1H).

4-(2-oxo-2-(piperazin-1-yl)ethoxy)benzaldehyde (55)

tert-Butyl 4-(2-(4-formylphenoxy)acetyl)piperazine-1-carboxylate (54) was treated in an analogous manner to compound 50 to yield the desired product (60%) as a pale yellow solid. LCMS: 97% (M$^+$+1).

4-(2-(4-(2-hydroxypropyl)piperazin-1-yl)-2-oxoethoxy)benzaldehyde (56)

4-(2-oxo-2-(piperazin-1-yl)ethoxy)benzaldehyde (55) was treated in an analogous manner to compound 51 to yield the desired product (66%) as a colorless oil. LCMS: 96% (M$^+$+1).

Compound CCXLII

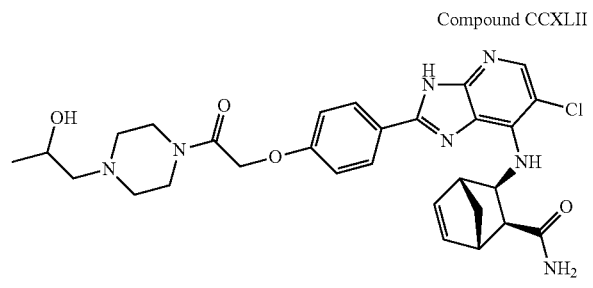 [SMILES: CC(O)CN1CCN(C(=O)COc2ccc(-c3nc4c(N[C@H]5[C@@H](C(N)=O)[C@@H]6C=C[C@H]5C6)c(Cl)cnc4[nH]3)cc2)CC1]

(1S,2S,3R,4R)-3-(6-chloro-2-(4-(2-(4-(2-hydroxypropyl)piperazin-1-yl)-2-oxoethoxy)phenyl)-3H-imidazo[4,5-b]pyridin-7-ylamino)bicyclo[2.2.1]hept-5-ene-2-carboxamide (Compound CCXLII)

(1S,2S,3R,4R)-3-(2,3-Diamino-5-chloro-pyridin-4-ylamino)-bicyclo[2.2.1]hept-5-ene-2-carboxylic acid amide (1 eq.) and 4-(2-(4-(2-hydroxypropyl)piperazin-1-yl)-2-oxoethoxy)benzaldehyde (56) (1.1 eq) were reacted in an analogous manner as compound CCXXIII to yield the desired product (33%) as a white solid, TFA salt. NMR: δ ($^1$H, 400 MHz, DMSO-d$_6$): 1.25 (3H, d, J=6.0 Hz), 1.57 (1H, d, J=8.4 Hz), 2.28 (1H, d, J=8.8 Hz), 2.76 (1H, d, J=8.0 Hz), 3.0-3.35 (5H, m), 3.45-3.6 (2H, m), 3.7-4.3 (3H, m), 4.8-5.00 (5H, m), 5.25 (2H, d, J=6.4 Hz), 6.45-6.47 (2H, m), 7.17 (2H, d, J=8.0 Hz), 8.08 (2H, d, J=8.4 Hz), 8.12 (1H, s), LCMS (254 nm): [M+H]$^+$ 580.10 (97.07%), HPLC: 98.37% (254 nm), 96.60% (220 nm).

3-(2-(4-methylpiperazin-1-yl)-2-oxoethoxy)benzaldehyde (57)

2-(3-Formylphenoxy)acetic acid (48) was treated with 1-methylpiperidine in an analogous manner to Compound 49 to afford the desired product (57%) as a colorless oil. LCMS: 99.0% (M$^+$+1).

Compound CCXLIII

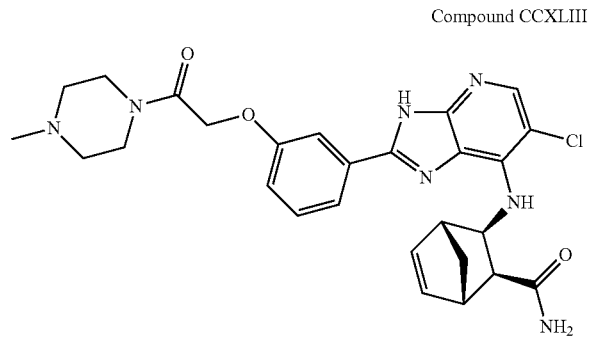 [SMILES: CN1CCN(C(=O)COc2cccc(-c3nc4c(N[C@H]5[C@@H](C(N)=O)[C@@H]6C=C[C@H]5C6)c(Cl)cnc4[nH]3)c2)CC1]

(1S,2S,3R,4R)-3-(6-chloro-2-(3-(2-(4-methylpiperazin-1-yl)-2-oxoethoxy)phenyl)-3H-imidazo[4,5-b]pyridine-7-ylamino)pyridin[2.2.1]hept-5-ene-2-carboxamide (Compound CCXLIII)

(1S,2S,3R,4R)-3-(2,3-Diamino-5-chloro-pyridin-4-ylamino)-bicyclo[2.2.1]hept-5-ene-2-carboxylic acid amide (1 eq.) and 3-(2-(4-methylpiperazin-1-yl)-2-oxoethoxy)benzaldehyde (57) (1.1 eq) were reacted in an analogous manner as compound CCXXIII to yield the desired product (59%) as a white solid. NMR: δ ($^1$H, 400 MHz, DMSO-d$_6$): 1.38 (1H, d, J=8.4 Hz), 2.19 (3H, s), 2.23 (1H, d, J=8.8 Hz) 2.25-2.28 (2H, m), 2.30-2.40 (2H, m), 2.62 (1H, d, J=8.4 Hz), 2.80 (1H, s), 2.90 (1H, s), 3.40-3.50 (4H, m), 4.91 (2H, s), 5.12 (1H, t, J=8 Hz), 6.35-6.41 (2H, m), 7.02-7.05 (1H, m), 7.23-7.25 (2H, m), 7.45 (1H, t, J=8 Hz), 7.68-7.77 (3H, m), 7.96 (1H, s), 13.29 (1H, bs).

LCMS (254 nm): [M+H]$^+$ 536.25 (98.87%).

HPLC: 98.43% (254 nm), 97.34% (220 nm).

4-(2-(4-methylpiperazin-1-yl)-2-oxoethoxy)benzaldehyde (58)

2-(4-Formylphenoxy)acetic acid (53) was treated with 1-methylpiperidine in an analogous manner to Compound 49 to afford the desired product (66%) as a colorless oil. LCMS: 99.0% (M$^+$+1).

Compound CCXLIV

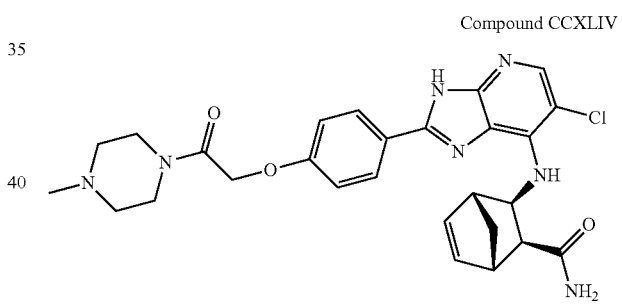

(1S,2S,3R,4R)-3-(6-chloro-2-(4-(2-(4-methylpiperazin-1-yl)-2-oxoethoxy)phenyl)-3H-imidazo[4,5-b]pyridin-7-ylamino)bicyclo[2.2.1]hept-5-ene-2-carboxamide (Compound CCXLIV)

(1S,2S,3R,4R)-3-(2,3-Diamino-5-chloro-pyridin-4-ylamino)-bicyclo[2.2.1]hept-5-ene-2-carboxylic acid amide (1 eq.) and 4-(2-(4-methylpiperazin-1-yl)-2-oxoethoxy)benzaldehyde (58) (1.1 eq) were reacted in an analogous manner as compound CCXXIII to yield the desired product (26%) as an off white solid. NMR: δ ($^1$H, 400 MHz, DMSO-d$_6$): 1.38 (1H, d, J=8 Hz), 2.19 (3H, s), 2.20-2.35 (5H, m), 2.62 (1H, d, J=8.4 Hz), 2.78 (1H, s), 2.89 (1H, s), 3.40-3.50 (4H, m), 4.91 (2H, s), 5.16 (1H, t, J=8 Hz), 6.36-6.40 (2H, m), 7.08 (2H, d, J=8.4 Hz), 7.11-7.14 (1H, m), 7.22 (1H, bs), 7.76 (1H, bs), 7.92 (1H, s), 8.05 (2H, d, J=8.4 Hz).

LCMS (254 nm): [M+H]$^+$ 536.25 (99.03%).

HPLC: 98.52% (254 nm), 98.73% (220 nm).

Compound CCXLV

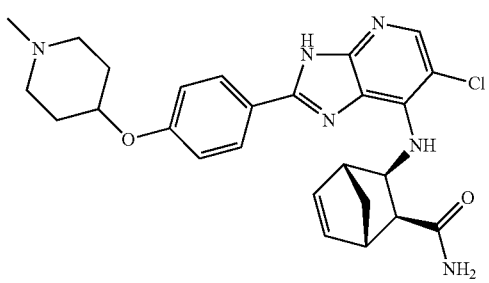

(1S,2S,3R,4R)-3-(6-chloro-2-(4-(1-methylpiperidin-4-yloxy)phenyl)-3H-imidazo[4,5-b]pyridin-7-ylamino)bicyclo[2.2.1]hept-5-ene-2-carboxamide (Compound CCXLV)

Procedure as 232yridine232 in the general procedure for benzimidazole derivatives. Off white solid (TFA salt).
Yield: 51%.
NMR: δ ($^1$H, 400 MHz, CD$_3$OD): 1.55 (1H, d, J=9.2 Hz), 2.00-2.20 (2H, m), 2.25-2.50 (3H, m), 2.74 (1H, d, J=9.6 Hz), 2.88 (1H, s), 2.94 (3H, s), 2.98 (1H, s), 3.10-3.70 (5H, m), 5.35 (1H, d, J=8 Hz), 6.36-6.38 (1H, m), 6.42-6.44 (1H, m), 7.18 (2H, d, J=8.8 Hz), 7.91 (1H, s), 8.07 (2H, d, J=8.8 Hz).
LCMS (254 nm): [M+H]$^+$ 493.18 (99.89%).
HPLC: 99.908% (254 nm); 97.968% (220 nm).

Compound CCXLVI

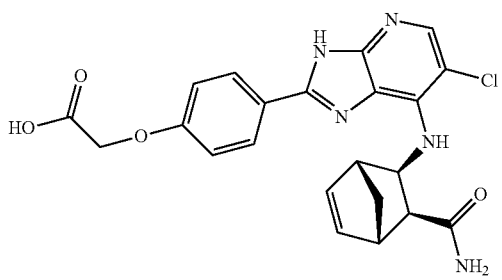

2-(4-(7-((1R,2R,3S,4S)-3-carbamoylbicyclo[2.2.1]hept-5-en-2-ylamino)-6-chloro-3H-imidazo[4,5-b]pyridin-2-yl)phenoxy)acetic acid (Compound CCXLVI)

(1S,2S,3R,4R)-3-(2,3-Diamino-5-chloro-pyridin-4-ylamino)-bicyclo[2.2.1]hept-5-ene-2-carboxylic acid amide (1 eq.) and 2-(4-Formylphenoxy)acetic acid (53) (1.1 eq) were reacted in an analogous manner as compound CCXXIII to yield the desired product (29%) as a white solid. NMR: δ ($^1$H, 400 MHz, DMSO-d$_6$): 1.37 (1H, d, J=8.4 Hz), 2.23 (1H, d, J=8.4 Hz), 2.62 (1H, d, J=7.6 Hz), 2.77 (1H, s), 2.88 (1H, s), 4.31 (2H, bs), 5.20 (1H, t, J=8.8 Hz), 6.34-6.41 (2H, m), 6.77 (1H, d, J=8.8 Hz), 6.95 (2H, d, J=8 Hz), 7.07 (1H, d, J=8.8 Hz), 7.20-7.25 (1H, m), 7.75 (1H, bs), 7.90 (1H, s), 8.02 (2H, d, J=8.0 Hz).
LCMS (254 nm): [M+H]$^+$ (454.05, 97.811%).
HPLC: 96.901% (254 nm).

Scheme 16

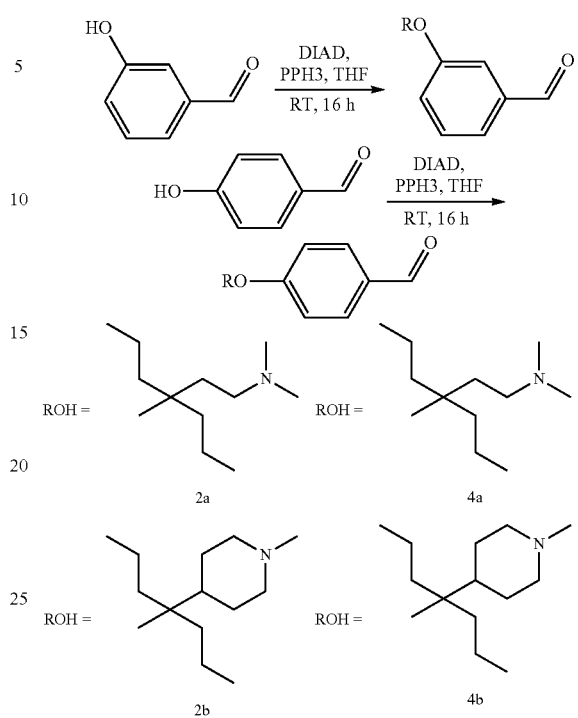

General Procedure for 2a, 2b, 4a, 4b:

Ph$_3$P (1.5 eq) was taken in THF, cooled to 0° C. and DIAD (1.5 eq) was added dropwise followed by addition of aldehyde (2a, 2b, 4a, 4b) (1 eq) at 0° C. The reaction mixture then stirred at rt for 15 min when ROH (1.25 eq) was added at rt and stirred for further 24 h when LCMS showed the desired conversion. The reaction mixture was concentrated and diluted with ether and hexane was added dropwise to precipitate out the Ph$_3$PO which was filtered. The filtrate was concentrated and purified by column chromatography using silica gel (100-200 mesh) to afford the pure product.

3-(2-(dimethylamino)ethoxy)benzaldehyde (2a)

brown sticky oil.
Yield: 52%.
LCMS: 88% (M$^+$+1).

3-(1-methylpiperidin-4-yloxy)benzaldehyde (2b)

colorless oil.
Yield: 70%.
LCMS: 74.11% (M$^+$+1).

4-(2-(dimethylamino)ethoxy)benzaldehyde (4a)

colorless oil.
Yield: 51%.
LCMS: 98% (M$^+$+1).

4-(1-methylpiperidin-4-yloxy)benzaldehyde (4b): colorless oil.
Yield: 61%.
LCMS: 89.78% (M$^+$+1).

Compound CCXLVII

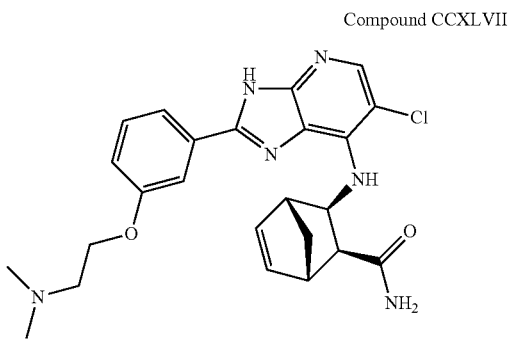 [SMILES: CN(C)CCOc1cccc(-c2nc3c(N[C@H]4[C@@H](C(N)=O)[C@@H]5C=C[C@H]4C5)c(Cl)cnc3[nH]2)c1]

(1S,2S,3R,4R)-3-(6-chloro-2-(3-(2-(dimethylamino)
ethoxy)phenyl)-3H-imidazo[4,5-b]234yridine-7-
ylamino)pyridin[2.2.1]hept-5-ene-2-carboxamide
(Compound CCXLVII)

Procedure was analogous to the general procedure for benzimidazole derivatives. Product was an off white solid (TFA Salt).

Yield: 70%.

NMR: δ (¹H, 400 MHz, CD₃OD): 1.58 (1H, d, J=9.2 Hz), 2.31 (1H, d, J=9.2 Hz), 2.76 (1H, d, J=8 Hz), 3.04 (6H, s), 3.02-3.10 (2H, m), 3.69 (2H, t, J=4.8 Hz), 4.49 (2H, t, J=4.8 Hz), 5.29 (1H, d, J=8.4 Hz), 6.44-6.50 (2H, m), 7.23 (1H, m), 7.54 (1H, t, J=8 Hz), 7.79-7.82 (2H, m), 8.14 (1H, s).

LCMS (254 nm): [M+H]⁺ 467.05 (99.308%).

HPLC: 96.88% (254 nm), 97.098% (220 nm).

Compound CCXLVIII (1S,2S,3R,4R)-3-(6-chloro-2-(3-(1-methylpiperidin-
4-yloxy)phenyl)-3H-imidazo[4,5-b]pyridin-7-
ylamino)bicyclo[2.2.1]hept-5-ene-2-carboxamide
(Compound CCXLVIII)

Procedure was analogous to the general procedure for benzimidazole derivatives. Product was a white solid.

Yield: 48%.

NMR: δ (¹H, 400 MHz, CD₃OD): 1.56 (1H, d, J=9.2 Hz), 1.92-2.46 (5H, m), 2.71-2.76 (1H, m), 2.91-3.03 (5H, m), 3.17-3.49 (4H, m), 3.65 (1H, d, J=12.4 Hz), 5.29 (1H, d, J=7.6 Hz), 6.4-6.5 (2H, m), 7.19 (1H, t, J=9.2 Hz), 7.48-7.52 (1H, m), 7.69-7.77 (2H, m), 8.08 (1H, s).

LCMS (254 nm): [M+H]⁺ 493.30 (100%).

HPLC: 99.908% (254 nm); 97.968% (220 nm).

Compound CCXLIX

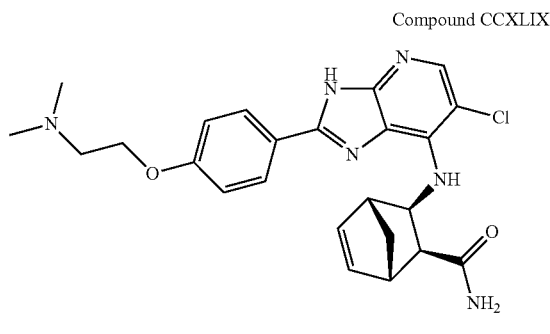 [SMILES: CN(C)CCOc1ccc(-c2nc3c(N[C@H]4[C@@H](C(N)=O)[C@@H]5C=C[C@H]4C5)c(Cl)cnc3[nH]2)cc1]

(1S,2S,3R,4R)-3-(6-chloro-2-(4-(2-(dimethylamino)
ethoxy)phenyl)-3H-imidazo[4,5-b]pyridin-7-
ylamino)bicyclo[2.2.1]hept-5-ene-2-carboxamide
(Compound CCXLIX)

Procedure was analogous to the general procedure for benzimidazole derivatives. Product was an off white solid.

Yield: 46%.

NMR: δ (¹H, 400 MHz, CD₃OD):): 1.58 (1H, d, J=8.8 Hz), 2.29 (1H, d, J=9.2 Hz), 2.77 (1H, d, J=8 Hz), 3.03 (6H, s), 3.07 (2H, s), 3.66 (2H, t, J=5.2 Hz), 4.48 (2H, t, J=5.2 Hz), 5.26 (1H, d, J=7.6 Hz), 6.45-6.50 (2H, m), 7.23 (2H, d, J=9.2 Hz), 8.12 (2H, d, J=9.2 Hz), 8.15 (1H, s).

LCMS (254 nm): [M+H]⁺ 467.05 (99.308%).

HPLC: 99.551% (254 nm), 99.015% (220 nm).

Scheme 17

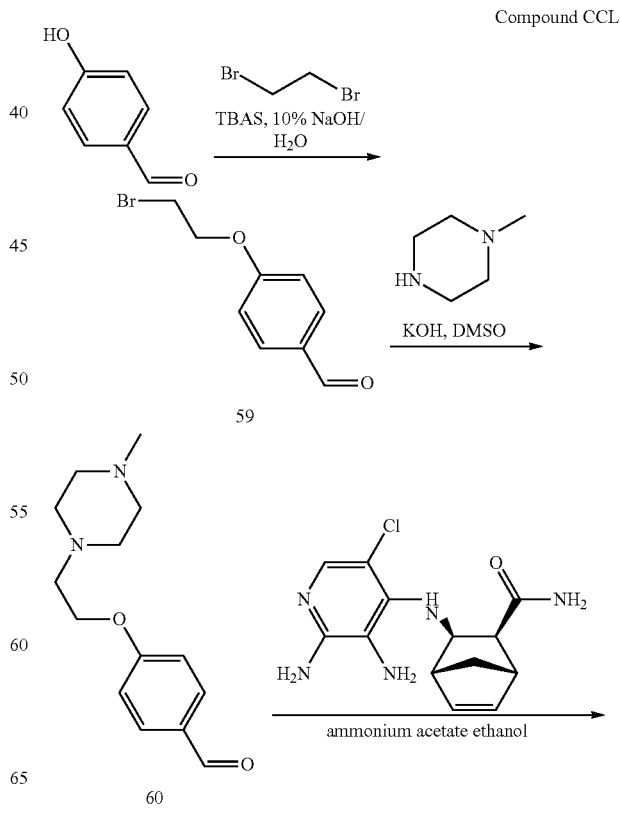

Compound CCL

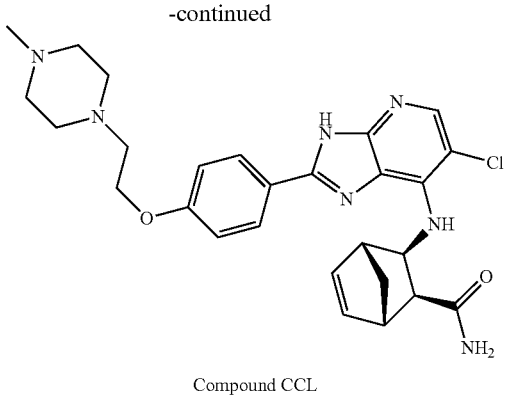

Compound CCL

4-(2-bromoethoxy)benzaldehyde (59)

4-hydroxy benzaldehyde (700 mg, 5.7 mmol) and dibromoethane (1.2 ml, 0.46 mmol) were taken in 10% NaOH solution (0.7 ml) and TBAS (2.5 g, 13.7 mmol) and heated at 70° C. for 16 h when TLC indicated completion of reaction. The reaction mixture was cooled to rt and poured into water and extracted with ethyl acetate. The combined organic extracts was washed with water, dried and purified by column chromatography using silica gel (100-200 mesh) to afford the pure product as colorless oil in 19% yield.

NMR: δ 3.674 (t, J=6.4 Hz, 2H), 4.381 (t, J=6.4 Hz, 2H), 7.024 (d, 8.8 Hz, 2H), 7.855 (d, J=8.8 Hz, 2H), 9.904 (s, 1H).

4-(2-(4-methylpiperazin-1-yl)ethoxy)benzaldehyde (60)

4-(2-bromoethoxy)benzaldehyde (4) (55 mg, 0.241 mmol) was taken in DMSO (1 ml) and N-methyl piperazine (24 mg, 0.241 mmol) and KOH (26 mg, 0.48 mmol) were added. The reaction mixture was stirred at rt for 16 h and completion of reaction was checked by TLC. The reaction mixture was diluted with DCM and the organic extract was washed with water, dried and purified by column chromatography using silica gel (100-200 mesh) to afford the pure product as a colorless oil in 23% yield.

NMR: δ 2.327 (s, 3H), 2.861 (t, J=5.6 Hz, 2H), 2.45-2.62 (m, 8H), 4.191 (t, J=6 Hz, 2H), 7.00 (d, J=8.4 Hz, 2H), 7.834 (d, J=8.4 Hz, 2H), 9.889 (s, 1H).

(1S,2S,3R,4R)-3-(6-chloro-2-(4-(2-(4-methylpiperazin-1-yl)ethoxy)phenyl)-3H-imidazo[4,5-b]pyridin-7-ylamino)bicyclo[2.2.1]hept-5-ene-2-carboxamide (Compound CCL)

Procedure was analogous to the general procedure for benzimidazole derivatives. Product was an off white solid. Yield: 26%

NMR: δ ($^1$H, 400 MHz, DMSO-d$_6$): 1.39 (1H, d, J=8.4 Hz), 2.22-2.4 (4H, m), 2.14 (3H, s), 2.61-28 (6H, m), 3.0-3.5 (4H, m), 4.14 (2H, t, J=5.6 Hz), 5.19 (1H, t, J=8.4 Hz), 6.36-6.40 (2H, m), 7.10 (2H, d, J=8.8 Hz), 7.22 (2H, bs), 7.76 (1H, bs), 7.91 (1H, s), 8.06 (2H, d, J=8.8 Hz), 13.14 (1H, bs).

LCMS (254 nm): [M+H]$^+$ 522.20 (97.48%).

HPLC: 98.236% (254 nm), 98.302% (220 nm).

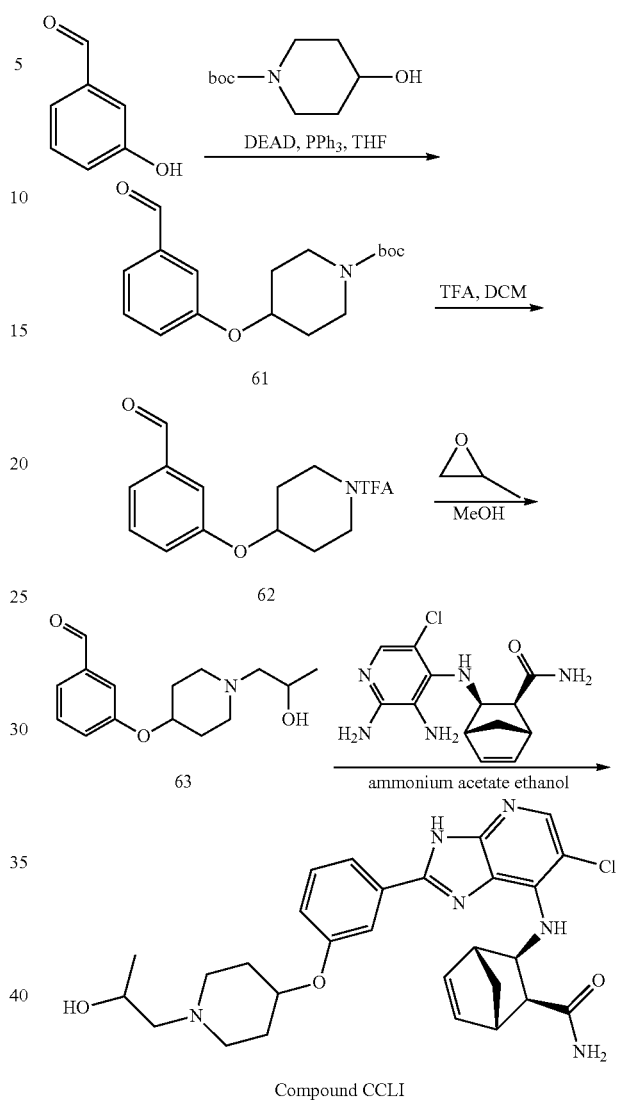

Scheme 18

Compound CCLI

Tert-butyl 4-(3-formylphenoxy)piperidine-1-carboxylate (61)

Ph$_3$P (1.8 eq) was taken in THF, cooled to 0° C. and DEAD (2 eq) was added dropwise followed by addition of aldehyde (1 eq) at 0° C. The reaction mixture then stirred at rt for 15 min when ROH (1.25 eq) was added at rt and stirred for further 24 h when LCMS showed the desired conversion. The reaction mixture was concentrated and diluted with ether and hexane was added dropwise to precipitate out the Ph$_3$PO which was filtered. The filtrate was concentrated and purified by column chromatography using silica gel (100-200 mesh) to afford the pure product as a colorless oil.

Yield: 22%.

NMR: δ 1.487 (s, 9H), 1.72-1.81 (m, 2H), 2.91-2.98 (m, 2H), 3.33-3.39 (m, 2H), 3.64-3.76 (m, 2H), 4.52-4.58 (m, 1H), 7.14-7.2 (m, 1H), 7.39-7.49 (m, 3H), 9.975 (s, 1H).

3-(1-(2,2,2-trifluoroacetyl)piperidin-4-yloxy)benzaldehyde (62)

tert-butyl 4-(3-formylphenoxy)piperidine-1-carboxylate (61) (5.55 mmol) was taken in DCM and cooled to 0° C. when TFA (5 ml) was added drop wise and then stirred at rt for 16 h when TLC confirmed completion of reaction. The reaction mixture was concentrated and used directly for the next step. White solid.

Yield: 78%.

LCMS: 99.72% (M⁺+1).

3-(1-(2-hydroxypropyl)piperidin-4-yloxy)benzaldehyde (63)

3-(1-(2,2,2-trifluoroacetyl)piperidin-4-yloxy)benzaldehyde (62) (1 eq) was taken in MeOH to which propylene oxide (4 eq) was added and the reaction mixture was heated in a sealed tube at 70° C. for 8 h when LCMS showed completion of reaction. The reaction mixture was concentrated and purified by column chromatography using silica gel (100-200 mesh) to afford the pure product as a colorless oil.

Yield: 78%.

LCMS: 88.26% (M⁺+1).

Compound CCLI (1S,2S,3R,4R)-3-(6-chloro-2-(3-(1-(2-hydroxypropyl)piperidin-4-yloxy)phenyl)-3H-imidazo[4,5-b]pyridine-7-ylamino)pyridin[2.2.1]hept-5-ene-2-carboxamide (Compound CCLI)

Procedure as analogous to the general procedure for benzimidazole derivatives. Yellow solid (TFA salt).

Yield: 32%.

NMR: δ (¹H, 400 MHz, CD₃OD): 1.26 (3H, d, J=5.6 Hz), 1.53 (1H, d, J=8.8 Hz), 2.0-2.50 (5H, m), 2.76 (1H, d, J=8.0 Hz), 2.96 (1H, s), 3.06-3.11 (3H, m), 3.22-3.25 (2H, m), 3.35-3.41 (1H, m), 3.55-3.62 (1H, m), 3.76-3.79 (1H, m), 4.24 (1H, bs), 5.08 (1H, d, J=7.2 Hz), 6.41-6.44 (2H, m), 7.15 (1H, d, J=7.6 Hz), 7.42-7.66 (3H, m), 8.06 (1H, s).

LCMS (254 nm): [M+H]⁺ 537.20 (99.90%).

HPLC: 99.587% (254 nm); 99.890% (220 nm).

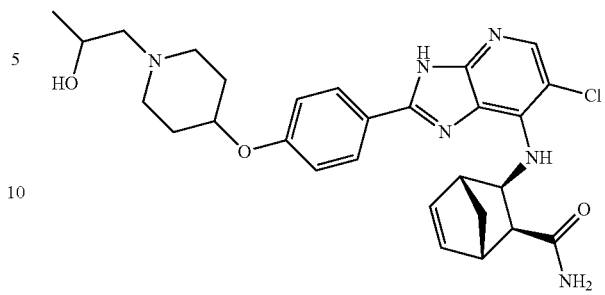

Compound CCLII

In an analogous manner to the synthesis of Compound CCLI (Scheme 18), Compound CCLII was synthesized starting from tert-butyl 4-(4-formylphenoxy)piperidine-1-carboxylate.

Tert-butyl 4-(4-formylphenoxy)piperidine-1-carboxylate colorless oil

Yield: 32%. NMR: δ 1.45 (s, 9H), 1.72-1.81 (m, 2H), 1.62-1.98 (m, 4H), 3.27-3.42 (m, 2H), 3.63-3.44 (m, 2H), 4.43-4.48 (m, 1H), 7.14-7.2 (m, 1H), 7.0 (d, J=8.4 Hz, 2H), 7.83 (d, J=8.4 Hz, 2H), 9.882 (s, 1H).

4-(1-(2,2,2-trifluoroacetyl)piperidin-4-yloxy)benzaldehyde pale yellow oil

Yield: 75%. LCMS: 91.17% (M⁺+1).

4-(1-(2-hydroxypropyl)piperidin-4-yloxy)benzaldehyde colorless oil

Yield: 62%. LCMS: 94.53% (M⁺+1).

(1S,2S,3R,4R)-3-(6-chloro-2-(4-(1-(2-hydroxypropyl)piperidin-4-yloxy)phenyl)-3H-imidazo[4,5-b]pyridin-7-ylamino)bicyclo[2.2.1]hept-5-ene-2-carboxamide (Compound CCLII)

Procedure was analogous to the general procedure for benzimidazole derivatives. Off white solid. Yield: 60%.

NMR: δ (¹H, 400 MHz, CD₃OD): 1.25 (3H, d, J=6 Hz), 1.57 (1H, d, J=8.8 Hz), 2.0-2.5 (5H, m), 2.76 (1H, d, J=8 Hz), 2.99-3.09 (4H, m), 3.21-3.25 (2H, m), 3.38-3.60 (3H, m), 4.21 (1H, bs), 5.27 (1H, d, J=8 Hz), 6.43-6.45 (1H, m), 6.46-6.49 (1H, m), 7.21 (2H, d, J=8.8 Hz), 8.00-8.11 (3H, m).

LCMS (254 nm): [M+H]⁺ (537.20, 99.881%).

HPLC: 99.765% (254 nm); 99.886% (220 nm).

Compound CCLIII

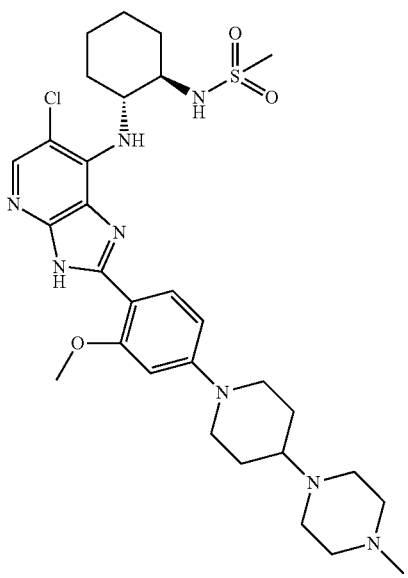

N-[1R,2R)-2-(6-Chloro-2-{2-methoxy-4-[4-(4-methyl-piperazin-1-yl)-piperidin-1-yl]-phenyl}-3H-imidazo[4,5-b]pyridin-7-ylamino)-cyclohexyl]-methanesulfonamide Using a procedure analogous to the synthesis of compound LXX N-[(1R,2R)-2-aminocyclohexyl]-methanesulfonamide (0.218 g, 1.05 mmol) (Kaik, M.; Gawronski, J. Tetrahedron: Asymmetry (2003), 14(11), 1559-1563) and 2-Methoxy-4-[4-(4-methyl-piperazin-1-yl)-piperidin-1-yl]-benzaldehyde was converted to the title compound isolated as a TFA salt (13.55 mgs, 0.5% yield). LC/MS. found 631 (M+H)+. $^{1}$H-NMR (dmso-d$_{6}$, 400 MHz): δ 12.42 (broad s, 1H), 8.09-7.99 (m, 2H), 7.53-7.47 (m, 1H). 6.77 (s, J=10.5 Hz, 1H), 6.65 (s, 1H), 6.40 (broad s, 1H), 4.74 (broad s, 1H), 4.07 (d, J=13.4 Hz, 2H), 3.99 (s, 3H), 3.62-2.94 (complex series of multiplets, 9H), 2.87 (s, 3H), 2.84-2.76 (m, 4H), 2.24-1.32 (complex series of multiplets, 14H).

Compound CCLIV

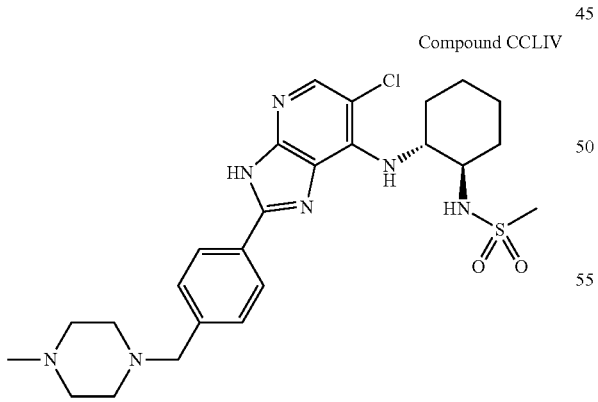

N-((1R,2R)-2-{6-Chloro-2-[4-(4-methyl-piperazin-1-ylmethyl)-phenyl]-3H-imidazo[4,5-b]pyridin-7-ylamino}-cyclohexyl)-methanesulfonamide Using procedures analogous to the synthesis of compound CCLIII, 4-(4-methyl-piperazin-1-ylmethyl)-benzaldehyde (72 mgs, 0.33 mmol) was converted to the title compound 33.2 mg (20%) as a yellowish foam. LC/MS. found 532.16 (M+H)+. $^{1}$H-NMR (CDCl$_{3}$, 400 MHz) δ 8.10 (s, 1H), 8.05 (d, J=8.0 Hz, 2H), 7.61 (d, J=8.4 Hz, 1H), 7.56 (d, J=8.4 Hz, 1H), 5.02 (d, J=8.0 Hz, 1H), 4.82-4.74 (m, 1H), 3.62 (s, 3H), 3.36-3.27 (m, 1H), 2.72 (s, 3H), 2.63-2.20 (complex series of multiplets, 8H), 1.89-0.98 (complex series of multiplets, 12H).

Compound CCLXIII

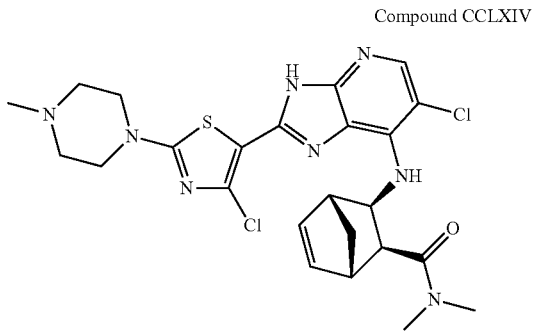

2-(3-(7-((1R,2R,3S,4S)-3-carbamoylbicyclo[2.2.1]hept-5-en-2-ylamino)-6-chloro-3H-imidazo[4,5-b]pyridin-2-yl)phenoxy)acetic acid (Compound CCLXIII)

(1S,2S,3R,4R)-3-(2,3-Diamino-5-chloro-pyridin-4-ylamino)-bicyclo[2.2.1]hept-5-ene-2-carboxylic acid amide (1 eq.) and 2-(3-Formylphenoxy)acetic acid (48) (1.1 eq) were reacted in an analogous manner as compound CCXXIII to yield the desired product (31%) as a brown solid. NMR: δ ($^{1}$H, 400 MHz, DMSO-d$_{6}$): 1.38 (1H, d, J=8.8 Hz), 2.23 (1H, d, J=8.4 Hz), 2.63 (1H, d, J=8 Hz), 2.78-2.88 (2H, m), 4.26 (2H, s), 5.20 (1H, t, J=8.4 Hz), 6.36-6.42 (2H, m), 6.90 (1H, d, J=8.8 Hz), 7.14 (1H, d, J=8.8 Hz), 7.21 (1H, bs), 7.36 (1H, t, J=7.2 Hz), 7.60-7.70 (2H, m), 7.78 (1H, s), 7.94 (1H, s).
LCMS (254 nm): [M+H]$^{+}$ 454.05 (99.226%).
HPLC: 98.900% (254 nm), 98.801% (220 nm).

Compound CCLXIV

Synthesis of (1S,2S,3R,4R)-3-((6-chloro-2-(4-chloro-2-(4-methylpiperazin-1-yl)thiazol-5-yl)-3H-imidazo[4,5-b]pyridin-7-yl)amino)-N,N-dimethylbicyclo[2.2.1]hept-5-ene-2-carboxamide (Compound CCLXIV)

This compound was synthesized in a similar fashion as for the synthesis of Compound CXCVII (Scheme 2). Yield:

22.5%. NMR: ($^1$H, 400M Hz, CDCl$_3$): 1.43 (1H, d, J=8.0 Hz), 2.03 (1H, d, J=8.0 Hz), 2.40-2.55 (m, 1H), 2.40-3.00 (m, 15H), 3.80-4.10 (m, 4H), 5.02 (d, 1H, J=8.0 Hz), 6.37 (s, 2H), 8.01 (s, 1H). LCMS: (254 nm): [M+H]$^+$ 547.10. HPLC: 99%.

General Experimental Methods:

G Method—Gradient elution (0 to 100%) acetonitrile (containing 0.1% trifluoroacetic acid):water (containing 0.1% trifluoroacetic acid) over five minutes on a 4.6×75 mm (2.5 micron) Zorbax XDB-C8 column at 2.5 ml/min.

The invention claimed is:

1. A compound of the general formula (I):

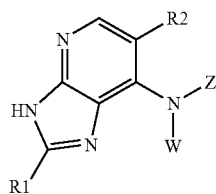

I and a salt thereof, wherein:

W is H and Z is selected from

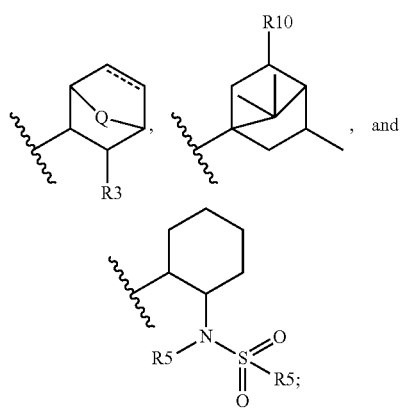

, and or

W and Z are taken together to form

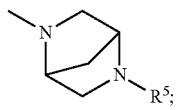

R$^1$ is selected from (C$_6$-C$_{10}$)aryl, aminophenyl, (C$_2$-C$_9$)heterocycloalkyl, (C$_1$-C$_9$)heteroaryl and a group of formula

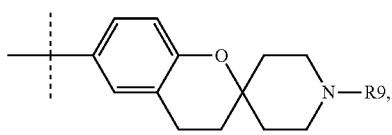

wherein any of the foregoing may be optionally substituted with one or more R$^6$ groups;

R$^2$ is selected from hydrogen and halogen;

R$^3$ is selected from CH$_2$OH and CONR$^4$R$^5$;

Q is selected from CH$_2$ and O;

"------" is either present so as to form a double bond or is absent;

R$^4$ and R$^5$ are each independently selected from H, (C$_1$-C$_6$)alkyl, (C$_3$-C$_8$)cycloalkyl, (C$_1$-C$_6$)alkyl(C$_3$-C$_8$)cycloalkyl, and (C$_1$-C$_6$)alkyl-OR$^9$ wherein any of the foregoing except for H may be optionally substituted with one or more R$^7$;

each R$^6$ is independently selected from (C$_0$-C$_4$)alkylCO$_2$R$^8$, (C$_0$-C$_4$)alkylCON(R$^8$)$_2$, (C$_0$-C$_4$)alkylCOR$^8$, (C$_0$-C$_4$)alkylN(R$^8$)$_2$, (C$_0$-C$_4$)OR$^9$, (C$_1$-C$_6$)alkoxy, (C$_1$-C$_6$)alkoxy(C$_2$-C$_9$)heterocycloalkyl, (C$_1$-C$_6$)alkoxy(C$_3$-C$_8$)cycloalkyl, (C$_1$-C$_6$)alkyl, (C$_1$-C$_6$)alkyl(C$_1$-C$_9$)heteroaryl, (C$_1$-C$_6$)alkyl(C$_2$-C$_9$)heterocycloalkyl, (C$_1$-C$_6$)alkyl(C$_3$-C$_8$)cycloalkyl, (C$_1$-C$_6$)alkyl(C$_6$-C$_{10}$)aryl, (C$_1$-C$_9$)heteroaryl, (C$_2$-C$_6$)alkenyl, (C$_2$-C$_9$)heterocycloalkyl, (C$_2$-C$_9$)heterocycloalkyloxy, (C$_3$-C$_8$)cycloalkyl, (C$_3$-C$_8$)cycloalkyloxy, (C$_3$-C$_9$)heterocycloalkenyl, (C$_6$-C$_{10}$)aryl, cyano, halo(C$_1$-C$_6$)alkoxy, halo(C$_1$-C$_6$)alkyl, halogen, O(C$_0$-C$_4$)alkylCO$_2$R$^8$, O(C$_0$-C$_4$)alkylCON(R$^8$)$_2$, O(C$_0$-C$_4$)alkylCOR$^8$, PO((C$_1$-C$_4$)alkyl)$_2$, and O(C$_0$-C$_4$)alkylN(R$^8$)$_2$, wherein any of the foregoing except for halogen, may be optionally substituted with one or more R$^7$;

each R$^7$ is independently selected from (C$_0$-C$_4$)alkylCO$_2$R$^8$, (C$_0$-C$_4$)alkylCON(R$^8$)$_2$, (C$_0$-C$_4$)alkylCOR$^8$, (C$_0$-C$_4$)OR$^9$, (C$_1$-C$_6$)alkoxy, (C$_1$-C$_6$)alkyl, (C$_1$-C$_6$)alkyl(C$_1$-C$_9$)heteroaryl, (C$_1$-C$_6$)alkyl(C$_2$-C$_9$)heterocycloalkyl, (C$_1$-C$_6$)alkyl(C$_3$-C$_8$)cycloalkyl, (C$_1$-C$_6$)alkyl(C$_6$-C$_{10}$)aryl, (C$_1$-C$_9$)heteroaryl, (C$_2$-C$_9$)heterocycloalkyl, (C$_2$-C$_9$)heterocycloalkyl optionally substituted with (C$_1$-C$_6$)alkyl, (C$_3$-C$_8$)cycloalkyl, (C$_6$-C$_{10}$)aryl, halo(C$_1$-C$_6$)alkoxy, halo(C$_1$-C$_6$)alkyl, halogen, hydroxy(C$_1$-C$_6$)alkyl, PO((C$_1$-C$_4$)alkyl)$_2$, and hydroxy(C$_1$-C$_6$)alkyl(C$_1$-C$_6$)alkoxy;

each R$^8$ is independently selected from H, (C$_1$-C$_6$)alkyl, and (C$_2$-C$_9$)heterocycloalkyl, or two R$^8$ are taken together with the nitrogen atom to which they are attached to form (C$_2$-C$_9$)heterocycloalkyl, wherein any of the foregoing except for H, may be optionally substituted with (C$_1$-C$_6$)alkyl, (C$_1$-C$_6$)alkoxy, halo(C$_1$-C$_6$)alkyl, halo(C$_1$-C$_6$)alkoxy, halogen, (C$_0$-C$_4$)alkylCO$_2$R$^9$, (C$_0$-C$_4$)alkylN(R$^9$)$_2$ or (C$_0$-C$_4$)alkylOR$^9$;

R$^9$ is independently selected from H and (C$_1$-C$_6$)alkyl; and

R$^{10}$ is independently a carbonyl or a hydroxyl group.

2. A compound according to claim 1 or a salt thereof, wherein Z is:

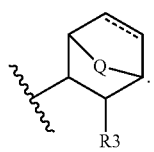

3. A compound according to claim 1 or a salt thereof, wherein Z is:

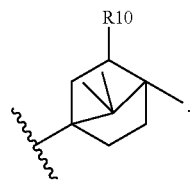

4. A compound according to claim 1 or a salt thereof, wherein Z is:

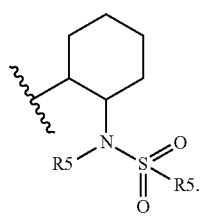

5. A compound according to claim 1, or a salt thereof, wherein Z is selected from:

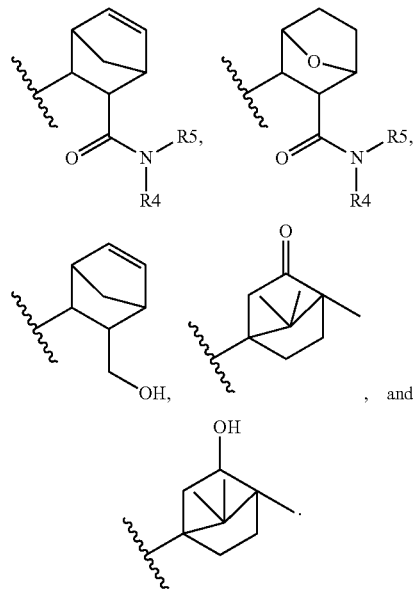

6. A compound according to claim 1, or a salt thereof, wherein W and Z are taken together to form

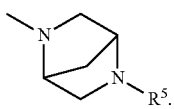

7. A compound according to claim 5, or a salt thereof, wherein Z is selected from:

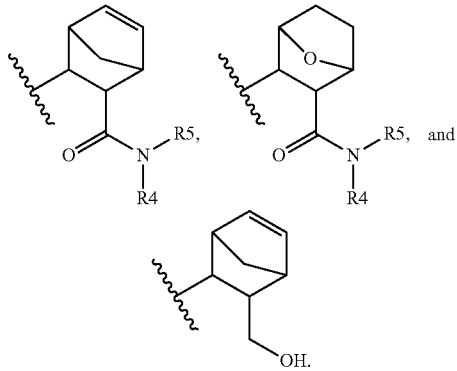

8. A compound according to claim 7, or a salt thereof, wherein Z is:

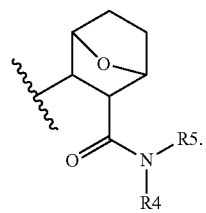

9. A compound according to claim 7, or a salt thereof, wherein Z is:

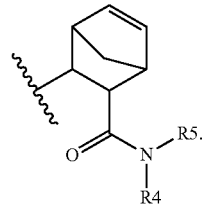

10. A compound according to claim 5, or a salt thereof, wherein Z is:

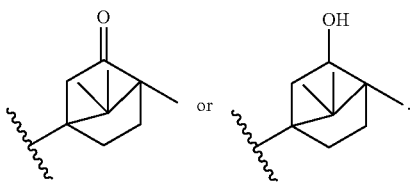 [SMILES: *C12CCC(C)(C(=O)C1)C2(C)C ; *C12CCC(C)(C(O)C1)C2(C)C]

11. A compound according to claim 7, or a salt thereof, wherein Z is

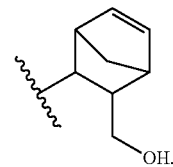

12. A compound according to claim 1, or a salt thereof, wherein $R^2$ is selected from hydrogen, chlorine and bromine.

13. A compound according to claim 9, or a salt thereof, wherein:

$R^1$ is selected from phenyl, piperidinyl, pyrazolyl, pyridinyl, pyrimidinyl, furanyl, pyrrolyl, thiophenyl, thiazolyl, isoxazolyl, tetrahydroimidazopyridinyl, and aminophenyl, wherein each of the foregoing may be optionally substituted with one or more $R^6$ groups;

$R^2$ is selected from hydrogen, chlorine and bromine; and $R^4$ and $R^5$ are each independently selected from hydrogen, methyl, isopropyl, hydroxyethyl, and cyclopropyl.

14. A compound according to claim 13 that is selected from the following:

(1S,2S,3R,4R)-3-[6-Chloro-2-(4-morpholin-4-ylmethyl-phenyl)-3H-imidazo[4,5-b]pyridine-7-ylamino]-bicyclo[2.2.1]hept-5-ene-2-carboxylic acid amide;
(1S,2S,3R,4R)-3-[6-Chloro-2-(4-morpholin-4-yl-phenyl)-3H-imidazo[4,5-b]pyridine-7-ylamino]-bicyclo[2.2.1]hept-5-ene-2-carboxylic acid amide;
(1S,2S,3R,4R)-3-[6-Chloro-2-(3-methoxy-phenyl)-3H-imidazo[4,5-b]pyridin-7-ylamino]-bicyclo[2.2.1]hept-5-ene-2-carboxylic acid amide;
(1S,2S,3R,4R)-3-[6-Chloro-2-(4-methoxy-phenyl)-3H-imidazo[4,5-b]pyridine-7-ylamino]-bicyclo[2.2.1]hept-5-ene-2-carboxylic acid amide;
(1S,2S,3R,4R)-3-[6-Chloro-2-(3-morpholin-4-yl-phenyl)-3H-imidazo[4,5-b]pyridine-7-ylamino]-bicyclo[2.2.1]hept-5-ene-2-carboxylic acid amide;
(1S,2S,3R,4R)-3-[6-Chloro-2-(1-methyl-1H-pyrazol-4-yl)-3H-imidazo[4,5-b]pyridin-7-ylamino]-bicyclo[2.2.1]hept-5-ene-2-carboxylic acid amide;
(1S,2S,3R,4R)-3-[6-Chloro-2-(2-methoxy-phenyl)-3H-imidazo[4,5-b]pyridine-7-ylamino]-bicyclo[2.2.1]hept-5-ene-2-carboxylic acid amide;
(1S,2S,3R,4R)-3-{6-Chloro-2-[4-(4-methyl-piperazin-1-yl)-phenyl]-3H-imidazo[4,5-b]pyridine-7-ylamino}-bicyclo[2.2.1]hept-5-ene-2-carboxylic acid amide;
3-[7-((1R,2R,3S,4S)-3-Carbamoyl-bicyclo[2.2.1]hept-5-en-2-ylamino)-6-chloro-3H-imidazo[4,5-b]pyridine-2-yl]-piperidine-1-carboxylic acid tert-butyl ester;
(1S,2S,3R,4R)-3-[6-Chloro-2-(3-dimethylamino-phenyl)-3H-imidazo[4,5-b]pyridin-7-ylamino]-bicyclo[2.2.1]hept-5-ene-2-carboxylic acid amide;
(1S,2S,3R,4R)-3-(6-Chloro-2-piperidin-3-yl-3H-imidazo[4,5-b]pyridin-7-ylamino)-bicyclo[2.2.1]hept-5-ene-2-carboxylic acid amide; (1S,2S,3R,4R)-3-[6-Chloro-2-(4-piperazin-1-yl-phenyl)-3H-imidazo[4,5-b]pyridin-7-ylamino]-bicyclo[2.2.1]hept-5-ene-2-carboxylic acid amide; (1S,2S,3R,4R)-3-[6-Chloro-2-(3-morpholin-4-ylmethyl-phenyl)-3H-imidazo[4,5-b]pyridin-7-ylamino]-bicyclo[2.2.1]hept-5-ene-2-carboxylic acid amide; (1S,2S,3R,4R)-3-[6-Chloro-2-(4-dimethylamino-2-methoxy-phenyl)-3H-imidazo[4,5-b]pyridine-7-ylamino]-bicyclo[2.2.1]hept-5-ene-2-carboxylic acid amide; (1S,2S,3R,4R)-3-[6-Chloro-2-(2-methoxy-4-trifluoromethoxy-phenyl)-3H-imidazo[4,5-b]pyridine-7-ylamino]-bicyclo[2.2.1]hept-5-ene-2-carboxylic acid amide; (1S,2S,3R,4R)-3-[6-Chloro-2-(2-methoxy-4-morpholin-4-yl-phenyl)-3H-imidazo[4,5-b]pyridine-7-ylamino]-bicyclo[2.2.1]hept-5-ene-2-carboxylic acid amide; (1S,2S,3R,4R)-3-{6-Chloro-2-[4-(4-methyl-piperazin-1-ylmethyl)-phenyl]-3H-imidazo[4,5-b]pyridin-7-ylamino}-bicyclo[2.2.1]hept-5-ene-2-carboxylic acid amide; (1S,2S,3R,4R)-3-{6-Chloro-2-[2-methoxy-4-(4-methyl-piperazin-1-yl)-phenyl]-3H-imidazo[4,5-b]pyridin-7-ylamino}-bicyclo[2.2.1]hept-5-ene-2-carboxylic acid amide;
(1S,2S,3R,4R)-3-[6-Bromo-2-(4-dimethylamino-phenyl)-3H-imidazo[4,5-b]pyridin-7-ylamino]-bicyclo[2.2.1]hept-5-ene-2-carboxylic acid amide;
(1S,2S,3R,4R)-3-[6-Bromo-2-(3-dimethylamino-phenyl)-3H-imidazo[4,5-b]pyridin-7-ylamino]-bicyclo[2.2.1]hept-5-ene-2-carboxylic acid amide;
(1S,2S,3R,4R)-3-{6-Bromo-2-[4-(4-methyl-piperazin-1-yl)-phenyl]-3H-imidazo[4,5-b]pyridin-7-ylamino}-bicyclo[2.2.1]hept-5-ene-2-carboxylic acid amide; (1S,2S,3R,4R)-3-[6-Bromo-2-(4-morpholin-4-yl-phenyl)-3H-imidazo[4,5-b]pyridin-7-ylamino]-bicyclo[2.2.1]hept-5-ene-2-carboxylic acid amide;
(1S,2S,3R,4R)-3-[6-Bromo-2-(4-morpholin-4-ylmethyl-phenyl)-3H-imidazo[4,5-b]pyridin-7-ylamino]-bicyclo[2.2.1]hept-5-ene-2-carboxylic acid amide;
(1S,2S,3R,4R)-3-[6-Bromo-2-(3-morpholin-4-ylmethyl-phenyl)-3H-imidazo[4,5-b]pyridin-7-ylamino]-bicyclo[2.2.1]hept-5-ene-2-carboxylic acid amide; 3-[6-Bromo-7-((1R,2R,3S,4S)-3-carbamoyl-bicyclo[2.2.1]hept-5-en-2-ylamino)-3H-imidazo[4,5-b]pyridin-2-yl]-piperidine-1-carboxylic acid tert-butyl ester;
(1S,2S,3R,4R)-3-[6-Bromo-2-(3-morpholin-4-yl-phenyl)-3H-imidazo[4,5-b]pyridin-7-ylamino]-bicyclo[2.2.1]hept-5-ene-2-carboxylic acid amide;
(1S,2S,3R,4R)-3-[6-Bromo-2-(4-dimethylamino-2-methoxy-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(1-methyl-1H-pyrazol-4-yl)-3H-imidazo[4,5-b]pyridin-7-ylamino]-bicyclo[2.2.1]hept-5-ene-2-carboxylic acid amide; (1S,2S,3R,4R)-3-[2-(4-Dimethylamino-phenyl)-3H-imidazo[4,5-b]pyridin-7-ylamino]-bicyclo[2.2.1]hept-5-ene-2-carboxylic acid amide; (1S,2S,3R,4R)-3-[2-(3-Dimethylamino-phenyl)-3H-imidazo[4,5-b]pyridin-7-ylamino]-bicyclo[2.2.1]hept-5-ene-2-carboxylic acid amide; (1S,2S,3R,4R)-3-{2-[4-(4-Methyl-piperazin-1-yl)-phenyl]-3H-imidazo[4,5-b]pyridin-7-ylamino}-bicyclo[2.2.1]hept-5-ene-2-carboxylic acid amide; (1S,2S,3R,4R)-3-[2-(4-Morpholin-4-yl-phenyl)-3H-imidazo[4,5-b]pyridin-7-ylamino]-bicyclo[2.2.1]hept-5-ene-2-carboxylic acid amide; (1S,2S,3R,4R)-3-[2-(4-Morpholin-4-ylmethyl-phenyl)-3H-imidazo[4,5-b]pyridin-7-ylamino]-bicyclo[2.2.1]hept-5-ene-2-carboxylic acid amide; (1S,2S,3R,4R)-3-[2-(3-Morpholin-4-ylmethyl-phenyl)-3H-imidazo[4,5-b]pyridin-7-ylamino]-bicyclo[2.2.1]hept-5-ene-2-carboxylic acid amide; 3-[7-((1R,2R,3S,4S)-3-Carbamoyl-bicyclo[2.2.1]hept-5-en-2-ylamino)-3H-imidazo[4,5-b]pyridin-2-yl]-piperidine-1-carboxylic acid tert-butyl ester;
(1S,2S,3R,4R)-3-[2-(4-Dimethylamino-2-methoxy-phenyl)-3H-imidazo[4,5-b]pyridin-7-ylamino]-bicyclo[2.2.1]hept-5-ene-2-carboxylic acid amide;
(1S,2S,3R,4R)-3-[2-(1-Methyl-1H-pyrazol-4-yl)-3H-imidazo[4,5-b]pyridin-7-ylamino]-bicyclo[2.2.1]hept-5-ene-2-carboxylic acid amide; (1S,2S,3R,4R)-3-{6-Chloro-2-[2-methoxy-4-(4-morpholin-4-yl-piperidin-1-yl)-phenyl]-3H-imidazo[4,5-b]pyridin-7-ylamino}-bicyclo[2.2.1]hept-5-ene-2-carboxylic acid amide; (1S,2S,3R,4R)-3-(6-Chloro-2-{2-methoxy-4-[4-(4-methyl-piperazin-1-yl)-piperidin-1-yl]-phenyl}-3H-imidazo[4,5-b]pyridin-7-ylamino)-bicyclo[2.2.1]hept-5-ene-2-carboxylic acid amide; (1S,2S,3R,4R)-3-{2-[2-Methoxy-4-(4-methyl-piperazin-1-yl)-phenyl]-3H-imidazo[4,5-b]pyridin-7-ylamino}-bicyclo[2.2.1]hept- 5-ene-2-carboxylic acid amide; (1S,2S,3R,4R)-3-{6-Bromo-2-[2-methoxy-4-(4-methyl-piperazin-1-yl)-phenyl]-3H-imidazo[4,5-b]pyridin-7-ylamino}-bicyclo[2.2.1]hept-5-ene-2-carboxylic acid amide; (1S,2S,3R,4R)-3-{6-Bromo-2-[2-methoxy-4-(4-morpholin-4-yl-piperidin-1-yl)-phenyl]-3H-imidazo[4,5b]pyridin-7-ylamino}-bicyclo[2.2.1]hept-5-ene-2-carboxylic acid amide; (1S,2S,3R,4R)-3-(6-Bromo-2-{2-methoxy-4-[4-(4-methyl-piperazin-1-yl)-piperidin-1-yl]-phenyl}-3H-imidazo[4,5-b]pyridin-7-ylamino)-bicyclo[2.2.1] hept-5-ene-2-carboxylic acid amide; (1S,2S,3R,4R)-3-(2-{2-Methoxy-4-[4-(4-methyl-piperazin-1-yl)-piperidin-1-yl]-phenyl}-3H-imidazo[4,5-b]pyridin-7-ylamino)-bicyclo[2.2.1]hept-5-ene-2-carboxylic acid amide; (1R,2R,3S,4S)-3-[6-Chloro-2-(3-dimethylamino-phenyl)-3H-imidazo[4,5-b]pyridine-7-ylamino]-bicyclo[2.2.1]hept-5-ene-2-carboxylic acid amide; (1R,2R,3S,4S)-3-[6-Chloro-2-(3-morpholin-4-yl-phenyl)-3H-imidazo[4,5-b]pyridine-7-ylamino]-bicyclo[2.2.1]hept-5-ene-2-carboxylic acid amide; (1R,2R,3S,4S)-3-{6-Chloro-2-[4-(4-methyl-piperazin-1-yl)-phenyl]-3H-imidazo[4,5-b]pyridine-7-ylamino}-bicyclo[2.2.1]hept-5-ene-2-carboxylic acid amide; (1R,2R,3S,4S)-3-{6-Chloro-2-[2-methoxy-4-(4-morpholin-4-yl-piperidin-1-yl)-phenyl]-3H-imidazo[4,5-b]pyridin-7-ylamino}-bicyclo[2.2.1]hept-5-ene-2-carboxylic acid amide;

(1R,2R,3S,4S)-3-{6-Chloro-2-[2-methoxy-4-(4-methyl-piperazin-1-yl)-phenyl]-3H-imidazo[4,5-b]pyridin-7-ylamino}-bicyclo[2.2.1]hept-5-ene-2-carboxylic acid amide; 4-{2-[7-((1R,2R,3S,4S)-3-Carbamoyl-bicyclo[2.2.1]hept-5-en-2-ylamino)-6-chloro-3H-imidazo[4,5-b]pyridine-2-yl}-5-methoxy-phenyl}-piperidinej-1-carboxylic acid tert-butyl ester (1S,2S,3R,4R)-3-[6-Chloro-2-(4-methoxy-2-piperidin-4-yl-phenyl)-3H-imidazo[4,5-b]pyridine-7-ylamino]-bicyclo[2.2.1]hept-5-ene-2-carboxylic acid amide; (1S,2S,3R,4R)-3-(6-Chloro-2-{2-[1-((R)-2-hydroxypropyl)-piperidin-4-yl]-4-methoxy-phenyl}-3H-imidazo[4,5-b]pyridin-7-ylamino)-bicyclo[2.2.1]hept-5-ene-2-carboxylic acid amide; (1S,2S,3R,4R)-3-(6-Chloro-2-{2-[1-((S)-2-hydroxypropyl)-piperidin-4-yl]-4-methoxy-phenyl}-3H-imidazo[4,5-b]pyridin-7-ylamino)-bicyclo[2.2.1]hept-5-ene-2-carboxylic acid amide; (1S,2S,3R,4R)-3-(6-Chloro-2-{2-[1-((S)-2,3-dihydroxypropyl)-piperidin-4-yl]-4-methoxy-phenyl}-3H-imidazo[4,5-b]pyridin-7-ylamino)-bicyclo[2.2.1]hept-5-ene-2-carboxylic acid amide; (1S,2S,3R,4R)-3-[6-Chloro-2-(2-chloro-4-morpholin-4-yl-phenyl)-3H-imidazo[4,5-b]pyridin-7-ylamino]-bicyclo[2.2.1]hept-5-ene-2-carboxylic acid amide; (1S,2S,3R,4R)-3-[6-Chloro-2-(2-methyl-4-morpholin-4-yl-phenyl)-3H-imidazo[4,5-b]pyridin-7-ylamino]-bicyclo[2.2.1]hept-5-ene-2-carboxylic acid amide; (1S,2S,3R,4R)-3-[6-Chloro-2-(1,3-dimethyl-5-morpholin-4-yl-1H-pyrazol-4-yl)-3H-imidazo[4,5-b]pyridin-7-ylamino]-bicyclo[2.2.1]hept-5-ene-2-carboxylic acid amide; (1S,2S,3R,4R)-3-[6-Chloro-2-(2-methoxy-pyridin-3-yl)-3H-imidazo[4,5-b]pyridin-7-ylamino]-bicyclo[2.2.1]hept-5-ene-2-carboxylic acid amide; (1S,2S,3R,4R)-3-{6-Bromo-2-[4-(4-methyl-piperazin-1-ylmethyl)-phenyl]-3H-imidazo[4,5-b]pyridin-7-ylamino-bicyclo[2.2.1]hept-5-ene-2-carboxylic acid amide; (1S,2S,3R,4R)-3-[6-Bromo-2-(2-methoxy-pyridin-3-yl)-3H-imidazo[4,5-b]pyridin-7-ylamino]-bicyclo[2.2.1]hept-5-ene-2-carboxylic acid amide; (1S,2S,3R,4R)-3-[6-Bromo-2-(2-morpholin-4-yl-pyridin-3-yl)-3H-imidazo[4,5-b]pyridin-7-ylamino]-bicyclo[2.2.1]hept-5-ene-2-carboxylic acid amide; (1S,2S,3R,4R)-3-[6-Bromo-2-(4-methoxy-pyridin-3-yl)-3H-imidazo[4,5-b]pyridin-7-ylamino]-bicyclo[2.2.1]hept-5-ene-2-carboxylic acid amide; (1S,2S,3R,4R)-3-[6-Bromo-2-(2-pyrazol-1-yl-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(2-pyrrolidin-1-yl-pyridin-3-yl)-3H-imidazo[4,5-b]pyridin-7-ylamino]-bicyclo[2.2.1]hept-5-ene-2-carboxylic acid amide; (1S,2S,3R,4R)-3-[6-Chloro-2-(2-morpholin-4-yl-pyridin-3-yl)-3H-imidazo[4,5-b]pyridine-7-ylamino]-bicyclo[2.2.1]hept-5-ene-2-carboxylic acid amide; (1S,2S,3R,4R)-3-[6-Chloro-2-(4-methoxy-pyridin-3-yl)-3H-imidazo[4,5-b]pyridine-7-ylamino]-bicyclo[2.2.1]hept-5-ene-2-carboxylic acid amide; (1S,2S,3R,4R)-3-[6-Bromo-2-(2,6-dimethoxy-phenyl)-3H-imidazo[4,5-b]pyridin-7-ylamino]-bicyclo[2.2.1]hept-5-ene-2-carboxylic acid amide;

(1S,2S,3R,4R)-3-(6-Bromo-2-pyrimidin-5-yl-3H-imidazo[4,5-b]pyridin-7-ylamino)-bicyclo[2.2.1]hept-5-ene-2-carboxylic acid amide; (1S,2S,3R,4R)-3-(6-Bromo-2-furan-3-yl-3H-imidazo[4,5-b]pyridin-7-ylamino)-bicyclo[2.2.1]hept-5-ene-2-carboxylic acid amide; (1S,2S,3R,4R)-3-[6-Bromo-2-(1-methyl-1H-pyrrol-2-yl)-3H-imidazo[4,5-b]pyridin-7-ylamino]-bicyclo[2.2.1]hept-5-ene-2-carboxylic acid amide; (1S,2S,3R,4R)-3-[6-Bromo-2-(5-methyl-furan-2-yl)-3H-imidazo[4,5-b]pyridin-7-ylamino]-bicyclo[2.2.1]hept-5-ene-2-carboxylic acid amide;

(1S,2S,3R,4R)-3-(6-Bromo-2-thiophen-3-yl-3H-imidazo[4,5-b]pyridin-7-ylamino)-bicyclo[2.2.1]hept-5-ene-2-carboxylic acid amide; (1S,2S,3R,4R)-3-[6-Bromo-2-(6-morpholin-4-yl-pyridin-3-yl)-3H-imidazo[4,5-b]pyridin-7-ylamino]-bicyclo[2.2.1]hept-5-ene-2-carboxylic acid amide; (1R,2S,3R,4S)-3-{6-Bromo-2-[4-(4-methyl-piperazin-1-yl)-phenyl]-3H-imidazo[4,5-b]pyridin-7-ylamino}-bicyclo[2.2.1]heptane-2-carboxylic acid amide; (1S,2S,3R,4R)-3-[6-Chloro-2-(6-methoxy-pyridin-2-yl)-3H-imidazo[4,5-b]pyridin-7-ylamino]-bicyclo[2.2.1]hept-5-ene-2-carboxylic acid amide; (1S,2S,3R,4R)-3-[6-Chloro-2-(3-pyrazol-1-yl-phenyl)-3H-imidazo[4,5-b]pyridin-7-ylamino]-bicyclo[2.2.1]hept-5-ene-2-carboxylic acid amide; (1S,2S,3R,4R)-3-[6-Chloro-2-(2-morpholin-4-yl-pyridin-4-yl)-3H-imidazo[4,5-b]pyridin-7-ylamino]-bicyclo[2.2.1]hept-5-ene-2-carboxylic acid amide; (1S,2S,3R,4R)-3-[6-Chloro-2-(2-fluoro-phenyl)-3H-imidazo[4,5-b]pyridin-7-ylamino]-bicyclo[2.2.1]hept-5-ene-2-carboxylic acid amide;

1S,2S,3R,4R)-3-[6-Chloro-2-(3-fluoro-phenyl)-3H-imidazo[4,5-b]pyridin-7-ylamino]-bicyclo[2.2.1]hept-5-ene-2-carboxylic acid amide; (1S,2S,3R,4R)-3-[6-Chloro-2-(4-fluoro-phenyl)-3H-imidazo[4,5-b]pyridin-7-ylamino]-bicyclo[2.2.1]hept-5-ene-2-carboxylic acid amide; (1S,2S,3R,4R)-3-[6-Chloro-2-(2-methoxy-4-morpholin-4-yl-phenyl)-3H-imidazo[4,5-b]pyridine-7-ylamino]-bicyclo[2.2.1]hept-5-ene-2-carboxylic acid amide; (1S,2S,3R,4R)-3-{6-Chloro-2-[2-methoxy-4-(4-methyl-piperazin-1-ylmethyl)-phenyl]-3H-imidazo[4,5-b]pyridine-7-ylamino}-bicyclo[2.2.1]hept-5-ene-2-carboxylic acid amide;

(1S,2S,3R,4R)-3-{6-Chloro-2-[2-methoxy-4-(4-methyl-piperazin-1-ylmethyl)-phenyl]-3H-imidazo[4,5-b]pyridine-7-ylamino}-bicyclo[2.2.1]hept-5-ene-2-carboxylic acid amide; (1S,2S,3R,4R)-3-{6-Chloro-2-[2-methoxy-4-pyrrolidin-1-ylmethyl)-phenyl]-3H-imidazo[4,5-b]pyridine-7-ylamino}-bicyclo[2.2.1]

hept-5-ene-2-carboxylic acid amide; (1S,2S,3R,4R)-3-[6-Chloro-2-(2-methoxy-4-piperazin-1-ylmethyl-phenyl)-3H-imidazo[4,5-b]pyridine-7-ylamino]-bicyclo[2.2.1]hept-5-ene-2-carboxylic acid amide; (1S,2S,3R,4R)-3-(6-Chloro-2-{4-[4-((S)-2-hydroxypropyl)-piperazin-1-ylmethyl]-2-methoxyphenyl}-3H-imidazo[4,5-b]pyridine-7-ylamino)-bicyclo[2.2.1]hept-5-ene-2-carboxylic acid amide; (1S,2S,3R,4R)-3-[6-Bromo-2-(2-methyl-4-morpholin-4-yl-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(2-fluoro-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(3-fluoro-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(4-fluoro-phenyl)-3H-imidazo[4,5-b]pyridin-7-ylamino]-bicyclo[2.2.1]hept-5-ene-2-carboxylic acid amide; (1S,2S,3R,4R)-3-(6-Chloro-2-{4-[4-((R)-2-hydroxypropyl)-piperazin-1-ylmethyl]-2-methoxyphenyl}-3H-imidazo[4,5-b]pyridine-7-ylamino)-bicyclo[2.2.1]hept-5-ene-2-carboxylic acid amide; (1S,2S,3R,4R)-3-(6-Chloro-2-{4-[1-((S)-2-hydroxypropyl)-piperidin-4-yl]-2-methoxyphenyl}-3H-imidazo[4,5-b]pyridine-7-ylamino)-bicyclo[2.2.1]hept-5-ene-2-carboxylic acid amide; (1S,2S,3R,4R)-3-[6-Bromo-2-(2-chloro-4-morpholin-4-yl-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(3-chloro-4-morpholin-4-yl-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(2-morpholin-4-yl-pyridin-4-yl)-3H-imidazo[4,5-b]pyridin-7-ylamino]-bicyclo[2.2.1]hept-5-ene-2-carboxylic acid amide; (1S,2S,3R,4R)-3-[6-Chloro-2-(3-chloro-4-morpholin-4-yl-phenyl)-3H-imidazo[4,5-b]pyridin-7-ylamino]-bicyclo[2.2.1]hept-5-ene-2-carboxylic acid amide; (1S,2S,3R,4R)-3-[6-Chloro-2-(4-dimethylaminomethyl-2-methoxyphenyl)-3H-imidazo[4,5-b]pyridine-7-ylamino]-bicyclo[2.2.1]hept-5-ene-2-carboxylic acid amide; (1S,2S,3R,4R)-3-[6-Chloro-2-(3-chloro-4-morpholin-4-yl-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(6-trifluoromethyl-pyridin-3-yl)-3H-imidazo[4,5-b]pyridin-7-ylamino]-bicyclo[2.2.1]hept-5-ene-2-carboxylic acid amide; (1S,2S,3R,4R)-3-(6-Chloro-2-[4-((R)-3-hydroxy-pyrrolidin-1-ylmethyl)-2-methoxyphenyl]-3H-imidazo[4,5-b]pyridine-7-ylamino)-bicyclo[2.2.1]hept-5-ene-2-carboxylic acid amide; (1S,2S,3R,4R)-3-(6-chloro-2-(4-morpholinophenyl)-3H-imidazo[4,5-b]pyridin-7-ylamino)-N,N-dimethylbicyclo[2.2.1]hept-5-ene-2-carboxamide; (1S,2S,3R,4R)-3-(6-chloro-2-(4-morpholinophenyl)-3H-imidazo[4,5-b]pyridin-7-ylamino)-N-isopropylbicyclo[2.2.1]hept-5-ene-2-carboxamide; (1S,2S,3R,4R)-3-(6-chloro-2-(1-methyl-1H-pyrazol-4-yl)-3H-imidazo[4,5-b]pyridin-7-ylamino)-N-isopropylbicyclo[2.2.1]hept-5-ene-2-carboxamide; (1S,2S,3R,4R)-3-(6-chloro-2-(4-(4-methylpiperazin-1-yl)phenyl)-3H-imidazo[4,5-b]pyridin-7-ylamino)-N-(2-hydroxyethyl)bicyclo[2.2.1]hept-5-ene-2-carboxamide; (1S,2S,3R,4R)-3-(6-chloro-2-(thiazol-5-yl)-3H-imidazo[4,5-b]pyridin-7-ylamino)bicyclo[2.2.1]hept-5-ene-2-carboxamide; (1S,2S,3R,4R)-3-(6-chloro-2-(2-methylthiazol-5-yl)-3H-imidazo[4,5-b]pyridin-7-ylamino)bicyclo[2.2.1]hept-5-ene-2-carboxamide; (1S,2S,3R,4R)-3-(6-chloro-2-(4-chloro-2-(4-methylpiperazin-1-yl)thiazol-5-yl)-3H-imidazo[4,5-b]pyridin-7-ylamino)bicyclo[2.2.1]hept-5-ene-2-carboxamide; (1S,2S,3R,4R)-3-(6-chloro-2-(5,6,7,8-tetrahydroimidazo[1,2-a]pyridin-2-yl)-3H-imidazo[4,5-b]pyridin-7-ylamino)bicyclo[2.2.1]hept-5-ene-2-carboxamide; (1S,2S,3R,4R)-3-[6-Chloro-2-(3-chloro-phenyl)-3H-imidazo[4,5-b]pyridin-7-ylamino]-bicyclo[2.2.1]hept-5-ene-2-carboxylic acid amide; (1S,2S,3R,4R)-3-[6-Chloro-2-(4-chloro-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(3-chloro-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(4-chloro-phenyl)-3H-imidazo[4,5-b]pyridin-7-ylamino]-bicyclo[2.2.1]hept-5-ene-2-carboxylic acid amide; (1S,2S,3R,4R)-3-(6-Chloro-2-{4-[1-((S)-2-hydroxypropyl)-1,2,3,6-tetrahydro-pyridin-4-yl]-2-methoxyphenyl}-3H-imidazo[4,5-b]pyridine-7-ylamino)-bicyclo[2.2.1]hept-5-ene-2-carboxylic acid amide; (1S,2S,3R,4R)-3-[6-Chloro-2-(3-cyano-phenyl)-3H-imidazo[4,5-b]pyridin-7-ylamino]-bicyclo[2.2.1]hept-5-ene-2-carboxylic acid amide; (1S,2S,3R,4R)-3-[6-Chloro-2-(4-cyano-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(3-cyano-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(4-cyano-phenyl)-3H-imidazo[4,5-b]pyridin-7-ylamino]-bicyclo[2.2.1]hept-5-ene-2-carboxylic acid amide; (1S,2S,3R,4R)-3-[6-Chloro-2-(2-methoxy-5-morpholin-4-ylphenyl)-3H-imidazo[4,5-b]pyridine-7-ylamino)-bicyclo[2.2.1]hept-5-ene-2-carboxylic acid amide; 4-{4-[7-((1R,2R,3S,4S)-3-Carbamoyl-bicyclo[2.2.1]hept-5-en-2-ylamino)-6-chloro-3H-imidazo[4,5-b]pyridine-2-yl]-pyrazol-1-yl}-piperidine-1-carboxylic acid tert-butyl ester; (1S,2S,3R,4S)-3-{2-[4-(4-Acetyl-piperazin-1-ylmethyl)-2-methoxyphenyl]-6-chloro-3H-imidazo[4,5-b]pyridine-7-ylamino}-bicyclo[2.2.1]hept-5-ene-2-carboxylic acid amide; (1S,2S,3R,4R)-3-(6-chloro-2-(4-(4-methylpiperazin-1-yl)phenyl)-3H-imidazo[4,5-b]pyridin-7-ylamino)-N-methylbicyclo[2.2.1]hept-5-ene-2-carboxamide; (1S,2S,3R,4R)-3-(6-chloro-2-(2-methoxy-4-morpholinophenyl)-3H-imidazo[4,5-b]pyridin-7-ylamino)-N-methylbicyclo[2.2.1]hept-5-ene-2-carboxamide; (1S,2S,3R,4R)-3-(6-chloro-2-(4-(4-methylpiperazin-1-yl)phenyl)-3H-imidazo[4,5-b]pyridin-7-ylamino)-N-isopropyl bicyclo[2.2.1]hept-5-ene-2-carboxamide; (1S,2S,3R,4R)-3-(6-chloro-2-(2-methoxy-4-morpholinophenyl)-3H-imidazo[4,5-b]pyridin-7-ylamino)-N-(2-hydroxyethyl)bicyclo[2.2.1]hept-5-ene-2-carboxamide; (1S,2S,3R,4R)-3-(6-chloro-2-(2-methoxythiazol-5-yl)-3H-imidazo[4,5-b]pyridin-7-ylamino)bicyclo[2.2.1]hept-5-ene-2-carboxamide; (1S,2S,3R,4R)-3-(6-chloro-2-(2-(4-methylpiperazin-1-yl)thiazol-5-yl)-3H-imidazo[4,5-b]pyridin-7-ylamino)bicyclo[2.2.1]hept-5-ene-2-carboxamide; tert-butyl 4-(7-((1R,2R,3S,4S)-3-carbamoylbicyclo[2.2.1]hept-5-en-2-ylamino)-6-chloro-3H-imidazo[4,5-b]pyridin-2-yl)piperidine-1-carboxylate; (1S,2S,3R,4R)-3-(6-chloro-2-(2-morpholinothiazol-5-yl)-3H-imidazo[4,5-b]pyridin-7- ylamino)bicyclo[2.2.1]hept-5-ene-2-carboxamide; (1S,2S,3R,4R)-3-[6-Chloro-2-(2-chloro-phenyl)-3H-imidazo[4,5-b]pyridin-7-ylamino]-bicyclo[2.2.1]hept-5-ene-2-carboxylic acid amide; (1S,2S,3R,4R)-3-[6-Bromo-2-(2-chloro-phenyl)-3H-imidazo[4,5-b]pyridin-7-ylamino]-bicyclo[2.2.1]hept-5-ene-2-carboxylic acid amide;

(1S,2S,3R,4R)-3-[6-Chloro-2-(2-methoxy-3-morpholin-4-ylmethyl-phenyl)-3H-imidazo[4,5-b]pyridine-7-ylamino]-bicyclo[2.2.1]hept-5-ene-2-carboxylic acid amide; (1S,2S,3R,4R)-3-[6-Chloro-2-(1-methyl-piperidin-4-yl)-3H-imidazo[4,5-b]pyridin-7-ylamino]-bicyclo[2.2.1]hept-5-ene-2-carboxylic acid amide;

(1S,2S,3R,4R)-3-[6-Chloro-2-(1,3,5-trimethyl-1H-pyrazol-4-yl)-3H-imidazo[4,5-b]pyridin-7-ylamino]-bicyclo[2.2.1]hept-5-ene-2-carboxylic acid amide;

(1S,2S,3R,4R)-3-[6-Bromo-2-(1,3,5-trimethyl-1H-pyrazol-4-yl)-3H-imidazo[4,5-b]pyridin-7-ylamino]-bicyclo[2.2.1]hept-5-ene-2-carboxylic acid amide;

(1S,2S,3R,4R)-3-(6-Chloro-2-{4-[1-(R)-2-hydroxy-3-methoxypropyl)-piperidin-4-yl]-2-methoxyphenyl}-3H-imidazo[4,5-b]pyridine-7-ylamino}-bicyclo[2.2.1]hept-5-ene-2-carboxylic acid amide; (1S,2S,3R,4R)-3-{6-Chloro-2-[4-((S)-3-hydroxy-pyrrolidin-1-ylmethyl)-2-methoxyphenyl]-3H-imidazo[4,5-b]pyridine-7-ylamino}-bicyclo[2.2.1]hept-5-ene-2-carboxylic acid amide; (1S,2S,3R,4R)-3-(6-chloro-2-(1-methyl-1H-pyrazol-4-yl)-3H-imidazo[4,5-b]pyridin-7-ylamino)-N-methylbicyclo[2.2.1]hept-5-ene-2-carboxamide; (1S,2S,3R,4R)-3-(6-chloro-2-(4-morpholinophenyl)-3H-imidazo[4,5-b]pyridin-7-ylamino)-N-(2-hydroxyethyl)bicyclo[2.2.1]hept-5-ene-2-carboxamide; (1S,2S,3R,4R)-3-(6-chloro-2-(2-methoxy-4-(4-methylpiperazin-1-yl)phenyl)-3H-imidazo[4,5-b]pyridin-7-ylamino)-N-(2-hydroxyethyl)bicyclo[2.2.1]hept-5-ene-2-carboxamide;

(1S,2S,3R,4R)-3-(6-chloro-2-(4-(4-methylpiperazin-1-yl)phenyl)-3H-imidazo[4,5-b]pyridin-7-ylamino)-N-isopropyl-bicyclo[2.2.1]hept-5-ene-2-carboxamide;

(1S,2S,3R,4R)-3-[2-(4-Allyl-2-methoxy-phenyl)-6-chloro-3H-imidazo[4,5-b]pyridine-7-ylamino}-bicyclo[2.2.1]hept-5-ene-2-carboxylic acid amide;

(1S,2S,3R,4R)-3-(6-chloro-2-(2-methoxy-4-morpholinophenyl)-3H-imidazo[4,5-b]pyridin-7-ylamino)-N,N-dimethylbicyclo[2.2.1]hept-5-ene-2-carboxamide;

(1S,2S,3R,4R)-3-(6-chloro-2-(2-methoxy-4-morpholinophenyl)-3H-imidazo[4,5-b]pyridin-7-ylamino)-N,N-dimethylbicyclo[2.2.1]hept-5-ene-2-carboxamide;

(1S,2S,3R,4R)-3-(6-chloro-2-(2-methoxy-4-(4-methylpiperazin-1-yl)phenyl)-3H-imidazo[4,5-b]pyridin-7-ylamino)-N,N-dimethylbicyclo[2.2.1]hept-5-ene-2-carboxamide; (1S,2S,3R,4R)-3-[6-Chloro-2-(1-piperidin-4-yl-1H-pyrazol-4-yl)-3H-imidazo[4,5-b]pyridine-7-ylamino]-bicyclo[2.2.1]hept-5-ene-2-carboxylic acid amide; (1S,2S,3R,4R)-3-(6-Chloro-2-{1-[1-((R)-2-hydroxypropyl)-piperidin-4-yl]-1H-pyrazol-4-yl}-3H-imidazo[4,5-b]pyridine-7-ylamino)-bicyclo[2.2.1]hept-5-ene-2-carboxylic acid amide; (1S,2S,3R,4R)-3-(6-Chloro-2-{1-[1-((S)-2-hydroxypropyl)-piperidin-4-yl]-1H-pyrazol-4-yl}-3H-imidazo[4,5-b]pyridine-7-ylamino)-bicyclo[2.2.1]hept-5-ene-2-carboxylic acid amide; (1S,2S,3R,4R)-3-(6-Chloro-2-{1-[1-((R)-2-hydroxy-3-methoxy-propyl)-piperidin-4-yl]-1H-pyrazol-4-yl}-3H-imidazo[4,5-b]pyridine-7-ylamino)-bicyclo[2.2.1]hept-5-ene-2-carboxylic acid amide; (1S,2S,3R,4R)-3-(6-Chloro-2-pyridin-3-yl-3H-imidazo[4,5-b]pyridin-7-ylamino)-bicyclo[2.2.1]hept-5-ene-2-carboxylic acid amide; (1S,2S,3R,4R)-3-[6-Chloro-2-(4-chloro-2-dimethylamino-thiazol-5-yl)-3H-imidazo[4,5-b]pyridin-7-ylamino]-bicyclo[2.2.1]hept-5-ene-2-carboxylic acid amide; (1S,2S,3R,4R)-3-[6-Bromo-2-(4-chloro-2-dimethylamino-thiazol-5-yl)-3H-imidazo[4,5-b]pyridin-7-ylamino]-bicyclo[2.2.1]hept-5-ene-2-carboxylic acid amide; (1S,2S,3R,4R)-3-{2-[1-(1-Acetyl-piperidin-4-yl)-1H-pyrazol-4-yl]-6-chloro-3H-imidazo[4,5-b]pyridine-7-ylamino}-bicyclo[2.2.1]hept-5-ene-2-carboxylic acid amide; 4-{4-[7-((1R,2R,3S,4S)-3-Carbamoyl-bicyclo[2.2.1]hept-5-ene-2-ylamino)-6-chloro-3H-imidazo[4,5-b]pyridine-2-yl]-pyrazol-1-yl)-piperidine-1-carboxylic acid ethylamide; (1S,2S,3R,4R)-3-{6-Chloro-2-[2-methoxy-4-(morpholine-4-carbonyl)-phenyl]-3H-imidazo[4,5-b]pyridine-7-ylamino}-bicyclo[2.2.1]hept-5-ene-2-carboxylic acid amide; (1S,2S,3R,4R)-3-(6-Chloro-2-{4-[1-((R)-2-hydroxy-propyl)-piperidin-4-yl]-2-methoxy-phenyl}-3H-imidazo[4,5-b]pyridin-7-ylamino)-bicyclo[2.2.1]hept-5-ene-2-carboxylic acid amide; (1S,2S,3R,4R)-3-{6-Chloro-2-[2-methoxy-4-(1-methyl-piperidin-4-yl)-phenyl]-3H-imidazo[4,5-b]pyridin-7-ylamino}-bicyclo[2.2.1]hept-5-ene-2-carboxylic acid amide; (1S,2S,3R,4R)-3-(6-Chloro-2-{4-[1-((R)-2,3-dihydroxy-propyl)-piperidin-4-yl]-2-methoxy-phenyl}-3H-imidazo[4,5-b]pyridin-7-ylamino)-bicyclo[2.2.1]hept-5-ene-2-carboxylic acid amide; (1S,2S,3R,4R)-3-(6-Chloro-2-{4-[1-((S)-2-hydroxy-3-methoxy-propyl)-piperidin-4-yl]-2-methoxy-phenyl}-3H-imidazo[4,5-b]pyridin-7-ylamino)-bicyclo[2.2.1]hept-5-ene-2-carboxylic acid amide; (1S,2S,3R,4R)-3-[6-Chloro-2-(4-methyl-2-piperidin-4-yl-thiazol-5-yl)-3H-imidazo[4,5-b]pyridin-7-ylamino]-bicyclo[2.2.1]hept-5-ene-2-carboxylic acid amide; (1S,2S,3R,4R)-3-{2-[4-(4-Acetyl-piperazin-1-ylmethyl)-phenyl]-6-bromo-3H-imidazo[4,5-b]pyridin-7-ylamino}-bicyclo[2.2.1]hept-5-ene-2-carboxylic acid amide; (1S,2S,3R,4R)-3-{2-[4-(4-Acetyl-piperazin-1-ylmethyl)-phenyl]-6-chloro-3H-imidazo[4,5-b]pyridin-7-ylamino}-bicyclo[2.2.1]hept-5-ene-2-carboxylic acid amide;

(1S,2S,3R,4R)-3-{2-[2-(1-Carbamoylmethyl-piperidin-4-yl)-4-methyljj-thiazol-5-yl]-6-chloro-3H-imidazo[4,5-b]pyridine-7-ylamino}-bicyclo[2.2.1]hept-5-ene-2-carboxylic acid amide; (1S,2S,3R,4R)-3-{2-[1-(1-Carbamoylmethyl-piperidin-4-yl)-1H-pyrazol-4-yl]-6-chloro-3H-imidazo[4,5-b]pyridine-7-ylamino}-bicyclo[2.2.1]hept-5-ene-2-carboxylic acid amide; (1S,2S,3R,4R)-3-{2-[1-(1-Carbamoylmethyl-piperidin-4-yl)-1H-pyrazol-4-yl]-6-chloro-3H-imidazo[4,5-b]pyridin-7-ylamino}-bicyclo[2.2.1]hept-5-ene-2-carboxylic acid amide;

(1S,2S,3R,4R)-3-(6-chloro-2-(3-methoxyphenyl)-3H-imidazo[4,5-b]pyridin-7-ylamino)bicyclo[2.2.1]hept-5-ene-2-carboxamide; (1S,2S,3R,4R)-3-(6-chloro-2-(3-(2-morpholinoethoxy)phenyl)-3H-imidazo[4,5-b]yridine-7-ylamino)yridin[2.2.1]hept-5-ene-2-carboxamide; (1S,2S,3R,4R)-3-(6-chloro-2-(2-methoxy-4-morpholinophenyl)-3H-imidazo[4,5-b]pyridin-7-ylamino)-N-isopropylbicyclo[2.2.1]hept-5-ene-2-carboxamide; (1S,2S,3R,4R)-3-(6-chloro-2-(2-methoxy-4-(4-methylpiperazin-1-yl)phenyl)-3H-imidazo[4,5-b]pyridin-7-ylamino)-N-methylbicyclo[2.2.1]hept-5-ene-2-carboxamide; (1S,2S,3R,4R)-3-(6-chloro-2-(4-morpholinophenyl)-3H-imidazo[4,5-b]pyridin-7-ylamino)-N-methylbicyclo[2.2.1]hept-5-ene-2-carboxamide; (1S,2S,3R,4R)-3-(6-chloro-2-(1- methyl-1H-pyrazol-4-yl)-3H-imidazo[4,5-b]pyridin-7-ylamino)-N-(2-hydroxyethyl)bicyclo[2.2.1]hept-5-ene-2-carboxamide; (1S,2S,3R,4R)-3-(6-chloro-2-(4-(4-methylpiperazin-1-yl)phenyl)-3H-imidazo[4,5-b]pyridin-7-ylamino)-N,N-dimethylbicyclo[2.2.1]hept-5-ene-2-carboxamide; (1S,2S,3R,4R)-3-(6-chloro-2-(5,6,7,8-tetrahydroimidazo[1,2-a]pyridin-2-yl)-3H-imidazo[4,5-b]pyridin-7-ylamino)bicyclo[2.2.1]hept-5-ene-2-carboxamide; 2-(4-(7-((1R,2R,3S,4S)-3-carbamoylbicyclo[2.2.1]hept-5-en-2-ylamino)-6-chloro-3H-imidazo[4,5-b]pyridin-2-yl)phenoxy)acetic acid; (1S,2S,3R,4R)-3-(6-chloro-2-(4-(2-morpholinoethoxy)phenyl)-3H-imidazo[4,5-b]pyridin-7-ylamino)bicyclo[2.2.1]hept-5-ene-2-carboxamide; 4-(7-((1R,2R,3S,4S)-3-carbamoylbicyclo[2.2.1]hept-5-en-2-ylamino)-6-chloro-3H-imidazo[4,5-b]pyridin-2-yl)benzoic acid; (1S,2S,3R,4R)-3-(6-chloro-2-(4-hydroxyphenyl)-3H-imidazo[4,5-b]pyridin-7-ylamino)bicyclo[2.2.1]hept-5-ene-2-carboxamide;
(1S,2S,3R,4R)-3-(6-chloro-2-(4-methoxyphenyl)-3H-imidazo[4,5-b]pyridin-7-ylamino)bicyclo[2.2.1]hept-5-ene-2-carboxamide; (1S,2S,3R,4R)-3-(6-chloro-2-(3-hydroxyphenyl)-3H-imidazo[4,5-b]pyridin-7-ylamino)pyridin[2.2.1]hept-5-ene-2-carboxamide; (1S,2S,3R,4R)-3-(6-Chloro-2-phenylamino-3H-imidazo[4,5-b]pyridine-7-ylamino)-bicyclo[2.2.1]hept-5-ene-2-carboxylic acid amide; 2-(3-(7-((1R,2R,3S,4S)-3-carbamoylbicyclo[2.2.1]hept-5-en-2-ylamino)-6-chloro-3H-imidazo[4,5-b]pyridin-2-yl)phenoxy)acetic acid; (1S,2S,3R,4R)-3-(2-(3-(2-amino-2-oxoethoxy)phenyl)-6-chloro-3H-imidazo[4,5-b]pyridin-7-ylamino)bicyclo[2.2.1]hept-5-ene-2-carboxamide; (1S,2S,3R,4R)-3-(2-(4-(2-amino-2-oxoethoxy)phenyl)-6-chloro-3H-imidazo[4,5-b]pyridin-7-ylamino)bicyclo[2.2.1]hept-5-ene-2-carboxamide; (1S,2S,3R,4R)-3-[6-Chloro-2-(4-chloro-2-morpholin-4-yl-thiazol-5-yl)-3H-imidazo[4,5-b]pyridin-7-ylamino]-bicyclo[2.2.1]hept-5-ene-2-carboxylic acid amide; (1S,2S,3R,4R)-3-[6-Bromo-2-(4-chloro-2-morpholin-4-yl-thiazol-5-yl)-3H-imidazo[4,5-b]pyridin-7-ylamino]-bicyclo[2.2.1]hept-5-ene-2-carboxylic acid amide; (1S,2S,3R,4R)-3-(6-chloro-2-(4-(2-(dimethylamino)ethoxy)phenyl)-3H-imidazo[4,5-b]pyridin-7-ylamino)bicyclo[2.2.1]hept-5-ene-2-carboxamide; (1S,2S,3R,4R)-3-((6-chloro-2-(4-chloro-2-(4-methylpiperazin-1-yl)thiazol-5-yl)-3H-imidazo[4,5-b]pyridin-7-yl)amino)-N-isopropylbicyclo[2.2.1]hept-5-ene-2-carboxamide; (1S,2S,3R,4R)-3-((6-chloro-2-(4-chloro-2-(4-methylpiperazin-1-yl)thiazol-5-yl)-3H-imidazo[4,5-b]pyridin-7-yl)amino)-N,N-dimethylbicyclo[2.2.1]hept-5-ene-2-carboxamide;
(1S,2S,3R,4R)-3-[6-Chloro-2-(2-methoxy-phenylamino)-3H-imidazo[4,5-b]pyridine-7-ylamino]-bicyclo[2.2.1]hept-5-ene-2-carboxylic acid amide;
(1S,2S,3R,4R)-3-(6-chloro-2-(3-(1-methylpiperidin-4-yloxy)phenyl)-3H-imidazo[4,5-b]pyridin-7-ylamino)bicyclo[2.2.1]hept-5-ene-2-carboxamide;
(1S,2S,3R,4R)-3-(6-chloro-2-(3-(2-(dimethylamino)ethoxy)phenyl)-3H-imidazo[4,5-b]yridine-7-ylamino)pyridin[2.2.1]hept-5-ene-2-carboxamide;
(1S,2S,3R,4R)-3-(6-chloro-2-(3-(2-(4-methylpiperazin-1-yl)-2-oxoethoxy)phenyl)-3H-imidazo[4,5-b]yridine-7-ylamino)pyridin[2.2.1]hept-5-ene-2-carboxamide;
(1S,2S,3R,4R)-3-(6-chloro-2-(4-(2-(4-methylpiperazin-1-yl)-2-oxoethoxy)phenyl)-3H-imidazo[4,5-b]pyridin-7-ylamino)bicyclo[2.2.1]hept-5-ene-2-carboxamide; 2-(3-(7-((1R,2R,3S,4S)-3-carbamoylbicyclo[2.2.1]hept-5-en-2-ylamino)-6-chloro-3H-imidazo[4,5-b]pyridin-2-yl)benzamido)acetic acid; (1S,2S,3R,4R)-3-[6-Chloro-2-(2-methoxy-4-morpholin-4-ylmethyl-phenylamino)-3H-imidazo[4,5-b]pyridin-7-ylamino]-bicyclo[2.2.1]hept-5-ene-2-carboxylic acid amide;
(1S,2S,3R,4R)-3-[6-Chloro-2-(4-chloro-2-morpholin-4-yl-thiazol-5-yl)-3H-imidazo[4,5-b]pyridin-7-ylamino]-bicyclo[2.2.1]hept-5-ene-2-carboxylic acid dimethylamide; (1S,2S,3R,4R)-3-[6-Chloro-2-(4-chloro-2-morpholin-4-yl-thiazol-5-yl)-3H-imidazo[4,5-b]pyridin-7-ylamino]-bicyclo[2.2.1]hept-5-ene-2-carboxylic acid isopropylamide; (1S,2S,3R,4R)-3-(6-chloro-2-(4-(1-methylpiperidin-4-yloxy)phenyl)-3H-imidazo[4,5-b]pyridin-7-ylamino)bicyclo[2.2.1]hept-5-ene-2-carboxamide; (1S,2S,3R,4R)-3-(6-chloro-2-(4-(4-methylpiperazine-1-carbonyl)phenyl)-3H-imidazo[4,5-b]pyridin-7-ylamino)bicyclo[2.2.1]hept-5-ene-2-carboxamide; (1S,2S,3R,4R)-3-(6-chloro-2-(3-(2-(dimethylamino)ethylcarbamoyl)phenyl)-3H-imidazo[4,5-b]pyridine-7-ylamino)pyridin[2.2.1]hept-5-ene-2-carboxamide; (1S,2S,3R,4R)-3-(6-chloro-2-(3-(4-methylpiperazine-1-carbonyl)phenyl)-3H-imidazo[4,5-b]pyridin-7-ylamino)bicyclo[2.2.1]hept-5-ene-2-carboxamide; (1S,2S,3R,4R)-3-(6-chloro-2-(3-(2-(4-(2-hydroxypropyl)piperazin-1-yl)-2-oxoethoxy)phenyl)-3H-imidazo[4,5-b]pyridin-7-ylamino)bicyclo[2.2.1]hept-5-ene-2-carboxamide; (1S,2S,3R,4R)-3-(6-chloro-2-(4-(2-(4-methylpiperazin-1-yl)ethoxy)phenyl)-3H-imidazo[4,5-b]pyridin-7-ylamino)bicyclo[2.2.1]hept-5-ene-2-carboxamide; (1S,2S,3R,4R)-3-(6-chloro-2-(3-(piperazine-1-carbonyl)phenyl)-3H-imidazo[4,5-b]pyridin-7-ylamino)bicyclo[2.2.1]hept-5-ene-2-carboxamide; (1S,2S,3R,4R)-3-[6-Chloro-2-(4-chloro-2-pyrrolidin-1-yl-thiazol-5-yl)-3H-imidazo[4,5-b]pyridin-7-ylamino]-bicyclo[2.2.1]hept-5-ene-2-carboxylic acid dimethylamide; (1S,2S,3R,4R)-3-[6-Chloro-2-(4-chloro-2-pyrrolidin-1-yl-thiazol-5-yl)-3H-imidazo[4,5-b]pyridin-7-ylamino]-bicyclo[2.2.1]hept-5-ene-2-carboxylic acid isopropylamide;
(1S,2S,3R,4R)-3-[6-Chloro-2-(4-chloro-2-pyrrolidin-1-yl-thiazol-5-yl)-3H-imidazo[4,5-b]pyridin-7-ylamino]-bicyclo[2.2.1]hept-5-ene-2-carboxylic acid amide; (1S,2S,3R,4R)-3-[6-Bromo-2-(4-chloro-2-pyrrolidin-1-yl-thiazol-5-yl)-3H-imidazo[4,5-b]pyridin-7-ylamino]-bicyclo[2.2.1]hept-5-ene-2-carboxylic acid amide; (1S,2S,3R,4R)-3-{6-Chloro-2-[4-chloro-2-((R)-3-hydroxy-pyrrolidin-1-yl)-thiazol-5-yl]-3H-imidazo[4,5-b]pyridin-7-ylamino}-bicyclo[2.2.1]hept-5-ene-2-carboxylic acid dimethylamide; (1S,2S,3R,4R)-3-{6-Chloro-2-[4-chloro-2-((R)-3-hydroxy-pyrrolidin-1-yl)-thiazol-5-yl]-1H-imidazo[4,5-b]pyridin-7-ylamino}-bicyclo[2.2.1]hept-5-ene-2-carboxylic acid isopropylamide;
(1S,2S,3R,4R)-3-{6-Chloro-2-[4-chloro-2-((R)-3-hydroxy-pyrrolidin-1-yl)-thiazol-5-yl]-1H-imidazo[4,5-b]pyridin-7-ylamino}-bicyclo[2.2.1]hept-5-ene-2-carboxylic acid isopropylamide; (1S,2S,3R,4R)-3-{6-Bromo-2-[4-chloro-2-((R)-3-hydroxy-pyrrolidin-1-yl)-thiazol-5-yl]-3H-imidazo[4,5-b]pyridin-7-ylamino}-bicyclo[2.2.1]hept-5-ene-2-carboxylic acid amide; (1S,2S,3R,4R)-3-[6-Chloro-2-(4-chloro-2-pyrrolidin-1-yl-thiazol-5-yl)-3H-imidazo[4,5-b]pyridin-7-ylamino]-bicyclo[2.2.1]hept-5-ene-2-carboxylic acid cyclopropylamide; (1S,2S,3R,4R)-3-{6-Chloro-2-[4-chloro-2-((R)-3-hydroxy-pyrrolidin-1-yl)-thiazol-5-yl]-3H-imidazo[4,5-b]pyridin-7-ylamino}-bicyclo[2.2.1]hept-5-ene-2-carboxylic acid cyclopropylamide;

(1S,2S,3R,4R)-3-[6-Chloro-2-(4-chloro-2-morpholin-4-yl-thiazol-5-yl)-3H-imidazo[4,5-b]pyridin-7-ylamino]-bicyclo[2.2.1]hept-5-ene-2-carboxylic acid cyclopropylamide; (1S,2S,3R,4R)-3-(6-chloro-2-(4-(piperazine-1-carbonyl)phenyl)-3H-imidazo[4,5-b]pyridin-7-ylamino)bicyclo[2.2.1]hept-5-ene-2-carboxamide; (1S,2S,3R,4R)-3-{6-Chloro-2-[4-(2-dimethylamino-ethylcarbamoyl)-phenyl]-3H-imidazo[4,5-b]pyridine-7-ylamino}-bicyclo[2.2.1]hept-5-ene-2-carboxylic acid amide; (1S,2S,3R,4R)-3-(6-chloro-2-(4-(4-(2-hydroxypropyl)piperazine-1-carbonyl)phenyl)-3H-imidazo[4,5-b]pyridin-7-ylamino)pyridin[2.2.1]hept-5-ene-2-carboxamide; (1S,2S,3R,4R)-3-(6-chloro-2-(4-(1-(2-hydroxypropyl)piperidin-4-yloxy)phenyl)-3H-imidazo[4,5-b]pyridin-7-ylamino)bicyclo[2.2.1]hept-5-ene-2-carboxamide; (1S,2S,3R,4R)-3-(6-chloro-2-(3-(1-(2-hydroxypropyl)piperidin-4-yloxy)phenyl)-3H-imidazo[4,5-b]pyridine-7-ylamino)pyridin[2.2.1]hept-5-ene-2-carboxamide; 1S,2S,3R,4R)-3-(6-chloro-2-(3-(4-(2-hydroxypropyl)piperazine-1-carbonyl)phenyl)-3H-imidazo[4,5-b]pyridine-7-ylamino)pyridin[2.2.1]hept-5-ene-2-carboxamide;
(1S,2S,3R,4R)-3-(6-chloro-2-(4-(2-(4-(2-hydroxypropyl)piperazin-1-yl)-2-oxoethoxy)phenyl)-3H-imidazo[4,5-b]pyridin-7-ylamino)bicyclo[2.2.1]hept-5-ene-2-carboxamide; 4-(3-(7-((1R,2R,3S,4S)-3-carbamoylbicyclo[2.2.1]hept-5-en-2-ylamino)-6-chloro-3H-imidazo[4,5-b]pyridine-2-yl)benzoyl)piperazine-2-carboxylic acid; 2-(4-(7-((1R,2R,3S,4S)-3-carbamoylbicyclo[2.2.1]hept-5-en-2-ylamino)-6-chloro-3H-imidazo[4,5-b]pyridine-2-yl)benzamido)acetic acid;
(1S,2S,3R,4R)-3-(6-Chloro-2-{4-[2-(4-methyl-piperazin-1-yl)-ethoxy]-phenyl}-3H-imidazo[4,5-b]pyridin-7-ylamino)-bicyclo[2.2.1]hept-5-ene-2-carboxylic acid dimethylamide; (1S,2S,3R,4R)-3-{6-Chloro-2-[4-(2-dimethylamino-ethoxy)-phenyl]-3H-imidazo[4,5-b]pyridin-7-ylamino}-bicyclo[2.2.1]hept-5-ene-2-carboxylic acid dimethylamide; 2-(4-(7-((1R,2R,3S,4S)-3-carbamoylbicyclo(2.2.1)hept-5-en-2-ylamino)-6-chloro-3H-imidazo[4,5-b]pyridine-2-yl)benzamido)-3-hydroxypropanoic acid; 4-(4-(7-((1R,2R,3S,4S)-3-carbamoylbicyclo[2.2.1]hept-5-en-2-ylamino)-6-chloro-3H-imidazo[4,5-b]yridine-2-yl)benzoyl)piperazine-2-carboxylic acid; and
(2-(3-(7-((1R,2R,3S,4S)-3-carbamoylbicyclo(2.2.1)hept-5-en-2-ylamino)-6-chloro-3H-imidazo[4,5-b]pyridine-2-yl)benzamido)-3-hydroxypropanoic acid;
or a salt thereof.

15. A compound according to claim 9, or a salt thereof, wherein:
R$^1$ is

R$^2$ is selected from hydrogen, bromine and chlorine; and R$^4$, R$^5$, and R$^9$ are each H.

16. A compound according to claim 4, or a salt thereof, wherein:
R$^1$ is phenyl, optionally substituted with one or more R$^6$ groups; and each R$^5$ is independently selected from hydrogen and methyl.

17. A compound according to claim 15 that is selected from the following:
2S,3R,4R)-3-[(6-bromo-2-spiro[chromane-2,4'-piperidine]-6-yl-3H-imidazo[4,5-b]pyridin-7-yl)amino]bicyclo[2.2.1]hept-5-ene-2-carboxamide and
(1S,2S,3R,4R)-3-[(6-chloro-2-spiro[chromane-2,4'-piperidine]-6-yl-3H-imidazo[4,5-b]pyridin-7-yl)amino]bicyclo[2.2.1]hept-5-ene-2-carboxamide;
or a salt thereof.

18. A compound according to claim 16 that is selected from the following:
N-[(1R,2R)-2-(6-Chloro-2-{2-methoxy-4-[4-(4-methyl-piperazin-1-yl)-piperidin-1-yl]-phenyl}-3H-imidazo[4,5-b]pyridin-7-ylamino)-cyclohexyl]-methanesulfonamide;
N-((1R,2R)-2-{6-Chloro-2-[4-(4-methyl-piperazin-1-ylmethyl)-phenyl]-3H-imidazo[4,5-b]pyridin-7-ylamino}-cyclohexyl)-methanesulfonamide;
N-{(1R,2R)-2-[6-Chloro-2-(2-methoxy-4-morpholin-4-ylmethyl-phenyl)-3H-imidazo[4,5-b]pyridine-7-ylamino]-cyclohexyl}-methanesulfonamide;
N-((1R,2R)-2-{6-Chloro-2-[2-methoxy-4-(4-methyl-piperazin-1-ylmethyl)-phenyl]-3H-imidazo[4,5-b]pyridine-7-ylamino}-cyclohexyl)-methanesulfonamide;
N-{(1R,2R)-2-[6-Chloro-2-(2-methoxy-4-morpholin-4-yl-phenyl)-3H-imidazo[4,5-b]pyridine-7-ylamino]-cyclohexyl}-methanesulfonamide;
N-((1R,2R)-2{6-Chloro-2-[2-methoxy-4-(4-morpholin-4-yl-piperidin-1-yl)-phenyl]-3H-imidazo[4,5-b]pyridine-7-ylamino}-cyclohexyl)-methanesulfonamide;
N-{(1R,2R)-2-[6-Chloro-2-(2-methoxy-5-morpholin-4-ylmethyl-phenyl)-3H-imidazo[4,5-b]pyridine-7-ylamino]-cyclohexyl}-methanesulfonamide; and
N-((1R,2R)-2-{6-Chloro-2-[4-((R)-3-hydroxy-pyrrolidin-1-ylmethyl)-2-methoxy-phenyl]-3H-imidazo[4,5-b]pyridine-7-ylamino}-cyclohexyl)-methanesulfonamide;
or a salt thereof.

19. A compound according to claim 8, or a salt thereof, wherein:
R$^1$ is selected from phenyl and pyrazolyl, each optionally substituted with one or more R$^6$ groups.

20. A compound according to claim 19 that is selected from the following:
(1S,2R,3S,4R)-3-(6-chloro-2-(1-methyl-1H-pyrazol-4-yl)-3H-imidazo[4,5-b]pyridin-7-ylamino)-7-oxabicyclo[2.2.1]heptane-2-carboxamide; (1S,2R,3S,4R)-3-(6-chloro-2-(4-morpholinophenyl)-3H-imidazo[4,5-b]pyridin-7-ylamino)-7-oxabicyclo[2.2.1]heptane-2-carboxamide; and (1S,2R,3S,4R)-3-(6-chloro-2-(2-methoxy-4-morpholinophenyl)-3H-imidazo[4,5-b]pyridin-7-ylamino)-7-oxabicyclo[2.2.1]heptane-2-carboxamide;
or a salt thereof.

21. A compound according to claim 6 that is selected from the following:
(1S,4S)-5-[6-Chloro-2-(2-methoxy-4-morpholinj-4-yl-phenyl)-3H-imidazo[4,5-b]pyridine-7-yl]-2,5-diaza-bicyclo[2.2.1]heptane-2-carboxylic acid tert-butyl ester;
6-Chloro-7-(1S,4S)-2,5-diaza-bicyclo[2.2.1]hept-2-yl-2-(2-methoxy-4-morpholin-4-yl-phenyl)-3H-imidazo[4,5-b]pyridine; and
(S)-1-{(1S,4S)-5-[6-Chloro-2-(methoxy-4-morpholin-4-yl-phenyl)-3H-imidazo[4,5-b]pyridine-7-yl]-2,5-diaza-bicyclo[2.2.1]hept-2-yl}-propan-2-ol;
or a salt thereof.

22. A compound according to claim 10, or a salt thereof, wherein Z is

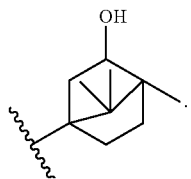 [SMILES: *C12CCC(C)(C(O)C1)C2(C)C]

23. A compound according to claim 22 that is selected from the following:
- 4-(6-chloro-2-(2-methoxy-4-morpholinophenyl)-3H-imidazo[4,5-b]pyridin-7-ylamino)-1,7,7-trimethylbicyclo[2.2.1]heptan-2-ol;
- (4S)-4-(6-chloro-2-(1-methyl-1H-pyrazol-4-yl)-3H-imidazo[4,5-b]pyridin-7-ylamino)-1,7,7-trimethylbicyclo[2.2.1]heptan-2-ol; and
- 4-(6-chloro-2-(4-morpholinophenyl)-3H-imidazo[4,5-b]pyridin-7-ylamino)-1,7,7-trimethylbicyclo[2.2.1]heptan-2-ol;

or a salt thereof.

24. A compound according to claim 10, or a salt thereof, wherein Z is

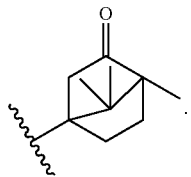 [SMILES: *C12CCC(C)(C(=O)C1)C2(C)C]

25. A compound according to claim 24 that is selected from the following:
- 4-(6-chloro-2-(4-morpholinophenyl)-3H-imidazo[4,5-b]pyridin-7-ylamino)-1,7,7-trimethylbicyclo[2.2.1]heptan-2-one;
- 4-(6-chloro-2-(2-methoxy-4-morpholinophenyl)-3H-imidazo[4,5-b]pyridin-7-ylamino)-1,7,7-trimethylbicyclo[2.2.1]heptan-2-one; and
- 4-(6-chloro-2-(1-methyl-1H-pyrazol-4-yl)-3H-imidazo[4,5-b]pyridin-7-ylamino)-1,7,7-trimethylbicyclo[2.2.1]heptan-2-one;

or a salt thereof.

26. A compound according to claim 11 that is {(diexo)-3-[6-Chloro-2-(2-methoxy-4-morpholin-4-ylmethylphenyl)-3H-imidazo[4,5-b]pyridine-7-ylamino]-bicyclo[2.2.1]hept-5-en-2-yl}-methanol, or a salt thereof.

27. A pharmaceutical composition comprising a compound according to claim 1, or a pharmaceutically acceptable salt thereof and one or more pharmaceutically acceptable excipients.

28. A method of treating a disease or disorder mediated by ALK kinase and/or JAK2 kinase comprising administering to a subject suffering from such a disease or disorder a compound according to claim 1, or a pharmaceutically acceptable salt thereof, wherein said disease or disorder is selected from colon cancer, breast cancer, non-small cell lung cancer, neuroblastoma, esophageal squamous carcinoma, hemangioma, head and neck squamous cell carcinoma, prostate cancer, myeloid leukemia, melanoma, glioblastoma, astrocytoma, anaplastic large cell lymphoma, inflammatory myofibroblastic tumor, and myeloproliferative neoplasms (MPN).

* * * * *